United States Patent
Tojo et al.

(10) Patent No.: US 10,703,755 B2
(45) Date of Patent: Jul. 7, 2020

(54) SUBSTITUTED PURINE DERIVATIVE

(71) Applicant: SUMITOMO DAINIPPON PHARMA CO., LTD., Osaka-shi, Osaka (JP)

(72) Inventors: Shingo Tojo, Osaka (JP); Yoshiaki Isobe, Osaka (JP); Eiji Ideue, Osaka (JP); Hiroaki Fujiwara, Tokyo (JP); Daisuke Urabe, Osaka (JP)

(73) Assignee: SUMITOMO DAINIPPON PHARMA CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 16/095,822

(22) PCT Filed: Apr. 25, 2017

(86) PCT No.: PCT/JP2017/016445
§ 371 (c)(1),
(2) Date: Oct. 23, 2018

(87) PCT Pub. No.: WO2017/188287
PCT Pub. Date: Nov. 2, 2017

(65) Prior Publication Data
US 2019/0169191 A1    Jun. 6, 2019

(30) Foreign Application Priority Data
Apr. 26, 2016    (JP) .................. 2016-087656

(51) Int. Cl.
| | |
|---|---|
| A61K 31/52 | (2006.01) |
| A61K 31/5377 | (2006.01) |
| A61K 45/06 | (2006.01) |
| C07D 473/16 | (2006.01) |
| C07D 473/18 | (2006.01) |
| C07D 473/40 | (2006.01) |
| C07D 519/00 | (2006.01) |
| A61P 37/06 | (2006.01) |
| C07D 473/34 | (2006.01) |
| C07D 473/28 | (2006.01) |

(52) U.S. Cl.
CPC ............ *C07D 473/18* (2013.01); *A61K 31/52* (2013.01); *A61K 31/5377* (2013.01); *A61K 45/06* (2013.01); *A61P 37/06* (2018.01); *C07D 473/16* (2013.01); *C07D 473/28* (2013.01); *C07D 473/34* (2013.01); *C07D 473/40* (2013.01); *C07D 519/00* (2013.01)

(58) Field of Classification Search
CPC .... A61K 31/52; A61K 31/5377; A61K 45/06; C07D 473/16; C07D 473/18; C07D 473/40; C07D 519/00
See application file for complete search history.

(56) References Cited

FOREIGN PATENT DOCUMENTS

| | | |
|---|---|---|
| CA | 2 315 736 A1 | 7/1999 |
| CA | 2 376 835 A1 | 1/2001 |
| WO | 03/002566 A1 | 1/2003 |
| WO | 03/006465 A1 | 1/2003 |
| WO | 03/051882 A1 | 6/2003 |
| WO | 2005/025583 A2 | 3/2005 |
| WO | 2009/005687 A1 | 1/2009 |
| WO | 2009/052310 A1 | 4/2009 |
| WO | 2011/059207 A2 | 5/2011 |

OTHER PUBLICATIONS

National Center for Biotechnology Information. PubChem Database. CID=12136911, https://pubchem.ncbi.nlm.nih.gov/compound/12136911 (accessed on Jul. 2, 2019).*
National Center for Biotechnology Information. PubChem Database. CID=12136912, https://pubchem.ncbi.nlm.nih.gov/compound/12136912 (accessed on Jul. 2, 2019).*
National Center for Biotechnology Information. PubChem Database. CID=12136915, https://pubchem.ncbi.nlm.nih.gov/compound/12136915 (accessed on Jul. 2, 2019).*
National Center for Biotechnology Information. PubChem Database. CID=22133976, https://pubchem.ncbi.nlm.nih.gov/compound/22133976 (accessed on Jul. 2, 2019).*
Sala, et al., "Purine analogs as phosphatidylinositol 4-kinase IIIβ inhibitors", Bioorganic & Medicinal Chemistry Letters, 2016, pp. 2706-2712, vol. 26 (7 pages total).
Chorvat, et al., "Synthesis, Corticotropin-Releasing Factor Receptor Binding Affinity, and Pharmacokinetic Properties of Triazolo-, Imidazo-, and Pyrrolopyrimidines and -pyridines", J. Med. Chem, 1999, pp. 838-848, vol. 42, No. 5 (16 pages total).
Shi, et al., "Oxygen as an oxidant in palladium/copper-cocatalyzed oxidative C—H/C—H cross-coupling between two heteroarenes", Science China Chemistry, Aug. 2015, pp. 1292-1296, vol. 58, No. 8 (5 pages total).

(Continued)

*Primary Examiner* — Brenda L Coleman
(74) *Attorney, Agent, or Firm* — Sughrue Mion, PLLC

(57) ABSTRACT

The present invention relates to a substituted purine derivative of formula (1) wherein $R^1$ is alkoxy or the like, $R^2$ is alkyl or the like, Ring $Q^1$ is aryl or the like, $W^1$ is alkylene or the like, Ring $Q^2$ is aromatic carbocyclyl or the like, n is 1-4, $R^3$ is hydrogen atom or the like, $X^1$ is single bond or the like, $W^2$ is alkylene or the like, and $R^4$ is hydrogen atom or the like, or a pharmaceutically acceptable salt thereof, which has a potent inhibitory effect against TLR7, and thereby is useful for treating autoimmune disease.

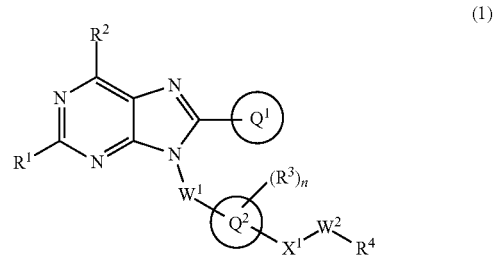

(1)

27 Claims, No Drawings

(56) References Cited

OTHER PUBLICATIONS

Liu, et al., "Parallel Solution-Phase Synthesis of a 2,6,8,9-Tetrasubstituted Purine Library via a Sulfur Intermediate", J. Comb. Chem, 2005, pp. 627-636, vol. 7, No. 4 (10 pages total).

Yang, et al., "Preparation of a Fully Substituted Purine Library", J. Comb. Chem, 2005, pp. 474-482, vol. 7, No. 3 (9 pages total).

Smith, et al., "An infrared study of the association between some 2,6-diamino-8, 9-disubstituted purines and phenobarbitone in chloroform", Journal of Pharmacy and Pharmacology, 1972, pp. 111-114, vol. 24 (6 pages total).

Sasai, et al., "Love Triangle between Unc9361, TLR7, and TLR9 Prevents Fatal Attraction", Immunity, Jul. 22, 2011, pp. 3-5, vol. 35 (3 pages total).

Savarese, et al., "Requirement of Toll-like Receptor 7 for Pristane-Induced Production of Autoantibodies and Development of Murine Lupus Nephritis", Arthritis & Rheumatism, Apr. 2008, pp. 1107-1115, vol. 58, No. 4 (9 pages total).

Christensen, et al., "Toll-like Receptor 7 and TLR9 Dictate Autoantibody Specificity and Have Opposing Inflammatory and Regulatory Roles in a Murine Model of Lupus", Immunity, Sep. 2006, pp. 417-428, vol. 25 (12 pages total).

Yokogawa, et al., "Epicutaneous Application of Toll-like Receptor 7 Agonists Leads to Systemic Autoimmunity in Wild-Type Mice", Arthritis & Rheumatology, Mar. 2014, pp. 694-706, vol. 66, No. 3 (13 pages total).

Rutz, et al., "Toll-like receptor 9 binds single-stranded CpG-DNA in a sequence- and pH-dependent manner", Eur. J. Immunol., 2004, pp. 2541-2550, vol. 34 (10 pages total).

International Search Report, issued by International Searching Authority in corresponding International Application No. PCT/JP2017/016445, dated Jun. 13, 2017.

International Preliminary Report on Patentability with translation of the Written Opinion issued from the International Bureau in counterpart International Application No. PCT/JP2017/016445, dated Nov. 8, 2018.

Extended European Search Report dated Sep. 16, 2019 in European Patent Application No. 17789569.5.

\* cited by examiner

SUBSTITUTED PURINE DERIVATIVE

CROSS REFERENCE TO RELATED APPLICATIONS

This application is a National Stage of International Application No. PCT/JP2017/016445 filed Apr. 25, 2017, claiming priority based on Japanese Patent Application No. 2016-087656 filed Apr. 26, 2016.

TECHNICAL FIELD

The present invention relates to a substituted purine derivative useful as a medicament and a pharmaceutically acceptable salt thereof, as well as a medicament for preventing and treating autoimmune disease comprising the derivative or a salt thereof as an active ingredient.

BACKGROUND ART

Autoimmune disease is a collective term of a disease that makes innate immune system (having an inherent role in detecting a foreign substance from outside such as pathogenic microorganism and in excluding it) function abnormally, i.e., the abnormally functioned immune system recognizes ingredients composing self-cells or self-tissues as foreign substance to allow autoantibody or self-reactive lymphocyte to constantly arise excessively, and thereby inflammation arises systemically or organ-specifically with the production of cytokine to lead to histologic damage.

Despite such a bad disease, however, until now there has not been therapeutic approach to exhibit some sufficient effect for treating autoimmune disease without severe side effect, except a few diseases such as rheumatoid arthritis. Accordingly, it has been strongly desired to develop a new drug for treating autoimmune disease with high therapeutic effect and high safety.

Recently, it has been found that Toll-like receptor (TLR), especially TLR7 is deeply involved in the pathology of autoimmune disease (Non-Patent Literatures 1 and 2). Thus, it is expected that a compound acting on TLR could selectively control the immunoreactions initiated from pathogenic microorganism, autoantibody, or self-reactive lymphocyte, that is, such compound acting on TLR is expected as a new medicament for treating autoimmune disease which can completely cure the disease. On the other hand, recent reports based on studies using model animals suggests that medicaments for treating autoimmune disease which have inhibitory effect to TLR9 could induce the reduction of the drug efficacy or the safety problem (Non-Patent Literatures 3 and 4).

As a medicament for treating autoimmune disease which has inhibitory effect to TLR, for example, chloroquine, hydroxychloroquine, and the like are known (Non-Patent Literature 5).

PRIOR ART

Non-Patent Reference

[Non-Patent Literature 1] Immunity, 2011, 35, 3-5
[Non-Patent Literature 2] Arthritis & Rheumatism 2000, 58, 1107-1115
[Non-Patent Literature 3] immunity 2006, 25, 417
[Non-Patent Literature 4] ARTHRITIS & RHEUMATOLOGY 2014, 66, 694
[Non-Patent Literature 5] European Journal of Immunology, 2004, 34, 2541-2550

SUMMARY OF INVENTION

Technical Problem

The purpose of the present invention may be to provide a medicament for preventing and/or treating autoimmune disease, specifically a disease involving autoimmunity (connective tissue disease such as systemic lupus erythematosus, inflammation, allergy, asthma, transplant rejection, graft-versus-host disease, infection, cancer), immunodeficiency, pain, or central nervous system disease (neurodegenerative disease such as Alzheimer's disease and Parkinson's disease). In addition, the present invention provides a medicament useful for preventing and/or treating autoimmune disease, by finding a suitable compound inhibiting TLR, especially TLR7.

Solution to Problem

The present inventors have extensively studied to reach the above purpose, and then have found that a compound of formula (1) shown below or a pharmaceutically acceptable salt thereof (hereinafter, it may be referred to as "the present compound") has a potent inhibitory effect against TLR7, and thereby the present compound may be a very useful medicament for preventing and/or treating autoimmune disease. Based upon the new findings, the present invention has been completed.

The present invention can show as follows.
(Term 1)
A compound of formula (1):

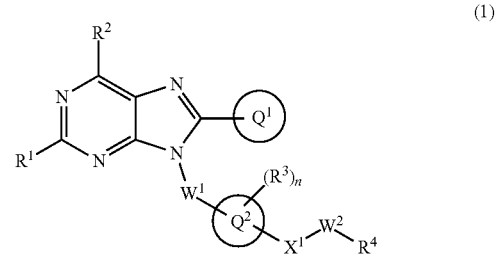

or a pharmaceutically acceptable salt thereof
wherein
$R^1$ optionally-substituted $C_{1-6}$ alkoxy, optionally-substituted $C_{3-7}$ cycloalkoxy, optionally-substituted 4- to 10-membered saturated heterocyclyloxy, optionally-substituted $C_{1-6}$ alkyl, optionally-substituted cycloalkyl, optionally-substituted $C_{1-6}$ alkylthio, optionally-substituted 4- to 10-membered saturated heterocyclyl, optionally-substituted amino, halogen atom, or hydroxy;
$R^2$ is optionally-substituted $C_{1-6}$ alkyl, optionally-substituted $C_{3-7}$ cycloalkyl, or optionally-substituted amino;
Ring $Q^1$ is optionally-substituted $C_{5-10}$ aryl, or optionally-substituted 5- to 10-membered heteroaryl;
$W^1$ is single bond, or optionally-substituted $C_{1-4}$ alkylene;
Ring $Q^2$ is $C_{6-10}$ aromatic carbocyclyl, or 5- to 10-membered aromatic heterocyclyl;
n is 1, 2, 3, or 4;
$R^3$ is, independently if there are plural $R^3$, hydrogen atom, halogen atom, cyano, hydroxy, optionally-substituted $C_{1-6}$ alkyl, optionally-substituted $C_{1-6}$ alkoxy, optionally-substituted C$_{3-7}$ cycloalkyl, optionally-substituted C$_{3-7}$ cycloalkoxy, or optionally-substituted amino;

Q$^2$-X$^1$— is Q$^2$-(single bond)-, Q$^2$-(CH$_2$)$_m$—O—, Q$^2$-(CH$_2$)$_m$—S—, Q$^2$-(CH$_2$)$_m$—S(O)$_2$—, Q$^2$-(CH$_2$)$_m$—NR$^a$S(O)$_2$, Q$^2$-(CH$_2$)$_m$—S(O)$_2$NR$^a$—, Q$^2$-(CH$_2$)$_m$—C(O)—, Q$^2$-(CH$_2$)$_m$—NR$^a$—, Q$^2$-(CH$_2$)$_m$—NR$^a$C(O)—, or Q$^2$-(CH$_2$)$_m$—C(O)NR$^a$—, wherein R$^a$ is hydrogen atom or C$_{1-6}$ alkyl; m is 0, 1, or 2;

W$^2$ is single bond, or optionally-substituted C$_{1-8}$ alkylene; and

R$^4$ is hydrogen atom, —OR$^b$ (wherein R$^b$ is hydrogen atom, optionally-substituted C$_{1-6}$ alkyl, optionally-substituted C$_{1-6}$ alkylcarbonyl, optionally-substituted aminocarbonyl, or optionally-substituted C$_{1-6}$ alkylsulfonyl), —NR$^c$R$^d$ (wherein R$^c$ is hydrogen atom or optionally-substituted C$_{1-6}$ alkyl; and R$^d$ is hydrogen atom, optionally-substituted C$_{1-6}$ alkyl, optionally-substituted C$_{1-6}$ alkylcarbonyl, optionally-substituted C$_{1-6}$ alkoxycarbonyl, or optionally-substituted C$_{1-6}$ alkylsulfonyl), optionally-substituted 4- to 10-membered saturated heterocyclyl, or optionally-substituted 5- to 10-membered heteroaryl.

(Term 2)

A compound of formula (1):

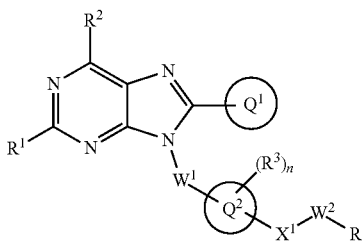

(1)

or a pharmaceutically acceptable salt thereof
wherein

R$^1$ is optionally-substituted C$_{1-6}$ alkoxy, optionally-substituted C$_{3-7}$ cycloalkoxy, optionally-substituted 4- to 7-membered saturated heterocyclyloxy, optionally-substituted C$_{1-6}$ alkyl, optionally-substituted C$_{3-7}$ cycloalkyl, optionally-substituted C$_{1-6}$ alkylthio, optionally-substituted 4- to 7-membered saturated heterocyclyl, optionally-substituted amino, or halogen atom;

R$^2$ is optionally-substituted C$_{1-6}$ alkyl, optionally-substituted C$_{3-7}$ cycloalkyl, or optionally-substituted amino;

Ring Q$^1$ optionally-substituted C$_{6-10}$ aryl, or optionally-substituted 5- to 10-membered heteroaryl;

W$^1$ is single bond, or optionally-substituted C$_{1-4}$ alkylene;

Ring Q$^2$ is C$_{6-10}$ aromatic carbocyclyl, or 5- to 10-membered aromatic heterocyclyl;

n is 1, 2, 3, or 4;

R$^3$ is, independently if there are plural R$^3$, hydrogen atom, halogen atom, cyano, hydroxy, optionally-substituted C$_{1-6}$ alkyl, optionally-substituted C$_{1-6}$ alkoxy, optionally-substituted C$_{3-7}$ cycloalkyl, optionally-substituted C$_{3-7}$ cycloalkoxy, or optionally-substituted amino;

Q$^2$-X$^1$— is Q$^2$-(single bond)-, Q$^2$-(CH$_2$)$_m$—O—, Q$^2$-(CH$_2$)$_m$—S—, Q$^2$-(CH$_2$)$_m$—S(O)$_2$—, Q$^2$-(CH$_2$)$_m$—NR$^a$S(O)$_2$—, Q$^2$-(CH$_2$)$_m$—S(O)$_2$NR$^a$—, Q$^2$-(CH$_2$)$_m$—C(O)—, Q$^2$-(CH$_2$)$_m$—NR$^a$—, Q$^2$-(CH$_2$)$_m$—NR$^a$C(O)—, or Q$^2$-(CH$_2$)$_m$—C(O)NR$^a$—, wherein R$^a$ is hydrogen atom or C$_{1-6}$ alkyl; m is 0, 1, or 2;

W$^2$ is single bond, or optionally-substituted C$_{1-8}$ alkylene; and

R$^4$ is hydrogen atom, —OR$^b$ (wherein R$^b$ is hydrogen atom, optionally-substituted C$_{1-6}$ alkyl, optionally-substituted C$_{1-6}$ alkylcarbonyl, optionally-substituted aminocarbonyl, or optionally-substituted C$_{1-6}$ alkylsulfonyl), —NR$^c$R$^d$ (wherein R$^c$ is hydrogen atom or optionally-substituted C$_{1-6}$ alkyl; and R$^d$ is hydrogen atom, optionally-substituted C$_{1-6}$ alkyl, optionally-substituted C$_{1-6}$ alkylcarbonyl, optionally-substituted C$_{1-6}$ alkoxycarbonyl, or optionally-substituted C$_{1-6}$ alkylsulfonyl), optionally-substituted 4- to 10-membered saturated heterocyclyl, or optionally-substituted 5- to 10-membered heteroaryl.

(Term 3)

The compound of Term 1 or a pharmaceutically acceptable salt thereof, wherein

R$^1$ is (1) C$_{1-6}$ alkoxy which may be substituted with 1-3 the same or different substituents selected from the group consisting of
 (a) halogen atom,
 (b) hydroxy,
 (c) C$_{1-6}$ alkoxy which may be substituted with 1-3 the same or different halogen atoms,
 (d) C$_{3-7}$ cycloalkyl which may be substituted with 1-4 the same or different substituents selected from the group consisting of halogen atom, C$_{1-6}$ alkyl, and C$_{1-6}$ alkoxy,
 (e) C$_{3-7}$ cycloalkoxy which may be substituted with 1-4 the same or different substituents selected from the group consisting of halogen atom, C$_{1-6}$ alkyl, and C$_{1-6}$ alkoxy,
 (f) phenyl which may be substituted with 1-4 the same or different substituents selected from the group consisting of halogen atom, C$_{1-6}$ alkyl, and C$_{1-6}$ alkoxy,
 (g) 5- or 6-membered heteroaryl which may be substituted with 1-4 the same or different substituents selected from the group consisting of halogen atom, C$_{1-6}$ alkyl, and C$_{1-6}$ alkoxy, and
 (h) 4- to 7-membered saturated heterocyclyl which may be substituted with 1-4 the same or different substituents selected from the group consisting of halogen atom, C$_{1-6}$ alkyl, and C$_{1-6}$ alkoxy, (2) C$_{3-7}$ cycloalkoxy which may be substituted with 1-4 the same or different substituents selected from the group consisting of halogen atom, C$_{1-6}$ alkyl, and C$_{1-6}$ alkoxy, (3) 4- to 10-membered saturated heterocyclyloxy which may be substituted with 1-4 the same or different substituents selected from the group consisting of halogen atom, C$_{1-6}$ alkyl, and C$_{1-6}$ alkoxy, (4) C$_{1-6}$ alkyl which may be substituted 1-3 the same or different substituents selected from the group consisting of halogen atom, hydroxy, and C$_{1-6}$ alkoxy, (5) C$_{3-7}$ cycloalkyl which may be substituted with 1-4 the same or different substituents selected from the group consisting of halogen atom, C$_{1-6}$ and C$_{1-6}$ alkoxy, (6) C$_{1-6}$ alkylthio which may be substituted with 1-3 the same or different halogen atoms, (7) 4- to 10-membered saturated heterocyclyl which may be substituted with 1-4 the same or different substituents selected from the group consisting of halogen atom, C$_{1-6}$ alkyl and C$_{1-6}$ alkoxy, (8) amino which may be substituted with 1-2 the same or different C$_{1-6}$ alkyl which may be substituted with 1-3 the same or different halogen atoms, (9) halogen atom, or

(10) hydroxy;

R$^2$ is C$_{6-10}$ alkyl (which may be substituted with 1-3 the same or different halogen atoms), C$_{3-7}$ cycloalkyl, or amino (which may be substituted with 1-2 the same or different C$_{1-6}$ alkyl);

Ring $Q^1$ is (1) $C_{1-6}$ aryl which may be substituted with 1-5 the same or different substituents selected from the group consisting of
  (a) halogen atom,
  (b) cyano,
  (c) $C_{1-6}$ alkyl which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
  (d) $C_{1-6}$ alkylsulfonyl which may be substituted with 1-3 the same or different halogen atoms,
  (e) $C_{1-6}$ alkoxy which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
  (f) $C_{3-7}$ cycloalkyl which may be substituted with 1-4 the same or different substituents selected from the group consisting of halogen atom, $C_{1-6}$ alkyl, and $C_{1-6}$ alkoxy,
  (g) $C_{3-7}$ cycloalkoxy which may be substituted with 1-4 the same or different substituents selected from the group consisting of halogen atom, $C_{1-6}$ alkyl, and $C_{1-6}$ alkoxy,
  (h) amino which may be substituted with 1-2 the same or different $C_{1-6}$ alkyl which may be substituted with 1-3 the same or different halogen atoms,
  (i) phenyl which may be substituted with 1-4 the same or different substituents selected from the group consisting of halogen atom, $C_{1-6}$ alkyl, and $C_{1-6}$ alkoxy, and
  (j) 5- or 6-membered heteroaryl which may be substituted with 1-4 the same or different substituents selected from the group consisting of halogen atom, $C_{1-6}$ alkyl, and $C_{1-6}$ alkoxy, or (2) 5- to 10-membered heteroaryl which may be substituted with 1-4 the same or different substituents selected from the group consisting of (a)-(j) in the above (1) $C_{6-10}$ aryl;

$W^1$ is single bond, or $C_{1-4}$ alkylene which may be substituted with 1-4 the same or different substituents selected from the group consisting of halogen atom, hydroxy, and $C_{1-6}$ alkoxy;

Ring $Q^2$ is $C_{6-10}$ aromatic carbocyclyl, or 5- to 10-membered aromatic heterocyclyl;

n is 1, 2, 3, or 4;

$R^3$ is, independently if there are plural $R^3$,
  (1) hydrogen atom,
  (2) halogen atom,
  (3) cyano,
  (4) hydroxy,
  (5) $C_{1-6}$ alkyl which may be substituted with 1-3 the same or different substituents selected from the group consisting of halogen atom, hydroxy, and $C_{1-6}$ alkoxy,
  (6) $C_{1-6}$ alkoxy which may be substituted with 1-3 the same or different substituents selected from the group consisting of halogen atom, hydroxy, and $C_{1-6}$ alkoxy,
  (7) $C_{3-7}$ cycloalkyl which may be substituted with 1-4 the same or different substituents selected from the group consisting of halogen atom, $C_{1-6}$ alkyl, and $C_{1-6}$ alkoxy,
  (8) $C_{3-7}$ cycloalkoxy which may be substituted with 1-4 the same or different substituents selected from the group consisting of halogen atom, $C_{1-6}$ alkyl, and $C_{1-6}$ alkoxy, or
  (9) amino which may be substituted with 1-2 the same or different $C_{1-6}$ alkyl which may be substituted with 1-3 the same or different halogen atoms;

$Q^2$-$X^1$— is $Q^2$-(single bond)-, $Q^2$-$(CH_2)_m$—O—, $Q^2$-$(CH_2)_m$—S—, $Q^2$-$(CH_2)_m$—$S(O)_2$—, $Q^2$-$(CH_2)_m$—$NR^aS(O)_2$—, $Q^2$-$(CH_2)_m$—$S(O)_2NR^a$—, $Q^2$-$(CH_2)_m$—C(O)—, $Q^2$-$(CH_2)_m$—$NR^a$—, $Q^2$-$(CH_2)_m$—$NR^aC(O)$—, or $Q^2$-$(CH_2)_m$—$C(O)NR^a$—, wherein $R^a$ is hydrogen atom or $C_{1-6}$ alkyl; m is 0, 1, or 2;

$W^2$ is single bond, or $C_{1-8}$ alkylene which may be substituted with 1-4 the same or different substituents selected from the group consisting of halogen atom, hydroxy, and $C_{1-6}$ alkoxy; and $R^4$ is
  (1) hydrogen atom,
  (2) —$OR^b$ wherein $R^b$ is hydrogen atom, $C_{1-6}$ alkyl, $C_{1-6}$ alkylcarbonyl, mono- or di-$C_{1-6}$ alkyl-aminocarbonyl, or $C_{1-6}$ alkylsulfonyl,
  (3) —$NR^cR^d$ wherein $R^c$ is hydrogen atom or $C_{1-6}$ alkyl which may be substituted with 1-3 the same or different halogen atoms; and $R^d$ is hydrogen atom, $C_{1-6}$ alkyl (which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy), $C_{1-6}$ alkylcarbonyl (which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy), $C_{1-6}$ alkoxycarbonyl, or $C_{1-6}$ alkylsulfonyl,
  (4) 4- to 10-membered saturated heterocyclyl which may be substituted with 1-4 the same or different substituents selected from the group consisting of
    (a) halogen atom,
    (b) hydroxy,
    (c) cyano,
    (d) $C_{1-6}$ alkyl which may be substituted with 1-3 the same or different substituents selected from the group consisting of halogen atom, hydroxy, and $C_{1-6}$ alkoxy,
    (e) alkoxy which may be substituted with 1-3 the same or different substituents selected from the group consisting of halogen atom, hydroxy, and $C_{1-6}$ alkoxy,
    (f) $C_{3-7}$ cycloalkyl,
    (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy,
    (h) $C_{1-6}$ alkoxycarbonyl,
    (i) 4- to 7-membered saturated heterocyclyl which may be substituted with 1-4 the same or different substituents selected from the group consisting of halogen atom, $C_{1-6}$ alkyl, and $C_{1-6}$ alkoxy,
    (j) phenyl which may be substituted with 1-4 the same different substituents selected from the group consisting of halogen atom, $C_{1-6}$ alkyl, and $C_{1-6}$ alkoxy,
    (k) 5- or 6-membered heteroaryl which may be substituted with 1-4 the same or different substituents selected from the group consisting of halogen atom, $C_{1-6}$ alkyl, and $C_{1-6}$ alkoxy, and
    (l) oxo, or
  (5) 5- to 10-membered heteroaryl which may be substituted with 1-4 the same or different substituents selected from the group consisting of halogen atom, $C_{1-6}$ alkyl, and $C_{1-6}$ alkoxy.

(Term 4)

The compound of Term 2 or a pharmaceutically acceptable salt thereof, wherein $R^1$ is (1) $C_{1-6}$ alkoxy which may be substituted with 1-3 the same or different substituents selected from the group consisting of (a) halogen atom,
(b) hydroxy,
(c) $C_{1-6}$ alkoxy which may be substituted with 1-3 the same or different halogen atoms,
(d) $C_{3-7}$ cycloalkyl which may be substituted with 1-4 the same or different substituents selected from the group consisting of halogen atom, $C_{1-6}$ alkyl, and $C_{1-6}$ alkoxy,
(e) $C_{3-7}$ cycloalkoxy which may be substituted with 1-4 the same or different substituents selected from the group consisting of halogen atom, $C_{1-6}$ alkyl, and $C_{1-6}$ alkoxy,
(f) phenyl which may be substituted with 1-4 the same or different substituents selected from the group consisting of halogen atom, $C_{1-6}$ alkyl, and $C_{1-6}$ alkoxy,
(g) 5- or 6-membered heteroaryl which may be substituted with 1-4 the same or different substituents selected from the group consisting of halogen atom, $C_{1-6}$ alkyl, and $C_{1-6}$ alkoxy, and
(h) 4- to 7-membered saturated heterocyclyl which may be substituted with 1-4 the same or different substituents selected from the group consisting of halogen atom, $C_{1-6}$ alkyl, and $C_{1-6}$ alkoxy,
(2) $C_{3-7}$ cycloalkoxy which may be substituted with 1-4 the same or different substituents selected from the group consisting of halogen atom, $C_{1-6}$ alkyl, and $C_{1-6}$ alkoxy,
(3) 4- to 7-membered saturated heterocyclyloxy which may be substituted with 1-4 the same or different substituents selected from the group consisting of halogen atom, $C_{1-6}$ alkyl, and $C_{1-6}$ alkoxy,
(4) $C_{1-6}$ alkyl which may be substituted with 1-3 the same or different substituents selected from the group consisting of halogen atom, hydroxy, and alkoxy,
(5) $C_{3-7}$ cycloalkyl which may be substituted with 1-4 the same or different substituents selected from the group consisting of halogen atom, $C_{1-6}$ alkyl, and $C_{1-6}$ alkoxy,
(6) $C_{1-6}$ alkylthio which may be substituted with 1-3 the same or different halogen atoms,
(7) 4- to 7-membered saturated heterocyclyl which may be substituted with 1-4 the same or different substituents selected from the group consisting of halogen atom, $C_{1-6}$ alkyl, and $C_{1-6}$ alkoxy,
(8) amino which may be substituted with 1-2 the same or different $C_{1-6}$ alkyl which may be substituted with 1-3 the same or different halogen atoms, or
(9) halogen atom;
$R^2$ is $C_{1-6}$ alkyl (which may be substituted with 1-3 the same or different halogen atoms), $C_{3-7}$ cycloalkyl, or amino (which may be substituted with 1-2 the same or different $C_{1-6}$ alkyl);
Ring $Q^1$ is
(1) $C_{6-10}$ aryl which may be substituted with 1-5 the same or different substituents selected from the group consisting of
(a) halogen atom,
(b) cyano,
(c) $C_{1-6}$ alkyl which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
(d) $C_{1-6}$ alkylsulfonyl which may be substituted with 1-3 the same or different halogen atoms,
(e) $C_{1-6}$ alkoxy which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
(f) $C_{3-7}$ cycloalkyl which may be substituted with 1-4 the same or different substituents selected from the group consisting of halogen atom, $C_{1-6}$ alkyl, and $C_{1-6}$ alkoxy,
(g) $C_{3-7}$ cycloalkoxy which may be substituted with 1-4 the same or different substituents selected from the group consisting of halogen atom, $C_{1-6}$ alkyl, and $C_{1-6}$ alkoxy,
(h) amino which may be substituted with 1-2 the same or different $C_{1-6}$ alkyl which may be substituted with 1-3 the same or different halogen atoms,
(i) phenyl which may be substituted with 1-4 the same or different substituents selected from the group consisting of halogen atom, $C_{1-6}$ alkyl, and $C_{1-6}$ alkoxy, and
(j) 5- or 6-membered heteroaryl which may be substituted with 1-4 the same or different substituents selected from the group consisting of halogen atom, $C_{1-6}$ alkyl, and $C_{1-6}$ alkoxy, or
(2) 5- or 10-membered heteroaryl which may be substituted with 1-4 the same or different substituents selected from the group consisting of (a)-(j) in the above (1) $C_{6-10}$ aryl;
$W^1$ is single bond, or $C_{1-4}$ alkylene which may be substituted with 1-4 the same or different substituents selected from the group consisting of halogen atom, hydroxy, and $C_{1-6}$ alkoxy;
Ring $Q^2$ is $C_{6-10}$ aromatic carbocyclyl, or 5- to 10-membered aromatic heterocyclyl;
n is 1, 2, 3, or 4;
$R^3$ is, independently if there are plural $R^3$,
(1) hydrogen atom,
(2) halogen atom,
(3) cyano,
(4) hydroxy,
(5) $C_{1-6}$ alkyl which may be substituted with 1-3 the same or different substituents selected from the group consisting of halogen atom, hydroxy, and $C_{1-6}$ alkoxy,
(6) $C_{1-6}$ alkoxy which may be substituted with 1-3 the same or different substituents selected from the group consisting of halogen atom, hydroxy, and $C_{1-6}$ alkoxy,
(7) $C_{3-7}$ cycloalkyl which may be substituted with 1-4 the same or different substituents selected from the group consisting of halogen atom, $C_{1-6}$ alkyl, and $C_{1-6}$ alkoxy,
(8) $C_{3-7}$ cycloalkoxy which may be substituted with 1-4 the same or different substituents selected from the group consisting of halogen atom, $C_{1-6}$ alkyl, and $C_{1-6}$ alkoxy, or
(9) amino which may be substituted with 1-2 the same different $C_{1-6}$ alkyl which may be substituted with 1-3 the same or different halogen atoms;
$Q^2$-$X^1$— is $Q^2$-(single bond)-, $Q^2$-$(CH_2)_m$—O—, $Q^2$-$(CH_2)_m$—S—, $Q^2$-$(CH_2)_m$—$S(O)_2$—, $Q^2$-$(CH_2)_m$—$NR^aS(O)_2$—, $Q^2$-$(CH_2)_m$—$S(O)_2NR^a$—, $Q^2$-$(CH_2)_m$—C(O)—, $Q^2$-$(CH_2)_m$—$NR^a$—, $Q^2$-$(CH_2)_m$—$NR^aC(O)$—, or $Q^2$-$(CH_2)_m$—$C(O)NR^a$—, wherein $R^a$ is hydrogen atom or $C_{1-6}$ alkyl; m is 0, 1, or 2;
$W^2$ is single bond, or $C_{1-6}$ alkylene which may be substituted with 1-4 the same or different substituents selected from the group consisting of halogen atom, hydroxy, and $C_{1-6}$ alkoxy; and
$R^4$ is
(1) hydrogen atom,
(2) —$OR^b$ wherein $R^b$ is hydrogen atom, $C_{1-6}$ alkyl, $C_{1-6}$ alkylcarbonyl, mono- or di-$C_{1-6}$ alkyl-aminocarbonyl, or $C_{1-6}$ alkylsulfonyl,
(3) —$NR^cR^d$ wherein $R^c$ is hydrogen atom or $C_{1-6}$ alkyl which may be substituted with 1-3 the same or different halogen atoms; and $R^d$ is hydrogen atom, $C_{1-6}$ alkyl (which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy), $C_{1-6}$ alkylcarbonyl (which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy), $C_{1-6}$ alkoxycarbonyl, or $C_{1-6}$ alkylsulfonyl, (4) 4- to 10-membered saturated heterocyclyl which may be substituted with 1-4 the same or different substituents selected from the group consisting of
  (a) halogen atom,
  (b) hydroxy,
  (c) cyano,
  (d) $C_{1-6}$ alkyl which may be substituted with 1-3 the same or different substituents selected from the group consisting of halogen atom, hydroxy, and $C_{1-6}$ alkoxy,
  (e) $C_{1-6}$ alkoxy which may be substituted with 1-3 the same or different substituents selected from the group consisting of halogen atom, hydroxy, and $C_{1-6}$ alkoxy,
  (f) $C_{3-7}$ cycloalkyl,
  (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy,
  (h) $C_{1-6}$ alkoxycarbonyl,
  (i) 4- to 7-membered saturated heterocyclyl which may be substituted with 1-4 the same or different substituents selected from the group consisting of halogen atom, $C_{1-6}$ alkyl, and $C_{1-6}$ alkoxy,
  (j) phenyl which may be substituted with 1-4 the same or different substituents selected from the group consisting of halogen atom, $C_{1-6}$ alkyl, and $C_{1-6}$ alkoxy, and
  (k) 5- or 6-membered heteroaryl which may be substituted with 1-4 the same or different substituents selected from the group consisting of halogen atom, $C_{1-6}$ alkyl, and $C_{1-6}$ alkoxy, or (5) 5- to 10-membered heteroaryl which may be substituted with 1-4 the same or different substituents selected from the group consisting of halogen atom, $C_{1-6}$ alkyl, and $C_{1-6}$ alkoxy.

(Term 5)

The compound of Term 1 or 3 or a pharmaceutically acceptable salt thereof, wherein $R^1$ is $C_{1-6}$ alkoxy (which may be substituted with 1-3 the same or different substituents selected from the group consisting of halogen atom, hydroxy, $C_{1-6}$ alkoxy, $C_{3-7}$ cycloalkyl and 4- to 7-membered saturated heterocyclyl), 4- to 10-membered saturated heterocyclyloxy (which may be substituted with 1-4 the same or different substituents selected from the group consisting of halogen atom, and $C_{1-6}$ alkyl), $C_{1-6}$ alkyl (which may be substituted with 1-3 the same or different substituents selected from the group consisting of halogen atom, hydroxy, and $C_{1-6}$ alkoxy), 4- to 10-membered saturated heterocyclyl (which may be substituted with 1-4 the same or different substituents selected from the group consisting of halogen atom, $C_{1-6}$ alkyl, and $C_{1-6}$ alkoxy), amino (which may be substituted with 1-2 the same or different $C_{1-6}$ alkyl), halogen atom, or hydroxy.

(Term 5')

The compound of Term 2 or 4 or a pharmaceutically acceptable salt thereof, wherein $R^1$ is $C_{1-6}$ alkoxy (which may be substituted with 1-3 the same or different substituents selected from the group consisting of halogen atom, hydroxy, $C_{1-6}$ alkoxy, $C_{3-7}$ cycloalkyl and 4- to 7-membered saturated heterocyclyl), 4- to 7-membered saturated heterocyclyloxy (which may be substituted with 1-4 the same or different substituents selected from the group consisting of halogen atom, and $C_{1-6}$ alkyl), $C_{1-6}$ alkyl (which may be substituted with 1-3 the same or different substituents selected from the group consisting of halogen atom, hydroxy, and $C_{1-6}$ alkoxy), 4- to 7-membered saturated heterocyclyl (which may be substituted with 1-4 the same or different substituents selected from the group consisting of halogen atom, $C_{1-6}$ alkyl, and $C_{1-6}$ alkoxy), amino (which may be substituted with 1-2 the same or different $C_{1-6}$ alkyl), or halogen atom.

(Term 6)

The compound any one of Terms 1-5 or a pharmaceutically acceptable salt thereof, wherein $R^1$ is $C_{1-6}$ alkoxy (which may be substituted with 1-3 the same or different substituents selected from the group consisting of halogen atom, hydroxy, and $C_{1-6}$ alkoxy), or halogen atom.

(Term 7)

The compound of any one of Terms 1-6 or a pharmaceutically acceptable salt thereof, wherein $R^2$ is $C_{1-6}$ alkyl or amino.

(Term 8)

The compound of any one of Terms 1-7 or a pharmaceutically acceptable salt thereof, wherein Ring $Q^1$ is (1) $C_{6-10}$ aryl which may be substituted with 1-5 the same or different substituents selected from the group consisting of
  (a) halogen atom,
  (b) cyano,
  (c) $C_{1-6}$ alkyl which may be substituted with 1-3 the same or different substituents selected from the group consisting of halogen atom, hydroxy, $C_{1-6}$ alkoxy, and 4- to 7-membered saturated heterocyclyl,
  (d) $C_{1-6}$ alkylsulfonyl,
  (e) $C_{1-6}$ alkoxy which may be substituted with 1-3 the same or different substituents selected from the group consisting of halogen atom, hydroxy, $C_{1-6}$ alkoxy, and 4- to 7-membered saturated heterocyclyl, and
  (f) amino which may be substituted with 1-2 the same or different $C_{1-6}$ alkyl, or (2) 5- to 10-membered heteroaryl which may be substituted with 1-4 the same or different substituents selected from the group consisting of (a)-(f) in the above (1) $C_{6-10}$ aryl.

(Term 9)

The compound of any one of Terms 1-8 or a pharmaceutically acceptable salt thereof, wherein Ring $Q^1$ is (1) phenyl which may be substituted with 1-5 the same or different substituents selected from the group consisting of
  (a) halogen atom,
  (b) cyano,
  (c) $C_{1-6}$ alkyl which may be substituted with 1-3 the same or different substituents selected from the group consisting of halogen atom, hydroxy, and $C_{1-6}$ alkoxy, and
  (d) $C_{1-6}$ alkoxy which may be substituted with 1-3 the same or different substituents selected from the group consisting of halogen atom, hydroxy, and $C_{1-6}$ alkoxy, (2) pyridyl which may be substituted with 1-4 the same or different substituents selected from the group consisting of (a)-(d) in the above (1), (3) pyrimidinyl which may be substituted with 1-3 the same or different substituents selected from the group consisting of (a)-(d) in the above (1), (4) pyridazinyl which may be substituted with 1-3 the same or different substituents selected from the group consisting of (a)-(d) in the above (1), (5) pyrazolyl which may be substituted with 1-3 the same or different substituents selected from the group consisting of (a)-(d) in the above (1), (6) furyl which may be substituted with 1-3 the same or different substituents selected from the group consisting of (a)-(d) in the above (1), or (7) isoxazolyl which may be substituted with 1-2 the same or different substituents selected from the group consisting of (a)-(d) in the above (1).

(Term 10)

The compound of any one of Terms 1-9 or a pharmaceutically acceptable salt thereof, wherein Ring $Q^1$ is (1) pyridyl which may be substituted with 1-5 the same or different substituents selected from the group consisting of (a) halogen atom, (b) cyano, (c) $C_{1-6}$ alkyl which may be substituted with 1-3 the same or different halogen atoms, and (d) $C_{1-6}$ alkoxy which may be substituted with 1-3 the same or different halogen atoms, or (2) pyrimidinyl which may be substituted with 1-3 the same or different substituents selected from the group consisting of (a)-(d) in the above (1).

(Term 11)

The compound of any one of Terms 1-10 or a pharmaceutically acceptable salt thereof, wherein Ring $Q^1$ is pyridyl which may be substituted with 1-4 the same or different substituents selected from the group consisting of halogen atom, cyano, $C_{1-6}$ alkyl (which may be substituted with 1-3 the same or different halogen atoms), and $C_{1-6}$ alkoxy (which may be substituted with 1-3 the same or different halogen atoms).

(Term 12)

The compound of any one of Terms 1-11 or a pharmaceutically acceptable salt thereof, wherein $W^1$ is methylene.

(Term 13)

The compound of any one of Terms 1-12 or pharmaceutically acceptable salt thereof, wherein Ring $Q^2$ is benzene ring group, or 5- or 6-membered aromatic heterocyclyl.

(Term 14)

The compound of any one of Terms 1-13 or a pharmaceutically acceptable salt thereof, wherein Ring $Q^2$ is pyridine ring group, pyrazole ring group, isoxazole ring group, or benzene ring group.

(Term 15)

The compound of any one of Terms 1-14 or a pharmaceutically acceptable salt thereof, wherein. Ring $Q^2$ is pyridine ring group, or pyrazole ring group.

(Term 16)

The compound of any one of Terms 1-15 or pharmaceutically acceptable salt thereof, wherein $R^3$ is hydrogen atom, halogen atom, cyano, hydroxy, $C_{1-6}$ alkyl (which may be substituted with 1-3 the same or different halogen atoms), or $C_{1-6}$ alkoxy (which may be substituted with 1-3 the same or different halogen atoms).

(Term 17)

The compound of any one of Terms 1-16 or a pharmaceutically acceptable salt thereof, wherein $R^3$ is hydrogen atom, halogen atom, cyano, $C_{1-6}$ alkyl (which may be substituted with 1-3 the same or different halogen atoms), or $C_{1-6}$ alkoxy (which may be substituted with 1-3 the same or different halogen atoms).

(Term 18)

The compound of any one of Terms 1-17 or a pharmaceutically acceptable salt thereof, wherein $Q^2$-$X^1$— is $Q^2$-(single bond)-, $Q^2$-$(CH_2)_m$—O—, $Q^2$-$(CH_2)_m$—C(O)—, $Q^2$-$(CH_2)_m$—$NR^a$—, or $Q^2$-$(CH_2)_m$—C(O)$NR^a$—, wherein $R^a$ is hydrogen atom or $C_{1-6}$ alkyl; m is 0, 1, or 2.

(Term 19)

The compound of any one of Terms 1-18 or a pharmaceutically acceptable salt thereof, wherein $X^1$ is single bond or —O—.

(Term 20)

The compound of any one of Terms 1-19 or a pharmaceutically acceptable salt thereof, wherein $W^2$ is single bond or $C_{1-3}$ alkylene.

(Term 21)

The compound of any one of Terms 1-20 or a pharmaceutically acceptable salt thereof, wherein $W^2$ is single bond or methylene.

(Term 22)

The compound of any one of Terms 1-3 and 5-21 or a pharmaceutically acceptable salt thereof, wherein $R^4$ is (1) hydrogen atom, (2) —$OR^b$ wherein $R^b$ is hydrogen atom, $C_{1-6}$ alkyl, or $C_{1-6}$ alkylsulfonyl, (3) —$NR^cR^d$ wherein $R^c$ and $R^d$ are independently hydrogen atom or $C_{1-6}$ alkyl which may be substituted with 1-3 the same or different halogen atoms, (4) 4- to 10-membered saturated heterocyclyl which may be substituted with 1-4 the same or different substituents selected from the group consisting of (a) halogen atom, (b) hydroxy, (c) cyano, (d) $C_{1-6}$ alkyl which may be substituted with 1-3 the same or different substituents selected from the group consisting of halogen atom, hydroxy, and $C_{1-6}$ alkoxy, (e) $C_{1-6}$ alkoxy which may be substituted with 1-3 the same or different substituents selected from the group consisting of halogen atom, hydroxy, and $C_{1-6}$ alkoxy, (f) $C_{3-7}$ cycloalkyl, (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, (h) alkoxycarbonyl, (i) 4- to 7-membered saturated heterocyclyl which may be substituted with 1-4 the same or different substituents selected from the group consisting of halogen atom, $C_{1-6}$ alkyl, and $C_{1-6}$ alkoxy, and (j) oxo, or (5) to 10-membered heteroaryl which may be substituted with 1-4 the same or different substituents selected from the group consisting of halogen atom, $C_{1-6}$ alkyl, and $C_{1-6}$ alkoxy.

(Term 23)

The compound of any one of Terms 1-22 or a pharmaceutically acceptable salt thereof, wherein $R^4$ is (1) —$NR^cR^d$ wherein $R^c$ and $R^d$ are independently hydrogen atom or $C_{1-6}$ alkyl which may be substituted with 1-3 the same or different halogen atoms, or (2) 4- to 10-membered saturated nitrogen-containing heterocyclyl which may be substituted with 1-4 the same or different substituents selected from the group consisting of (a) halogen atom, (b) hydroxy, (c) cyano, (d) $C_{1-6}$ alkyl which may be substituted with 1-3 the same or different substituents selected from the group consisting of halogen atom, hydroxy, and $C_{1-6}$ alkoxy, (e) $C_{1-6}$ alkoxy which may be substituted with 1-3 the same or different substituents selected from the group consisting of halogen atom, hydroxy, and $C_{1-6}$ alkoxy, (f) $C_{3-7}$ cycloalkyl, (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, and (h) 4- to 7-membered saturated heterocyclyl.

(Term 24)

The compound of Term 1 or a pharmaceutically acceptable salt thereof, wherein formula (1) is represented as formula (1a):

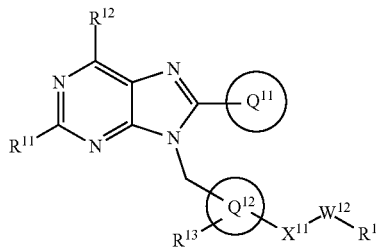

(1a)

wherein $R^{11}$ is $C_{1-6}$ alkoxy (which may be substituted with 1-3 the same or different substituents selected from the group consisting halogen atom, hydroxy, $C_{1-6}$ alkoxy, $C_{3-7}$ cycloalkyl and 4- to 7-membered saturated heterocyclyl), 4- to 10-membered saturated heterocyclyloxy (which may be substituted with 1-4 the same or different substituents selected from the group consisting of halogen atom, and $C_{1-6}$ alkyl), $C_{1-6}$ alkyl (which may be substituted with 1-3 the same or different substituents selected from the group consisting of halogen atom, hydroxy, and $C_{1-6}$ alkoxy), 4- to 10-membered saturated heterocyclyl (which may be substituted with 1-4 the same or different substituents selected from the group consisting of halogen atom, $C_{1-6}$ alkyl, and $C_{1-6}$ alkoxy), amino (which may be substituted with 1-2 the same or different $C_{1-6}$ alkyl), halogen atom, or hydroxy;

$R^{12}$ is $C_{1-6}$ alkyl or amino;

Ring $Q^{11}$ is (1) $C_{6-10}$ aryl which may be substituted with 1-5 the same or different substituents selected from the group consisting of (a) halogen atom, (b) cyano, (c) $C_{1-6}$ alkyl which may be substituted with 1-3 the same or different substituents selected from the group consisting of halogen atom, hydroxy, $C_{1-6}$ alkoxy, and 4- to 7-membered saturated heterocyclyl, (d) $C_{1-6}$ alkylsulfonyl, (e) $C_{1-6}$ alkoxy which may be substituted with 1-3 the same or different substituents selected from the group consisting of halogen atom, hydroxy, and 4- to 7-membered saturated heterocyclyl, and (f) amino which may be substituted with 1-2 the same or different $C_{1-6}$ alkyl, or (2) 5- to 10-membered heteroaryl which may be substituted with 1-4 the same or different substituents selected from the group consisting of (a)-(f) in the above (1) $C_{6-10}$ aryl;

Ring $Q^{12}$ is benzene ring group, or 5- or 6-membered aromatic heterocyclyl;

$R^{13}$ is hydrogen atom, halogen atom, hydroxy, $C_{1-6}$ alkyl (which may be substituted with 1-3 the same or different halogen atoms), or $C_{1-6}$ alkoxy (which may be substituted with 1-3 the same or different halogen atoms);

$Q^{12}$-$X^{11}$— is $Q^{12}$-(single bond)-, $Q^{12}$-$(CH_2)_m$—O—, $Q^{12}$-$(CH_2)_m$—C(O)—, $Q^{12}$-$(CH_2)_m$—$NR^a$—, or $Q^{12}$-$(CH_2)_m$—C(O)$NR^a$—, wherein $R^a$ is hydrogen atom or $C_{1-6}$ alkyl; m is 0, 1, or 2;

$W^{12}$ is single bond or $C_{1-3}$ alkylene; and $R^{14}$ is (1) hydrogen atom, (2) —$OR^b$ wherein $R^b$ is hydrogen atom, $C_{1-6}$ alkyl, or $C_{1-6}$ alkylsulfonyl, (3) —$NR^cR^d$ wherein $R^c$ and $R^d$ are independently hydrogen atom, or $C_{1-6}$ alkyl which may be substituted with 1-3 the same or different halogen atoms, (4) 4- to 10-membered saturated heterocyclyl which may be substituted with 1-4 the same or different substituents selected from the group consisting of (a) halogen atom, (b) hydroxy, (c) $C_{1-6}$ alkyl which may be substituted with 1-3 the same or different substituents selected from the group consisting of halogen atom, hydroxy, and $C_{1-6}$ alkoxy, (e) $C_{1-6}$ alkoxy which may be substituted with 1-3 the same or different substituents selected from the group consisting of halogen atom, hydroxy, and $C_{1-6}$ alkoxy, (f) $C_{3-7}$ cycloalkyl, (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, (h) $C_{1-6}$ alkoxycarbonyl, (i) 4- to 7-membered saturated heterocyclyl which may be substituted with 1-4 the same or different substituents selected from the group consisting of halogen atom, $C_{1-6}$ alkyl, and $C_{1-6}$ alkoxy, and (j) oxo, or (5) 5- to 10-membered heteroaryl which may be substituted with 1-4 the same or different substituents selected from the group consisting of halogen atom, $C_{1-6}$ alkyl, and $C_{1-6}$ alkoxy.

(Term 25)

The compound of Term 1 or a pharmaceutically acceptable salt thereof, wherein formula (1) is represented as formula (1a):

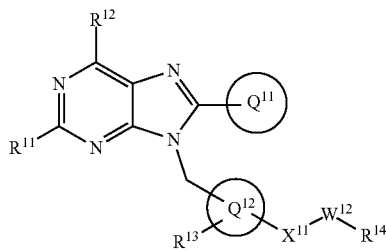

(1a)

wherein

R$^{11}$ is alkoxy which may be substituted with 1-3 the same or different substituents elected from the group consisting of halogen atom, hydroxy, and C$_{1-6}$ alkoxy;

R$^{12}$ is C$_{1-6}$ alkyl or amino;

Ring Q$^{11}$ is pyridyl which may be substituted with 1-4 the same or different substituents selected from the group consisting of halogen atom, cyano, C$_{1-6}$ alkyl (which may be substituted with 1-3 the same or different halogen atoms), and C$_{1-6}$ alkoxy (which may be substituted with 1-3 the same or different halogen atoms);

Ring Q$^{12}$ is benzene ring group, or 5- or 6-membered aromatic heterocyclyl;

R$^{13}$ is hydrogen atom, halogen atom, C$_{1-6}$ alkyl (which may be substituted with 1-3 the same or different halogen atoms), or C$_{1-6}$ alkoxy (which may be substituted with 1-3 the same or different halogen atoms);

X$^{11}$ is single bond or —O—;

W$^{12}$ is single bond or methylene;

R$^{14}$ is (1) amino which may be substituted with 1-2 the same or different C$_{1-6}$ alkyl which may be substituted with 1-3 the same or different halogen atoms, or (2) 4- to 10-membered saturated nitrogen-containing heterocyclyl which may be substituted with 1-4 the same or different substituents selected from the group consisting of (a) halogen atom, (b) hydroxy, (c) cyano, (d) C$_{1-6}$ alkyl which may be substituted with 1-3 the same or different substituents selected from the group consisting of halogen atom, hydroxy, and C$_{1-6}$ alkoxy, (e) C$_{1-6}$ alkoxy which may be substituted with 1-3 the same or different substituents selected from the group consisting of halogen atom, hydroxy, and C$_{1-6}$ alkoxy, (f) C$_{3-7}$ cycloalkyl, (g) C$_{1-6}$ alkylcarbonyl which may be substituted with 1-3 the same or different substituents selected from the group consisting of halogen atom, hydroxy, amino (which may be substituted with 1-2 the some or different C$_{1-6}$ alkyl), and C$_{1-6}$ alkoxy, and (h) 4- to 7-membered saturated heterocyclyl, (Term 26)

The compound of Term 24 or 25 or a pharmaceutically acceptable salt thereof, wherein R$^{12}$ is C$_{1-4}$ alkyl.

(Term 27)

The compound of any one of Terms 24-26 or a pharmaceutically acceptable salt thereof, wherein R$^{13}$ is hydrogen atom or halogen atom.

(Term 28)

The compound of any one of Terms 24, 26, and 27 or a pharmaceutically acceptable salt thereof, wherein Ring Q$^{11}$ is (1) pyridyl which may be substituted with 1-4 the same or different substituents selected from the group consisting of (a) halogen atom, (b) cyano, (c) C$_{1-6}$ alkyl which may be substituted with 1-3 the same or different halogen atoms, and (d) C$_{1-6}$ alkoxy which may be substituted with 1-3 the same or different halogen atoms, or (2) pyrimidinyl which may be substituted with 1-3 the same or different substituents selected from the group consisting of (a)-(d) in the above (1).

(Term 29)

The compound of any one of Terms 24-28 or a pharmaceutically acceptable salt thereof, wherein Ring Q$^{11}$ is pyridyl substituted with 1-4 the same or different halogen atoms.

(Term 30)

The compound of any one of Terms 24, and 26-29 or a pharmaceutically acceptable salt thereof, wherein Ring Q$^{11}$ is 5-fluoropyridin-3-yl, 5-cyanopyridin-3-yl, pyridin-3-yl, or pyrimidinyl.

(Term 31)

The compound any one of Terms 24-30 or a pharmaceutically acceptable salt thereof, wherein Ring Q$^{11}$ is 5-fluoropyridin-3-yl.

(Term 32)

The compound of any one of Terms 24-31 or a pharmaceutically acceptable salt thereof, wherein Q$^{12}$ is pyridine ring group, pyrazole ring group, isoxazole ring group, or benzene ring group.

(Term 33)

The compound of any one of Terms 24-32 or a pharmaceutically acceptable salt thereof, wherein Ring Q$^{12}$ is pyridine ring group, or pyrazole ring group.

(Term 34)

The compound of any one of Terms 24-33 or a pharmaceutically acceptable salt thereof, wherein R$^{14}$ is the following formula (2), (3), (4), (5), (6), (7), (8), (9), (10), (11), (12), (13), (14), (15), or (16):

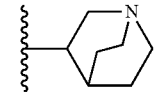

(2)

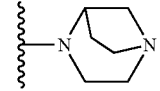

(3)

(4)

(5)

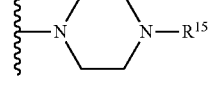

(6)

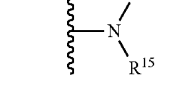

(7)

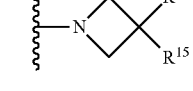

(8)

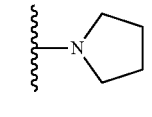

(9)

-continued

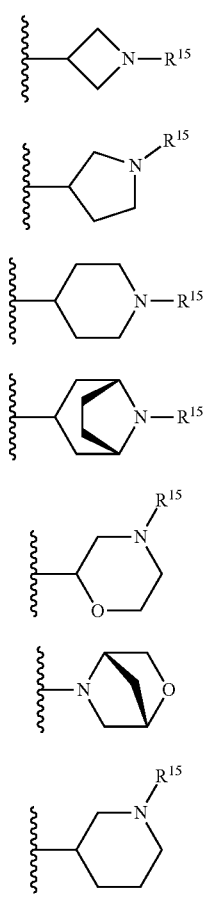

(10)

(11)

(12)

(13)

(14)

(15)

(16)

wherein

R[15] is halogen, hydroxy, C[1-6] alkyl (which may be substituted with 1-3 the same or different substituents selected from the group consisting of halogen atom, hydroxy, and C[1-6] alkoxy), C[3-7] cycloalkyl, C[1-6] alkylcarbonyl (which may be substituted with one amino which may be substituted with 1-2 the same or different C[1-6]alkyl), or 4- to 7-membered saturated heterocyclyl.

(Term 35)

The compound any one of Terms 24-34 a pharmaceutically acceptable salt thereof, wherein R[14] is the following formula (2), (3), (4), (5), (6), (7), (8), (9), or (10):

(2)

(3)

(4)

-continued (5)

(6)

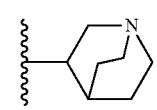

(7)

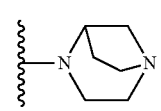

(8)

(9)

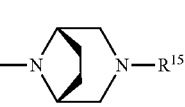

(10)

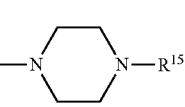

wherein

R[15] halogen, hydroxy, C[1-6] alkyl (which may be substituted with 1-3 the same or different substituents selected from group consisting of halogen atom, hydroxy, and C[1-6] alkoxy), C[3-7] cycloalkyl, C[1-6] alkylcarbonyl (which may be substituted with one amino which may be substituted with 1-2 the same or different C[1-6] alkyl), or 4- to 7-membered saturated heterocyclyl.

(Term 36)

The compound of any one of Terms 24-35 or a pharmaceutically acceptable salt thereof, wherein R[14] is the following formula (2), (3), (4), (5), or (6):

(2)

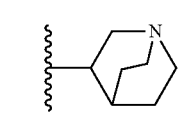

(3)

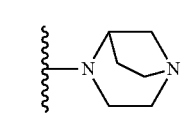

(4)

(5)

(6)

wherein

R$^{15}$ is C$_{1-6}$ alkyl (which may be substituted with 1-3 the same or different substituents selected from the group consisting of halogen atom, hydroxy, and C$_{1-6}$ alkoxy), C$_{3-7}$ cycloalkyl, C$_{1-6}$ alkylcarbonyl, or 4- to 7-membered saturated heterocyclyl.

(Term 37)

The compound of any one of Terms 34-36 or a pharmaceutically acceptable salt thereof, wherein R$^{14}$ is formula (2).

(Term 38)

The compound of Term 1 which is selected from the following compounds, or a pharmaceutically acceptable salt thereof:

Example 69: 9-({6-[(3S)-1-azabicyclo[2.2.2]oct-3-yloxy]pyridin-3-yl}methyl)-8-(5-fluoropyridin-3-yl)-2-methoxy-6-methyl-9H-purine, Example 71: 9-({6-[(3S)-1-azabicyclo[2.2.2]oct-3-yloxy]pyridin-3-yl}methyl)-2-ethoxy-8-(5-fluoropyridin-3-yl)-6-methyl-9H-purine, Example 107: 8-(5-fluoropyridin-3-yl)-2-methoxy-6-methyl-9-(4-{[(1S,4S)-5-methyl-2,5-diazabicyclo[2.2.1]hept-2-yl]methyl}benzyl)-9H-purine, Example 109: 2-ethoxy-8-(5-fluoropyridin-3-yl)-6-methyl-9-(4-{[(1S,4S)-5-methyl-2,5-diazabicyclo[2.2.1]hept-2-yl]methyl}benzyl)-9H-purine, Example 110: 2-ethoxy-8-(5-fluoropyridin-3-yl)-6-methyl-9-(4-{[(1R,4R)-5-methyl-2,5-diazabicyclo[2.2.1]hept-2-yl]methyl}benzyl)-9H-purine, Example 131: 2-ethoxy-9-(4-{[(1S,4S)-5-ethyl-2,5-diazabicyclo[2.2.1]hept-2-yl]methyl}benzyl)-8-(5-fluoropyridin-3-yl)-6-methyl-9H-purine, Example 132: 9-(4-{[(1S,4S)-5-ethyl-2,5-diazabicyclo[2.2.1]hept-2-yl]methyl}benzyl)-8-(5-fluoropyridin-3-yl)-2-methoxy-6-methyl-9H-purine, Example 133: 8-(5-fluoropyridin-3-yl)-2-methoxy-6-methyl-9-(4-{[(1S,4S)-5-propyl-2,5-diazabicyclo[2.2.1]hept-2-yl]methyl}benzyl)-9H-purine, Example 174: 9-{4-[(5R)-1,4-diazabicyclo[3.2.1]oct-4-ylmethyl]benzyl}-2-ethoxy-8-(5-fluoropyridin-3-yl)-6-methyl-9H-purine, Example 178: 9-{4-[(3S)-1-azabicyclo[2.2.2]oct-3-yl]benzyl}-8-(5-fluoropyridin-3-yl)-2-methoxy-6-methyl-9H-purine, Example 262: 2-ethoxy-8-(5-fluoropyridin-3-yl)-6-methyl-9-{4-[4-methylpiperazine-1-yl)methyl]benzyl}-9H-purine, Example 372: 9-[4-(1-azabicyclo[2.2.2]oct-3-yl)-2-methoxybenzyl]-2-ethoxy-8-(5-fluoropyridin-3-yl)-6-methyl-9H-purine, Examples 394, 395: 2-(1-azabicyclo[2.2.2]oct-3-yl)-5-{[2-ethoxy-8-(5-fluoropyridin-3-yl)-6-methyl-9H-purin-9-yl]methyl}benzonitrile, Examples 398, 399: 9-{[1-(1-azabicyclo[2.2.2]oct-3-ylmethyl)-1H-pyrazol-4-yl]methyl}-2-ethoxy-8-(5-fluoropyridin-3-yl)-6-methyl-9H-purine, Examples 400, 401: 2-(1-azabicyclo[2.2.2]oct-3-yl)-5-{[8-(5-fluoropyridin-3-yl)-2-methoxy-6-methyl-9H-purin-9-yl]methyl}benzonitrile, Example 283: 9-2-fluoro-4-[(1-methylpiperidin-4-yl)methyl]benzyl}-(5-fluoropyridin-3-yl)-2-methoxy-6-methyl-9H-purine, Example 286: 9-{2-fluoro-4-[(1-methylazetidin-3-yl)methoxy]benzyl}-8-(5-fluoropyridin-3-yl)-2-methoxy-6-methyl-9H-purine, Example 289: 5-{9-[4-(1-ethylpiperidin-4-yl)-2-fluorobenzyl]-2-methoxy-6-methyl-9H-purin-8-yl}pyridine-3-carbonitrile, Example 290: 9-[2-fluoro-4-(1-methylpyrrolidin-3-yl)benzyl]-8-(5-fluoropyridin-3-yl)-2-methoxy-6-methyl-9H-purine, Example 291: 9-[4-(1-ethylpyrrolidin-3-yl)-2-fluorobenzyl]-8-(5-fluoropyridin-3-yl)-2-methoxy-6-methyl-9H-purine, Example 292: 9-[2-fluoro-4-(1-methylpiperidin-4-yl)benzyl]-2-methoxy-6-methyl-8-(pyridin-3-yl)-9H-purine, Example 293: 9-[4-(1-ethylpiperidin-4-yl)-2-fluorobenzyl]-2-methoxy-6-methyl-8-(pyridin-3-yl)-9H-purine, Example 297: 9-(2-fluoro-4-{[(3-endo)-8-methyl-8-azabicyclo[3.2.1]oct-3-yl]oxy}benzyl)-2-methoxy-6-methyl-8-(pyridin-3-yl)-9H-purine, Example 32: 9-{4-[(3S)-1-azabicyclo[2.2.2]oct-3-yloxy]-2-fluorobenzyl}-2-methoxy-6-methyl-8-(pyrimidin-5-yl)-9H-purine, Example 344: 3-{9-[4-(1-azabicyclo[2.2.2]oct-3-yl)-2-fluorobenzyl]-2-methoxy-6-methyl-9H-purin-8-yl}benzonitrile, Example 377: 9-[4-(1-azabicyclo[2.2.2]oct-3-yl)-3-fluorobenzyl]-8-(5-fluoropyridin-3-yl)-2-methoxy-6-methyl-9H-purine, Example 386: 9-[3-(1-azabicyclo[2.2.2]oct-3-yl)benzyl]-8-(5-fluoropyridin-3-yl)-2-methoxy-6-methyl-9H-purine, Examples 396, 397: 9-{[6-(1-azabicyclo[2.2.2]oct-3-yl)-2-methylpyridin-3-yl]methyl}-2-ethoxy-8-(5-fluoropyridin-3-yl)-6-methyl-9H-purine, Example 410: 9-{4-[(3S)-1-azabicyclo[2.2.2]oct-3-yloxy]-2-fluorobenzyl}-2-methoxy-6-methyl-8-(pyridin-3-yl)-9H-purine, Example 411: 9-{2-fluoro-4-[(1-methylpiperidin-4-yl)oxy]benzyl}-8-(5-fluoropyridin-3-yl)-2-methoxy-6-methyl-9H-purine, Example 414: 9-(2-fluoro-4-{[(3S)-1-methylpyrrolidin-3-yl]oxy}benzyl)-8-(5-fluoropyridin-3-yl)-2-methoxy-6-methyl-9H-purine, Example 415: 9-(2-fluoro-4-{[(3R)-1-methylpyrrolidin-3-yl]oxy}benzyl)-8-(5-fluoropyridin-3-yl)-2-methoxy-6-methyl-9H-purine, Example 416: 9-{2-fluoro-4-[(1-methylazetidin-3-yl)oxy]benzyl}-8-(5-fluoropyridin-3-yl)-2-methoxy-6-methyl-9H-purine, Example 259: 1-(3-fluoro-4-{[8-(5-fluoropyridin-3-yl)-2-methoxy-6-methyl-9H-purin-9-yl]methyl}phenyl)-N,N-dimethylmethanamine, Example 260: 9-[4-(azetidin-1-ylmethyl)-2-fluorobenzyl]-8-(5-fluoropyridin-3-yl)-2-methoxy-6 methyl-9H-purine, Example 280: 9-(2-fluoro-4-{[(1S,4S)-5-methyl-2,5-diazabicyclo[2.2.1]hept-2-yl]methyl}benzyl)-8-(5-fluoropyridin-3-yl)-2-methoxy-6-methyl-9H-purine, Example 282: 9-[2-fluoro-4-(1-methylpiperidin-4-yl)benzyl]-8-(5-fluoropyridin-3-yl)-2-methoxy-6-methyl-9H-purine, Example 284: 9-[4-(1-ethylpiperidin-4-yl)-2-fluorobenzyl]-8-(5-fluoropyridin-3-yl)-2-methoxy-6-methyl-9H-purine, Example 285: 9-(2-fluoro-4-{[(3-endo)-8-methyl-8-azabicyclo[3.2.1]oct-3-yl]oxy}benzyl)-8-(5-fluoropyridin-3-yl)-2-methoxy-6-methyl-9H-purine, Example 294: 9-(2-fluoro-4-{[(3-endo)-8-methyl-8-azabicyclo[3.2.1]oct-3-yl]oxy}benzyl)-2-methoxy-6-methyl-8-(pyrimidin-5-yl)-9H-purine, Example 295: 5-[9-(2-fluoro-4-{[(3-endo)-8-methyl-8-azabicyclo[3.2.1]oct-3-yl]oxy}benzyl)-2-methoxy-6-methyl-9H-purin-8-yl]pyridine-3-carbonitrile, Example 296: 5-[9-(4-{[(3-endo)-8-ethyl-8-azabicyclo[3.2.1]oct-3-yl]oxy}-2-fluorobenzyl)-2-methoxy-6-methyl-9H-purin-8-yl]pyridine-3-carbonitrile, Example 303: 9-[4-(1-azabicyclo[2.2.2]oct-3-yl)-2-fluorobenzyl]-2-methoxy-6-methyl-8-(pyridin-3-yl)-9H-purine, Example 304: 9-[4-(1-azabicyclo[2.2.2]oct-3-yl)-2-fluorobenzyl]-2-methoxy-6-methyl-8-(4-methylpyridin-3-yl)-9H-purine, Example 305: 9-[4-(1-azabicyclo[2.2.2]oct-3-yl)-2-fluorobenzyl]-2-methoxy-6-methyl-8-(5-methylpyridin-3-yl)-9H-purine, Example 308: 5-[9-(2-fluoro-4-{[(1S,4S)-5-methyl-2,5-diazabicyclo[2.2.1]hept-2-yl]methyl}benzyl)-2-methoxy-6-methyl-9H-purin-8-yl]pyridine-3-carbonitrile, Example 309: 5-[9-(4-{[(1S,4S)-5-ethyl-2,5-diazabicyclo[2.2.1]hept-2-yl]methyl}-2-fluorobenzyl)-2-methoxy-6-methyl-9H-purin-8-yl]pyridine-3-carbonitrile, Example 310: 9-(2-fluoro-4-{[(1S,4S)-5-methyl-2,5-diazabicyclo[2.2.1]hept-2-yl]methyl}benzyl)-2-methoxy-6-methyl-8-(pyridin-3-yl)-9H-purine, Example 311: 5-[2-ethoxy-9-(2-fluoro-4-([{(1S,4S)-5-methyl-2,5-diazabicyclo[2.2.1]hept-2-yl]methyl}benzyl)-6-methyl-9H-purin-8-yl]pyridine-3-carbonitrile, Example 312: 2-ethoxy-9-(2-fluoro-4-{[(1S,4S)-5-methyl-2,5-diazabicyclo[2.2.1]hept-2-yl]methyl}benzyl)-6-methyl-8-(pyrimidin-5-yl)-9H-purine, Example 313: 2-ethoxy-9-(2-fluoro-4-{[(1S,4S)-5-methyl-2,5-diazabicyclo[2.2.1]hept-2-yl]methyl}benzyl)-8-(5-fluoropyridin-3-yl)-6-methyl-9H-purine, Example 322: 5-(9-{4-[(3S)-1-azabicyclo[2.2.2]oct-3-yloxy]-2-fluorobenzyl}-2-methoxy-6-methyl-9H-purin-8-yl)pyridine-3-carbonitrile, Examples 390, 391: 9-{[6-(1-azabicyclo[2.2.2]oct-3-yl)pyridin-3-yl]methyl}-2-ethoxy-8-(5-fluoropyridin-3-yl)-6-methyl-9H-purine, Examples 392, 393: 9-[4-(1-azabicyclo[2.2.2]oct-3-yl)-2-fluorobenzyl]-8-(5-fluoropyridin-3-yl)-2-methoxy-6-methyl-9H-purine, Examples 402, 403: 5-{9-[4-(1-azabicyclo[2.2.2]oct-3-yl)-2-fluorobenzyl]-2-methoxy-6-methyl-9H-purin-8-yl}pyridine-3-carbonitrile, Example 412: 9-{4-[(3S)-1-azabicyclo[2.2.2]oct-3-yloxy]-2-fluorobenzyl}-8-(5-fluoropyridin-3-yl)-2-methoxy-6-methyl 9H-purine, Example 413: 9-{4-[(3R)-1-azabicyclo[2.2.2]oct-3-yloxy]-2-fluorobenzyl}-8-(5-fluoropyridin-3-yl)-2-methoxy-6-methyl-9H-purine, Example 418: 9-(2-fluoro-4-{[(3-exo)-8-methyl-8-azabicyclo[3.2.1]oct-3-yl]oxy}benzyl)-8-(5-fluoropyridin-3-yl)-2-methoxy-6-methyl-9H-purine, and Example 443: 9-[5-(1-azabicyclo[2.2.2]oct-3-yl)-2-fluorobenzyl]-8-(5-fluoropyridin-3-yl)-2-methoxy-6-methyl-9H-purine.
(Term 39)
The compound of Term 1 which is selected from the following compounds, or a pharmaceutically acceptable salt thereof:

Example 259: 1-(3-fluoro-4-{[8-(5-fluoropyridin-3-yl)-2-methoxy-6-methyl-9H-purin-9-yl]methyl}phenyl)-N,N-dimethylmethanamine, Example 260: 9-[4-(azetidin-1-ylmethyl)-2-fluorobenzyl]-8-(5-fluoropyridin-3-yl)-2-methoxy-6-methyl-9H-purine, Example 280: 9-(2-fluoro-4-{[(1S,4S)-5-methyl-2,5-diazabicyclo[2.2.1]hept-2-yl]methyl}benzyl)-8-(5-fluoropyridin-3-yl)-2-methoxy-6-methyl-9H-purine, Example 282: 9-[2-fluoro-4-(1-methylpiperidin-4-yl)benzyl]-8-(5-fluoropyridin-3-yl)-2-methoxy-6-methyl-9H-purine, Example 284: 9-[4-(1-ethylpiperidin-4-yl)-2-fluorobenzyl]-8-(5-fluoropyridin-3-yl)-2-methoxy-6-methyl-9H-purine, Example 285: 9-(2-fluoro-4-{[(3-endo)-8-methyl-8-azabicyclo[3.2.1]oct-3-yl]oxy}benzyl)-8-(5-fluoropyridin-3-yl)-2-methoxy-6-methyl-9H-purine, Example 294: 9-(2-fluoro-4-{[(3-endo)-8-methyl-8-azabicyclo[3.2.1]oct-3-yl]oxy}benzyl)-2-methoxy-6-methyl-8-(pyrimidin-5-yl)-9H-purine, Example 295: 5-[9-(2-fluoro-4-{[(3-endo)-8-methyl-8-azabicyclo[3.2.1]oct-3-yl]oxy}benzyl)-2-methoxy-6-methyl-9H-purin-8-yl]pyridine-3-carbonitrile, Example 296: 5-[9-(4-{[(3-endo)-8-ethyl-8-azabicyclo[3.2.1]oct-3-yl]oxy}-2-fluorobenzyl)-2-methoxy-6-methyl-9H-purin-8-yl]pyridine-3-carbonitrile, Example 303: 9-[4-(1-azabicyclo[2.2.2]oct-3-yl)-2-fluorobenzyl]-2-methoxy-6-methyl-8-(pyridin-3-yl)-9H-purine, Example: 304: 9-[4-(1-azabicyclo[2.2.2]oct-3-yl)-2-fluorobenzyl]-2-methoxy-6-methyl-8-(4-methylpyridin-3-yl)-9H-purine, Example 305: 9-[4-(1-azabicyclo[2.2.2]oct-3-yl)-2-fluorobenzyl]-2-methoxy-6-methyl-8-(5-methylpyridin-3-yl)-9H-purine, Example 308: 5-[9-(2-fluoro-4-{[(1S,4S)-5-methyl-2,5-diazabicyclo[2.2.1]hept-2-yl]methyl}benzyl)-2-methoxy-6-methyl-9H-purin-8-yl]pyridine-3-carbonitrile, Example 309: 5-[9-(4-{[(1S,4S)-5-ethyl-2,5-diazabicyclo[2.2.1]hept-2-yl]methyl}-2-fluorobenzyl)-2-methoxy-6-methyl-9H-purin-8-yl]pyridine-3-carbonitrile, Example 310: 9-(2-fluoro-4-{[(1S,4S)-5-methyl-2,5-diazabicyclo[2.2.1]hept-2-yl]methyl}benzyl)-2-methoxy-6-methyl-8-(pyridin-3-yl)-9H-purine, Example 311: 5-[2-ethoxy-9-(2-fluoro-4-{[(1S,4S)-5-methyl-2,5-diazabicyclo[2.2.1]hept-2-yl]methyl}benzyl)-6-methyl-9H-purin-8-yl]pyridine-3-carbonitrile, Example 312: 2-ethoxy-9-(2-fluoro-4-{[(1S,4S)-5-methyl-2,5-diazabicyclo[2.2.1]hept-2-yl]methyl}benzyl)-6-methyl-8-(pyrimidin-5-yl)-9H-purine, Example 313: 2-ethoxy-9-(2-fluoro-4-{[(1S,4S)-5-methyl-2,5-diazabicyclo[2.2.1]hept-2-yl]methyl}benzyl)-8-(5-fluoropyridin-3-yl)-6-methyl-9H-purine, Example 322: 5-(9-{4-[(3S)-1-azabicyclo[2.2.2]oct-3-yloxy]-2-fluorobenzyl}-2-methoxy-6-methyl-9H-purin-8-yl)pyridine-3-carbonitrile, Examples 390, 391: 9-{[[6-(1-azabicyclo[2.2.2]oct-3-yl)pyridin-3-yl]methyl}-2-ethoxy-8-(5-fluoropyridin-3-yl)-6-methyl-9H-purine, Examples 392, 393: 9-[4-(1-azabicyclo[2.2.2]oct-3-yl)-2-fluorobenzyl]-8-(5-fluoropyridin-3-yl)-2-methoxy-6-methyl-9H-purine, Examples 402, 403: 5-{9-[4-(1-azabicyclo[2.2.2]oct-3-yl)-2-fluorobenzyl]-2-methoxy-6-methyl-9H-purin-8-yl}pyridine-3-carbonitrile, Example 412: 9-{4-[(3S)-1-azabicyclo[2.2.2]oct-3-yloxy]-2-fluorobenzyl}-8-(5-fluoropyridin-3-yl)-2-methoxy-6-methyl-9H-purine, Example 413: 9-{4-[(3R)-1-azabicyclo[2.2.2]oct-3-yloxy]-2-fluorobenzyl}-8-(5-fluoropyridin-3-yl)-2-methoxy-6-methyl-9H-purine, Example 418: 9-(2-fluoro-4-{[(3-exo)-8-methyl-8-azabicyclo[3.2.1]oct-3-yl]oxy}benzyl)-8-(5-fluoropyridin-3-yl)-2-methoxy-6-methyl-9H-purine, and Example 443: 9-[5-(1-azabicyclo[2.2.2]oct-3-yl)-2-fluorobenzyl]-8-(5-fluoropyridin-3-yl)-2-methoxy-6-methyl-9H-purine.

(Term 40)

A medicament comprising the compound of any one Terms 1-39 or a pharmaceutically acceptable salt thereof as an active ingredient.

(Term 41)

A medicament for treating autoimmune disease, comprising the compound of any one of Terms 1-39 or a pharmaceutically acceptable salt thereof as an active ingredient.

(Term 42)

An TLR7 inhibitor comprising the compound of any one of Terms 1-39 or a pharmaceutically acceptable salt thereof as an active ingredient.

(Term 43)

A medicament for treating systemic lupus erythematosus, lupus nephritis, Sjogren's syndrome, idiopathic thrombocytopenic purpura, psoriasis, rheumatoid arthritis, polymyositis, dermatomyositis, Behcet's disease, multiple sclerosis, or pemphigus, comprising the compound of any one of Terms 1-39 or a pharmaceutically acceptable salt thereof as an active ingredient.

(Term 44)

A medicament comprising the compound of any one of Terms 1-39 or a pharmaceutically acceptable salt thereof in combination with at least one agent selected from steroid drugs, immunosuppressive drugs, B cell-specific agent, TLR inhibitors, and other agents for treating autoimmune disease.

(Term 45)

Use of the compound of any one of Terms 1-39 or a pharmaceutically acceptable salt thereof, in the preparation of a medicament for treating systemic lupus erythematosus, lupus nephritis, Sjogren's syndrome, idiopathic thrombocytopenic purpura, psoriasis, rheumatoid arthritis, polymyositis, dermatomyositis, Behcet's disease, multiple sclerosis, or pemphigus.

(Term 46)

A method for treating systemic lupus erythematosus, lupus nephritis, Sjogren's syndrome, idiopathic thrombocytopenic purpura, psoriasis, rheumatoid arthritis, polymyositis, dermatomyositis, Behcet's disease, multiple sclerosis, or pemphigus, comprising administering a therapeutically effective amount of the compound of any one of Terms 1-39 or a pharmaceutically acceptable salt thereof to a mammal.

Effect of the Invention

The compound of the present invention has a potent inhibitory activity against TLR7. Additionally, in a preferred embodiment, the compound of the present invention has a high bioavailability when it is orally administered. Accordingly, the compound of the present invention is useful as an orally-available medicament for preventing and/or treating autoimmune disease.

DESCRIPTION OF EMBODIMENTS

Hereinafter, the present invention is described in detail. In the description, the number of carbon atoms in the definition of "substituents" can indicates, for example, "$C_{1-6}$". The specific definition "$C_{1-6}$ alkyl" means an alkyl group having 1 to 6 carbon atoms.

The "halogen atom" includes, for example, fluorine atom, chlorine atom, bromine atom, and iodine atom.

The "$C_{1-6}$ alkyl" used herein means straight or branched chain saturated hydrocarbon group having 1 to 6 carbon atoms. Preferably, it is "$C_{1-6}$ alkyl group". The "$C_{1-6}$ alkyl group" includes, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The "$C_{3-7}$ cycloalkyl" used herein means 3- to 7-membered mono-cyclic saturated or partially-unsaturated hydrocarbon group. Preferably, it is "$C_{3-6}$ cycloalkyl". The "$C_{3-7}$ cycloalkyl" includes, for example, cyclopropyl, cyclobutyl, cyclopentyl, cyclohexyl, cyclopentenyl, and cyclohexenyl.

The "$C_{1-8}$ alkylene" used herein means straight or branched chain bivalent saturated hydrocarbon group having 1 to 8 carbon atoms, or bivalent saturated hydrocarbon group having a cyclic structure which has 3 to 8 carbon atoms.

The straight or branched chain "$C_{1-8}$ alkylene" includes, for example, methylene, ethylene, trimethylene, tetramethylene, 1-methylmethylene, 1-ethylmethylene, 1-propylmethylene, 1-methylethylene, 2-methylethylene, and 1-ethylethylene, preferably methylene, and ethylene.

The "$C_{3-8}$ alkylene" having a cyclic structure includes, for example, the following groups.

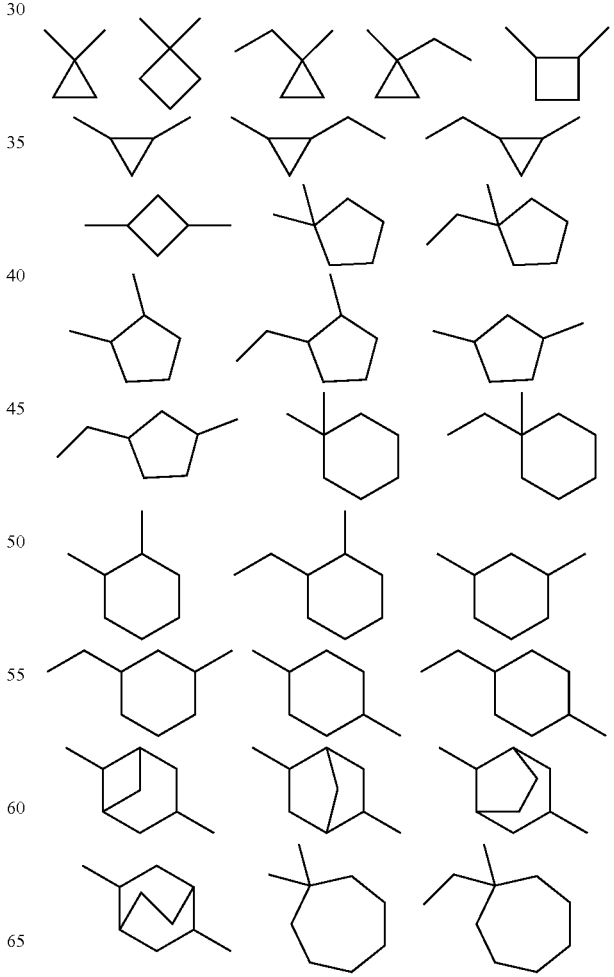

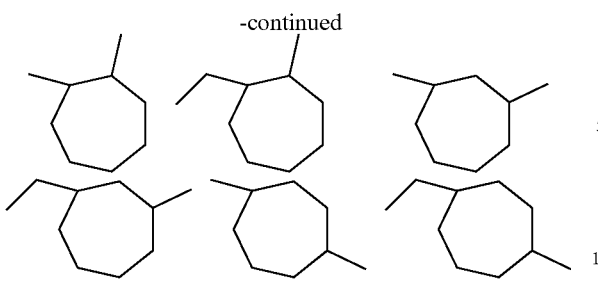

The "$C_{1-6}$ alkyl" moiety in the "$C_{1-6}$ alkoxy" is as defined in the aforementioned "$C_{1-6}$ alkyl". Preferably, it is "$C_{1-4}$ alkoxy". The "$C_{1-6}$ alkoxy" includes, for example, methoxy, ethoxy, propoxy, isopropoxy, butoxy, isobutoxy, sec-butoxy, and tert-butoxy.

The "$C_{3-7}$ cycloalkoxy" has the same meaning of "$C_{3-7}$ cycloalkyloxy", and the "$C_{3-7}$ cycloalkyl" moiety therein is as defined in the aforementioned "$C_{3-7}$ cycloalkyl". The "$C_{3-7}$ cycloalkoxy" includes, for example, cyclopropyloxy, cyclobutyloxy, cyclopentyloxy, and cyclohexyloxy.

The "$C_{1-6}$ alkyl" moiety in the "$C_{1-6}$ alkylthio" is as defined in the aforementioned "$C_{1-6}$ alkyl". Preferably, it is "$C_{1-4}$ alkylthio". The "$C_{1-6}$ alkylthio" includes, for example, methylthio, ethylthio, propylthio, isopropylthio, butylthio, isobutylthio, sec-butylthio, and tert-butylthio.

The "$C_{1-6}$ alkyl" moiety in the "$C_{1-6}$ alkylcarbonyl" is as defined in the aforementioned "$C_{1-6}$ alkyl". Preferably, it is "$C_{1-4}$ alkylcarbonyl". The "$C_{1-6}$ alkylcarbonyl" includes, for example, methylcarbonyl (acetyl), ethylcarbonyl, propylcarbonyl, isopropylcarbonyl, butylcarbonyl, pentylcarbonyl, and hexylcarbonyl.

The "$C_{1-6}$ alkyl" moiety in the "$C_{1-6}$ alkylsulfonyl" is as defined in the aforementioned "$C_{1-6}$ alkyl". Preferably, it is "$C_{1-4}$ alkylsulfonyl". The "$C_{1-6}$ alkylsulfonyl" includes, for example, methylsulfonyl (mesyl), ethylsulfonyl, propylsulfonyl, isopropylsulfonyl, butylsulfonyl, pentylsulfonyl, and hexylsulfonyl.

The "$C_{6-10}$ aryl" used herein means aromatic hydrocarbon group having 6-10 carbon atoms. Preferably, it is "$C_6$ aryl" (phenyl). The "$C_{6-10}$ aryl" includes, for example, phenyl, 1-naphthyl, and 2-naphthyl.

The "$C_{6-10}$ aryl" also includes a phenyl-fused ring group with a 5- to 7-membered ring having one or more the same or different heteroatoms selected from the group consisting of nitrogen atom, sulfur atom, and oxygen atom (for example, 1-4 heteroatoms), or a 5- to 7-membered saturated hydrocarbon ring (for example, cyclopentane, or cyclohexane). In case of the polycyclic "$C_{6-10}$ aryl group" which is a fused ring with an aromatic ring and a non-aromatic ring, however, only the aromatic ring has its "binding site".

The above fused ring group includes, for example, the following groups. In the following groups, the "binding bar" crossing each ring means that the "binding bar" attaches at a substitutable site of the ring.

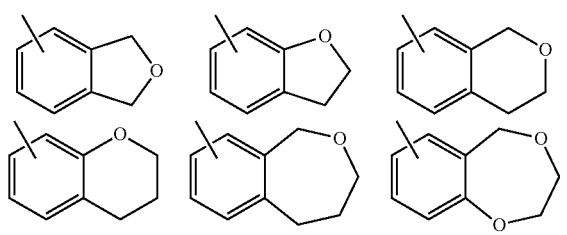

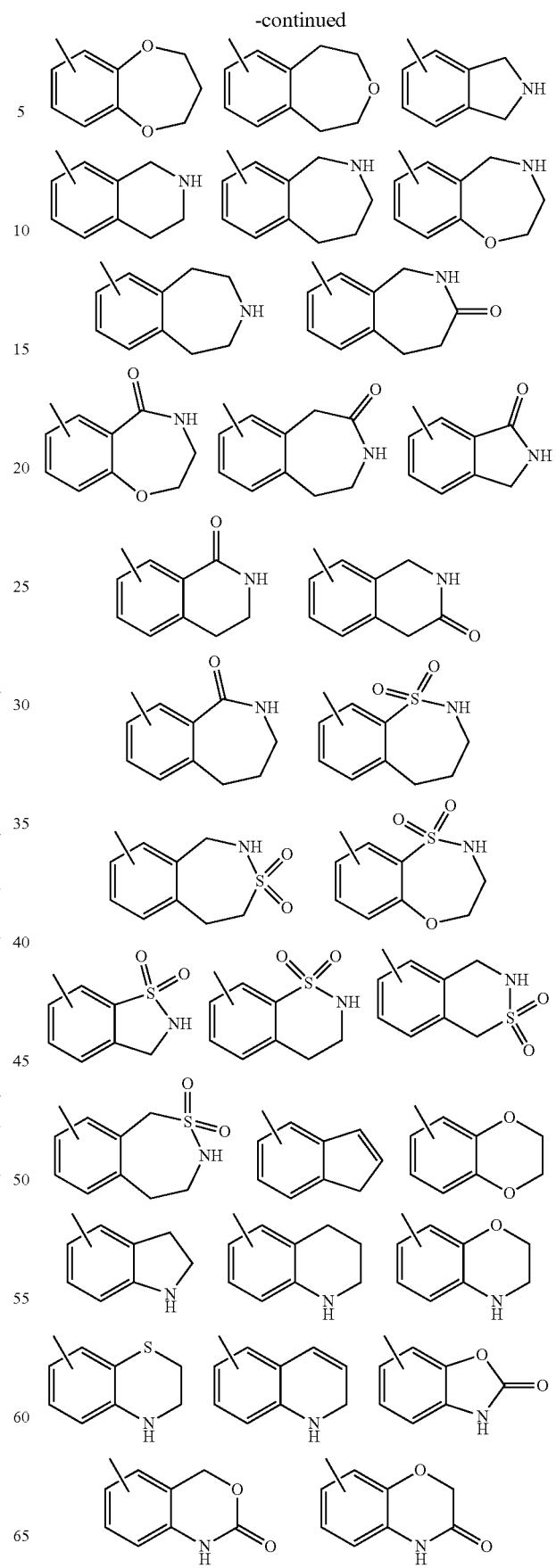

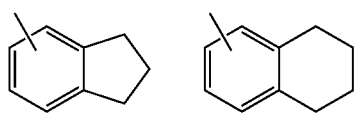

The "$C_{6-10}$ aromatic carbocyclyl" defined in Ring $Q^2$ means an aromatic carbocyclyl having 6-10 carbon atoms. Preferably, it is benzene ring group (phenylene).

The "$C_{6-10}$ aromatic carbocyclyl" also includes a benzene-fused ring group with a 5- to 7-membered ring having one or more the same or different heteroatoms selected from the group consisting of nitrogen atom, sulfur atom, and oxygen atom (for example, 1-4 heteroatoms), or a 5- to 7-membered saturated hydrocarbon ring (for example, cyclopentane, cyclohexane, or cycloheptane).

In this case, $W^1$ binds to only the aromatic ring. $X^1$ and $R^3$ can bind to a substitutable site of the aromatic ring or non-aromatic ring. The above fused ring group includes, for example, the following groups.

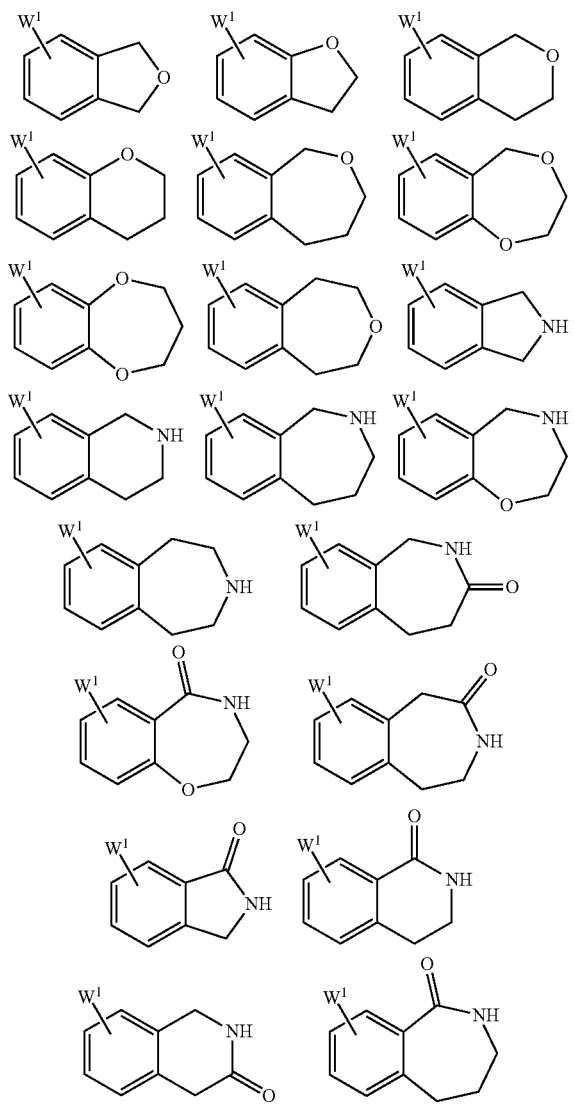

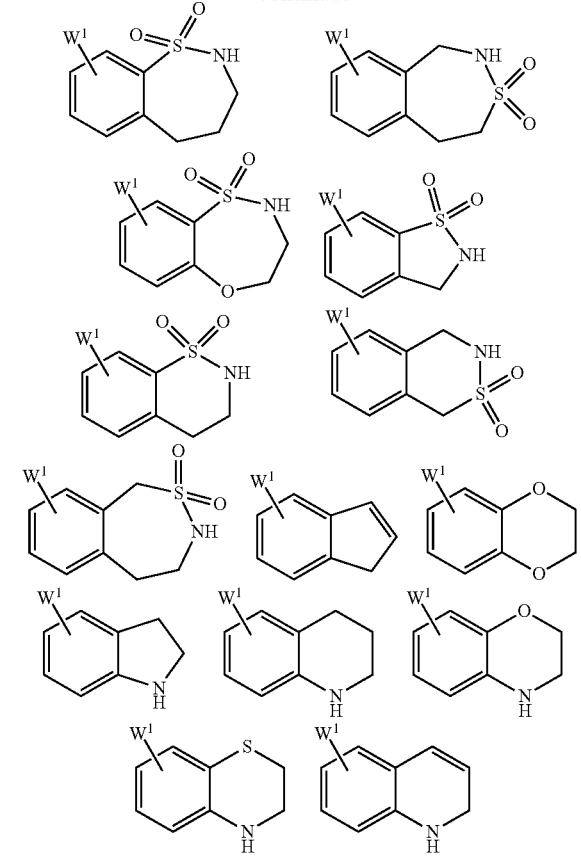

The "5- to 10-membered heteroaryl" includes, for example, 5- to 10-membered mono- or bi-cyclic aromatic hetero-ring group which has one or more the same or different heteroatoms selected from the group consisting of nitrogen atom, sulfur atom, and oxygen atom (for example, 1-4 heteroatoms). The bi-cyclic heteroaryl group also includes a mono-cyclic heteroaryl-fused ring with an aromatic ring (such as benzene and pyridine), or a non-aromatic ring (such as cyclohexane and piperidine). The "heteroaryl ring" includes, for example, the following groups.

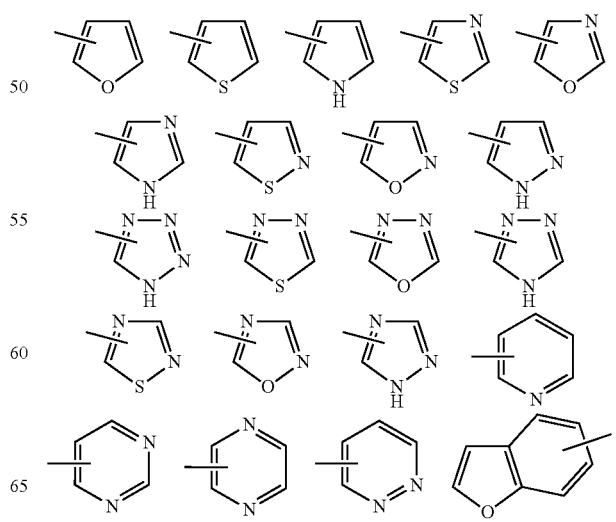

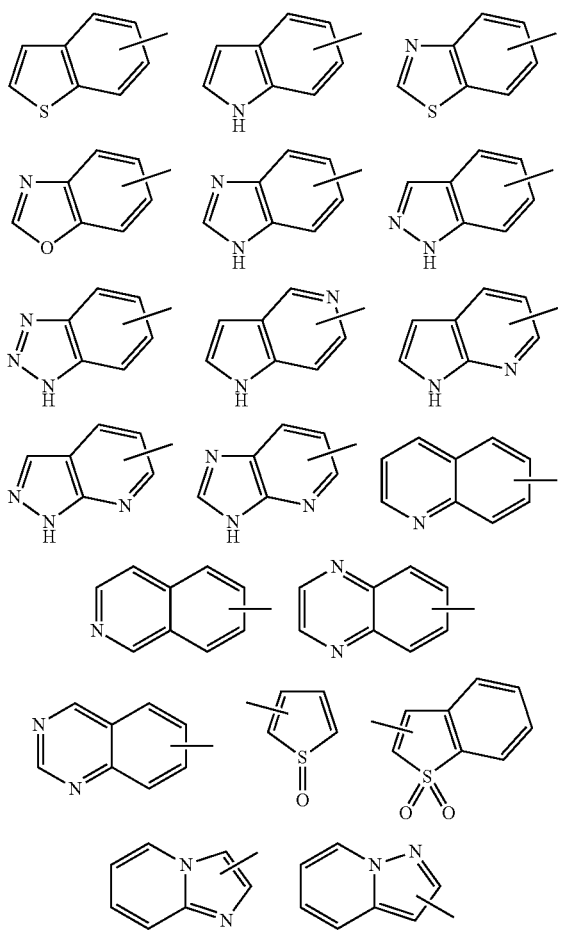

In the above groups, the "binding bar" crossing each ring means that the "binding bar" attaches at a substitutable site of the ring. For example, the following heteroaryl means 2-pyridyl, 3-pyridyl, or 4-pyridyl.

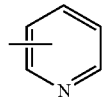

In case that the "heteroaryl" is a bi-cyclic group, for example, the following group may be 1-benzimidazolyl or 2-benzimidazolyl, as well as 4-, 5-, 6-, or 7-benzimidazolyl.

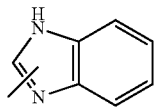

In case of the polycyclic heteroaryl group which is a fused ring of an aromatic ring and a non-aromatic ring (such as cyclohexane and piperidine), however, only the aromatic ring has its "binding site". For example, the following "polycyclic heteroaryl group" means that there is the binding site at 2-, 3-, or 4-position.

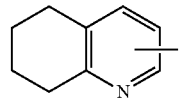

The "5- to 10-membered aromatic heterocyclyl" defined in Ring $Q^2$ includes, for example, 5- to 10-membered mono- or bi-cyclic aromatic hetero-ring group which has one or more the same or different heteroatoms selected from the group consisting of nitrogen atom, sulfur atom, and oxygen atom (for example, 1-4 heteroatoms). The bi-cyclic aromatic hetero-ring also includes a mono-cyclic aromatic hetero-ring-fused ring with an aromatic ring (such as benzene and pyridine), or a non-aromatic ring (such as cyclohexane and piperidine).

When the "5- to 10-membered aromatic heterocyclyl" is an aromatic heterocyclyl wherein a mono-cyclic aromatic heterocycle is fused with an aromatic ring or a non-aromatic ring, $W^1$ binds to only the aromatic ring (cycle).

$X^1$ and $R^3$ can bind to any substitutable site of the aromatic ring (cycle) or the non-aromatic ring.

The "4- to 10-membered saturated heterocyclyl" includes, for example, 4- to 10-membered mono- or poly-cyclic saturated heterocyclyl having 1-3 the same or different heteroatoms selected from the group consisting of nitrogen atom, oxygen atom, and sulfur atom. All the nitrogen atom, oxygen atom, and sulfur atom are atoms composing the ring(s). The heterocyclyl may be a saturated ring or a partially-unsaturated ring. Preferably, it is a saturated heterocyclyl, more preferably 5- or 6-membered saturated heterocyclyl. It includes, for example, pyranyl, dihydropyranyl, tetrahydropyranyl, tetrahydrofuryl, azetidinyl, pyrrolidinyl, imidazolidinyl, piperidinyl, piperazinyl, azepanyl, morpholinyl, thiomorpholinyl, dioxothiomorpholinyl, hexamethyleneiminyl, oxazolidinyl, thiazolidinyl, oxo-oxozolidinyl, dioxo-oxazolidinyl, dioxothiazolidinyl, 5-oxo-1,2,4-oxadiazol-3-yl, 5-oxo-1,2,4-thiadiazol-3-yl, and 5-thioxo-1,2,4-oxadiazol-3-yl. The binding site thereof may be any carbon atom or nitrogen atom which composes the ring(s).

The "4- to 10-membered saturated nitrogen-containing heterocyclyl" includes, for example, 4- to 10-membered mono- or poly-cyclic saturated heterocyclyl having 1-3 nitrogen atoms and optionally-having 1-2 the same or different atoms selected from oxygen atom and sulfur atom. All the nitrogen atom, oxygen atom, and sulfur atom are atoms composing the ring(s). The heterocyclyl may be a saturated ring or a partially-unsaturated ring. It includes, for example, azetidinyl, pyrrolidinyl, piperidinyl, piperazinyl, azepanyl, morpholinyl, thiomorpholinyl, dioxothiomorpholinyl, hexamethyleneiminyl, oxazolidinyl, thiazolidinyl, imidazolidinyl, oxo-oxazolidinyl, dioxo-oxazolidinyl, dioxothiazolidinyl, 5-oxo-1,2,4-oxadiazol-3-yl, 5-oxo-1,2,4-thiadiazol-3-yl, 5-thioxo-1,2,4-oxadiazol-3-yl, 1,2,3,6-tetrahydropyridin-4-yl, and 2,5-dihydro-1H-pyrrol-3-yl. The binding site thereof may be any carbon atom or nitrogen atom which composes the ring(s).

The "4- to 10-membered saturated nitrogen-containing heterocyclyl" also includes saturated bicyclyl, saturated fused cyclyl, and saturated spiro cyclyl which are in a scope of "4- to 10-membered saturated nitrogen-containing heterocyclyl" as a basic structure. It includes, for example, the following groups.

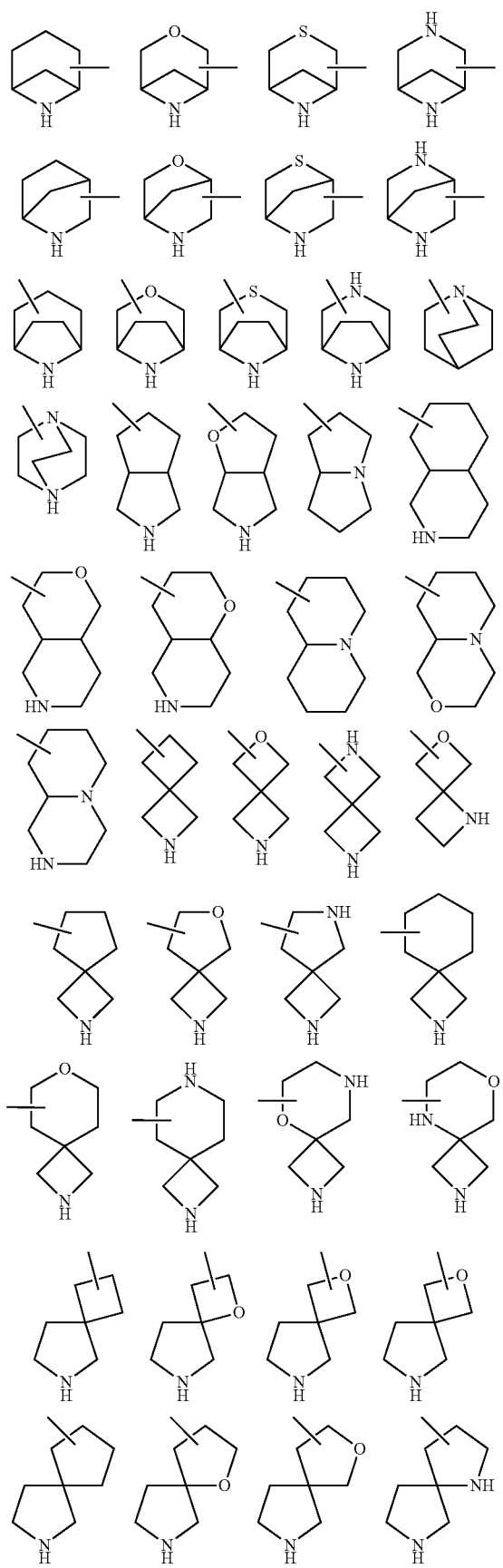
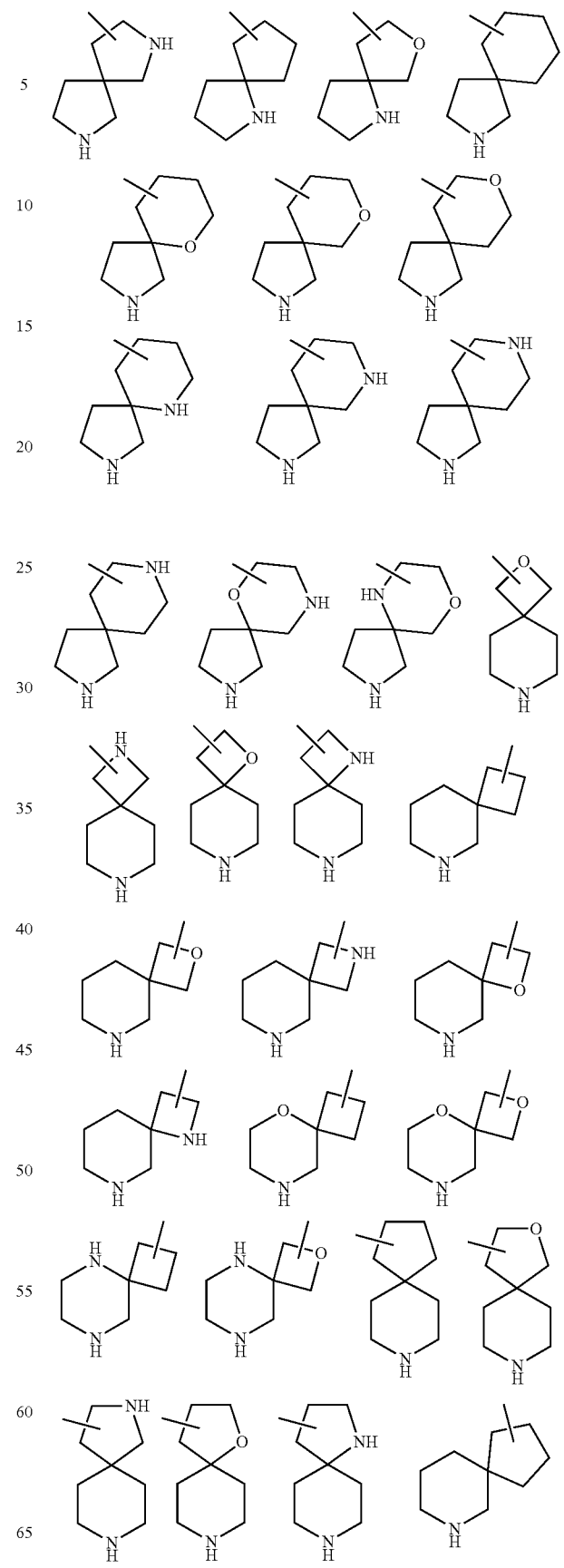

-continued

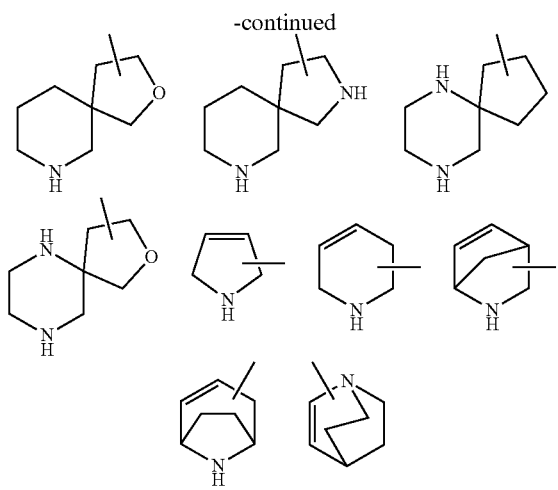

The substituent in the "optionally-substitute $C_{1-6}$ alkyl", the "optionally-substituted $C_{1-6}$ alkoxy", the "optionally-substituted $C_{1-6}$ alkylthio", the "optionally-substituted $C_{1-6}$ alkylcarbonyl", the "optionally-substituted $C_{1-6}$ alkoxycarbonyl", the "optionally-substituted $C_{1-6}$ alkylsulfonyl", and the "optionally-substituted $C_{1-4}$ alkylene" includes, for example, hydroxy, halogen atom, and $C_{1-6}$ alkoxy, preferably fluorine atom.

The substituent in the "optionally-substituted $C_{6-10}$ aryl", the "optionally-substituted 5- to 10-membered heteroaryl", the "optionally-substituted $C_{3-7}$ cycloalkyl", the "optionally-substituted $C_{3-7}$ cycloalkoxy", the "optionally-substituted saturated heterocyclyl", and the "optionally-substituted saturated heterocyclyloxy" includes, for example
(a) halogen atom,
(b) cyano,
(c) $C_{1-6}$ alkyl which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
(d) $C_{1-6}$ alkylsulfonyl which may be substituted with 1-3 the same or different halogen atoms,
(e) $C_{1-6}$ alkoxy which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
(f) $C_{3-7}$ cycloalkyl which may be substituted with 1-4 the same or different substituents selected from the group consisting of halogen atom, $C_{1-6}$ alkyl, and $C_{1-6}$ alkoxy,
(g) $C_{3-7}$ cycloalkoxy which may be substituted with 1-4 the same or different substituents selected from the group consisting of halogen atom, $C_{1-6}$ alkyl, and $C_{1-6}$ alkoxy,
(h) amino which may be substituted with 1-2 the same or different $C_{1-6}$ alkyl which may be substituted with 1-3 the same or different halogen atoms,
(i) phenyl which may be substituted with 1-4 the same or different substituents selected from the group consisting of halogen atom, $X_{1-6}$ alkyl, and $C_{1-6}$ alkoxy,
(j) 5- or 6-membered heteroaryl which may be substituted with 1-4 the same or different substituents selected from the group consisting of halogen atom, $C_{1-6}$ alkyl, and $C_{1-6}$ alkoxy,
(k) 4- to 7-membered saturated heterocyclyl which may be substituted with 1-4 the same or different substituents selected from the group consisting of halogen atom, $C_{1-6}$ alkyl, and $C_{1-6}$ alkoxy, (1) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy,
(m) phenoxy which may be substituted with 1-4 the same or different substituents selected from the group consisting of halogen atom, $C_{1-6}$ alkyl, and $C_{1-6}$ alkoxy,
(n) hydroxy, and
(o) aminocarbonyl wherein the amino may be substituted with 1-2 the same or different $C_{1-6}$ alkyl.

In another embodiment, the substituent in the "optionally-substituted amino" and the "optionally-substituted aminocarbonyl" includes, for example, $C_{1-6}$ alkyl.

In another embodiment, the substituent in the "optionally-substituted $C_{1-6}$ alkyl", the "optionally-substituted $C_{1-6}$-alkylthio", the "optionally-substituted $C_{1-6}$ alkylcarbonyl", the "optionally-substituted $C_{1-6}$ alkoxycarbonyl", the "optionally-substituted $C_{1-6}$ alkylsulfonyl", and the "optionally-substituted $C_{1-4}$ alkylene" includes, for example, hydroxy, halogen atom, and $C_{1-6}$ alkoxy, preferably fluorine atom.

In another embodiment, the substituent in the "optionally-substituted $C_{1-6}$ alkoxy", the "optionally-substituted $C_{6-10}$ aryl", the "optionally-substituted 5- to 10-membered heteroaryl", the "optionally-substituted $C_{3-7}$ cycloalkyl", the "optionally-substituted $C_{3-7}$ cycloalkoxy", the "optionally-substituted saturated heterocyclyl", and the "optionally-substituted saturated heterocyclyloxy" includes, for example
(a) halogen atom,
(b) cyano,
(c) $C_{1-6}$ alkyl which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
(d) $C_{1-6}$ alkylsulfonyl which may be substituted with 1-3 the same or different halogen atoms,
(e) $C_{1-6}$ alkoxy which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
(f) $C_{3-7}$ cycloalkyl which may be substituted with 1-4 the same or different substituents selected from the group consisting of halogen atom, $C_{1-6}$ alkyl, and $C_{1-6}$ alkoxy,
(g) $C_{3-7}$ cycloalkoxy which may be substituted with 1-4 the same or different substituents selected from the group consisting of halogen atom, $C_{1-6}$ alkyl, and $C_{1-6}$ alkoxy,
(h) amino which may be substituted with 1-2 the same or different $C_{1-6}$ alkyl which may be substituted with 1-3 the same or different halogen atoms,
(i) phenyl which may be substituted with 1-4 the same or different substituents selected from the group consisting of halogen atom, $C_{1-6}$ alkyl, and $C_{1-6}$ alkoxy,
(j) 5- or 6-membered heteroaryl which may be substituted with 1-4 the same or different substituents selected from the group consisting of halogen atom, $C_{1-6}$ alkyl, and $C_{1-6}$ alkoxy,
(k) 4- to 7-membered saturated heterocyclyl which may be substituted with 1-4 the same or different substituent selected from the group consisting of halogen atom, $C_{1-6}$ alkyl, and $C_{1-6}$ alkoxy,
(l) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, (m) phenoxy which may be substituted with 1-4 the same or different substituents selected from the group consisting of halogen atom, $C_{1-6}$ alkyl, and $C_{1-6}$ alkoxy, (n) hydroxy, (o) aminocarbonyl wherein the amino may be substituted with 1-2 the same or different $C_{1-6}$ alkyl, and (p) $C_{1-6}$ alkoxycarbonyl.

Preferred $R^1$, $R^2$, $R^3$, $W^1$, $W^2$, $X^1$, Ring $Q^1$, and Ring $Q^2$ in the present compound of formula (1) are shown below, but the technical scope of the present invention should not be limited the following compounds. The preferred embodiment of the corresponding $R^{11}$, $R^{12}$, $R^{13}$, $R^{14}$, $W^{12}$, $X^{11}$, Ring $Q^{11}$, and Ring $Q^{12}$ is also based on the followings.

Preferably, $R^1$ includes (1) $C_{1-6}$ alkoxy which may be substituted with 1-4 the same or different substituents selected from the group consisting of (a) halogen atom, (b) hydroxy, (c) $C_{1-6}$ alkoxy which may be substituted with 1-3 the same or different halogen atoms, (d) $C_{3-7}$ cycloalkyl which may be substituted with 1-4 the same or different substituents selected from the group consisting of halogen atom, $C_{1-6}$ alkyl, and $C_{1-6}$ alkoxy, (e) $C_{3-7}$ cycloalkoxy which may be substituted with 1-4 the same or different substituents selected from the group consisting of halogen atom, $C_{1-6}$ alkyl, and $C_{1-6}$ alkoxy, (f) phenyl which may be substituted with 1-4 the same or different substituents selected from the group consisting of halogen atom, $C_{1-6}$ alkyl, and $C_{1-6}$ alkoxy, (g) 5- or 6-membered heteroaryl which may be substituted with 1-4 the same or different substituents selected from the group consisting of halogen atom, $C_{1-6}$ alkyl, and $C_{1-6}$ alkoxy, and (h) 4- to 7-membered saturated heterocyclyl which may be substituted with 1-4 the same or different substituents selected from the group consisting of halogen atom, $C_{1-6}$ alkyl, and $C_{1-6}$ alkoxy, (2) $C_{3-7}$ cycloalkoxy which may be substituted with 1-4 the same or different substituents selected from the group consisting of halogen atom, $C_{1-6}$ alkyl, and $C_{1-6}$ alkoxy, (3) 4- to 7-membered saturated heterocyclyloxy which may be substituted with 1-4 the same or different substituents selected from the group consisting of halogen atom, $C_{1-6}$ alkyl, and $C_{1-6}$ alkoxy, (4) $C_{1-6}$ alkyl which may be substituted with 1-3 the same or different substituents selected from the group consisting of halogen atom, hydroxy, and $C_{1-6}$ alkoxy, (5) $C_{3-7}$ cycloalkyl which may be substituted with 1-4 the same or different substituents selected from the group consisting of halogen atom, $C_{1-6}$ alkyl, and $C_{1-6}$ alkoxy, (6) $C_{1-6}$ alkylthio which may be substituted with 1-3 the same or different halogen atoms, (7) 4- to 7-membered saturated heterocyclyl which may be substituted with 1-4 the same or different substituents selected from the group consisting of halogen atom, $C_{1-6}$ alkyl, and $C_{1-6}$ alkoxy, (8) amino which may be substituted with 1-2 the same or different $C_{1-6}$ alkyl which may be substituted with 1-3 the same or different halogen atoms, (9) halogen atom, and

(10) hydroxy.

More preferably, $R^1$ includes $C_{1-6}$ alkoxy (which may be substituted with 1-3 the same or different substituents selected from the group consisting of halogen atom, hydroxy, and $C_{1-6}$ alkoxy), and halogen atom; more preferably, $C_{1-6}$ alkoxy which may be substituted with 1-3 the same or different substituents selected from the group consisting of halogen atom, hydroxy, and $C_{1-6}$ alkoxy; more preferably, $C_{1-6}$ alkoxy which may be substituted with $C_{1-6}$ alkoxy.

In another embodiment, $R^1$ includes (1) $C_{1-6}$ alkoxy which may be substituted with 1-3 the same or different substituents selected from the group consisting of halogen atom, hydroxy, $C_{1-6}$ alkoxy, $C_{3-7}$ cycloalkyl and 4- to 10-membered saturated heterocyclyl, (2) 4- to 10-membered saturated heterocyclyloxy which may be substituted with 1-4 the same or different substituents selected from the group consisting of halogen atom, and $C_{1-6}$ alkyl, (3) $C_{1-6}$ alkyl which may be substituted with 1-3 the same or different substituents selected from the group consisting of halogen atom, hydroxy, and $C_{1-6}$ alkoxy, (4) 4- to 10-membered saturated heterocyclyl which may be substituted with 1-4 the same or different substituents selected from the group consisting of halogen atom, $C_{1-6}$ alkyl, and $C_{1-6}$ alkoxy, (5) amino which may be substituted with 1-2 the same or different $C_{1-6}$ alkyl;

(6) halogen atom, and (7) hydroxy.

Preferably, $R^2$ includes, $C_{1-6}$ alkyl (which may be substituted with 1-3 the same or different halogen atoms), $C_{3-7}$ cycloalkyl, and amino (which may be substituted with 1-2 the same or different $C_{1-6}$ alkyl). More preferably, it is $C_{1-6}$ alkyl or amino; even more preferably, $C_{1-4}$ alkyl.

Preferably, $R^3$ includes (1) hydrogen atom, (2) halogen atom, (3) cyano, (4) hydroxy, (5) $C_{1-6}$ alkyl which may be substituted with 1-3 the same or different substituents selected from the group consisting of halogen atom, hydroxy, and $C_{1-6}$ alkoxy, (6) $C_{1-6}$ alkoxy which may be substituted with 1-3 the same or different substituents selected from the group consisting of halogen atom, hydroxy, and $C_{1-6}$ alkoxy, (7) $C_{3-7}$ cycloalkyl which may be substituted with 1-4 the same or different substituents selected from the group consisting of halogen atom, $C_{1-6}$ alkyl, and $C_{1-6}$ alkoxy, (8) $C_{3-7}$ cycloalkoxy which may be substituted with 1-4 the same or different substituents selected from the group consisting of halogen atom, $C_{1-6}$ alkyl, and $C_{1-6}$ alkoxy, and (9) amino which may be substituted with 1-2 the same or different $C_{1-6}$ alkyl which may be substituted with 1-3 the same or different halogen atoms.

More preferably, $R^3$ includes hydrogen atom, halogen atom, cyano, $C_{1-6}$ alkyl (which may be substituted with 1-3 the same or different halogen atoms), and $C_{1-6}$ alkoxy (which may be substituted with 1-3 the same or different halogen atoms); more preferably, hydrogen atom, and halogen atom; more preferably, hydrogen atom and fluorine atom.

In another embodiment, $R^3$ includes hydrogen atom, halogen atom, cyano, $C_{1-6}$ alkyl (which may be substituted with 1-3 the same or different halogen atoms), $C_{1-6}$ alkoxy (which may be substituted with 1-3 the same or different halogen atoms), and hydroxy.

Preferably, $R^4$ includes (1) hydrogen atom, (2) —$OR^b$ wherein $R^b$ hydrogen atom, $C_{1-6}$ alkyl, $C_{1-6}$ alkylcarbonyl, mono- or di-$C_{1-6}$ alkyl-aminocarbonyl, or $C_{1-6}$ alkylsulfonyl, (3) —NR$^c$R$^d$ wherein R$^c$ is hydrogen atom or C$_{1-6}$ alkyl which may be substituted with 1-3 the same or different halogen atoms; and R$^d$ is hydrogen atom, C$_{1-6}$ alkyl (which may be substituted with 1-3 the same or different substituents selected from the group consisting of halogen atom, hydroxy, amino (which may be substituted with 1-2 the same or different C$_{1-6}$ alkyl), and C$_{1-6}$ alkoxy), C$_{1-6}$ alkylcarbonyl (which may be substituted with 1-3 the same or different substituents selected from the group consisting of halogen atom, hydroxy, amino (which may be substituted with 1-2 the same or different C$_{1-6}$ alkyl), and C$_{1-6}$ alkoxy), C$_{1-6}$ alkoxycarbonyl, or C$_{1-6}$ alkylsulfonyl, (4) 4- to 10-membered saturated heterocyclyl which may be substituted with 1-4 the same or different substituents selected from the group consisting of (a) halogen atom,
(b) hydroxy,
(c) cyano,
(d) C$_{1-6}$ alkyl which may be substituted with 1-3 the same or different substituents selected from the group consisting of halogen atom, hydroxy, and C$_{1-6}$ alkoxy,
(e) C$_{1-6}$ alkoxy which may be substituted with 1-3 the same or different substituents selected from the group consisting of halogen atom, hydroxy, and C$_{1-6}$ alkoxy,
(f) C$_{3-7}$ cycloalkyl,
(g) C$_{1-6}$ alkylcarbonyl which may be substituted with 1-3 the same or different substituents selected from the group consisting of halogen atom, hydroxy, amino (which may be substituted with 1-2 the same or different C$_{1-6}$ alkyl), and C$_{1-6}$ alkoxy,
(h) C$_{1-6}$ alkoxycarbonyl,
(i) 4- to 7-membered saturated heterocyclyl which may be substituted with 1-4 the same or different substituents selected from the group consisting of halogen atom, C$_{1-6}$ alkyl, and C$_{1-6}$ alkoxy,
(j) phenyl which may be substituted with 1-4 the same or different substituents selected from the group consisting of halogen atom, C$_{1-6}$ alkyl, and C$_{1-6}$ alkoxy,
(k) 5- or 6-membered heteroaryl which may be substituted with 1-4 the same or different substituents selected from the group consisting of halogen atom, C$_{1-6}$ alkyl, and C$_{1-6}$ alkoxy, and
(l) oxo, and (5) 5- to 10-membered heteroaryl which may be substituted with 1-4 the same or different substituents selected from the group consisting of halogen atom, C$_{1-6}$ alkyl, and C$_{1-6}$ alkoxy.

More preferably, R$^4$ includes
(1) —NR$^c$R$^d$ wherein R$^c$ and R$^d$ are independently hydrogen atom or C$_{1-6}$ alkyl which may be substituted with 1-3 the same or different halogen atoms, and
(2) 4- to 10-membered saturated nitrogen-containing heterocyclyl which may be substituted with 1-4 the same or different substituents selected from the group consisting of
(a) halogen atom,
(b) hydroxy,
(c) cyano,
(d) C$_{1-6}$ alkyl which may be substituted with 1-3 the same or different substituents selected from the group consisting of halogen atom, hydroxy, and C$_{1-6}$ alkoxy,
(e) C$_{1-6}$ alkoxy which may be substituted with 1-3 the same or different substituents selected from the group consisting of halogen atom, hydroxy, and C$_{1-6}$ alkoxy,
(f) C$_{3-7}$ cycloalkyl,
(g) C$_{1-6}$ alkylcarbonyl which may be substituted with 1-3 the same or different substituents selected from the group consisting of halogen atom, hydroxy, amino (which may be substituted with 1-2 the same or different C$_{1-6}$ alkyl), and C$_{1-6}$ alkoxy, and
(h) 4- to 7-membered saturated heterocyclyl.

More preferably, R$^4$ includes the following formulae (2), (3), (4), (5), and (6):

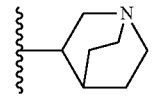

(2)

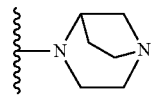

(3)

(4)

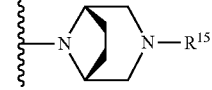

(5)

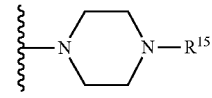

(6)

wherein R$^{15}$ is C$_{1-6}$ alkyl (which may be substituted with 1-3 the same or different substituents selected from the group consisting of halogen atom, hydroxy, and C$_{1-6}$ alkoxy), C$_{3-7}$ cycloalkyl, C$_{1-6}$ alkylcarbonyl, or 4- to 7-membered saturated heterocyclyl; more preferably a group of formula (2).

In another embodiment, R$^4$ includes
(1) hydrogen atom,
(2) —OR$^b$ wherein R$^b$ is hydrogen atom, C$_{1-6}$ alkyl, or C$_{1-6}$ alkylsulfonyl,
(3) —NR$^c$R$^d$ wherein R$^c$ and R$^d$ are independently hydrogen atom, or C$_{1-6}$ alkyl which may be substituted with 1-3 the same or different halogen atoms,
(4) 4- to 10-membered saturated heterocyclyl which may be substituted with 1-4 the same or different substituents selected from the group consisting of
(a) halogen atom,
(b) hydroxy,
(d) C$_{1-6}$ alkyl which may be substituted with 1-3 the same or different substituents selected from the group consisting of halogen atom, hydroxy, and C$_{1-6}$ alkoxy,
(e) C$_{1-6}$ alkoxy which may be substituted with 1-3 the same or different substituents selected from the group consisting of halogen atom, hydroxy, and C$_{1-6}$ alkoxy,
(f) C$_{3-7}$ cycloalkyl,
(g) C$_{1-6}$ alley carbonyl which may be substituted with 1-3 the same or different substituents selected from the group consisting of halogen atom, hydroxy, amino (which may be substituted with 1-2 the same or different C$_{1-6}$ alkyl), and C$_{1-6}$ alkoxy,
(h) C$_{1-6}$ alkoxycarbonyl,
(i) 4- to 7-membered saturated heterocyclyl which may be substituted with 1-4 the same or different substituents selected from the group consisting of halogen atom, C$_{1-6}$ alkyl, and C$_{1-6}$ alkoxy, and (j) oxo, and (5) 5- to 10-membered heteroaryl which may be substituted with 1-4 the same or different substituents selected from the group consisting of halogen atom, $C_{1-6}$ alkyl, and $C_{1-6}$ alkoxy.

In another embodiment, $R^4$ includes the following formulae (2), (3), (4), (5), (6), (7), (8), (9), (10), (11), (12), (13), (14), and (16):

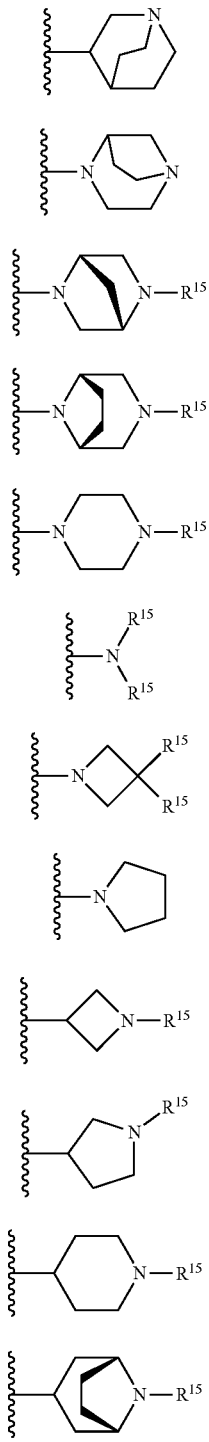

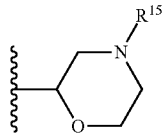

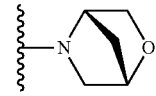

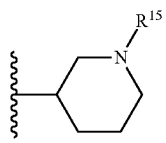

wherein $R^{15}$ halogen, hydroxy, $C_{1-6}$ alkyl (which may be substituted with 1-3 the same or different substituents selected from the group consisting of halogen atom, hydroxy, and $C_{1-6}$ alkoxy), $C_{3-7}$ cycloalkyl, $C_{1-6}$ alkylcarbonyl (which may be substituted with one amino which may be substituted with 1-2 the same or different $C_{1-6}$ alkyl), 4- to 7-membered saturated heterocyclyl.

In another embodiment, $R^4$ includes the following formulae (2), (3), (4), (5), (6), (7), (8), (9), and (10):

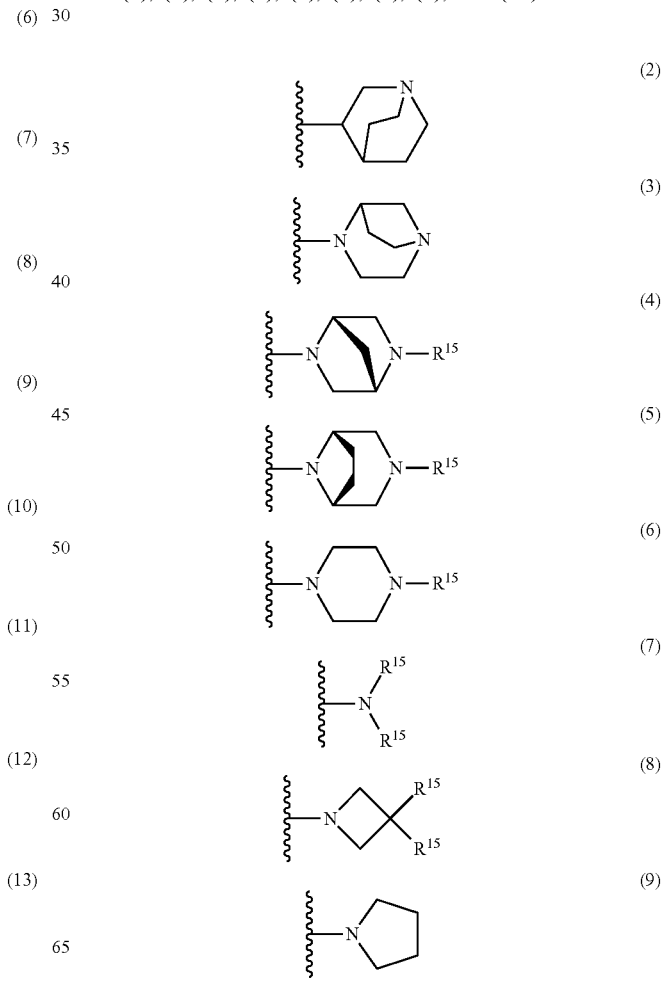

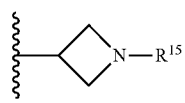

wherein $R^{15}$ is halogen, hydroxy, $C_{1-6}$ alkyl (which may be substituted with 1-3 the same or different substituents selected from the group consisting of halogen atom, hydroxy, and $C_{1-6}$ alkoxy), $C_{3-7}$ cycloalkyl, $C_{1-6}$ alkylcarbonyl (which may be substituted with one amino which may be substituted with 1-2 the same or different $C_{1-6}$ alkyl), or 4- to 7-membered saturated heterocyclyl.

Preferably, $W^1$ includes single bond and $C_{1-4}$ alkylene which may be substituted with 1-4 the same or different substituents selected from the group consisting of halogen atom, hydroxy, and $C_{1-6}$ alkoxy. More preferably, it is $C_{1-4}$ alkylene; even more preferably methylene.

Preferably, $W^2$ includes single bond and $C_{1-4}$ alkylene which may be substituted with 1-4 the same or different substituents selected from the group consisting of halogen atom, hydroxy, and $C_{1-6}$ alkoxy. More preferably, it is single bond or methylene; even more preferably single bond.

In another embodiment, $W^2$ includes single bond and $C_{1-3}$ alkylene.

Preferably, $X^1$ includes single bond, $-(CH_2)_n-O-$, $-(CH_2)_m-S-$, $-(CH_2)_m-S(O)_2-$, $-(CH_2)_m-NR^aS(O)_2-$, $-(CH_2)_m-S(O)_2NR^a-$, $-(CH_2)_m-C(O)-$, $-(CH_2)_m-NR^a-$, $-(CH_2)_m-NR^aC(O)-$, and $-(CH_2)_m-C(O)NR^a-$, wherein $R^a$ is hydrogen atom or $C_{1-6}$ alkyl; m is 0, 1, or 2. More preferably, it is single bond or $-O-$; even more preferably single bond.

In another embodiment, $X^1$ includes single bond, $-(CH_2)_m-O-$, $-(CH_2)_m-C(O)-$, $-(CH_2)_m-NR^a-$, and $-(CH_2)_m-C(O)NR^a-$, wherein $R^a$ is hydrogen atom or $C_{1-6}$ alkyl; m is 0, 1, or 2.

More preferably, Ring $Q^1$ includes
(1) $C_{6-10}$ aryl which may be substituted with 1-5 the same or different substituents selected from the group consisting of
 (a) halogen atom,
 (b) cyano,
 (c) $C_{1-6}$ alkyl which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
 (d) $C_{1-6}$ alkylsulfonyl which may be substituted with 1-3 the same or different halogen atoms,
 (e) $C_{1-6}$ alkoxy which may be substituted with 1-3 the same or different substituents selected from the group consisting of halogen atom, hydroxy, $C_{3-7}$ cycloalkyl, $C_{1-6}$ alkoxy, and 4- to 7-membered saturated heterocyclyl,
 (f) $C_{3-7}$ cycloalkyl which may be substituted with 1-4 the same or different substituents selected from the group consisting of halogen atom, $C_{1-6}$ alkyl, and $C_{1-6}$ alkoxy,
 (g) $C_{3-7}$ cycloalkoxy which may be substituted with 1-4 the same or different substituents selected from the group consisting of halogen atom, $C_{1-6}$ alkyl, and $C_{1-6}$ alkoxy,
 (h) amino which may be substituted with 1-2 the same or different $C_{1-6}$ alkyl which may be substituted with 1-3 the same or different halogen atoms,
 (i) phenyl which may be substituted with 1-4 the same or different substituents selected from the group consisting of halogen atom, $C_{1-6}$ alkyl, and $C_{1-6}$ alkoxy, and
 (j) 5- or 6-membered heteroaryl which may be substituted with 1-4 the same or different substituents selected from the group consisting of halogen atom, $C_{1-6}$ alkyl, and $C_{1-6}$ alkoxy, or
(2) 5- to 10-membered heteroaryl which may be substituted with 1-4 the same or different substituents selected from the group consisting of (a)-(j) in the above (1) $C_{6-10}$ aryl.

More preferably, Ring $Q^1$ includes pyridyl which may be substituted with 1-4 the same or different substituents selected from the group consisting of halogen atom, cyano, $C_{1-6}$ alkyl (which may be substituted with 1-3 the same or different halogen atoms), and $C_{1-6}$ alkoxy (which may be substituted with 1-3 the same or different halogen atoms); more preferably pyridyl substituted with 1-4 the same or different halogen atoms; even more preferably 5-fluoropyridin-3-yl.

In another embodiment, Ring $Q^1$ includes
(1) $C_{6-10}$ aryl which may be substituted with 1-3 the same or different substituents selected from the group consisting of
 (a) halogen atom,
 (b) cyano,
 (c) $C_{1-6}$ alkyl which may be substituted with 1-3 the same or different substituents selected from the group consisting of halogen atom, hydroxy, $C_{1-6}$ alkoxy, and 4- to 7-membered saturated heterocyclyl,
 (d) $C_{1-6}$ alkylsulfonyl,
 (e) $C_{1-6}$ alkoxy which may be substituted with 1-3 the same or different substituents selected from the group consisting of halogen atom, hydroxy, and 4- to 7-membered saturated heterocyclyl, and
 (f) amino which may be substituted with 1-2 the same or different $C_{1-6}$ alkyl, or
(2) 5- to 10-membered heteroaryl which may be substituted with 1-4 the same or different substituents selected from the group consisting of (a)-(f) in the above (1) $C_{6-10}$ aryl.

In another embodiment, Ring $Q^1$ includes
(1) pyridyl which may be substituted with 1-5 the same or different substituents selected from the group consisting of
 (a) halogen atom,
 (b) cyano,
 (c) $C_{1-6}$ alkyl which may be substituted with 1-3 the same or different halogen atoms, and
 (d) $C_{1-6}$ alkoxy which may be substituted with 1-3 the same or different halogen atoms, or
(2) pyrimidinyl which may be substituted with 1-3 the same or different substituents selected from the group consisting of (a)-(d) in the above (1).

In another embodiment, Ring $Q^1$ includes
(1) pyridyl which may be substituted with 1-4 the same or different substituents selected from the group consisting of
 (a) halogen atom, and
 (b) cyano, or
(2) pyrimidinyl which may be substituted with 1-3 the same or different substituents selected from the group consisting of (a)-(b) in the above (1).

In another embodiment, Ring $Q^1$ includes 5-fluoropyridin-3-yl, 5-cyanopyridin-3-yl, pyridin-3-yl, and pyrimidinyl.

Preferably, Ring $Q^2$ includes benzene ring group, and 5- or 6-membered aromatic heterocyclyl. More preferably, it is phenylene, pyridinediyl, or pyrazolediyl; even more preferably pyridinediyl or pyrazolediyl.

In another embodiment, Ring $Q^2$ includes pyridinediyl, pyrazolediyl, isoxazoldiyl, and benzenediyl.

In another embodiment, Ring $Q^2$ includes pyridinediyl, pyrazolediyl, and benzenediyl.

One embodiment of the compound (1) includes the following: the compound or a pharmaceutically acceptable salt thereof, wherein $R^1$ is $C_{1-6}$ alkoxy which may be substituted with 1-3 the same or different substituents selected from the group consisting of halogen atom, hydroxy, and $C_{1-6}$ alkoxy;

$R^2$ is $C_{1-6}$ alkyl or amino;

Ring $Q^1$ is (1) pyridyl which may be substituted with 1-5 the same different substituents selected from the group consisting of
  (a) halogen atom,
  (b) cyano,
  (c) $C_{1-6}$ alkyl which may be substituted with 1-3 the same or different halogen atoms, and
  (d) $C_{1-6}$ alkoxy which may be substituted with 1-3 the same or different halogen atoms, or (2) pyrimidinyl which may be substituted with 1-3 the same or different, substituents selected from the group consisting of (a)-(d) in the above (1);

Ring $Q^2$ is pyridinediyl, pyrazolediyl, or benzenediyl;

$R^3$ is hydrogen atom or fluorine atom;

$X^1$ is single bond or —O—;

$W^1$ is methylene;

$W^2$ is single bond or methylene;

$R^4$ is the following formula (2), (3), (4), (5), (6), (7), (8), (9), (10), (11), (12), (13), (14), (15), or (16):

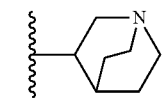
(2)

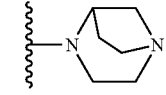
(3)

(4)

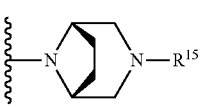
(5)

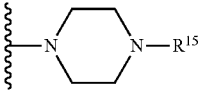
(6)

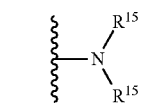
(7)

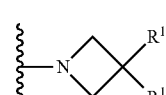
(8)

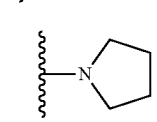
(9)

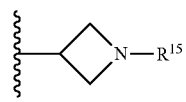
(10)

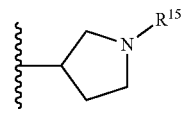
(11)

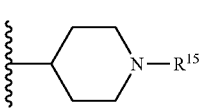
(12)

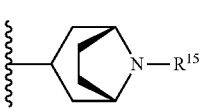
(13)

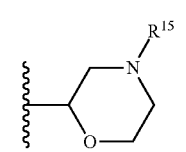
(14)

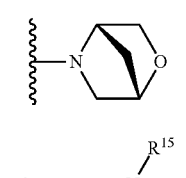
(15)

(16)

wherein $R^{15}$ is halogen, hydroxy, $C_{1-6}$ alkyl (which may be substituted with 1-3 the same or different substituents selected from the group consisting of halogen atom, hydroxy, and $C_{1-6}$ alkoxy), $C_{3-7}$ cycloalkyl, $C_{1-6}$ alkylcarbonyl (which may be substituted with one amino which may be substituted with 1-2 the same or different $C_{1-6}$ alkyl), or 4- to 7-membered saturated heterocyclyl.

The compound of the present invention may be is a form of hydrate and/or solvate, thus the compound of the present invention encompasses such hydrate thereof and solvate thereof such as ethanolate. In addition, the compound of the present invention also includes various embodiments of its crystal form.

The pharmaceutically acceptable salt of the compound of formula (1) includes, for example, a salt with an inorganic acid such as hydrochloride, hydrobromide, sulfate, phosphate, and nitrate; and a salt with an organic acid such as acetate, propionate, oxalate, succinate, lactate, malate, tartrate, citrate, maleate, fumarate, methanesulfonate, p-toluenesulfonate, benzenesulfonate, and ascorbate.

The compound of formula (1) can exist as a tautomer thereof. Thus, the compound of the present invention also includes a tautomer of compound (1).

The compound of formula (1) can have at least one chiral carbon. Thus, the compound of the present invention also includes a racemate of compound (1) as well as an optically active compound (1).

In addition, the compound of formula (1) in which any one or more $^1H$ atoms are replaced by $^2H$ (D) atoms (deuterium form) is within the scope of the present invention of formula (1).

Hereinafter, the processes to prepare the present compound of formula (1) are explained along with examples, but the present invention should not be limited to the examples.
Preparation Process The compounds of the present invention can be prepared by means of the preparation processes mentioned below, and known processes with known compounds.

Each compound in the following schemes sometimes exists as its salt, and as an example of such salt, the salt of Compound (1) can be exemplified. The reactions mentioned below are just examples, thus the compounds of the present invention may be prepared by other means based on the knowledge of a skilled person in organic synthesis.

If there is a function group that needs to be protected in each preparation process, the function group may be protected as appropriate and then deprotected after completing the reaction or the reaction sequences, unless there is any specific description of protecting groups.

The protecting group used herein includes, for example, general protecting groups described in T. W. Greene and P. G. M. Wuts, "Protective Groups in Organic Synthesis", 3rd Ed., John Wiley and Sons, inc., New York (1999); in more detail, it includes, for example, tert-butoxycarbonyl, benzyloxycarbonyl, dimethylformamide, p-toluenesulfonyl, o-nitrobenzenesulfonyl, and tetrahydropyranyl, for amino group; trialkylsilyl, acetyl, benzyl, tetrahydropyranyl, and methoxymethyl, for hydroxy group; dialkylacetal and cycloalkylacetal, for aldehyde group; and tert-butyl ester, orthoester, and acid amide, for carbonyl group.

The protection and deprotection can be carried out by conventional means in organic synthesis chemistry (for example, the methods described in T. W. Greene and P. G. M. Wuts, "Protective Groups in Organic Synthesis", 3rd Ed., John Wiley and Sons, inc., New York (1999)), or similar means to them.

Preparation Process 1

The compound of formula (1-6) can be prepared, for example, by the following process.

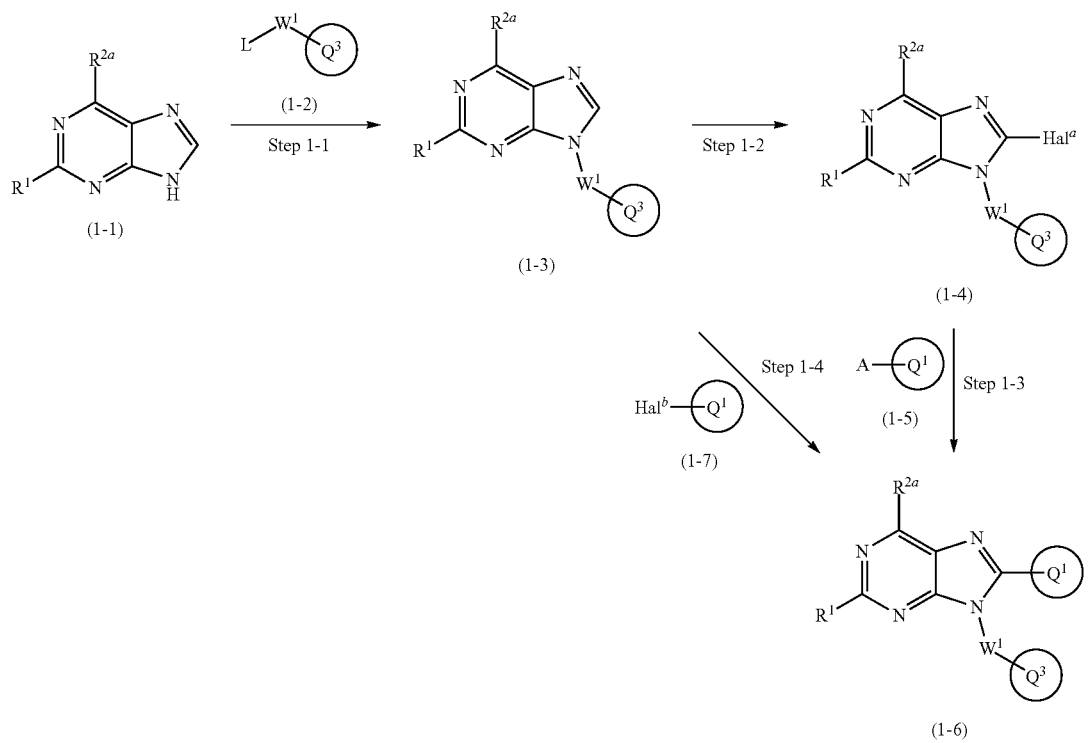

wherein $R^1$, Ring $Q^1$, and $W^1$ are as defined in the above Term 1; $R^{2a}$ is optionally-substituted amino; Ring $Q^3$ is optionally-substituted $C_{6\text{-}10}$ aryl, or optionally-substituted 5- to 10-membered heteroaryl; A is boronic acid, boronate, $BF_3K$, or $BF_3Na$; $Hal^a$ and $Hal^b$ are independently chlorine atom, bromine atom, or iodine atom; L is leaving group such as iodine atom, bromine atom, chlorine atom, and substituted sulfonyl (for example, methanesulfonyl, p-toluenesulfonyl, etc.).

Step 1-1: Preparation Step of Compound (1-3)

Compound (1-3) can be prepared by reacting compound (1-1) with compound (1-2) by a known synthetic method (for example, EP1550662, (2005); *Journal of Medicinal Chemistry*, 2964, (2010)) or a similar method. Compound (1-1) can be got as a marketed product or can be prepared by a known synthetic method (for example, EP1550662, (2005); EP1728792, (2006)) or a similar method. Compound (1-2) can be got as a marketed product or can be prepared by a known synthetic method (for example, EP1550662, (2005); EP1728792, 2006) or a similar method.

Step 1-2: Preparation Step of Compound (1-4)

Compound (1-4) can be prepared by halogenating compound (1-3) by a known synthetic method (for example, EP1550662, (2005); *Journal of Medicinal Chemistry*, 2964, (2010)) or a similar method.

Step 1-3: Preparation Step of Compound (1-6)

Compound (1-6) can be prepared by reacting compound (1-4) with compound (1-5), in the presence of a base and a palladium catalyst optionally along with a phosphine ligand, in an inert solvent. Compound (1-5) can be got as a marketed product or can be prepared by a known synthetic method (for example, *Journal of Organic Chemistry* 7508 (1995); Angewandte Chemie International Edition 928 (2008)) or a similar method.

The inert solvent includes, for example, ether solvents such as tetrahydrofuran, tetrahydropyran, 1,4-dioxane, and 1,2-dimethoxyethane; aromatic hydrocarbons such as toluene and xylene; aprotic polar solvents such as acetonitrile, propionitrile, N,N-dimethylformamide, N,N-dimethylacetamide, N-methyl-2-pyrrolidinone, and dimethylsulfoxide; protic polar solvents such as water; and mixture solvents thereof.

The palladium catalyst includes, for example, zero-valent catalysts such as tetrakis(triphenylphosphine)palladium, bis(t-butylphosphine)palladium, and tris(dibenzylidneacetone)dipalladium; and bi-valent catalysts such as bis(triphenylphosphine)palladium dichloride, palladium acetate, and bis(diphenylphosphino)ferrocene-palladium dichloride. Preferably, it is tetrakis(triphenylphosphine) palladium or palladium acetate.

The phosphine ligand includes, for example, monodentate ligands such as o-tolylphosphine, 2-dicyclohexylphosphino-2',6'-dimethoxy-1,1'-biphenyl, and 2-dicyclohexylphosphino-2',4',6'-triisopropyl-1,1'-biphenyl; and bidentate ligands such as 1,1'-bis(diphenylphosphino)ferrocene, 1,2-bis(diphenylphosphino)ethane, 1,3-bis(diphenylphosphino)propane, 1,4-bis(diphenylphosphino)butane, 2,2'-bis(diphenylphosphino)-1,1'-binaphthyl, 9,9-dimethyl-4,5-bis(diphenylphosphino)xanthine, and bis(2-diphenylphosphinophenyl) ether.

The base used herein includes, for example, inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogen phosphate, sodium phosphate, potassium hydroxide, and sodium hydroxide. Preferably, it is sodium carbonate, potassium carbonate, or potassium phosphate.

The reaction temperature is not limited to specific ones, but it is selected from the temperatures between room temperature and boiling point of the used solvent, preferably 60° C.-140° C., or 80° C.-140° C. under microwave irradiation. The reaction time is generally 30 minutes-24 hours.

Step 1-4: Preparation Step of Compound (1-6)

Compound (1-6) can be also prepared by reacting compound (1-3) with compound (1-7) in the presence of a base, copper reagent, and palladium catalyst, in an inert solvent. Compound (1-7) can be got as a marketed product or can be prepared by a known synthetic method (for example, *Synlett* 461 (2004); *Journal of Organic Chemistry* 5867 (2007)) or a similar method.

The inert solvent includes, for example, ether solvents such as tetrahydrofuran, tetrahydropyran, 1,4-dioxane, and 1,2-dimethoxyethane; aromatic hydrocarbons such as toluene and xylene; aprotic polar solvents such as acetonitrile, propionitrile, N,N-dimethylformamide, N,N-dimethylacetamide, N-methyl-2-pyrrolidinone, and dimethylsulfoxide; and mixture solvents thereof. Preferably, it is N,N-dimethylacetamide or N-methyl-2-pyrrolidinone.

The copper reagent includes, for example, copper chloride, copper bromide, copper iodide, and copper acetate. Preferably, it is copper iodide or copper acetate.

The palladium catalyst includes, for example, palladium acetate, palladium hydroxide on carbon, and tris(dibenzylideneacetone)dipalladium. Preferably, it is palladium acetate or tris(dibenzylideneacetone)dipalladium.

The base used herein includes, for example, inorganic bases such as potassium carbonate, sodium carbonate, and cesium carbonate; and organic bases such as diisopropylamine, diisobutylamine, and piperidine. Preferably, it is cesium carbonate.

The reaction temperature is not limited to specific ones, but it is selected from the temperatures between room temperature and boiling point of the used solvent, or 50° C.-180° C. under microwave irradiation. The reaction time is generally 30 minutes-24 hours.

Preparation Process 2

The compound of formula (2-12) can be prepared, for example, by the following process.

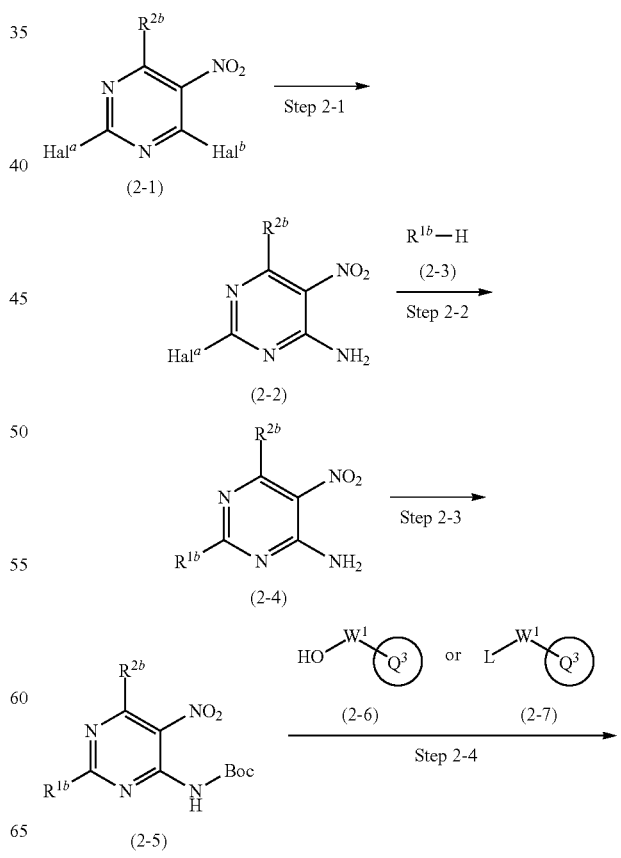

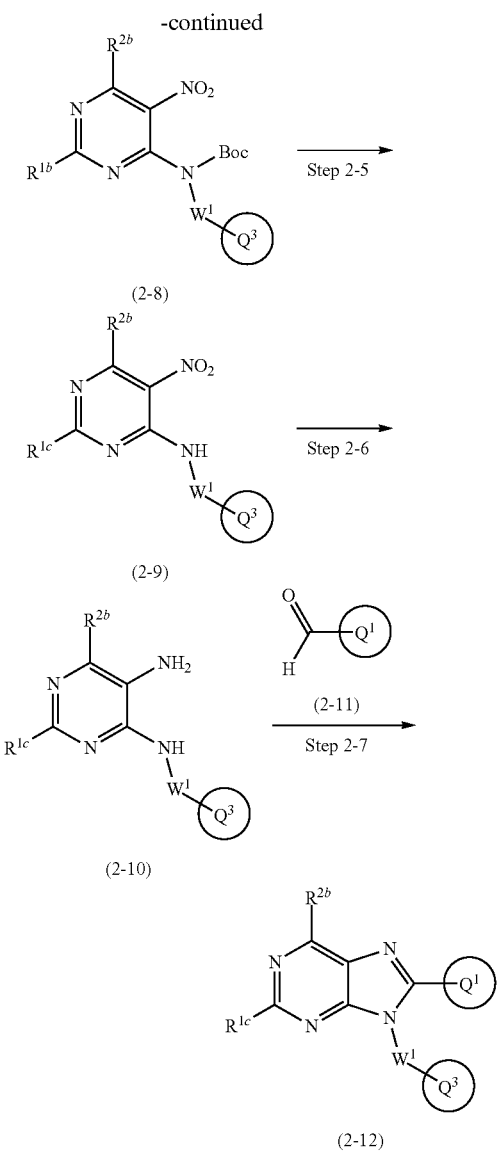

wherein Ring $Q^1$ and $W^1$ are as defined in the above Term 1; $R^{1b}$ is optionally-substituted $C_{1-6}$ alkoxy, optionally-substituted $C_{3-7}$ cycloalkoxy, optionally-substituted 4- to 7-membered saturated heterocyclyloxy, optionally-substituted $C_{1-6}$ alkylthio, or optionally-substituted amino; $R^{1c}$ is optionally-substituted $C_{1-6}$ alkoxy, optionally-substituted $C_{3-7}$ cycloalkoxy, optionally-substituted 4- to 7-membered saturated heterocyclyloxy, optionally-substituted $C_{1-6}$ alkylthio, optionally-substituted amino, or hydroxy; $R^{2b}$ is optionally-substituted $C_{1-6}$ alkyl, or optionally-substituted $C_{3-7}$ cycloalkyl; Ring $Q^3$ is optionally-substituted $C_{6-10}$ aryl, or optionally-substituted 5- to 10-membered heteroaryl; $Hal^a$ and $Hal^b$ are independently chlorine atom, bromine atom, or iodine atom; L is leaving group such as iodine atom, bromine atom, chlorine atom, and substituted sulfonyl (for example, methanesulfonyl, p-toluenesulfonyl, etc.).

Step 2-1: Preparation Step of Compound (2-2)

Compound (2-2) can be prepared by reacting compound (2-1) with ammonia in the presence of a base in an inert solvent. Compound (2-1) can be got as a marketed product or can be prepared by a known synthetic method (for example, WO2014127816; *Bioorganic and Medicinal Chemistry Letters,* 4879, (2006)) or a similar method.

The inert solvent includes, for example, ether solvents such as tetrahydrofuran, tetrahydropyran, 1,4-dioxane, and 1,2-dimethoxyethane; halogenated hydrocarbons such as chloroform, dichloromethane, and 1,2-dichloroethane; aprotic polar solvents such as acetonitrile, propionitrile, N,N-dimethylformamide, N,N-dimethylacetamide, N-methyl-2-pyrrolidinone, and dimethylsulfoxide; protic polar solvents such as water, methanol, ethanol, and isopropanol; and mixture solvents thereof. Preferably, it is tetrahydrofuran or methanol.

The base used herein includes, for example, triethylamine, and diisopropylethylamine.

The reaction temperature is not limited to specific ones, but is generally selected from the temperatures between −78° C. and boiling point of the used solvent. Preferably it is −78° C. to 0° C. The reaction time is generally 30 minutes-6 hours.

Step 2-2: Preparation Step of Compound (2-4)

Compound (2-4) can be prepared by reacting compound (2-2) with compound (2-3) in the presence of a base in an inert solvent. Compound (2-3) can be got as a marketed product or can be prepared by a known synthetic method (for example, WO200874752, WO200616178) or a similar method.

The inert solvent includes, for example, ether solvents such as tetrahydrofuran, tetrahydropyran, 1,4-dioxane, and 1,2-dimethoxyethane; protic polar solvents such as methanol, ethanol, 1-propanol, isopropanol, and 1-butanol; and mixture solvents thereof. Preferably, it is tetrahydrofuran or a protic polar solvent.

The base used herein includes, for example, metal alkoxides such as sodium methoxide, sodium ethoxide, sodium, and sodium 1-propoxide; and metal hydrides such as sodium hydride.

The reaction temperature is not limited to specific ones, but it is generally selected from the temperatures between −20° C. and boiling point of the used solvent. Preferably it is −20° C. to 20° C. The reaction time is generally 30 minutes-12 hours.

Step 2-3: Preparation Step of Compound (2-5)

Compound (2-5) can be prepared by reacting compound (2-4) with di-tert-butyl dicarbonate in the presence of a base in an inert solvent.

The inert solvent includes, for example, ether solvents such as tetrahydrofuran, tetrahydropyran, 1,4-dioxane, and 1,2-dimethoxyethane; aromatic hydrocarbons such as toluene and xylene; halogenated hydrocarbons such as chloroform, dichloromethane, and 1,2-dichloromethane; aprotic polar solvents such as acetonitrile, propionitrile, N,N-dimethylformamide, N,N-dimethylacetamide, N-methyl-2-pyrrolidinone, and dimethylsulfoxide; protic polar solvents such as water, methanol, ethanol, and isopropanol; and mixture solvents thereof. Preferably, it is tetrahydrofuran, chloroform, or dichloromethane.

The base used herein includes, for example, triethylamine, diisopropylethylamine, pyridine, and N,N-dimethylaminopyridine. Preferably, it is triethylamine or diisopropylethylamine in combination with N,N-dimethylaminopyridine.

The di-Boc compound which is produced as a side product in the reaction can be converted into compound (2-5) by adding a metal alkoxide to the reaction media in which compound (2-4) is exhausted. The metal alkoxide used herein includes sodium methoxide, sodium ethoxide, sodium, and sodium 1-propoxide.

The reaction temperature is not limited to specific ones, but it is generally selected from the temperatures between −20° C. and boiling point of the used solvent. Preferably it is 0° C. to 20° C. The reaction time is generally 1 hour-24 hours.

Step 2-4: Preparation Step of Compound (2-8)

Compound (2-8) can be prepared by reacting compound (2-5) with compound (2-6) in the presence of Mitsunobu reagent and a phosphine reagent, in an inert solvent. And, compound (2-8) can be also prepared from compound (2-5) and compound (2-7), according to the method described in Step 1-1. Compound (2-6) can be got as a marketed product or can be prepared by a known synthetic method (for example, WO200644454, WO201428669) or a similar method. Compound (2-7) can be got as a marketed product or can be prepared by a known synthetic method (for example, US2013/1503254; EP1679308, (2006)) or a similar method.

The inert solvent includes, for example, ether solvents such as tetrahydrofuran, tetrahydropyran, 1,4-dioxane, and 1,2-dimethoxyethane; aromatic hydrocarbons such as toluene and xylene; halogenated hydrocarbons such as chloroform, dichloromethane, and 1,2-dichloroethane; aprotic polar solvents such as acetonitrile, propionitrile, N,N-dimethylformamide, N,N-dimethylacetamide, N-methyl-2-pyrrolidinone, and dimethylsulfoxide; and mixture solvents thereof. Preferably, it is tetrahydrofuran, toluene, dichloromethane, or a mixture solvent thereof.

The Mitsunobu reagent includes, for example, diethyl azodicarboxylate, diisopropyl azodicarboxylate, dicyclohexyl azodicarboxylate, dibenzyl azodicarboxylate, tert-butyl azodicarboxylate, bis(2-methoxyethyl) azodicarboxylate, 1,1'-(azodicarbonyl)dipiperidine, and 1,1'-azobis(N,N-dimethylformamide).

The phosphine reagent includes, for example, triphenylphosphine, trimethylphosphine, tributylphosphine, and trioctylphosphine. Preferably, it is triphenylphosphine or tributylphosphine.

The reaction temperature is not limited to specific ones, but it is generally selected from the temperatures between 0° C. and boiling point of the used solvent. Preferably it is 0° C. to 60° C. The reaction time is generally 5 minutes-72 hours.

Step 2-5: Preparation Step of Compound (2-9)

Compound (2-9) can be prepared by reacting compound (2-8) with an acid in an inert solvent.

The inert solvent includes, for example, ether solvents such as tetrahydrofuran, tetrahydropyran, 1,4-dioxane, and 1,2-dimethoxyethane; aromatic hydrocarbons such as toluene and xylene; ester solvents such as methyl acetate and ethyl acetate; halogenated hydrocarbons such as chloroform, dichloromethane, and 1,2-dichloroethane; aprotic polar solvents such as acetonitrile, propionitrile, N,N-dimethylformamide, N,N-dimethylacetamide, N-methyl-2-pyrrolidinone, and dimethylsulfoxide; and mixture solvents thereof. Preferably, it is tetrahydrofuran, ethyl acetate, chloroform, or dichloromethane.

The acid used herein includes, for example, inorganic acids such as hydrochloric acid and sulfuric acid; and organic acids such as trifluoroacetic acid.

The reaction temperature is not limited to specific ones, but it is generally selected from the temperatures between −20° C. and boiling point of the used solvent. Preferably it is 0° C. to 60° C. The reaction time is generally 30 minutes-24 hours.

Step 2-6: Preparation Step of Compound (2-10)

Compound (2-10) can be prepared by reducing the nitro group in compound (2-9). For example, the applicable reduction includes, a reduction under acidic condition with a metal such as zinc, iron, and tin, or a metal salt such as tin(III) chloride; a reduction with a sulfide compound such as sodium dithionite; and a hydrogenation under hydrogen atmosphere with a metallic catalyst such as palladium/carbon, Raney nickel/carbon, platinum oxide/carbon, and rhodium/carbon.

In the reduction with a metal or a metal salt, the amount of the metal or metal salt used herein is generally 1 mole-100 moles, preferably 2 moles-20 moles, per one mole of compound (2-9). The amount of the acid used herein is generally 1 mole-100 moles, preferably 1 mole-20 moles, per one mole of compound (2-9). The reduction reaction is carried out in an inert solvent. The inert solvent includes, for example, ether solvents such as tetrahydrofuran, tetrahydropyran, 1,4-dioxane, and 1,2-dimethoxyethane; ester solvents such as methyl acetate and ethyl acetate; protic polar solvents such as water, methanol, ethanol, and isopropanol; and mixture solvents thereof. The reaction temperature is not limited to specific ones, but it is generally selected from the temperatures between 0° C. and 100° C. The reaction time is generally 30 minutes-12 hours.

The reaction can be carried out in the presence of an acid as appropriate. The acid used herein includes, for example, organic acids such as formic acid, acetic acid, and trifluoroacetic acid; and inorganic acids such as ammonium chloride. The amount of the acid used herein is 0.1 mole or more per one mole of compound (2-9).

In the hydrogenation, the amount of the metallic catalyst used herein is generally 0.1-1000 wt %, preferably 1-100 wt % per weight of compound (2-9). The reaction is carried out in an inert solvent. The inert solvent includes, for example, ether solvents such as tetrahydrofuran, tetrahydropyran, 1,4-dioxane, and 1,2-dimethoxyethane; ester solvents such as methyl acetate and ethyl acetate; protic polar solvents such as water, methanol, ethanol, and isopropanol; and mixture solvents thereof. The hydrogen pressure is generally about 1-about 100 atm, preferably about 1-about 5 atm. The reaction temperature is not limited to specific ones, but it is generally selected from the temperatures between 0° C. and 120° C., preferably 20° C. to 80° C. The reaction time is generally 30 minutes-72 hours, preferably 1 hour-24 hours.

The reaction may be carried out in the presence of an acid catalyst as appropriate. The acid catalyst used herein includes, for example, organic acids such as formic acid, acetic acid, and trifluoroacetic acid; and inorganic hydrobromic acid. The amount of the acid used herein is 0.1 mole or more per one mole of compound (2-9).

Step 2-7: Preparation Step of Compound (2-12)

Compound (2-12) can be prepared by reacting compound (2-10) with compound (2-11) in the presence of an oxidizing agent in an inert solvent. Compound (2-11) can be got as a marketed product or can be prepared by known synthetic method (for example, US200619965; *Journal of Medicinal Chemistry*, 3680, (2003)) or a similar method.

The inert solvent includes, for example, ether solvents such as tetrahydrofuran, tetrahydropyran, 1,4-dioxane, and 1,2-dimethoxyethane; aprotic polar solvents such as acetonitrile, propionitrile, N,N-dimethylformamide, N,N-dimethylacetamide, N-methyl-2-pyrrolidinone, and dimethylsulfoxide; protic polar solvents such as water, methanol, ethanol, and isopropanol; and mixture solvents thereof. Preferably, it is N,N-dimethylformamide, dimethylsulfoxide, water, ethanol, or isopropanol.

The oxidizing agent includes, for example, ferric(III) chloride and oxone.

The reaction temperature is not limited to specific ones, but it is generally selected from the temperatures between 0° C. and boiling point of the used solvent. Preferably it is 0° C. to 100° C. The reaction time is generally 30 minutes-24 hours.

Preparation Process 3

The compound of formula (2-9) can be also prepared, for example, by the following process.

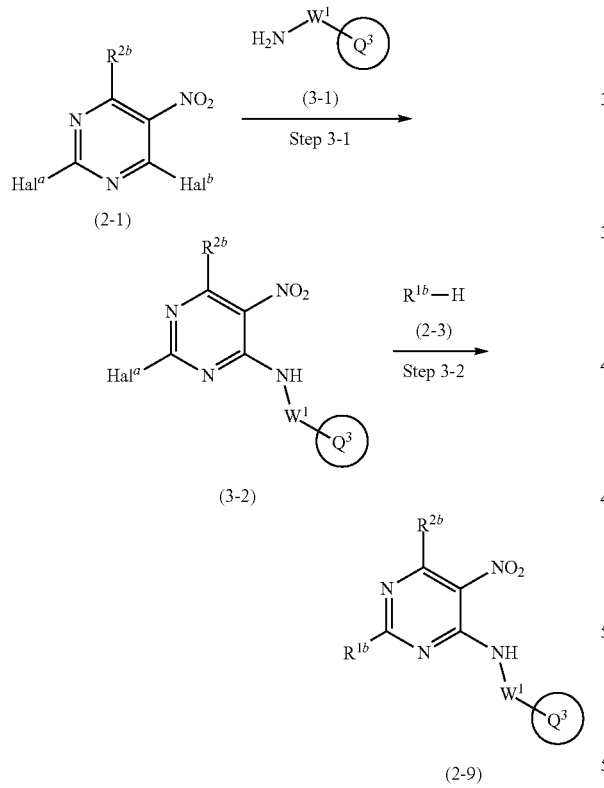

wherein $W^1$ is as defined in the above Term 1; $R^{1b}$ is optionally-substituted $C_{1-6}$ alkoxy, optionally-substituted $C_{3-7}$ cycloalkoxy, optionally-substituted 4- to 7-membered saturated heterocyclyloxy, optionally-substituted $C_{1-6}$ alkylthio, or optionally-substituted amino; $R^{2b}$ is optionally-substituted $C_{1-6}$ alkyl, or optionally-substituted $C_{3-7}$ cycloalkyl; Ring $Q^3$ is optionally-substituted $C_{6-10}$ aryl or optionally-substituted 5- to 10-membered heteroaryl; $Hal^a$ and $Hal^b$ are independently chlorine atom, bromine atom, or iodine atom.

Step 3-1: Preparation Step of Compound (3-2)

Compound (3-2) can be prepared by reacting compound (2-1) with compound (3-1) in the presence of a base in an inert solvent. Compound (2-1) can be got as a marketed product or can be prepared by a known synthetic method (for example, WO201514993; *Bioorganic and Medicinal Chemistry*, 3720, (2014)) or a similar method.

The inert solvent includes, for example, ether solvents such as tetrahydrofuran, tetrahydropyran, 1,4-dioxane, and 1,2-dimethoxyethane; halogenated hydrocarbons such as chloroform, dichloromethane, and 1,2-dichloroethane; aprotic polar solvents such as acetonitrile, N,N-dimethylformamide, N,N-dimethylacetamide, N-methyl-2-pyrrolidinone, and dimethylsulfoxide; and mixture solvents thereof. Preferably, it is tetrahydrofuran, dichloromethane, or N,N-dimethylformamide.

The base used herein includes, for example, organic bases such as triethylamine, diisopropylethylamine, and pyridine; and inorganic bases such as potassium carbonate, sodium carbonate, and cesium carbonate. Preferably, it is trimethylamine, diisopropylamine, or potassium carbonate.

The reaction temperature is not limited to specific ones, but it is generally selected from the temperatures between −20° C. and boiling point the used solvent. Preferably it is 0° C. to 60° C. The reaction time generally 30 minutes-72 hours Step 3-2: Preparation Step of Compound (2-9)

Compound (2-9) can be also prepared from compound (3-2) and compound (2-3) according to the method described in Step 2-2.

Preparation Process 4

The compound of formula (4-5) which is in the scope of the compound of formula (1) can be also prepared, for example, by the following process.

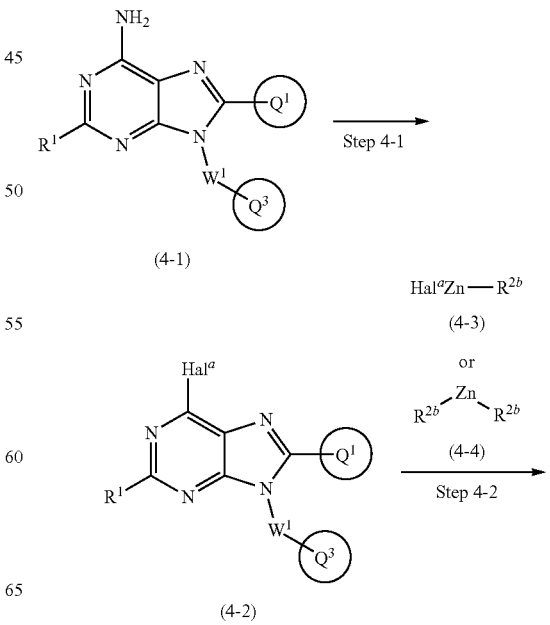

-continued

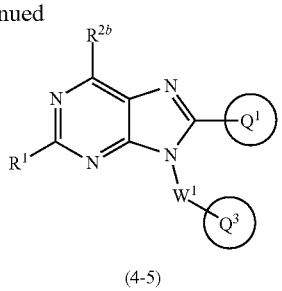

(4-5)

wherein $R^1$, Ring $Q^1$, and $W^1$ are as defined in the above Term 1; $R^{2b}$ is optionally-substituted $C_{1-6}$ alkyl, or optionally-substituted $C_{3-7}$ cycloalkyl; Ring $Q^3$ is optionally-substituted $C_{6-10}$ aryl, or optionally-substituted 5- to 10-membered heteroaryl; $Hal^a$ is chlorine atom, bromine atom or iodine atom.

Step 4-1: Preparation Step of Compound (4-2)

Compound (4-2) can be prepared by reacting compound (4-1) with a nitrite ester/sodium nitrite and a halide, in the presence of an additive agent as appropriate, in an inert solvent. Compound (4-1) used herein can be prepared according to the method described in Preparation Process 1.

The inert solvent includes, for example, halogenated hydrocarbons such as chloroform, dichloromethane, and 1,2-dichloroethane; aprotic polar solvents such as acetonitrile, dimethylformamide, N-methyl-2-pyrrolidinone, and dimethylsulfoxide; protic polar solvents such as water; and mixture solvents thereof. Preferably, it is dichloromethane or 1,2-dichloroethane.

The addictive agent includes for example, halogenated trialkylsilanes such as chlorotrimethylsilane, bromotrimethylsilane, and iodotrimethylsilane.

The nitrite ester includes, for example, ethyl nitrite, isopropyl nitrite, isoamyl nitrite, tert-butyl nitrite, and isobutyl nitrite.

The halide includes, for example, metallic halides such as copper chloride, copper bromide, and potassium iodide; and organic halides such as tetraethylammonium chloride, tetraethylammonium bromide, tetraethylammonium iodide, benzyltriethylammonium chloride, benzyltriethylammonium bromide, benzyltriethylammonium iodide, tetrabutylammonium chloride, tetrabutylammonium bromide, and tetrabutylammonium iodide. Preferably, it is benzyltriethylammonium halide.

The reaction temperature is not limited to specific ones, but it is generally selected from the temperatures between 0° C. and boiling point of the used solvent. Preferably it is 20° C. to 80° C. The reaction time is generally 30 minutes-24 hours.

Step 4-2: Preparation Step of Compound (4-5)

Compound (4-5) can be prepared by reacting compound (4-2) with compound (4-3) or compound (4-4), in the presence of a palladium catalyst optionally along with a phosphine ligand, in an inert solvent. Compound (4-3) and compound (4-4) can be got as a marketed product or can be prepared by a known synthetic method (for example, WO200624493, WO200883070) or a similar method.

The inert solvent includes, for example, ether solvents such as tetrahydrofuran, tetrahydropyran, 1,4-dioxane, and 1,2-dimethoxyethane; aromatic hydrocarbon such as toluene and xylene; aprotic polar solvents such as N,N-dimethylformamide, N,N-dimethylacetamide, and N-methyl-2-pyrrolidinone; and mixture solvents thereof. Preferably, it is tetrahydrofuran.

The palladium catalyst includes, for example, zero-valent catalysts such as tetrakis(triphenylphosphine)palladium, bis(t-butylphosphine)palladium, and tris(dibenzylideneacetone)dipalladium; and bi-valent catalysts such as bis(triphenylphosphine)palladium dichloride, palladium acetate, and bis(diphenylphosphino)ferrocene-palladium dichloride. Preferably, it is tetrakis(triphenylphosphine)palladium or bis(t-butylphosphine)palladium.

The phosphine ligand includes, for example, monodentate ligands such as o-tolylphosphine, 2-dicyclohexylphosphino-2',6'-dimethoxy-1,1'-biphenyl, and 2-dicyclohexylphosphino-2',4',6'-triisopropyl-1,1'-biphenyl; and bidentate ligands such as 1,1'-bis(diphenylphosphino)ferrocene, 1,2-bis(diphenylphosphino)ethane, 1,3-bis(diphenylphosphino)propane, 1,4-bis(diphenylphosphino)butane, 2,2'-bis(diphenylphosphino)-1,1'-binaphthyl, 9,9-dimethyl-4,5-bis(diphenylphosphino)xanthine, and bis(2-diphenylphosphinophenyl)ether.

The reaction temperature is not limited to specific ones, but it is generally selected from the temperatures between −20° C. and boiling point of the used solvent, preferably 0° C. to 60° C. The reaction time is generally 5 minutes-24 hours, preferably 5 minutes-6 hours.

Preparation Process 5

The compound of formula (5-4) which is in the scope of the compound of formula (1) can be also prepared, for example, by the following process.

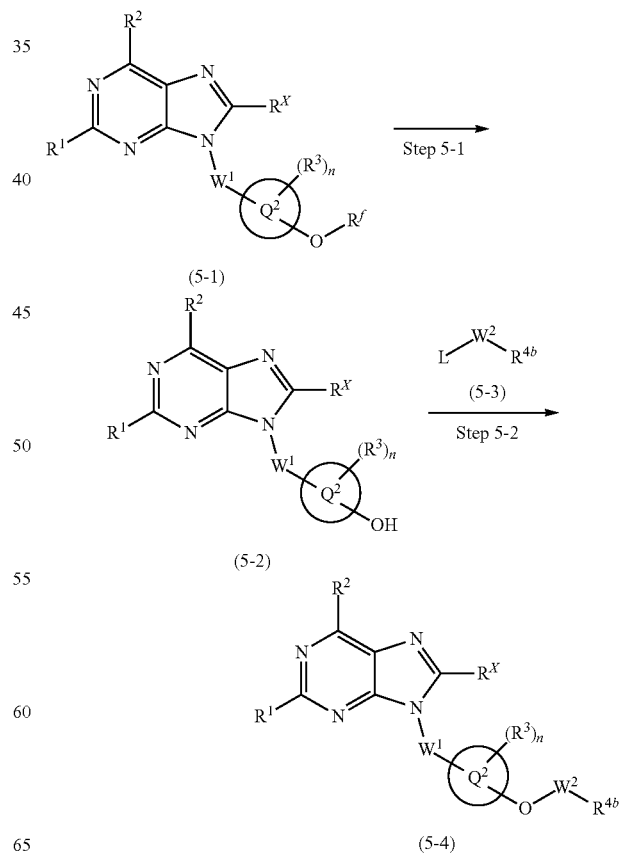

wherein $R^1$, $R^2$, $R^3$, Ring $Q^2$, $W^1$, $W^2$, and n are as defined in the above Term 1; $R^X$ is hydrogen atom, halogen atom, optionally-substituted $C_{6-10}$ aryl, or optionally-substituted 5- to 10-membered heteroaryl; $R^{4b}$ is optionally-substituted amino, or optionally-substituted 4- or 10-membered saturated heterocyclyl; $R^f$ is substituted sulfonyl (for example, methanesulfonyl, p-toluenesulfonyl, etc.); L is leaving group such as iodine atom, bromine atom, chlorine atom, and substituted sulfonyl (for example, methanesulfonyl, p-toluenesulfonyl, etc.).

Step 5-1: Preparation Step of Compound (5-2)

Compound (5-2) can be prepared by reacting compound (5-1) with a base in an inert solvent. Compound (5-1) used herein can be prepared according to the method described in Preparation Process 1. The compounds in the present process wherein $R^X$ is hydrogen atom or halogen atom may be used as intermediates in Preparation Process 1.

The inert solvent includes, for example, ether solvents such as tetrahydrofuran, tetrahydropyran, 1,4-dioxane, and 1,2-dimethoxyethane; aromatic hydrocarbon such as toluene and xylene; halogenated hydrocarbons such as chloroform, dichloromethane, and 1,2-dichloroethane; aprotic polar solvents such as acetonitrile, propionitrile, N,N-dimethylformamide, N,N-dimethylacetamide, and N-methyl-2-pyrrolidinone; protic polar solvents such as methanol, ethanol, and water; and mixture solvents thereof. Preferably, it is tetrahydrofuran, acetonitrile, or N,N-dimethylformamide.

The base used herein includes, for example, inorganic bases such as lithium hydroxide, sodium hydroxide, and potassium hydroxide; and organic bases such as sodium methoxide, sodium ethoxide, sodium tert-butoxide, potassium tert-butoxide, lithium trimethylsilyloxide, sodium trimethylsilyloxide, and potassium trimethylsilyloxide. Preferably, it is potassium trimethylsilyloxide.

The reaction temperature is not limited to specific ones, but it is generally selected from the temperatures between −20° C. and boiling point of the used solvent. Preferably it is 0° C. to 60° C. The reaction time is generally 30 minutes-48 hours.

Step 5-2: Preparation Step of Compound (5-4)

Compound (5-4) can be prepared from compound (5-2) and compound (5-3), according to the method described in Step 1-1. Compound (5-3) can be got as a marketed product or can be prepared by a known synthetic method (for example, WO201364919, WO200952065) or a similar method. When $R^2$ is amino group, the amino group may be protected before the reaction, by reacting the amino group with dimethylformamide in the presence of a reaction accelerator, to convert its N,N-dimethylimido-formamide. And, after the reaction, the protective group can be removed under a basic condition to obtain compound (5-4).

Preparation Process 6

The compounds of formulae (6-2), (6-5), (6-6), and (6-7) which are in the scope of the compound of formula (1) can be prepared, for example, by the following process.

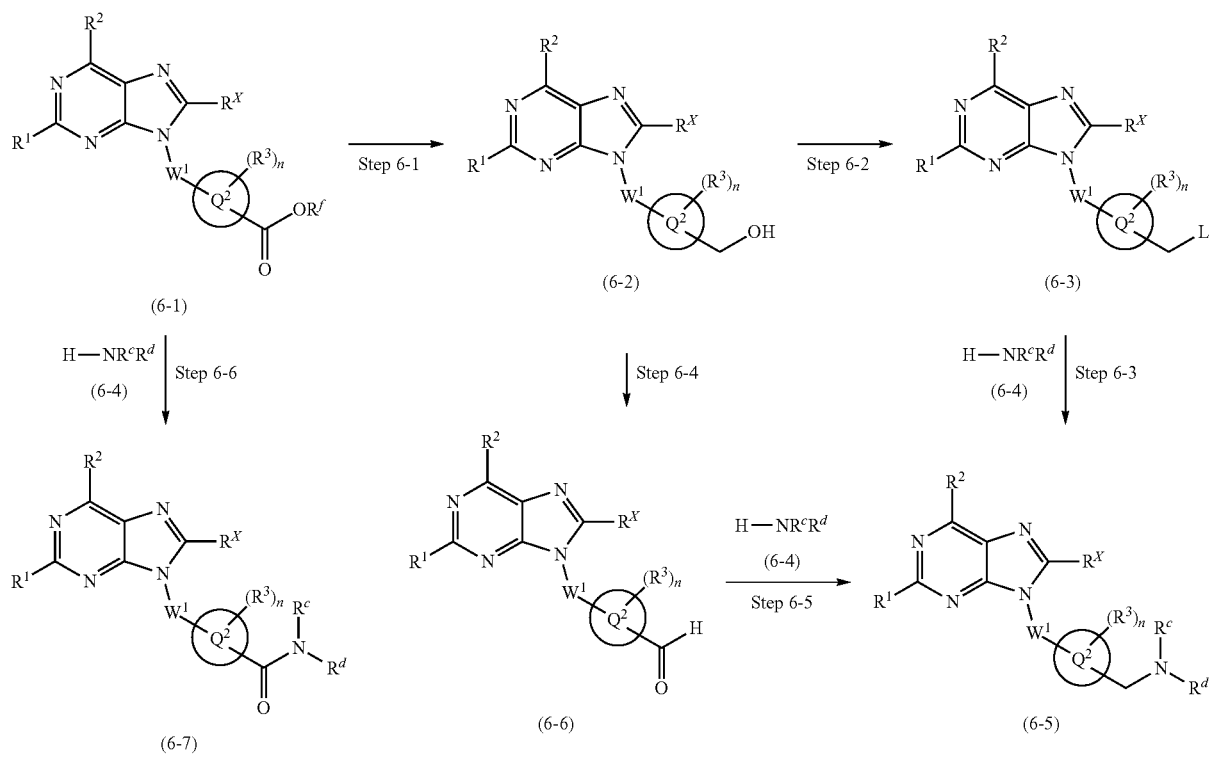

wherein $R^1$, $R^2$, $R^3$, Ring $Q^2$, $W^1$, and n are as defined in the above Term 1; $R^X$ is hydrogen atom, halogen atom, optionally-substituted $C_{6-10}$ aryl, or optionally-substituted 5- to 10-membered heteroaryl; $R^c$, $R^d$, and $R^f$ are independently hydrogen atom or optionally-substituted $C_{1-6}$ alkyl, or $R^c$ and $R^d$ may be combined together with the nitrogen atom to which they are attached to form optionally-substituted 4- to 10-membered saturated heterocycle; and L is leaving group such as iodine atom, bromine atom, chlorine atom, and substituted sulfonyl (for example, methanesulfonyl, p-toluenesulfonyl, etc.).

Step 6-1: Preparation Step of Compound (6-2)

Compound (6-2) can be prepared by reacting compound (6-1) with a hydride reducing agent in an inert solvent. Compound (6-1) used herein can be prepared according to the method described in Preparation Process 1. The compounds in the present process wherein $R^X$ is hydrogen atom or halogen atom may be used as intermediates in Preparation Process 1.

The inert solvent includes, for example, ether solvents such as tetrahydrofuran, tetrahydropyran, 1,4-dioxane, and 1,2-dimethoxyethane; aromatic hydrocarbon such as toluene and xylene; halogenated hydrocarbons such as chloroform, dichloromethane, and 1,2-dichloroethane; and mixture solvents thereof.

The hydride reducing agent includes, for example, sodium borohydride, lithium borohydride, lithium aluminum hydride, sodium cyanoborohydride, lithium triethylborohydride, diisobutylaluminum hydride, sodium bis(2-methoxyethoxy)aluminum hydride, lithium borodeuteride, and lithium aluminum deuteride. Preferably, it is diisobutylaluminum hydride or lithium aluminum hydride.

The reaction temperature is not limited to specific ones, but it is generally selected from the temperatures between −78° C. and boiling point of the used solvent. Preferably it is −20° C. to 20° C. The reaction time is generally 5 minutes-24 hours.

Step 6-2: Preparation Step of Compound (6-3)

Compound (6-3) wherein L is a substituted sulfonyl group can be prepared by reacting compound (6-2) with a sulfonyl chloride in the presence of a base in an inert solvent. Compound (6-3) wherein is halogen can be prepared by reacting compound (6-2) with a halogenating agent in an inert solvent.

The inert solvent includes, for example, ether solvents such as tetrahydrofuran, tetrahydropyran, 1,4-dioxane, and 1,2-dimethoxyethane; aromatic hydrocarbon such as toluene and xylene; halogenated hydrocarbons such as chloroform, dichloromethane, and 1,2-dichloroethane; aprotic polar solvents such as acetonitrile, N,N-dimethylformamide, N,N-dimethylacetamide, and N-methyl-2-pyrrolidinone; and mixture solvents thereof. Preferably, it is tetrahydrofuran, chloroform, or dichloromethane.

The base used herein includes, for example, organic bases such as triethylamine, diisopropylethylamine, pyridine, 2,4,6-trimethylpyridine, and 4-dimethylaminopyridine. Preferably, it is triethylamine or diisopropylamine.

The substituted sulfonyl chloride includes, for example, methanesulfonyl chloride, monochloromethanesulfonyl chloride, benzenesulfonyl chloride, p-toluenesulfonyl chloride, o-nitrobenzenesulfonyl chloride, and p-nitrobenzenesulfonyl chloride. Preferably, it is methanesulfonyl chloride.

The halogenating agent includes, for example, thionyl chloride, oxalyl dichloride, and phosphorus tribromide. Preferably, it is thionyl chloride, or phosphorus tribromide.

The reaction temperature is not limited to specific ones, but it is generally selected from the temperatures between −20° C. and boiling point of the used solvent. Preferably it is 0° C. to 60° C. The reaction time is generally 5 minutes-24 hours.

Step 6-3: Preparation Step of Compound (6-5)

Compound (6-5) can be prepared by reacting compound (6-3) with compound (6-4) in the presence of a base optionally along with a halide, in an inert solvent. Compound (6-4) can be got as a marketed product or can be prepared by a known synthetic method (for example, WO20073965, US2010216812) or a similar method.

The inert solvent includes, for example, ether solvents such as tetrahydrofuran, tetrahydropyran, 1,4-dioxane, and 1,2-dimethoxyethane; halogenated hydrocarbons such as chloroform, dichloromethane, and 1,2-dichloroethane; aprotic polar solvents such as acetonitrile, N,N-dimethylformamide, N,N-dimethylacetamide, N-methyl-2-pyrrolidinone, and dimethylsulfoxide; and mixture solvents thereof. Preferably, it is tetrahydrofuran, dichloromethane, or N,N-dimethylformamide.

The base used herein includes, for example, organic bases such as triethylamine, diisopropylethylamine, pyridine, 2,4,6-trimethylpyridine, and 4-dimethylaminopyridine; and inorganic bases such as potassium carbonate, sodium carbonate, and cesium carbonate.

The halide includes, for example, organic halides such as tetrabutylammonium iodide, and tetrabutylammonium bromide; and inorganic halides such as potassium iodide, potassium bromide, sodium iodide, and sodium bromide.

The reaction temperature is not limited to specific ones, but it is generally selected from the temperatures between −20° C. and boiling point of the used solvent or compound (6-4). Preferably it is 0° C. to 120° C. The reaction time is generally 30 minutes-72 hours.

Step 6-4: Preparation Step of Compound (6-6)

Compound (6-6) can be prepared by reacting compound (6-2) with an oxidizing agent, in the presence of a base as appropriate, in an inert solvent.

The inert solvent includes, for example, ether solvents such as tetrahydrofuran, tetrahydropyran, 1,4-dioxane, and 1,2-dimethoxyethane; halogenated hydrocarbons such as chloroform, dichloromethane, and 1,2-dichloroethane; aprotic polar solvents such as acetonitrile, propionitrile, N,N-dimethylformamide, N,N-dimethylacetamide, N-methyl-2-pyrrolidinone, and dimethylsulfoxide; and mixture solvents thereof.

The oxidizing agent includes, for example, manganese dioxide, pyridine-sulfur trioxide complex, and Dess-Martin reagent.

The base used herein includes, for example, organic bases such as triethylamine, diisopropylethylamine, pyridine, 2,4,6-trimethylpyridine, and 4-dimethylaminopyridine; and inorganic bases such as sodium bicarbonate, potassium bicarbonate, sodium carbonate, potassium carbonate, and cesium carbonate.

The reaction temperature is not limited to specific ones, but it is generally selected from the temperatures between 0° C. and boiling point of the used solvent. Preferably it is 0° C. to 20° C. The reaction time is generally 30 minutes-72 hours.

Step 6-5: Preparation Step of Compound (6-5)

Compound (6-5) can be prepared by reacting compound (6-6) with compound (6-4) in the presence of a borohydride compound optionally along with an acid, in an inert solvent.

The inert solvent includes, for example, ether solvents such as tetrahydrofuran, tetrahydropyran, 1,4-dioxane, and 1,2-dimethoxyethane; halogenated hydrocarbons such ac chloroform, dichloromethane, and 1,2-dichloroethane; protic polar solvents such as methanol, ethanol, 1-propanol, 2-propanol, and water; and mixture solvents thereof. Preferably, it is tetrahydrofuran, dichloromethane, chloroform, or methanol.

The acid used herein includes, for example, carboxylic acids such as formic at propionic acid, acetic acid, and trifluoroacetic acid; and mineral acids such as hydrochloric acid.

The borohydride compound includes, for example, sodium cyanoborohydride, sodium triacetoxyborohydride, and sodium borohydride. Preferably, it is sodium cyanoborohydride and sodium triacetoxyborohydride.

The reaction temperature is not limited to specific ones, but it is generally selected from the temperatures between 0° C. and boiling point of the used solvent. Preferably is 0° C. to 20° C. The reaction time generally 30 minutes-72 hours.

Step 6-6: Preparation Step of Compound (6-7)

Compound (6-7) can be prepared by reacting compound (6-1) and compound (6-4) with a condensing agent, in the presence of a base and an additive agent as appropriate, in an inert solvent.

The inert solvent includes, for example, ether solvents such as tetrahydrofuran, tetrahydropyran, 1,4-dioxane, and 1,2-dimethoxyethane; aromatic hydrocarbon such as toluene and xylene; aprotic polar solvents such as acetonitrile, propionitrile, N,N-dimethylformamide, N,N-dimethylacetamide, N-methyl-2-pyrrolidinone, and dimethylsulfoxide; and mixture solvents thereof. Preferably, it is N,N-dimethylacetamide or N-methyl-2-pyrrolidinone.

The condensing agent includes, for example, dicyclohexylcarbodiimide, diisopropylcarbodiimide, 1-ethyl-3-(3-dimethylaminopropyl)-carbodiimide, benzotriazol-1-yloxy-tris (dimethylamino)phosphonium hexafluorophosphate, diphenylphosphonyl azide, N,N'-carbonyldiimidazole, O-(benzotriazol-1-yl)-N,N,N',N'-tetramethyluronium hexafluorophosphate, and O-(7-azabenzotriazol-1-yl)-N,N,N',N'-tetramethyluronium hexafluorophosphate.

The additive agent includes, for example, N-hydroxysuccinimide, 1-hydroxybenzotriazole, and 3-hydroxy-4-oxo-3,4-dihydro-1,2,3-benzotriazine, which can be used in the reaction.

The base used herein includes, for example, organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogen phosphate, sodium phosphate, potassium hydroxide, sodium hydroxide, and sodium hydride; and metal alkoxides such as sodium methoxide and potassium tert-butoxide.

The reaction temperature is not limited to specific ones, but it is generally selected from the temperatures between −20° C. and boiling point of the used solvent. Preferably it is 0° C. to 20° C. The reaction time is generally 10 minutes-48 hours.

Preparation Process 7

The compounds of formulae (7-3) and (7-4) which are in the scope of the compound of formula (1) can be prepared, for example, by the following process.

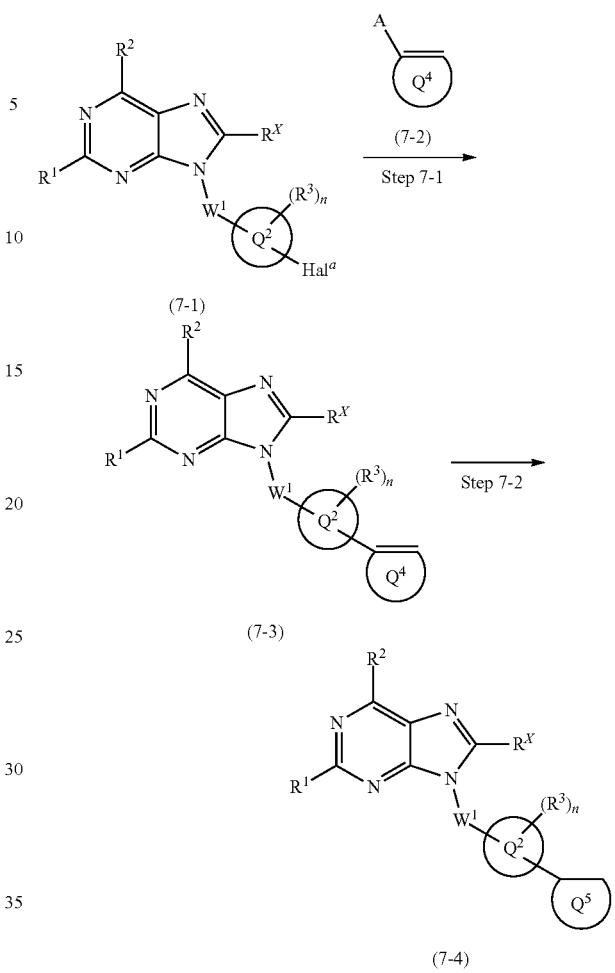

wherein $R^1$, $R^2$, $R^3$, Ring $Q^1$, $W^1$, and n are as defined in the above Term 1; $R^X$ is hydrogen atom, optionally-substituted $C_{6-10}$ aryl, or optionally-substituted 5- to 10-membered heteroaryl; $Hal^a$ is chlorine atom, bromine atom, or iodine atom; A is boronic acid, boronate, $BF_3K$, or $BF_3Na$; $Q^4$ is optionally-substituted 4- to 10-membered partially-unsaturated carbon-ring group, or optionally-substituted 4- to 10-membered partially-unsaturated hetero-ring group; and $Q^5$ is $C_{4-10}$ cycloalkyl, or optionally-substituted 4- to 10-membered saturated heterocyclyl.

Step 7-1: Preparation Step of Compound (7-3)

Compound (7-3) can be prepared from compound (7-1) and compound (7-2), according to the method described in Step 1-3. Compound (7-2) used herein can be got as a marketed product or can be prepared according to the method to prepare compound (1-5). compound (7-1) used herein can be prepared according to the method described in Preparation Process 1. The compounds in the present process wherein $R^X$ hydrogen atom or halogen atom may be used as intermediates in Preparation Process 1.

Step 7-2: Preparation Step of Compound (7-4)

Compound (7-4) can be prepared by hydrogenating compound (7-3) under hydrogen atmosphere in the presence of a metallic catalyst in an inert solvent.

The inert solvent includes, for example, ether solvents such as tetrahydrofuran, tetrahydropyran, 1,4-dioxane, and 1,2-dimethoxyethane; protic polar solvents such as water, methanol, ethanol, and isopropanol; and mixture solvents thereof.

The metallic catalyst includes, for example, palladium/carbon, palladium hydroxide/carbon, Raney nickel, platinum oxide/carbon, and rhodium/carbon. Preferably, it is palladium/carbon or palladium hydroxide/carbon. The amount of the metallic catalyst used herein is generally 0.1-1000 wt %, preferably 1-100 wt % per weight of compound (7-3).

The reaction may be carried out in the presence of an acid as appropriate. The acid used herein includes, for example, organic acids such as formic acid, acetic acid, and trifluoroacetic acid. The amount of the acid used herein is 0.1 mole or more per one mole of compound (7-3).

The hydrogen pressure is generally about 1-about 100 atm, preferably about 1-about 5 atm. The reaction temperature is not limited to specific ones, but it is generally 0° C.-120° C., preferably 20° C.-80° C. The reaction time is generally 30 minutes-72 hours, preferably 1 hour-24 hours.

Preparation Process 8

The compound of formula (8-4) which is in the scope of the compound of formula (1) can be prepared, for example, by the following process.

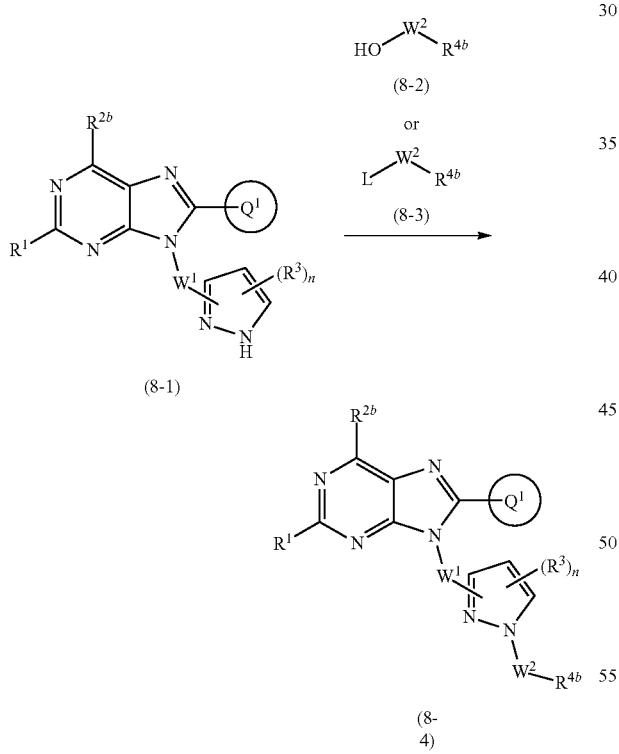

wherein $R^1$, $R^3$, Ring $Q^1$, $W^1$, $W^2$, and n are as defined in the above Term 1; $R^{2b}$ is optionally-substituted $C_{1-6}$ alkyl, or optionally-substituted $C_{3-7}$ cycloalkyl; $R^{4b}$ is optionally-substituted amino, or optionally-substituted 4- to 10-membered saturated heterocyclyl; L is leaving group such as iodine atom, bromine atom, chlorine atom, and substituted sulfonyl (for example, methanesulfonyl p-toluenesulfonyl etc.).

Compound (8-4) can be prepared by reacting compound (8-1) with compound (8-2) in the presence of Mitsunobu reagent and phosphine reagent, or Tsunoda reagent, in an inert solvent. Compound (8-2) can be got as a marketed product or can be prepared by a known synthetic method (for example, US2003220341, US2003229092) or a similar method. Compound (8-1) used herein can be prepared according to the method described in Preparation Process 2.

The inert solvent includes, for example, ether solvents such as tetrahydrofuran, tetrahydropyran, 1,4-dioxane, and 1,2-dimethoxyethane; aromatic hydrocarbon such as toluene and xylene; halogenated hydrocarbons such as chloroform, dichloromethane, and 1,2-dichloroethane; aprotic polar solvents such as acetonitrile, propionitrile, N,N-dimethylformamide, N,N-dimethylacetamide, N-methyl-2-pyrrolidinone, and dimethylsulfoxide; and mixture solvents thereof. Preferably, it is tetrahydrofuran, toluene, or a mixture solvent thereof.

The Mitsunobu reagent includes, for example, diethyl azodicarboxylate, diisopropyl azodicarboxylate, dicyclohexyl azodicarboxylate, dibenzyl azodicarboxylate, tert-butyl azodicarboxylate, bis(2-methoxyethyl) azodicarboxylate, 1,1'-(azodicarbonyl)dipiperidine, and 1,1'-azobis(N,N-dimethylformamide).

The phosphine reagent includes, for example, triphenylphosphine, trimethylphosphine, tributylphosphine, and trioctylphosphine. Preferably, it is triphenylphosphine or tributylphosphine.

The Tsunoda reagent includes, for example, (cyanomethylene)tributylphosohorane and (cyanomethylene)trimethylphosphorane. Preferably, it is (cyanomethylene)tributylphosphorane.

The reaction temperature is not limited to specific ones, but it is generally selected from the temperatures between 0° C. and boiling point of the used solvent. Preferably it is 20° C. to 100° C. The reaction time is generally 10 minutes-72 hours.

Compound (8-4) can be also prepared from compound (8-1) and compound (8-3), according to the method described in Step 5-2. Compound (8-3) can be got as a marketed product or can be prepared by a known synthetic method (for example, WO200620415, WO2007102883) or a similar method.

Preparation Process 9

The compound of formula (9-4) can be prepared, for example, by the following process.

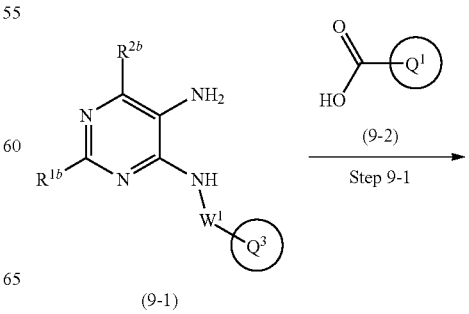

-continued

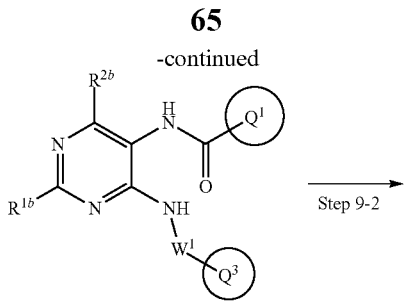

(9-3)

Step 9-2

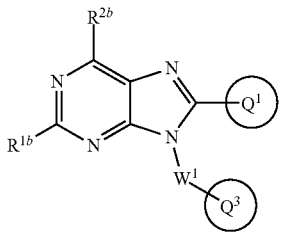

(9-4)

wherein Ring $Q^1$ and $W^1$ are as defined in the above Term 1; $R^{1b}$ is optionally-substituted $C_{1-6}$ alkoxy, optionally-substituted $C_{3-7}$ cycloalkoxy, optionally-substituted 4- to 7-membered saturated heterocyclyloxy, optionally-substituted $C_{1-6}$ alkylthio, or optionally-substituted amino; $R^{2b}$ is optionally-substituted $C_{1-6}$ alkyl, or optionally-substituted $C_{3-7}$ cycloalkyl; and Ring $Q^3$ is optionally-substituted $C_{6-10}$ aryl, or optionally-substituted 5- to 10-membered heteroaryl.

Step 9-1: Preparation Step of Compound (9-3)

Compound (9-3) can be prepared from compound (9-1) and compound (9-2), according to the method described in Step 6-6. compound (9-2) can be got as a marketed product or can be prepared by a known synthetic method (for example, WO200870150, WO200870150) or a similar method. Compound (9-1) used herein can be prepared according to the method described in Preparation Process 2.

Step 9-2: Preparation Step of Compound (9-4)

Compound (9-4) can be prepared by reacting compound (9-3) with a silylation agent, in the presence of an additive agent as appropriate, in an inert solvent.

The inert solvent includes, for example, ether solvents such as tetrahydrofuran, tetrahydropyran, 1,4-dioxane, and 1,2-dimethoxyethane; aromatic hydrocarbon such as toluene and xylene; aprotic polar solvents such as acetonitrile, propionitrile, N,N-dimethylformamide, N,N-dimethylacetamide, N-methyl-2-pyrrolidinone, and dimethylsulfoxide; halogenated hydrocarbons such as chloroform, dichloromethane, and 1,2-dichloroethane; and mixture solvents thereof.

The additive agent includes, for example, 1-(3-dimethylaminopropyl)3-ethylurea, N-hydroxysuccinimide, 1-hydroxybenzotriazole, 3-hydroxy-4-oxo-3,4-dihydro-1,2,3-benzotriazine, bis(trimethylsilyl)amine, N,N-dimethyl-4-pyridine, and pyridine, which can be used in the reaction.

The silylation agent includes, for example, N,O-bis(trimethylsilyl)acetamide, N,O-bis(trimethylsilyl)trifluoroacetamide, and trimethylchlorosilane. Preferably, it is N,O-bis(trimethylsilyl)acetamide N,O-bis(trimethylsilyl)trifluoroacetamide.

The reaction temperature is not limited to specific ones, but it is generally selected from the temperatures between about −20° C. and boiling point of the used solvent. Preferably it is 20° C. to 120° C. The reaction time is generally 10 minutes-48 hours.

Preparation Process 10

The compound of formula (10-4) can be prepared, for example, by the following process.

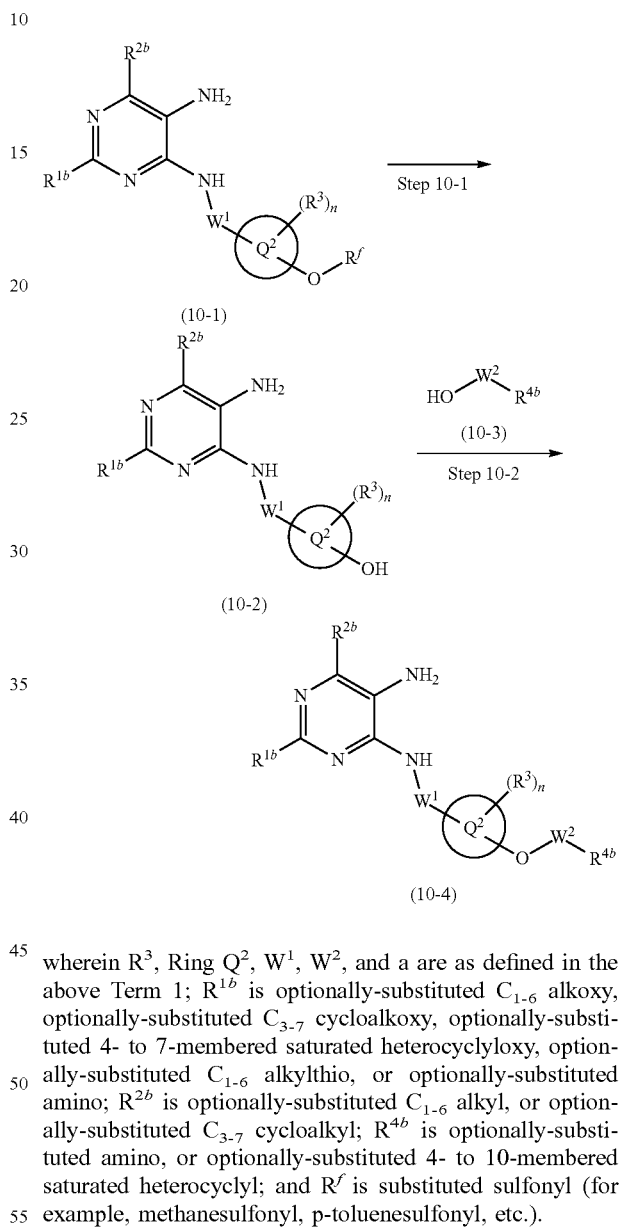

wherein $R^3$, Ring $Q^2$, $W^1$, $W^2$, and a are as defined in the above Term 1; $R^{1b}$ is optionally-substituted $C_{1-6}$ alkoxy, optionally-substituted $C_{3-7}$ cycloalkoxy, optionally-substituted 4- to 7-membered saturated heterocyclyloxy, optionally-substituted $C_{1-6}$ alkylthio, or optionally-substituted amino; $R^{2b}$ is optionally-substituted $C_{1-6}$ alkyl, or optionally-substituted $C_{3-7}$ cycloalkyl; $R^{4b}$ is optionally-substituted amino, or optionally-substituted 4- to 10-membered saturated heterocyclyl; and $R^f$ is substituted sulfonyl (for example, methanesulfonyl, p-toluenesulfonyl, etc.).

Step 10-1: Preparation Step of Compound (10-2)

Compound (10-2) can be prepared by reacting compound (10-1) with a base in an inert solvent. compound (10-1) used herein can be prepared according to the method described in Preparation Process 2.

The inert solvent includes, for example, ether solvents such as tetrahydrofuran, tetrahydropyran, 1,4-dioxane, and 1,2-dimethoxyethane; protic polar solvents such as methanol, ethanol, and water; and mixture solvents thereof. Preferably, it is tetrahydrofuran, methanol, or ethanol.

The base used herein includes, for example, inorganic bases such as lithium hydroxide, sodium hydroxide, and potassium hydroxide; and organic bases such as sodium methoxide, sodium ethoxide, sodium tert-butoxide, potassium tert-butoxide, lithium trimethylsilyloxide, sodium trimethylsilyloxide, and potassium trimethylsilyloxide. Preferably, it is lithium hydroxide, sodium hydroxide, or potassium hydroxide.

The reaction temperature is not limited to specific ones, but it is generally selected from the temperatures between −20° C. and boiling point of the used solvent. Preferably it is −20° C. to 60° C. The reaction time is generally 30 minutes-48 hours.

Step 10-2: Preparation Step of Compound (10-4)

Compound (10-4) can be prepared from compound (10-2) and compound (10-3), according to the method described in Preparation Process 8. Compound (10-3) can be got as a marketed product or can be prepared by a known synthetic method (for example, US2003220341, US2003229092) or a similar method.

Preparation Process 11

The compound of formula (11-4) can be prepared, for example, by the following process.

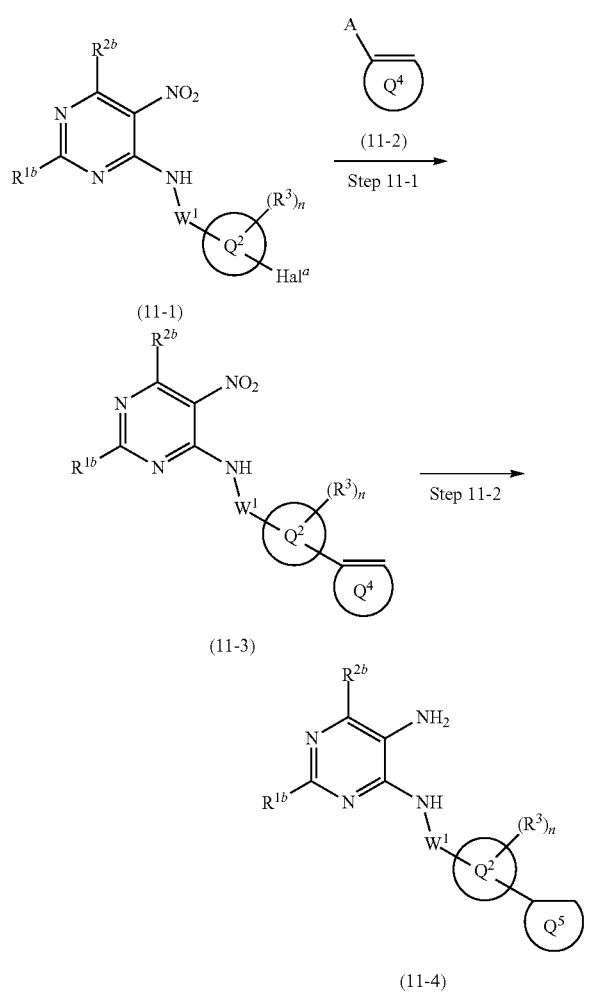

wherein $R^3$, Ring $Q^2$, $W^1$, and n are as defined in the above Term 1; $R^{1b}$ is optionally-substituted $C_{1-6}$ alkoxy, optionally-substituted $C_{3-7}$ cycloaloxy, optionally-substituted 4- to 7-membered saturated heterocyclyloxy, optionally-substituted $C_{1-6}$ alkylthio, or optionally-substituted amino; $R^{2b}$ is optionally-substituted $C_{1-6}$ alkyl, or optionally-substituted $C_{3-7}$ cycloalkyl; $Hal^a$ is chlorine atom, bromine atom, or iodine atom; A is boronic acid, boronate, $BF_3K$, or $BF_3Na$; $Q^4$ is optionally-substituted 4- to 10-membered partially-unsaturated carbon-ring group, or optionally-substituted 4- to 10-membered partially-unsaturated hetero-ring group; $Q^5$ is $C_{4-10}$ cycloalkyl, or optionally-substituted 4- to 10-membered saturated heterocyclyl.

Step 11-1: Preparation Step of Compound (11-3)

Compound (11-3) can be prepared from compound (11-1), according to the method described in Step 7-1. Compound (11-2) used herein can be got as a marketed product or can be prepared by a known method which is according to the method to prepare compound (1-5). Compound (11-1) used herein can be prepared according to the method described in Preparation Process 2 or Preparation Process 3.

Step 11-2: Preparation Step of Compound (11-4)

Compound (11-4) can be prepared from compound (11-3), according to the method described in Step 7-2.

Preparation Process 12

The compound of formula (12-5) can be prepared, for example, by the following process.

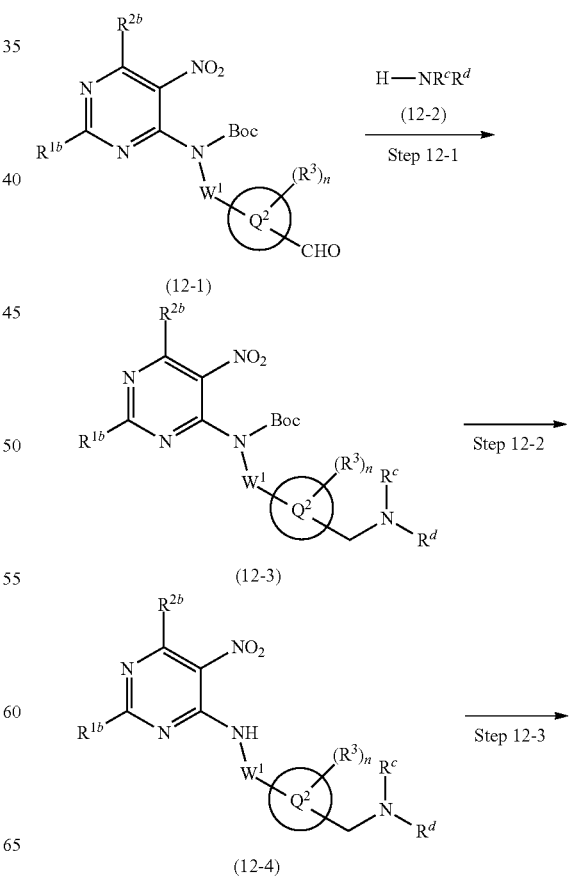

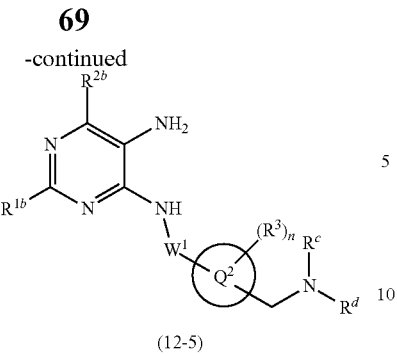

(12-5)

wherein $R^3$, Ring $Q^2$, $W^1$, and n are as defined in the above Term 1; $R^{1b}$ is optionally-substituted $C_{1-6}$ alkoxy, optionally-substituted $C_{3-7}$ cycloalkoxy, optionally-substituted 4- to 7-membered saturated heterocyclyloxy, optionally-substituted $C_{1-6}$ alkylthio, or optionally-substituted amino; $R^{2b}$ optionally-substituted $C_{1-6}$ alkyl, or optionally-substituted $C_{3-7}$ cycloalkyl; and $R^c$ and $R^d$ are independently hydrogen atom or optionally-substituted $C_{1-6}$ alkyl, or $R^c$ and $R^d$ may be combined together with the nitrogen atom to which they are attached to form optionally-substituted 4- to 10-membered saturated heterocycle.

Step 12-1: Preparation Step of Compound (12-3)

Compound (12-3) can be prepared from compound (12-1), according to the method described in Step 6-5. Compound (12-2) can be got as a marketed product or can be prepared by a known synthetic method (for example, WO20073965, US2010216812) a similar method. Compound (12-1) used herein can be prepared according to the method described in Preparation Process 2.

Step 12-2: Preparation Step of Compound (12-4)

Compound (12-4) can be prepared from compound (12-3), according to the method described in Step 2-5.

Step 12-3: Preparation Step of Compound (12-5)

Compound (12-5) can be prepared from compound (12-4), according to the method described in Step 2-6.

Preparation Process 13

The compound of formula (13-2) can be prepared, for example, by the following process.

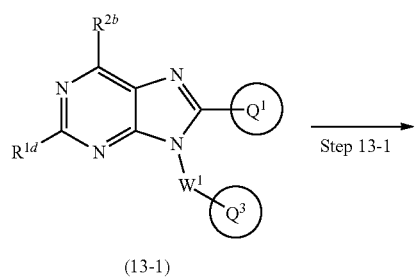

(13-1)

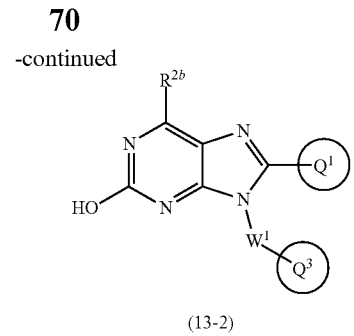

(13-2)

wherein Ring $Q^1$ and $W^1$ are as defined in the above Term 1; $R^{1d}$ is optionally-substituted $C_{1-6}$ alkoxy; $R^{2b}$ is optionally-substituted $C_{1-6}$ alkyl, or optionally-substituted $C_{3-7}$ cycloalkyl; and Ring $Q^3$ is optionally-substituted $C_{6-10}$ aryl, or optionally-substituted 5- to 10-membered heteroaryl.

Step 13-1: Preparation Step of Compound (13-2)

Compound (13-2) can be prepared by reacting compound (13-1) with an acid in an inert solvent.

The inert solvent includes, for example, ether solvents such as tetrahydrofuran, tetrahydropyran, 1,4-dioxane, and 1,2-dimethoxyethane; protic polar solvents such as methanol, ethanol, and water; ester solvents such as methyl acetate and ethyl acetate; halogenated hydrocarbons such as chloroform, dichloromethane, and 1,2-dichloroethane; and mixture solvents thereof.

The acid used herein includes, for example, inorganic acids such as hydrochloric acid and sulfuric acid.

The reaction temperature is not limited to specific ones, but it is generally selected from the temperatures between 20° C. and boiling point of the used solvent. Preferably it 20° C. to 60° C. The reaction time is generally 30 minutes-24 hours.

The present compound having a desired functional group at a desired position can be prepared by suitably combining the above preparation processes. The isolation and purification of each intermediate or product in the above preparation processes can be carried out by conventional manners an organic synthesis, for example, by suitably combining filtration, extraction, washing, drying, concentration, crystallization, various chromatography, etc. Or, some intermediates may be sometimes used in the next step without purification.

Some starting compounds or intermediates in the above preparation processes can exist in a salt form such as hydrochloride, but can be used as free form thereof. When starting compounds or intermediates that are in salt form need to be used or obtained as free form thereof, they can be transformed to free forms thereof by dissolving or suspending them in an appropriate solvent and neutralizing the solution or suspension with a base such as aqueous sodium bicarbonate.

Some of compound (1) or a pharmaceutically acceptable salt thereof can exist as isomers such as tautomer (for example, keto-enol form), regioisomer, geometrical isomer, and optical isomer. The present invention encompasses every possible isomer including the above, and a mixture thereof which has various mixture proportions.

And, optical isomers thereof can be resolved by a known manner such as chromatography with an optically-active column and fractional crystallization at a suitable step in the above-mentioned preparation processes. And, an optically-active starting material can be also used for this purpose.

In order to obtain compound (1) as a salt thereof, when the product is a salt of compound (1), the product should be directly purified; or when the product is in free form of compound (1), the product should be dissolved or suspended in an appropriate solvent and then an acid or a base should be added thereto to form a salt thereof. And, some of compound (1) or a pharmaceutically acceptable salt thereof can exist as a hydrate thereof or a solvate thereof with various solvents, which are also included in the present invention.

Autoimmune disease is a generic term of diseases progressing to histological damage which can be developed as follows; innate immune system which intrinsically has a role to recognize foreign substances from outside such as pathogenic microorganisms and then exclude them gets abnormal, recognizes autologous cells or tissues as foreign substances to produce excess autoantibody and lymphocyte, and causes inflammation systemically or organ-specifically with producing cytokine. It includes, for example, systemic lupus erythematosus, lupus nephritis, central nervous system lupus, cutaneous lupus erythematosus (e.g. discoid lupus erythematosus, lupus erythematosus profundus), Sjogren's syndrome, idiopathic thrombocytopenic purpura, autoimmune blood disease (e.g. autoimmune hemolytic anemia, episodic thrombocytopenia), psoriasis (e.g. plaque psoriasis, psoriasis arthropathica, pustular psoriasis, guttate psoriasis), pemphigus (e.g. pemphigus vulgaris, bullous pemphigoid), rheumatoid arthritis, antiphospholipid antibody syndrome, Aicardi-Goutieres syndrome, IgG4-related disease, polymyositis, dermatomyositis, Behcet's disease, type 1 diabetes, rapidly progressive glomerulonephritis, multiple sclerosis, Crohn's disease, ulcerative colitis, Hashimoto's disease, scleroderma, systemic sclerema, polyarteritis nodosa, allergic granulomatous angiitis, primary myxedema, thyrotoxicosis, pernicious anemia, Goodpasture's syndrome, myasthenia gravis, insulin-resistant diabetes, juvenile diabetes, Addison's disease, atrophic gastritis, male sterility, early-onset climacteric, lens-induced uveitis, primary biliary cirrhosis, chronic active hepatitis, paroxysmal hemoglobinuria, primary biliary cirrhosis, Guillain-Barre syndrome, Graves' disease, interstitial pulmonary fibrosis, and mixed connective tissue disease.

The pharmaceutical formulation of the present invention can be prepared by mixing an active ingredient with one or more pharmaceutically acceptable carriers and processing it by a conventional manner in drug formulation field. The pharmaceutically acceptable carrier used herein includes, for example, lactose, mannitol, glucose, starch, magnesium stearate, glycerate ester, distilled water for injection, saline, propylene glycol, polyethylene glycol, and ethanol. And, the pharmaceutical formulation of the present invention may comprise various other excipient, lubrication agent, lubricant, binder, disintegrant, tonicity agent, emulsifier, and the like.

As for the administration route of the present invention, a route to bring into the most effective therapy is preferable, which includes oral administration, and parenteral administration such as intravenous, transdermal, inhalational, and ophthalmic, preferably oral administration. The dosage form of the present invention includes, for example, tablet and injection, preferably tablet. The dose of the present pharmaceutical composition and the frequency of administration depend on dosage form, disease and symptom of patients, age and body weight of patients, etc. Thus, they cannot be clearly determined, but the present pharmaceutical composition may be administered to an adult a few times per day, preferably 1-3 times per day, wherein the daily dose of the active ingredient is a range of about 0.0001-about 5000 mg, preferably about 0.001-about 1000 mg, more preferably about. 0.1-about 500 mg, particularly preferably about 1-about 300 mg.

The present compound may be used in combination with other drugs to strengthen the efficacy and/or reduce side effects. For example, the present compound may be used in combination with another drug such as a steroid drug, an immunosuppressive drug, B cell-specific agent, and TLR inhibitor. The "B cell-specific agent" means an antibody drug whose target is B cells. The "TLR inhibitor" includes, for example, hydroxychloroquine and chloroquine.

Hereinafter, a drug which can be used in combination with the present compound is called a combination drug for short.

The combination drug used herein includes, for example, a steroid drug, an immunosuppressive drug, a B cell-specific agent, a TLR inhibitor, and other agents for treating autoimmune disease.

The administration interval between the present compound and a combination drug should not be limited. These may be administered to a subject simultaneously or with time lag. And, the present compound and a combination drug may be a "drug-combination" thereof. The dose of a combination drug can be suitably determined based on the dose that the combination drug has been clinically used. The ratio of the present compound and a combination drug may be determined based on its subject, administration route, disease, symptom, combination, etc. For example, in case that the subject is a human, 0.01-100 parts by weight of a combination drug may be used per one part by weight of the present compound (1). In addition, in order to suppress its side effect, other drugs such as an antiemetic drug, a sleep-inducing drug, and an anticonvulsant drug (i.e., concurrent drug) may be used in combination.

The dose of each compound can depend on patient's disease, age, body weight, gender, symptom, and the administration route, etc. In general, the present compound is administered to an adult (body weight: 50 kg) by 0.1-1000 mg/day, preferably 0.1-300 mg/day, once a day or in 2-3 doses. Or, it may be administered once in a few days to a few weeks.

EXAMPLES

The present invention is explained in more detail in the following by referring to Examples, Reference examples, and Tests; however, the technical scope of the present invention is not limited thereto. The compound names used in Examples and Reference examples are not always based on IUPAC nomenclature system.

In the present specification, the abbreviations shown below may be sometimes used.
(Boc)$_2$O: di-tert-butyl dicarbonate
Tf: trifluoromethanesulfonyl
DMAP: N,N-dimethyl-4-aminopyridine
EDCI: 1-(3-dimethylaminopropyl)-3-ethylcarbodiimide
EDCI·HCl: 1-(3-dimethylaminopropyl)-3-ethylcarbodiimide hydrochloride
HOBt: 1-hydroxybenzotriazole
HOBt·H$_2$O: 1-hydroxybenzotriazole monohydrate
Boc: tert-butoxycarbonyl
Me: methyl
Et: ethyl
Tf: trifluoromethanesulfonyl
Rt: retention time In the following Examples and Reference examples, the reaction device shown below was used as appropriate.
Microwave reactor: Biotage AB Initiator The physicochemical data of each compound in Examples and Reference examples were obtained with the instrument shown below.

$^1$H-NMR: JEOL JNM-AL400; Brucker AVANCE 400 Spectrometer

The LC/MS data of each compound in Examples and Reference examples were obtained with the instrument shown below.
Detector: ACQUITY™ SQ deteceter (Waters)
HPLC: ACUITY™ UPLC
SYSTEM Column: Waters ACQUITY™ UPLC BEH C18 (1.7 μm, 2.1 mm×30 mm)

The analytical conditions are as follows.

| Method | Solvent | Gradient condition |
|---|---|---|
| Method A | A: 0.05% formic acid/water<br>B: acetonitrile | 0.0-1.3 min Linear gradient from B 2% to 96% |
| Method B | A: 0.05% formic acid water<br>B: acetonitrile | 0.0-1.3 min Linear gradient from B 1% to 95% |
| Method C | A: 0.05% formic acid/water<br>B: acetonitrile | 0.0-1.3 min Linear gradient from B 10% to 95% |
| Method D | A: 0.06% formic acid/water<br>B: 0.06% formic acid/acetonitrile | 0.0-1.3 min Linear gradient from B 2% to 96% |

Flow rate: 0.8 mL/min; Detection UV: 220 nm and 254 nm; Temperature: 40° C.

The compound names in Examples and Reference examples were determined with ACD/Name (ACD/Labs 12.0, Advanced Chemistry Development Inc.).

Example 1

9-Benzyl-2-butoxy-8-(5-fluoropyridin-3-yl)-9H-purine-6-amine

To a solution of 9-benzyl-8-bromo-2-butoxy-9H-purine-6-amine (70.1 mg) in a mixture of 1,4-dioxane (3 mL)/water (1 mL) were added 3-fluoropyridine-5-boronic acid pinacol ester (46.4 mg), potassium carbonate (77.6 g), and tetrakis (triphenylphosphine)palladium (0.021 g), and the mixture was stirred at 120° C. under microwave irradiation for one hour. The reaction mixture was cooled to room temperature, and then water was added thereto. The mixture was extracted with ethyl acetate. The organic layer was dried over sodium sulfate, filtrated, and then concentrated in vacuo. The residue was purified by silica gel column chromatography (chloroform/methanol) to give the title compound (22.6 mg).

LC-MS [M+H]$^+$/Rt (min): 393.0/0.988 (Method A); $^1$H-NMR (400 MHz, DMSO-d$_6$) δ: 8.67 (1H, t, J=1.8 Hz), 8.67 (1H, d, J=7.9 Hz), 7.98-7.95 (1H, m), 7.47 (2H, brs), 7.28-7.19 (3H, m), 6.99-6.96 (2H, m), 5.47 (2H, s), 4.22 (2H, t, J=6.4 Hz), 1.64 (2H, tt, C=6.4, 7.9 Hz), 1.38 (2H, qt, J=7.3, 7.9 Hz), 0.90 (3H, t, J=7.3 Hz).

Examples 2-46

According to the method of Example 1, Examples 2-46 were prepared by using the corresponding material compounds. As appropriate, some reactions were carried out under reflux or under microwave irradiation.

| Example | Chemical Structure | Instrumental analysis data |
|---|---|---|
| 2 | 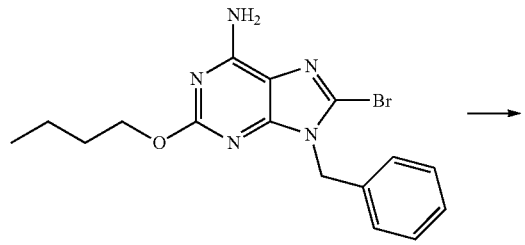 | LC-MS [M + H]$^+$/Rt (min): 375.0/0.899 (Method A); $^1$H-NMR (400 MHz, DMSO-d$_6$) δ: 8.81 (1H, d, J = 1.8 Hz), 8.63 (1H, dd, J = 1.2, 4.9 Hz), 8.02 (1H, dt, J = 1.8, 7.9 Hz), 7.48 (1H, dd, J = 4.9, 7.9 Hz), 7.42 (2H, brs), 7.27-7.19 (3H, m), 6.97 (2H, d, J = 6.7 Hz), 5.43 (2H, s), 4.21 (2H, t, J = 6.7 Hz), 1.64 (2H, tt, J = 6.7, |

-continued

| Example | Chemical Structure | Instrumental analysis data |
|---|---|---|
| | | 7.9 Hz), 1.38 (2H, qt, J = 7.3, 7.9 Hz), 0.90 (3H, t, J = 7.3 Hz). |
| 3 | 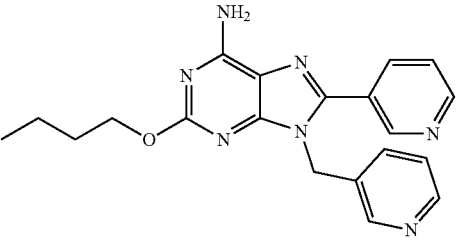 [SMILES: CCCCOc1nc(N)c2nc(-c3cccnc3)n(Cc3cccnc3)c2n1] | LC-MS [M + H]⁺/Rt (min): 376.1/0.643 (Method A); ¹H-NMR (400 MHz, DMSO-d₆) δ: 8.83 (1H, d, J = 1.2 Hz), 8.65 (1H, dd, J = 1.2, 4.9 Hz), 8.41 (1H, dd, J = 1.8, 4.9 Hz), 8.27 (1H, d, J = 1.2 Hz), 8.04 (1H, ddd, J = 1.8, 1.8 7.9 Hz), 7.51 (1H, dd, J = 4.9, 7.9 Hz), 7.49 (2H, brs), 7.35-7.34 (1H, m), 7.26 (1H, dd, J = 4.9, 7.9), 5.46 (2H, s), 4.21 (2H, t, J = 6.7 Hz), 1.64 (2H, tt, J = 6.7, 7.9 Hz), 1.38 (2H, qt, J = 7.3, 7.9 Hz), 0.90 (3H, t, J = 7.3 Hz). |
| 4 | 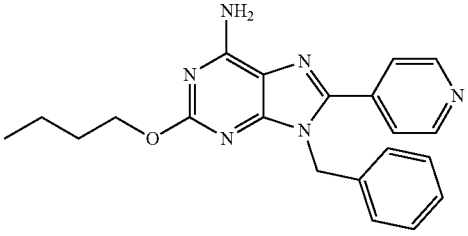 [SMILES: CCCCOc1nc(N)c2nc(-c3ccncc3)n(Cc3ccccc3)c2n1] | LC-MS [M + H]⁺/Rt (min): 375.1/0.891 (Method A); ¹H-NMR (400 MHz, DMSO-d₆) δ: 8.64 (2H, dd, J = 1.8, 4.3 Hz), 7.64 (2H, dd, J = 1.8, 4.3 Hz), 7.49 (2H, brs), 7.28-7.19 (3H, m), 7.00 (2H, d, J = 6.7 Hz), 5.50 (2H, s), 4.21 (2H, t, J = 6.7 Hz), 1.63 (2H, tt, J = 6.7, 7.9 Hz), 1.38 (2H, qt, J = 7.3, 7.9 Hz), 0.89 (3H, t, J = 7.3 Hz). |
| 5 | 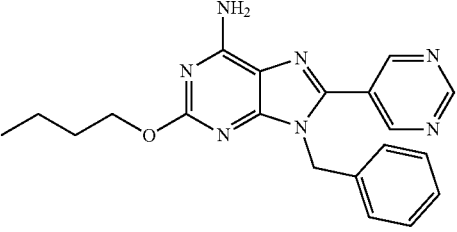 [SMILES: CCCCOc1nc(N)c2nc(-c3cncnc3)n(Cc3ccccc3)c2n1] | LC-MS [M + H]⁺/Rt (min): 376.1/0.891 (Method A); ¹H-NMR (400 MHz, DMSO-d₆) δ: 9.23 (1H, s), 9.03 (1H, s), 9.02 (1H, s), 7.50 (2H, brs), 7.28-7.19 (3H, m), 6.99 (2H, d, J = 6.7 Hz), 5.49 (2H, s), 4.23 (2H, t, J = 6.7 Hz), 1.64 (2H, tt, J = 6.7, 7.9 Hz), 1.39 (2H, qt, J = 7.3, 7.9 Hz), 0.90 (3H, t, J = 7.3 Hz). |
| 6 | 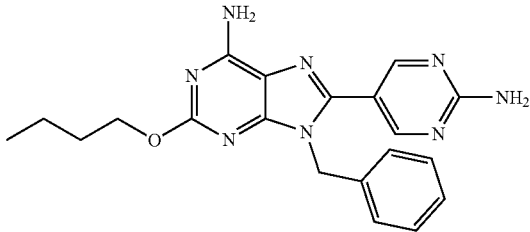 [SMILES: CCCCOc1nc(N)c2nc(-c3cnc(N)nc3)n(Cc3ccccc3)c2n1] | LC-MS [M + H]⁺/Rt (min): 391.1/0.833 (Method A); ¹H-NMR (400 MHz, DMSO-d₆) δ: 8.40 (2H, s), 7.35-7.21 (5H, m), 7.07 (2H, s), 7.01 (2H, d, J = 6.7 Hz), 5.38 (2H, s), 4.19 (2H, t, J = 6.7 Hz), 1.63 (2H, tt, J = 6.7, 7.9 Hz), 1.37 (2H, qt, J = 7.3, 7.9 Hz), 0.89 (3H, t, J = 7.3 Hz). |
| 7 | 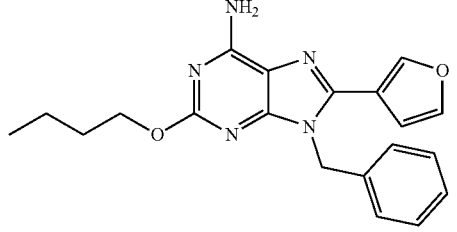 [SMILES: CCCCOc1nc(N)c2nc(-c3ccoc3)n(Cc3ccccc3)c2n1] | LC-MS [M + H]⁺/Rt (min): 364.1/1.008 (Method A); ¹H-NMR (400 MHz, DMSO-d₆) δ: 8.05 (1H, s), 7.77 (1H, dd, J = 1.2, 1.8 Hz), 7.32-7.20 (5H, m), 7.05 (2H, d, J = 7.3 Hz), 6.85 (1H, d, J = 1.8 Hz), 5.46 (2H, s), 4.19 (2H, t, J = 6.7 Hz), 1.63 (2H, tt, J = 6.7, 7.9 Hz), 1.37 (2H, qt, J = 7.3, 7.9 Hz), 0.89 (3H, t, J = 7.3 Hz). |

| Example | Chemical Structure | Instrumental analysis data |
|---|---|---|
| 8 | 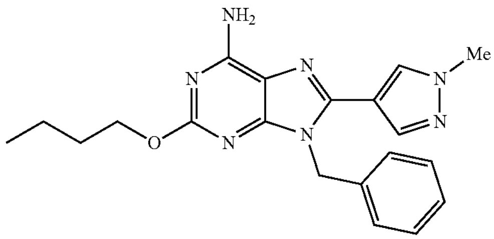 [SMILES: CCCCOc1nc(N)c2nc(-c3cnn(C)c3)n(Cc3ccccc3)c2n1] | ¹H-NMR (400 MHz, DMSO-d₆) δ: 8.11 (1H, s), 7.76 (1H, s), 7.33-7.21 (5H, m), 5.46 (2H, s), 4.19 (2H, t, J = 6.5 Hz), 3.86 (3H, s), 1.63 (2H, tt, J = 6.5, 7.9 Hz), 1.38 (2H, qt, J = 7.3, 7.9 Hz), 0.90 (3H, t, J = 7.3 Hz). |
| 9 | 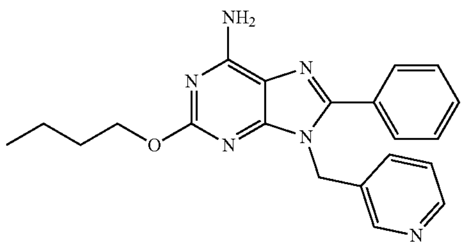 [SMILES: CCCCOc1nc(N)c2nc(-c3ccccc3)n(Cc3cccnc3)c2n1] | ¹H-NMR (400 MHz, DMSO-d₆) δ: 8.43-8.41 (1H, m), 8.27-8.26 (1H, m), 7.67-7.48 (5H, m), 7.45-7.34 (3H, m), 7.30-7.26 (1H, m), 5.44 (2H, s), 4.21 (2H, t, J = 6.6 Hz), 1.65 (2H, tt, J = 6.6, 7.9 Hz), 1.38 (2H, qt, J = 7.3, 7.9 Hz), 0.91 (3H, t, J = 7.3 Hz). |
| 10 | 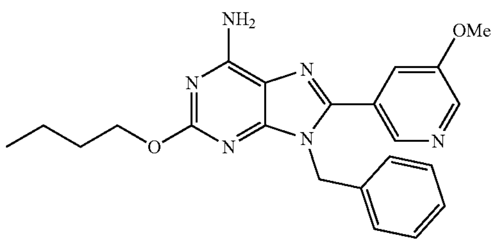 [SMILES: CCCCOc1nc(N)c2nc(-c3cncc(OC)c3)n(Cc3ccccc3)c2n1] | ¹H-NMR (400 MHz, DMSO-d₆) δ: 8.41 (1H, d, J = 1.7 Hz), 8.36 (1H, d, J = 2.8 Hz), 7.53-7.37 (3H, m), 7.32-7.20 (3H, m), 7.03-7.00 (2H, m), 5.45 (2H, s), 4.22 (2H, t, J = 6.6 Hz), 1.66 (2H, tt, J = 6.6, 7.9 Hz), 1.39 (2H, qt, J = 7.3, 7.9 Hz), 0.91 (3H, t, J = 7.3 Hz). |
| 11 | 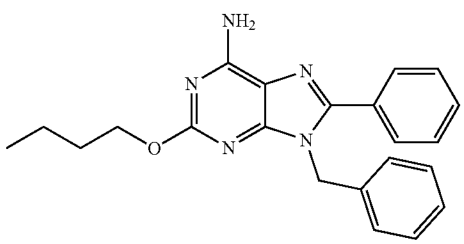 [SMILES: CCCCOc1nc(N)c2nc(-c3ccccc3)n(Cc3ccccc3)c2n1] | LC-MS: [M + H]⁺/Rt (min): 374.1/1.078 (Method A); ¹H-NMR (400 MHz, DMSO-d₆) δ: 7.65-7.61 (2H, m), 7.47-7.43 (3H, m), 7.33 (2H, brs), 7.28-7.19 (3H, m), 6.97 (2H, d, J = 6.7 Hz), 5.38 (2H, s), 4.20 (2H, t, J = 6.7 Hz), 1.63 (2H, tt, J = 6.7, 7.9 Hz), 1.37 (2H, qt, J = 7.3, 7.9 Hz), 0.89 (3H, t, J = 7.3 Hz). |
| 12 | 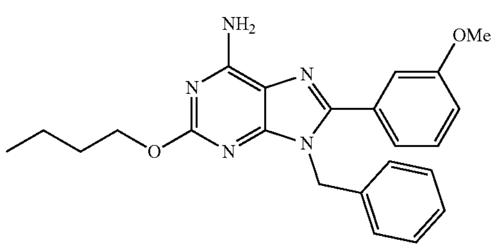 [SMILES: CCCCOc1nc(N)c2nc(-c3cccc(OC)c3)n(Cc3ccccc3)c2n1] | LC-MS: [M + H]⁺/Rt (min): 404.2/1.091 (Method A); ¹H-NMR (400 MHz, DMSO-d₆) δ: 7.39-7.31 (3H, m), 7.30-7.19 (4H, m), 7.11-7.09 (1H, m), 7.04-6.98 (3H, m), 5.38 (2H, s), 4.19 (2H, t, J = 6.7 Hz), 3.66 (3H, s), 1.63 (2H, tt, J = 6.7, 7.9 Hz), 1.36 (2H, qt, J = 7.3, 7.9 Hz), 0.89 (3H, t, J = 7.3 Hz). |
| 13 | 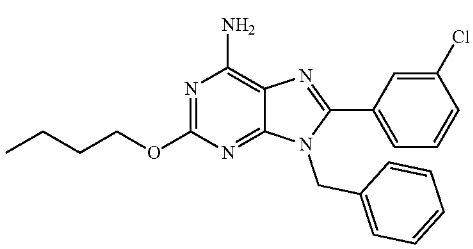 [SMILES: CCCCOc1nc(N)c2nc(-c3cccc(Cl)c3)n(Cc3ccccc3)c2n1] | LC-MS: [M + H]⁺/Rt (min): 408.1/1.162 (Method A); ¹H-NMR (400 MHz, DMSO-d₆) δ: 7.68-7.66 (1H, m), 7.61-7.57 (1H, m), 7.59-7.50 (1H, m), 7.49 (2H, dd, J = 7.3, 7.9 Hz), 7.40 (2H, brs), 7.29-7.20 (3H, m), 6.99 (2H, d, J = 7.3 Hz), 5.41 (2H, s), 4.20 (2H, t, J = 6.7 Hz), 1.64 (2H, tt, J = 6.7, 7.9 Hz), 1.37 (2H, qt, J = 7.3, 7.9 Hz), 0.89 (3H, t, J = 7.3 Hz). |

| Example | Chemical Structure | Instrumental analysis data |
|---|---|---|
| 14 | 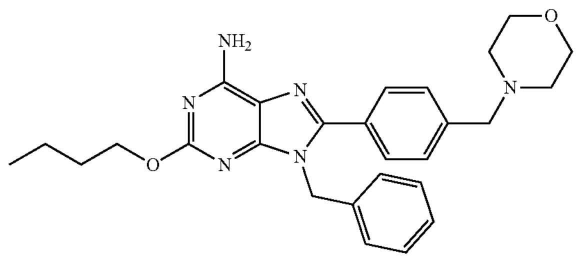 [SMILES: CCCCOc1nc(N)c2nc(-c3ccc(CN4CCOCC4)cc3)n(Cc3ccccc3)c2n1] | ¹H-NMR (400 MHz, DMSO-d₆) δ: 7.65 (2H, d, J = 8.1 Hz), 7.45 (2H, d, J = 8.1 Hz), 7.41 (2H, brs), 7.35-7.26 (3H, m), 7.06-7.03 (2H, m), 5.46 (2H, s), 4.27 (2H, t, J = 6.6 Hz), 3.66-3.62 (4H, m), 3.56 (2H, m), 2.44-2.38 (4H, m), 1.70 (2H, tt, J = 6.6, 7.9 Hz), 1.44 (2H, qt, J = 7.3, 7.9 Hz), 0.97 (3H, t, J = 7.3 Hz). |
| 15 | 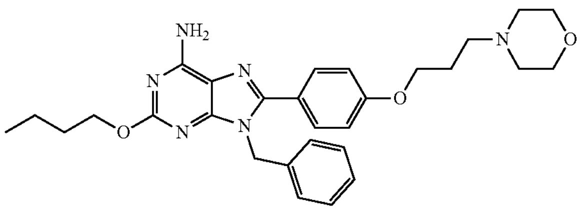 [SMILES: CCCCOc1nc(N)c2nc(-c3ccc(OCCCN4CCOCC4)cc3)n(Cc3ccccc3)c2n1] | ¹H-NMR (400 MHz, DMSO-d₆) δ: 7.56 (2H, d, J = 8.8 Hz), 7.55-7.20 (5H, m), 7.03-6.98 (4H, m), 5.38 (2H, s), 4.19 (2H, t, J = 6.6 Hz), 4.04 (2H, t, J = 6.4 Hz), 3.59-3.55 (4H, m), 2.41 (2H, t, J = 7.1 Hz), 2.38-2.33 (4H, m), 1.88 (2H, tt, J = 6.4, 7.1 Hz), 1.64 (2H, tt, J = 6.6, 7.9 Hz), 1.38 (2H, qt, J = 7.3, 7.9 Hz), 0.90 (3H, t, J = 7.3 Hz). |
| 16 | 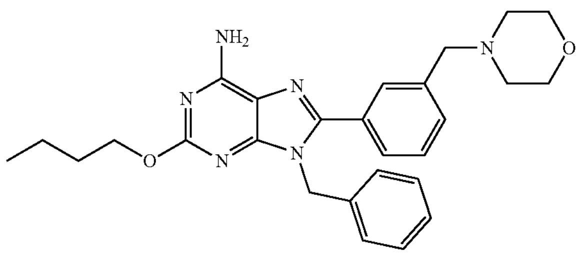 [SMILES: CCCCOc1nc(N)c2nc(-c3cccc(CN4CCOCC4)c3)n(Cc3ccccc3)c2n1] | ¹H-NMR (400 MHz, DMSO-d₆) δ: 7.58-7.51 (2H, m), 7.43-7.34 (4H, m), 7.18-7.20 (3H, m), 6.99 (2H, d, J = 6.8 Hz), 5.38 (2H, s), 4.21 (2H, t, J = 6.6 Hz), 3.56-3.49 (4H, m), 3.43 (2H, s), 2.31-2.24 (4H, m), 1.65 (2H, tt, J = 6.6, 7.9 Hz), 1.38 (2H, qt, J = 7.3, 7.9 Hz), 0.91 (3H, t, J = 7.3 Hz). |
| 17 | 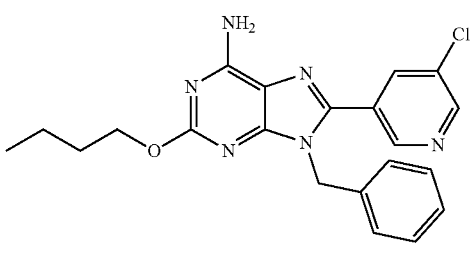 [SMILES: CCCCOc1nc(N)c2nc(-c3cncc(Cl)c3)n(Cc3ccccc3)c2n1] | LC-MS: [M + H]⁺/Rt (min): 409.1/1.048 (Method A); ¹H-NMR (400 MHz, DMSO-d₆) δ: 8.75 (1H, d, J = 1.8 Hz), 8.69 (1H, d, J = 2.4 Hz), 8.15-8.13 (1H, m), 7.47 (2H, brs), 7.29-7.19 (3H, m), 7.01-6.98 (2H, m), 5.47 (2H, s), 4.22 (2H, t, J = 6.7 Hz), 1.64 (2H, tt, J = 6.7, 7.9 Hz), 1.38 (2H, qt, J = 7.3, 7.9 Hz), 0.90 (3H, t, J = 7.3 Hz). |
| 18 | 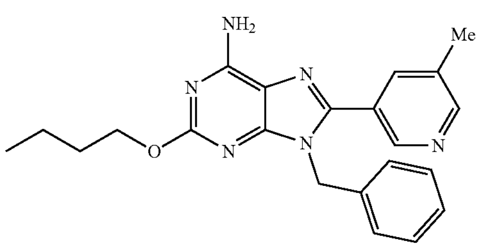 [SMILES: CCCCOc1nc(N)c2nc(-c3cncc(C)c3)n(Cc3ccccc3)c2n1] | LC-MS: [M + H]⁺/Rt (min): 389.3/0.940 (Method A); ¹H-NMR (400 MHz, DMSO-d₆) δ: 8.60 (1H, d J = 1.8 Hz), 8.47 (1H, d, J = 1.2 Hz), 7.84-7.83 (1H, m), 7.40 (2H, brs), 7.29-7.20 (3H, m), 7.01-6.98 (2H, m), 5.42 (2H, s), 4.21 (2H, t, J = 6.7 Hz), 2.30 (3H, s), 1.64 (2H, tt, J = 6.7, 7.9 Hz), 1.38 (2H, qt, J = 7.3, 7.9 Hz), 0.90 (3H, t, J = 7.3 Hz). |
| 19 | 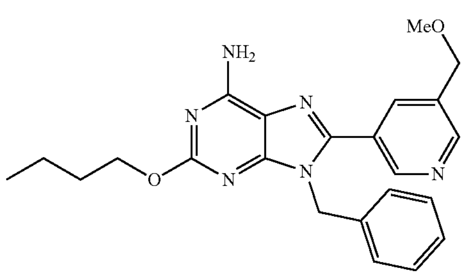 [SMILES: CCCCOc1nc(N)c2nc(-c3cncc(COC)c3)n(Cc3ccccc3)c2n1] | LC-MS [M + H]⁺/Rt (min): 419.6/0.939 (Method A); ¹H-NMR (400 MHz, DMSO-d₆) δ: 8.60 (1H, d J = 1.8 Hz), 8.47 (1H, d, J = 1.2 Hz), 7.84-7.83 (1H, m), 7.40 (2H, brs), 7.29-7.20 (3H, m), 7.01-6.98 (2H, m), 5.42 (2H, s), 4.21 (2H, t, J = 6.7 Hz), 2.30 (3H, s), 1.64 (2H, tt, J = 6.7, 7.9 Hz), 1.38 (2H, qt, J = 7.3, 7.9 Hz), 0.90 (3H, t, J = 7.3 Hz). |

-continued

| Example | Chemical Structure | Instrumental analysis data |
|---|---|---|
| 20 | 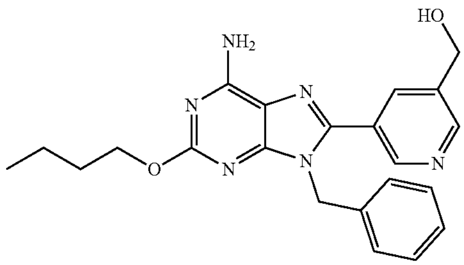 [SMILES: CCCCOc1nc(N)c2nc(-c3cncc(CO)c3)n(Cc3ccccc3)c2n1] | LC-MS: [M + H]⁺/Rt (min): 405.1/0.824 (Method A); ¹H-NMR (400 MHz, DMSO-d₆) δ: 8.67 (1H, d, J = 2.4 Hz), 8.56 (1H, d, J = 1.8 Hz), 8.02-7.99 (1H, m), 7.42 (2H, brs), 7.28-7.19 (3H, m), 7.00 (2H, d, J = 6.7 Hz), 5.44 (2H, s), 5.39 (1H, t, J = 5.5 Hz), 4.55 (2H, d, J = 5.5 Hz), 4.21 (2H, t, J = 6.7 Hz), 1.64 (2H, tt, J = 6.7, 7.9 Hz), 1.38 (2H, qt, J = 7.3, 7.9), 0.90 (3H, t, J = 7.3 Hz). |
| 21 | 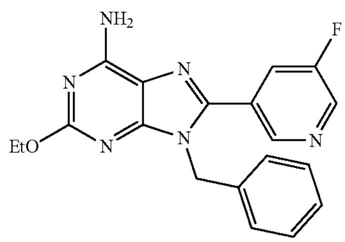 [SMILES: CCOc1nc(N)c2nc(-c3cncc(F)c3)n(Cc3ccccc3)c2n1] | LC-MS [M + H]⁺/Rt (min): 365.5/0.845 (Method A); ¹H-NMR (400 MHz, DMSO-d₆) δ: 8.71-8.69 (1H, m), 8.67 (1H, d, J = 2.8 Hz), 8.00-7.96 (1H, m), 7.50 (2H, brs), 7.29-7.20 (3H, m), 6.99 (2H, d, J = 6.8 Hz), 5.48 (2H, s), 4.27 (2H, q, J = 7.1 Hz), 1.28 (3H, t, J = 7.1 Hz). |
| 22 | 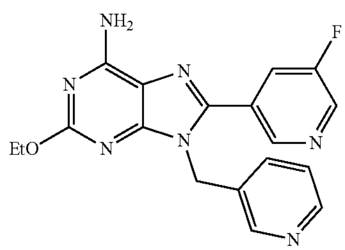 [SMILES: CCOc1nc(N)c2nc(-c3cncc(F)c3)n(Cc3cccnc3)c2n1] | LC-MS [M + H]⁺/Rt (min): 366.4/0.587 (Method A); ¹H-NMR (400 MHz, DMSO-d₆) δ: 8.71-8.68 (2H, m), 8.41 (1H, dd, J = 1.2, 4.9 Hz), 8.29 (1H, d, J = 1.8 Hz), 8.04-8.00 (1H, m), 7.48 (2H, brs), 7.38-7.35 (1H, m), 7.27 (1H, dd, J = 4.9, 7.9 Hz), 5.50 (2H, s), 4.26 (2H, q, J = 7.3 Hz), 1.27 (3H, t, J = 7.3 Hz). |
| 23 | 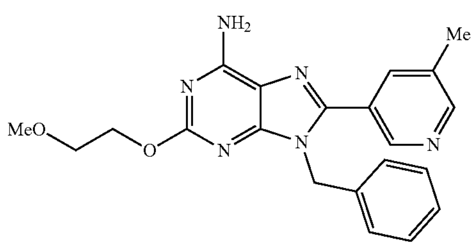 [SMILES: COCCOc1nc(N)c2nc(-c3cncc(C)c3)n(Cc3ccccc3)c2n1] | ¹H-NMR (400 MHz, DMSO-d₆) δ: 8.60 (1H, d, J = 1.8 Hz), 8.47 (1H, d, J = 1.2 Hz), 7.85-7.82 (1H, m), 7.44 (2H, brs), 7.31-7.19 (3H, m), 7.01-6.98 (2H, m), 5.42 (2H, s), 4.33 (2H, t, J = 4.9 Hz), 3.60 (2H, t, J = 4.9 Hz), 3.27 (3H, s), 2.30 (3H, s). |
| 24 | 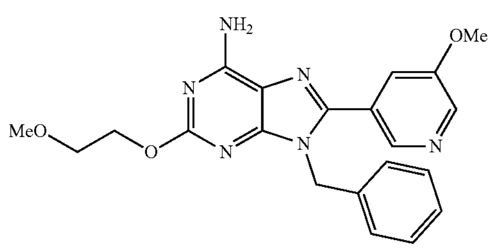 [SMILES: COCCOc1nc(N)c2nc(-c3cncc(OC)c3)n(Cc3ccccc3)c2n1] | LC-MS [M + H]⁺/Rt (min): 407.1/0.773 (Method A); ¹H-NMR (400 MHz, DMSO-d₆) δ: 8.40 (1H, d, J = 1.8 Hz), 8.35 (1H, d, J = 3.1 Hz), 7.51 (1H, dd, J = 1.8, 2.4 Hz), 7.46 (2H, brs), 7.31-7.21 (3H, m), 7.03-6.98 (2H, m), 5.43 (2H, s), 4.33 (2H, t, J = 4.9 Hz), 3.76 (3H, s), 3.60 (2H, t, J = 4.9 Hz), 3.27 (3H, s). |
| 25 | 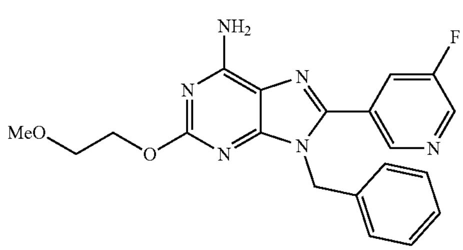 [SMILES: COCCOc1nc(N)c2nc(-c3cncc(F)c3)n(Cc3ccccc3)c2n1] | LC-MS: [M + H]⁺/Rt (min): 395.6/0.799 (Method A); ¹H-NMR (400 MHz, DMSO-d₆) δ: 8.69 (1H, d, J = 1.8 Hz), 8.66 (1H, d, J = 3.1 Hz), 7.98-7.94 (1H, m), 7.50 (2H, brs), 7.28-7.19 (3H, m), 6.99-6.96 (2H, m), 5.47 (2H, s), 4.34 (2H, t, J = 4.9 Hz), 3.61 (2H, t, J = 4.9 Hz), 3.27 (3H, s). |

| Example | Chemical Structure | Instrumental analysis data |
| --- | --- | --- |
| 26 | 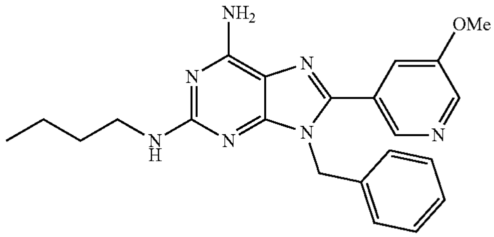 [SMILES: CCCCNc1nc(N)c2nc(-c3cncc(OC)c3)n(Cc3ccccc3)c2n1] | LC-MS: [M + H]$^+$/Rt (min): (404.2/0.813 (Method A); $^1$H-NMR (400 MHz, DMSO-d$_6$) δ: 8.38 (1H, d, J = 1.2 Hz), 8.30 (1H, d, J = 2.4 Hz), 7.46-7.44 (1H, m), 7.30-7.19 (3H, m), 7.03 (2H, d, J = 7.3 Hz), 6.87 (2H, brs), 6.42-6.37 (1H, m), 5.37 (2H, s), 3.74 (3H, s), 3.22 (2H, dt, J = 6.4, 6.7 Hz), 1.47 (2H, tt, J = 6.7, 7.3 Hz), 1.28 (2H, qt, J = 7.3, 7.3 Hz), 0.85 (3H, t, J = 7.3 Hz). |
| 27 | 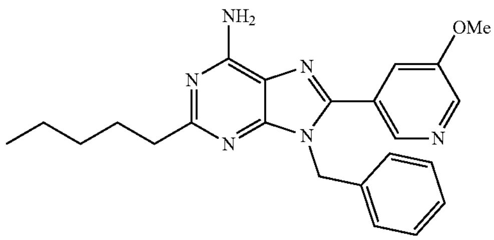 [SMILES: CCCCCc1nc(N)c2nc(-c3cncc(OC)c3)n(Cc3ccccc3)c2n1] | LC-MS: [M + H]$^+$/Rt (min): 403.2/0.861 (Method A); $^1$H-NMR (400 MHz, DMSO-d$_6$) δ: 8.41 (1H, d, J = 1.2 Hz), 8.36 (1H, d, J = 3.1 Hz), 7.53-7.51 (1H, m), 7.31 (2H, brs), 7.29-7.20 (3H, m), 6.97 (2H, d, J = 6.7 Hz), 5.50 (2H, s), 3.75 (3H, s), 2.65 (2H, t, J = 7.3 Hz), 1.71 (2H, tt, J = 6.7, 7.3 Hz), 1.32-1.23 (4H, m), 0.83 (3H, t, J = 6.7 Hz). |
| 28 | 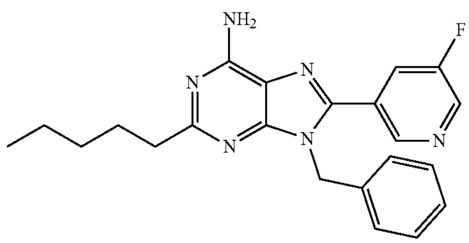 [SMILES: CCCCCc1nc(N)c2nc(-c3cncc(F)c3)n(Cc3ccccc3)c2n1] | $^1$H-NMR (400 MHz, DMSO-d$_6$) δ: 8.71-8.68 (2H, m), 8.02-7.99 (1H, m), 7.39 (2H, brs), 7.28-7.19 (3H, m), 6.98-6.95 (2H, m), 2.67 (2H, t, J = 7.4 Hz), 1.77-1.69 (2H, m), 1.34-1.23 (4H, m), 0.85 (3H, t, J = 6.8 Hz). |
| 29 | 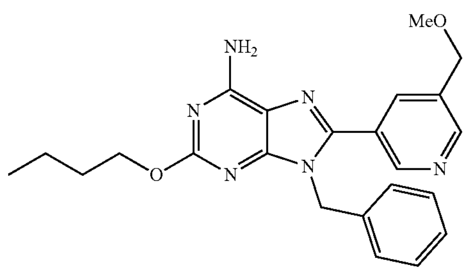 [SMILES: CCCCOc1nc(N)c2nc(-c3cncc(COC)c3)n(Cc3ccccc3)c2n1] | $^1$H-NMR (400 MHz, DMSO-d$_6$) δ: 8.75-8.74 (1H, m), 8.59-8.58 (1H, s), 7.98 (1H, s), 7.45 (2H, brs), 7.30-7.21 (3H, m), 7.02-7.00 (2H, m), 5.45 (2H, s), 4.47 (2H, s), 4.23 (2H, t, J = 6.6 Hz), 3.28 (3H, s), 1.66 (2H, tt, J = 6.6, 7.9 Hz), 1.39 (2H, qt, J = 7.3, 7.9 Hz), 0.91 (3H, t, J = 7.3 Hz). |
| 30 | 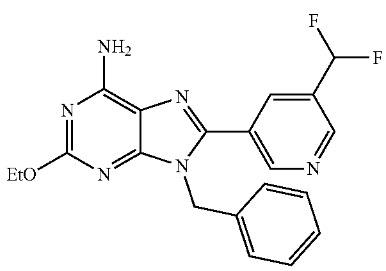 [SMILES: CCOc1nc(N)c2nc(-c3cncc(C(F)F)c3)n(Cc3ccccc3)c2n1] | LC-MS: [M + H]$^+$/Rt (min): 397.1/0.877 (Method A); $^1$H-NMR (400 MHz, DMSO-d$_6$) δ: 8.96 (1H, s), 8.82 (1H, s), 8.23 (1H, s), 7.48 (2H, brs), 7.28-7.19 (3H, m), 7.17 (1H, t, J = 54.9 Hz), 7.00 (2H, d, J = 7.3 Hz), 5.48 (2H, s), 4.27 (2H, q, J = 7.3 Hz), 1.27 (3H, t, J = 7.3 Hz). |
| 31 | 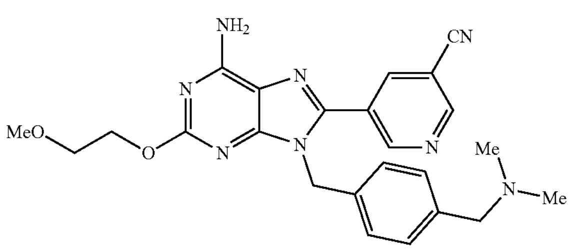 [SMILES: COCCOc1nc(N)c2nc(-c3cncc(C#N)c3)n(Cc3ccc(CN(C)C)cc3)c2n1] | LC-MS [M + H]$^+$/Rt (min): 459.1/0.497 (Method A); $^1$H-NMR (400 MHz, DMSO-d$_6$) δ: 9.06 (1H, d, J = 1.8 Hz), 9.04 (1H, d, J = 2.4 Hz), 8.50 (1H, dd, J = 1.8, 2.4 Hz), 7.52 (2H, brs), 7.13 (1H, d, J = 7.9 Hz), 6.91 (1H, d, J = 7.9 Hz), 5.47 (2H, s), 4.35 (2H, t, J = 4.9 Hz), 3.61 (2H, t, J = 4.9 Hz), 3.31 (3H, s), 3.27 (2H, s), 2.07 (6H, s). |

| Example | Chemical Structure | Instrumental analysis data |
|---|---|---|
| 32 | 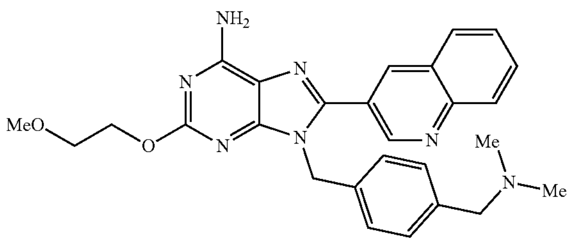 [SMILES: COCCOc1nc(N)c2nc(-c3cnc4ccccc4c3)n(Cc3ccc(CN(C)C)cc3)c2n1] | LC-MS [M + H]⁺/Rt (min): 484.2/0.566 (Method A); ¹H-NMR (400 MHz, DMSO-d₆) δ: 9.18 (1H, d, J = 2.4 Hz), 8.58 (1H, d, J = 1.8 Hz), 8.03 (1H, d, J = 8.5 Hz), 7.93 (1H, d, J = 7.9 Hz), 7.84-7.79 (1H, m), 7.68-7.64 (1H, m), 7.50 (2H, brs), 7.13 (2H, d, J = 7.9 Hz), 6.97 (2H, d, J = 7.9 Hz), 5.55 (2H, s), 4.36 (2H, t, J = 4.9 Hz), 3.62 (2H, t, J = 4.9 Hz), 3.28 (3H, s), 3.25 (2H, s), 2.01 (6H, s). |
| 33 | 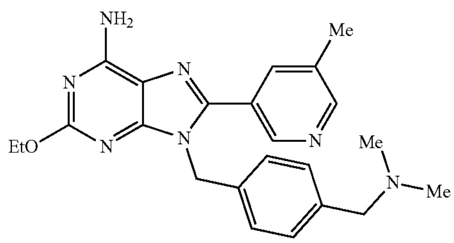 [SMILES: CCOc1nc(N)c2nc(-c3cncc(C)c3)n(Cc3ccc(CN(C)C)cc3)c2n1] | LC-MS: [M + H]⁺/Rt (min): 418.5/0.538 (Method A); ¹H-NMR (400 MHz, DMSO-d₆) δ: 8.58 (1H, d, J = 1.8 Hz), 8.46 (1H, d, J = 1.8 Hz), 7.80-7.79 (1H, m), 7.39 (2H, brs), 7.16 (1H, d, J = 7.9 Hz), 6.93 (2H, d, J = 7.9 Hz), 5.40 (2H, s), 4.26 (2H, q, J = 7.3 Hz), 3.28 (2H, s), 2.28 (3H, s), 2.05 (6H, s), 1.27 (3H, t, J = 7.3 Hz). |
| 34 | 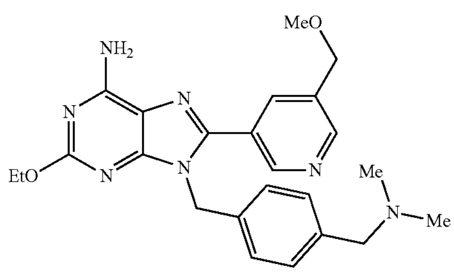 [SMILES: CCOc1nc(N)c2nc(-c3cncc(COC)c3)n(Cc3ccc(CN(C)C)cc3)c2n1] | LC-MS: [M + H]⁺/Rt (min): 448.2/0.537 (Method A); ¹H-NMR (400 MHz, DMSO-d₆) δ: 8.73 (1H, d, J = 1.8 Hz), 8.56 (1H, d, J = 2.4 Hz), 7.95-7.93 (1H, m), 7.42 (2H, brs), 7.16 (2H, d, J = 7.9 Hz), 6.94 (2H, d, J = 7.9 Hz), 5.41 (2H, s), 4.44 (2H, s), 4.26 (2H, q, J = 7.3 Hz), 3.28 (2H, s), 3.26 (3H, s), 2.06 (6H, s), 1.27 (3H, t, J = 7.3 Hz). |
| 35 | 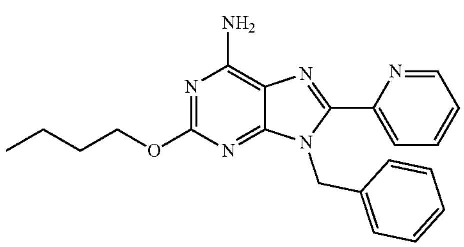 [SMILES: CCCCOc1nc(N)c2nc(-c3ccccn3)n(Cc3ccccc3)c2n1] | LC-MS [M + H]⁺/Rt (min): 375.4/1.070 (Method C); ¹H-NMR (CDCl₃) δ: 8.64 (1H, d, J = 4.9 Hz), 8.17 (1H, d, J = 7.9 Hz), 7.76 (1H, td, J = 1.6, 7.9 Hz), 7.31-7.24 (3H, m), 7.21-7.16 (3H, m), 6.06 (2H, s), 5.59 (2H, br s), 4.37 (2H, t, J = 6.7 Hz), 1.83-1.76 (2H, m), 1.56-1.47 (2H, m), 0.97 (3H, t, J = 7.3 Hz). |
| 36 | 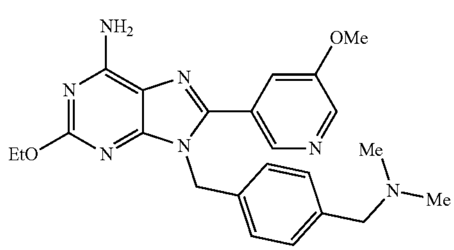 [SMILES: CCOc1nc(N)c2nc(-c3cncc(OC)c3)n(Cc3ccc(CN(C)C)cc3)c2n1] | LC-MS [M + H]⁺/Rt (min): 434.5/0.590 (Method B); ¹H-NMR (CDCl₃) δ: 8.43 (1H, s), 8.38-8.37 (1H, m), 7.32-7.32 (1H, m), 7.22 (2H, d, J = 7.9 Hz), 7.05 (2H, d, J = 7.9 Hz), 5.52 (2H, s), 5.40 (2H, s), 4.40 (2H, q, J = 7.2 Hz), 3.75 (3H, s), 3.36 (2H, s), 2.19 (6H, s), 1.41 (3H, t, J = 7.2 Hz). |
| 37 | 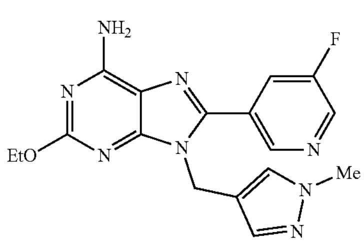 [SMILES: CCOc1nc(N)c2nc(-c3cncc(F)c3)n(Cc3cnn(C)c3)c2n1] | LC-MS [M + H]⁺/Rt (min): 369.0/0.535 (Method C); ¹H-NMR (CDCl₃) δ: 8.43 (1H, s), 8.38-8.37 (1H, m), 7.32-7.32 1H, m), 7.22 (2H, d, J = 7.9 Hz), 7.05 (2H, d, J = 7.9 Hz), 5.52 (2H, s), 5.40 (2H,s), 4.40 (2H, q, J = 7.2 Hz), 3.75 (3H, s), 3.36 (2H, s), 2.19 (6H, s), 1.41 (3H, t, J = 7.2 Hz). |

| Example | Chemical Structure | Instrumental analysis data |
|---|---|---|
| 38 | 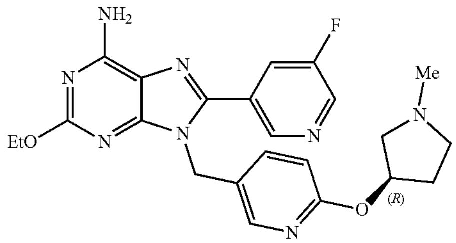 | LC-MS [M + H]⁺/Rt (min): 465.3/0.545 (Method D); ¹H-NMR (CDCl₃) δ: 8.63 (1H, br s), 8.59 (1H, br s), 7.86 (1H, s), 7.65 (1H, dd, J = 1.5, 8.9 Hz), 7.35 (1H, d, J = 8.5 Hz), 6.65 (1H, d, J = 8.5 Hz), 5.55 (2H, br s), 5.37-5.34 (3H, m), 4.41 (2H, q, J = 7.0 Hz), 2.87-2.78 (2H, m), 2.70-2.67 (1H, m), 2.37-2.29 (5H, m), 1.95-1.90 (1H, m), 1.43 (3H, t, J = 7.0 Hz). |
| 39 | 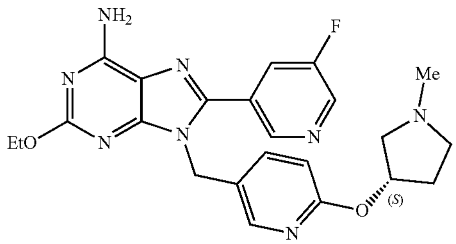 | LC-MS [M + H]⁺/Rt (min): 465.3/0.514 (Method D); ¹H-NMR (CDCl₃) δ: 8.68 (1H, br s), 8.59 (1H, d, J = 2.4 Hz), 7.86 (1H, s), 7.66 (1H, d, J = 9.2 Hz), 7.34 (1H, d, J = 8.5 Hz), 6.66 (1H, d, J = 8.5 Hz), 5.52 (2H, s), 5.37-5.34 (3H, m), 4.41 (2H, q, J = 7.1 Hz), 2.87-2.78 (2H, m), 2.71-2.67 (1H, m), 2.37-2.32 (5H, m), 1.92 (1H, br s), 1.43 (3H, t, J = 7.3 Hz). |
| 40 | 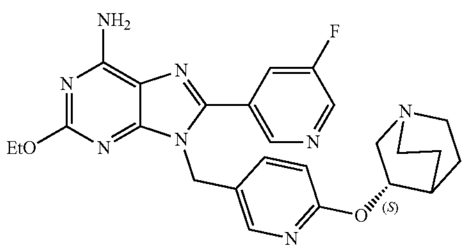 | LC-MS [M + H]⁺/Rt (min): 491.4/0.661 (Method C); ¹H-NMR (CDCl₃) δ: 8.68 (1H, br s), 8.59 (1H, d, J = 2.4 Hz), 7.86 (1H, d, J = 1.8 Hz), 7.68-7.65 (1H, m), 7.36 (1H, dd, J = 2.4, 8.5 Hz), 6.64 (1H, d, J = 8.5 Hz), 5.55 (2H, s), 5.35 (2H, s), 4.97-4.94 (1H, m), 4.42 (2H, q, J = 7.1 Hz), 3.34-3.27 (1H, m), 2.94-2.71 (5H, m), 2.13-2.09 (1H, m), 1.97-1.88 (1H, m), 1.74-1.66 (1H, m), 1.63-1.54 (1H, m), 1.44-1.34 (4H, m). |
| 41 | 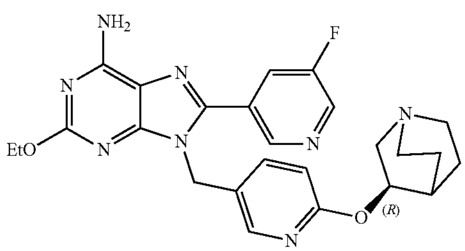 | LC-MS [M + H]⁺/Rt (min): 491.4/0.652 (Method C); ¹H-NMR (CDCl₃) δ: 8.68 (1H, br s), 8.59 (1H, d, J = 2.4 Hz), 7.86 (1H, d, J = 1.8 Hz), 7.68-7.65 (1H, m), 7.36 (1H, dd, J = 2.4, 8.5 Hz), 6.64 (1H, d, J = 8.5 Hz), 5.54 (2H, s), 5.35 (2H, s), 4.97-4.93 (1H, m), 4.42 (2H, q, J = 7.1 Hz), 3.34-3.27 (1H, m), 2.98-2.70 (5H, m), 2.12-2.09 (1H, m), 1.97-1.88 (1H, m), 1.74-1.65 (1H, m), 1.63-1.58 (1H, m), 1.44-1.34 (4H, m). |
| 42 | 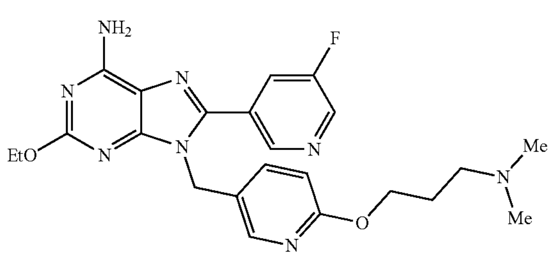 [SMILES: CCOc1nc(N)c2nc(-c3cncc(F)c3)n(Cc3ccc(OCCCN(C)C)nc3)c2n1] | LC-MS: [M + H]⁺/Rt (min): 467.0/0.465 (Method C); ¹H-NMR (CDCl₃) δ: 8.68 (1H, s), 8.59 (1H, d, J = 2.4 Hz), 7.88 (1H, s), 7.67-7.65 (1H, m), 7.37-7.34 (1H, m), 6.63 (1H, d, J = 8.5 Hz), 5.54 (2H, s), 5.35 (2H, s), 4.42 (2H, q, J = 7.1 Hz), 4.28 (2H, t, J = 6.7 Hz), 2.40 (2H, t, J = 7.3 Hz), 2.23 (6H, s), 1.94-1.87 (2H, m), 1.43 (3H, t, J = 7.6 Hz). |

-continued

| Example | Chemical Structure | Instrumental analysis data |
|---|---|---|
| 43 | 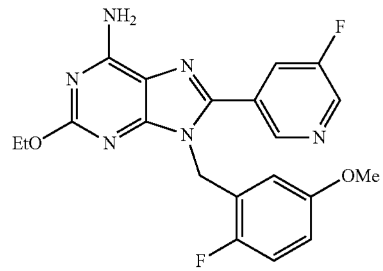 [SMILES: CCOc1nc(N)c2nc(-c3cncc(F)c3)n(Cc3cc(OC)ccc3F)c2n1] | LC-MS [M + H]$^+$/Rt (min): 413.0/0.787 (Method C); $^1$H-NMR (400 MHz, CDCl$_3$) δ: 8.64-8.61 (1H, m), 8.54 (1H, d, J = 2.4 Hz), 7.66-7.59 (1H, m), 6.96 (1H, dd, J = 9.2, 9.2 Hz), 6.77-6.70 (1H, m), 6.50 (1H, dd, J = 5.5, 3.1 Hz), 5.61 (2H, s), 5.42 (2H, s), 4.38 (2H, q, J = 7.1 Hz), 3.64 (3H, s), 1.39 (3H, t, J = 7.1 Hz). |
| 44 | 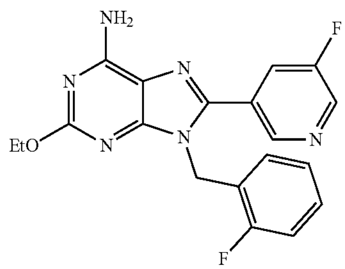 [SMILES: CCOc1nc(N)c2nc(-c3cncc(F)c3)n(Cc3ccccc3F)c2n1] | LC-MS [M + H]$^+$/Rt (min): 383.0/0.785 (Method C); $^1$H-NMR (CDCl$_3$) δ: 8.63-8.59 (1H, m), 8.54 (1H, d, J = 3.1 Hz), 7.64-7.59 (1H, m), 7.06-6.98 (2H, m), 6.98-6.93 (1H, m), 5.63 (2H, s), 5.47 (2H, s), 4.37 (2H, q, J = 7.1 Hz), 1.38 (3H, t, J = 7.1 Hz). |
| 45 | 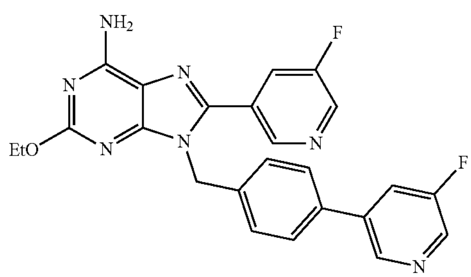 [SMILES: CCOc1nc(N)c2nc(-c3cncc(F)c3)n(Cc3ccc(-c4cncc(F)c4)cc3)c2n1] | LC-MS [M + H]$^+$/Rt (min): 460.4/0.805 (method C); $^1$H-NMR (CDCl$_3$) δ: 8.68-8.65 (1H, m), 8.64-8.61 (1H, m), 8.56 (1H, d, J = 2.4 Hz), 8.46 (1H, d, J = 2.4 Hz), 7.70-7.66 (1H, m), 7.57-7.50 (3H, m), 7.22 (2H, d, J = 8.5 Hz), 5.64 (2H, s), 5.50 (2H, s), 4.41 (2H, q, J = 7.3 Hz), 1.42 (3H, t, J = 7.3 Hz). |
| 46 | 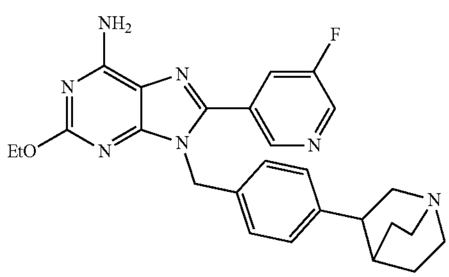 [SMILES: CCOc1nc(N)c2nc(-c3cncc(F)c3)n(Cc3ccc(C4CN5CCC4CC5)cc3)c2n1] | LC-MS[M + H]$^+$/Rt (min): 474.5/0.519 (Method C); $^1$H-NMR (400 MHz, (CDCl$_3$) δ: 8.68-8.65 (1H, m), 8.56 (1H, d, J = 3.1 Hz), 7.67-7.60 (1H, m), 7.21 (2H, d, J = 7.9 Hz), 7.08 (2H, d, J = 7.9 Hz), 5.64 (2H, s), 5.43 (2H, s), 4.42 (2H, q, J = 7.0 Hz), 3.40-3.31 (1H, m), 3.13-3.05 (1H, m), 3.05-2.84 (5H, m), 1.95-1.91 (1H, m), 1.81-1.75 (2H, m), 1.69-1.58 (1H, m), 1.43 (3H, t, J = 7.0 Hz), 1.41-1.35 (1H, m). |

Example 47

2-Ethoxy-8-(5-fluoropyridin-3-yl)-9-{4-[2-(pyrrolidin-1-yl)ethoxy]benzyl}-9H-purine-6-amine

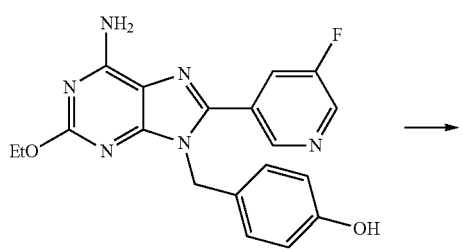

→

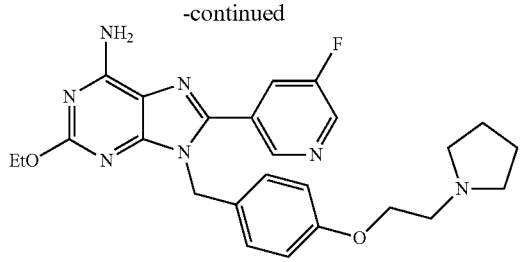

To a solution of the compound of Example 208 (44.0 mg) in N,N-dimethylformamide (2.5 mL) were added 1-(2-chloroethyl)pyrrolidine hydrochloride (35.8 mg), potassium carbonate (80.0 mg), and potassium iodide (11.5 mg), and the mixture was stirred at room temperature for 2 days. To the reaction mixture was added water, and the mixture was extracted with chloroform/methanol. The organic layer was dried over sodium sulfate, filtrated, and then concentrated in vacuo. The residue was purified by silica gel column chromatography (chloroform/methanol) to give the title compound (5.4 mg).

LC-MS [M+H]⁺/Rt (min): 478.51/0.574 (Method C); ¹H-NMR (400 MHz, CDCl₃) δ: 8.69-8.67 (1H, m), 8.56 (1H, d, J=3.1 Hz), 7.64-7.61 (1H, m), 7.01 (2H, d, J=9.2 Hz), 6.83 (2H, d, J=9.2 Hz), 5.63 (2H, s), 5.37 (2H, s), 4.42 (2H, q, J=7.3 Hz), 4.07 (2H, t, J=6.1 Hz), 2.89 (2H, t, J=6.1 Hz), 2.64-2.61 (4H, m), 1.83-1.80 (4H, m), 1.43 (3H, t, J=7.3 Hz).

Examples 48-56

According to the method of Example 47, Examples 48-56 were prepared by using the corresponding material compounds.

| Example | Chemical Structure | Instrumental analysis data |
|---|---|---|
| 48 | 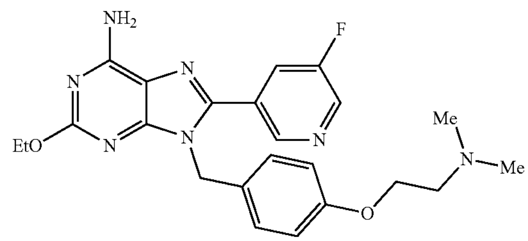 [SMILES: CCOc1nc(N)c2nc(-c3cncc(F)c3)n(Cc3ccc(OCCN(C)C)cc3)c2n1] | ¹H-NMR (400 MHz, CDCl₃) δ: 8.72-8.63 (1H, m), 8.56 (1H, d, J = 2.4 Hz), 7.71-7.53 (1H, m), 7.01 (2H, d, J = 9.2 Hz), 6.83 (2H, d, J = 9.2 Hz), 5.66 (2H, s), 5.37 (2H, s), 4.42 (2H, q, J = 7.1 Hz), 4.02 (2H, t, J = 5.8 Hz), 2.71 (2H, t, J = 5.8 Hz), 2.33 (6H, s), 1.43 (3H, t, J = 7.1 Hz). |
| 49 | 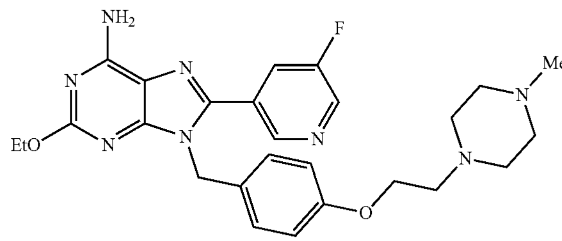 [SMILES: CCOc1nc(N)c2nc(-c3cncc(F)c3)n(Cc3ccc(OCCN4CCN(C)CC4)cc3)c2n1] | ¹H-NMR (400 MHz, CDCl₃) δ: 8.68-8.66 (1H, m), 8.56 (1H, d, J = 2.4 Hz), 7.67-7.60 (1H, m), 7.01 (2H, d, J = 8.5 Hz), 6.81 (2H, d, J = 8.5 Hz), 5.63 (2H, s), 5.36 (2H, s), 4.42 (2H, q, J = 6.9 Hz), 4.06 (2H, t, J = 5.8 Hz), 2.80 (2H, t, J = 5.8 Hz), 2.74-2.34 (8H, m), 2.30 (3H, s), 1.43 (3H, t, J = 6.9 Hz). |
| 50 | 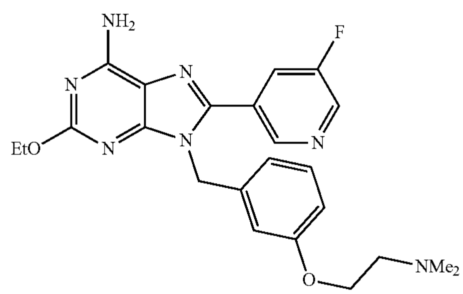 [SMILES: CCOc1nc(N)c2nc(-c3cncc(F)c3)n(Cc3cccc(OCCN(C)C)c3)c2n1] | ¹H-NMR (400 MHz, CDCl₃) δ: 8.69-8.65 (1H, m), 8.56-8.50 (1H, m), 7.63 (1H, d, J = 9.2 Hz), 7.22 (1H, dd, J = 7.9, 8.0 Hz), 6.82 (1H, d, J = 7.9 Hz), 6.68-6.62 (2H, m), 5.64 (2H, s), 5.40 (2H, s), 4.41 (2H, q, J = 7.3 Hz), 3.98 (2H, t, J = 5.8 Hz), 2.68 (2H, t, J = 5.8 Hz), 2.31 (6H, s), 1.42 (3H, t, J = 7.3 Hz). |
| 51 | 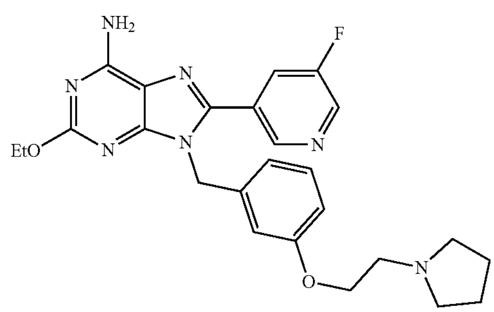 [SMILES: CCOc1nc(N)c2nc(-c3cncc(F)c3)n(Cc3cccc(OCCN4CCCC4)c3)c2n1] | ¹H-NMR (400 MHz, CDCl₃) δ: 8.67 (1H, s), 8.54 (1H, d, J = 2.4 Hz), 7.65-7.60 (1H, m), 7.21 (1H, dd, J = 8.2, 8.0 Hz), 6.82 (1H, d, J = 9.2 Hz), 6.68-6.62 (2H, m), 5.77 (2H, s), 5.39 (2H, s), 4.40 (2H, q, J = 7.3 Hz), 4.03 (2H, t, J = 5.8 Hz), 2.88 (2H, t, J = 5.8 Hz), 2.68-2.58 (4H, m), 1.87-1.77 (4H, m), 1.41 (3H, t, J = 7.3 Hz). |
| 52 | 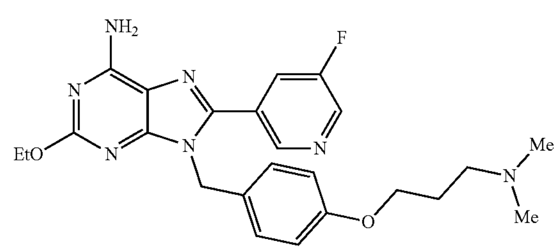 [SMILES: CCOc1nc(N)c2nc(-c3cncc(F)c3)n(Cc3ccc(OCCCN(C)C)cc3)c2n1] | ¹H-NMR (400 MHz, CDCl₃) δ: 8.70-8.65 (1H, m), 8.55 (1H, d, J = 3.1 Hz), 7.65-7.59 (1H, m), 7.00 (2H, d, J = 8.5 Hz), 6.80 (2H, d, J = 8.5 Hz), 5.75 (2H, s), 5.36 (2H, s), 4.42 (3H, q, J = 7.0 Hz), 3.97 (2H, t, J = 6.8 Hz), 2.44 (2H, t, J = 6.8 Hz), 2.25 (6H, s), 1.97-1.90 (2H, m), 1.43 (3H, t, J = 7.0 Hz). |

-continued

| Example | Chemical Structure | Instrumental analysis data |
|---|---|---|
| 53 | 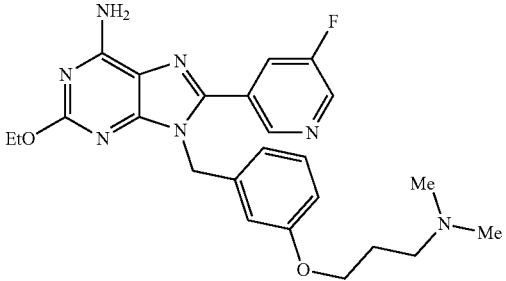 [SMILES: CCOc1nc(N)c2nc(-c3cncc(F)c3)n(Cc3cccc(OCCCN(C)C)c3)c2n1] | $^1$H-NMR (400 MHz, CDCl$_3$) δ: 8.69-8.65 (1H, m), 8.56-8.51 (1H, m), 7.63 (1H, d, J = 8.4 Hz), 7.20 (1H, dd, J = 6.8, 8.4 Hz), 6.80 (1H, d, J = 7.9 Hz), 6.66-6.61 (2H, m), 5.78 (2H, s), 5.39 (2H, s), 4.41 (2H, q, J = 7.3 Hz), 3.93 (2H, t, J = 6.4 Hz), 2.46 (2H, t, J = 7.3 Hz), 2.28 (6H, s), 1.99-1.88 (2H, m), 1.42 (3H, t, J = 7.3 Hz). |
| 54 | 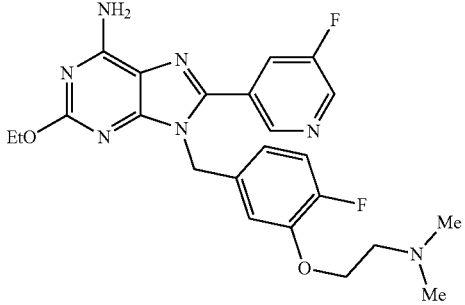 [SMILES: CCOc1nc(N)c2nc(-c3cncc(F)c3)n(Cc3ccc(F)c(OCCN(C)C)c3)c2n1] | $^1$H-NMR (400 MHz, CDCl$_3$) δ: 8.69-8.65 (1H, m), 8.57 (1H, d, J = 2.4 Hz), 7.68-7.62 (1H, m), 6.99 (1H, dd, J = 8.2, 10.7 Hz), 6.80 (1H, dd, J = 2.1, 7.6 Hz), 6.64-6.58 (1H, m), 5.60 (2H, s), 5.37 (2H, s), 4.42 (2H, q, J = 7.1 Hz), 4.02 (2H, t, J = 5.8 Hz), 2.73 (2H, t, J = 5.8 Hz), 2.33 (6H, s), 1.44 (4H, t, J = 7.1 Hz). |
| 55 | 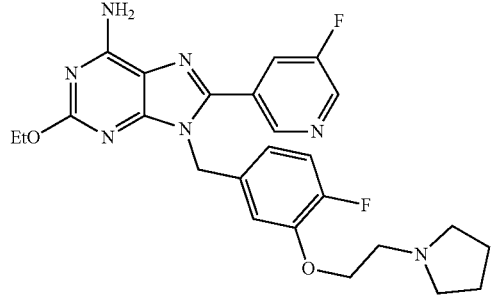 [SMILES: CCOc1nc(N)c2nc(-c3cncc(F)c3)n(Cc3ccc(F)c(OCCN4CCCC4)c3)c2n1] | $^1$H-NMR (400 MHz, CDCl$_3$) δ: 8.69-8.64 (1H, m), 8.57 (1H, d, J = 2.4 Hz), 7.67-7.61 (1H, m), 6.99 (1H, dd, J = 8.5, 11.0 Hz), 6.79 (1H, dd, J = 2.4, 7.6 Hz), 6.63-6.57 (1H, m), 5.71 (2H, s), 5.37 (2H, s), 4.42 (2H, q, J = 7.1 Hz), 4.05 (2H, t, J = 6.1 Hz), 2.89 (2H, t, J = 6.1 Hz), 2.66-2.53 (4H, m), 1.85-1.76 (4H, m), 1.43 (3H, t, J = 7.1 Hz). |
| 56 | 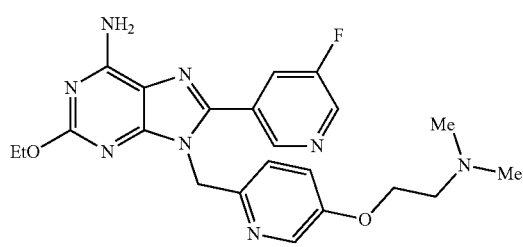 [SMILES: CCOc1nc(N)c2nc(-c3cncc(F)c3)n(Cc3ccc(OCCN(C)C)cn3)c2n1] | LC-MS [M + H]$^+$/Rt (min): 453.4/0.602 (Method C); $^1$H-NMR (CDCl$_3$) δ: 8.90 (1H, br s), 8.54 (1H, d, J = 3.1 Hz), 8.26 (1H, d, J = 2.4 Hz), 8.10-8.06 (1H, m), 7.27-7.25 (1H, m), 7.17 (1H, dd, J = 3.1, 8.5 Hz), 5.57 (2H, s), 5.43 (2H, s), 4.38 (2H, q, J = 7.1 Hz), 4.08 (2H, t, J = 5.6 Hz), 2.72 (2H, t, J = 5.6 Hz), 2.33 (6H, s), 1.40 (3H, t, J = 7.1 Hz). |

Example 57

9-({2-[2-(Dimethylamino)ethoxy]pyridin-4-yl)methyl}-2-ethoxy-8-(5-fluoropyridin-3-yl)-9H-purine-6-amine

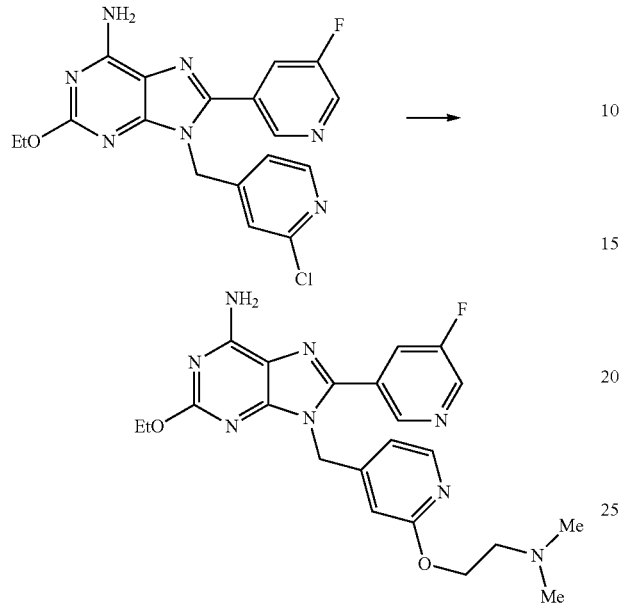

To a solution of N,N-dimethylethanolamine (111 mg) in 1,4-dioxane (1.5 mL) was added sodium hydride (27.3 mg), and the mixture was stirred at room temperature for 10 minutes. Then, the compound of Example 191 (50.0 mg) was added thereto. The reaction solution was heated to 80° C. and stirred with heating for 6 hours. To the reaction mixture was added 35% hydrochloric acid (54 μl), and the mixture was extracted with chloroform/methanol solution. The organic layer was dried over sodium sulfate, filtrated, and then concentrated in vacuo. The residue was purified by silica gel column chromatography (chloroform/methanol) to give the title compound (11.8 mg).

$^1$H-NMR (400 MHz, CDCl$_3$) δ: 8.64-8.60 (1H, m), 8.55 (1H, d, J=2.4 Hz), 8.10 (1H, d, J=4.9 Hz), 7.70-7.64 (1H, m), 6.64 (1H, d, J=4.9 Hz), 6.44-6.40 (1H, m), 5.72 (2H, s), 5.37 (2H, s), 4.38 (2H, d, J=7.0 Hz), 4.36 (2H, t, J=5.5 Hz), 2.67 (2H, t, J=5.5 Hz), 2.30 (6H, s), 1.40 (3H, t, J=7.0 Hz).

Examples 58-63

According to the method of Example 57, Examples 58-63 were prepared by using the corresponding material compounds.

| Example | Chemical Structure | Instrumental analysis data |
|---|---|---|
| 58 | 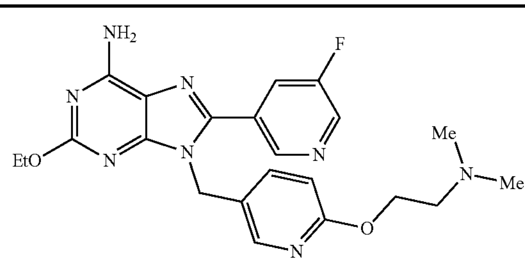 | $^1$H-NMR (400 MHz, CDCl$_3$) δ: 8.71-8.66 (1H, m), 8.60 (1H, d, J = 3.1 Hz), 7.89 (1H, s), 7.69-7.63 (1H, m), 7.39-7.34 (1H, m), 6.71 (1H, dd, J = 3.1, 8.5 Hz), 5.67 (2H, s), 5.36 (2H, s), 4.43 (2H, q, J = 7.1 Hz), 4.36 (2H, t, J = 5.5 Hz), 2.69 (2H, t, J = 5.5 Hz), 2.31 (6H, s), 1.43 (3H, t, J = 7.1 Hz). |
| 59 | 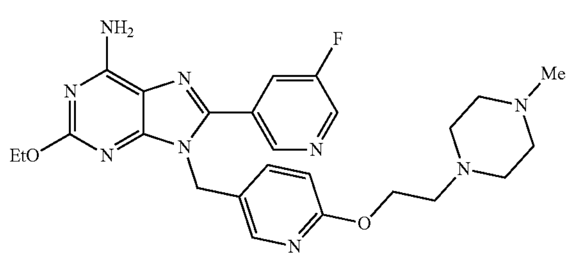 [SMILES: CCOc1nc(N)c2nc(-c3cncc(F)c3)n(Cc3ccc(OCCN4CCN(C)CC4)nc3)c2n1] | $^1$H-NMR (400 MHz, CDCl$_3$) δ: 8.69-8.67 (1H, m), 8.59 (1H, d, J = 2.4 Hz), 7.89 (1H, d, J = 2.4 Hz), 7.69-7.63 (1H, m), 7.36 (1H, dd, J = 2.4, 8.5 Hz), 6.67 (1H, d, J = 8.5 Hz), 5.75 (2H, s) 5.35 (2H, s), 4.43 (2H, t, J = 5.8 Hz), 4.40 (2H, q, J = 7.0 Hz), 2.77 (2H, t, J = 5.8 Hz), 2.71-2.31 (8H, m), 2.29 (3H, s), 1.43 (3H, t, J = 7.0 Hz). |
| 60 | 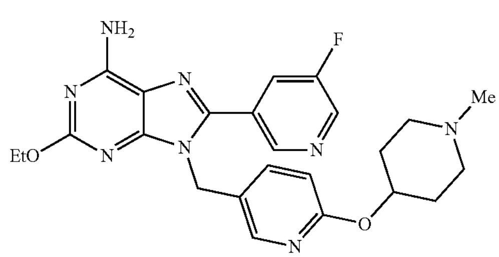 [SMILES: CCOc1nc(N)c2nc(-c3cncc(F)c3)n(Cc3ccc(OC4CCN(C)CC4)nc3)c2n1] | $^1$H-NMR (400 MHz, CDCl$_3$) δ: 8.71-8.67 (1H, m), 8.60 (1H, d, J = 2.4 Hz), 7.87 (1H, d, J = 2.4 Hz), 7.70-7.64 (1H, m), 7.37 (2H, dd, J = 2.4, 8.5 Hz), 6.63 (1H, d, J = 8.5 Hz), 5.69 (2H, s), 5.35 (2H, s), 5.04-4.97 (1H, m), 4.42 (2H, q, J = 7.1 Hz), 2.77-2.64 (2H, m), 2.31 (3H, s), 2.33-2.24 (2H, m), 2.09-1.94 (2H, m), 1.85-1.73 (2H, m), 1.44 (3H, t, J = 7.1 |

-continued

| Example | Chemical Structure | Instrumental analysis data |
|---|---|---|
| 61 | 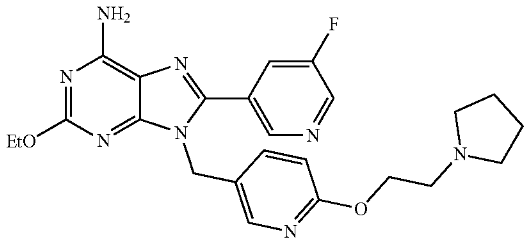 [SMILES: CCOc1nc(N)c2nc(-c3cncc(F)c3)n(Cc3ccc(OCCN4CCCC4)nc3)c2n1] | Hz). <br> $^1$H-NMR (400 MHz, CDCl$_3$) δ: 8.70-8.67 (1H, m), 8.60 (1H, d, J = 2.4 Hz), 7.89 (1H, d, J = 2.1 Hz), 7.69-7.63 (1H, m), 7.37 (1H, dd, J = 2.1, 8.5 Hz), 6.70 (1H, d, J = 8.5 Hz), 5.72 (2H, s), 5.36 (2H, s), 4.43 (2H, t, J = 5.8 Hz), 4.40 (2H, q, J = 7.0 Hz), 2.86 (2H, t, J = 5.8 Hz), 2.63-2.55 (4H, m), 1.82-1.76 (4H, m), 1.44 (3H, t, J = 7.0 Hz). |
| 62 | 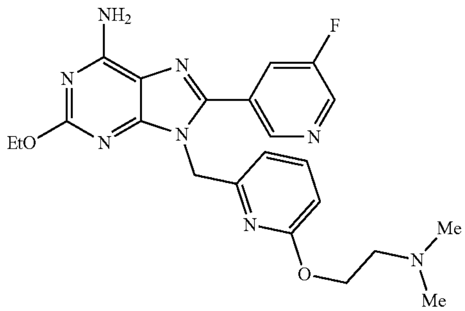 [SMILES: CCOc1nc(N)c2nc(-c3cncc(F)c3)n(Cc3cccc(OCCN(C)C)n3)c2n1] | $^1$H-NMR (400 MHz, CDCl$_3$) δ: 8.98-8.92 (1H, m), 8.58-8.50 (1H, m), 8.18-8.09 (1H, m), 7.53 (1H, d, J = 13.4 Hz), 6.91 (1H, d, J = 6.1 Hz), 6.73-6.65 (1H, m), 5.74 (2H, s), 5.40 (2H, s), 4.38 (2H, q, J = 6.7 Hz), 4.24 (2H, t, J = 5.8 Hz), 2.60 (2H, t, J = 5.8 Hz), 2.27 (6H, s), 1.40 (3H, t, J = 6.7 Hz). |
| 63 | 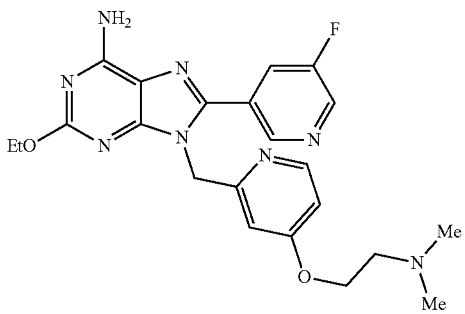 [SMILES: CCOc1nc(N)c2nc(-c3cncc(F)c3)n(Cc3cc(OCCN(C)C)ccn3)c2n1] | $^1$H-NMR (400 MHz, CDCl$_3$) δ: 8.87-8.81 (1H, m), 8.54 (1H, d, J = 1.2 Hz), 8.39 (1H, d, J = 5.5 Hz), 8.01 (1H, dd, J = 1.2, 9.5 Hz), 6.81-6.71 (2H, m), 5.76 (2H, s), 5.45 (2H, s), 4.39 (2H, q, J = 7.1 Hz), 4.05 (2H, t, J = 5.2 Hz), 2.70 (2H, t, J = 5.2 Hz), 2.31 (6H, s), 1.40 (3H, t, J = 7.1 Hz). |

Example 64

N-(5-{[6-Amino-2-ethoxy-8-(5-fluoropyridin-3-yl)-9H-purin-9-yl]methyl}pyridin-2-yl)-N,N',N'-trimethylethane-1,2-diamine

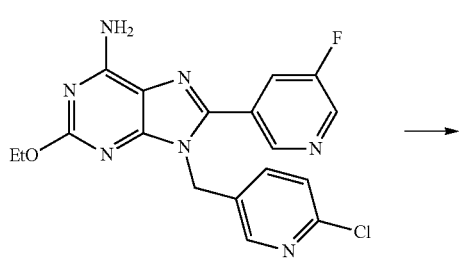

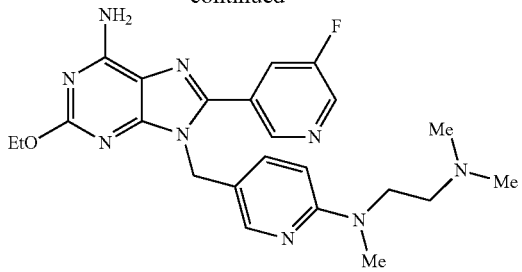

A suspension of the compound of Example 189 (70 mg) and N,N,N'-trimethylethylenediamine (683 μL) was stirred at 120° C. for 6 hours. The reaction mixture was cooled to room temperature, and then water was added thereto. The mixture was extracted with ethyl acetate, and the organic layer was concentrated in vacuo. The residue was purified by silica gel column chromatography (chloroform/methanol) to give the title compound (34 mg).

LC-MS [M+H]$^+$/Rt (min): 466.6/0.559 (Method B); $^1$H-NMR (CDCl$_3$) δ: 8.71 (1H, s), 8.58 (1H, d, J=3.1 Hz), 7.88 (1H, d, J=2.4 Hz), 7.69-7.66 (1H, m), 7.22 (1H, dd, J=2.4, 8.5 Hz), 6.37 (1H, d, J=8.5 Hz), 5.56 (2H, s), 5.28

(2H, s), 4.43 (2H, q, J=7.1 Hz), 3.61 (2H, t, J=7.0 Hz), 3.01 (3H, s), 2.45 (2H, t, J=7.0 Hz), 2.27 (6H, s), 1.44 (3H, t, J=7.1 Hz).

Example 65

According to the method of Example 64, Example 65 was prepared by using the corresponding material compound.

| Example | Chemical Structure | Instrumental analysis data |
|---|---|---|
| 65 | 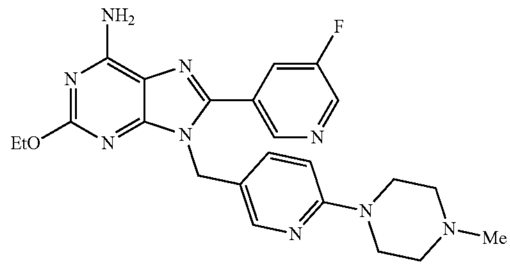 [SMILES: CCOc1nc(N)c2nc(-c3cncc(F)c3)n(Cc3ccc(N4CCN(C)CC4)nc3)c2n1] | LC-MS [M + H]⁺/Rt (min): 464.5/0.543 (Method B); ¹H-NMR (CDCl₃) δ: 8.70 (1H, s), 8.59-8.58 (1H, m), 7.94 (1H, s), 7.68 (1H, d, J = 8.5 Hz), 7.27-7.26 (1H, m), 6.55-6.52 (1H, m), 5.55 (2H, s), 5.30 (2H, s), 4.46-4.39 (2H, m), 3.53 (4H, br s), 2.49 (4H, br s), 2.33 (3H, br s), 1.46-1.41 (3H, m). |

Example 66

9-{4-[(3S)-1-Azabicyclo[2.2.2]oct-3-yloxy]benzyl}-2-ethoxy-8-(5-fluoropyridin-3-yl)-9H-purine-6-amine

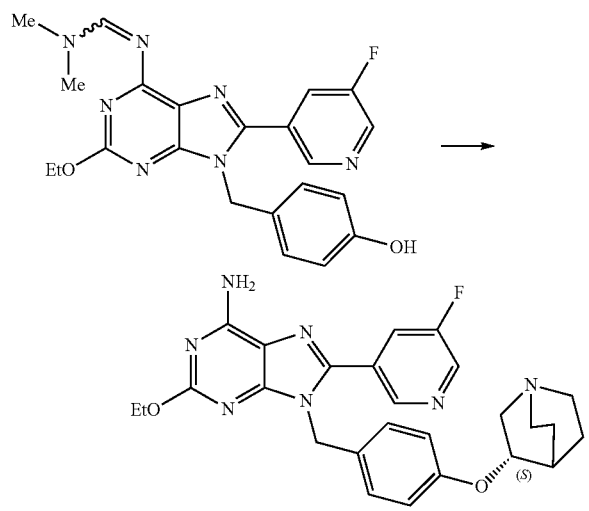

To an ice-cooled solution of the compound of Reference example 121 (602 mg) in tetrahydrofuran (13.8 mL) were added (R)-3-quinuclidinol (703 mg), triphenylphosphine (1.45 g), and diisopropyl azodicarboxylate (1.09 mL), and the mixture was stirred at room temperature for 3 days. To the reaction mixture was added water, and the mixture was extracted with chloroform/methanol. The organic layer was washed with brine, dried over sodium sulfate, filtrated, and then concentrated in vacuo. To a solution of the obtained residue methanol (13.8 mL) was added 28% ammonia (13.8 mL), and the mixture was stirred at 60° C. for 2.5 hours. To the reaction mixture was added water, and the mixture was extracted with chloroform/methanol. The organic layer was washed with brine, dried over sodium sulfate, filtrated, and then concentrated in vacuo. The residue was purified by silica gel column chromatography (chloroform/methanol) to give the title compound (248 mg).

LC-MS [M+H]⁺/Rt (min): 490.5/0.659 (Method B); ¹H-NMR (CDCl₃) δ: 8.67 (1H, br s), 8.55 (1H, d, J=2.7 Hz), 7.65-7.61 (1H, m), 7.00 (2H, d, J=8.4 Hz), 6.75 (2H, d, J=8.4 Hz), 5.57 (2H, s), 5.35 (2H, s), 4.41 (2H, q, J=6.8 Hz), 4.32-4.30 (1H, m), 3.24 (1H, dd, J=8.0, 13.9 Hz), 3.00-2.75 (5H, m), 2.10 (1H, br s), 1.99-1.92 (1H, m), 1.76-1.49 (2H, m), 1.46-1.33 (4H, m).

Example 67

According to the method of Example 66, Example 67 was prepared by using the corresponding material compound.

| Example | Chemical Structure | Instrumental analysis data |
|---|---|---|
| 67 | 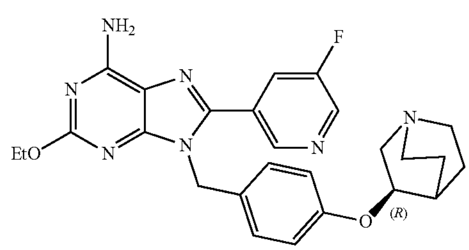 | LC-MS [M + H]⁺/Rt (min): 490.3/0.641 (Method B); ¹H-NMR (CDCl₃) δ: 8.66 (1H, br s), 8.55 (1H, d, J = 3.1 Hz), 7.65-7.61 (1H, m), 7.01 (2H, d, J = 8.5 Hz), 6.75 (2H, d, J = 8.5 Hz), 5.57 (2H, br s), 5.35 (2H, s), 4.44-4.35 (3H, m), 3.32-3.27 (1H, m), 3.06-2.84 (5H, m), 2.17 (1H, br s), 2.04-2.01 (1H, m), 1.81-1.59 (2H, m), 1.48-1.40 (4H, m). |

Example 68

2-Ethoxy-8-(5-fluoropyridin-3-yl)-9-[4-(4-methyl-piperazin-1-yl)benzyl]-9H-purine-6-amine

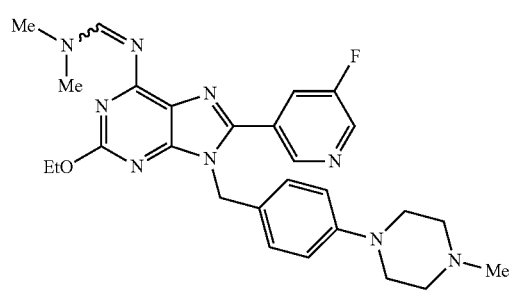

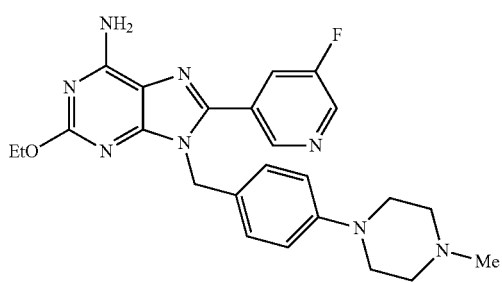

To a solution of the compound of Reference example 123 (11.3 mg) in methanol was added 28% ammonia (0.8 mL) at room temperature. The reaction mixture was stirred at 60° C. for 4 hours, and then extracted with chloroform/methanol. The organic layer was dried over sodium sulfate, filtrated, and then concentrated in vacuo. The residue was purified by silica gel column chromatography (chloroform/methanol) to give the title compound (7.1 mg).

LC-MS [M+H]$^+$/Rt (min): 463.4/0.495 (Method C); $^1$H-NMR (400 MHz, CDCl$_3$) δ: 8.72-8.67 (1H, m), 8.56 (1H, d, J=3.1 Hz), 7.68-7.62 (1H, m), 7.01 (2H, d, J=8.5 Hz), 6.83 (2H, d, J=8.5 Hz), 5.62 (2H, s), 5.35 (2H, s), 4.43 (2H, q, J=7.1 Hz), 3.32-3.19 (4H, m), 2.77-2.53 (4H, m), 2.40 (3H, s), 1.44 (3H, t, J=7.1 Hz).

Example 69

9-({6-[(3S)-1-Azabicyclo[2.2.2]oct-3-yloxy]pyridin-3-yl}methyl)-8-(5-fluoropyridin-3-yl)-2-methoxy-6-methyl-9H-purine

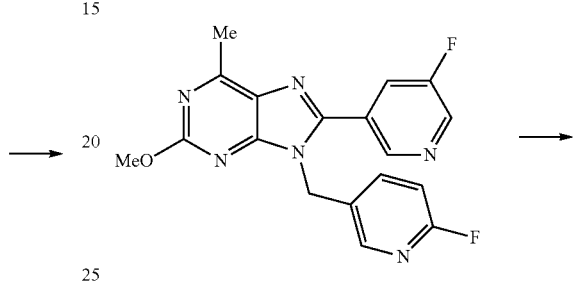

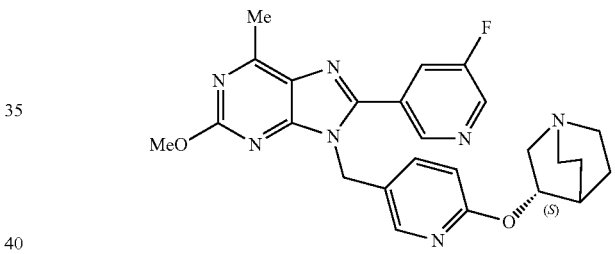

To an ice-cooled solution of (S)-(+)-3-quinuclidinol (135 mg) in tetrahydrofuran (1.0 mL) was added potassium tert-butoxide (119 mg), and the mixture was stirred for 15 minutes. A solution of the compound of Example 204 (150 mg) in tetrahydrofuran (3 mL) was added thereto, and the mixture was stirred in ice bath for 1.5 hours. To the reaction mixture was added water, and the mixture was extracted with ethyl acetate. The organic layer was washed with brine, dried over sodium sulfate, filtrated, and then concentrated in vacuo. The obtained residue was purified by amino silica gel column chromatography (chloroform/methanol), and then purified by silica gel column chromatography (chloroform/methanol) to give the title compound (91 mg).

LC-MS [M+H]$^+$/Rt (min): 476.4/0.557 (Method C); $^1$H-NMR (CDCl$_3$) δ: 8.71 (1H, br s), 8.63 (1H, d, J=2.4 Hz), 7.85 (1H, d, J=2.4 Hz), 7.75-7.72 (1H, m), 7.34 (1H, dd, J=2.4, 8.5 Hz), 6.64 (1H, d, J=8.5 Hz), 5.40 (2H, s), 4.96-4.93 (1H, m), 4.08 (3H, s), 3.33-3.27 (1H, m), 2.97-2.70 (8H, m), 2.11-2.09 (1H, m), 1.96-1.87 (1H, m), 1.74-1.66 (1H, m), 1.62-1.58 (1H, m), 1.42-1.34 (1H, m).

Examples 70-76

According to the method of Example 69, Examples 70-76 were prepared by using the corresponding material compounds.

| Example | Chemical Structure | Instrumental analysis data |
|---|---|---|
| 70 | 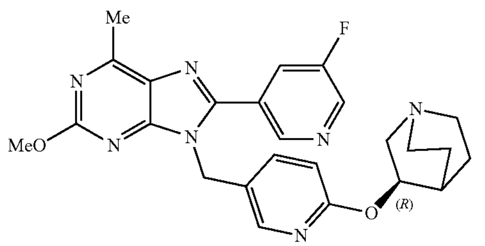 | LC-MS [M + H]⁺/Rt (min): 476.4/0.529 (Method C); ¹H-NMR (CDCl₃) δ: 8.72-8.71 (1H, m), 8.63 (1H, d, J = 2.4 Hz), 7.85 (1H, d, J = 2.4 Hz), 7.75-7.71 (1H, m), 7.34 (1H, dd, J = 8.4, 2.7 Hz), 6.64 (1H, d, J = 8.4 Hz), 5.40 (2H, s), 4.96-4.93 (1H, m), 4.08 (3H, s), 3.33-3.27 (1H, m), 2.97-2.70 (8H, m), 2.11-2.08 (1H, m), 1.96-1.87 (1H, m), 1.70-1.65 (1H, m), 1.62-1.54 (1H, m), 1.41-1.33 (1H, m). |
| 71 | 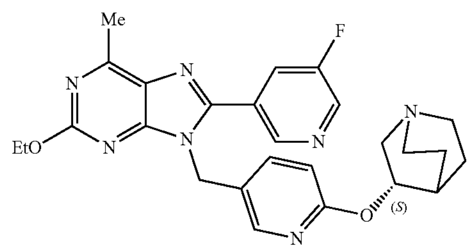 | LC-MS [M + H]⁺/Rt (min): 490.4/0.684 (Method C); ¹H-NMR (CDCl₃) δ: 8.71-8.70 (1H, m), 8.63 (1H, d, J = 2.4 Hz), 7.84 (1H, d, J = 2.4 Hz), 7.74-7.71 (1H, m), 7.33 (1H, dd, J = 8.5, 2.4 Hz), 6.64 (1H, d, J = 8.5 Hz), 5.39 (2H, s), 4.97-4.93 (1H, m), 4.49 (2H, q, J = 7.1 Hz), 3.33-3.27 (1H, m), 2.97-2.71 (8H, m), 2.12-2.09 (1H, m), 1.96-1.88 (1H, m), 1.74-1.66 (1H, m), 1.63-1.55 (1H, m), 1.47 (3H, t, J = 7.1 Hz), 1.42-1.34 (1H, m). |
| 72 | 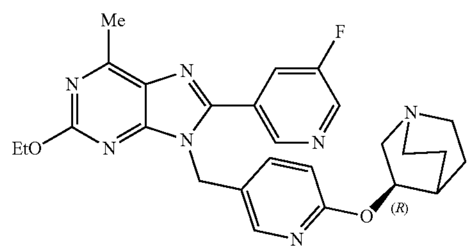 | LC-MS [M + H]⁺/Rt (min): 490.4/0.690 (Method C); ¹H-NMR (CDCl₃) δ: 8.71-8.71 (1H, m), 8.63 (1H, d, J = 3.1 Hz), 7.84 (1H, d, J = 2.4 Hz), 7.75-7.71 (1H, m), 7.33 (1H, dd, J = 2.4, 8.5 Hz), 6.64 (1H, d, J = 8.5 Hz), 5.40 (2H, s), 4.97-4.93 (1H, m), 4.49 (2H, q, J = 7.1 Hz), 3.34-3.28 (1H, m), 2.98-2.71 (8H, m), 2.13-2.09 (1H, m), 1.97-1.88 (1H, m), 1.75-1.55 (2H, m), 1.47 (3H, t, J = 7.0 Hz), 1.43-1.35 (1H, m). |
| 73 | 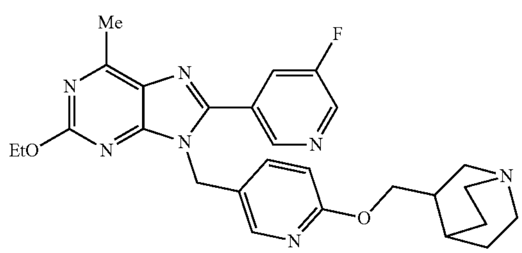 [SMILES: CCOc1nc(C)c2nc(-c3cncc(F)c3)n(Cc3ccc(OCC4CN5CCC4CC5)nc3)c2n1] | LC-MS [M + H]⁺/Rt (min): 504.4/0.0597 (Method D); ¹H-NMR (CDCl₃) δ: 8.71 (1H, br s), 8.63 (1H, d, J = 3.1 Hz), 7.88 (1H, d, J = 1.8 Hz), 7.75-7.72 (1H, m), 7.34 (1H, dd, J = 3.1, 8.5 Hz), 6.63 (1H, d, J = 8.5 Hz), 5.41 (2H, s), 4.50 (2H, q, J = 6.9 Hz), 4.21 (2H, d, J = 7.9 Hz), 3.11-3.05 (1H, m), 2.88-2.79 (7H, m), 2.49-2.44 (1H, m), 2.15-2.07 (1H, m), 1.87-1.85 (1H, m), 1.75-1.53 (3H, m), 1.48 (3H, t, J = 7.0 Hz), 1.44-1.36 (1H, m). |
| 74 | 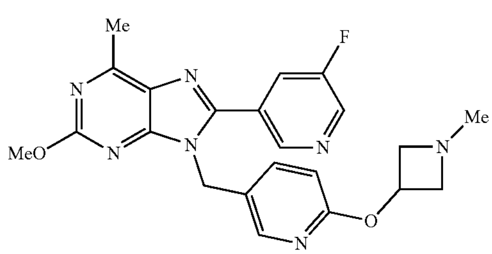 [SMILES: COc1nc(C)c2nc(-c3cncc(F)c3)n(Cc3ccc(OC4CN(C)C4)nc3)c2n1] | LC-MS [M + H]⁺/Rt (min): 450.3/0.554 (Method D); ¹H-NMR (CDCl₃) δ: 8.69 (1H, t, J = 1.5 Hz), 8.62 (1H, d, J = 2.4 Hz), 7.84 (1H, d, J = 2.4 Hz), 7.73-7.70 (1H, m), 7.34 (1H, dd, J = 2.4, 8.5 Hz), 6.65 (1H, d, J = 8.5 Hz), 5.39 (2H, s), 5.17-5.11 (1H, m), 4.49 (2H, q, J = 7.1 Hz), 3.77-3.74 (2H, m), 3.09-3.05 (2H, m), 2.81 (3H, s), 2.38 (3H, s), 1.47 (3H, t, J = 7.1 Hz). |

| Example | Chemical Structure | Instrumental analysis data |
|---|---|---|
| 75 | (structure) | LC-MS [M + H]⁺/Rt (min): 504.2/0.603 (Method C); ¹H-NMR (CDCl₃) δ: 8.71 (1H, br s), 8.63 (1H, d, J = 2.4 Hz), 7.84 (1H, d, J = 2.4 Hz), 7.74-7.71 (1H, m), 7.33 (1H, dd, J = 2.4, 8.5 Hz), 6.64 (1H, d, J = 8.5 Hz), 5.40 (2H, s), 4.97-4.93 (1H, m), 4.39 (2H, t, J = 6.7 Hz), 3.33-3.27 (1H, m), 2.97-2.71 (8H, m), 2.11-2.09 (1H, m), 1.93-1.86 (3H, m), 1.74-1.54 (2H, m), 1.41-1.34 (1H, m), 1.08 (3H, t, J = 7.6 Hz). |
| 76 | (structure) | LC-MS [M + H]⁺/Rt (min): 500.1/0.580 (Method C); ¹H-NMR (CDCl₃) δ: 8.67 (1H, d, J = 1.8 Hz), 8.59 (1H, d, J = 2.0 Hz), 7.84 (1H, d, J = 2.4 Hz), 7.77 (1H, br s), 7.34 (1H, dd, J = 2.4, 8.5 Hz), 6.63 (1H, d, J = 8.5 Hz), 5.36 (2H, s), 4.97-4.93 (1H, m), 4.38 (2H, t, J = 6.7 Hz), 3.34-3.29 (1H, m), 2.94-2.71 (8H, m), 2.41 (3H, s), 2.11-2.10 (1H, m), 1.96-1.84 (3H, m), 1.74-1.55 (2H, m), 1.42-1.35 (1H, m), 1.08 (3H, t, J = 7.6 Hz). |

Example 77

(4-{[6-Amino-2-ethoxy-8-(5-fluoropyridin-3-yl)-9H-purin-9-yl]methyl}phenyl)methanol

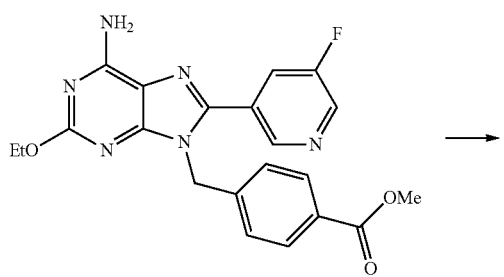

→

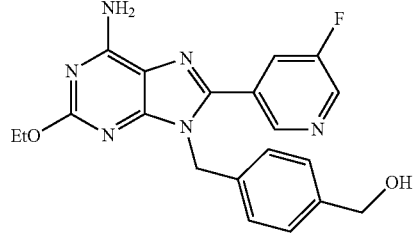

To an ice-cooled solution of the compound of Example 182 (385 mg) in tetrahydrofuran (50 mL) was added diisobutylaluminum hydride (1.02 mol/L hexane solution, 8.2 mL), and the mixture was stirred for 2.5 hours. To the reaction mixture were added ethyl acetate (5 mL) and aqueous saturated potassium sodium tartrate, and the mixture was stirred at room temperature overnight. The mixture was extracted with chloroform. The organic layer was dried over sodium sulfate, filtrated, and then concentrated in vacuo. The residue was purified by silica gel column chromatography (chloroform/methanol) to give the title compound (220 mg).

LC-MS ([M+H]⁺/Rt (min.)): 395.4/0.671 (Method A); ¹H-NMR (400 MHz, DMSO-d₆) δ: 8.70 (1H, dd, J=1.2, 1.8 Hz), 8.66 (1H, d, J=3.1 Hz), 8.01-7.96 (1H, m), 7.46 (2H, brs), 7.19 (2H, d, J=7.9 Hz), 6.94 (2H, d, J=7.9 Hz), 5.45 (2H, s), 5.12 (1H, t, J=5.5 Hz), 4.40 (2H, d, J=5.5 Hz), 4.26 (2H, q, J=6.7 Hz), 1.27 (3H, t, J=6.7 Hz).

Examples 78-79

According to the method of Example 77, Examples 78-79 were prepared by using the corresponding material compounds.

| Example | Chemical Structure | Instrumental analysis data |
|---|---|---|
| 78 | ![structure] | LC-MS [M + H]⁺/Rt (min): 394.4/0.760 (Method A) |
| 79 | ![structure] | LC-MS [M + H]⁺/Rt (min): 422.1/0.892 (Method A) |

Example 80

9-{4-[(Dimethylamino)methyl]benzyl}-2-ethoxy-8-(5-fluoropyridin-3-yl)-9H-purine-6-amine

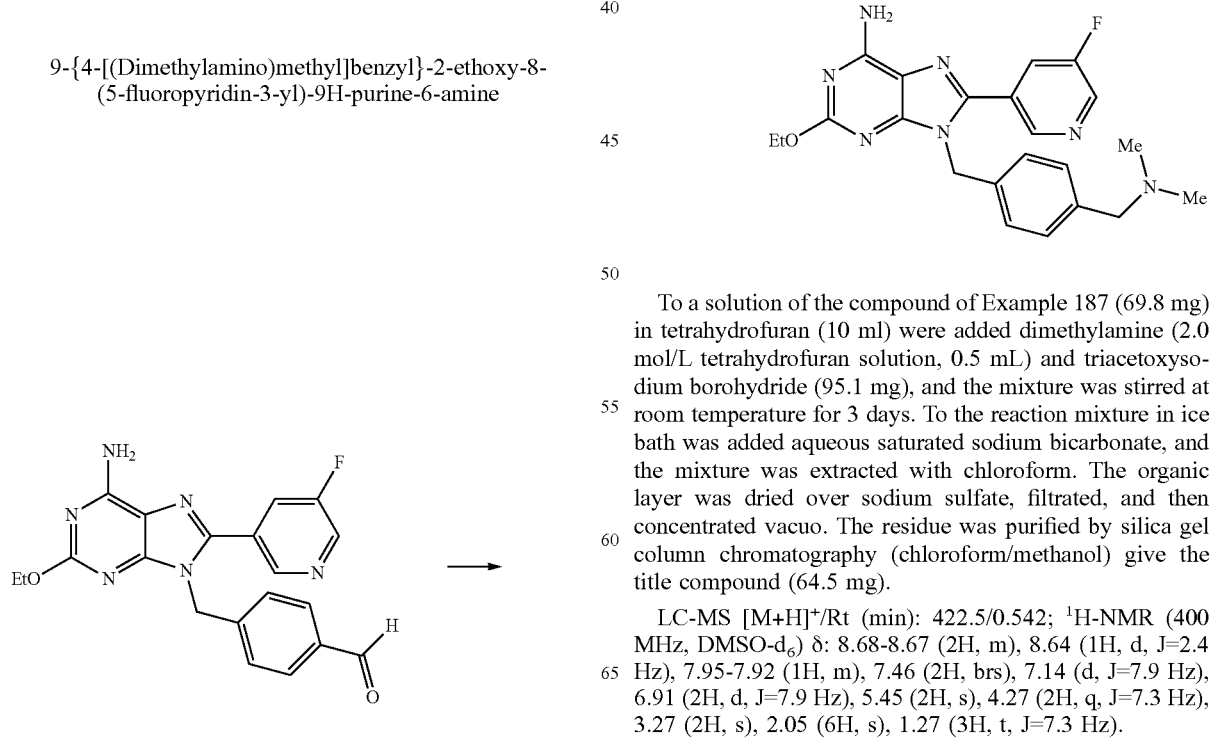

To a solution of the compound of Example 187 (69.8 mg) in tetrahydrofuran (10 ml) were added dimethylamine (2.0 mol/L tetrahydrofuran solution, 0.5 mL) and triacetoxysodium borohydride (95.1 mg), and the mixture was stirred at room temperature for 3 days. To the reaction mixture in ice bath was added aqueous saturated sodium bicarbonate, and the mixture was extracted with chloroform. The organic layer was dried over sodium sulfate, filtrated, and then concentrated vacuo. The residue was purified by silica gel column chromatography (chloroform/methanol) give the title compound (64.5 mg).

LC-MS [M+H]⁺/Rt (min): 422.5/0.542; ¹H-NMR (400 MHz, DMSO-d₆) δ: 8.68-8.67 (2H, m), 8.64 (1H, d, J=2.4 Hz), 7.95-7.92 (1H, m), 7.46 (2H, brs), 7.14 (d, J=7.9 Hz), 6.91 (2H, d, J=7.9 Hz), 5.45 (2H, s), 4.27 (2H, q, J=7.3 Hz), 3.27 (2H, s), 2.05 (6H, s), 1.27 (3H, t, J=7.3 Hz).

Examples 81-122

According to the method of Example 80, Examples 81-122 were prepared by using the corresponding material compounds.

| Example | Chemical Structure | Instrumental analysis data |
| --- | --- | --- |
| 81 | 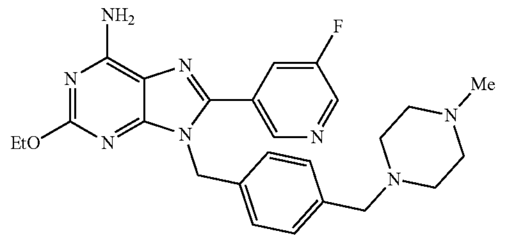 | LC-MS [M + H]+/Rt (min): 477.4/0.539; ¹H-NMR (400 MHz, DMSO-d₆) δ: 8.68-8.67 (1H, m), 8.64 (1H, d, J = 3.0 Hz), 7.95-7.92 (1H, m), 7.46 (2H, brs), 7.15 (2H, d, J = 7.9 Hz), 6.91 (2H, d, J = 7.9 Hz), 5.44 (2H, s), 4.27 (2H, q, J = 7.3 Hz), 3.34 (2H, s), 2.40-2.12 (8H, m), 2.11 (3H, s), 1.27 (3H, t, J = 7.3 Hz). |
| 82 | 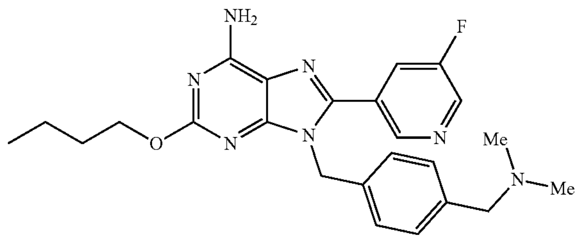 [SMILES: CCCCOc1nc(N)c2nc(-c3cncc(F)c3)n(Cc3ccc(CN(C)C)cc3)c2n1] | LC-MS [M + H]+/Rt (min): 450.2/0.637 (Method A); ¹H-NMR (400 MHz, DMSO-d₆) δ: 8.67 (1H, dd, J = 1.2, 1.8 Hz), 8.64 (1H, d, J = 3.1 Hz), 7.96-7.91 (1H, m), 7.46 (2H, brs), 7.14 (2H, d, J = 7.9 Hz), 6.91 (2H, d, J = 7.9 Hz), 5.45 (2H, s), 4.22 (2H, t, J = 6.4 Hz), 3.27 (2H, s), 2.05 (6H, s), 1.64 (2H, tt, J = 6.4, 7.9 Hz), 1.38 (2H, qt, J = 7.3, 7.9 Hz), 0.90 (3H, t, J = 7.3 Hz). |
| 83 | 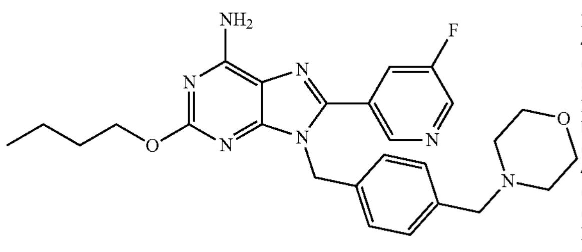 | LC-MS [M + H]+/Rt (min): 492.2/0.647 (Method A); ¹H-NMR (400 MHz, DMSO-d₆) δ: 8.68-8.66 (1H, m), 8.64 (1H, d, J = 3.1 Hz), 7.96-7.91 (1H, m), 7.46 (2H, brs), 7.16 (2H, d, J = 7.9 Hz), 6.92 (2H, d, J = 7.9 Hz), 5.45 (2H, s), 4.22 (2H, t, J = 6.7 Hz), 3.53-3.49 (4H, m), 3.35 (2H, s), 2.26-2.23 (4H, m), 1.64 (2H, tt, J = 6.7, 7.9 Hz), 1.38 (2H, qt, J = 7.3, 7.9 Hz), 0.90 (3H, t, J = 7.3 Hz). |
| 84 | 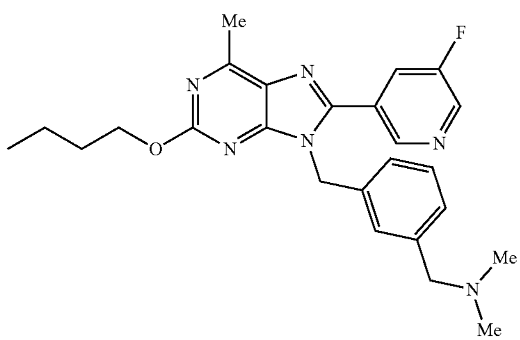 [SMILES: CCCCOc1nc(C)c2nc(-c3cncc(F)c3)n(Cc3cccc(CN(C)C)c3)c2n1] | LC-MS [M + H]+/Rt (min): 450.2/0.648 (Method A); ¹H-NMR (400 MHz, DMSO-d₆) δ: 8.67 (1H, dd, J = 1.2, 1.8 Hz), 8.63 (1H, J = 2.4 Hz), 7.96-7.91 (1H, m), 7.46 (2H, brs), 7.18 (1H, dd, J = 7.3, 7.9 Hz), 7.09 (1H, d, J = 7.3 Hz), 6.92-6.90 (1H, m), 6.83 (1H, d J = 7.9 Hz), 5.47 (2H, s), 4.23 (2H, t, J = 6.7 Hz), 3.23 (2H, s), 2.00 (3H, s), 1.65 (2H, tt, J = 6.7, 7.9 Hz), 1.38 (2H, qt, J = 7.3, 7.9 Hz), 0.90 (3H, t, J = 7.3 Hz). |
| 85 | 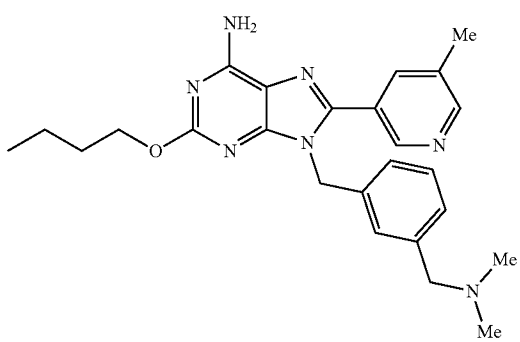 [SMILES: CCCCOc1nc(N)c2nc(-c3cncc(C)c3)n(Cc3cccc(CN(C)C)c3)c2n1] | LC-MS [M + H]+/Rt (min): 446.2/0.643 (Method A); ¹H-NMR (400 MHz, DMSO-d₆) δ: 8.59 (1H, d, J = 1.8 Hz) 8.45 (1H, d, J = 1.3 Hz), 7.83-7.81 (1H, m), 7.40 (2H, brs), 7.19 (1H, dd, J = 7.3, 7.9 Hz), 7.10 (1H, d, J = 7.3 Hz) 6.94-6.92 (1H, m), 6.85 (1H, d J = 7.9 Hz), 5.42 (2H, s), 4.22 (2H, t, J = 6.7 Hz), 3.24 (2H, s), 2.29 (3H, s), 2.01 (6H, s), 1.65 (2H, tt, J = 6.7, 7.9 Hz), 1.38 (2H, qt, J = 7.3, 7.9 Hz), 0.90 (3H, t, J = 7.3 Hz). |

| Example | Chemical Structure | Instrumental analysis data |
|---|---|---|
| 86 | 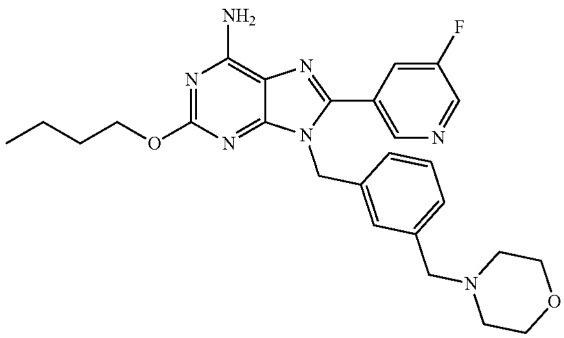 [SMILES: CCCCOc1nc(N)c2nc(-c3cncc(F)c3)n(Cc3cccc(CN4CCOCC4)c3)c2n1] | LC-MS [M + H]⁺/Rt (min): 492.2/0.635 (Method A); ¹H-NMR (400 MHz, DMSO-d₆) δ: 8.69-8.66 (1H, m), 8.64 (1H, d, J = 2.4 Hz), 7.98-7.93 (1H, m), 7.47 (2H, brs), 7.19 (1H, dd, J = 7.3, 7.9 Hz), 7.11 (1H, d, J = 7.3 Hz), 6.93-6.90 (1H, m), 6.86 (1H, d J = 7.9 Hz), 5.48 (2H, s), 4.23 (2H, t, J = 6.7 Hz), 3.50-3.45 (4H, m), 3.31 (2H, s), 2.25-2.15 (4H, m), 1.65 (2H, tt, J = 6.7, 7.9 Hz), 1.39 (2H, qt, J = 7.3, 7.9 Hz), 0.90 (3H, t, J = 7.3 Hz). |
| 87 | 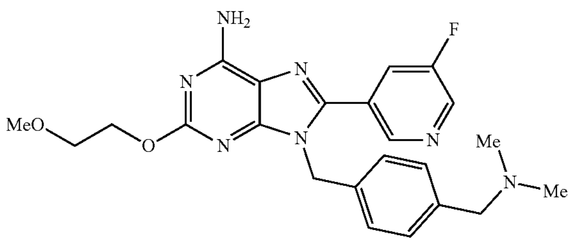 [SMILES: COCCOc1nc(N)c2nc(-c3cncc(F)c3)n(Cc3ccc(CN(C)C)cc3)c2n1] | LC-MS [M + H]⁺/Rt (min): 452.2/0.516 (Method A); ¹H-NMR (400 MHz, DMSO-d⁶) δ: 8.67 (1H, dd, J = 1.2, 1.8 Hz), 8.65 (1H, d, J = 3.1 Hz), 7.96-7.92 (1H, m), 7.50 (2H, brs), 7.15 (2H, d, J = 7.9 Hz), 6.91 (2H, d, J = 7.9 Hz), 5.45 (2H, s), 4.34 (2H, t, J = 4.9 Hz), 3.61 (2H, t, J = 4.9 Hz), 3.32 (3H, s), 3.27 (2H, s), 2.05 (6H, s). |
| 88 | 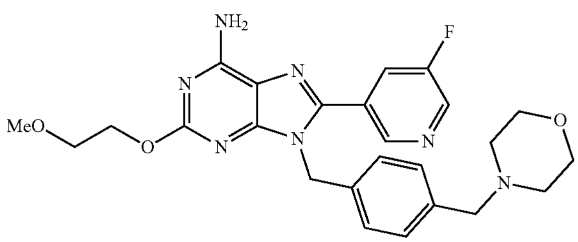 [SMILES: COCCOc1nc(N)c2nc(-c3cncc(F)c3)n(Cc3ccc(CN4CCOCC4)cc3)c2n1] | LC-MS [M + H]⁺/Rt (min): 494.2/0.511 (Method A); ¹H-NMR (400 MHz, DMSO-d₆) δ: 8.68-8.66 (1H, m), 8.65 (1H, d, J = 2.4 Hz), 7.96-7.92 (1H, m), 7.50 (2H, brs), 7.17 (2H, d, J = 7.9 Hz), 6.92 (2H, d, J = 7.9 Hz), 5.45 (2H, s), 4.34 (2H, t, J = 4.9 Hz), 3.61 (2H, t, J = 4.9 Hz), 3.53-3.49 (4H, m), 3.35 (3H, s), 3.27 (2H, s), 2.26-2.23 (4H, m). |
| 89 | 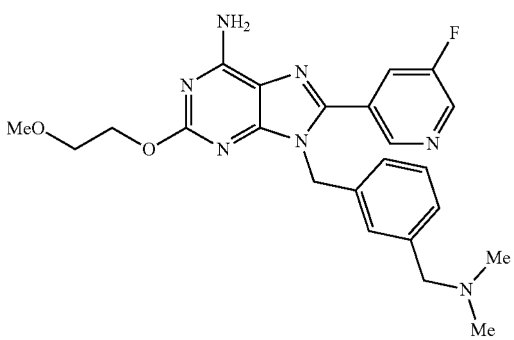 [SMILES: COCCOc1nc(N)c2nc(-c3cncc(F)c3)n(Cc3cccc(CN(C)C)c3)c2n1] | LC-MS [M + H]⁺/Rt (min): 452.1/0.524 (Method A); ¹H-NMR (400 MHz, DMSO-d₆) δ: 8.68-8.66 (1H, m), 8.64 (1H, d, J = 2.4 Hz), 7.97-7.92 (1H, m), 7.50 (2H, brs), 7.19 (1H, dd, J = 7.3, 7.9 Hz), 7.10 (1H, d, J = 7.3 Hz), 6.91-6.90 (1H, m), 6.84 (1H, d, J = 7.9 Hz), 5.48 (2H, s), 4.35 (2H, t, J = 4.9 Hz), 3.61 (2H, t, J = 4.9 Hz), 3.27 (3H, s), 3.24 (2H, s), 2.00 (6H, s). |
| 90 | 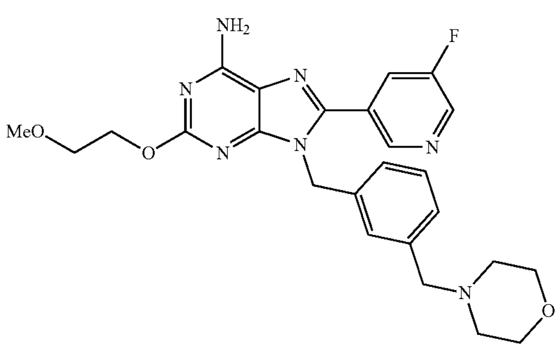 [SMILES: COCCOc1nc(N)c2nc(-c3cncc(F)c3)n(Cc3cccc(CN4CCOCC4)c3)c2n1] | LC-MS [M + H]⁺/Rt (min): 494.1/0.533 (Method A); ¹H-NMR (400 MHz DMSO-d₆) δ: 8.68-8.66 (1H, m), 8.65 (1H, d, J = 2.4 Hz), 7.98-7.94 (1H, m), 7.52 (2H, brs), 7.20 (1H, dd, J = 7.3, 7.9 Hz), 7.11 (1H, d, J = 7.3 Hz), 6.91-6.89 (1H, m), 6.86 (1H, d, J = 7.9 Hz), 5.48 (2H, s), 4.34 (2H, t, J = 4.9 Hz), 3.61 (2H, t, J = 4.9 Hz), 3.51-3.45 (4H, m), 3.31 (2H, s), 3.27 (3H, s), 2.22-2.16 (4H, m). |

| Example | Chemical Structure | Instrumental analysis data |
|---|---|---|
| 91 | 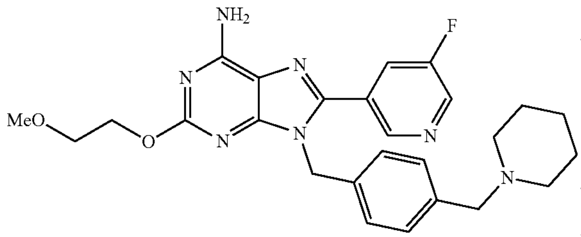 | LC-MS [M + H]⁺/Rt (min): 492.5/0.559 (Method A); ¹H-NMR (400 MHz, DMSO-d₆) δ: 8.69-8.67 (1H, m), 8.65 (1H, d, J = 2.7 Hz), 7.96-7.92 (1H, m), 7.49 (2H, brs), 7.14 (2H, d, J = 8.2 Hz), 6.91 (2H, d, J = 8.2 Hz), 5.45 (2H, s), 4.34 (2H, t, J = 4.8 Hz), 3.61 (2H, t, J = 4.8 Hz), 3.30 (2H, s), 3.27 (3H, s), 2.26-2.16 (4H, m), 1.46-1.38 (4H, m), 1.37-1.30 (2H, m). |
| 92 | 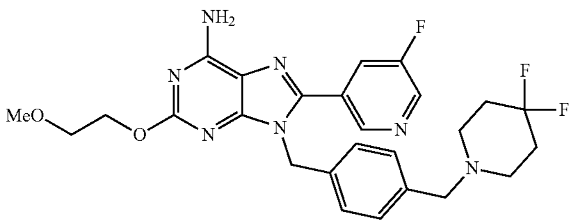 [SMILES: COCCOc1nc(N)c2nc(-c3cncc(F)c3)n(Cc3ccc(CN4CCC(F)(F)CC4)cc3)c2n1] | LC-MS [M + H]⁺/Rt (min): 528.5/0.584 (Method A); ¹H-NMR (400 MHz, DMSO-d₆) δ: 8.68-8.67 (1H, m), 8.65 (1H, d, J = 2.7 Hz), 7.96-7.93 (1H, m), 7.49 (2H, brs), 7.17 (2H, d, J = 8.2 Hz), 6.93 (2H, d, J = 8.2 Hz), 5.45 (2H, s), 4.34 (2H, t, J = 4.6 Hz), 3.61 (2H, t, J = 4.6 Hz), 3.44 (2H, s), 3.27 (3H, s), 2.42-2.35 (4H, m), 1.95-1.83 (4H, m). |
| 93 | 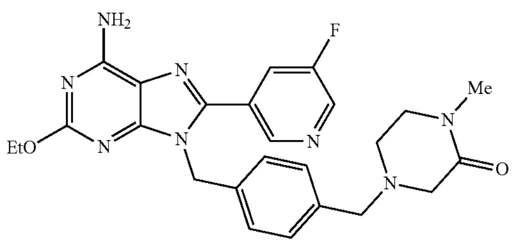 [SMILES: CCOc1nc(N)c2nc(-c3cncc(F)c3)n(Cc3ccc(CN4CCN(C)C(=O)C4)cc3)c2n1] | LC-MS [M + H]⁺/Rt (min): 491.5/0.581 (Method A); ¹H-NMR (400 MHz, DMSO-d₆) δ: 8.67-8.66 (1H, m), 8.64 (1H, d, J = 3.1 Hz), 7.96-7.92 (1H, m), 7.47 (2H, brs), 7.18 (2H, d, J = 7.9 Hz), 6.94 (2H, d, J = 7.9 Hz), 5.46 (2H, s), 4.26 (2H, q, J = 7.3 Hz), 3.43 (2H, s), 3.19 (2H, t, J = 5.5 Hz), 2.86 (2H, s), 2.77 (3H, s), 2.52 (2H, t, J = 5.5 Hz), 1.27 (3H, t, J = 7.3 Hz). |
| 94 | 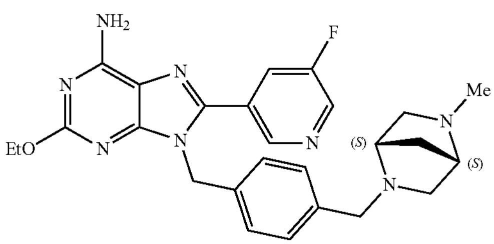 | LC-MS [M + H]⁺/Rt (min): 489.2/0.508 (Method A); ¹H-NMR (400 MHz DMSO-d₆) δ: 8.68-8.67 (1H, m), 8.65 (1H, d, J = 2.4 Hz), 7.97-7.93 (1H, m), 7.47 (2H, brs), 7.19 (2H, d, J = 7.9 Hz), 6.91 (2H, d, J = 7.9 Hz), 5.44 (2H, s), 4.26 (2H, q, J = 7.3 Hz), 3.37-3.24 (4H, m), 3.17 (1H, brs), 2.84-2.75 (1H, m), 2.59-2.53 (2H, m), 2.33 (2H, s), 1.27 (3H, t, J = 7.3 Hz). |
| 95 | 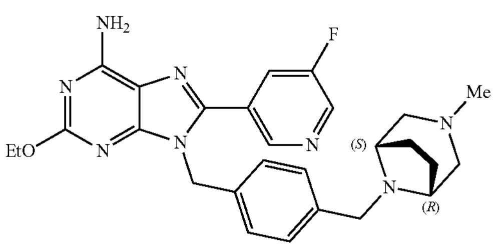 | LC-MS [M + H]⁺/Rt (min): 503.5/0.553 (Method A); ¹H-NMR (400 MHz, DMSO-d₆) δ: 3.69-8.68 (1H, m), 8.65 (1H, d, J = 2.4 Hz), 7.96-7.92 (1H, m), 7.46 (2H, brs), 7.21 (2H, d, J = 7.9 Hz), 6.91 (2H, d, J = 7.9 Hz), 5.44 (2H, s), 4.27 (2H, q, J = 7.3 Hz), 3.36 (2H, s), 2.93-3.88 (2H, m), 2.46-2.40 (2H, m), 2.10-2.04 (5H, m), 1.83-1.76 (2H, m), 1.67-1.61 (2H, m), 1.27 (3H, t, J = 7.3 Hz). |
| 96 | 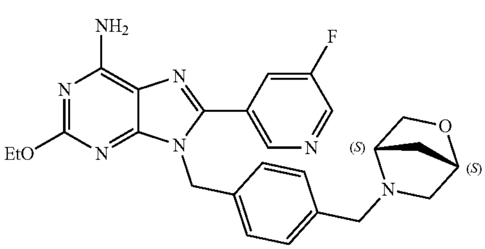 | LC-MS [M + H]⁺/Rt (min): 476.5/0.530 (Method A); ¹H-NMR (400 MHz, DMSO-d₆) δ: 8.68-8.67 (1H, m), 8.65 (1H, d, J = 3.0 Hz), 7.97-7.93 (1H, m), 7.46 (2H, brs), 7.19 (2H, d, J = 7.9 Hz), 6.91 (2H, d, J = 7.9 Hz), 5.44 (2H, s), 4.30-4.29 (1H, m), 4.28 (2H, q, J = 7.3 Hz), 3.84 (1H, d, J = 7.3 Hz), 3.63 (1H, d, J = 13.4 Hz), 3.58 (1H, d, J = 13.4 Hz), 3.46 (1H, dd, J = 1.8, 7.3 Hz), 3.34-3.30 (1H, m), 2.52 (1H, dd, J = 1.8, 9.4 Hz), 1.72 (1H, dd, J = 1.8, 9.4), 1.55-1.51 (1H, m), 1.27 (3H, t, J = 7.3 Hz). |

| Example | Chemical Structure | Instrumental analysis data |
|---|---|---|
| 97 | 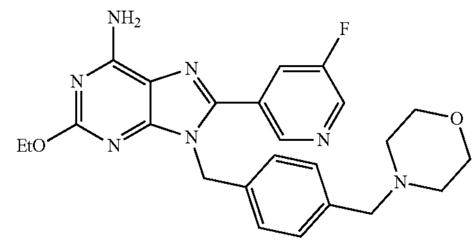 [SMILES: CCOc1nc(N)c2nc(-c3cncc(F)c3)n(Cc3ccc(CN4CCOCC4)cc3)c2n1] | LC-MS [M + H]⁺/Rt (min): 464.4/0.528 (Method A); ¹H-NMR (400 MHz, DMSO-d₆) δ: 8.68-8.67 (1H, m), 8.64 (1H, d J = 2.4 Hz), 7.95-7.92 (1H, m), 7.46 (2H, brs), 7.17 (2H, d, J = 7.9 Hz), 6.92 (2H, d, J = 7.9 Hz), 5.45 (2H, s), 4.27 (2H, q, J = 7.3 Hz) 3.52-3.50 (4H, m), 3.35 (2H, s), 2.28-2.22 (4H, m), 1.27 (3H, t, J = 7.3 Hz). |
| 98 | 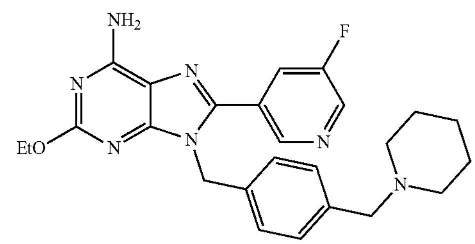 [SMILES: CCOc1nc(N)c2nc(-c3cncc(F)c3)n(Cc3ccc(CN4CCCCC4)cc3)c2n1] | LC-MS [M + H]⁺/Rt (min): 462.3/0.583 (Method A); ¹H-NMR (400 MHz, CDCl₃) δ: 8.59-8.58 (1H, m), 8.46 (1H, d, J = 3.1 Hz), 7.55-7.51 (1H, m), 7.16 (2H, d, J = 7.9 Hz), 6.94 (2H, d, J = 7.9 Hz), 5.51 (2H, brs), 5.34 (2H, s), 4.33 (2H, q, J = 7.3 Hz), 3.34 (2H, s), 2.28-2.20 (4H, m), 1.51-1.44 (4H, m), 1.38-1.30 (2H, m), 1.34 (3H, t, J = 7.3 Hz). |
| 99 | 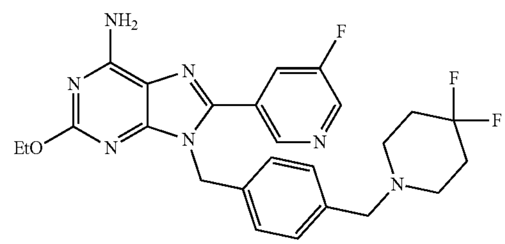 [SMILES: CCOc1nc(N)c2nc(-c3cncc(F)c3)n(Cc3ccc(CN4CCC(F)(F)CC4)cc3)c2n1] | LC-MS [M + H]⁺/Rt (min): 498.3/0.603 (Method A); ¹H-NMR (400 MHz, CDCl₃) δ: 8.63-8.62 (1H, m), 8.51 (1H, d, J = 2.4 Hz), 7.61-7.57 (1H, m), 7.21 (2H, d, J = 7.9 Hz) 7.01 (2H, d, J = 7.9 Hz), 5.56 (2H, brs), 5.39 (2H, s), 4.38 (2H, q, J = 7.3 Hz), 3.47 (2H, s), 2.50-2.44 (4H, m), 2.01-1.89 (4H, m), 1.39 (3H, t, J = 7.3 Hz). |
| 100 | 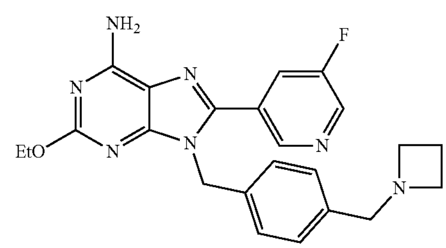 [SMILES: CCOc1nc(N)c2nc(-c3cncc(F)c3)n(Cc3ccc(CN4CCC4)cc3)c2n1] | LC-MS [M + H]⁺/Rt (min): 434.3/0.545 (Method A); ¹H-NMR (400 MHz, CDCl₃) δ: 8.58-8.57 (1H, m), 8.45 (1H, d, J = 3.1 Hz), 7.54-7.50 (1H, m), 7.12 (2H, d, J = 7.9 Hz), 6.94 (2H, d, J = 7.9 Hz), 5.52 (2H, brs), 5.33 (2H, s), 4.32 (2H, J = 7.3 Hz), 3.44 (2H, s), 3.11 (4H, t, J = 6.7 Hz), 2.00 (2H, quin, J = 6.7 Hz), 1.34 (3H, t, J = 7.3 Hz). |
| 101 | 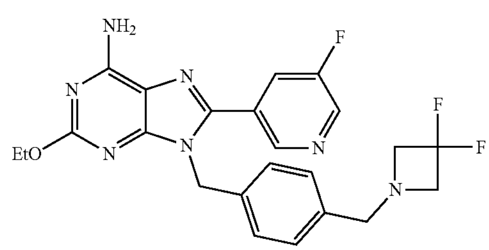 [SMILES: CCOc1nc(N)c2nc(-c3cncc(F)c3)n(Cc3ccc(CN4CC(F)(F)C4)cc3)c2n1] | LC-MS [M + H]⁺/Rt (min): 470.3/0.632 (Method A); ¹H-NMR (400 MHz, CDCl₃) δ: 8.62-8.61 (1H, m), 8.51 (1H, d, J = 2.4 Hz), 7.60-7.57 (1H, m), 7.19 (2H, d, J = 8.5 Hz), 7.02 (2H, d, J = 8.5 Hz), 5.56 (2H, brs), 5.39 (2H, s), 4.37 (2H, q, J = 7.3 Hz), 3.67 (2H, s), 3.62-3.50 (5H, m), 1.39 (3H, t, J = 7.3 Hz). |
| 102 | 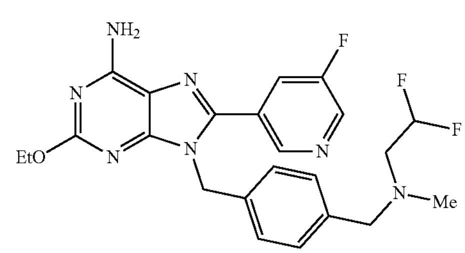 [SMILES: CCOc1nc(N)c2nc(-c3cncc(F)c3)n(Cc3ccc(CN(C)CC(F)F)cc3)c2n1] | LC-MS [M + H]⁺/Rt (min): 472.1/0.647 (Method A); ¹H-NMR (400 MHz, DMSO-d₆) δ: 8.66 (1H, dd, J = 1.8, 1.8 Hz), 8.64 (1H, d, J = 2.4 Hz), 7.95-7.91 (1H, m), 7.46 (2H, brs), 7.17 (2H, d J = 7.9 Hz), 6.93 (2H, d, J = 7.9 Hz), 6.06 (1H, tt, J = 4.2, 47.6 Hz), 5.45 (2H, s), 4.27 (2H, q, J = 7.3 Hz), 3.51 (2H, s), 2.68 (2H, dt, J = 4.2, 11.0 Hz), 2.15 (3H, s), 1.27 (3H, t, J = 7.3 Hz). |

-continued

| Example | Chemical Structure | Instrumental analysis data |
|---|---|---|
| 103 | 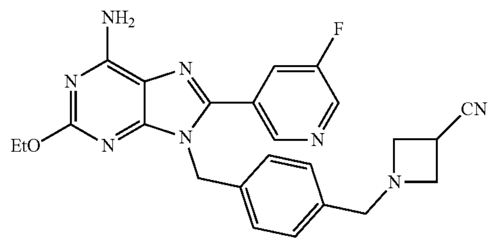 [SMILES: CCOc1nc(N)c2nc(-c3cncc(F)c3)n(Cc3ccc(CN4CC(C#N)C4)cc3)c2n1] | LC-MS [M + H]⁺/Rt (min): 459.1/0.556 (Method A); ¹H-NMR (400 MHz, DMSO-d$_6$) δ: 8.67-8.65 (2H, m), 7.97-7.92 (1H, m), 7.46 (2H, brs), 7.13 (2H, d, J = 7.3 Hz), 6.92 (2H, d, J = 7.3 Hz), 5.44 (2H, s), 4.26 (2H, q, J = 7.3 Hz), 3.47 (2H, s), 3.45-3.38 (1H, m), 3.35 (2H, t, J = 6.1 Hz), 3.18 (2H, t, J = 6.1 Hz), 1.27 (3H, t, J = 7.3 Hz). |
| 104 | 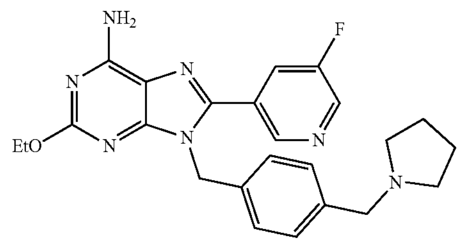 | LC-MS [M + H]⁺/Rt (min): 448.5/0.561 (Method A); ¹H-NMR (400 MHz, DMSO-d$_6$) δ: 8.68 (1H, d, J = 1.8 Hz), 8.65 (1H, d, J = 2.4 Hz), 7.97-7.92 (1H, m), 7.46 (2H, brs), 7.16 (2H, d, J = 7.3 Hz), 6.91 (2H, d, J = 7.3 Hz), 5.45 (2H, s), 4.27 (2H, q, J = 7.3 Hz), 3.46 (2H, s), 2.38-2.35 (4H, m), 1.63-1.59 (4H, m), 1.27 (3H, t, J = 7.3 Hz). |
| 105 | 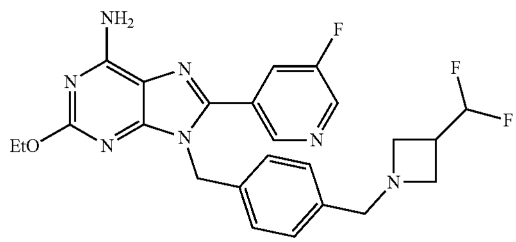 [SMILES: CCOc1nc(N)c2nc(-c3cncc(F)c3)n(Cc3ccc(CN4CC(C(F)F)C4)cc3)c2n1] | LC-MS [M + H]⁺/Rt (min): 484.5/0.605 (Method A); ¹H-NMR (400 MHz, DMSO-d$_6$) δ: 8.68-8.66 (1H, m), 8.65 (1H, d, J = 2.7 Hz), 7.96-7.92 (1H, m), 7.45 (2H, brs), 7.13 (2H, d, J = 8.2 Hz), 6.91 (2H, d, J = 8.2 Hz), 6.18 (1H, dt, J = 5.2, 56.9 Hz), 5.43 (2H, s), 4.26 (2H, q, J = 7.3 Hz), 3.45 (2H, s), 3.19 (2H, t, J = 7.7 Hz), 3.00 (2H, t, J = 7.7 Hz), 2.88-2.74 (1H, m), 1.27 (3H, t, J = 7.3 Hz). |
| 106 | 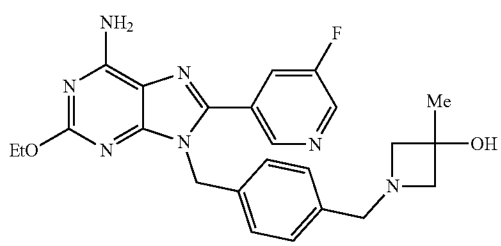 [SMILES: CCOc1nc(N)c2nc(-c3cncc(F)c3)n(Cc3ccc(CN4CC(C)(O)C4)cc3)c2n1] | LC-MS [M + H]⁺/Rt (min): 464.1/0.540 (Method A); ¹H-NMR (400 MHz, DMSO-d$_6$) δ: 8.68-8.67 (1H, m), 8.66 (1H, d, J = 2.4 Hz), 7.97-7.93 (1H, m), 7.47 (2H, brs), 7.12 (2H, d, J = 7.9 Hz), 6.90 (2H, d, J = 7.9 Hz), 5.43 (2H, s), 5.10 (1H, s), 4.26 (2H, q, J = 7.3 Hz), 3.46 (2H, s), 3.06 (2H, d, J = 7.3 Hz), 2.78 (2H, d, J = 7.3 Hz), 1.30 (3H, s), 1.27 (3H, t, J = 7.3 Hz). |
| 107 | 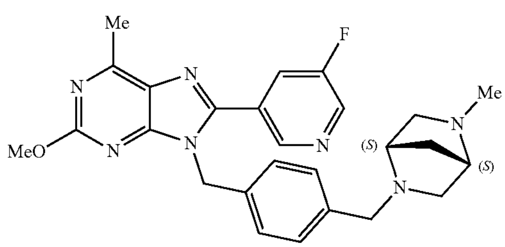 | LC-MS [M + H]⁺/Rt (min): 474.4/0.525 (Method A); ¹H-NMR (CDCl$_3$) δ: 8.73-8.72 (2H, m), 8.06-8.02 (1H, m), 7.17 (2H, d, J = 6.7 Hz), 6.91 (2H, d, J = 6.7 Hz), 5.54 (2H, s), 3.95 (3H, s), 3.57 (1H, d, J = 13.4 Hz), 3.50 (1H, d, J = 13.4 Hz), 3.07 (2H, d, J = 9.8 Hz), 2.71 (3H, s), 2.61 (1H, d, J = 9.8 Hz), 2.46-2.40 (2H, m), 2.21 (3H, s), 1.53 (3H, s). |
| 108 | 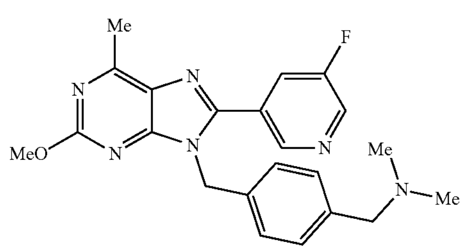 [SMILES: COc1nc(C)c2nc(-c3cncc(F)c3)n(Cc3ccc(CN(C)C)cc3)c2n1] | LC-MS [M + H]⁺/Rt (min): 421.4/0.587 (Method A); ¹H-NMR (CDCl$_3$) δ: 8.73-8.70 (2H, m), 8.05-8.00 (1H, m), 7.14 (2H, d, J = 7.9 Hz), 6.92 (2H, d, J = 7.9 Hz), 5.53 (2H, s), 4.38 (2H, q, J = 7.3 Hz), 3.27 (2H, s), 2.70 (3H, s), 2.04 (6H, s), 1.33 (3H, t, J = 7.3 Hz). |

-continued

| Example | Chemical Structure | Instrumental analysis data |
|---|---|---|
| 109 | [Structure] | LC-MS [M + H]+/Rt (min): 488.5/0.573 (Method A); ¹H-NMR (400 MHz DMSO-d₆) δ: 8.73-8.71 (2H, m), 8.05-8.01 (1H, m), 7.18 (1H, d, J = 7.9 Hz), 6.91 (2H, d, J = 7.9 Hz), 5.52 (2H, s), 4.38 (2H, q, J = 7.3 Hz), 3.58 (1H, d, J = 13.4 Hz), 3.51 (1H, d, J = 13.4 Hz), 3.31 (2H, s), 3.17 (1H, s), 3.13 (1H, s) 2.70 (3H, s), 2.54-2.44 (4H, m), 2.28 (3H, s), 1.59 (2H, s), 1.33 (3H, t, J = 7.3 Hz). |
| 110 | [Structure] | LC-MS [M + H]+/Rt (min): 488.5/0.596 (Method A); ¹H-NMR (400 MHz, DMSO-d₆) δ: 8.73-8.71 (2H, m), 8.05-8.01 (1H, m), 7.18 (1H, d, J = 7.9 Hz), 6.91 (2H, d, J = 7.9 Hz), 5.52 (2H, s), 4.38 (2H, q, J = 7.3 Hz), 3.57 (1H, d, J = 13.4 Hz), 3.50 (1H, d, J = 13.4 Hz), 3.31 (2H, s), 3.10 (2H, s), 2.70 (3H, s), 2.63 (1H, d, J = 9.2 Hz), 2.51-2.42 (3H, m), 2.23 (3H, s), 1.55 (2H, s), 1.33 (3H, t, J = 7.3 Hz). |
| 111 | [Structure] | ¹H-NMR (400 MHz, DMSO-d₆) δ: 8.74-8.72 (2H, m), 8.05-8.01 (1H, m), 7.15 (1H, d, J = 8.1 Hz), 6.93 (2H, d, J = 8.1 Hz), 5.55 (2H, s), 4.35 (2H, t, J = 6.6 Hz), 2.71 (3H, s), 2.05 (6H, s), 1.73 (2H, tt, J = 6.6, 7.9 Hz), 1.42 (2H, qt, J = 7.3, 7.9), 0.93 (3H, t, J = 7.3 Hz). |
| 112 | [Structure] | ¹H-NMR (400 MHz, DMSO-d₆) δ: 8.73-8.72 (2H, m), 8.05-8.01 (1H, m), 7.24 (1H, d, J = 8.1 Hz), 6.94 (2H, d, J = 8.1 Hz), 5.55 (2H, s), 4.35 (2H, t, J = 6.6 Hz), 2.71 (3H, s), 2.28-2.22 (4H, s), 1.72 (2H, tt, J = 6.6, 7.9 Hz), 1.42 (2H, qt, J = 7.3, 7.9), 0.93 (3H, t, J = 7.3 Hz). |
| 113 | [Structure] | LC-MS [M + H]+/Rt (min): 451.2/0.537 (Method A); ¹H-NMR (400 MHz, DMSO-d₆) δ: 8.73-8.71 (2H, m), 8.05-8.01 (1H, m), 7.14 (2H, d, J = 7.9 Hz), 6.92 (2H, d, J = 7.9 Hz), 5.54 (2H, s), 4.46 (2H, t, J = 4.9 Hz), 3.67 (2H, t, J = 4.9 Hz), 3.31 (3H, s), 3.27 (2H, s), 2.71 (3H, s), 2.04 (6H, s). |
| 114 | [Structure] | LC-MS [M + H]+/Rt (min): 493.1/0.562 (Method A) |

-continued

| Example | Chemical Structure | Instrumental analysis data |
|---|---|---|
| 115 | 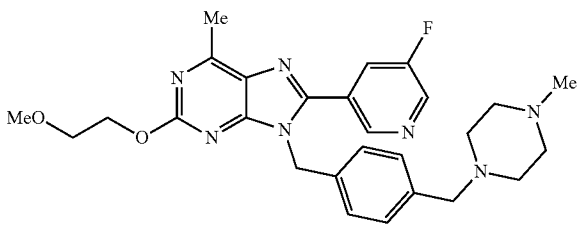 [SMILES: COCCOc1nc(C)c2nc(-c3cncc(F)c3)n(Cc3ccc(CN4CCN(C)CC4)cc3)c2n1] | LC-MS [M + H]⁺/Rt (min): 506.2/0.578 (Method A) |
| 116 | 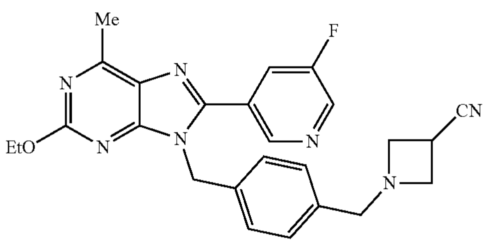 [SMILES: CCOc1nc(C)c2nc(-c3cncc(F)c3)n(Cc3ccc(CN4CC(C#N)C4)cc3)c2n1] | LC-MS [M + H]⁺/Rt (min): 458.5/0.611 (Method A); ¹H-NMR (400 MHz, DMSO-d₆) δ: 8.73 (1H, d, J = 3.1 Hz) 8.71-8.70 (1H, m), 8.05-8.02 (1H, m), 7.12 (2H, d, J = 7.9 Hz), 6.92 (2H, d, J = 7.9 Hz), 5.52 (2H, s), 4.38 (2H, q, J = 7.3 Hz), 3.46 (2H, s), 3.45-3.38 (1H, m), 3.34 (2H, t, J = 6.7 Hz), 3.18 (2H, t, J = 6.7 Hz), 2.70 (3H, s), 1.33 (3H, t, J = 7.3 Hz). |
| 117 | 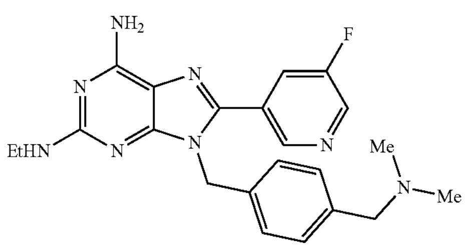 | LC-MS [M + H]⁺/Rt (min): 421.4/0.473 (Method A); ¹H-NMR (400 MHz, DMSO-d₆) δ: 8.68 (1H, s), 8.58 (1H, d, J = 2.4 Hz), 7.89-7.86 (1H, m), 7.15 (2H, d, J = 7.9 Hz), 6.93 (2H, d, J = 7.9 Hz), 6.93 (2H, brs), 6.44 (1H, t, J = 5.5 Hz), 5.40 (2H, s), 3.31-3.23 (4H, m), 2.05 (6H, s), 1.08 (3H, t, J = 7.3 Hz). |
| 118 | 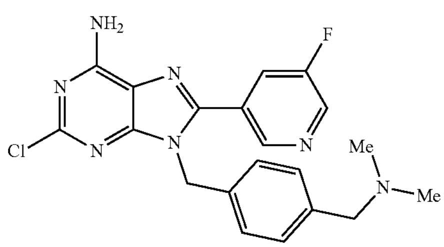 [SMILES: CN(C)Cc1ccc(Cn2c(-c3cncc(F)c3)nc3c(N)nc(Cl)nc32)cc1] | LC-MS [M + H]⁺/Rt (min): 412.3/0.396 (Method C); ¹H-NMR (CDCl₃) δ: 8.66 (1H, s), 8.58-8.56 (1H, m), 7.61-7.58 (1H, m), 7.27-7.24 (2H, m), 6.98 (2H, d, J = 8.5 Hz), 6.10-5.92 (2H, m), 5.47 (2H, s), 3.40 (2H, s), 2.21 (6H, s). |
| 119 | 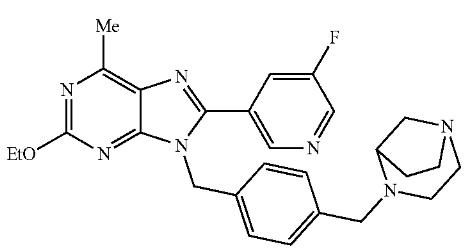 [SMILES: CCOc1nc(C)c2nc(-c3cncc(F)c3)n(Cc3ccc(CN4CCN5CCC4C5)cc3)c2n1] | ¹H-NMR (400 MHz, CDCl₃) δ: 8.70-8.67 (1H, m), 8.58 (1H, d, J = 2.4 Hz), 7.71-7.64 (1H, m), 7.25 (3H, d, J = 7.9 Hz), 7.01 (2H, d, J = 7.9 Hz), 5.47 (2H, s), 4.49 (2H, q, J = 7.1 Hz), 3.36 (2H, dd, J = 13.4, 19.5 Hz), 3.15-3.10 (1H, m), 3.06-2.94 (2H, m), 2.84 (3H, s), 2.83-2.74 (1H, m), 2.64 (1H, dd, J = 4.0, 13.4 Hz), 2.58-2.51 (1H, m), 2.48 (1H, dd, J = 4.6, 11.9 Hz), 2.32-2.23 (1H, m), 2.05-1.95 (1H, m), 1.47 (3H, t, J = 7.1 Hz). |
| 120 | 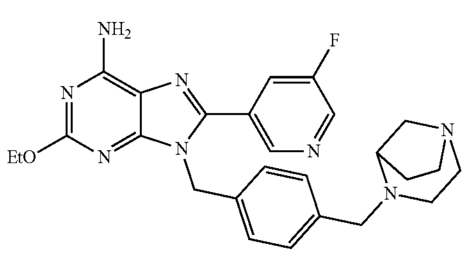 [SMILES: CCOc1nc(N)c2nc(-c3cncc(F)c3)n(Cc3ccc(CN4CCN5CCC4C5)cc3)c2n1] | ¹H-NMR (400 MHz, CDCl₃) δ: 8.69-8.61 (1H, m), 8.56-8.49 (1H, m), 7.60 (1H, d, J = 8.5 Hz), 7.24 (2H, d, J = 6.1 Hz), 7.02 (2H, d, J = 6.1 Hz), 5.83 (2H, s), 5.41 (2H, s), 4.39 (2H, q, J = 7.0 Hz), 3.33 (2H, dd, J = 13.4, 17.1 Hz), 3.11-3.03 (1H, m), 3.02-2.82 (3H, m), 2.79-2.67 (1H, m), 2.62-2.52 (1H, m), 2.52-2.36 (2H, m), 2.02-1.88 (1H, m), 1.41 (3H, t, J = 7.0 Hz). |

-continued

| Example | Chemical Structure | Instrumental analysis data |
|---|---|---|
| 121 | 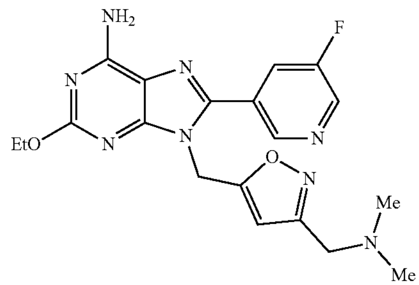 [SMILES: CCOc1nc(N)c2nc(-c3cncc(F)c3)n(Cc3cc(CN(C)C)no3)c2n1] | ¹H-NMR (400 MHz, CDCl₃) δ: 8.80-8.77 (1H, m), 8.63 (1H, d, J = 2.4 Hz), 7.83-7.77 (1H, m), 6.20 (1H, s), 5.57 (2H, s), 4.41 (2H, q, J = 7.1 Hz), 2.24 (6H, s), 1.44 (3H, t, J = 7.1 Hz). |
| 122 | 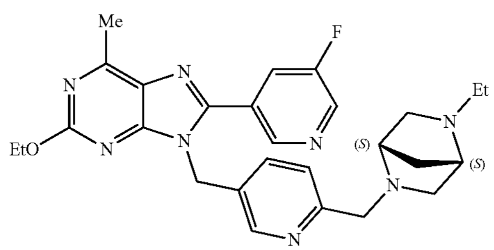 | ¹H-NMR (400 MHz, CDCl₃) δ: 8.91-8.88 (1H, m), 8.56 (1H, d, J = 3.1 Hz), 8.47 (1H, d, J = 1.8 Hz), 8.13-8.08 (1H, m), 7.66 (1H, dd, J = 1.8, 7.9 Hz), 7.25-7.22 (1H, m), 5.50 (2H, s), 4.42 (2H, q, J = 7.1 Hz), 3.86-3.79 (2H, m), 3.67 (1H, d, J = 13.4 Hz), 3.44-3.37 (1H, m), 3.19-3.07 (1H, m), 3.07-2.91 (2H, m), 2.90-2.81 (1H, m), 2.80 (3H, s), 2.70 (1H, d, J = 9.2 Hz), 2.05-1.93 (2H, m), 1.42 (3H, t, J = 7.1 Hz), 1.33 (3H, t, J = 7.2 Hz). |

Example 123

9-{4-[(1S,4S)-2,5-Diazabicyclo[2.2.1]hept-2-ylmethyl]benzyl}-2-ethoxy-8-(5-fluoropyridin-3-yl)-6-methyl-9H-purine

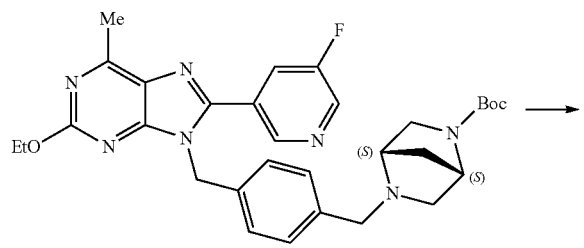
→
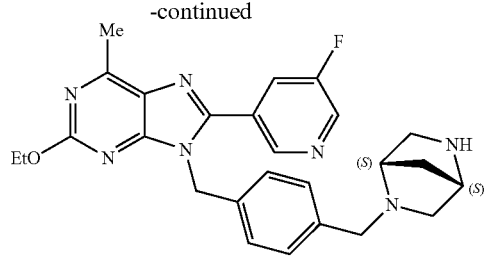

To the compound of Example 225 (138 mg) was added trifluoroacetic acid (1.5 mL), and the mixture was stirred at room temperature for 3 hours. The reaction mixture was diluted with toluene, and then concentrated in vacuo. To the reaction mixture in ice bath was added aqueous saturated sodium bicarbonate, and the mixture was extracted with chloroform-methanol (20:1). The organic layer was dried over sodium sulfate, filtrated, and then concentrated in vacuo. The residue was purified by amino silica gel column chromatography (chloroform/methanol) to give the title compound (105 mg).

LC-MS [M+H]⁺/Rt (min): 474.5/0.531 (Method A); ¹H-NMR (400 MHz, DMSO-d₆) δ: 8.72-8.71 (1H, m), 8.31-8.30 (1H, m), 8.05-8.01 (1H, m), 7.18 (1H, d, J=7.3 Hz), 6.90 (2H, d, J=7.3 Hz), 5.52 (2H, s), 4.42-4.35 (2H, m), 3.14-3.13 (1H, m), 2.92 (1H, d, J=9.8 Hz), 2.70 (3H, s), 2.65-2.50 (3H, m), 2.19 (1H, d, J=9.2 Hz), 1.58 (1H, d, J=9.2 Hz), 1.35-1.31 (4H, m).

Examples 124-125

According to the method of Example 123, Examples 124-125 were prepared by using the corresponding material compounds.

| Example | Chemical Structure | Instrumental analysis data |
|---|---|---|
| 124 | 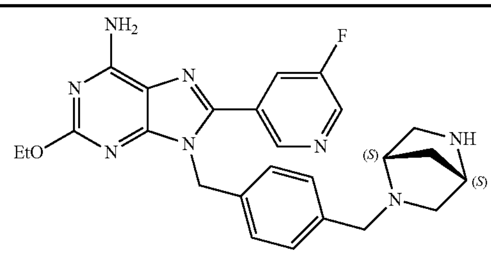 | LC-MS [M + H]⁺/Rt (min): 475.5/0.518 (Method A); $^1$H-NMR (DMSO-$d_6$) δ: 8.68-8.67 (1H, m), 8.65 (1H, d, J = 3.1 Hz), 7.97-7.92 (1H, m), 7.46 (2H, brs), 7.18 (1H, d, J = 7.9 Hz), 6.90 (2H, d, J = 7.9 Hz), 5.43 (2H, s), 4.26 (2H, q, J = 7.3 Hz), 3.58 (1H, d, J = 13.4 Hz), 3.52 (1H, d, J = 13.4 Hz), 3.15 (1H, brs), 2.93 (1H, d, J = 9.8 Hz), 2.64-4.48 (2H, m), 2.20 (1H, d, J = 9.2 Hz), 1.59 (1H, d, J = 8.5 Hz), 1.34 (1H, d, J = 9.2 Hz), 1.27 (3H, t, J = 7.3 Hz). |
| 125 | 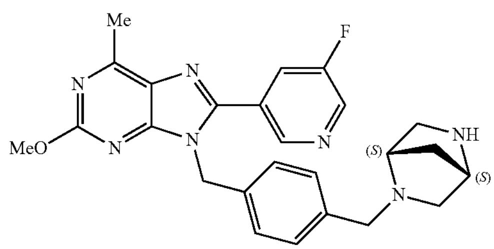 | LC-MS [M + H]⁺/Rt (min): 460.5/0.555 (Method A); $^1$H-NMR (400 MHz DMSO-$d_6$) δ: 8.73-8.72 (2H, m), 8.06-8.01 (1H, m), 7.16 (1H, d, J = 7.9 Hz), 6.90 (2H, d, J = 7.9 Hz), 5.33 (2H, s), 3.95 (3H, s), 3.58 (1H, d, J = 13.4 Hz), 3.51 (1H, d, J = 13.4 Hz), 3.14 (1H, brs), 2.92 (1H, d, J = 9.8 Hz), 2.70 (3H, s), 2.64-2.54 (2H, m), 2.19 (1H, d, J = 9.2 Hz), 1.58 (1H, d, J = 9.2 Hz), 1.33 (1H, d, J = 9.2 Hz). |

Example 126

1-[(1S,4S)-5-(4-{[6-Amino-2-ethoxy-8-(5-fluoropyridin-3-yl)-9H-purin-9-yl]methyl}benzyl)-2,5-diazabicyclo[2.2.1]hept-2-yl]ethanone

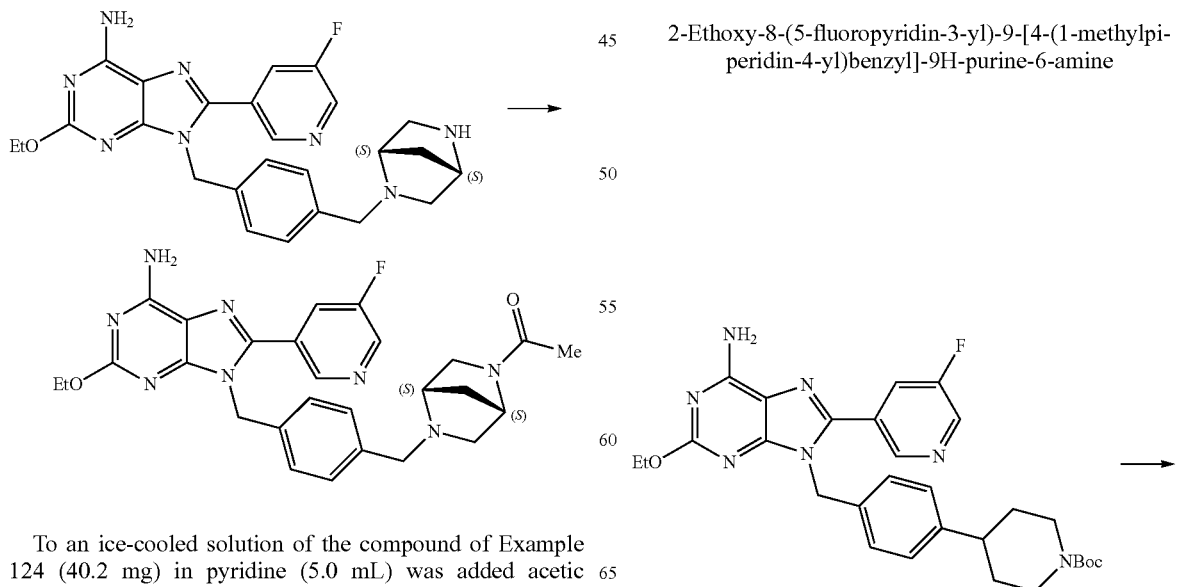

To an ice-cooled solution of the compound of Example 124 (40.2 mg) in pyridine (5.0 mL) was added acetic anhydride (0.050 ml). The reaction mixture was stirred at room temperature for 4.5 hours, and then concentrated. The obtained residue was purified by silica gel column chromatography (chloroform/methanol) to give the title compound (38.2 mg).

LC-MS [M+H]⁺/Rt (min): 517.5/0.517 (Method A)

Example 127

2-Ethoxy-8-(5-fluoropyridin-3-yl)-9-[4-(1-methylpiperidin-4-yl)benzyl]-9H-purine-6-amine

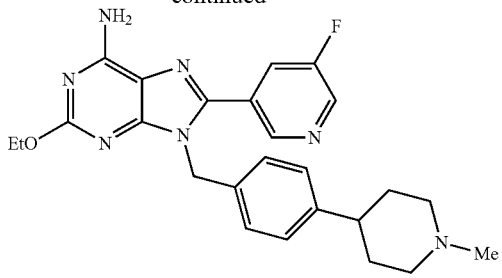

To an ice-cooled solution of the compound of Example 194 (145 mg) in chloroform (3 mL) was added trifluoroacetic acid (0.409 ml). The reaction mixture was warmed to room temperature, stirred for 2 days, and then concentrated. The obtained residue was dissolved in tetrahydrofuran (3 ml). To the solution were added sodium acetate (65.3 mg), 37% formaldehyde solution (0.041 ml) and triacetoxysodium borohydride (112 mg) under ice temperature. Then, the mixture was warmed to room temperature, and stirred for one hour. To the reaction mixture in ice bath was added aqueous saturated sodium bicarbonate, and the mixture was extracted with chloroform. The organic layer was dried over sodium sulfate, filtrated, and then concentrated in vacuo. The residue was purified by silica gel column chromatography (chloroform/methanol) to give the title compound (72 mg).

LC-MS ([M+H]$^+$/Rt (min)): 462.5/0.461 (Method C); $^1$H-NMR (400 MHz, CDCl$_3$) δ: 8.71-8.62 (1H, m), 8.55 (1H, d, J=3.1 Hz), 7.67-7.58 (1H, m), 7.15 (2H, d, J=7.9 Hz), 7.03 (2H, d, J=7.9 Hz), 5.80 (2H, s), 5.40 (2H, s), 4.41 (2H, q, J=7.1 Hz), 2.98 (2H, d, J=11.6 Hz), 2.51-2.38 (1H, m), 2.33 (3H, s), 2.13-2.00 (2H, m), 1.86-1.72 (4H, m), 1.41 (3H, t, J=7.1 Hz).

Examples 128-139

According to the methods of Examples 80 and 127, Examples 128-139 were prepared by using the corresponding material compounds.

| Example | Chemical Structure | Instrumental analysis data |
|---|---|---|
| 128 | 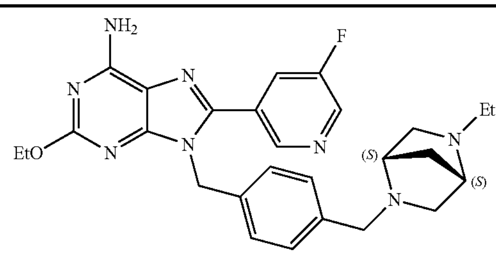 | LC-MS [M + H]$^+$/Rt (min): 503.5/0.536 (Method A); $^1$H-NMR (DMSO-d$_6$) δ: 8.68-8.67 (1H, m), 8.65 (1H, d, J = 3.1 Hz), 7.96-7.93 (1H, m), 7.46 (2H, brs), 7.18 (2H, d, J = 7.9 Hz), 6.90 (2H, d, J = 7.9 Hz), 5.43 (2H, br s), 4.26 (2H, q, J = 7.3 Hz), 3.58 (1H, d, J = 14.0 Hz), 3.50 (1H, d, J = 14.0 Hz), 3.22 (1H, s), 3.11 (1H, s), 2.58 (1H, d, J = 9.8 Hz), 2.54-2.34 (3H, m), 1.53 (2H, q, J = 7.3 Hz), 1.27 (3H, t, J = 7.3 Hz), 0.93 (3H, t, J = 7.3 Hz). |
| 129 | 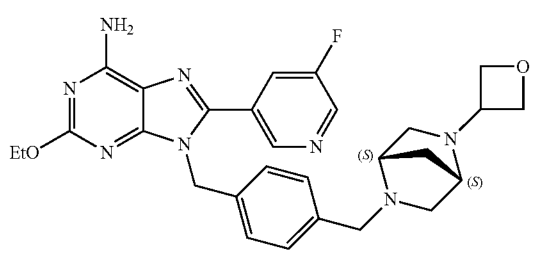 | LC-MS [M + H]$^+$/Rt (min): 531.6/0.552 (Method A); $^1$H-NMR (DMSO-d$_6$) δ: 8.68-8.67 (1H, m), 8.65 (1H, d, J = 3.1 Hz), 7.96-7.92 (1H, m), 7.46 (2H, brs), 7.19 (2H, d, J = 8.5 Hz), 6.90 (2H, d, J = 8.5 Hz), 5.43 (2H, s), 4.54 (1H, t, J = 6.7 Hz), 4.49 (1H, t, J = 6.7 Hz), 4.36 (1H, t, J = 5.5 Hz), 4.33-4.24 (3H, m), 3.83-3.77 (1H, m), 3.59 (1H, d, J = 14.0 Hz), 3.50 (1H, d, J = 14.0 Hz), 3.15 (2H, s), 2.72 (1H, d, J = 9.2 Hz), 2.47-2.35 (3H, m), 1.55 (1H, d, J = 9.7 Hz), 1.49 (1H, d, J = 9.7 Hz), 1.27 (3H, t, J = 7.3 Hz). |
| 130 | 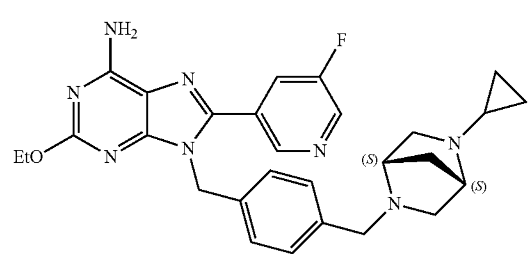 | LC-MS [M + H]$^+$/Rt (min): 515.6/0.584 (Method A); $^1$H-NMR (DMSO-d$_6$) δ: 8.68-8.67 (1H, m), 8.65 (1H, d, J = 2.4 Hz), 7.96-7.92 (1H, m), 7.46 (2H, brs), 7.19 (2H, d, J = 8.5 Hz), 5.43 (2H, s), 4.27 (2H, q, J = 7.3 Hz), 3.59 (1H, d, J = 14.0 Hz), 3.52 (1H, d, J = 14.0 Hz), 3.22 (1H, m), 3.13 (1H, m), 2.62 (1H, dd, J = 2.4, 9.2 Hz), 2.75 (1H, d, J = 9.2 Hz), 2.55 (1H, d, J = 9.2 Hz), 2.50-2.43 (3H, m), 1.95-1.90 (1H, m), 1.56 (1H, d, J = 9.2 Hz), 1.51 (1H, d, J = 9.2 Hz), 1.27 (3H, t, J = 7.3 Hz), 0.36-0.28 (2H, m), 0.25- |

| Example | Chemical Structure | Instrumental analysis data |
|---|---|---|
| | | 0.21 (2H, m). |
| 131 | 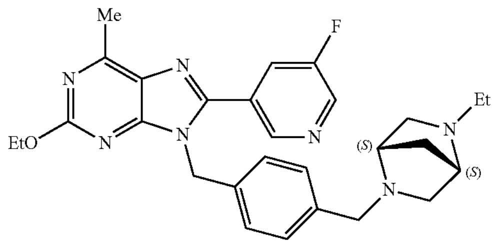 | LC-MS [M + H]⁺/Rt (min): 502.2/0.628 (Method A); ¹H-NMR (DMSO-d$_6$)8.73-8.71 (2H, m), 8.05-8.01 (1H, m), 7.18 (2H, d, J = 7.9 Hz), 6.91 (2H, d, J = 7.9 Hz), 5.52 (2H, s), 4.38 (2H, q, J = 7.3 Hz), 3.58 (1H, d, J = 14.0 Hz), 3.50 (1H, d, J = 14.0 Hz), 3.11 (1H, s), 2.70 (3H, s), 2.55-2.34 (3H m), 1.60-1.48 (2H, m), 1.33 (3H, t, J = 7.3 Hz), 0.93 (3H, t, J = 7.3 Hz). |
| 132 | 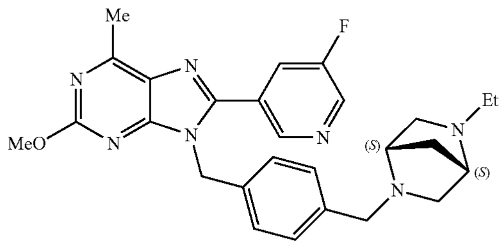 | LC-MS [M + H]⁺/Rt (min): 488.5/0.611 (Method A); ¹H-NMR (DMSO-d$_6$) δ: 8.73-8.71 (2H, m), 8.06-8.01 (1H, m), 7.18 (2H, d, J = 7.7 Hz), 6.91 (2H, d, J = 7.7 Hz), 5.54 (2H, s), 3.95 (3H, s), 3.58 (1H, d, J = 14.2 Hz), 3.51 (1H, d, J = 14.2 Hz), 3.13 (1H, s), 2.71 (3H, s), 2.70-2.38 (5H m), 1.62-1.51 (2H, m), 0.95 (3H, t, J = 7.3 Hz). |
| 133 | 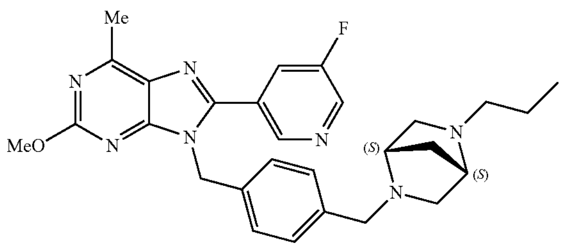 | LC-MS [M + H]⁺/Rt (min): 502.5/0.775 (Method A); ¹H-NMR (DMSO-d$_6$) δ: 8.73-8.72 (2H, m), 8.05-8.02 (1H, m), 7.17 (2H, d, J = 7.3 Hz), 6.90 (2H, d, J = 7.3 Hz), 5.53 (2H, br s), 3.95 (3H, s), 3.57 (1H, d, J = 14.0 Hz), 3.50 (1H, d, J = 14.0 Hz), 3.17 (1H, s), 3.08 (1H, s), 2.71 (3H, s), 2.56-2.47 (2H, m), 2.44-2.38 (2H, m), 2.33-2.23 (1H, m), 1.55-1.47 (2H, m), 1.36-1.27 (2H, m), 0.82 (3H, t, J = 7.9 Hz). |
| 134 | 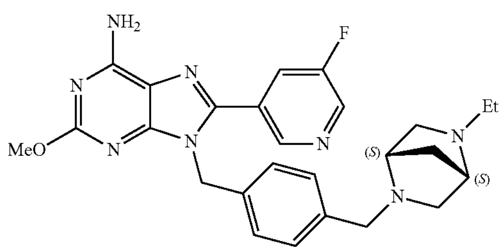 | LC-MS [M + H]⁺/Rt (min): 489.5/0.526 (Method B); ¹H-NMR (CDCl$_3$) δ: 8.66-8.65 (1H, m), 8.54 (1H, d, J = 3.1 Hz), 7.63-7.59 (1H, m), 7.28-7.26 (2H, m), 7.02 (2H, d, J = 8.0 Hz), 5.61 (2H, br s), 5.41 (2H, s), 3.98 (3H, s), 3.71 (1H, d, J = 13.2 Hz), 3.62 (1H, d, J = 13.2 Hz), 3.42 (1H, s), 3.24 (1H, s), 2.80-2.53 (5H, m), 1.76-1.74 (3H, m), 1.10 (3H, t, J = 7.0 Hz). |
| 135 | 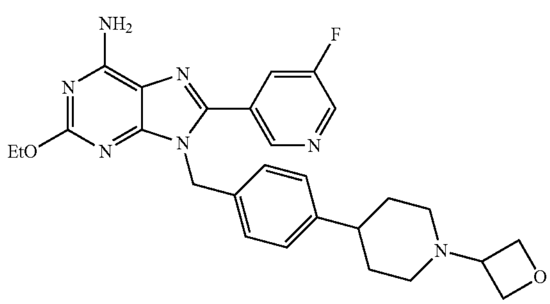 [SMILES: CCOc1nc(N)c2nc(-c3cncc(F)c3)n(Cc3ccc(C4CCN(C5COC5)CC4)cc3)c2n1] | ¹H-NMR (400 MHz, CDCl$_3$) δ: 8.67-8.63 (1H, m), 8.55 (1H, d, J = 1.8 Hz), 7.67-7.60 (1H, m), 7.16 (2H, d, J = 7.9 Hz), 7.03 (2H, d, J = 7.9 Hz), 5.73 (2H, s), 5.41 (2H, s), 4.72-4.62 (4H, m), 4.41 (2H, q, J = 6.9 Hz), 3.51 (1H, dd, J = 6.0, 6.2 Hz), 2.91-2.81 (2H, m), 2.56-2.43 (1H, m), 1.99-1.71 (6H, m), 1.42 (3H, t, J = 6.9 Hz). |

| Example | Chemical Structure | Instrumental analysis data |
|---|---|---|
| 136 | 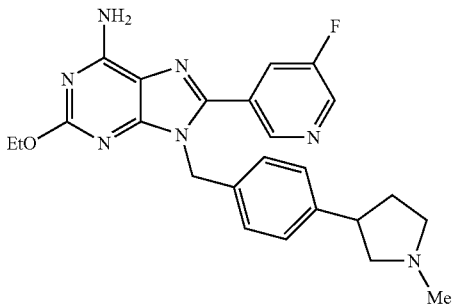 [SMILES: CCOc1nc(N)c2nc(-c3cncc(F)c3)n(Cc3ccc(C4CCN(C)C4)cc3)c2n1] | $^1$H-NMR (400 MHz, CDCl$_3$) δ: 8.69-8.63 (1H, m), 8.56 (1H, d, J = 2.4 Hz), 7.67-7.61 (1H, m), 7.21 (2H, d, J = 7.9 Hz), 7.03 (2H, d, J = 7.9 Hz), 5.69 (2H, s), 5.41 (2H, s), 4.41 (2H, q, J = 7.0 Hz), 3.45-3.31 (1H, m), 3.09-3.00 (1H, m), 2.91-2.78 (1H, m), 2.77-2.63 (1H, m), 2.60-2.48 (1H, m), 2.45 (3H, s), 2.40-2.27 (1H, m), 1.93-1.79 (1H, m), 1.42 (3H, t, J = 7.0 Hz). |
| 137 | 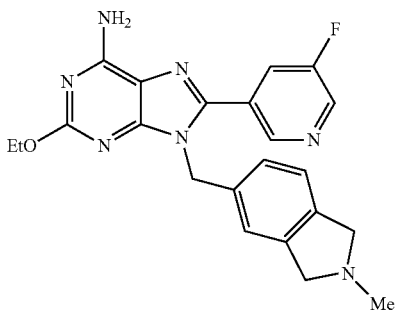 [SMILES: CCOc1nc(N)c2nc(-c3cncc(F)c3)n(Cc3ccc4c(c3)CN(C)C4)c2n1] | LC-MS: [M + H]$^+$/Rt (min): 420.4/0.388 (Method C); $^1$H-NMR (400 MHz, CDCl$_3$): δ: 8.67-8.65 (1H, m), 8.55 (1H, d, J = 3.1 Hz), 7.65-7.58 (1H, m), 7.12 (1H, d, J = 8.5 Hz), 6.92-6.91 (2H, m), 5.93 (2H, s), 5.41 (2H, s), 4.41 (2H, q, J = 7.1 Hz), 3.91 (2H, s), 3.86 (2H, s), 2.58 (3H, s), 1.42 (3H, t, J = 7.0 Hz). |
| 138 | 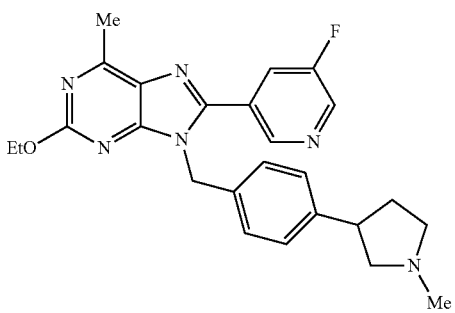 [SMILES: CCOc1nc(C)c2nc(-c3cncc(F)c3)n(Cc3ccc(C4CCN(C)C4)cc3)c2n1] | LC-MS [M + H]$^+$/Rt (min): 447.3/0.663 (Method C); $^1$H-NMR (400 MHz, CDCl$_3$) δ: 8.73-8.65 (1H, m), 8.59 (1H, d, J = 2.4 Hz), 7.73-7.67 (1H, m), 7.20 (2H, d, J = 7.9 Hz), 7.00 (2H, d, J = 7.9 Hz), 5.45 (2H, s), 4.49 (2H, q, J = 7.1 Hz), 3.41-3.27 (1H, m), 2.98 (1H, dd, J = 8.5, 8.5 Hz), 2.84 (3H, s), 2.81-2.73 (1H, m), 2.69-2.60 (1H, m), 2.46 (1H, dd, J = 8.0, 8.5 Hz), 2.41 (3H, s), 2.38-2.27 (1H, m), 1.89-1.77 (1H, m), 1.47 (3H, t, J = 7.1 Hz). |
| 139 | 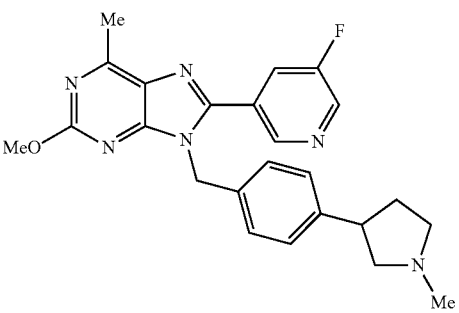 [SMILES: COc1nc(C)c2nc(-c3cncc(F)c3)n(Cc3ccc(C4CCN(C)C4)cc3)c2n1] | LC-MS [M + H]$^+$/Rt (min): 434.3/0.539 (Method C); $^1$H-NMR (400 MHz, CDCl$_3$) δ: 8.72-8.68 (1H, m), 8.60 (1H, d, J = 2.4 Hz), 7.74-7.67 (1H, m), 7.20 (2H, d, J = 7.9 Hz), 7.00 (2H, d, J = 7.9 Hz), 5.46 (2H, s), 4.08 (3H, s), 3.40-3.29 (1H, m), 2.96 (1H, dd, J = 8.8, 9.2 Hz), 2.85 (3H, s), 2.80-2.72 (1H, m), 2.69-2.58 (1H, m), 2.48-2.42 (1H, m), 2.40 (3H, s), 2.37-2.26 (1H, m), 1.87-1.76 (1H, m). |

Example 140

9-(4-{[2-(Dimethylamino)ethoxy]methyl}benzyl)-2-ethoxy-8-(5-fluoropyridin-3-yl)-9H-purine-6-amine

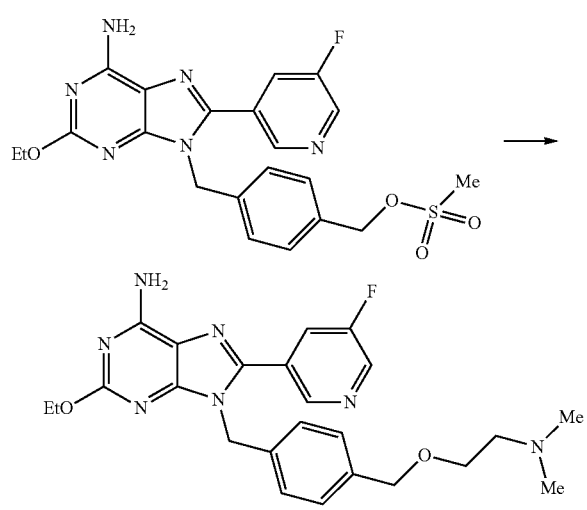

To an ice-cooled solution of sodium hydride (13.9 mg, purity: 55%) tetrahydrofuran (0.5 mL) was added N,N-dimethylethanolamine (0.032 mL), and the mixture was stirred for 10 minutes. Then, a solution of the compound of Example 232 (50 mg) tetrahydrofuran (0.56 mL) was added thereto, and the mixture was stirred at room temperature for 3 hours. To the reaction mixture was added water, and the mixture was extracted with ethyl acetate. The organic layer was washed with brine, dried over sodium sulfate, filtrated, and then concentrated in vacuo. The obtained residue was purified by amino silica gel column chromatography (chloroform/ethyl acetate/methanol), and then the residue was purified by silica gel column chromatography (chloroform/methanol) to give the title compound (4.0 mg).

LC-MS [M+H]$^+$/Rt (min): 466.1/0.479 (Method C); $^1$H-NMR (CDCl$_3$) δ: 8.67 (1H, br s), 8.55 (1H, d, J=2.7), 7.65-7.61 (1H, m), 7.00 (2H, d, J=8.4 Hz), 6.75 (2H, d, J=8.4 Hz), 5.57 (2H, s), 5.35 (2H, s), 4.41 (2H, q, J=6.8 Hz), 4.32-4.30 (1H, m), 3.24 (1H, dd, J=13.9, 8.0 Hz), 3.00-2.75 (5H, m), 2.10 (1H, br s), 1.99-1.92 (1H, m), 1.76-1.49 (2H, m), 1.46-1.33 (4H, m).

Example 141

9-Benzyl-2-butoxy-8-(5-fluoropyridin-3-yl)-6-methyl-9H-purine

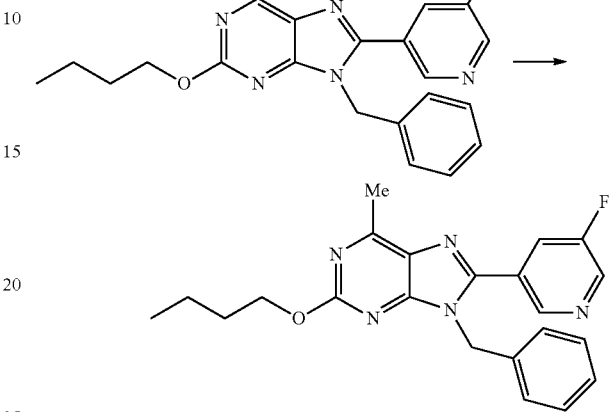

To an ice-cooled solution of sodium hydride (13.9 mg, purity: 55%) in tetrahydrofuran (0.5 mL) was added N,N-dimethylethanolamine (0.032 mL), and the mixture was stirred for 10 minutes. Then, a solution of the compound of Reference example 135 (50.0 mg) in tetrahydrofuran (0.56 mL) was added thereto, and the mixture was stirred at room temperature for 3 hours. To the reaction mixture was added water, and the mixture was extracted with ethyl acetate. The organic layer was washed with brine, dried over sodium sulfate, filtrated, and then concentrated in vacuo. The obtained residue was purified by amino silica gel column chromatography (chloroform/ethyl acetate/methanol), and then the residue was purified by silica gel column chromatography (chloroform/methanol) to give the title compound (4.0 mg).

LC-MS [M+H]$^+$/Rt (min): 466.1/0.479 (Method C); $^1$H-NMR (DMSO-d$_6$) δ: 8.67 (1H, br s), 8.55 (1H, d, J=2.7 Hz), 7.65-7.61 (1H, m), 7.00 (2H, d, J=8.4 Hz), 6.75 (2H, d, J=8.4 Hz), 5.57 (2H, s), 5.35 (2H, s), 4.41 (2H, q, J=6.8 Hz), 4.32-4.30 (1H, m), 3.24 (1H, dd, J=13.9, 8.0 Hz), 3.00-2.75 (5H, m), 2.10 (1H, br s), 1.99-1.92 (1H, m), 1.76-1.49 (2H, m), 1.46-1.33 (4H, m).

Example 142

According to the method of Example 141, Example 142 was prepared by using the corresponding material compound.

| Example | ChemicalStructure | Instrumental analysis data |
|---|---|---|
| 142 | ![structure] | LC-MS [M + H]$^+$/Rt (min): 404.0/1.056 (Method A); $^1$H-NMR (400 MHz, DMSO-d$_6$) δ: 8.45-8.41 (2H, m), 7.56 (1H, dd, J = 1.8, 2.4), 7.30-7.20 (3H, m), 7.02-6.99 (2H, m), 5.52 (2H, s), 4.32 (2H, t, J = 6.4 Hz), 3.78 (3H, s), 2.70 (3H, s), 1.70 (2H, tt, J = 6.4, 7.9 Hz), 1.41 (2H, qt, J = 7.3, 7.9 Hz), 0.91 (3H, t, J = 7.3 Hz). |

Example 143

(4-{[6-Amino-2-ethoxy-8-(5-fluoropyridin-3-yl)-9H-purin-9-yl]methyl}phenyl) (4-methylpiperazin-1-yl) methanone

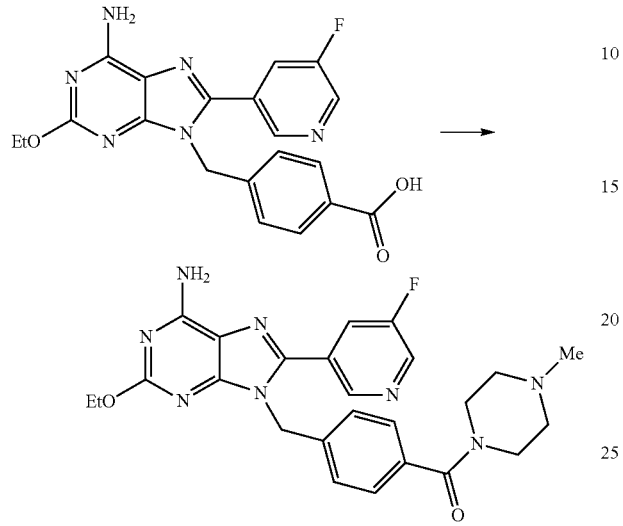

To a solution of the compound of Example 235 (66.3 mg) in dimethylformamide (5 mL) were added EDCl·HCl (63.3 mg), HOBT (21.7 mg), 1-methylpiperazine (0.027 mL), and diisopropylethylamine (0.056 mL), and the mixture was stirred at room temperature for 2 days. To the reaction mixture was added aqueous saturated sodium bicarbonate, and the mixture was extracted with chloroform. The organic layer was dried over sodium sulfate, filtrated, and then concentrated in vacuo. The residue was purified by silica gel column chromatography (chloroform/methanol) to give the title compound (60.5 mg).

LC-MS ([M+H]$^+$/Rt (min.)): 491.4/0.507; $^1$H-NMR (400 MHz, DMSO-d$_6$) δ: 8.68-8.67 (1H, m), 8.65 (1H, d, J=3.1 Hz), 7.98-7.94 (1H, m), 7.48 (2H, brs), 7.25 (2H, d, J=7.9 Hz), 7.03 (2H, d, J=7.9 Hz), 5.50 (2H, s), 4.26 (2H, t, J=4.9 Hz), 3.64-3.46 (2H, m), 3.24-3.10 (2H, m), 2.35-2.14 (4H, m), 2.16 (3H, s), 1.27 (3H, t, J=6.7 Hz).

Examples 144-147

According to the method of Example 143, Examples 144-147 were prepared by using the corresponding material compounds.

| Example | Chemical Structure | Instrumental analysis data |
|---|---|---|
| 144 | 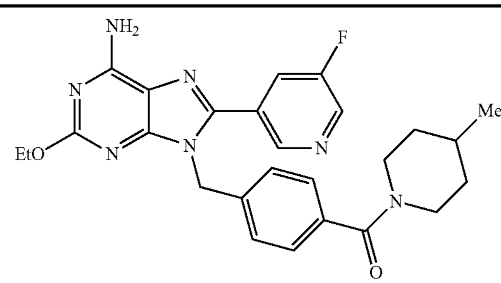 | LC-MS [M + H]$^+$/Rt (min): 490.5/0.891 (Method A); $^1$H-NMR (400 MHz, DMSO-d$_6$) δ: 8.68-8.67 (1H, m), 8.65 (1H, d, J = 2.4 Hz), 7.98-7.94 (1H, m), 7.48 (2H, brs), 7.23 (2H, d, J = 7.9 Hz), 7.02 (2H, d, J = 7.9 Hz), 5.50 (2H, s), 4.43-4.31 (1H, m), 4.27 (2H, q, J = 6.7 Hz), 3.40-3.27 (2H, m), 2.98-2.84 (1H, m), 2.76-2.62 (1H, m), 1.70-1.45 (2H, m), 1.27 (3H, t, J = 6.7 Hz), 1.08-0.93 (2H, m), 0.88 (3H, d, J = 6.1 Hz). |
| 145 | 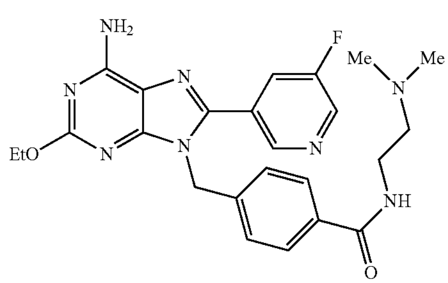 [SMILES: CCOc1nc(N)c2nc(-c3cncc(F)c3)n(Cc3ccc(C(=O)NCCN(C)C)cc3)c2n1] | LC-MS [M + H]$^+$/Rt (min): 479.5/0.541 (Method A); $^1$H-NMR (400 MHz, DMSO-d$_6$) δ: 8.69-8.68 (1H, m), 8.66 (1H, d, J = 2.4 Hz), 8.30 (1H, t, J = 5.5 Hz), 7.99-7.95 (1H, m), 7.70 (2H, d, J = 7.9 Hz), 7.48 (2H, brs), 7.06 (2H, d, J = 7.9 Hz), 5.52 (2H, s), 4.26 (2H, q, J = 7.3 Hz), 3.31-3.27 (2H, m), 2.34 (2H, t, J = 6.7 Hz), 2.13 (6H, s), 1.26 (3H, t, J = 7.3 Hz). |
| 146 | 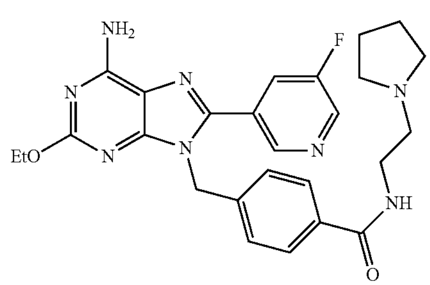 [SMILES: CCOc1nc(N)c2nc(-c3cncc(F)c3)n(Cc3ccc(C(=O)NCCN4CCCC4)cc3)c2n1] | LC-MS [M + H]$^+$/Rt (min): 505.1/0.569 (Method A); $^1$H-NMR (400 MHz, DMSO-d$_6$) δ: 8.69-8.68 (1H, m), 8.66 (1H, d, J = 2.4 Hz), 8.36 (1H, t, J = 5.5 Hz), 8.00-7.96 (1H, m), 7.70 (2H, d, J = 7.9 Hz), 7.49 (2H, brs), 7.06 (2H, d, J = 7.9 Hz), 5.52 (2H, s), 4.25 (2H, q, J = 7.3 Hz), 2.54-2.40 (8H, m), 1.68-1.61 (4H, m), 1.26 (3H, t, J = 7.3 Hz). |

| Example | Chemical Structure | Instrumental analysis data |
|---|---|---|
| 147 | 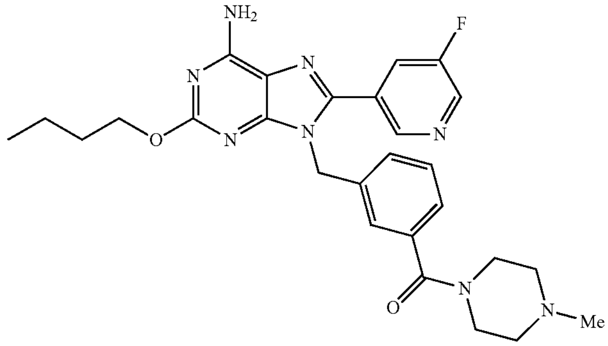 [SMILES: CCCCOc1nc(N)c2nc(-c3cncc(F)c3)n(Cc3cccc(C(=O)N4CCN(C)CC4)c3)c2n1] | LC-MS [M + H]+/Rt (min): 519.2/0.621 (Method A); 1H-NMR (400 MHz, DMSO-d6) δ: 8.68-8.67 (1H, m), 8.65 (1H, d, J = 2.4 Hz), 8.00-7.95 (1H, m), 7.50 (2H, brs), 7.33 (1H, dd, J = 7.3, 7.9 Hz), 7.21 (1H, d, J = 7.3 Hz), 7.06 (1H, d, J = 7.9 Hz), 6.94 (1H, s), 5.52 (2H, s), 4.22 (2H, t, J = 6.7 Hz), 3.60-3.46 (2H, m), 3.15-3.02 (2H, m), 2.34-2.20 (2H, m), 2.16 (3H, s), 2.14-2.02 (2H, m), 1.65 (2H, tt, J = 6.7, 7.9 Hz), 1.38 (2H, qt, J = 7.3, 7.9 Hz), 0.90 (3H, t, J = 7.3 Hz). |

Example 148

1-[4-(4-{[6-Amino-2-ethoxy-8-(5-fluoropyridin-3-yl)-9H-purin-9-yl]methyl}phenyl)piperidin-1-yl]-2-(dimethylamino)ethanone

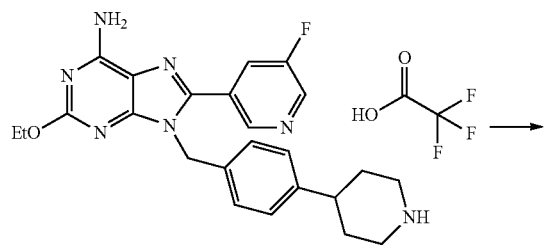

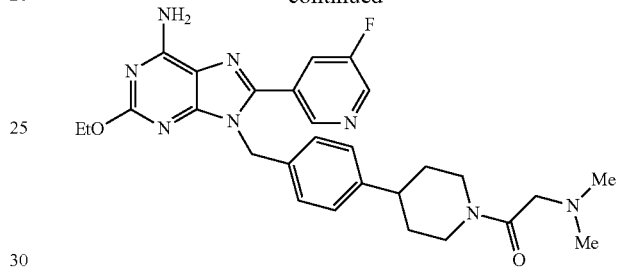

To a solution of the compound of Example 227 (68 mg) in N,N-dimethylformamide (4 mL) were added N,N-dimethylglycine hydrochloride (27.7 mg), N,N-diisopropylethylamine (0.070 mL), and HATU (64.5 mg) at room temperature. The reaction mixture was stirred for 16 hours, and then concentrated in vacuo. The residue was purified by silica gel column chromatography (chloroform/methanol) to give the title compound (40.7 mg).

LC-MS [M+H]+/Rt (min): 533.5/0.498 (Method C)

Example 149

According to the method of Example 148, Example 149 was prepared by using the corresponding material compound.

| Example | Chemical Structure | Instrumental analysis data |
|---|---|---|
| 149 | 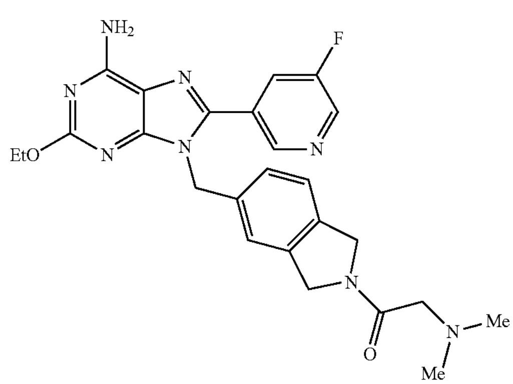 [SMILES: CCOc1nc(N)c2nc(-c3cncc(F)c3)n(Cc3ccc4c(c3)CN(C(=O)CN(C)C)C4)c2n1] | 1H-NMR (400 MHz, CDCl3) (mixture of rotamers, 1:1) δ: 8.66-8.63 (1H, m), 8.57-8.54 (1H, m), 7.66 (1H, ddd, J = 2.0, 6.8, 8.8 Hz), 7.22 (1H, dd, J = 23.8, 7.9 Hz), 7.09-6.92 (2H, m), 5.75 (2H, s), 5.45 (2H, s), 4.88 (1H, s), 4.84 (1H, s), 4.79 (1H, s), 4.75 (1H, s), 4.41 (2H, q, J = 7.1 Hz), 3.22 (1H, s), 3.20 (1H, s), 2.40 (3H, s), 2.38 (3H, s), 1.42 (3H, t, J = 7.1 Hz). |

Example 150

9-{4-[(Dimethylamino)methyl]benzyl}-8-(5-fluoro-pyridin-3-yl-2-methoxy-9H-purine-6-amine

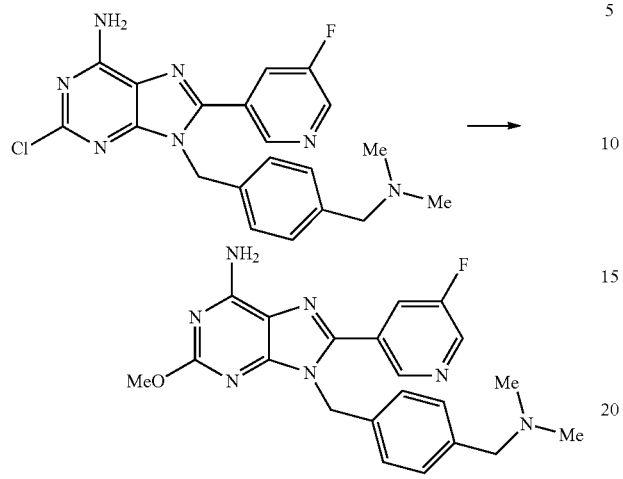

To a solution of the compound of Example 118 (70 mg) in 1,4-dioxane (1.9 mL) was added sodium methoxide (46 mg), and the mixture was stirred at 100° C. for 3 hours. To the reaction mixture was added water under ice temperature, and the mixture was extracted with ethyl acetate. The organic layer was washed with brine, dried over sodium sulfate, filtrated, and then concentrated in vacuo. The residue was purified by silica gel column chromatography (chloroform/methanol). The obtained solid was triturated with diethyl ether to give the title compound (20 mg).

LC-MS [M+H]$^+$/Rt (min): 408.5/0.498 (Method B); $^1$H-NMR (CDCl$_3$) δ: 8.65 (1H, br s), 8.53 d, J=2.4 Hz), 7.62-7.59 (1H, m), 7.26-7.24 (2H, m), 7.05 (2H, d, J=8.5 Hz), 5.58 (2H, br s), 5.43 (2H, s), 3.97 (3H, s), 3.45 (2H, s), 2.25 (6H, brs).

Examples 151-155

According to the method of Example 150, Examples 151-155 were prepared by using the corresponding material compounds.

| Example | Chemical Structure | Instrumental analysis data |
|---|---|---|
| 151 | 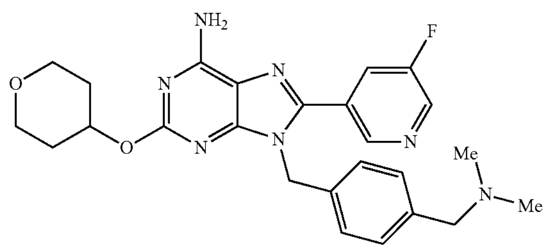 [SMILES: CN(C)Cc1ccc(Cn2c(-c3cncc(F)c3)nc3c(N)nc(OC4CCOCC4)nc32)cc1] | LC-MS [M + H]$^+$/Rt (min): 478.5/0.544 (Method B); $^1$H-NMR (CDCl$_3$) δ: 8.65 (1H, br s), 8.53 (1H, d, J = 3.1 Hz), 7.60-7.58 (1H, m), 7.23 (2H, d, J = 7.9 Hz), 7.02 (2H, d, J = 7.9 Hz), 5.70 (2H, s), 5.40 (2H, s), 5.22-5.16 (1H, m), 4.03-3.98 (2H, m), 3.61-3.55 (2H, m), 3.41 (2H, s), 2.22 (6H, s), 2.08-2.04 (2H, m), 1.90-1.82 (2H, m). |
| 152 | 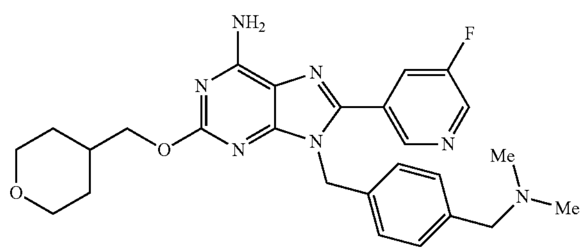 [SMILES: CN(C)Cc1ccc(Cn2c(-c3cncc(F)c3)nc3c(N)nc(OCC4CCOCC4)nc32)cc1] | LC-MS [M + H]$^+$/Rt (min): 492.6/0.582 (Method B); $^1$H-NMR (CDCl$_3$) δ: 8.64 (1H, s), 8.53 (1H, d, J = 2.4 Hz), 7.61-7.57 (1H, m), 7.26-7.24 (2H, m), 7.04 (2H, d, J = 7.9 Hz), 5.67 (2H, s), 5.42 (2H, s), 4.19 (2H, d, J = 6.7 Hz), 4.00 (2H, dd, J = 3.1, 11.6 Hz), 3.49-3.38 (4H, m), 2.28 (6H, s), 2.13-2.04 (2H, m), 1.79-1.76 (1H, m), 1.49-1.41 (2H, m). |
| 153 | 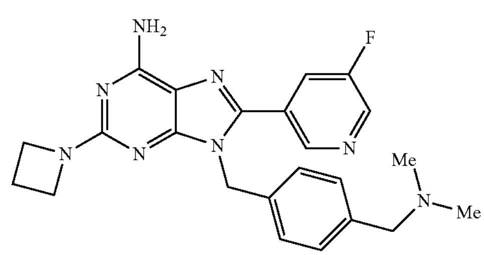 [SMILES: CN(C)Cc1ccc(Cn2c(-c3cncc(F)c3)nc3c(N)nc(N4CCC4)nc32)cc1] | LC-MS [M + H]$^+$/Rt (min): 433.5/0.501 (Method B); $^1$H-NMR (CDCl$_3$) δ: 8.63 (1H, br s), 8.47 (1H, d, J = 3.1 Hz), 7.59-7.55 (1H, m), 7.21 (2H, d, J = 7.9 Hz), 7.05 (2H, d, J = 7.9 Hz), 5.55 (2H, s), 5.35 (2H, s), 4.14-4.09 (4H, m), 3.37 (2H, s), 2.35-2.20 (2H, m), 2.20 (6H, s). |

| Example | Chemical Structure | Instrumental analysis data |
|---|---|---|
| 154 | 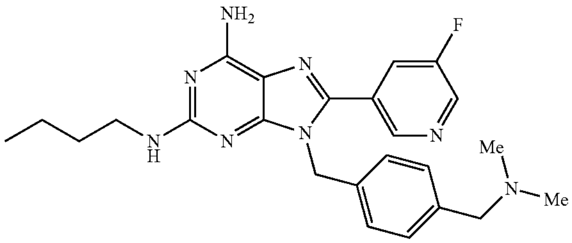 [SMILES: CCCCNc1nc(N)c2nc(-c3cncc(F)c3)n(Cc3ccc(CN(C)C)cc3)c2n1] | LC-MS [M + H]⁺/Rt (min): 449.5/0.551 (Method B); ¹H-NMR (CDCl₃) δ: 8.63 (1H, br s), 8.48 (1H, d, J = 2.7 Hz), 7.59-7.56 (1H, m), 7.22 (2H, d, J = 7.8 Hz), 7.06 (2H, d, J = 7.8 Hz), 5.45 (2H, s), 5.34 (2H, s), 4.91-4.89 (1H, m) 3.43-3.38 (4H, m), 2.21 (6H, s), 1.60-1.53 (2H, m), 1.43-1.34 (2H, m), 0.92 (3H, t, J = 7.3 Hz). |
| 155 | 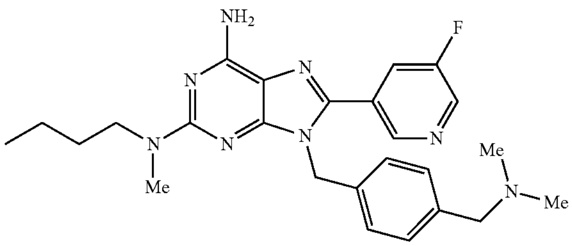 [SMILES: CCCCN(C)c1nc(N)c2nc(-c3cncc(F)c3)n(Cc3ccc(CN(C)C)cc3)c2n1] | LC-MS [M + H]⁺/Rt (min): 463.5/0.653 (Method B); ¹H-NMR (CDCl₃) δ: 8.64 (1H, br s), 8.47 (1H, d, J = 3.1 Hz), 7.61-7.58 (1H, m), 7.23 (2H, d, J = 8.4 Hz), 7.09 (2H, d, J = 8.4 Hz), 5.34 (2H, s), 5.29 (2H, s), 3.62 (2H, t, J = 7.3 Hz), 3.39 (2H, s), 3.13 (3H, s), 2.22 (6H, s), 1.61-1.54 (2H, m), 1.34-1.25 (2H, m), 0.90 (3H, t, J = 7.3 Hz). |

Example 156

9-{4-[(Dimethylamino)methyl]benzyl}-8-(5-fluoropyridin-3-yl)-2-methyl-9H-purine-6-amine

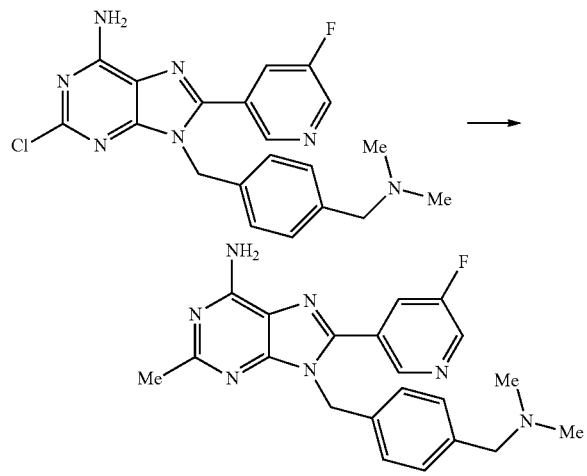

To a solution of the compound of Example 118 (30 mg) in tetrahydrofuran (0.728 mL) were added his (tri-tert-butylphosphine)palladium (7.4 mg) and methyltin chloride (2.0 mol/L a tetrahydrofuran solution, 0.182 mL), and the mixture was stirred at 60° C. for 4 hours. To the reaction mixture was added water, and the mixture was extracted with ethyl acetate. The organic layer was concentrated in vacuo. The residue was purified by amino silica gel column chromatography (chloroform/ethyl acetate). The obtained residue was purified by reverse-phase column chromatography (water/acetonitrile) to give the title compound (11.2 mg).

LC-MS [M+H]⁺/Rt (min): 392.4/0.411 (Method B); ¹H-NMR (CDCl₃) δ: 8.65 (1H, br s), 8.53 (1H, d, J=2.7 Hz), 7.61-7.58 (1H, m), 7.22 (2H, d, J=8.2 Hz), 6.98 (2H, d, J=8.2 Hz), 5.77 (2H, s), 5.48 (2H, s), 3.38 (2H, s), 2.62 (3H, s), 2.20 (6H, s).

Example 157

According to the method of Example 156, Example 157 was prepared by using the corresponding material compound.

| Example | Chemical Structure | Instrumental analysis data |
|---|---|---|
| 157 | 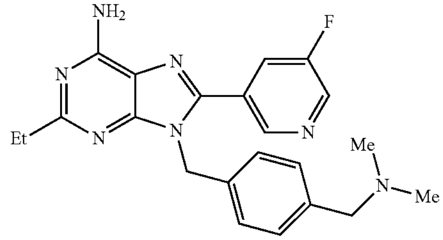 [SMILES: CCc1nc(N)c2nc(-c3cncc(F)c3)n(Cc3ccc(CN(C)C)cc3)c2n1] | LC-MS [M + H]⁺/Rt (min): 406.4/0.466 (Method B); ¹H-NMR (CDCl₃) δ: 8.66 (1H, br s), 8.54 (1H, d, J = 2.4 Hz), 7.62-7.59 (1H, m), 7.23 (2H, d, J = 8.2 Hz), 7.02 (2H, d, J = 8.2 Hz), 5.66 (2H, s), 5.49 (2H, s), 3.39 (2H, s), 2.87 (2H, q, J = 7.7 Hz), 2.22 (6H, s), 1.36 (3H, t, J = 7.7 Hz). |

Example 158

9-{4-[(Dimethylamino)methyl]benzyl}-8-(5-fluoro-pyridin-3-yl)-2-[(1-methoxypropan-2-yl)oxy]-9H-purine-6-amine

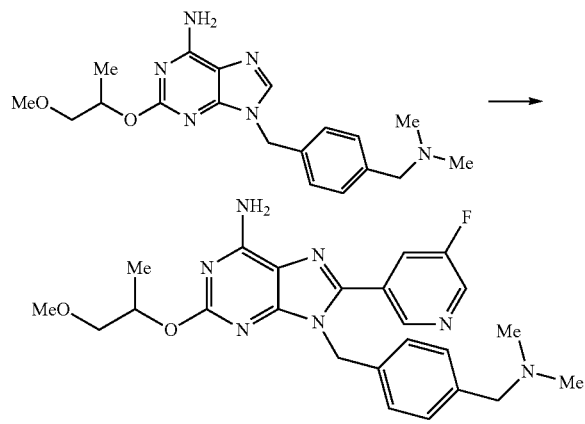

To a solution of the compound of Reference example 136 (105 mg) in N-methyl-2-pyrrolidone (1.42 mL) were added 3-bromo-5-fluoropyridine (0.058 mL), copper(I) iodide (162 mg), cesium carbonate (231 mg), and palladium(II) acetate 6.4 mg), and the mixture was stirred at 160° C. under microwave irradiation for 2 hours. The reaction mixture was filtrated through Celite. The filtrate was diluted with 28% ammonia, and extracted with ethyl acetate. The organic layer was washed with brine, dried over sodium sulfate, filtrated, and then concentrated in vacuo. The residue was purified by silica gel column chromatography (chloroform/methanol), and then purified by reverse-phase column chromatography (water/acetonitrile) to give the title compound (16.4 mg).

LC-MS [M+H]$^+$/Rt (min): 466.5/0.578 (Method B); $^1$H-NMR (CDCl$_3$) δ: 8.65-8.63 (1H, m), 8.52 (1H, d, J=2.4 Hz), 7.61-7.57 (1H, m), 7.23 (2H, d, J=7.9 Hz), 7.02 (2H, d, J=7.9 Hz), 5.69 (2H, br s), 5.40-5.35 (3H, m), 3.67-3.63 (1H, m), 3.50-3.46 (1H, m), 3.39-3.38 (5H, m), 2.21 (6H, s), 1.35 (3H, d, J=6.7 Hz).

Examples 159-162

According to the method of Example 158, Examples 159-162 were prepared by using the corresponding material compounds. As appropriate, microwave irradiation was used.

| Example | Chemical Structure | Instrumental analysis data |
|---|---|---|
| 159 | 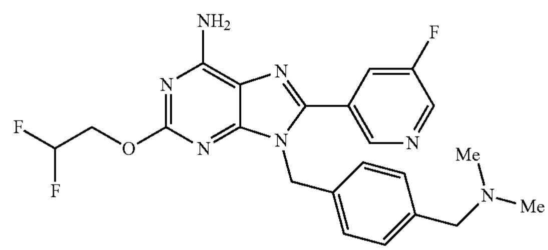 [SMILES: CN(C)Cc1ccc(Cn2c(-c3cncc(F)c3)nc3c(N)nc(OCC(F)F)nc32)cc1] | LC-MS [M + H]$^+$/Rt (min): 458.4/0.589 (Method B); $^1$H-NMR (CDCl$_3$) δ: 8.65 (1H, br s), 8.55 (1H, d, J = 3.1 Hz), 7.62-7.59 (1H, m), 7.26-7.24 (2H, m), 7.01 (2H, d, J = 7.9 Hz), 6.12 (1H, tt, J = 4.3, 55.5 Hz), 5.72 (2H, br s), 5.42 (2H, s), 4.56 (2H, td, J = 4.5, 13.3 Hz), 3.42 (2H, s), 2.23 (6H, s). |
| 160 | 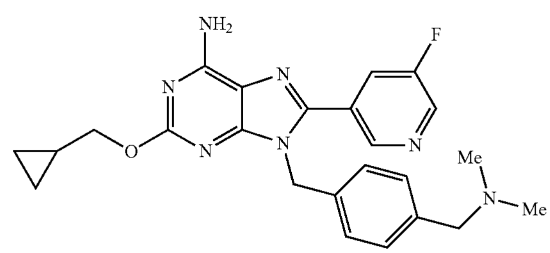 [SMILES: CN(C)Cc1ccc(Cn2c(-c3cncc(F)c3)nc3c(N)nc(OCC4CC4)nc32)cc1] | LC-MS [M + H]$^+$/Rt (min): 448.4/0.613 (Method B); $^1$H-NMR (CDCl$_3$) δ: 8.64 (1H, br s), 8.52 (1H, d, J = 2.4 Hz), 7.60-7.57 (1H, m), 7.23 (2H, d, J = 7.9 Hz), 7.02 (2H, d, J = 7.9 Hz), 5.68 (2H, s), 5.41 (2H, s), 4.17 (2H, d, J = 7.3 Hz), 3.39 (2H, s), 2.21 (6H, s), 1.34-1.25 (1H, m), 0.61-0.56 (2H, m), 0.37-0.33 (2H, m). |
| 161 | 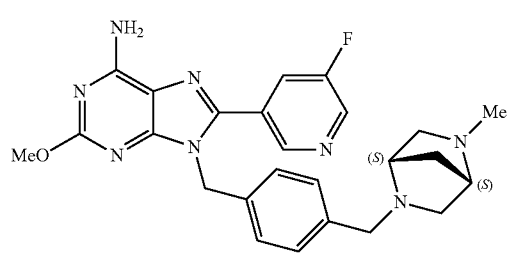 | LC-MS [M + H]$^+$/Rt (min): 475.4/0.562 (Method B); $^1$H-NMR (CDCl$_3$) δ: 8.66 (1H, br s), 8.54 (1H, d, J = 2.7 Hz), 7.62-7.59 (1H, m), 7.30-7.26 (2H, m), 7.02 (2H, d, J = 8.2 Hz), 5.58 (2H, s), 5.41 (2H, s), 3.98 (3H, s), 3.70 (1H, d, J = 13.4 Hz), 3.63 (1H, d, J = 13.4 Hz), 3.24 (2H, s), 2.88 (1H, br s), 2.74-2.61 (3H, m), 2.41 (3H, s), 1.73 (2H, br s). |

-continued

| Example | Chemical Structure | Instrumental analysis data |
|---|---|---|
| 162 | 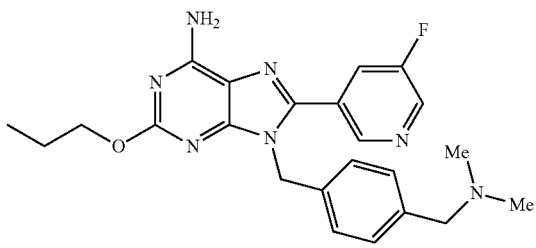 [SMILES: CCCOc1nc(N)c2nc(-c3cncc(F)c3)n(Cc3ccc(CN(C)C)cc3)c2n1] | LC-MS [M + H]⁺/Rt (min): 436.4/0.724 (Method C); ¹H-NMR (CDCl₃) δ: 8.66 (1H, br s), 8.54 (1H, d, J = 2.7 Hz), 7.62-7.59 (1H, m), 7.30-7.26 (2H, m), 7.02 (2H, d, J = 8.2 Hz), 5.58 (2H, s), 5.41 (2H, s), 3.98 (3H, s), 3.70 (1H, d, J = 13.4 Hz), 3.63 (1H, d, J = 13.4 Hz), 3.24 (2H, s), 2.88 (1H, br s), 2.74-2.61 (3H, m), 2.41 (3H, s), 1.73 (2H, br s). |

Example 163

9-{[1-(1-Azabicyclo[2.2.2]oct-3-ylmethyl)-1H-pyrazol-4-yl]methyl}-2-ethoxy-8-(5-fluoropyridin-3-yl)-6-methyl-9H-purine

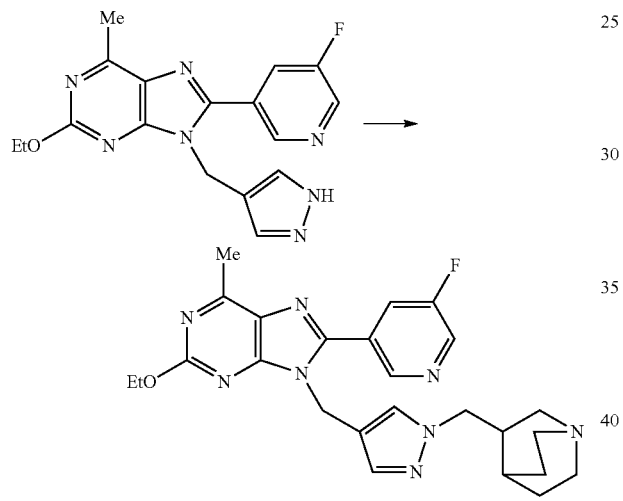

To a solution of the compound of Example 207 (50 mg) in tetrahydrofuran (0.70 mL) were added 1-azabicyclo[2,2,2]oct-3-ylmethanol (24 mg) and (cyanomethylene)tributylphosphorane (0.056 mL), and the mixture was stirred at 80° C. for 3 hours. To the reaction mixture was added water, and the mixture was extracted with ethyl acetate. The organic layer was concentrated in vacuo. The obtained residue was purified by amino silica gel column chromatography (chloroform/methanol), and then purified by purified by reverse-phase silica gel column chromatography (acetonitrile/water) to give the title compound. (24 mg).

LC-MS [M+H]⁺/Rt (min): 477.1/0.467 (Method C); ¹H-NMR (CDCl₃) δ: 8.78 (1H, s), 8.62 (1H, d, J=3.1 Hz), 7.79-7.76 (1H, m), 7.32 (1H, s), 7.22 (1H, s), 5.31 (2H, s), 4.51 (2H, q, J=7.1 Hz), 4.00 (2H, d, J=7.9 Hz), 2.98-2.93 (1H, m), 2.87-2.71 (7H, m), 2.38-2.33 (1H, m), 2.19-2.13 (1H, m), 1.68-1.55 (2H, m), 1.49-1.40 (6H, m).

Example 164

According to the method of Example 163, Example 164 was prepared by using the corresponding material compound.

| Example | Chemical Structure | Instrumental analysis data |
|---|---|---|
| 164 | 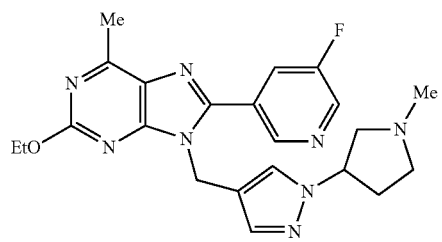 [SMILES: CCOc1nc(C)c2nc(-c3cncc(F)c3)n(Cc3cnn(C4CCN(C)C4)c3)c2n1] | LC-MS [M + H]⁺/Rt (min): 437.1/0.455 (Method C); ¹H-NMR (CDCl₃) δ: 8.79 (1H, t, J = 1.5 Hz), 8.63 (1H, d, J = 3.1 Hz), 7.80-7.77 (1H, m), 7.45 (1H, s), 7.31 (1H, s), 5.30 (2H, s), 4.81-4.74 (1H, m), 4.52 (2H, q, J = 7.1 Hz), 2.89-2.73 (6H, m), 2.48-2.36 (5H, m), 2.07-1.98 (1H, m), 1.49 (3H, t, J = 7.1 Hz). |

Example 165

9-[4-(1-Azabicyclo[2.2.2]oct-3-yl)benzyl]-8-(5-fluoropyridin-3-yl)-2-methoxy-6-methyl-9H-purine

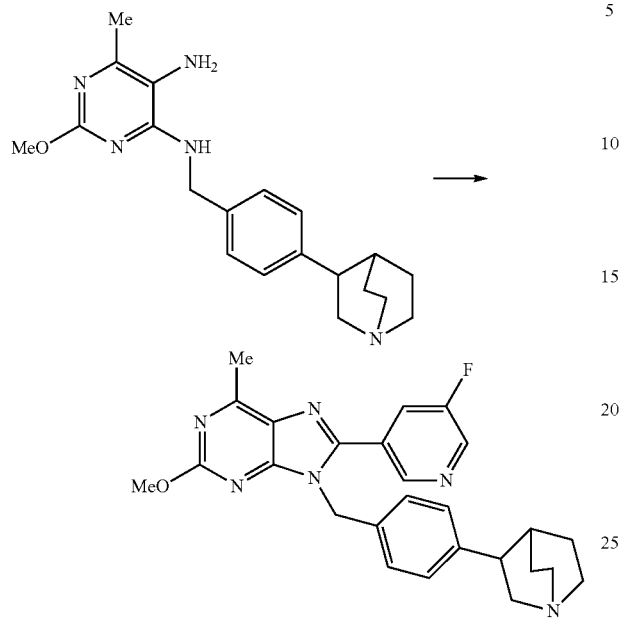

To a solution of the compound of Reference example 107 (299 mg) in 2-propanol (4 mL) were added 5-fluoronicotinaldehyde (159 mg) and ferric(III) chloride (549 mg) at room temperature, and the mixture was refluxed with heating. The reaction mixture was stirred for 2 hours. To the reaction mixture was added water, and the mixture was extracted with chloroform/methanol. The organic layer was dried over sodium sulfate, filtrated, and then concentrated in vacuo. The residue was purified by silica gel column chromatography (chloroform/methanol) to give the title compound (231 mg).

LC-MS [M+H]$^+$/Rt (min): 459.1/0.488 (Method C); $^1$H-NMR (400 MHz, CDCl$_3$) δ: 8.69-8.65 (1H, m), 8.57 (1H, d, J=3.1 Hz), 7.70-7.66 (1H, m), 7.18 (2H, d, J=7.9 Hz), 7.02 (2H, d, J=7.9 Hz), 5.46 (2H, s), 4.06 (3H, s), 3.33-3.24 (1H, m), 3.04-2.96 (1H, m), 2.96-2.77 (8H, m), 1.88-1.82 (1H, m), 1.75-1.67 (2H, m), 1.59-1.50 (1H, m), 1.39-1.26 (1H, m).

Examples 1.66-172

According to the method of Example 165, Examples 166-172 were prepared by using the corresponding material compounds.

| Example | Chemical Structure | Instrumental analysis data |
|---|---|---|
| 166 | 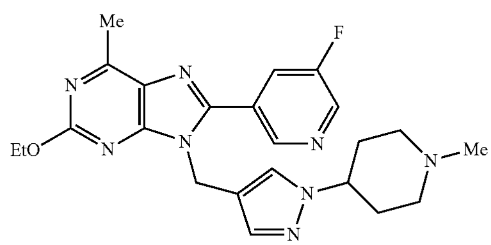 [SMILES: CCOc1nc(C)c2nc(-c3cncc(F)c3)n(Cc3cnn(C4CCN(C)CC4)c3)c2n1] | LC-MS [M + H]$^+$/Rt (min): 451.1/0.471 (Method C); $^1$H-NMR (CDCl$_3$) δ: 8.78-8.78 (1H, m), 8.63 (1H, d, J = 3.1 Hz), 7.80-7.76 (1H, m), 7.33 (1H, s), 7.30 (1H, s), 5.31 (2H, s), 4.52 (2H, q, J = 7.1 Hz), 4.07-4.00 (1H, m), 2.96-2.93 (2H, m), 2.80 (3H, s), 2.31 (3H, s), 2.17-1.85 (6H, m), 1.49 (3H, t, J = 7.1 Hz). |
| 167 | 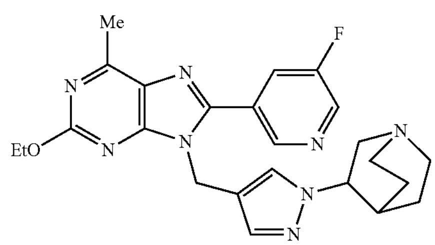 [SMILES: CCOc1nc(C)c2nc(-c3cncc(F)c3)n(Cc3cnn(C4CN5CCC4CC5)c3)c2n1] | LC-MS [M + H]$^+$/Rt (min): 463.0/0.504 (Method C); $^1$H-NMR (CDCl$_3$) δ: 8.80 (1H, br s), 8.64 (1H, d, J = 2.4 Hz), 7.82-7.79 (1H, m), 7.38 (1H, s), 7.36 (1H, s), 5.34 (2H, s), 4.53 (2H, q, J = 7.1 Hz), 4.29-4.26 (1H, m), 3.51-3.46 (1H, m), 3.34-3.28 (1H, m), 3.06-2.81 (7H, m), 2.04-2.02 (1H, m), 1.79-1.77 (6H, m), 1.41-1.34 (1H, m). |
| 168 | 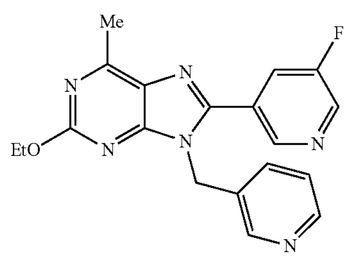 [SMILES: CCOc1nc(C)c2nc(-c3cncc(F)c3)n(Cc3cccnc3)c2n1] | LC-MS [M + H]$^+$/Rt (min): 365.2/0.685 (Method C); $^1$H-NMR (400 MHz, CDCl$_3$) δ: 8.69-8.66 (1H, m), 8.61 (1H, d, J = 2.7 Hz), 8.55-8.52 (1H, m), 8.41 (1H, d, J = 1.8 Hz), 7.73-7.68 (1H, m), 7.41-7.36 (1H, m), 7.22 (1H, dd, J = 4.8, 8.0 Hz), 5.50 (2H, s), 4.47 (2H, q, J = 7.2 Hz), 2.82 (3H, s), 1.45 (3H, t, J = 7.2 Hz). |

| Example | Chemical Structure | Instrumental analysis data |
|---|---|---|
| 169 | (structure) | ¹H-NMR (CDCl₃) δ: 7.99-7.96 (1H, m), 7.87 (1H, d, J = 2.4 Hz), 7.00-6.96 (1H, m), 6.48 (2H, d, J = 7.9 Hz), 6.31 (2H, d, J = 7.9 Hz), 4.75 (2H, s), 3.77 (2H, q, J = 7.1 Hz), 2.63-2.55 (1H, m), 2.35-2.27 (1H, m), 2.26-2.08 (8H, m), 1.19-1.14 (1H, m), 1.04-0.98 (2H, m), 0.94-0.82 (1H, m), 0.74 (3H, t, J = 7.1 Hz), 0.67-0.58 (1H, m). |
| 170 | (structure) | LC-MS [M + H]⁺/Rt (min): 447.3/0.581 (Method C); ¹H-NMR (CDCl₃) δ: 8.69-8.65 (1H, m), 8.56 (1H, d, J = 2.4 Hz), 7.67-7.62 (1H, m), 7.24 (2H, d, J = 7.9 Hz), 6.99 (2H, d, J = 7.9 Hz), 5.44 (2H, s), 4.47 (2H, q, J = 7.1 Hz), 3.22-3.16 (1H, m), 2.97 (1H, dd, J = 9.2, 9.2 Hz), 2.82 (3H, s), 2.24 (1H, dd, J = 9.2, 17.6 Hz), 2.17-2.06 (4H, m), 1.98-1.82 (1H, m), 1.82-1.71 (1H, m), 1.71-1.62 (1H, m), 1.44 (3H, t, J = 7.1 Hz). |
| 171 | (structure) | ¹H-NMR (CDCl₃) δ: 8.69-8.66 (1H, m), 8.60 (1H, d, J = 3.1 Hz), 8.33 (1H, d, J = 2.4 Hz), 7.74-7.69 (1H, m), 7.32 (1H, dd, J = 7.9, 2.4 Hz), 7.10 (1H, d, J = 7.9 Hz), 5.46 (2H, s), 4.47 (2H, q, J = 7.1 Hz), 3.46-3.37 (1H, m), 3.22-3.13 (1H, m), 3.04-2.82 (4H, m), 2.81 (3H, s), 2.79-2.73 (1H, m), 2.00-1.95 (1H, m), 1.74-1.68 (2H, m), 1.59-1.47 (1H, m), 1.45 (3H, t, J = 7.1 Hz), 1.32-1.22 (1H, m). |

-continued

| Example | Chemical Structure | Instrumental analysis data |
|---|---|---|
| 172 | (structure shown) | $^1$H-NMR (CDCl$_3$) δ: 8.67-8.63 (1H, m), 8.57 (1H, d, J = 2.4 Hz), 7.73-7.65 (1H, m), 6.98-6.85 (3H, m), 5.49 (2H, s), 4.45 (2H, q, J = 7.1 Hz), 3.32-3.23 (1H, m), 2.99-2.79 (6H, m), 2.81 (3H, s), 1.91-1.82 (1H, m), 1.73-1.66 (2H, m), 1.60-1.48 (1H, m), 1.43 (3H, t, J = 7.1 Hz), 1.39-1.27 (1H, m). |

Examples 173, 174

9-{4-[(5S)-1,4-Diazabicyclo[3.2.1]oct-4-ylmethyl]benzyl}-2-ethoxy-8-(5-fluoropyridin-3-yl)-6-methyl-9H-purine; 9-{4-[(5R)-1,4-diazabicyclo[3.2.1]oct-4-ylmethyl]benzyl}-2-ethoxy-8-(5-fluoropyridin-3-yl)-6-methyl-9H-purine

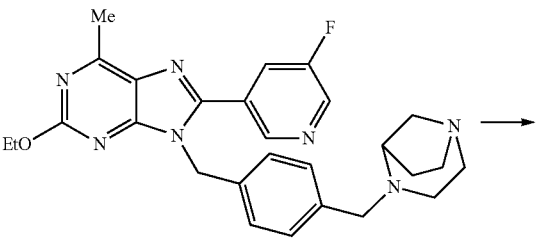

The compound of Example 119 (180 mg) was optically separated in the following conditions to obtain the title compounds (Example 173: 75.4 mg-first peak: 33.0 min, Example 174: 70.2 mg-second peak: 43.1 min).

Column: CHIRALPAK™ AD-H; Solvent: Solution A: hexane, Solution B: ethanol/2-propanol/diethylamine=2/1/0.3%; Mobile phase condition: A/B=70/30; Flow rate: 10 mL/min; Detection UV: 220 nm; Column temperature: 40° C.

| Example | Instrumental analysis data |
|---|---|
| 173 | $^1$H-NMR (400 MHz, CDCl$_3$) δ: 8.70-8.67 (1H, m), 8.58 (1H, d, J = 2.4 Hz), 7.71-7.64 (1H, m), 7.25 (3H, d, J = 7.9 Hz), 7.01 (2H, d, J = 7.9 Hz), 5.47 (2H, s), 4.49 (2H, q, J = 7.1 Hz), 3.36 (2H, dd, J = 13.4, 19.5 Hz), 3.15-3.10 (1H, m), 3.06-2.94 (2H, m), 2.84 (3H, s), 2.83-2.74 (1H, m), 2.64 (1H, dd, J = 4.0, 13.4 Hz), 2.58-2.51 (1H, m), 2.48 (1H, dd, J = 4.6, 11.9 Hz), 2.32-2.23 (1H, m), 2.05-1.95 (1H, m), 1.47 (3H, t, J = 7.1 Hz). |
| 174 | $^1$H-NMR (400 MHz, CDCl$_3$) δ: 8.70-8.67 (1H, m), 8.58 (1H, d, J = 2.4 Hz), 7.71-7.64 (1H, m), 7.25 (3H, d, J = 7.9 Hz), 7.01 (2H, d, J = 7.9 Hz), 5.47 (2H, s), 4.49 (2H, q, J = 7.1 Hz), 3.36 (2H, dd, J = 13.4, 19.5 Hz), 3.15-3.10 (1H, m), 3.06-2.94 (2H, m), 2.84 (3H, s), 2.83-2.74 (1H, m), 2.64 (1H, dd, J = 4.0, 13.4 Hz), 2.58-2.51 (1H, m), 2.48 (1H, dd, J = 4.6, 11.9 Hz), 2.32-2.23 (1H, m), 2.05-1.95 (1H, m), 1.47 (3H, t, J = 7.1 Hz). |

Examples 175, 176

9-{4-[(3R)-1-Azabicyclo[2.2.2]oct-3-yl]benzyl}-2-ethoxy-8-(5-fluoropyridin-3-yl)-9H-purine-6-amine;
9-{4-[(3S)-1-azabicyclo[2.2.2]oct-3-yl]benzyl}-2-ethoxy-8-(5-fluoropyridin-3-yl)-9H-purine-6-amine

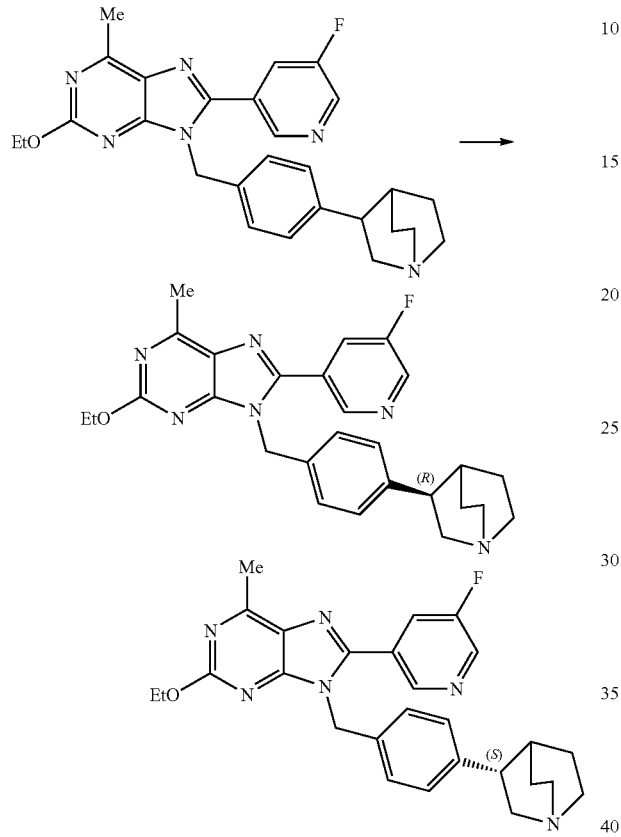

The compound of Example 46 (13.0 mg) was optically separated in the following conditions to obtain the title compounds (Example 175: 6.1 mg-first peak: 61.4 min, Example 176: 6.1 mg-second peak: 78.8 min).

Column: CHIRALPAK™ AS-H; Solvent: Solution A: hexane, Solution B: ethanol/2-propanol/diethylamine=2/1/0.3%; Mobile phase condition: A/B=93/7; Flow rate: 10 mL/min; Detection UV: 220 nm; Column temperature: 40° C.

| Example | Instrumental analysis data |
|---------|----------------------------|
| 175 | $^1$H-NMR (400 MHz, CDCl$_3$) δ: 8.63-8.65 (1H, m), 8.56 (1H, d, J = 3.1 Hz), 7.67-7.60 (1H, m), 7.21 (2H, d, J = 7.9 Hz), 7.08 (2H, d, J = 7.9 Hz), 5.64 (2H, s), 5.43 (2H, s), 4.42 (2H, q, J = 7.0 Hz), 3.40-3.31 (1H, m), 3.13-3.05 (1H, m), 3.05-2.84 (5H, m), 1.95-1.91 (1H, m), 1.81-1.75 (2H, m), 1.69-1.58 (1H, m), 1.43 (3H, t, J = 7.0 Hz), 1.41-1.35 (1H, m). |
| 176 | $^1$H-NMR (400 MHz, CDCl$_3$) δ: 8.68-8.65 (1H, m), 8.56 (1H, d, J = 3.1 Hz), 7.67-7.60 (1H, m), 7.21 (2H, d, J = 7.9 Hz), 7.08 (2H, d, J = 7.9 Hz), 5.64 (2H, s), 5.43 (2H, s), 4.42 (2H, q, J = 7.0 Hz), 3.40-3.31 (1H, m), 3.13-3.05 (1H, m), 3.05-2.84 (5H, m), 1.95-1.91 (1H, m), 1.81-1.75 (2H, m), 1.69-1.58 (1H, m), 1.43 (3H, t, J = 7.0 Hz), 1.41-1.35 (1H, m). |

Examples 177 and 178

9-{4-[(3R)-1-Azabicyclo[2.2.2]oct-3-yl]benzyl}-8-(5-fluoropyridin-3-yl)-2-methoxy-6-methyl-9H-purine; 9-{4-[(3S)-1-azabicyclo[2.2.2]oct-3-yl]benzyl}-8-(5-fluoropyridin-3-yl)-2-methoxy-6-methyl-9H-purine

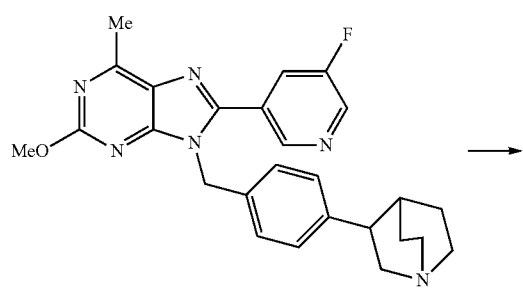 →

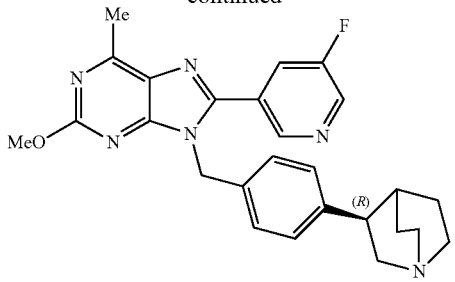

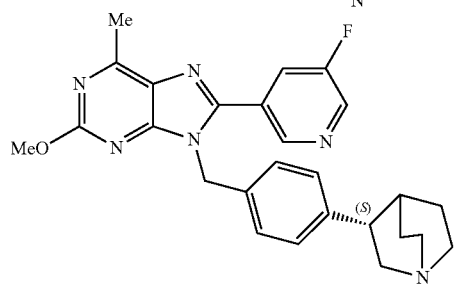

The compound of Example 165 (30.0 mg) was optically separated in the following conditions to obtain the title compounds (Example 177: 8.6 mg-first peak: 24.1 min, Example 178: 6.6 mg-second peak: 34.5 min).

Column: CHIRALPAK™ AS-H; Solvent: Solution A: hexane, Solution B: ethanol/2-propanol/diethylamine/methanol=2/1/0.3/2%; Mobile phase condition: A/B=93/7; Flow rate: 10 mL/min; Detection UV: 220 nm; Column temperature: 40° C.

| Example | Instrumental analysis data |
|---|---|
| 177 | $^1$H-NMR (400 MHz, CDCl$_3$) δ: 8.69-9.65 (1H, m), 8.57 (1H, d, J = 3.1 Hz), 7.70-7.66 (1H, m), 7.18 (2H, d, J = 7.9 Hz), 7.02 (2H, d, J = 7.9 Hz), 5.46 (2H, s), 4.06 (3H, s), 3.33-3.24 (1H, m), 3.04-2.96 (1H, m), 2.96-2.77 (8H, m), 1.88-1.82 (1H, m), 1.75-1.67 (2H, m), 1.59-1.50 (1H, m), 1.39-1.26 (1H, m). |
| 178 | $^1$H-NMR (400 MHz, CDCl$_3$) δ: 8.69-9.65 (1H, m), 8.57 (1H, d, J = 3.1 Hz), 7.70-7.66 (1H, m), 7.18 (2H, d, J = 7.9 Hz), 7.02 (2H, d, J = 7.9 Hz), 5.46 (2H, s), 4.06 (3H, s), 3.33-3.24 (1H, m), 3.04-2.96 (1H, m), 2.96-2.77 (8H, m), 1.88-1.82 (1H, m), 1.75-1.67 (2H, m), 1.59-1.50 (1H, m), 1.39-1.26 (1H, m). |

Examples 179-199

According to the method of Example 1, Examples 179-199 were prepared by using the corresponding material compounds. As appropriate, microwave irradiation was used.

| Example | Chemical Structure | Instrumental analysis data |
|---|---|---|
| 179 | 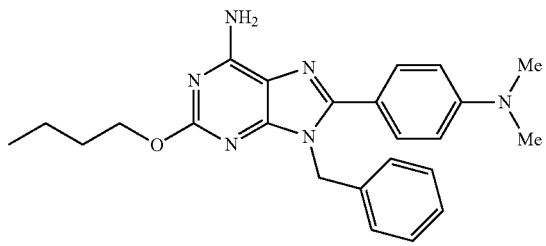 [SMILES: CCCCOc1nc(N)c2nc(-c3ccc(N(C)C)cc3)n(Cc3ccccc3)c2n1] | LC-MS [M + H]$^+$/Rt (min): 417.3/1.105 (Method A); $^1$H-NMR (400 MHz, DMSO-d$_6$) δ: 7.48-7.44 (2H, m), 7.31-7.20 (5H, s), 7.02 (2H, d, J = 6.7 Hz), 5.36 (2H, s), 4.17 (2H, t, J = 6.7 Hz), 2.93 (6H, s), 1.61 (2H, tt, J = 6.7, 7.9 Hz), 1.36 (2H, qt, J = 7.3, 7.9 Hz), 0.88 (3H, t, J = 7.3 Hz). |

-continued

| Example | Chemical Structure | Instrumental analysis data |
|---|---|---|
| 181 | | LC-MS: [M + H]⁺/Rt (min): 428.2/0.621 (Method A); $^1$H-NMR (400 MHz, DMSO-d$_6$) δ: 8.68-8.66 (2H, m), 8.52-8.50 (2H, m), 7.99-7.95 (1H, m), 7.59 (2H, brs), 7.37 (2H, d J = 6.1 Hz), 7.22-7.18 (3H, m), 6.93-6.90 (2H, m), 5.46 (2H, s), 5.40 (2H, s). |
| 181 | | LC-MS: [M + H]⁺/Rt (min): 512.3/0.486 (Method A); $^1$H-NMR (400 MHz, DMSO-d$_6$) δ: 9.10-9.08 (2H, m), 8.54-8.53 (1H, m), 7.58 (2H, brs), 7.17 (2H, d, J = 7.9 Hz), 6.98 (2H, d, J = 7.9 Hz), 5.50 (2H, s), 4.35 (2H, t, J = 4.8 Hz), 3.61 (2H, t, J = 4.8 Hz), 3.28 (3H, s), 3.26 (2H, s), 2.06 (6H, s). |
| 182 | 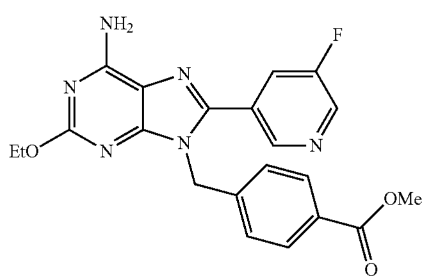 [SMILES: CCOc1nc(N)c2nc(-c3cncc(F)c3)n(Cc3ccc(C(=O)OC)cc3)c2n1] | LC-MS [M + H]⁺/Rt (min): 423.5/0.844 (Method A) |
| 183 | 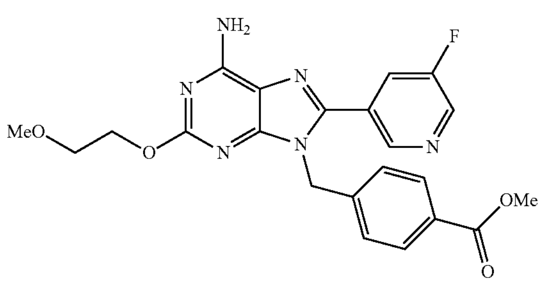 [SMILES: COCCOc1nc(N)c2nc(-c3cncc(F)c3)n(Cc3ccc(C(=O)OC)cc3)c2n1] | LC-MS [M + H]⁺/Rt (min): 453.1/0.778 (Method A) |
| 184 | 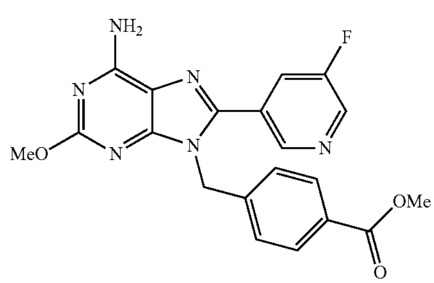 [SMILES: COC(=O)c1ccc(Cn2c(-c3cncc(F)c3)nc3c(N)nc(OC)nc32)cc1] | LC-MS [M + H]⁺/Rt (min): 409.4/0.813 (Method A) |

-continued

| Example | Chemical Structure | Instrumental analysis data |
|---|---|---|
| 185 | 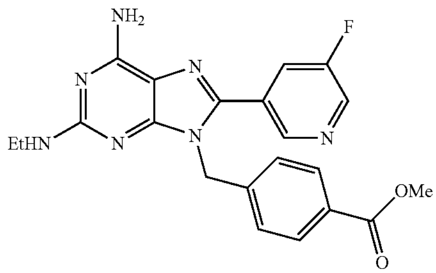 | LC-MS [M + H]⁺/Rt (min): 422.4/0.721 (Method A) |
| 186 | 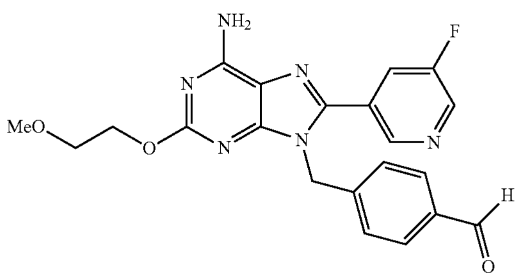 [SMILES: COCCOc1nc(N)c2nc(-c3cncc(F)c3)n(Cc3ccc(C=O)cc3)c2n1] | LC-MS [M + H]⁺/Rt (min): 423.3/0.714 (Method A) |
| 187 | 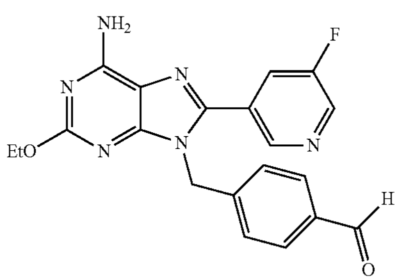 [SMILES: CCOc1nc(N)c2nc(-c3cncc(F)c3)n(Cc3ccc(C=O)cc3)c2n1] | LC-MS [M + H]⁺/Rt (min): 393.3/0.775 (Method A) |
| 188 | 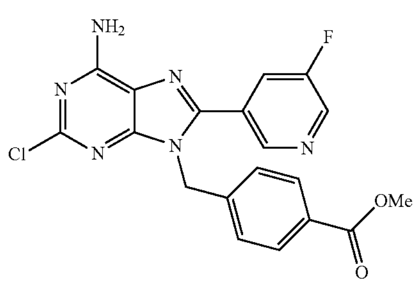 [SMILES: COC(=O)c1ccc(Cn2c(-c3cncc(F)c3)nc3c(N)nc(Cl)nc32)cc1] | ¹H-NMR (CDCl₃) δ: 8.63-8.58 (2H, m), 7.98 (2H, d, J = 8.2 Hz), 7.62-7.59 (1H, m), 7.11 (2H, d, J = 8.2 Hz), 5.91 (2H, br s), 5.54 (2H, s), 3.90 (3H, s). |
| 189 | 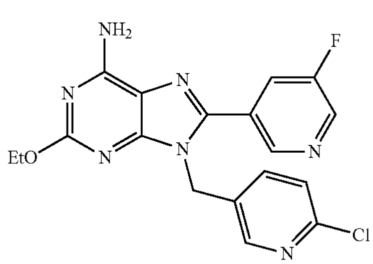 [SMILES: CCOc1nc(N)c2nc(-c3cncc(F)c3)n(Cc3ccc(Cl)nc3)c2n1] | ¹H-NMR (CDCl₃) δ: 8.65-8.60 (2H, m), 8.21 (1H, d, J = 2.7 Hz), 7.70-7.63 (1H, m), 7.43 (1H, dd, J = 2.7, 8.2 Hz), 7.27-7.25 (1H, m), 5.64 (2H, br s), 5.42 (2H, s), 4.39 (2H, q, J = 7.2 Hz), 1.42 (3H, t, J = 7.2 Hz). |

| Example | Chemical Structure | Instrumental analysis data |
| --- | --- | --- |
| 190 | 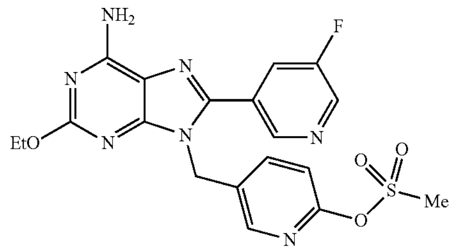 [SMILES: CCOc1nc(N)c2nc(-c3cncc(F)c3)n(Cc3ccc(OS(C)(=O)=O)nc3)c2n1] | ¹H-NMR (DMSO-D₆) δ: 8.81-8.80 (1H, m), 8.66 (1H, d, J = 3.1 Hz), 8.46 (1H, d, J = 3.1 Hz), 8.18-8.15 (1H, m), 7.80 (1H, dd, J = 2.4, 8.5 Hz), 7.50-7.44 (3H, m), 5.55 (2H, s), 4.23 (2H, q, J = 7.1 Hz), 3.42 (3H, s), 1.24 (3H, t, J = 7.1 Hz). |
| 191 | 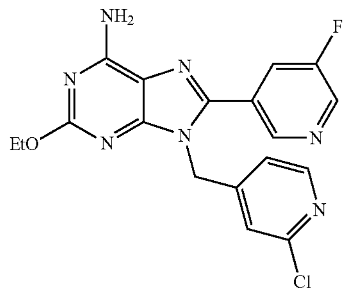 [SMILES: CCOc1nc(N)c2nc(-c3cncc(F)c3)n(Cc3ccnc(Cl)c3)c2n1] | LC-MS [M + H]⁺/Rt (min): 400.3/0.664 (Method C); ¹H-NMR (400 MHz, CDCl₃) δ: 8.59-8.55 (2H, m), 8.35 (1H, d, J = 5.2 Hz), 7.69-7.64 (1H, m), 7.06 (1H, s), 6.94 (1H, dd, J = 5.2, 1.5 Hz), 5.71 (2H, s), 5.41 (2H, S), 4.37 (2H, q, J = 7.1 Hz), 1.40 (3H, t, J = 7.1 Hz). |
| 192 | 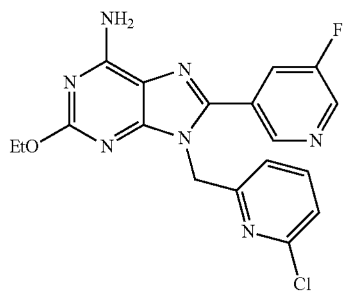 [SMILES: CCOc1nc(N)c2nc(-c3cncc(F)c3)n(Cc3cccc(Cl)n3)c2n1] | LC-MS [M + H]⁺/Rt (min): 400.4/0.664 (Method C); ¹H-NMR (400 MHz, CDCl₃) δ: 8.81 (1H, s), 8.59-8.55 (1H, m), 8.04-7.98 (1H, m), 7.62 (1H, dd, J = 7.6, 7.9 Hz), 7.29-7.26 (1H, m), 7.15 (1H, d, J = 7.9 Hz), 5.61 (2H, s), 5.45 (2H, s), 4.36 (2H, q, J = 6.9 Hz), 1.39 (3H, t, J = 6.9 Hz) |
| 193 | 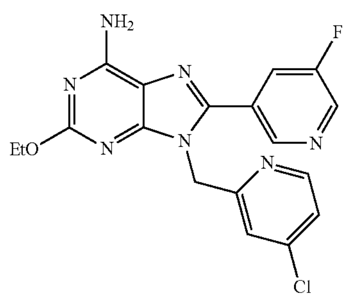 [SMILES: CCOc1nc(N)c2nc(-c3cncc(F)c3)n(Cc3cc(Cl)ccn3)c2n1] | ¹H-NMR (400 MHz, CDCl₃) δ: 8.90-8.86 (1H, m), 8.57 (1H, d, J = 3.1 Hz), 8.46 (1H, d, J = 5.5 Hz), 8.08-8.04 (1H, m), 7.39 (1H, d, J = 1.2 Hz), 7.25-7.23 (1H, m), 5.60 (2H, s), 5.46 (2H, s), 4.39 (2H, q, J = 7.1 Hz), 1.41 (3H, t, J = 7.1 Hz). |
| 194 | 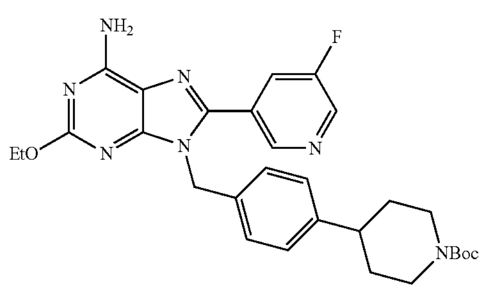 [SMILES: CCOc1nc(N)c2nc(-c3cncc(F)c3)n(Cc3ccc(C4CCN(C(=O)OC(C)(C)C)CC4)cc3)c2n1] | LC-MS [M + H]⁺/Rt (min): 548.5/1.105 (Method C); ¹H-NMR (400 MHz, CDCl₃) δ: 8.65-8.63 (1H, m), 8.54 (1H, d, J = 2.7 Hz), 7.62 (1H, ddd, J = 2.0, 2.7, 9.2 Hz), 7.12 (2H, d, J = 8.2 Hz), 7.02 (2H, d, J = 8.2 Hz), 5.63 (2H, s), 5.39 (2H, s), 4.40 (2H, q, J = 7.1 Hz), 4.30-4.13 (2H, m), 2.83-2.72 (2H, m), 2.66-2.54 (1H, m), 1.82-1.72 (2H, m), 1.61-1.49 (2H, m), 1.47 (9H, s), 1.41 (3H, t, J = 7.1 Hz). |

| Example | Chemical Structure | Instrumental analysis data |
|---|---|---|
| 195 | 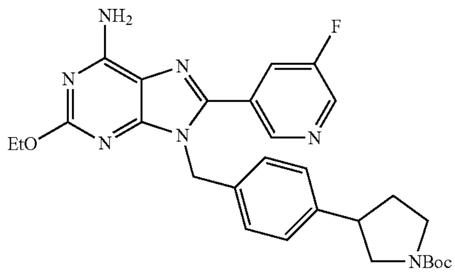 [SMILES: CCOc1nc(N)c2nc(-c3cncc(F)c3)n(Cc3ccc(C4CCN(C(=O)OC(C)(C)C)C4)cc3)c2n1] | LC-MS [M + H]⁺/Rt (min): 534.5/0.997 (Method C); ¹H-NMR (400 MHz, CDCl₃) δ: 8.66-8.61 (1H, m), 8.56 (1H, d, J = 2.4 Hz), 7.68-7.59 (1H, m), 7.17 (2H, d, J = 7.9 Hz), 7.04 (2H, d, J = 7.9 Hz), 6.06 (2H, br s), 5.41 (2H, s), 4.42 (3H, q, J = 7.1 Hz), 3.85-3.69 (1H, m), 3.66-3.46 (1H, m), 3.44-3.19 (2H, m), 2.26-2.19 (1H, m), 1.98-1.87 (2H, m), 1.47 (9H, s), 1.42 (3H, t, J = 7.1 Hz). |
| 196 | 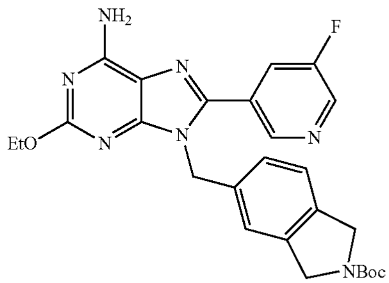 [SMILES: CCOc1nc(N)c2nc(-c3cncc(F)c3)n(Cc3ccc4c(c3)CN(C(=O)OC(C)(C)C)C4)c2n1] | LC-MS [M + H]⁺/Rt (min): 506.5/0.942 (Method C); ¹H-NMR (400 MHz, CDCl₃) δ: 8.63 (1H, s), 8.56-8.51 (1H, m), 7.62 (1H, d, J = 9.2 Hz), 7.17 (1H, dd, J = 23.8, 7.9 Hz), 7.02-6.88 (2H, m), 5.71 (2H, s), 5.42 (2H, s), 4.67-4.53 (4H, m), 4.39 (2H, q, J = 7.0 Hz), 1.49 (9H, s), 1.40 (3H, t, J = 7.0 Hz). |
| 197 | 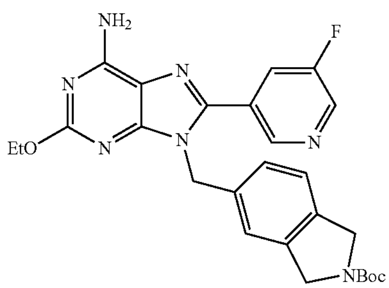 [SMILES: CCOc1nc(N)c2nc(-c3cncc(F)c3)n(Cc3ccc4c(c3)CN(C(=O)OC(C)(C)C)C4)c2n1] | LC-MS [M + H]⁺/Rt (min): 428.4/0.709 (Method C); ¹H-NMR (400 MHz, CDCl₃) δ: 8.78-8.72 (1H, m), 8.63 (1H, d, J = 1.8 Hz), 7.84-7.75 (1H, m), 6.60 (1H, s), 5.64 (2H, s), 5.54 (2H, s), 4.49-4.31 (4H, m), 1.46-1.33 (6H, m). |
| 198 | 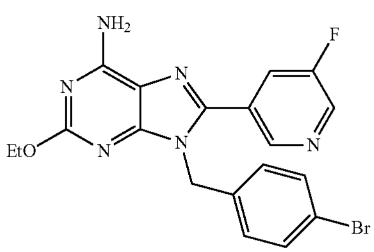 [SMILES: CCOc1nc(N)c2nc(-c3cncc(F)c3)n(Cc3ccc(Br)cc3)c2n1] | ¹H-NMR (400 MHz, CDCl₃) δ: 8.70-8.66 (1H, m), 8.66-8.62 (1H, m), 8.58 (1H, d, J = 2.4 Hz), 8.48 (1H, d, J = 2.4 Hz), 7.70 (1H, ddd, J = 2.0, 2.4, 4.8 Hz), 7.59-7.53 (1H, m), 7.53 (2H, d, J = 7.9 Hz), 7.24 (2H, d, J = 7.9 Hz), 5.65 (2H, s), 5.51 (2H, s), 4.43 (2H, q, J = 7.3 Hz), 1.43 (3H, t, J = 7.3 Hz). |
| 199 | 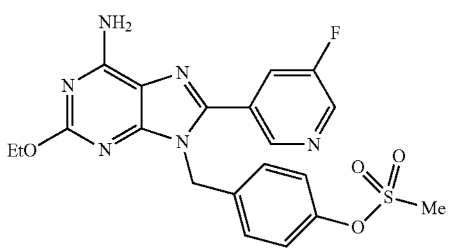 [SMILES: CCOc1nc(N)c2nc(-c3cncc(F)c3)n(Cc3ccc(OS(C)(=O)=O)cc3)c2n1] | ¹H-NMR (400 MHz, CDCl₃) δ: 8.66-8.62 (1H, m), 8.58 (1H, d, J = 2.4 Hz), 7.68-7.62 (1H, m), 7.24 (2H, d, J = 9.2 Hz), 7.18 (2H, d, J = 9.2 Hz), 5.62 (2H, s), 5.45 (2H, s), 4.41 (2H, q, J = 7.1 Hz), 3.14 (3H, s), 1.43 (3H, t, J = 7.0 Hz). |

Reference Examples 200-207

According to the method of Example 165, Examples 200-207 were prepared by using the corresponding material compounds.

| Example | Chemical Structure | Instrumental analysis data |
| --- | --- | --- |
| 200 | 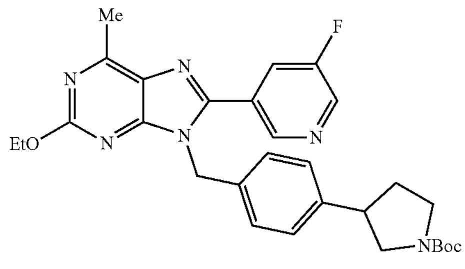 [SMILES: CCOc1nc(C)c2nc(-c3cncc(F)c3)n(Cc3ccc(C4CCN(C(=O)OC(C)(C)C)C4)cc3)c2n1] | LC-MS [M + H]⁺/Rt (min): 533.5/1.12 (Method C); ¹H-NMR (400 MHz, CDCl₃) δ: 8.69-8.66 (1H, m), 8.58 (1H, d, J = 2.4 Hz), 7.73-7.67 (1H, m), 7.15 (2H, d, J = 7.9 Hz), 7.01 (2H, d, J = 7.9 Hz), 5.45 (2H, s), 4.47 (2H, q, J = 7.1 Hz), 3.82-3.70 (1H, m), 3.64-3.48 (1H, m), 3.43-3.16 (3H, m), 2.82 (3H, s), 2.26-2.17 (1H, m), 1.97-1.85 (1H, m), 1.50-1.41 (12H, m). |
| 201 | 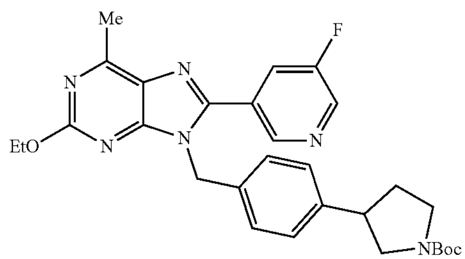 [SMILES: CCOc1nc(C)c2nc(-c3cncc(F)c3)n(Cc3ccc(C4CCN(C(=O)OC(C)(C)C)C4)cc3)c2n1] | LC-MS [M + H]⁺/Rt (min): 519.4/1.048 (Method D); ¹H-NMR (400 MHz, CDCl₃) δ: 8.69-8.66 (1H, m), 8.60-8.56 (1H, m), 7.80-7.73 (1H, m), 7.15 (2H, d, J = 7.9 Hz), 7.02 (2H, d, J = 7.9 Hz), 5.46 (2H, s), 4.06 (3H, s), 3.85-3.70 (1H, m), 3.64-3.48 (1H, m), 3.42-3.17 (3H, m), 2.84 (3H, s), 2.26-2.17 (1H, m), 1.97-1.85 (1H, m), 1.46 (9H, s). |
| 202 | 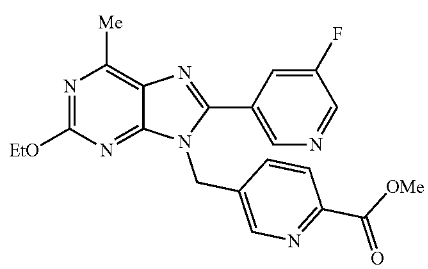 [SMILES: CCOc1nc(C)c2nc(-c3cncc(F)c3)n(Cc3ccc(C(=O)OC)nc3)c2n1] | LC-MS [M + H]⁺/Rt (min): 423.3/0.892 (Method C); ¹H-NMR (400 MHz, CDCl₃) δ: 9.12 (1H, d, J = 1.8 Hz), 8.88-8.85 (1H, m), 8.58 (1H, d, J = 2.4 Hz), 8.27 (1H, dd, J = 2.4, 8.5 Hz), 8.08-8.03 (1H, m), 7.37 (1H, d, J = 8.5 Hz), 5.59 (2H, s), 4.42 (2H, q, J = 7.1 Hz), 3.94 (3H, s), 2.82 (3H, s), 1.42 (3H, t, J = 7.1 Hz). |
| 203 | 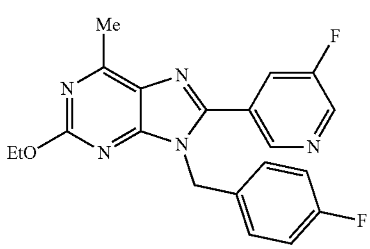 [SMILES: CCOc1nc(C)c2nc(-c3cncc(F)c3)n(Cc3ccc(F)cc3)c2n1] | ¹H-NMR (CDCl₃) δ: 8.68-8.64 (2H, m), 8.02 (1H, d, J = 2.4 Hz), 7.75-7.72 (1H, m), 7.58-7.53 (1H, m), 6.87 (1H, dd, J = 8.5, 3.1 Hz), 5.48 (2H, s), 4.48 (2H, q, J = 6.9 Hz), 2.82 (3H, s), 1.46 (3H, q, J = 6.9 Hz). |
| 204 | 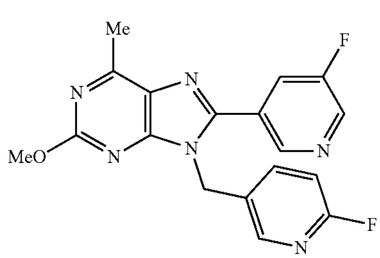 [SMILES: COc1nc(C)c2nc(-c3cncc(F)c3)n(Cc3ccc(F)nc3)c2n1] | ¹H-NMR (CDCl₃) δ: 8.69 (1H, br s), 8.65 (1H, d, J = 2.4 Hz), 8.02-8.01 (1H, m), 7.75-7.73 (1H, m), 7.59-7.55 (1H, m), 6.89-6.86 (1H, m), 5.49 (2H, s), 4.08 (3H, s), 2.83 (3H, s). |

| Example | Chemical Structure | Instrumental analysis data |
|---|---|---|
| 205 | 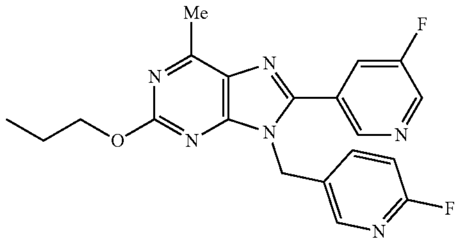 [SMILES: CCCOc1nc(C)c2nc(-c3cncc(F)c3)n(Cc3ccc(F)nc3)c2n1] | ¹H-NMR (CDCl₃) δ: 8.68 (1H, br s), 8.64 (1H, d, J = 3.1 Hz), 8.02-8.01 (1H, m), 7.75-7.71 (1H, m), 7.58-7.53 (1H, m), 6.87 (1H, dd, J = 3.1, 8.5 Hz), 5.49 (2H, s), 4.37 (2H, t, J = 6.7 Hz), 2.82 (3H, s), 1.92-1.83 (2H, m), 1.07 (3H, t, J = 7.3 Hz). |
| 206 | 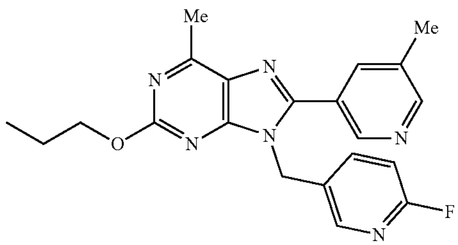 [SMILES: CCCOc1nc(C)c2nc(-c3cncc(C)c3)n(Cc3ccc(F)nc3)c2n1] | LC-MS [M + H]⁺/Rt (min): 393.0/0.769 (Method C) |
| 207 | 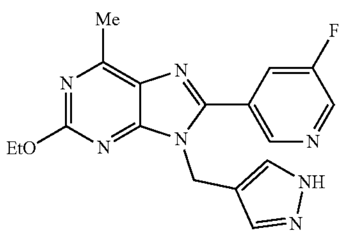 [SMILES: CCOc1nc(C)c2nc(-c3cncc(F)c3)n(Cc3cn[nH]c3)c2n1] | LC-MS [M + H]⁺/Rt (min): 354.0/0.561 (Method C) |

Example 208

4-{[6-Amino-2-ethoxy-8-(5-fluoropyridin-3-yl)-9H-purin-9-yl]methyl}phenol

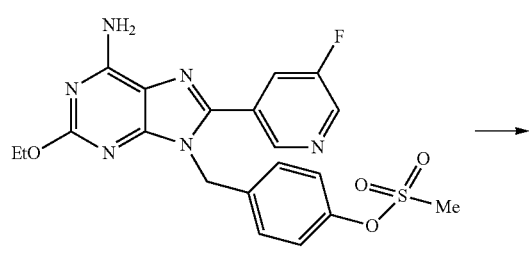

→

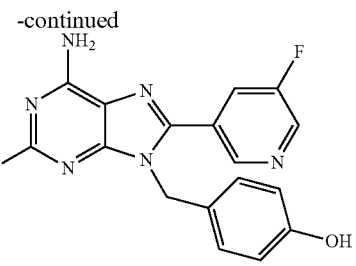

To an ice-cooled solution of the compound of Example 199 (53.9 mg) in acetonitrile (4 mL) was added potassium trimethylsilanolate (272 mg). The reaction mixture was warmed to room temperature, and then stirred for 24 hours. To the reaction mixture were added acetic acid (0.121 mL) and water, and the mixture was extracted with chloroform/methanol. The organic layer was dried over sodium sulfate, filtrated, and then concentrated in vacuo. The residue was purified by silica gel column chromatography (chloroform/methanol) to give the title compound (36.2 mg).

LC-MS [M+H]⁺/Rt (min): 381.36/0.608 (Method C); ¹H-NMR (400 MHz, CDCl₃) δ: 8.68-8.64 (1H, m), 8.56 (1H, d, J=3.1 Hz), 7.71-7.66 (1H, m), 6.94 (2H, d, J=8.5 Hz), 6.71 (2H, d, J=8.5 Hz), 5.68 (2H, s), 5.36 (2H, s), 4.42 (2H, q, J=7.1 Hz), 1.42 (4H, t, J=7.1 Hz).

Example 209

According to the method of Example 208, Example 209 was prepared by using, the corresponding material compound.

| Example | Chemical Structure | Instrumental analysis data |
|---|---|---|
| 209 | 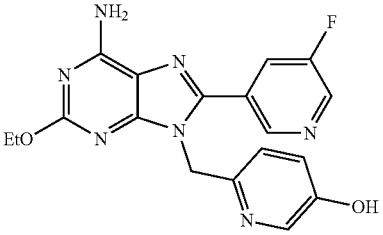 [SMILES: CCOc1nc(N)c2nc(-c3cncc(F)c3)n(Cc3ccc(O)cn3)c2n1] | LC-MS [M + H]$^+$/Rt (min): 382.3/0.690 (Method C) |

Examples 210-215

According to the method of Example 77, Examples 210-215 were prepared by using the corresponding material compounds.

| Example | Chemical Structure | Instrumental analysis data |
|---|---|---|
| 210 | 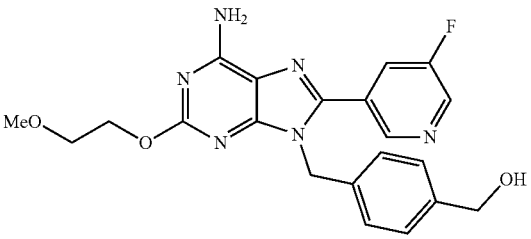 [SMILES: COCCOc1nc(N)c2nc(-c3cncc(F)c3)n(Cc3ccc(CO)cc3)c2n1] | LC-MS [M + H]$^+$/Rt (min): 425.1/0.640 (Method A) |
| 211 | 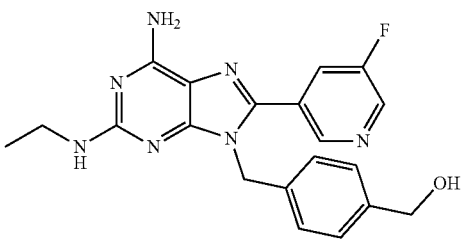 [SMILES: CCNc1nc(N)c2nc(-c3cncc(F)c3)n(Cc3ccc(CO)cc3)c2n1] | LC-MS [M + H]$^+$/Rt (min): 394.4/0.602 (Methog A) |
| 212 | 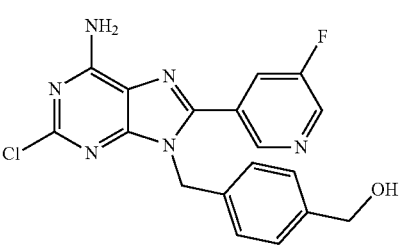 [SMILES: Nc1nc(Cl)nc2c1nc(-c1cncc(F)c1)n2Cc1ccc(CO)cc1] | $^1$H-NMR (DMSO-D$_6$) δ: 8.71-8.70 (2H, m), 8.03-7.99 (3H, m), 7.20 (2H, d, J = 7.9 Hz), 6.92 (2H, d, J = 7.9 Hz), 5.49 (2H, s), 5.13 (1H, t, J = 5.5 Hz), 4.41 (2H, d, J = 6.1 Hz). |
| 213 | 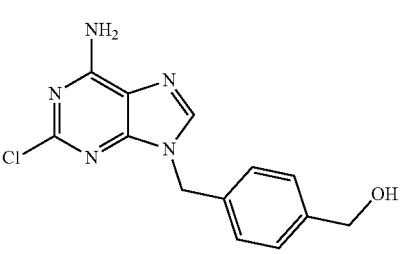 [SMILES: Nc1nc(Cl)nc2c1ncn2Cc1ccc(CO)cc1] | $^1$H-NMR (DMSO-D$_6$) δ: 8.23 (1H, s), 7.76 (2H, s), 7.28-7.22 (4H, m), 5.29 (2H, s), 5.14 (1H, t, J = 5.7 Hz), 4.44 (2H, d, J = 5.5 Hz). |

| Example | Chemical Structure | Instrumental analysis data |
|---|---|---|
| 214 | 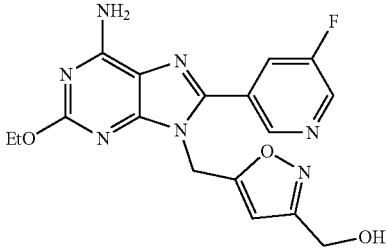 [SMILES: CCOc1nc(N)c2nc(-c3cncc(F)c3)n(Cc3cc(CO)no3)c2n1] | $^1$H-NMR (400 MHz, CDCl$_3$) δ: 8.74-8.71 (1H, m), 8.59 (1H, d, J = 2.4 Hz), 7.82-7.77 (1H, m), 6.27 (1H, s), 5.90 (2H, s), 5.46 (2H, s), 4.69 (2H, s), 4.37 (2H, q, J = 7.1 Hz), 1.39 (3H, t, J = 7.1 Hz). |
| 215 | 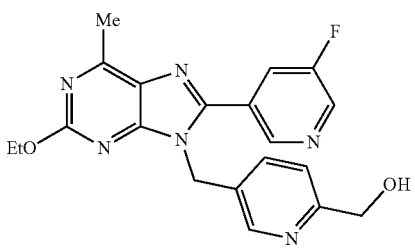 [SMILES: CCOc1nc(C)c2nc(-c3cncc(F)c3)n(Cc3ccc(CO)nc3)c2n1] | LC-MS [M + H]$^+$/Rt (min): 395.3/0.715 (Method C); $^1$H-NMR (400 MHz, CDCl$_3$) δ: 8.90-8.86 (1H, m), 8.56 (1H, d, J = 1.8 Hz), 8.51-8.47 (1H, m), 8.13-8.05 (1H, m), 7.69 (1H, d, J = 7.9 Hz), 7.30-7.26 (1H, m), 5.53 (2H, s), 4.71 (2H, s), 4.42 (2H, q, J = 7.0 Hz), 2.81 (3H, s), 1.42 (3H, t, J = 7.0 Hz). |

Example 216

4-{[2-Ethoxy-8-(5-fluoropyridin-3-yl)-6-methyl-9H-purin-9-yl]methyl}benzaldehyde

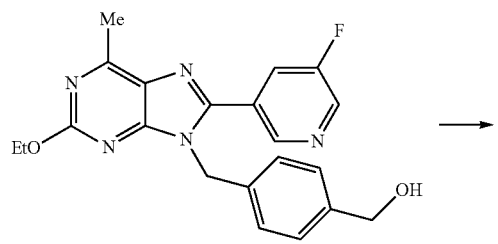

→

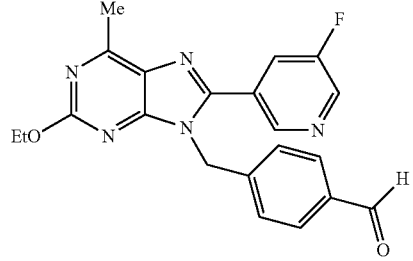

To a solution of the compound of Example 78 (826 mg) in tetrahydrofuran (30 mL) was added manganese dioxide (3.22 g), and the mixture was stirred at room temperature for 2 days. The reaction mixture was filtrated through Celite, and the filtrate was concentrated in vacuo. The residue was tied by silica gel column chromatography (chloroform/methanol) give the title compound (719 mg).

LC-MS ([M+H]$^+$/Rt (m 392.4/0.858 (Method A)

Examples 217-223

According to the method of Example 216, Examples 217-223 were prepared by using the corresponding material compounds.

| Example | Chemical Structure | Instrumental analysis data |
|---|---|---|
| 217 | 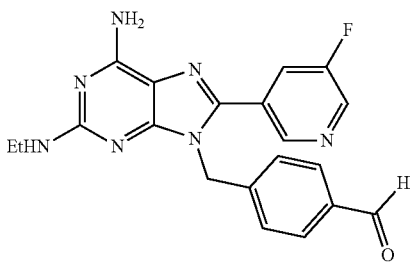 | LC-MS: [M + H]$^+$/Rt (min): 392.4/0.666 (Method A) |

| Example | Chemical Structure | Instrumental analysis data |
|---|---|---|
| 218 | 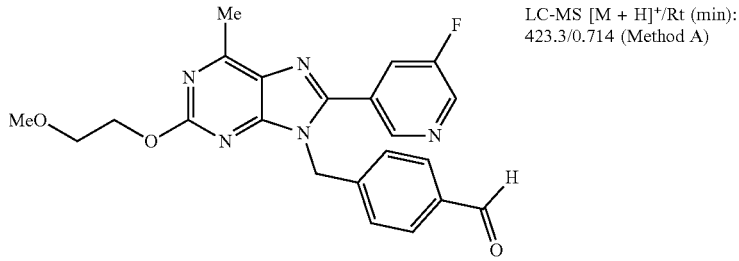 | LC-MS [M + H]+/Rt (min): 423.3/0.714 (Method A) |
| 219 | 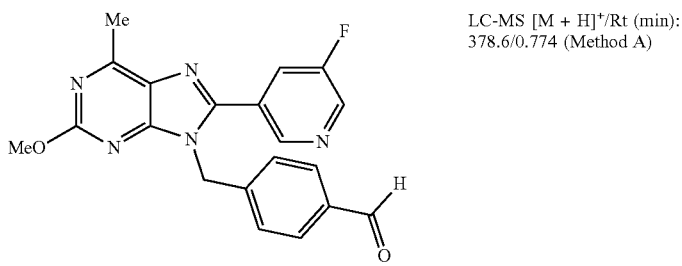 | LC-MS [M + H]+/Rt (min): 378.6/0.774 (Method A) |
| 220 | 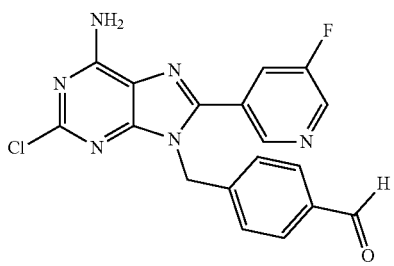 [SMILES: Nc1nc(Cl)nc2c1nc(-c1cncc(F)c1)n2Cc1ccc(C=O)cc1] | LC-MS [M + H]+/Rt (min): 383.3/0.672 (Method C) |
| 221 | 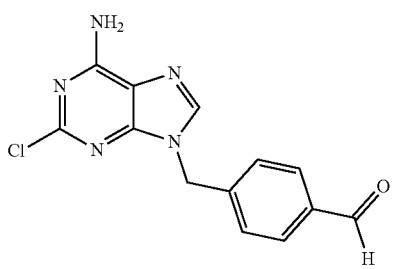 [SMILES: Nc1nc(Cl)nc2c1ncn2Cc1ccc(C=O)cc1] | $^1$H-NMR (DMSO-D$_6$) δ: 9.97 (1H, s), 8.28 (1H, s), 7.89-7.82 (4H, m), 7.43 (2H, d, J = 7.9 Hz), 5.45 (2H, s). |
| 222 | 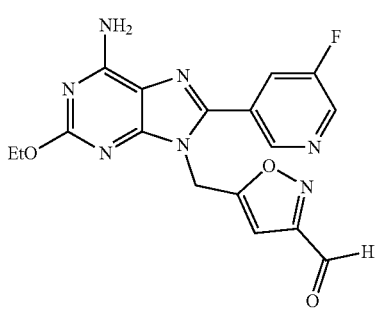 [SMILES: CCOc1nc(N)c2nc(-c3cncc(F)c3)n(Cc3cc(C=O)no3)c2n1] | LC-MS: [M + H]+/Rt (min): 386.4/0.479 (Method C) |

| Example | Chemical Structure | Instrumental analysis data |
|---|---|---|
| 223 | (structure) | ¹H-NMR (400 MHz, CDCl₃) δ: 10.08 (1H, s), 8.98 (1H, d, J = 1.8 Hz), 8.87-8.85 (1H, m), 8.58 (1H, d, J = 3.1 Hz), 8.16 (1H, dd, J = 7.9, 2.4 Hz), 8.07-8.01 (1H, m), 7.47 (1H, d, J = 7.9 Hz), 5.61 (2H, s), 4.41 (3H, q, J = 7.1 Hz), 2.82 (3H, s), 1.41 (3H, t, J = 7.1 Hz). |

Examples 224-226

According to the method of Example 80, Examples 224-226 were prepared by using the corresponding material compounds.

| Example | Chemical Structure | Instrumental analysis data |
|---|---|---|
| 224 | (structure) | LC-MS [M + H]⁺/Rt (min): 575.6/0.681 (Method A) |
| 225 | (structure) | LC-MS [M + H]⁺/Rt (min): 574.5/0.731 (Method A) |
| 226 | (structure) | LC-MS [M + H]⁺/Rt (min): 560.4/0.703 (Method A) |

Example 227

2-Ethoxy-8-(5-fluoropyridin-3-yl)-9-[4-(piperidin-4-yl)benzyl]-9H-purine-6-amine trifluoroacetate

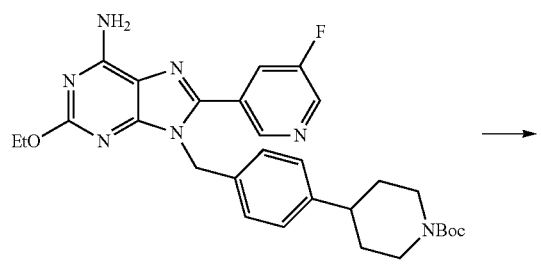

→

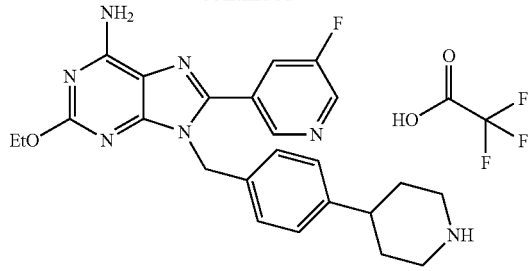

To an ice-cooled solution of the compound of Example 194 (219 mg) in chloroform (3 mL) was added trifluoroacetic acid (0.308 mL). The reaction mixture was warmed to room temperature, and stirred for 18 hours. The reaction mixture was concentrated to give the title compound (240 mg).

$^1$H-NMR (400 MHz, CDCl$_3$) δ: 8.69-8.58 (2H, m), 7.70 (1H, d, J=7.9 Hz), 7.21 (2H, d, J=7.9 Hz), 7.04 (2H, d, J=7.9 Hz), 5.44 (2H, s), 4.58 (2H, q, J=7.3 Hz), 3.64-3.47 (2H, m), 3.11-2.95 (2H, m), 2.84-2.71 (1H, m), 2.16-1.86 (4H, m), 1.47 (3H, q, J=7.3 Hz).

Examples 228-231

According to the methods of Example 123 and Example 227, Examples 228-231 were prepared using the corresponding material compounds.

| Example | Chemical Structure | Instrumental analysis data |
|---|---|---|
| 228 | (structure) | $^1$H-NMR (CDCl$_3$) δ: 8.65 (1H, s), 8.53 (1H, d, J = 2.4 Hz), 7.62-7.60 (1H, m), 7.27-7.26 (2H, m), 7.02 (2H, d, J = 8.8 Hz), 5.61 (2H, s), 5.41 (2H, s), 3.98 (3H, s), 3.71-3.62 (2H, m), 3.54 (1H, s), 3.31 (1H, s), 3.19-3.16 (1H, m), 2.87-2.80 (2H, m), 2.41 (1H, d, J = 9.2 Hz), 1.80 (1H, d, J = 9.2 Hz), 1.57-1.55 (2H, m). |
| 229 | (structure) | LC-MS [M + H]$^+$/Rt (min): 406.4/0.346 (Method C); $^1$H-NMR (CD$_3$OD) δ: 8.64-8.61 (1H, m), 8.59 (1H, d, J = 2.4 Hz), 7.95-7.90 (1H, m), 7.36 (1H, d, J = 7.9 Hz), 7.17-7.11 (2H, m), 5.59 (2H, s), 4.56 (2H, s), 4.52 (2H, s), 4.47 (2H, q, J = 7.0 Hz), 1.40 (3H, t, J = 7.0 Hz). |
| 230 | (structure) | LC-MS [M + H]$^+$/Rt (min): 433.4/0.601 (Method C); $^1$H-NMR (CDCl$_3$) δ: 8.69-8.66 (1H, m), 8.57 (1H, d, J = 1.2 Hz), 7.71-7.66 (1H, m), 7.15 (2H, d, J = 7.3 Hz), 6.99 (2H, d, J = 7.3 Hz), 5.44 (2H, s), 4.47 (2H, q, J = 7.1 Hz), 3.37-3.29 (1H, m), 3.23-3.03 (3H, m), 2.86-2.75 (4H, m), 2.26-2.16 (1H, m), 1.84-1.73 (1H, m), 1.45 (3H, t, J = 7.1 Hz), 1.24 (1H, s). |

| Example | Chemical Structure | Instrumental analysis data |
|---|---|---|
| 231 | 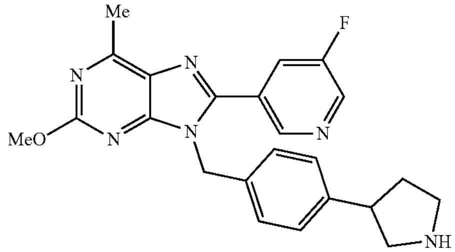 [SMILES: COc1nc(C)c2nc(-c3cncc(F)c3)n(Cc3ccc(C4CCNC4)cc3)c2n1] | LC-MS [M + H]⁺/Rt (min): 419.3/0.586 (Method D); ¹H-NMR (CDCl₃) δ: 8.69-8.65 (1H, m), 8.58 (1H, d, J = 2.4 Hz), 7.72-7.67 (1H, m), 7.15 (2H, d, J = 7.9 Hz), 6.99 (2H, d, J = 7.9 Hz), 5.45 (2H, s), 4.06 (3H, s), 3.32 (1H, dd, J = 10.7, 7.6 Hz), 3.21-3.02 (3H, m), 2.82 (3H, s), 2.78 (1H, dd, J = 10.7, 8.2 Hz), 2.24-2.15 (1H, m), 1.82-1.72 (1H, m). |

Example 232

4-{[6-Amino-8-(5-fluoropyridin-3-yl)-9H-purin-9-yl]methyl}benzyl methanesulfonate

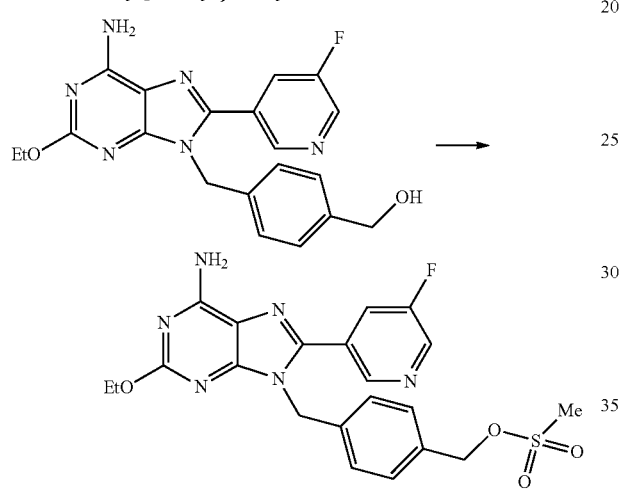

To an ice-cooled suspension of the compound of Example 77 (400 mg) in tetrahydrofuran (3.4 mL) were added triethylamine (0.424 mL) and methanesulfonyl chloride (0.118 mL), and the mixture was stirred in ice bath for 2 hours. To the reaction mixture was added water, and the mixture was extracted with chloroform/methanol. The organic layer was dried over sodium sulfate, filtrated, and then concentrated in vacuo to give the title compound (465 mg).

¹H-NMR (CDCl₃) δ: 8.62-8.61 (1H, m), 8.54 (1H, d, J=2.4 Hz), 7.64-7.61 (1H, m), 7.36 (2H, d, J=8.5 Hz), 7.13 (2H, d, J=8.5 Hz), 5.62 (2H, s), 5.45 (2H, s), 5.20 (2H, s), 4.39 (2H, q, J=7.1 Hz), 2.92 (3H, s), 1.40 (3H, t, J=7.1 Hz).

Examples 233-234

According to the method of Example 141, Examples 233-234 were prepared by using the corresponding material compounds.

| Example | Chemical Structure | Instrumental analysis data |
|---|---|---|
| 233 | 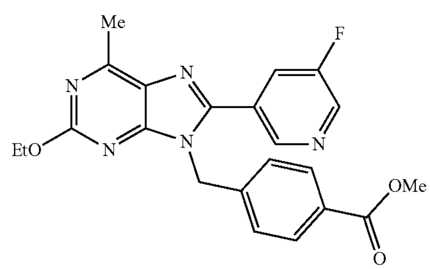 [SMILES: CCOc1nc(C)c2nc(-c3cncc(F)c3)n(Cc3ccc(C(=O)OC)cc3)c2n1] | LC-MS [M + H]⁺/Rt (min): 422.4/0.930 (Method A) |
| 234 | 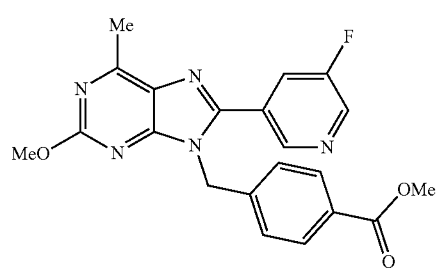 [SMILES: COC(=O)c1ccc(Cn2c(-c3cncc(F)c3)nc3c(C)nc(OC)nc32)cc1] | LC-MS [M + H]⁺/Rt (min): 408.3/0.890 (Method A) |

Example 235

4-{[6-Amino-2-ethoxy-8-(5-fluoropyridin-3-yl)-9H-purin-9-yl]methyl}benzoic acid

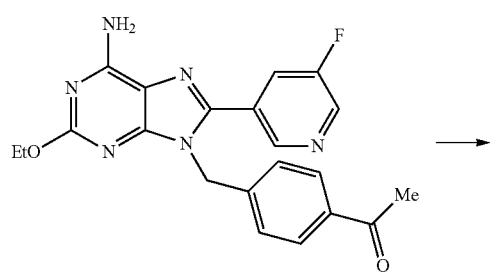

→

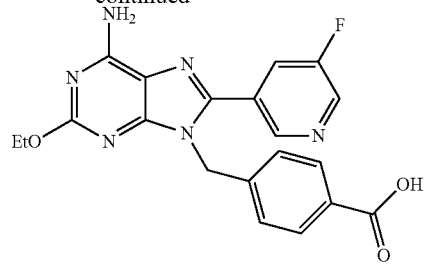

To a solution of the compound of Example 182 (302 mg) in a mixture of tetrahydrofuran (5 mL) and methanol (9 mL) was added 1 mol/L aqueous sodium hydroxide (4 mL), and the mixture was stirred at room temperature for 20 hours. The reaction mixture was concentrated in vacuo. To the residue was added 1 mol/L hydrochloric acid under ice temperature. The precipitated solid was collected on a filter, washed with water and methyl tert-butyl ether, and then dried in vacuo to give the title compound (244 mg).
LC-MS ([M+H]$^+$/Rt (min)): 409.3/0.679 (Method A)

Example 236

According to the method of Example 158, Example 236 was prepared by using the corresponding material compound. As appropriate, microwave irradiation was used.

| Example | Chemical Structure | Instrumental analysis data |
|---|---|---|
| 236 | 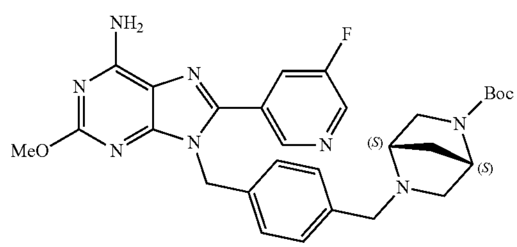 | LC-MS [M + H]$^+$/Rt (min): 561.5/0.668 (Method B) |

Example 237-241

According to the method of Example 1, Examples 237-241 were prepared by using the corresponding material compounds. As appropriate, some reactions were carried out under reflux or under microwave irradiation.

| Example | Chemical Structure | Instrumental analysis data |
|---|---|---|
| 237 | 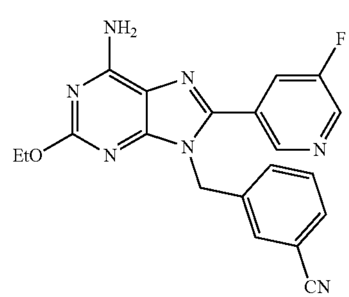 [SMILES: CCOc1nc(N)c2nc(-c3cncc(F)c3)n(Cc3cccc(C#N)c3)c2n1] | LC-MS [M + H]$^+$/Rt (min): 389.97/0.706 (method C); $^1$H-NMR (CDCl$_3$) δ: 8.61-8.58 (2H, m), 7.68-7.64 (1H, m), 7.60 (1H, d, J = 7.9 Hz), 7.49-7.40 (2H, m), 7.34 (1H, d, J = 7.9 Hz), 5.72 (2H, s), 5.47 (2H, s), 4.40 (2H, q, J = 7.1 Hz), 1.42 (3H, t, J = 7.1 Hz). |

| Example | Chemical Structure | Instrumental analysis data |
|---|---|---|
| 238 | 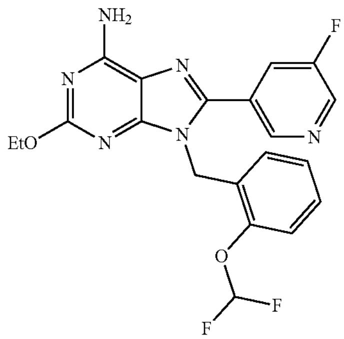 [SMILES: CCOc1nc(N)c2nc(-c3cncc(F)c3)n(Cc3ccccc3OC(F)F)c2n1] | $^1$H-NMR (CDCl$_3$) δ: 8.72-8.47 (2H, m), 7.63 (1H, d, J = 8.5 Hz), 7.35-7.29 (1H, m), 7.17-7.08 (2H, m), 6.92 (1H, d, J = 7.3 Hz), 6.54 (1H, t, J = 73.4 Hz), 5.76 (2H, s), 5.51 (2H, s), 4.39 (2H, q, J = 7.1 Hz), 1.41 (3H, t, J = 7.1 Hz). |
| 239 | 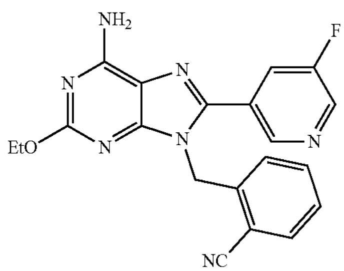 [SMILES: CCOc1nc(N)c2nc(-c3cncc(F)c3)n(Cc3ccccc3C#N)c2n1] | LC-MS [M + H]$^+$/Rt (min): 390.0/0.709 (Method C); $^1$H-NMR (CDCl$_3$) δ: 8.55 (1H, d, J = 3.1 Hz), 8.53-8.50 (1H, m), 7.69 (1H, dd, J = 7.9, 1.2 Hz), 7.65-7.60 (1H, m), 7.53-7.48 (1H, m), 7.40 (1H, dd, J = 7.3, 7.3 Hz), 6.99 (1H, d, J = 7.3 Hz), 5.66 (2H, s), 5.63 (2H, s), 4.33 (2H, q, J = 7.1 Hz), 1.36 (3H, t, J = 7.1 Hz). |
| 240 | 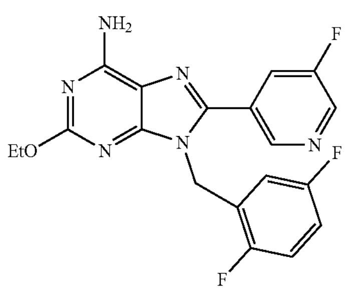 [SMILES: CCOc1nc(N)c2nc(-c3cncc(F)c3)n(Cc3cc(F)ccc3F)c2n1] | LC-MS [M + H]$^+$/Rt (min): 401.0/0.789 (Method C); $^1$H-NMR (CDCl$_3$) δ: 8.62-8.59 (1H, m), 8.56 (1H, d, J = 3.1 Hz), 7.68-7.61 (1H, m), 7.06-6.98 (1H, m), 6.98-6.90 (1H, m), 6.75-6.67 (1H, m), 5.65 (2H, s), 5.43 (2H, s), 4.38 (2H, q, J = 7.1 Hz), 1.40 (3H, t, J = 7.3 Hz). |
| 241 | 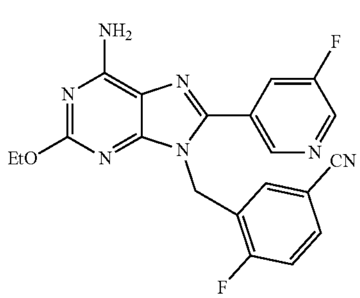 [SMILES: CCOc1nc(N)c2nc(-c3cncc(F)c3)n(Cc3cc(C#N)ccc3F)c2n1] | $^1$H-NMR (DMSO-D$_6$) δ: 8.74-8.71 (2H, m), 8.10-8.05 (1H, m), 7.86-7.81 (1H, m), 7.69 (1H, dd, J = 6.9, 2.3 Hz), 7.39 (1H, dd, J = 10.1, 8.7 Hz), 5.49 (2H, s), 4.25 (2H, q, J = 7.0 Hz), 1.26 (3H, t, J = 7.0 Hz). |

Example 242

2-Ethoxy-8-(5-fluoropyridin-3-yl)-6-methyl-9-[(1-methyl-1H-pyrazol-4-yl)methyl]-9H-purine

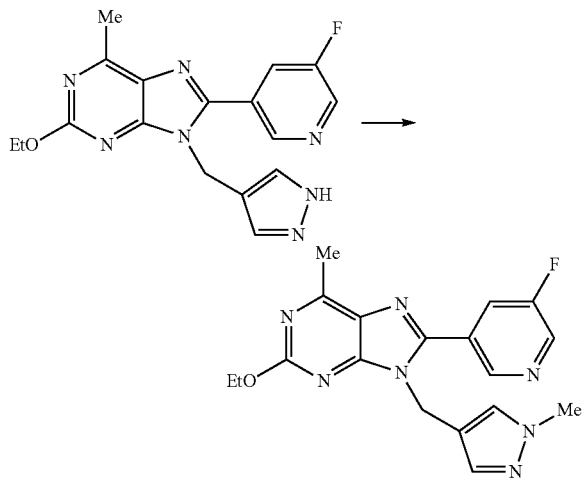

To a solution of the compound of Example 207 (120 mg) in N,N-dimethylformamide (6 mL) were added methyl iodide (72.1 mg) and potassium carbonate (93.7 mg), and the mixture was stirred at room temperature overnight. To the reaction mixture was added water, and the mixture was extracted with chloroform/methanol. The organic layer was dried over sodium sulfate, filtrated, and then concentrated in vacuo. The residue was purified by silica gel column chromatography (chloroform/methanol) to give the title compound (51.8 mg).

LC-MS [M+H]$^+$/Rt (min): 468.2/0.695 (Method A); $^1$H-NMR (400 MHz, CDCl$_3$) δ: 8.84-8.82 (1H, m), 8.67 (1H, d, J=2.5 Hz), 7.86-7.82 (1H, m), 7.36 (1H, brs), 7.28-7.27 (1H, m), 5.34 (2H, s), 4.55 (2H, q, J=7.0 Hz), 3.85 (3H, s), 2.83 (3H, s), 1.52 (3H, t, J=7.0 Hz).

Examples 243-257

According to the method of Example 242, Examples 243-257 were prepared by using the corresponding material compounds.

| Example | Chemical Structure | Instrumental analysis data |
|---|---|---|
| 243 | 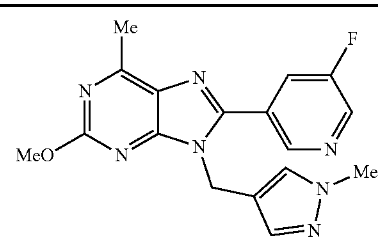 | LC-MS [M + H]$^+$/Rt (min): 354.3/0.630 (Method A); $^1$H-NMR (400 MHz, CDCl$_3$) δ: 8.84-8.82 (1H, m), 8.67 (1H, d, J = 3.0 Hz), 7.86-7.82 (1H, m), 7.36 (1H, brs), 7.30 (1H, brs), 5.34 (2H, s), 4.13 (3H, s), 3.85 (3H, s), 2.84 (3H, s). |
| 244 | 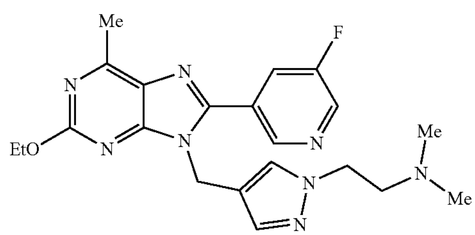 [SMILES: CCOc1nc(C)c2nc(-c3cncc(F)c3)n(Cc3cnn(CCN(C)C)c3)c2n1] | LC-MS [M + H]$^+$/Rt (min): 425.3/0.528 (Method A); $^1$H-NMR (400 MHz, CDCl$_3$) δ: 8.84-8.81 (1H, m), 8.66 (1H, d, J = 2.8 Hz), 7.86-7.79 (1H, m), 7.50 (2H, s), 5.38 (2H, s), 4.54 (2H, q, J = 7.2 Hz), 4.15 (2H, t, J = 6.4 Hz), 2.83 (3H, s), 2.70 (2H, t, J = 6.4 Hz), 2.25 (6H, s), 1.52 (3H, t, J = 7.2 Hz). |
| 245 | 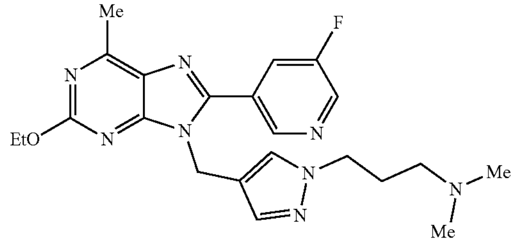 [SMILES: CCOc1nc(C)c2nc(-c3cncc(F)c3)n(Cc3cnn(CCCN(C)C)c3)c2n1] | LC-MS [M + H]$^+$/Rt (min): 439.3/0.549 (Method A); $^1$H-NMR (400 MHz, CDCl$_3$) δ: 8.84-8.81 (1H, m), 8.66 (1H, d, J = 3.0 Hz), 7.86-7.79 (1H, m), 7.37 (1H, s), 7.32 (1H, s), 5.34 (2H, s) 4.54 (2H, q, J = 7.0 Hz), 4.11 (2H, t, J = 7.0 Hz), 2.82 (3H, s), 2.22-2.13 (8H, m), 1.99-1.94 (2H, m), 1.51 (3H, t, J = 7.0 Hz). |

| Example | Chemical Structure | Instrumental analysis data |
|---|---|---|
| 246 | 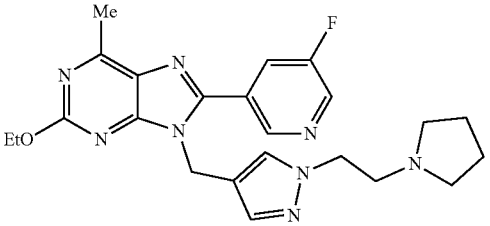 [SMILES: CCOc1nc(C)c2nc(-c3cncc(F)c3)n(Cc3cnn(CCN4CCCC4)c3)c2n1] | LC-MS [M + H]⁺/Rt (min): 451.3/0.540 (Method A); ¹H-NMR (400 MHz, CDCl₃) δ: 8.84-8.81 (1H, m), 8.66 (1H, d, J = 2.8 Hz), 7.86-7.79 (1H, m), 7.41-7.35 (2H, m), 5.34 (2H, s), 4.54 (2H, q, J = 7.2 Hz), 4.21 (2H, t, J = 6.8 Hz), 2.94-2.86 (2H, m), 2.83 (3H, s), 2.56-2.47 (4H, m), 1.52 (3H, t, J = 7.2 Hz). |
| 247 | 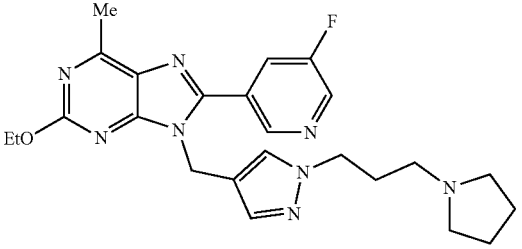 [SMILES: CCOc1nc(C)c2nc(-c3cncc(F)c3)n(Cc3cnn(CCCN4CCCC4)c3)c2n1] | LC-MS [M + H]⁺/Rt (min): 465.3/0.563 (Method A); ¹H-NMR (400 MHz, CDCl₃) δ: 8.84-8.81 (1H, m), 8.66 (1H, d, J = 2.5 Hz), 7.86-7.81 (1H, m), 7.37 (1H, s), 7.32 (1H, s), 5.34 (2H, s) 4.54 (2H, q, J = 7.0 Hz), 4.13 (2H, t, J = 7.0 Hz), 2.83 (3H, s), 2.49-2.41 (4H, m), 2.37 (2H, t, J = 7.0 Hz), 2.05-1.96 (2H, m), 1.74-1.82 (4H, m), 1.51 (3H, t, J = 7.5 Hz). |
| 248 | 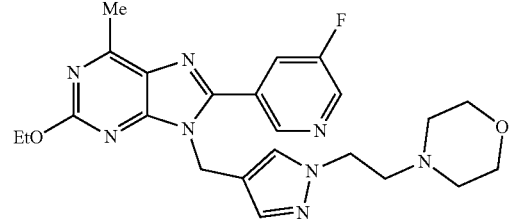 [SMILES: CCOc1nc(C)c2nc(-c3cncc(F)c3)n(Cc3cnn(CCN4CCOCC4)c3)c2n1] | LC-MS [M + H]⁺/Rt (min): 467.3/0.525 (Method A); ¹H-NMR (400 MHz, CDCl₃) δ: 8.84-8.81 (1H, m), 8.66 (1H, d, J = 3.0 Hz), 7.86-7.81 (1H, m), 7.39 (1H, s), 7.37 (1H, s), 5.34 (2H, s), 4.54 (2H, q, J = 7.0 Hz), 4.16 (2H, t, J = 6.5 Hz), 3.68-3.60 (4H, m), 2.83 (3H, s), 2.74 (2H, t, J = 6.5 Hz), 2.47-2.40 (4H, m), 1.51 (3H, t, J = 7.0 Hz). |
| 249 | 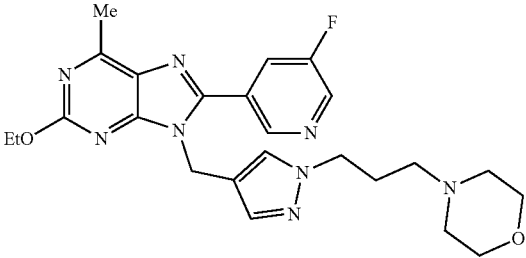 [SMILES: CCOc1nc(C)c2nc(-c3cncc(F)c3)n(Cc3cnn(CCCN4CCOCC4)c3)c2n1] | LC-MS [M + H]⁺/Rt (min): 481.3/0.547 (Method A); ¹H-NMR (400 MHz, CDCl₃) δ: 8.84-8.81 (1H, m), 8.66 (1H, d, J = 2.5 Hz), 7.86-7.79 (1H, m), 7.37 (1H, s), 7.30 (1H, s), 5.34 (2H, s) 4.54 (2H, q, J = 7.0 Hz), 4.12 (2H, t, J = 7.0 Hz), 3.67 (4H, t, J = 5.0 Hz), 2.83 (3H, s), 2.40-2.32 (4H, m), 2.24 (2H, t, J = 7.0 Hz), 2.03-1.92 (2H, m), 1.51 (3H, t, J = 7.0 Hz). |
| 250 | 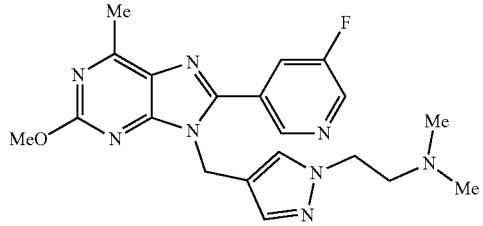 [SMILES: COc1nc(C)c2nc(-c3cncc(F)c3)n(Cc3cnn(CCN(C)C)c3)c2n1] | LC-MS [M + H]⁺/Rt (min): 411.3/0.455 (Method A); ¹H-NMR (400 MHz, CDCl₃) δ: 8.84-8.81 (1H, m), 8.66 (1H, d, J = 2.0 Hz), 7.86-7.79 (1H, m), 7.40 (1H, s), 7.37 (1H, s), 5.34 (2H, s), 4.18-4.08 (5H, m), 2.83 (3H, s), 2.68 (2H, t, J = 6.5 Hz), 2.23 (6H, s). |
| 251 | 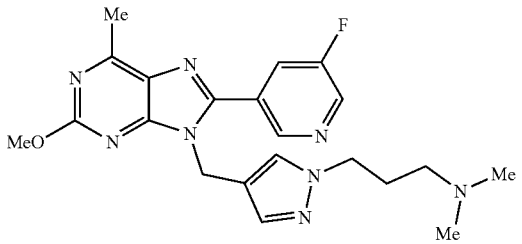 [SMILES: COc1nc(C)c2nc(-c3cncc(F)c3)n(Cc3cnn(CCCN(C)C)c3)c2n1] | LC-MS [M + H]⁺/Rt (min): 425.3/0.497 (Method A); ¹H-NMR (400 MHz, CDCl₃) δ: 8.84-8.81 (1H, m), 8.66 (1H, d, J = 2.8 Hz), 7.86-7.79 (1H, m), 7.39-7.31 (2H, m), 5.35 (2H, s), 4.22-4.02 (5H, m), 2.84 (3H, s), 2.26-2.10 (8H, m), 2.08-1.87 (2H, m). |

| Example | Chemical Structure | Instrumental analysis data |
|---|---|---|
| 252 | 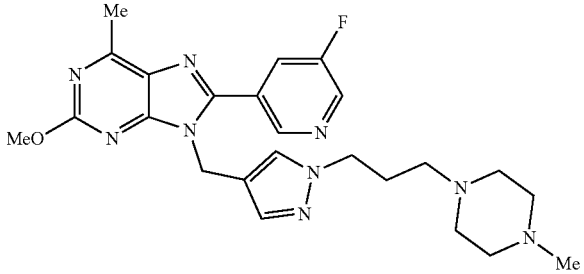 [SMILES: COc1nc(C)c2nc(-c3cncc(F)c3)n(Cc3cnn(CCCN4CCN(C)CC4)c3)c2n1] | LC-MS [M + H]⁺/Rt (min): 494.4/0.508 (Method A); ¹H-NMR (400 MHz, CDCl₃) δ: 8.84-8.81 (1H, m), 8.66 (1H, d, J = 2.5 Hz), 7.86-7.79 (1H, m), 7.36 (1H, s), 7.29 (1H, s), 5.34 (2H, s) 4.53 (2H, q, J = 7.0 Hz), 4.10 (2H, t, J = 7.0 Hz), 2.83 (3H, s), 2.57-2.30 (6H, m), 2.28 (3H, s), 2.24 (2H, t, J = 7.0 Hz), 2.00-1.92 (2H, m), 1.82-1.76 (2H, m), 1.51 (3H, t, J = 7.0 Hz). |
| 253 | 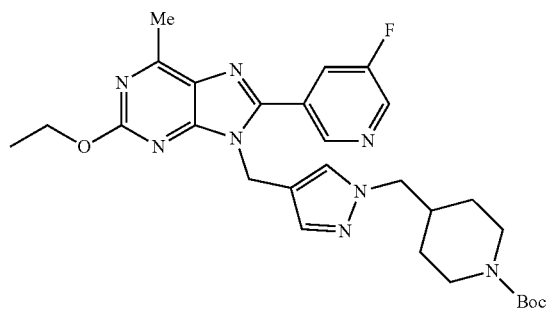 [SMILES: CCOc1nc(C)c2nc(-c3cncc(F)c3)n(Cc3cnn(CC4CCN(C(=O)OC(C)(C)C)CC4)c3)c2n1] | LC-MS [M + H]⁺/Rt (min): 552.40/0.985 (Method A); ¹H-NMR (CDCl₃) δ: 8.81 (1H, s), 8.65 (1H, d, J = 3.1 Hz), 7.84-7.79 (1H, m), 7.37 (1H, s), 7.23 (1H, s), 5.34 (2H, s), 4.54 (2H, q, J = 7.1 Hz), 4.17-4.03 (2H, m), 3.89 (2H, d, J = 7.3 Hz), 2.83 (3H, s), 2.73-2.58 (2H, m), 2.03-1.96 (1H, m), 1.55-1.39 (14H, m), 1.16-1.03 (2H, m). |
| 254 | 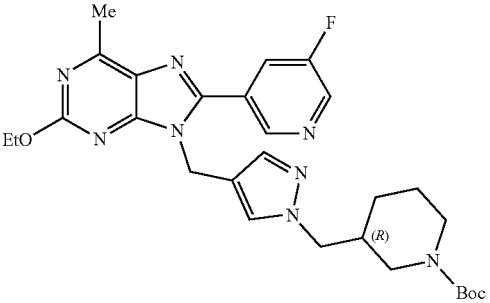 | LC-MS [M + H]⁺/Rt (min): 551.3/0.895 (Method C); ¹H-NMR (CDCl₃) δ: 8.79-8.76 (1H, m), 8.62 (1H, d, J = 3.1 Hz), 7.81-7.76 (1H, m), 7.33 (1H, s), 7.23 (1H, s), 5.35-5.26 (2H, m), 4.52 (2H, q, J = 7.2 Hz), 3.96-3.82 (2H, m), 3.78-3.64 (2H, m), 2.93-2.86 (1H, m), 2.81 (3H, s), 2.68-2.62 (1H, m), 2.03-1.96 (1H, m), 1.76-1.52 (3H, m), 1.48 (3H, t, J = 7.2 Hz), 1.38 (9H, brs), 1.16-1.04 (1H, m) |
| 255 | 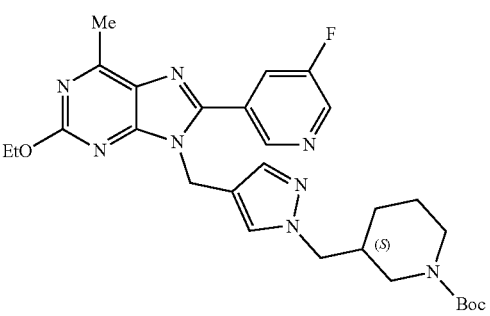 | LC-MS [M + H]⁺/Rt (min): 551.3/0.893 (Method C); ¹H-NMR (CDCl₃) δ: 8.79-8.76 (1H, m), 8.62 (1H, d, J = 2.4 Hz), 7.81-7.76 (1H, m), 7.33 (1H, s), 7.25-7.23 (1H, m), 5.35-5.26 (2H, m), 4.53 (2H, q, J = 7.2 Hz), 3.96-3.82 (2H, m), 3.76-3.64 (2H, m), 2.94-2.86 (1H, m), 2.83 (3H, s), 2.69-2.61 (1H, m), 2.04-1.96 (1H, m), 1.76-1.52 (3H, m), 1.48 (3H, t, J = 7.2 Hz), 1.38 (9H, brs), 1.16-1.04 (1H, m) |
| 256 | 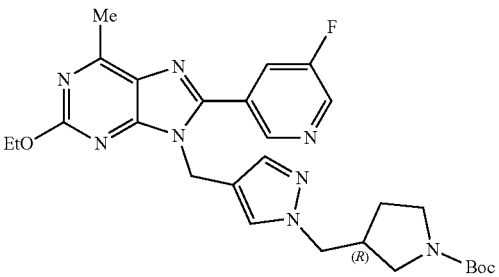 | LC-MS [M + H]⁺/Rt (min): 537.4/0.845 (Method C); ¹H-NMR (CDCl₃) δ: 8.77 (1H, s), 8.63 (1H, d, J = 2.4 Hz), 7.82-7.76 (1H, m), 7.33 (1H, s), 7.26-7.22 (1H, m), 5.31 (2H, s), 4.52 (2H, q, J = 7.0 Hz), 4.05-3.95 (2H, m), 3.47-3.34 (2H, m), 3.32-3.22 (1H, m), 3.04-2.95 (1H, m), 2.81 (3H, s), 2.70-2.61 (1H, m), 1.90-1.82 (1H, m), 1.72-1.52 (1H, m), 1.48 (3H, t, J = 7.0 Hz), 1.42 (9H, s) |

| Example | Chemical Structure | Instrumental analysis data |
|---|---|---|
| 257 | (structure: 6-Me, 2-EtO purine with 5-fluoropyridin-3-yl at 8-position; N9-CH2 linked to pyrazole-N-CH2-(S)-pyrrolidine-N-Boc) | LC-MS [M + H]$^+$/Rt (min): 537.4/0.847 (Method C); $^1$H-NMR (CDCl$_3$) δ: 8.77 (1H, s), 8.63 (1H, d, J = 3.1 Hz), 7.82-7.76 (1H, m), 7.33 (1H, s), 7.26-7.22 (1H, m), 5.31 (2H, s), 4.51 (2H, q, J = 7.0 Hz), 4.05-3.95 (2H, m), 3.45-3.34 (2H, m), 3.32-3.22 (1H, m), 3.04-2.95 (1H, m), 2.81 (3H, s), 2.70-2.60 (1H, m), 1.90-1.82 (1H, m), 1.67-1.52 (1H, m), 1.48 (3H, t, J = 7.0 Hz), 1.42 (9H, s) |

Example 258

According to the method of Example 77, Example 258 was prepared by using the corresponding material compound.

| Example | Chemical Structure | Instrumental analysis data |
|---|---|---|
| 258 | (structure: 6-Me, 2-MeO purine with 5-fluoropyridin-3-yl at 8-position; N9-CH2-(3-fluoro-4-(hydroxymethyl)phenyl)) | LC-MS [M + H]$^+$/Rt (min): 398.4/0.713 (Method A); $^1$H-NMR (400 MHz, DMSO-d$_6$) δ: 8.77-8.74 (2H, m), 8.16-8.11 (1H, m), 7.04-6.95 (3H, m), 5.56 (2H, s), 5.26 (1H, t, J = 5.5 Hz), 4.40 (2H, d, J = 5.5 Hz), 3.94 (3H, s), 2.69 (3H, s). |

Examples 259-266

According to the method of Example 80, Examples 259-266 were prepared by using the corresponding material compounds.

| Example | Chemical Structure | Instrumental analysis data |
|---|---|---|
| 259 | (structure: 6-Me, 2-MeO purine with 5-fluoropyridin-3-yl at 8-position; N9-CH2-(3-fluoro-4-((dimethylamino)methyl)phenyl)) | LC-MS [M + H]$^+$/Rt (min): 425.4/0.569 (Method A); $^1$H-NMR (400 MHz, DMSO-d$_6$) δ: 8.74-8.71 (2H, m), 8.12-8.07 (1H, m), 7.00-6.90 (3H, m), 5.57 (2H, s), 3.94 (3H, s), 3.28 (2H, s), 2.69 (3H, s), 2.04 (6H, s). |
| 260 | (structure: 6-Me, 2-MeO purine with 5-fluoropyridin-3-yl at 8-position; N9-CH2-(3-fluoro-4-(azetidin-1-ylmethyl)phenyl)) | LC-MS [M + H]$^+$/Rt (min): 437.4/0.574 (Method A); $^1$H-NMR (400 MHz, DMSO-d$_6$) δ: 8.74 (1H, d, J = 3.1 Hz), 8.73-8.71 (1H, m), 8.13-8.08 (1H, m), 6.97-6.88 (3H, m), 5.55 (2H, s), 3.93 (3H, s), 3.40 (2H, s), 3.02 (4H, t, J = 6.7 Hz), 2.69 (3H, s), 1.92 (2H, quin, J = 6.7 Hz). |

| Example | Chemical Structure | Instrumental analysis data |
|---|---|---|
| 261 | 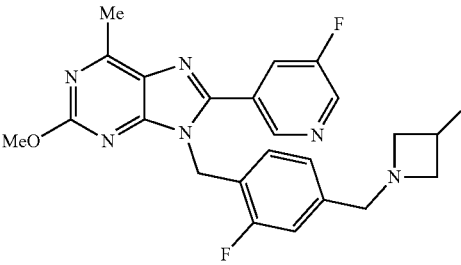 | LC-MS [M + H]⁺/Rt (min): 481.5/0.608 (Method A); ¹H-NMR (400 MHz, DMSO-d$_6$) δ: 8.75 (1H, d, J = 3.1 Hz), 8.71-8.69 (1H, m), 8.16-8.12 (1H, m), 7.29-7.26 (1H, m), 7.18-7.15 (1H, m), 7.11-7.07 (1H, m), 5.62 (2H, s), 4.37 (2H, s), 3.95 (3H, s), 3.11-3.04 (5H, m), 2.70 (3H, s), 1.25-1.19 (9H, m). |
| 262 | 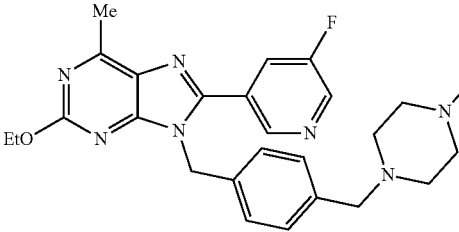 [SMILES: CCOc1nc(C)c2nc(-c3cncc(F)c3)n(Cc3ccc(CN4CCCCC4)cc3)c2n1] | LC-MS [M + H]⁺/Rt (min): 476.4/0.593 (Method A); ¹H-NMR (400 MHz, CDCl$_3$) δ: 8.66 (1H, dd, J = 1.2, 1.8 Hz), 8.55 (1H, d, J = 3.1 Hz), 7.66-7.62 (1H, m), 7.21 (2H, d, J = 7.9 Hz), 5.44 (2H, s), 4.45 (2H, q, J = 7.3 Hz), 3.43 (2H, s), 2.81 (3H, s), 2.50-2.30 (6H, m), 2.28 (3H, s), 1.66-1.54 (2H, m), 1.43 (3H, t, J = 7.3 Hz). |
| 263 | 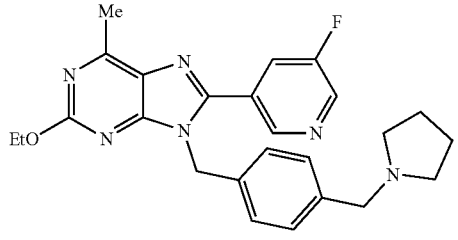 | LC-MS [M + H]⁺/Rt (min): 447.3/0.605 (Method A); ¹H-NMR (400 MHz, DMSO-d$_6$) δ: 8.74-8.73 (2H, m), 7.97-7.92 (1H, m), 7.18 (2H, d, J = 7.9 Hz), 6.93 (2H, d, J = 7.9 Hz), 5.54 (2H, s), 4.39 (2H, q, J = 7.3 Hz), 3.50 (2H, s), 2.71 (3H, s), 2.43-2.30 (4H, m), 1.68-1.60 (4H, m), 1.34 (3H, t, J = 7.3 Hz). |
| 264 | 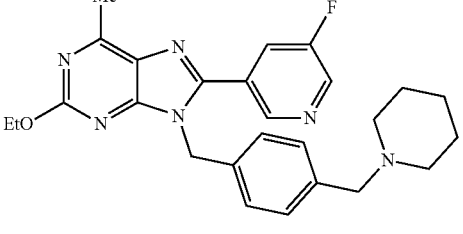 | LC-MS [M + H]⁺/Rt (min): 461.3/0.625 (Method A); ¹H-NMR (400 MHz, DMSO-d$_6$) δ: 8.76-8.70 (2H, m), 8.05-8.01 (1H, m), 7.15 (2H, d, J = 7.9 Hz), 6.93 (2H, d, J = 7.9 Hz), 5.54 (2H, s), 4.39 (2H, q, J = 7.3 Hz), 3.36-3.29 (4H, m), 2.71 (3H, s), 2.28-2.14 (4H, m), 1.48-1.39 (4H, m), 1.34 (3H, t, J = 7.3 Hz). |
| 265 | 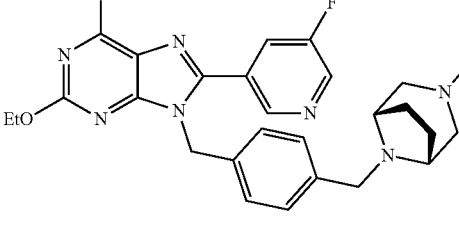 | LC-MS [M + H]⁺/Rt (min): 502.4/0.611 (Method A); ¹H-NMR (400 MHz, DMSO-d$_6$) δ: 8.74-8.72 (2H, m), 8.06-8.02 (1H, m), 7.22 (2H, d, J = 7.9 Hz), 6.93 (2H, d, J = 7.9 Hz), 5.54 (2H, s), 4.39 (2H, q, J = 7.3 Hz), 3.37 (2H, s), 2.95-2.89 (2H, m), 2.71 (3H, s), 2.48-2.41 (2H, m), 2.09 (3H, s), 1.84-1.76 (2H, m), 1.68-1.62 (2H, m), 1.34 (3H, t, J = 7.3 Hz). |
| 266 | 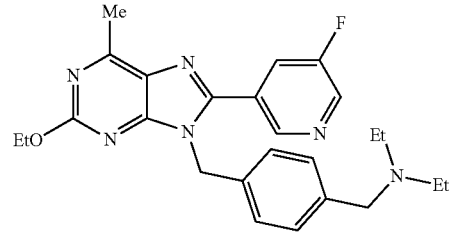 [SMILES: CCOc1nc(C)c2nc(-c3cncc(F)c3)n(Cc3ccc(CN(CC)CC)cc3)c2n1] | LC-MS [M + H]⁺/Rt (min): 449.3/0.620 (Method A); ¹H-NMR (400 MHz, DMSO-d$_6$) δ: 8.74-8.72 (2H, m), 8.06-8.01 (1H, m), 7.18 (2H, d, J = 7.9 Hz), 6.62 (2H, d, J = 7.9 Hz), 5.54 (2H, s), 4.39 (2H, q, J = 7.3 Hz), 3.42 (2H, s), 2.71 (3H, s), 2.36 (4H, q, J = 7.3 Hz), 1.34 (3H, t, J = 7.3 Hz), 0.91 (3H, t, J = 7.3 Hz). |

Examples 267-271

According to the method of Example 123, Examples 267-271 were prepared by using the corresponding material compounds.

| Example | Chemical Structure | Instrumental analaysis data |
|---|---|---|
| 267 | 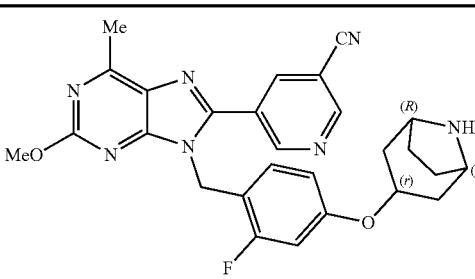 | LC-MS [M + 2H]$^{+2}$/2/Rt (min): 250.8/0.547 (Method C) 250.8/0.547 (Method C); $^1$H-NMR (CD$_3$OD) δ: 9.06 (2H, dd, J = 3.7, 2.4 Hz), 8.46 (1H, t, J = 1.8 Hz), 7.03 (1H, t, J = 8.9 Hz), 6.59-6.52 (2H, m), 5.56 (2H, s), 4.56-4.55 (1H, m), 4.08 (3H, s), 3.54-3.44 (2H, m), 2.77 (3H, s), 2.14-2.03 (3H, m), 1.93-1.75 (5H, m). |
| 268 | 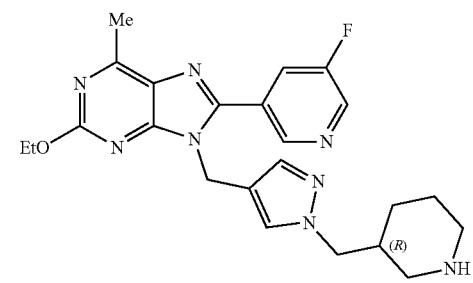 | LC-MS [M + 2H]$^{+2}$/2/Rt (min): 226.1/0.471 (Method C); $^1$H-NMR (CDCl$_3$) δ: 8.79-8.76 (1H, m), 8.62 (1H, d, J = 2.7 Hz), 7.80-7.76 (1H, m), 7.31 (1H, s), 7.21 (1H, s), 5.30 (2H, s), 4.50 (2H, q, J = 7.1 Hz), 3.96-3.84 (2H, m), 3.00-2.94 (1H, m), 2.88-2.81 (1H, m), 2.79 (3H, s), 2.59-2.52 (1H, m), 2.34-2.27 (1H, m), 2.08-1.99 (1H, m), 1.96-1.75 (1H, m), 1.68-1.58 (2H, m), 1.53-1.43 (1H, m), 1.47 (3H, t, J = 7.1 Hz), 1.12-1.01 (1H, m) |
| 269 | 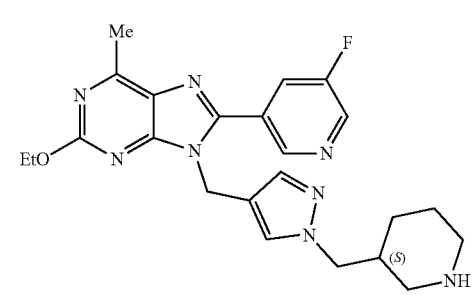 | LC-MS [M + 2H]$^{+2}$/2/Rt (min): 226.2/0.468 (Method C); $^1$H-NMR (CDCl$_3$) δ: 8.79-8.76 (1H, m), 8.62 (1H, d, J = 2.7 Hz), 7.80-7.76 (1H, m), 7.31 (1H, s), 7.21 (1H, s), 5.30 (2H, s), 4.50 (2H, q, J = 7.1 Hz), 3.96-3.84 (2H, m), 3.00-2.94 (1H, m), 2.88-2.81 (1H, m), 2.79 (3H, s), 2.59-2.52 (1H, m), 2.34-2.27 (1H, m), 2.08-1.99 (1H, m), 1.96-1.75 (1H, m), 1.68-1.58 (2H, m), 1.53-1.43 (1H, m), 1.47 (3H, t, J = 7.1 Hz), 1.12-1.01 (1H, m) |
| 270 | 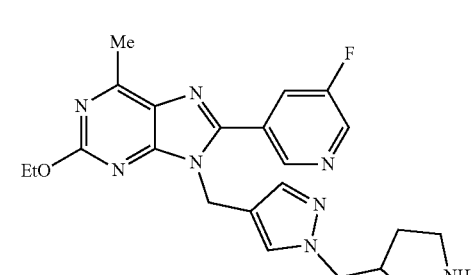 | LC-MS [M + 2H]$^{+2}$/2/Rt (min): 219.2/0.456 (Method C); $^1$H-NMR (CDCl$_3$) δ: 8.77 (1H, s), 8.62 (1H, d, J = 3.1 Hz), 7.81-7.76 (1H, m), 7.32 (1H, s), 7.27 (1H, s), 5.30 (2H, s), 4.50 (2H, q, J = 7.2 Hz), 3.99 (2H, d, J = 7.3 Hz), 3.04-2.90 (3H, m), 2.79 (3H, s), 2.66-2.58 (2H, m), 2.07-1.80 (2H, m), 1.50-1.38 (1H, m), 1.47 (3H, t, J = 7.2 Hz) |
| 271 | 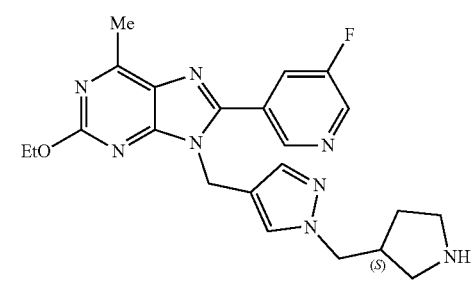 | LC-MS [M + 2H]$^{+2}$/2/Rt (min): 219.1/0.454 (Method C); $^1$H-NMR (CDCl$_3$) δ: 8.78-8.76 (1H, m), 8.62 (1H, d, J = 3.1 Hz), 7.81-7.76 (1H, m), 7.32 (1H, s), 7.27 (1H, s), 5.30 (2H, s), 4.50 (2H, q, J = 7.2 Hz), 3.99 (2H, d, J = 6.7 Hz), 3.04-2.89 (3H, m), 2.79 (3H, s), 2.66-2.57 (2H, m), 2.07-1.80 (2H, m), 1.50-1.37 (1H, m), 1.47 (3H, t, J = 7.2 Hz) |

Examples 272-298

According to the method of Example 127, Examples 272-298 were prepared by using the corresponding material compounds.

| Example | Chemical Structure | Instrumental analysis data |
|---|---|---|
| 272 | 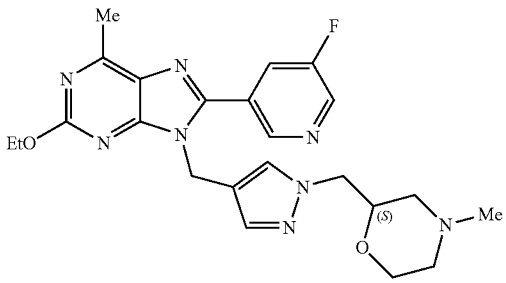 | LC-MS [M + H]⁺/Rt (min): 467.3/0.574 (Method A); ¹H-NMR (400 MHz, DMSO-d₆) δ: 8.81-8.78 (2H, m), 8.13-8.09 (1H, m), 7.43 (1H, s), 7.17 (1H, s), 5.37 (2H, s), 4.42 (2H, q, J = 7.3 Hz), 4.04-3.97 (2H, m), 3.71-3.68 (1H, m), 3.64-3.58 (1H, m), 3.40-3.33 (1H, m), 3.31-3.28 (1H, m), 2.67 (3H, s), 2.53-2.42 (1H, m), 2.09 (3H, s), 1.89-1.82 (1H, m), 1.55 (1H, dd, J = 10.4, 11.0 Hz), 1.36 (3H, t, J = 7.3 Hz). |
| 273 | 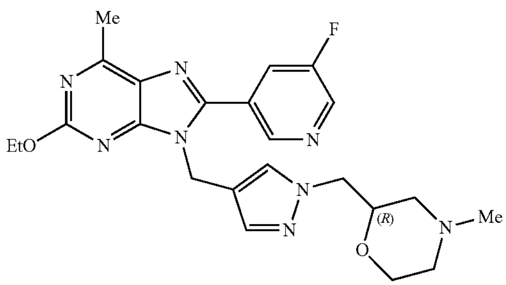 | LC-MS [M + H]⁺/Rt (min): 467.3/0.576 (Method A); ¹H-NMR (400 MHz, DMSO-d₆) δ: 8.81-8.78 (2H, m), 8.13-8.09 (1H, m), 7.43 (1H, s), 7.17 (1H, s), 5.37 (2H, s), 4.42 (2H, q, J = 7.3 Hz), 4.05-3.96 (2H, m), 3.71-3.66 (1H, m), 3.65-3.58 (1H, m), 3.40-3.33 (1H, m), 3.31-3.28 (1H, m), 2.67 (3H, s), 2.52-2.43 (1H, m), 2.09 (3H, s), 1.89-1.82 (1H, m), 1.55 (1H, dd, J = 10.4, 11.0 Hz), 1.36 (3H, t, J = 7.3 Hz). |
| 274 | 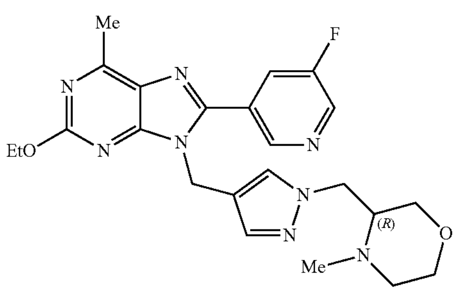 | LC-MS [M + H]⁺/Rt (min): 467.3/0.571 (Method A) |
| 275 | 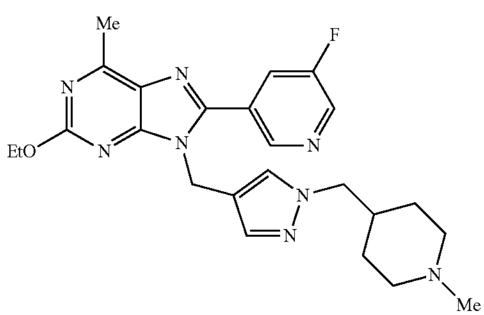 [SMILES: CCOc1nc(C)c2nc(-c3cncc(F)c3)n(Cc3cnn(CC4CCN(C)CC4)c3)c2n1] | LC-MS [M + H]⁺/Rt (min): 466.4/0.566 (Method A); ¹H-NMR (CDCl₃) δ: 8.19 (1H, d, J = 1.4 Hz), 8.02 (1H, d, J = 2.7 Hz), 7.20-7.15 (1H, m), 6.72 (1H, s), 6.60 (1H, s), 4.71 (2H, s), 3.91 (2H, q, J = 7.2 Hz), 3.26 (2H, d, J = 6.9 Hz), 2.22-2.16 (5H, m), 1.62 (3H, s), 1.28-1.11 (3H, m), 0.88 (3H, t, J = 7.2 Hz), 0.85-0.81 (2H, m), 0.70-0.56 (2H, m). |

| Example | Instrumental analysis data |
|---|---|
| 276 | LC-MS [M + 2H]⁺²/2/Rt (min): 233.2/0.459 (Method C); ¹H-NMR (CDCl₃) δ: 8.78-8.76 (1H, m), 8.61 (1H, d, J = 2.7 Hz), 7.80-7.76 (1H, m), 7.31 (1H, s), 7.26-7.24 (1H, m), 5.32-5.28 (2H, m), 4.50 (2H, q, J = 7.2 Hz), 3.96-3.92 (2H, m), 2.81-2.50 (2H, m), 2.79 (3H, s), 2.35-1.94 (5H, m), 1.91-1.51 (4H, m), 1.47 (3H, t, J = 7.2 Hz), 1.01-0.83 (1H, m). |
| 277 | LC-MS [M + 2H]⁺²/2/Rt (min): 233.2/0.466 (Method C); ¹H-NMR (CDCl₃) δ: 8.79-8.76 (1H, m), 8.61 (1H, d, J = 2.7 Hz), 7.80-7.76 (1H, m), 7.31 (1H, s), 7.26-7.24 (1H, m), 5.35-5.26 (2H, m), 4.50 (2H, q, J = 7.1 Hz), 4.01-3.88 (2H, m), 2.86-2.51 (2H, m), 2.79 (3H, s), 2.35-1.94 (5H, m), 1.91-1.51 (4H, m), 1.47 (3H, t, J = 7.1 Hz), 1.01-0.83 (1H, m). |
| 278 | LC-MS [M + 2H]⁺²/2/Rt (min): 226.1/0.453 (Method C); ¹H-NMR (CDCl₃) δ: 8.78-8.76 (1H, m), 8.62 (1H, d, J = 2.7 Hz), 7.79-7.76 (1H, m), 7.31 (1H, s), 7.28 (1H, s), 5.30 (2H, s), 4.50 (2H, q, J = 7.0 Hz), 4.09-3.96 (2H, m), 2.83-2.67 (2H, m), 2.79 (3H, s), 2.60-2.48 (2H, m), 2.47-2.33 (1H, m), 2.38 (3H, s), 2.02-1.91 (1H, m), 1.57-1.45 (1H, m), 1.47 (3H, t, J = 7.1 Hz). |
| 279 | LC-MS [M + H]⁺/Rt (min): 451.3/0.440 (Method C); ¹H-NMR (CDCl₃) δ: 8.78-8.76 (1H, m), 8.62 (1H, d, J = 2.7 Hz), 7.79-7.76 (1H, m), 7.31 (1H, s), 7.27 (1H, s), 5.30 (2H, s), 4.50 (2H, q, J = 7.0 Hz), 4.09-3.96 (2H, m), 2.81-2.62 (2H, m), 2.79 (3H, s), 2.55-2.46 (2H, m), 2.43-2.34 (1H, m), 2.36 (3H, s), 2.02-1.91 (1H, m), 1.56-1.44 (1H, m), 1.47 (3H, t, J = 7.1 Hz). |
| 280 | LC-MS [M + H]⁺/Rt (min): 492.5/0.578 (Method A); ¹H-NMR (DMSO-d₆) δ: 8.74-8.72 (2H, m), 8.12-8.08 (1H, m), 7.03-6.89 (3H, m), 5.55 (2H, s), 3.94 (3H, s), 3.57 (1H, d, J = 14.0 Hz), 3.50 (1H, d, J = 14.0 Hz), 3.09-3.06 (2H, m), 2.69 (3H, s), 2.59 (1H, d, J = 11.0), 2.52-2.48 (1H, m), 2.48-2.41 (2H, m), 2.21 (3H, s), 1.54 (2H, brs). |

-continued

| Example | Chemical Structure | Instrumental analysis data |
|---|---|---|
| 281 | 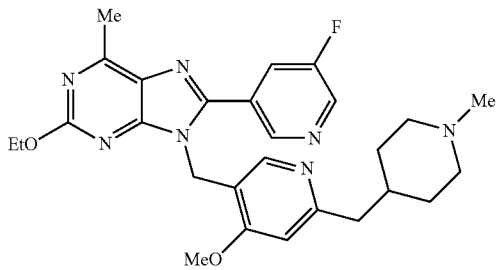 [SMILES: CCOc1nc(C)c2nc(-c3cncc(F)c3)n(Cc3cnc(CC4CCN(C)CC4)cc3OC)c2n1] | LC-MS [M + 2H]$^{+2}$/2/Rt (min): 253.6/0.394 (Method C); $^1$H-NMR (CDCl$_3$) δ: 8.72-8.70 (1H, m), 8.58 (1H, d, J = 3.0 Hz), 8.12 (1H, s), 7.76-7.71 (1H, m), 6.50 (1H, s), 5.41 (2H, s), 4.43 (2H, q, J = 7.1 Hz), 3.65 (3H, s), 2.87-2.80 (2H, m), 2.77 (3H, s), 2.59 (2H, d, J = 7.1 Hz), 2.26 (3H, s), 1.99-1.63 (3H, m), 1.59-1.52 (2H, m), 1.45-1.32 (2H, m), 1.42 (3H, t, J = 7.1 Hz). |
| 282 | 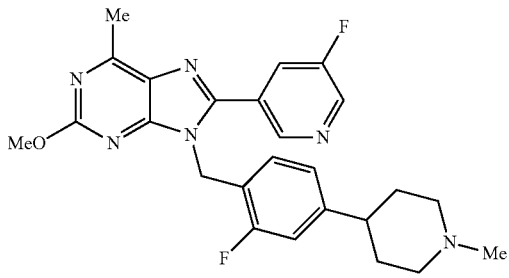 [SMILES: COc1nc(C)c2nc(-c3cncc(F)c3)n(Cc3ccc(C4CCN(C)CC4)cc3F)c2n1] | LC-MS [M + H]$^+$/Rt (min): 465.4/0.477 (Method C); $^1$H-NMR (CDCl$_3$) δ: 8.66-8.62 (1H, m), 8.57 (1H, d, J = 3.1 Hz), 7.72-7.66 (1H, m), 6.93-6.83 (3H, m), 5.47 (2H, s), 4.02 (3H, s), 3.21-3.06 (2H, m), 2.81 (3H, s), 2.57-2.38 (4H, m), 2.34-2.16 (2H, m), 2.05-1.77 (4H, m). |
| 283 | 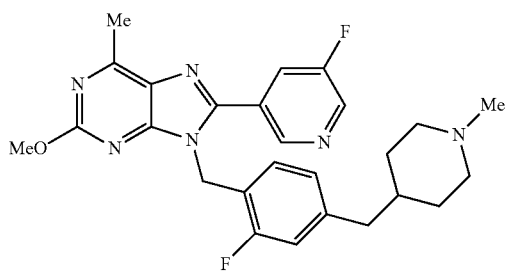 | LC-MS [M + 2H]$^{+2}$/2/Rt (min): 240.3/0.546 (Method C); $^1$H-NMR (CDCl$_3$) δ: 8.65-8.63 (1H, m), 8.56 (1H, d, J = 2.4 Hz), 7.70-7.64 (1H, m), 6.87-6.74 (3H, m), 5.47 (2H, s), 4.03 (3H, s), 3.00-2.86 (2H, m), 2.81 (3H, s), 2.47 (2H, d, J = 6.1 Hz), 2.33 (3H, s), 2.07-1.93 (2H, m), 1.62-1.53 (2H, m), 1.51-1.33 (3H, m). |
| 284 | 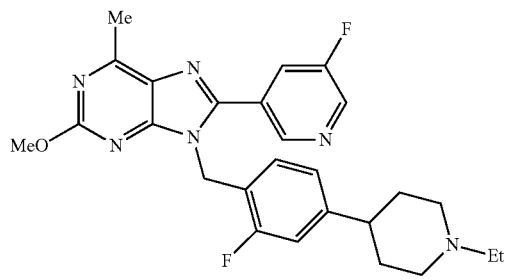 [SMILES: CCN1CCC(c2ccc(Cn3c(-c4cncc(F)c4)nc4c(C)nc(OC)nc43)c(F)c2)CC1] | LC-MS [M + 2H]$^{+2}$/2/Rt (min): 240.3/0.497 (Method C); $^1$H-NMR (CDCl$_3$) δ: 8.65-8.62 (1H, m), 8.57 (1H, d, J = 2.4 Hz), 7.71-7.65 (1H, m), 6.93-6.82 (3H, m), 5.47 (2H, s), 4.02 (3H, s), 3.35-3.03 (2H, m), 2.81 (3H, s), 2.69-2.39 (3H, m), 2.26-1.49 (6H, m), 1.28-1.08 (3H, m). |
| 285 | 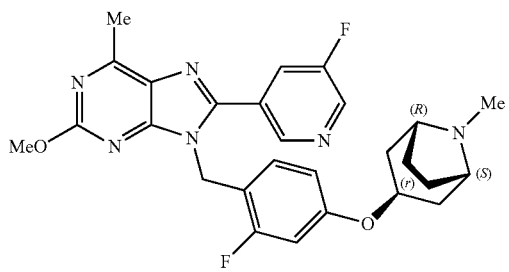 | LC-MS [M + 2H]$^{+2}$/2/Rt (min): 254.3/0.542 (Method C); $^1$H-NMR (CDCl$_3$) δ: 8.66-8.64 (1H, m), 8.58 (1H, d, J = 3.1 Hz), 7.72-7.67 (1H, m), 6.94-6.88 (1H, m), 6.50-6.42 (2H, m), 5.43 (2H, s), 4.51-4.42 (1H, m), 4.04 (3H, s), 3.40-3.19 (2H, m), 2.80 (3H, s), 2.60-1.87 (11H, m). |

-continued

| Example | Chemical Structure | Instrumental analysis data |
|---|---|---|
| 286 | 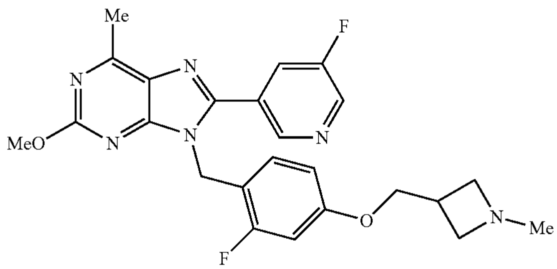 [SMILES: COc1nc(C)c2nc(-c3cncc(F)c3)n(Cc3ccc(OCC4CN(C)C4)cc3F)c2n1] | LC-MS [M + 2H]$^{+2}$/2/Rt (min): 234.3/ 0.491 (Method C); $^1$H-NMR (CDCl$_3$) δ: 8.68-8.64 (1H, m), 8.58 (1H, d, J = 3.0 Hz), 7.72-7.65 (1H, m), 6.96-6.85 (1H, m), 6.62-6.49 (2H, m), 5.43 (2H, s), 4.04 (3H, s), 4.01 (2H, d, J = 6.7 Hz), 3.40-3.33 (2H, m), 3.10-3.02 (2H, m), 2.85-2.76 (1H, m), 2.80 (3H, s), 2.30 (3H, s). |
| 287 | 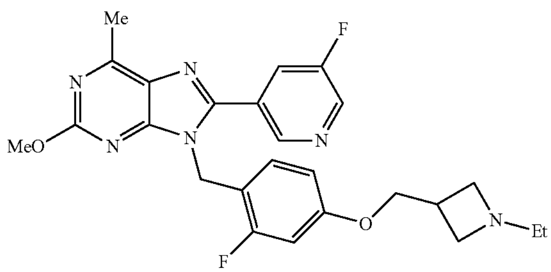 [SMILES: CCN1CC(COc2ccc(Cn3c(-c4cncc(F)c4)nc4c(C)nc(OC)nc43)c(F)c2)C1] | LC-MS [M + 2H]$^{+2}$/2/Rt (min): 241.4/ 0.538 (Method C) |
| 288 | 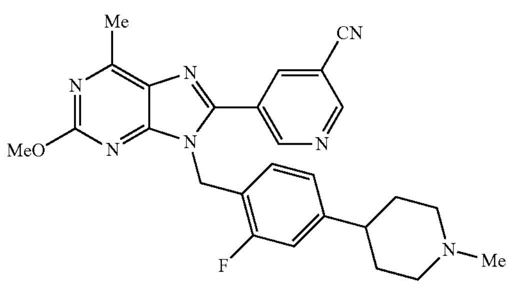 [SMILES: COc1nc(C)c2nc(-c3cncc(C#N)c3)n(Cc3ccc(C4CCN(C)CC4)cc3F)c2n1] | LC-MS [M + 2H]$^{+2}$/2/Rt (min): 236.8/ 0.481 (Method C); $^1$H-NMR (CDCl$_3$) δ: 9.01 (1H, d, J = 1.8 Hz), 8.94 (1H, d, J = 1.8 Hz), 8.20-8.17 (1H, m), 6.98-6.87 (3H, m), 5.46 (2H, s), 4.04 (3H, s), 3.16-3.02 (2H, m), 2.81 (3H, s), 2.55-2.35 (4H, m), 2.29-2.09 (2H, m), 2.00-1.75 (4H, m). |
| 289 | 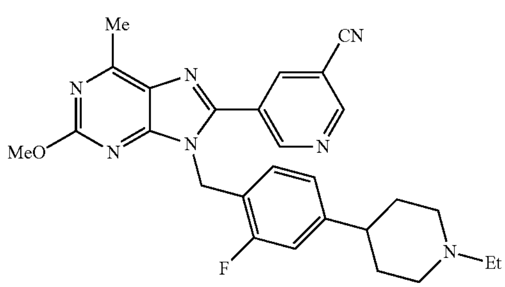 [SMILES: CCN1CCC(c2ccc(Cn3c(-c4cncc(C#N)c4)nc4c(C)nc(OC)nc43)c(F)c2)CC1] | LC-MS [M + 2H]$^{+2}$/2/Rt (min): 243.8/ 0.498 (Method C); $^1$H-NMR (CDCl$_3$) δ: 9.01 (1H, d, J = 2.4 Hz), 8.94 (1H, d, J = 2.4 Hz), 8.20-8.16 (1H, m), 6.97-6.85 (3H, m), 5.46 (2H, s), 4.04 (3H, s), 3.31-3.06 (2H, m), 2.81 (3H, s), 2.70-2.43 (3H, m), 2.27-1.69 (5H, m), 1.36-1.07 (4H, m). |
| 290 | 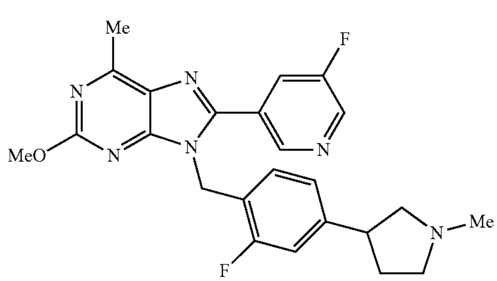 [SMILES: COc1nc(C)c2nc(-c3cncc(F)c3)n(Cc3ccc(C4CCN(C)C4)cc3F)c2n1] | LC-MS [M + 2H]$^{+2}$/2/Rt (min): 226.2/ 0.478 (Method C); $^1$H-NMR (CDCl$_3$) δ: 8.66-8.63 (1H, m), 8.57 (1H, d, J = 2.4 Hz), 7.73-7.66 (1H, m), 6.99-6.81 (3H, m), 5.47 (2H, s), 4.03 (3H, s), 3.35-3.24 (1H, m), 2.94-2.85 (1H, m), 2.81 (3H, s), 2.75-2.58 (2H, m), 2.48-2.40 (1H, m), 2.37 (3H, s), 2.34-2.24 (1H, m), 1.81-1.68 (1H, m). |

| Example | Chemical Structure | Instrumental analysis data |
|---------|-------------------|---------------------------|
| 291 | 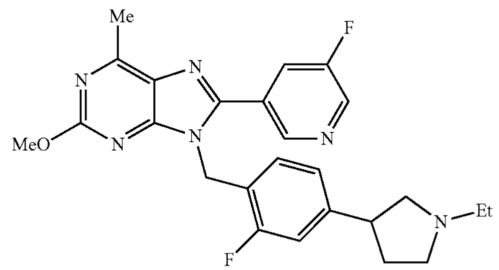 [SMILES: CCN1CCC(c2ccc(Cn3c(-c4cncc(F)c4)nc4c(C)nc(OC)nc43)c(F)c2)C1] | LC-MS [M + 2H]⁺²/2/Rt (min): 233.3/ 0.496 (Method C); ¹H-NMR (CDCl₃) δ: 8.67-8.63 (1H, m), 8.57 (1H, d, J = 2.4 Hz), 7.72-7.66 (1H, m), 6.99-6.82 (3H, m), 5.47 (2H, s), 4.03 (3H, s), 3.33-3.23 (1H, m), 3.00-2.93 (1H, m), 2.81 (3H, s), 2.79-2.73 (1H, m), 2.65-2.37 (4H, m), 2.32-2.21 (1H, m), 1.80-1.70 (1H, m), 1.10 (3H, t, J = 7.0 Hz). |
| 292 | 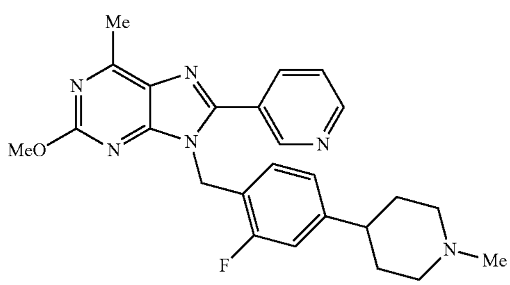 [SMILES: COc1nc(C)c2nc(-c3cccnc3)n(Cc3ccc(C4CCN(C)CC4)cc3F)c2n1] | LC-MS [M + 2H]⁺²/2/Rt (min): 224.3/ 0.439 (Method C); ¹H-NMR (CDCl₃) δ: 8.83-8.81 (1H, m), 8.72-8.69 (1H, m), 7.95-7.91 (1H, m), 7.41-7.37 (1H, m), 6.91-6.82 (3H, m), 5.45 (2H, s), 4.02 (3H, s), 3.17-3.02 (2H, m), 2.81 (3H, s), 2.53-2.36 (4H, m), 2.29-2.14 (2H, m), 1.98-1.75 (4H, m). |
| 293 | 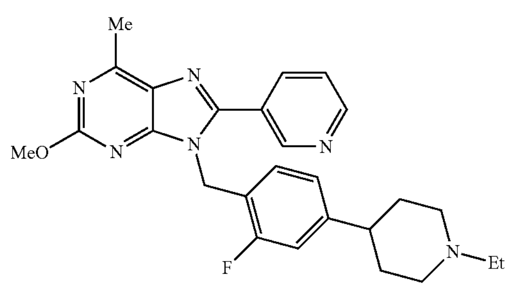 [SMILES: CCN1CCC(c2ccc(Cn3c(-c4cccnc4)nc4c(C)nc(OC)nc43)c(F)c2)CC1] | LC-MS [M + H]⁺/Rt (min): 461.5/0.441 (Method C); ¹H-NMR (CDCl₃) δ: 8.84-8.82 (1H, m), 8.72-8.68 (1H, m), 7.95-7.90 (1H, m), 7.41-7.35 (1H, m), 6.90-6.80 (3H, m), 5.45 (2H, s), 4.01 (3H, s), 3.16-3.02 (2H, m), 2.80 (3H, s), 2.55-2.38 (3H, m), 2.12-1.96 (2H, m), 1.87-1.69 (4H, m), 1.18-1.06 (3H, m). |
| 294 | 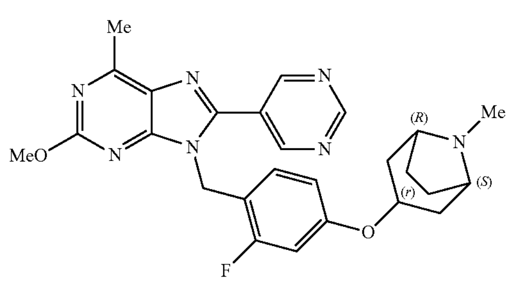 | LC-MS [M + 2H]⁺²/2/Rt (min): 245.7/0.465 (Method C); ¹H-MMR (CDCl₃) δ: 9.30 (1H, s), 8.98 (2H, s), 6.95-6.89 (1H, m), 6.50-6.43 (2H, m), 5.43 (2H, s), 4.51-4.45 (1H, m), 4.05 (3H, s), 3.42-3.27 (2H, m), 2.81 (3H, s), 2.59-2.39 (2H, m), 2.45 (3H, s), 2.18-2.04 (4H, m), 1.99-1.91 (2H, m). |
| 295 | 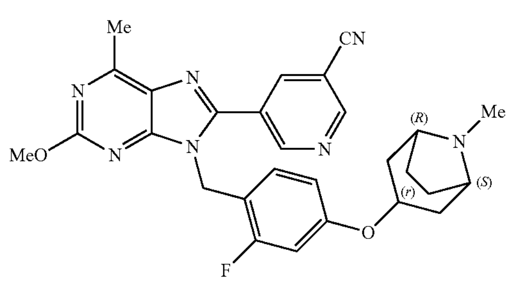 | LC-MS [M + 2H]²⁺/2/Rt min): 257.8/0.560 (Method C); ¹H-NMR (CD₃OD) δ: 9.05 (2H, dd, J = 6.1, 1.8 Hz), 8.46 (1H, t, J = 1.8 Hz), 7.02 (1H, t, J = 8.9 Hz), 6.58-6.50 (2H, m), 5.54 (2H, s), 4.50-4.44 (1H, m), 4.07 (3H, s), 3.19-3.07 (2H, m), 2.75 (3H, s), 2.28 (3H, s), 2.13-1.95 (8H, m). |

| Example | Chemical Structure | Instrumental analysis data |
|---|---|---|
| 296 | 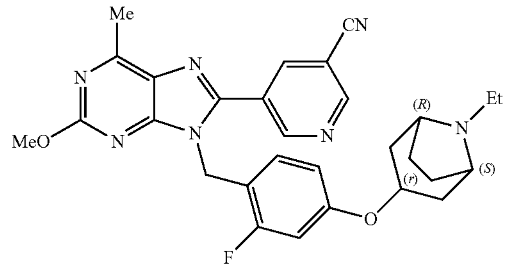 | LC-MS [M + 2H]$^{2+}$/2/Rt (min): 264.82/0.578 (Method C); $^1$H-NMR (CD$_3$OD) δ: 9.79-9.79 (2H, m), 9.25-9.23 (1H, m), 7.81-7.78 (1H, m), 7.49-7.38 (2H, m), 5.35 (2H, s), 4.53-4.34 (1H, m), 3.99 (3H, s), 3.48-3.44 (2H, m), 2.87 (3H, s), 2.51 (3H, q, J = 6.4 Hz), 2.06-2.01 (2H, m), 2.01-1.93 (4H, m), 1.92-1.89 (2H, m), 1.65 (3H, t, J = 10.0 Hz). |
| 297 | 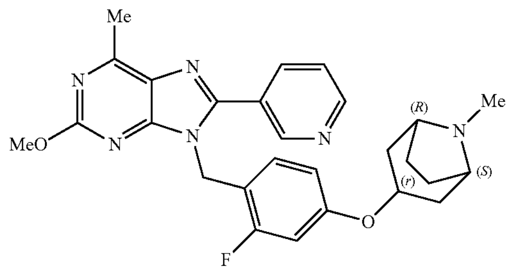 | LC-MS [M + 2H]$^{2+}$/2/Rt (min): 245.31/0.506 (Method C); $^1$H-NMR (CD$_3$OD) δ: 8.82 (1H, d, J = 1.2 Hz), 8.70 (1H, dd, J = 4.9, 1.2 Hz), 8.13 (1H, dt, J = 7.9, 1.8 Hz), 7.59 (1H, dd, J = 7.9, 4.9 Hz), 6.98 (1H, t, J = 8.9 Hz), 6.57-6.49 (2H, m), 5.52 (2H, s), 4.46 (1H, t, J = 4.9 Hz), 4.05 (3H, s), 3.17-3.09 (2H, m), 2.75 (3H, s), 2.28 (3H, s), 2.14-2.05 (2H, m), 2.05-1.95 (4H, m), 1.88-1.79 (2H, m). |
| 298 | 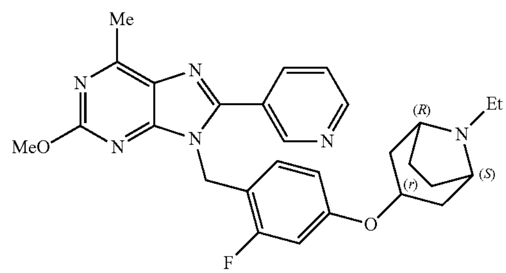 | LC-MS [M + 2H]$^{2+}$/2/Rt (min): 252.2/0.523 (Method C); $^1$H-NMR (CD$_3$OD) δ: 8.81 (1H, d, J = 1.8 Hz), 8.70 (1H, dd, J = 5.2, 1.5 Hz), 8.13 (1H, dt, J = 7.9, 1.8 Hz), 7.58 (1H, dd, J = 7.9, 4.9 Hz), 6.97 (1H, t, J = 8.9 Hz), 6.55-6.53 (1H, m), 6.53-6.50 (1H, m), 5.52 (2H, s), 4.52-4.45 (1H, m), 4.05 (3H, s), 3.29-3.22 (2H, m), 2.75 (3H, s), 2.48 (2H, q, J = 7.1 Hz), 2.15-2.04 (2H, m), 2.04-1.88 (4H, m), 1.87-1.76 (2H, m), 1.10 (3H, t, J = 7.3 Hz). |

Example 299 test-Butyl (1S,4S)-5-(3-fluoro-4-{[8-(5-fluoropyridin-3-yl)-2-methoxy-6-methyl-9H-purin-9-yl]methyl}benzyl)-2,5-diazabicyclo[2.2.1]heptane-2-carboxylate

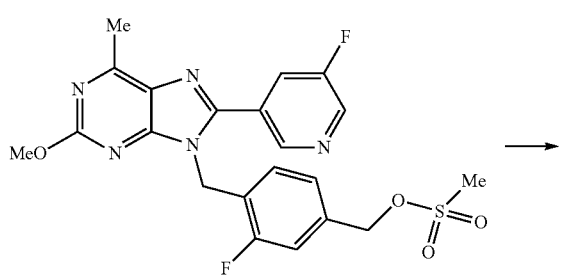

To an ice-cooled solution of the compound of Example 438 (40.1 mg) in N,N-dimethylformamide (5 mL) were added tert-butyl (1S,4S)-2,5-diazabicyclo[2.2.1]heptane-2-carboxylate (41.8 mg), potassium carbonate (43.1 mg), and potassium iodide (17.9 mg). The reaction mixture was stirred at room temperature overnight. To the reaction mixture was added aqueous saturated sodium bicarbonate, and the mixture was extracted with chloroform. The organic layer was dried over sodium sulfate, filtrated, and then concentrated in vacuo. The residue was purified by silica gel column chromatography (chloroform/methanol) to give the title compound (40.1 mg).

LC-MS [M+H]⁺/Rt (min): 578.5/0.704 (Method A)

Example 300

According to the method of Example 163, Example 300 was prepared by using the corresponding material compound.

| Example | Chemical Structure | Instrumental analysis data |
|---|---|---|
| 300 | (structure) | LC-MS [M + H]⁺/Rt (min): 480.4/0.538 (Method A); ¹H-NMR (CDCl₃) δ: 8.84-8.81 (1H, m), 8.66 (1H, d, J = 2.4 Hz), 7.86-7.79 (1H, m), 7.37 (2H, d, J = 5.2 Hz), 5.34 (2H, s), 4.54 (2H, q, J = 7.2 Hz), 4.16 (2H, t, J = 6.8 Hz), 2.83 (3H, s), 2.75 (2H, t, J = 6.4 Hz), 2.57-2.37 (8H, m), 2.31 (3H, s), 1.51 (3H, t, J = 7.2 Hz). |

Example 301

9-[4-(1-Azabicyclo[2.2.2]oct-3-yl)-2-fluorobenzyl]-2-methoxy-6-methyl-8-(pyrazin-2-yl)-9H-purine

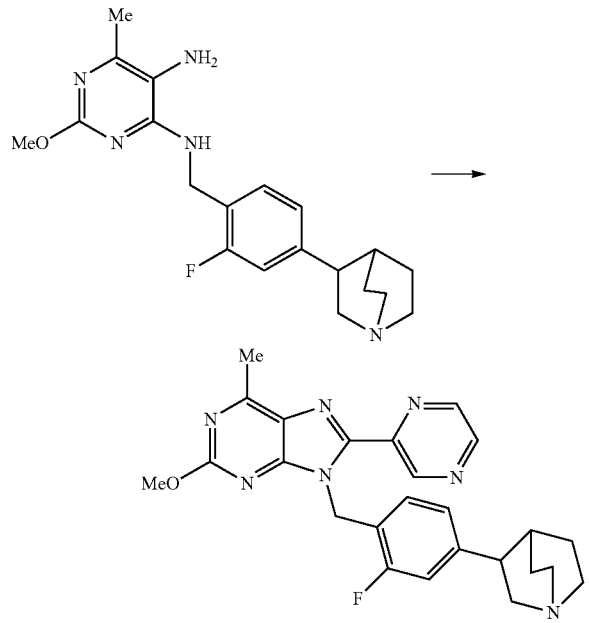

To a solution of the compound of Reference example 223 (187 mg) in chloroform (10 mL) were added pyrazine-2-carboxylic acid (187 mg), 1-ethyl-3-(3-dimethylaminopropyl)carbodiimide hydrochloride (290 mg), 1-hydroxybenzotriazole (204 mg), and N,N-diisopropylethylamine (0.514 mL), and the mixture was stirred at room temperature overnight. To the reaction mixture was added 50% aqueous potassium carbonate, and the mixture was extracted with chloroform/ethanol (3/1). The organic layer was dried over sodium sulfate, filtrated, and then concentrated in vacuo. To the obtained residue (904 mg) was added N,O-bis(trimethylsilyl)acetamide (4 mL), and the mixture was stirred at 55° C. for 2 hours. The reaction mixture was cooled to room temperature. 50% aqueous potassium carbonate was added thereto, and the mixture was extracted with chloroform/ethanol (3/1). The organic layer was dried over sodium sulfate, filtrated, and then concentrated in vacuo. The obtained residue was purified by amino silica gel column chromatography (chloroform/methanol) to give the title compound (119 mg).

LC-MS [M+H]⁺/Rt (min): 459.2/0.488 (Method C); ¹H-NMR (CDCl₃) δ: 9.55 (1H, d, J=1.2 Hz), 8.58 (1H, d, J=2.4 Hz), 0.54-8.53 (1H, m), 6.90-6.78 (3H, m), 6.06 (2H, s), 4.04 (3H, s), 3.40-3.26 (1H, m), 3.08-2.81 (6H, m), 2.83 (3H, s), 1.94-1.88 (1H, m), 1.82-1.69 (2H, m), 1.65-1.52 (1H, m), 1.46-1.33 (1H, m).

Examples 302-348

According to the method of Example 165 or Example 301, Examples 302-348 were prepared by the corresponding material compounds.

| Example | Chemical Structure | Instrumental analysis data |
|---|---|---|
| 302 | (structure) | LC-MS [M + 2H]²⁺/2/Rt (min): 245.4/0.523 (Method C); ¹H-NMR (CDCl₃) δ: 8.36-8.35 (2H, m), 7.39-7.37 (1H, m), 6.90-6.81 (3H, m), 5.44 (2H, s), 3.98 (3H, s), 3.77 (3H, s), 3.28-3.20 (1H, m), 2.94-2.78 (6H, m), 2.77 (3H, s), 1.86-1.73 (1H, m), 1.70-1.62 (2H, m), 1.54-1.44 (1H, m), 1.36-1.26 (1H, m). |

-continued

| Example | Chemical Structure | Instrumental analysis data |
|---------|-------------------|---------------------------|
| 303 | 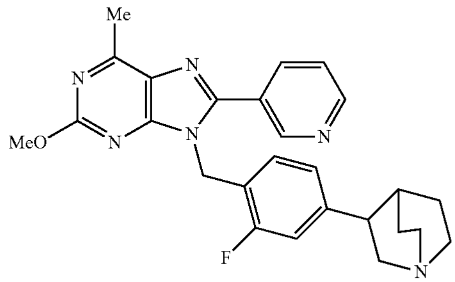 [SMILES: COc1nc(C)c2nc(-c3cccnc3)n(Cc3ccc(C4CN5CCC4CC5)cc3F)c2n1] | LC-MS [M + 2H]²⁺/2/Rt (min): 230.4/0.478 (Method C); ¹H-NMR (CDCl₃) δ: 8.79-8.78 (1H, m), 8.66 (1H, dd, J = 1.2, 3.7 Hz), 7.92-7.90 (1H, m), 7.35 (1H, dd, J = 3.1, 4.9 Hz), 6.88-6.84 (3H, m), 5.42 (2H, s), 3.98 (3H, s), 3.29-3.22 (1H, m), 2.96-2.78 (6H, m), 2.77 (3H, s), 1.86-1.82 (1H, m), 1.75-1.46 (3H, m), 1.36-1.27 (1H, m). |
| 304 | 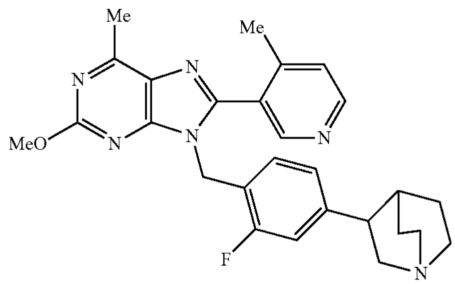 [SMILES: COc1nc(C)c2nc(-c3cnccc3C)n(Cc3ccc(C4CN5CCC4CC5)cc3F)c2n1] | ¹H-NMR (CDCl₃) δ: 8.56 (1H, d, J = 4.9 Hz), 8.42 (1H, s), 7.20 (1H, d, J = 5.5 Hz), 6.94-6.89 (1H, m), 6.86-6.83 (1H, m), 6.81-6.78 (1H, m), 5.26 (2H, s), 4.05 (3H, s), 3.32-3.24 (1H, m), 2.97-2.82 (6H, m), 2.78 (3H, s), 2.09 (3H, s), 1.88-1.82 (1H, m), 1.78-1.64 (2H, m), 1.56-1.46 (1H, m), 1.40-1.31 (1H, m). |
| 305 | 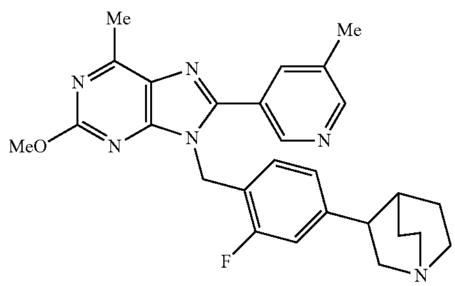 [SMILES: COc1nc(C)c2nc(-c3cncc(C)c3)n(Cc3ccc(C4CN5CCC4CC5)cc3F)c2n1] | LC-MS [M + 2H]²⁺/2/Et (min): 237.3/0.521 (Method C); ¹H-NMR (CDCl₃) δ: 8.55 (1H, d, J = 1.8 Hz), 8.49 (1H, d, J = 1.8 Hz), 7.73-7.71 (1H, m), 6.89-6.85 (3H, m), 5.42 (2H, s), 3.98 (3H, s), 3.29-3.21 (1H, m), 2.96-2.77 (6H, m), 2.77 (3H, s), 2.32 (3H, s), 1.86-1.81 (1H, m), 1.78-1.63 (2H, m), 1.57-1.45 (1H, m), 1.37-1.26 (1H, m). |
| 306 | 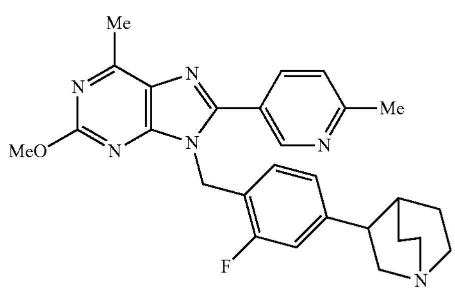 [SMILES: COc1nc(C)c2nc(-c3ccc(C)nc3)n(Cc3ccc(C4CN5CCC4CC5)cc3F)c2n1] | LC-MS [M + 2H]²⁺/2/Rt (min): 237.4/0.498 (Method C); ¹H-NMR (CDCl₃) δ: 8.65-8.64 (1H, m), 7.81 (1H, dd, J = 2.4, 5.5 Hz), 7.21-7.19 (1H, m), 6.90-6.79 (3H, m), 5.41 (2H, s), 3.96 (3H, s), 3.29-3.21 (1H, m), 2.95-2.78 (6H, m), 2.76 (3H, s), 2.56 (3H, s), 1.86-1.81 (1H, m), 1.72-1.61 (2H, m), 1.56-1.45 (1H, m), 1.36-1.26 (1H, m). |
| 307 | 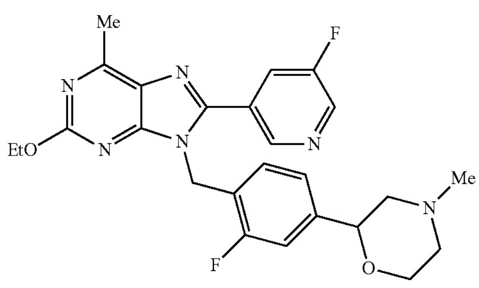 [SMILES: CCOc1nc(C)c2nc(-c3cncc(F)c3)n(Cc3ccc(C4CN(C)CCO4)cc3F)c2n1] | LC-MS [M + H]⁺/Rt (min): 481.5/0.655 (Method A); |

-continued

| Example | Chemical Structure | Instrumental analysis data |
|---|---|---|
| 308 | 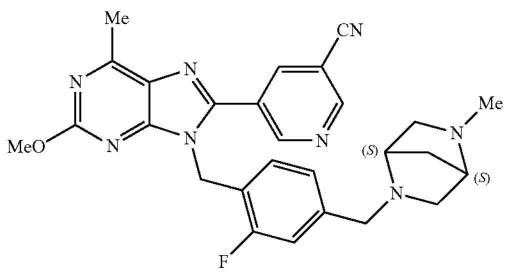 | LC-MS [M + H]⁺/Rt (min): 499.5/0.558 (Method A); 499.5/0.558 (Method A); $^1$H-NMR (DMSO-d$_6$) δ: 9.19 (1H, d, J = 1.8 Hz), 9.15 (1H, d, J = 1.8 Hz), 8.71-8.69 (1H, m), 7.06-6.95 (3H, m), 5.60 (2H, s), 3.98 (3H, s), 3.69-3.50 (2H, m), 3.12-3.09 (2H, m), 2.73 (3H, s), 2.64-2.61 (1H, m), 2.53-2.43 (2H, m), 1.57 (2H, brs), 1.46-1.32 (1H, m). |
| 309 | 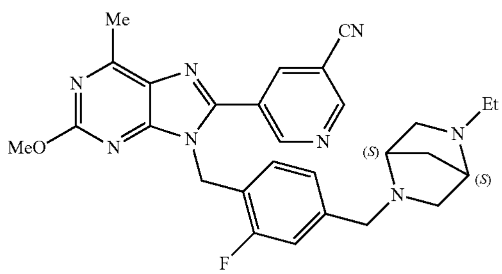 | LC-MS [M + H]⁺/Rt (min): 513.5/0.578 (Method A); |
| 310 | 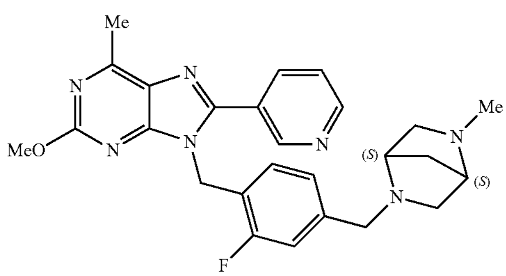 | LC-MS [M + H]⁺/Rt (min): 474.5/0.533 (Method A); |
| 311 | 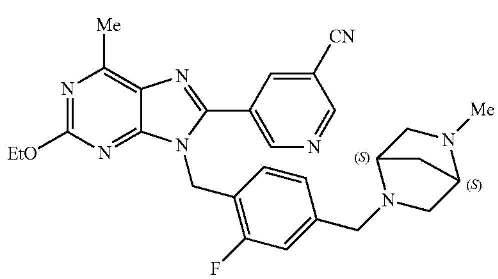 | LC-MS [M + H]⁺/Rt (min): 513.5/0.625 (Method A); 513.5/0.625 (Method A); $^1$H-NMR (DMSO-d$_6$) δ: 9.15 (1H, d, J = 1.8 Hz), 9.11 (1H, d, J = 1.8 Hz), 8.66-8.64 (1H, m), 7.03-6.91 (3H, m), 5.55 (2H, s), 4.38 (2H, q, J = 7.3 Hz), 3.57 (1H, d, J = 14.0 Hz), 3.50 (1H, d, J = 14.0 Hz), 3.08-3.07 (2H, m), 2.68 (3H, s), 2.61-2.59 (1H, m), 2.54-2.40 (2H, m), 2.22 (3H, s), 1.54 (2H, brs), 1.44-1.28 (1H, m), 1.32 (3H, t, J 7.3 Hz). |
| 312 | 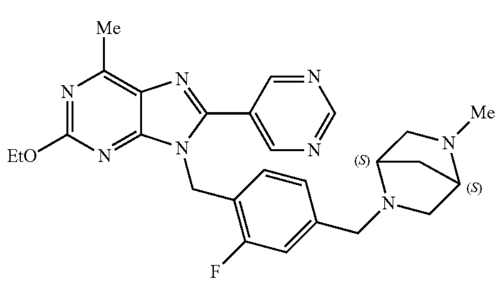 | LC-MS [M + H]⁺/Rt (min): 489.5/0.549 (Method A); 489.5/0.549 (Method A); $^1$H-NMR (DMSO-d$_6$) δ: 9.31 (1H, s), 9.12 (2H, s), 7.04-6.93 (3H, m), 5.55 (2H, s), 4.37 (2H, q, J = 7.3 Hz), 3.57 (1H, d, J = 14.0 Hz), 3.50 (1H, d, J = 14.0 Hz), 3.10-3.06 (2H, m), 2.68 (3H, s), 2.59 (1H, d, J = 11.0), 2.50-2.42 (2H, m), 2.21 (3H, s), 1.54 (2H, brs), 1.42-1.34 (1H, m), 1.32 (3H, t, J 7.3 Hz). |

| Example | Chemical Structure | Instrumental analysis data |
|---|---|---|
| 313 | 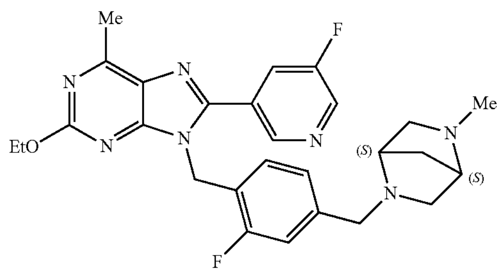 | LC-MS [M + H]⁺/Rt (min): ¹H-NMR (DMSO-d₆) δ: 8.75-8.73 (2H, m), 8.12-8.09 (1H, m), 7.05-6.97 (2H, m), 6.93-6.89 (1H, m), 5.55 (2H, s), 4.38 (2H, q, J = 7.3 Hz), 3.59 (1H, d, J = 14.0 Hz), 3.52 (1H, d, J = 14.0 Hz), 3.38-3.35 (1H, m), 3.10-3.07 (2H, m), 2.69 (3H, s), 2.60 (1H, d, J = 11.0), 2.47-2.41 (2H, m), 2.23 (3H, m), 1.55 (2H, brs), 1.44-1.30 (1H, m), 1.33 (3H, t, J 7.3 Hz). |
| 314 | 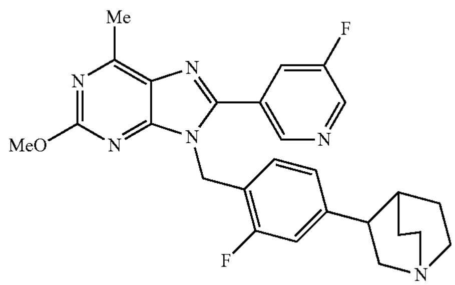 [SMILES: COc1nc(C)c2nc(-c3cncc(F)c3)n(Cc3ccc(C4CN5CCC4CC5)cc3F)c2n1] | LC-MS [M + H]⁺/Rt (min): 477.1/0.494 (Method C); ¹H-NMR (CDCl₃) δ: 8.70-8.67 (1H, m), 8.61 (1H, d, J = 2.4 Hz), 7.75-7.70 (1H, m), 6.99-6.91 (3H, m), 5.53 (2H, s), 4.08 (3H, s), 3.36-3.26 (1H, m), 3.01-2.80 (9H, m), 1.93-1.85 (1H, m), 1.77-1.65 (2H, m), 1.59-1.50 (1H, m), 1.42-1.30 (1H, m). |
| 315 | 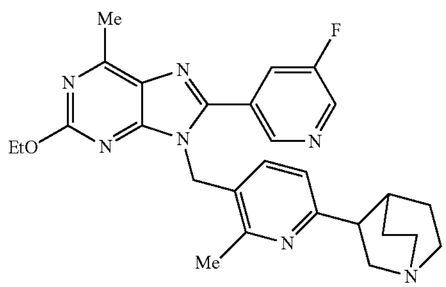 [SMILES: CCOc1nc(C)c2nc(-c3cncc(F)c3)n(Cc3ccc(C4CN5CCC4CC5)nc3C)c2n1] | LC-MS [M + H]⁺/Rt (min): 488.44/0.626 (Method A); ¹H-NMR (CDCl₃) δ: 6.62 (1H, s), 8.59 (1H, d, J = 3.0 Hz), 7.74-7.69 (1H, m), 6.92 (1H, d, J = 7.9 Hz), 6.84 (1H, d, J = 7.9 Hz), 5.46 (2H, s), 4.45 (2H, q, J = 7.1 Hz), 3.50-3.43 (1H, m), 3.24-3.16 (1H, m), 3.07-2.97 (2H, m), 2.96-2.88 (2H, m), 2.87 (3H, s), 2.85-2.77 (1H, m), 2.51 (3H, s), 2.02-1.97 (1H, m), 1.75-1.68 (2H, m), 1.66-1.57 (1H, m), 1.44 (3H, t, J = 7.1 Hz), 1.35-1.26 (1H, m). |
| 316 | 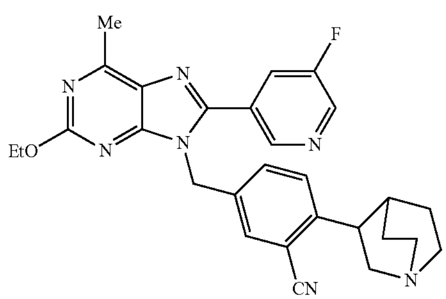 [SMILES: CCOc1nc(C)c2nc(-c3cncc(F)c3)n(Cc3ccc(C4CN5CCC4CC5)c(C#N)c3)c2n1] | LC-MS [M + H]⁺/Rt (min): 498.4/0.665 (Method A); ¹H-NMR (CDCl₃) δ: 8.68-8.60 (2H, m), 7.78-7.73 (1H, m), 7.50 (1H, d, J = 7.9 Hz), 7.40 (1H, d, J = 1.8 Hz), 7.32-7.29 (1H, m), 5.50 (2H, s), 4.50 (2H, q, J = 7.1 Hz), 3.44-3.38 (1H, m), 3.38-3.30 (1H, m), 3.10-3.00 (1H, m), 3.00-2.87 (4H, m), 2.86 (3H, s), 1.92-1.82 (2H, m), 1.79-1.73 (1H, m), 1.54-1.44 (4H, m), 1.42-1.33 (1H, m). |
| 317 | 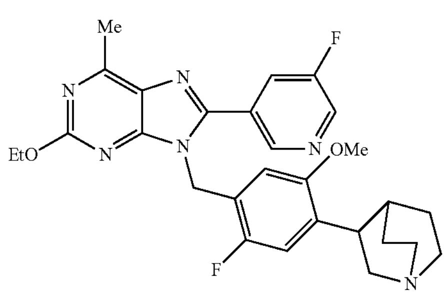 [SMILES: CCOc1nc(C)c2nc(-c3cncc(F)c3)n(Cc3cc(OC)c(C4CN5CCC4CC5)cc3F)c2n1] | LC-MS [M + H]⁺/Rt (min): 521.40/0.703 (Method A); ¹H-NMR (CDCl₃) δ: 8.72 (1H, s), 8.62 (1H, d, J = 3.0 Hz), 7.75-7.70 (1H, m), 6.98 (1H, d, J = 11.0 Hz), 6.55 (1H, d, J = 6.1 Hz), 5.50 (2H, s), 4.51 (2H, q, J = 7.1 Hz), 3.59 (3H, s), 3.42-3.32 (1H, m), 3.27-3.20 (1H, m), 3.03-2.91 (3H, m), 2.91-2.75 (5H, m), 1.80-1.62 (4H, m), 1.51-1.37 (4H, m). |

-continued

| Example | Chemical Structure | Instrumental analysis data |
|---|---|---|
| 318 | 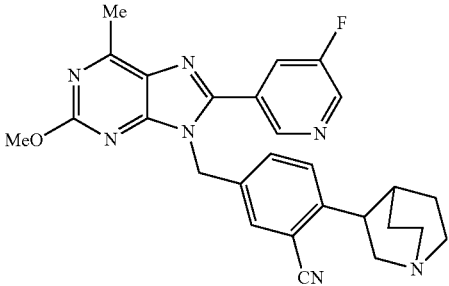 [SMILES: COc1nc(C)c2nc(-c3cncc(F)c3)n(Cc3ccc(C4CN5CCC4CC5)c(C#N)c3)c2n1] | LC-MS [M + H]⁺/Rt (min): 484.38/0.680 (Method A); ¹H-NMR (CDCl₃) δ: 8.65-8.62 (2H, m), 7.79-7.75 (1H, m), 7.50 (1H, d, J = 7.9 Hz), 7.41 (1H, d, J = 1.8 Hz), 7.33-7.29 (1H, m), 5.51 (2H, s), 4.09 (3H, s), 3.47-3.39 (1H, m), 3.39-3.32 (1H, m), 3.12-3.03 (1H, m), 3.02-2.89 (4H, m), 2.87 (3H, s), 1.94-1.90 (1H, m), 1.80-1.71 (1H, m), 1.56-1.45 (1H, m), 1.44-1.34 (1H, m), 1.34-1.25 (1H, m). |
| 319 | 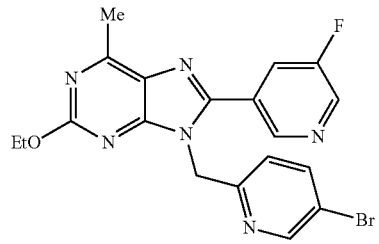 [SMILES: CCOc1nc(C)c2nc(-c3cncc(F)c3)n(Cc3ccc(Br)cn3)c2n1] | LC-MS [M + H]⁺/Rt (min): 445.17/1.044 (Method A); ¹H-NMR (CDCl₃) δ: 8.93-8.91 (1H, m), 8.63-8.59 (2H, m), 8.13-8.09 (1H, m), 7.82 (1H, dd, J = 8.2, 2.1 Hz), 7.26 (1H, d, J = 3.2 Hz), 5.50 (2H, s), 4.45 (2H, q, J = 7.1 Hz), 2.84 (3H, s), 1.45 (3H, t, J = 7.0 Hz). |
| 320 | 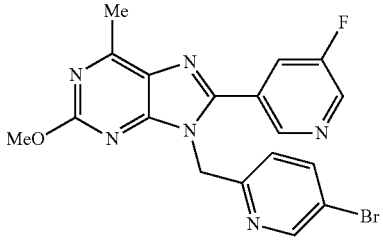 [SMILES: COc1nc(C)c2nc(-c3cncc(F)c3)n(Cc3ccc(Br)cn3)c2n1] | LC-MS [M + H]⁺/Rt (min): 431.2/0.968 (Method A); ¹H-NMR (CDCl₃) δ: 8.95-8.93 (1H, m), 8.63-8.60 (2H, m), 8.15-8.11 (1H, m), 7.82 (1H, dd, J = 8.5, 2.4 Hz), 7.29 (1H, d, J = 8.5 Hz), 5.50 (2H, s), 4.04 (3H, s), 2.84 (3H, s). |
| 321 | 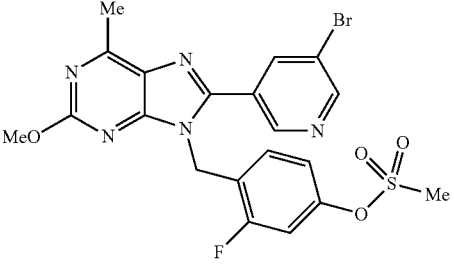 [SMILES: COc1nc(C)c2nc(-c3cncc(Br)c3)n(Cc3ccc(OS(C)(=O)=O)cc3F)c2n1] | LC-MS [M + H]⁺/Rt (min): 522.2/0.925 (Method A) |
| 322 | 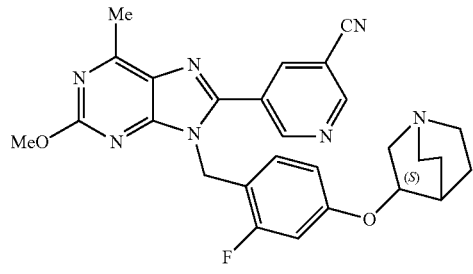 | LC-MS [M + 2H]²⁺/2/Rt (min): 250.67/0.538 (Method C); ¹H-NMR (CD₃OD) δ: 9.06 (2H, s), 8.46 (1H, t, J = 2.1 Hz), 7.04 (1H, t, J = 8.9 Hz), 6.66-6.56 (2H, m), 5.55 (2H, s), 4.50-4.41 (1H, m), 4.08 (3H, s), 3.29-3.22 (1H, m), 2.93-2.66 (5H, m), 2.76 (3H, s), 2.12-2.05 (1H, m), 1.98-1.87 (1H, m), 1.83-1.72 (1H, m), 1.71-1.57 (1H, m), 1.52-1.41 (1H, m). |

| Example | Chemical Structure | Instrumental analysis data |
|---|---|---|
| 323 | 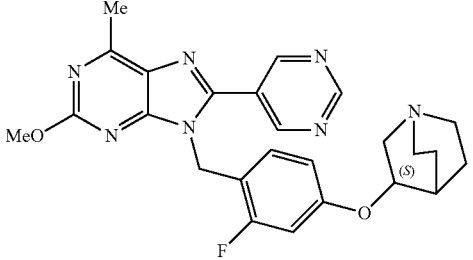 | LC-MS [M + 2H]$^{2+}$/2/Rt (min): 238.6/0.467 (Method C); $^1$H-NMR (CD$_3$OD) δ: 9.29 (1H, s), 9.08 (2H, s), 7.06 (1H, t, J = 8.9 Hz), 6.66-6.56 (2H, m), 5.56 (2H, s), 4.48-4.41 (1H, m), 4.06 (3H, s), 3.30-3.22 (1H, m), 2.92-2.77 (4H, m), 2.75 (3H, s), 2.72-2.66 (1H, m), 2.10-2.04 (1H, m), 1.97-1.85 (1H, m), 1.82-1.71 (1H, m), 1.69-1.57 (1H, m), 1.51-1.38 (1H, m). |
| 324 | 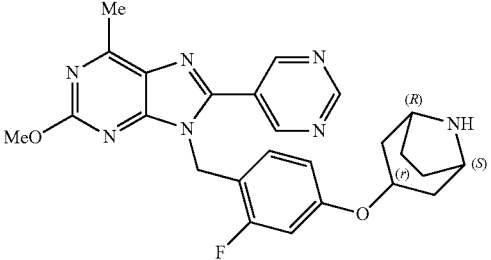 | LC-MS [M + 2H]$^{2+}$/2/Rt (min): 238.7/0.455 (Method C) |
| 325 | 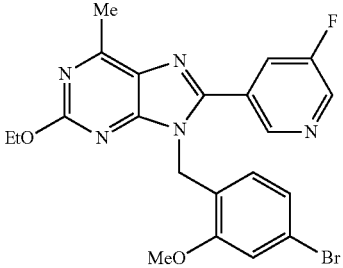 [SMILES: CCOc1nc(C)c2nc(-c3cncc(F)c3)n(Cc3ccc(Br)cc3OC)c2n1] | LC-MS [M + H]$^+$/Rt (min): 472.1/0.992 (Method C); $^1$H-NMR (CDCl$_3$) δ: 8.67-8.65 (1H, m), 8.56 (1H, d, J = 2.7 Hz), 7.73-7.68 (1H, m), 6.98-6.93 (2H, m), 6.72 (1H, d, J = 8.2 Hz), 5.39 (2H, s), 4.43 (2H, q, J = 7.0 Hz), 3.71 (3H, s), 2.81 (3H, s), 1.42 (3H, t, J = 7.0 Hz). |
| 326 | 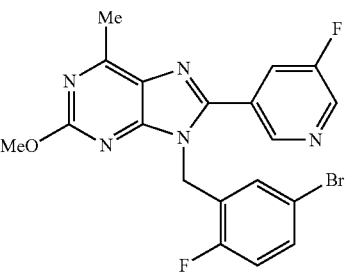 [SMILES: COc1nc(C)c2nc(-c3cncc(F)c3)n(Cc3cc(Br)ccc3F)c2n1] | LC-MS [M + H]$^+$/Rt (min): 446.3/0.949 (Method A); $^1$H-NMR (CDCl$_3$) δ: 8.65-8.63 (1H, m), 8.60 (1H, d, J = 3.0 Hz), 7.40-7.35 (1H, m), 7.17 (1H, dd, J = 2.4, 4.3), 6.93 (1H, dd, J = 9.1, 9.1 Hz), 5.46 (2H, s), 4.05 (3H, s), 2.82 (3H, s). |
| 327 | 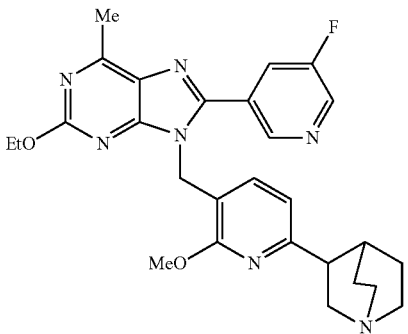 [SMILES: CCOc1nc(C)c2nc(-c3cncc(F)c3)n(Cc3ccc(C4CN5CCC4CC5)nc3OC)c2n1] | LC-MS [M + 2H]$^{2+}$/2/Rt (min): 252.7/0.588 (Method C); $^1$H-NMR (CDCl$_3$) δ: 8.67-8.66 (1H, m), 8.57 (1H, d, J = 3.0 Hz), 7.77-7.73 (1H, m), 7.09 (1H, d, J = 7.3 Hz), 6.63 (1H, d, J = 7.3 Hz), 5.39 (2H, s), 4.43 (2H, q, J = 7.0 Hz), 3.85 (3H, s), 3.60-3.51 (1H, m), 3.21-3.04 (2H, m), 3.03-2.82 (4H, m), 2.80 (3H, s), 1.98-1.94 (1H, m), 1.79-1.65 (3H, m), 1.42 (3H, t, J = 7.0 Hz), 1.39-1.29 (1H, m). |

| Example | Chemical Structure | Instrumental analysis data |
| --- | --- | --- |
| 328 | 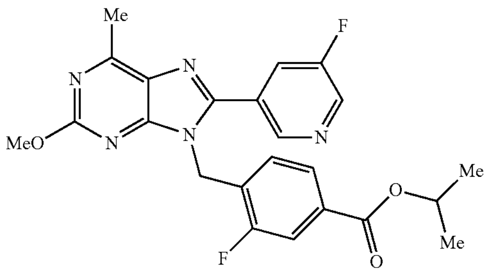 [SMILES: COc1nc(C)c2nc(-c3cncc(F)c3)n(Cc3ccc(C(=O)OC(C)C)cc3F)c2n1] | LC-MS [M + H]⁺/Rt (min): 454.5/1.016 (Method A) |
| 329 | 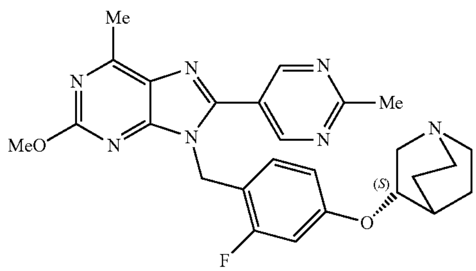 | LC-MS: [M + 2H]²⁺/2/Rt (min): 245.6/0.507 (Method C); ¹H-NMR (CD₃OD) δ: 8.95 (2H, s), 7.04 (1H, t, J = 8.5 Hz), 6.65-6.58 (2H, m), 5.54 (2H, s), 4.48-4.42 (1H, m), 4.06 (3H, s), 3.30-3.21 (1H, m), 2.91-2.79 (2H, m), 2.77 (3H, s), 2.76 (3H, s), 2.74-2.65 (2H, m), 2.11-2.04 (1H, m), 1.97-1.86 (1H, m), 1.82-1.71 (1H, m), 1.68-1.58 (1H, m), 1.49-1.39 (1H, m). |
| 330 | 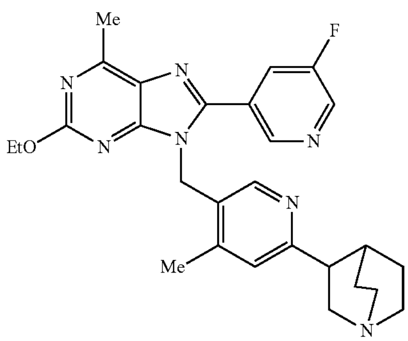 [SMILES: CCOc1nc(C)c2nc(-c3cncc(F)c3)n(Cc3cnc(C4CN5CCC4CC5)cc3C)c2n1] | LC-MS [M + 2H]²⁺/2/Rt (min): 244.7/0.507 (Method C); ¹H-NMR (CDCl₃) δ: 8.60-8.58 (1H, m), 8.55 (1H, d, J = 3.0 Hz), 7.83 (1H, s), 7.71-7.66 (1H, m), 6.96 (1H, s), 5.51-5.39 (2H, m), 4.42 (2H, q, J = 7.0 Hz), 3.43-3.36 (1H, m), 3.17-3.10 (1H, m), 2.97-2.70 (5H, m), 2.81 (3H, s), 2.18 (3H, s), 1.98-1.94 (1H, m), 1.73-1.46 (3H, m), 1.41 (3H, t, J = 7.0 Hz), 1.30-1.21 (1H, m). |
| 331 | 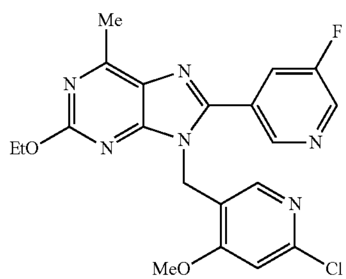 [SMILES: CCOc1nc(C)c2nc(-c3cncc(F)c3)n(Cc3cnc(Cl)cc3OC)c2n1] | LC-MS [M + H]⁺/Rt (min): 429.2/0.731 (Method C); ¹H-NMR (CDCl₃) δ: 8.71-8.70 (1H, m), 8.61 (1H, d, J = 3.0 Hz), 8.02 (1H, s), 7.78-7.74 (1H, m), 6.74 (1H, s), 5.40 (2H, s), 4.43 (2H, q, J = 7.0 Hz), 3.69 (3H, s), 2.79 (3H, s), 1.43 (3H, t, J = 7.0 Hz). |
| 332 | 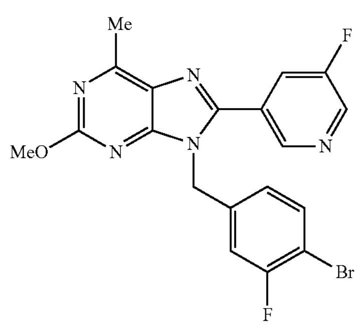 [SMILES: COc1nc(C)c2nc(-c3cncc(F)c3)n(Cc3ccc(Br)c(F)c3)c2n1] | LC-MS [M + H]⁺/Rt (min): 446.1/0.901 (Method C); ¹H-NMR (CDCl₃) δ: 8.64-8.63 (1H, m), 8.59 (1H, d, J = 3.0 Hz), 7.74-7.69 (1H, m), 7.50-7.44 (1H, m), 6.88-6.83 (1H, m), 6.75-6.70 (1H, m), 5.42 (2H, s), 4.04 (3H, s), 2.82 (3H, s). |

| Example | Chemical Structure | Instrumental analysis data |
|---|---|---|
| 333 | 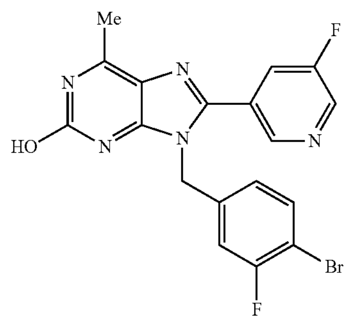 [SMILES: Cc1nc(O)nc2c1nc(-c1cncc(F)c1)n2Cc1ccc(Br)c(F)c1] | LC-MS [M + H]⁺/Rt (min): 432.0/0.632 (Method C); ¹H-NMR (DMSO-D₆) δ: 12.12 (1H, br s), 8.73 (1H, d, J = 2.4 Hz), 8.66-8.62 (1H, m), 8.02-7.96 (1H, m), 7.64-7.57 (1H, m), 7.13-7.08 (1H, m), 6.84-6.79 (1H, m), 5.32 (2H, s), 2.56 (3H, s). |
| 334 | 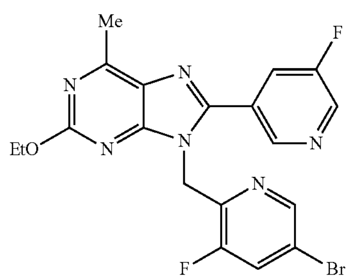 [SMILES: CCOc1nc(C)c2nc(-c3cncc(F)c3)n(Cc3ncc(Br)cc3F)c2n1] | LC-MS [M + H]⁺/Rt (min): 461.2/0.875 (Method C); ¹H-NMR (CDCl₃) δ: 8.85-8.83 (1H, m), 8.58 (1H, d, J = 2.4 Hz), 8.31-8.29 (1H, m), 8.01-7.96 (1H, m), 7.63-7.58 (1H, m), 5.54-5.52 (2H, m), 4.37 (2H, q, J = 7.0 Hz), 2.79 (3H, s), 1.39 (3H, t, J = 7.0 Hz). |
| 335 | 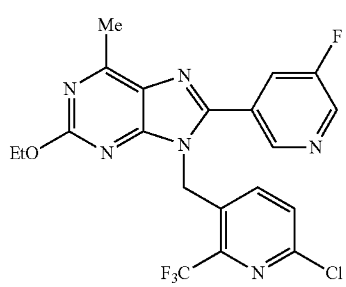 [SMILES: CCOc1nc(C)c2nc(-c3cncc(F)c3)n(Cc3ccc(Cl)nc3C(F)(F)F)c2n1] | LC-MS [M + H]⁺/Rt (min): 467.2/0.933 (Method C); ¹H-NMR (CDCl₃) δ: 8.59 (1H, d, J = 2.4 Hz), 8.53-8.51 (1H, m), 7.70-7.65 (1H, m), 7.41 (1H, d, J = 8.2 Hz), 7.13 (1H, d, J = 8.2 Hz), 5.65 (2H, s), 4.38 (2H, q, J = 7.0 Hz), 2.84 (3H, s), 1.39 (3H, t, J = 7.0 Hz). |
| 336 | 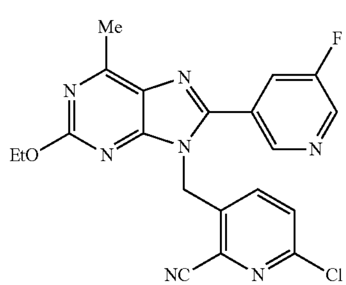 [SMILES: CCOc1nc(C)c2nc(-c3cncc(F)c3)n(Cc3ccc(Cl)nc3C#N)c2n1] | LC-MS [M + H]⁺/Rt (min): 424.3/0.801 (Method C); ¹H-NMR (CDCl₃) δ: 8.65 (1H, d, J = 2.4 Hz), 8.57-8.54 (1H, m), 7.77-7.73 (1H, m), 7.47-7.39 (2H, m), 5.65 (2H, s), 4.40 (2H, q, J = 7.0 Hz), 2.81 (3H, s), 1.42 (3H, t, J = 7.0 Hz). |
| 337 | 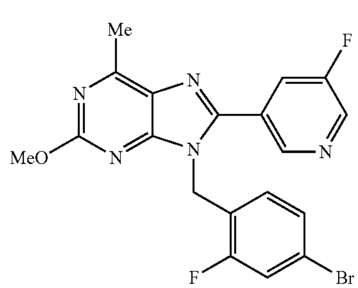 [SMILES: COc1nc(C)c2nc(-c3cncc(F)c3)n(Cc3ccc(Br)cc3F)c2n1] | LC-MS [M + H]⁺/Rt (min): 446.2/0.902 (Method C); ¹H-NMR (CDCl₃) δ: 8.65-8.62 (1H, m), 8.59 (1H, d, J = 3.0 Hz), 7.73-7.68 (1H, m), 7.25-7.20 (1H, m), 7.18-7.15 (1H, m), 6.89-6.83 (1H, m), 5.45 (2H, s), 4.02 (3H, s), 2.81 (3H, s). |

| Example | Chemical Structure | Instrumental analysis data |
|---|---|---|
| 338 | 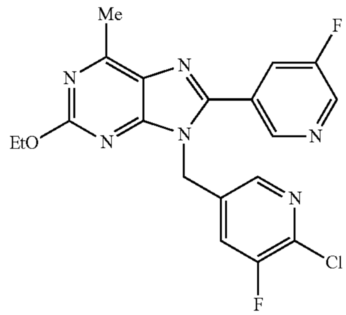 [SMILES: CCOc1nc(C)c2nc(-c3cncc(F)c3)n(Cc3cnc(Cl)c(F)c3)c2n1] | LC-MS [M + H]⁺/Rt (min): 417.3/0.820 (Method C); ¹H-NMR (CDCl₃) δ: 8.66-8.62 (2H, m), 8.00 (1H, d, J = 1.8 Hz), 7.76-7.71 (1H, m), 7.29-7.25 (1H, m), 5.47 (2H, s), 4.46 (2H, q, J = 7.0 Hz), 2.81 (3H, s), 1.45 (3H, t, J = 7.0 Hz). |
| 339 | 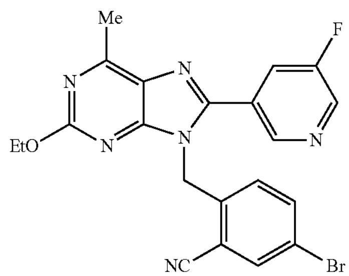 | LC-MS [M + H]⁺/Rt (min): 467.3/0.889 (Method C); ¹H-NMR (CDCl₃) δ: 8.61 (1H, d, J = 3.1 Hz), 8.53-8.52 (1H, m), 7.82 (1H, d, J = 2.0 Hz), 7.74-7.70 (1H, m), 7.61 (1H, dd, J = 8.0, 2.0 Hz), 6.85 (1H, d, J = 8.0 Hz), 5.60 (2H, s), 4.40 (2H, q, J = 7.0 Hz), 2.82 (3H, s), 1.41 (3H, t, J = 7.0 Hz). |
| 340 | 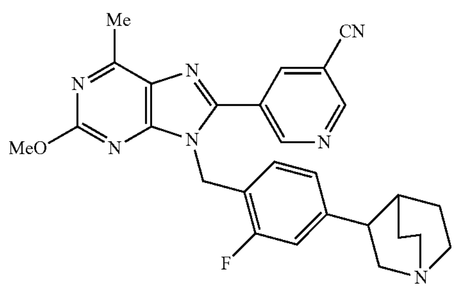 | LC-MS [M + H]⁺/Rt (min): 484.3/0.465 (Method C); ¹H-NMR (CDCl₃) δ: 9.03-9.01 (1H, m), 8.95-8.94 (1H, m), 8.21-8.19 (1H, m), 7.02-6.89 (3H, m), 5.48 (2H, s), 4.05 (3H, s), 3.38-3.29 (1H, m), 3.04-2.83 (6H, m), 2.81 (3H, s), 1.96-1.90 (1H, m), 1.81-1.72 (2H, m), 1.63-1.51 (1H, m), 1.47-1.34 (1H, m). |
| 341 | 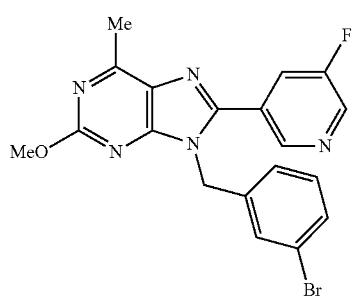 [SMILES: COc1nc(C)c2nc(-c3cncc(F)c3)n(Cc3cccc(Br)c3)c2n1] | LC-MS [M + H]⁺/Rt (min): 428.2/0.879 (Method C) |
| 342 | 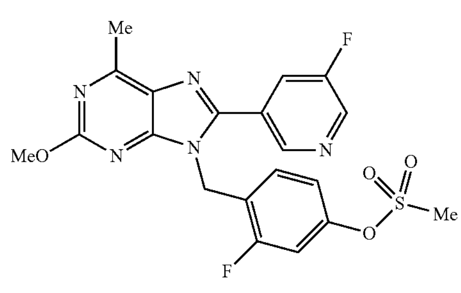 [SMILES: COc1nc(C)c2nc(-c3cncc(F)c3)n(Cc3ccc(OS(C)(=O)=O)cc3F)c2n1] | LC-MS [M + H]⁺/Rt (min): 462.3/0.728 (Method C); ¹H-NMR (CDCl₃) δ: 8.65-8.63 (1H, m), 8.60 (1H, d, J = 3.0 Hz), 7.74-7.70 (1H, m), 7.09-6.97 (3H, m), 5.51 (2H, s), 4.03 (3H, s), 3.14 (3H, s), 2.82 (3H, s). |

-continued

| Example | Chemical Structure | Instrumental analysis data |
| --- | --- | --- |
| 343 | 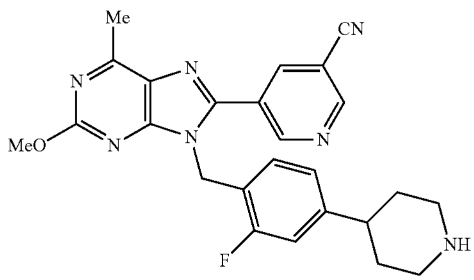 [SMILES: COc1nc(C)c2nc(-c3cncc(C#N)c3)n(Cc3ccc(C4CCNCC4)cc3F)c2n1] | LC-MS [M + 2H]$^{2+}$/2/Rt (min): 229.8/0.471 (Method C); $^1$H-NMR (CDCl$_3$) δ: 9.02-9.00 (1H, m), 8.95-8.93 (1H, m), 8.20-8.16 (1H, m), 6.99-6.85 (3H, m), 5.47 (2H, s), 4.05 (3H, s), 3.28-3.20 (2H, m), 2.81 (3H, s), 2.79-2.69 (2H, m), 2.64-2.53 (1H, m), 2.41-2.04 (1H, m), 1.92-1.76 (2H, m), 1.73-1.58 (2H, m). |
| 344 | 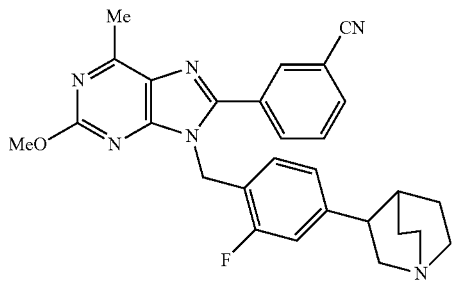 | LC-MS [M + 2H]$^{2+}$/2/Rt (min): 242.3/0.563 (Method C); $^1$H-NMR (CDCl$_3$) δ: 7.86-7.82 (2H, m), 7.77-7.73 (1H, m), 7.60-7.55 (1H, m), 6.99-6.89 (3H, m), 5.45 (2H, s), 4.04 (3H, s), 3.44-3.33 (1H, m), 3.13-2.87 (6H, m), 2.81 (3H, s), 2.00-1.93 (1H, m), 1.87-1.74 (2H, m), 1.68-1.55 (1H, m), 1.52-1.41 (1H, m). |
| 345 | 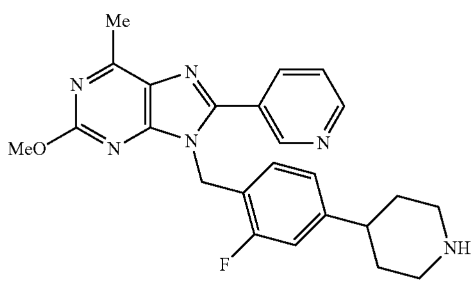 [SMILES: COc1nc(C)c2nc(-c3cccnc3)n(Cc3ccc(C4CCNCC4)cc3F)c2n1] | LC-MS [M + 2H]$^{2+}$/2/Rt (min): 217.2/0.440 (Method C); $^1$H-NMR (CDCl$_3$) δ: 8.84-8.80 (1H, m), 8.74-8.69 (1H, m), 7.96-7.91 (1H, m), 7.41-7.35 (1H, m), 6.90-6.79 (3H, m), 5.45 (2H, s), 4.02 (3H, s), 3.25-3.17 (2H, m), 2.81 (3H, s), 2.77-2.67 (2H, m), 2.61-2.51 (1H, m), 2.39-2.12 (1H, m), 1.83-1.74 (2H, m), 1.68-1.54 (2H, m). |
| 346 | 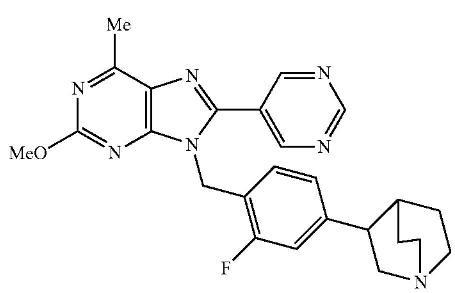 [SMILES: COc1nc(C)c2nc(-c3cncnc3)n(Cc3ccc(C4CN5CCC4CC5)cc3F)c2n1] | LC-MS [M + H]$^+$/Rt (min): 460.3/0.408 (Method C); $^1$H-NMR (CDCl$_3$) δ: 9.29 (1H, s), 8.98 (2H, s), 6.98-6.88 (3H, m), 5.49 (2H, s), 4.04 (3H, s), 3.52-3.32 (1H, m), 3.19-2.88 (6H, m), 2.82 (3H, s), 2.01-1.95 (1H, m), 1.90-1.76 (2H, m), 1.71-1.57 (1H, m), 1.55-1.41 (1H, m). |
| 347 | 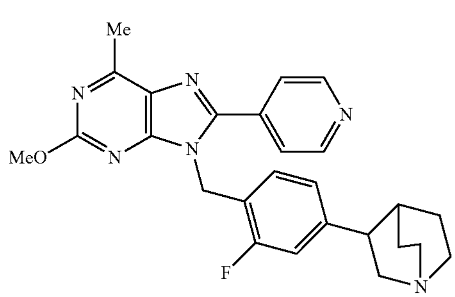 [SMILES: COc1nc(C)c2nc(-c3ccncc3)n(Cc3ccc(C4CN5CCC4CC5)cc3F)c2n1] | LC-MS [M + 2H]$^{2+}$/2/Rt (min): 230.3/0.446 (Method C); $^1$H-NMR (CDCl$_3$) δ: 8.73-8.69 (2H, m), 7.56-7.51 (2H, m), 7.00-6.82 (3H, m), 5.51 (2H, s), 4.02 (3H, s), 3.37-3.28 (1H, m), 3.05-2.78 (6H, m), 2.82 (3H, s), 1.94-1.88 (1H, m), 1.80-1.69 (2H, m), 1.63-1.52 (1H, m), 1.45-1.33 (1H, m). |

| Example | Chemical Structure | Instrumental analysis data |
|---|---|---|
| 348 | 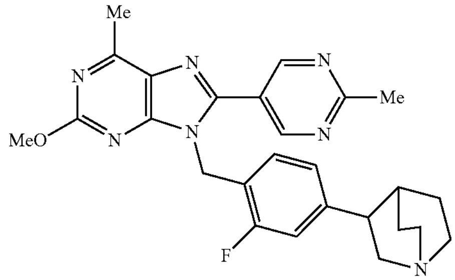 | LC-MS [M + 2H]$^{2+}$/2/Rt (min): 237.7/0.444 (Method C); $^1$H-NMR (CDCl$_3$) δ: 8.87 (2H, s), 6.97-6.88 (3H, m), 5.47 (2H, s), 4.02 (3H, s), 3.38-3.30 (1H, m), 3.05-2.84 (6H, m), 2.81 (3H, s), 2.79 (3H, s), 1.97-1.89 (1H, m), 1.82-1.71 (2H, m), 1.66-1.52 (1H, m), 1.47-1.35 (1H, m). |
| 349 | 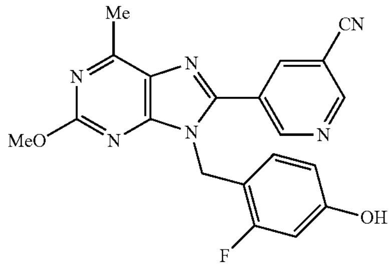 [SMILES: COc1nc(C)c2nc(-c3cncc(C#N)c3)n(Cc3ccc(O)cc3F)c2n1] | LC-MS [M + H]$^+$/Rt (min): 391.3/0.646 (Method C) |

Example 350

5-Bromo-2-{[2-ethoxy-8-(5-fluoropyridin-3-yl)-6-methyl-9H-purin-9-yl]methyl}phenol

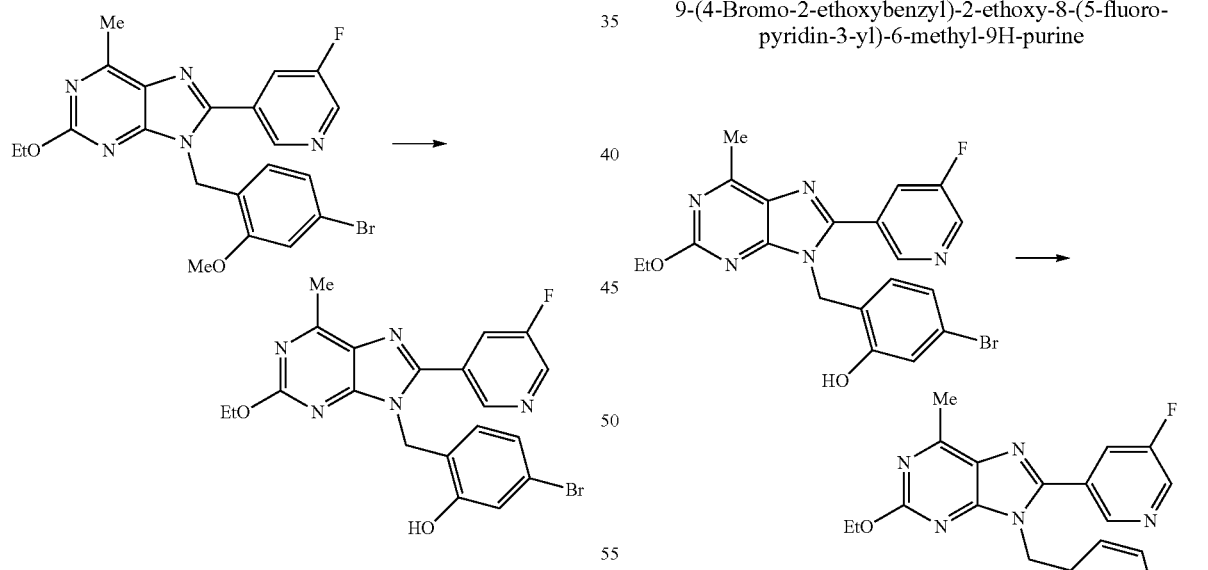

To the compound of Example 325 (236 mg) was added a solution of boron tribromide in dichloromethane (1 mol/L, 5 mL), and the mixture was stirred at room temperature for 5 days. To the reaction mixture was added methanol, and the solvent was removed under reduced pressure. The obtained residue was purified by silica gel column chromatography (hexane/ethyl acetate=>chloroform/methanol) and amino silica gel chromatography (chloroform/methanol) to give the title compound (60 mg).

LC-MS [M+H]$^+$/Rt (min): 458.1/0.851 (Method C); $^1$H-NMR (DMSO-d$_6$) δ: 10.26 (1H, br s), 8.75-8.71 (2H, m), 8.10-8.05 (1H, m), 6.88 (1H, d, J=1.8 Hz), 6.82 (1H, dd, J=7.9, 1.8 Hz), 6.71 (1H, d, J=7.9 Hz), 5.36 (2H, s), 4.35 (2H, q, J=7.0 Hz), 2.67 (3H, s), 1.31 (3H, t, J=7.0 Hz).

Example 351

9-(4-Bromo-2-ethoxybenzyl)-2-ethoxy-8-(5-fluoro-pyridin-3-yl)-6-methyl-9H-purine To a solution compound of Example 350 (55 mg) in N,N-dimethylformamide (6 mL) were added potassium carbonate (50 mg) and iodoethane (0.015 mL), and the mixture was stirred at room temperature for 1.5 hours. To the reaction mixture was water, and the mixture was extracted with ethyl acetate. The organic layer was washed with brine twice, dried over sodium sulfate, filtrated, and then concentrated in vacuo. The obtained residue was purified by silica gel column chromatography (hexane/ethyl acetate) to give the title compound (54 mg).

LC-MS [M+H]⁺/Rt (min): 486.1/1.060 (Method C); ¹H-NMR (CDCl₃) δ: 8.67-8.64 (1H, m), 8.54 (1H, d, J=3.0 Hz), 7.72-7.67 (1H, m), 6.96 (1H, d, J=1.8 Hz), 6.91 (1H, dd, J=8.2, 1.8 Hz), 6.62 (1H, d, J=8.2 Hz), 5.41 (2H, s), 4.43 (2H, q, J=7.2 Hz), 3.97 (2H, q, J=6.8 Hz), 2.80 (3H, d, J=10.4 Hz), 1.42 (3H, t, J=7.2 Hz), 1.28 (3H, t, J=6.8 Hz).

Example 352

9-{[5-(1-Azabicyclo[2.2.2]oct-2-en-3-yl)pyridin-2-yl]methyl}-2-ethoxy-8-(5-fluoropyridin-3-yl)-6-methyl-9H-purine

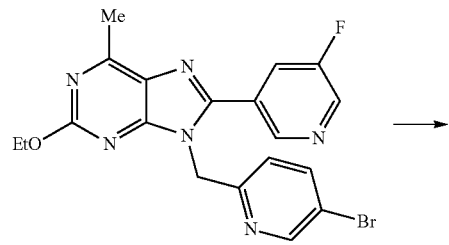

→

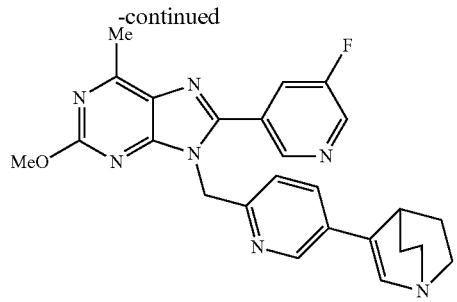

To a solution of the compound of Example 319 (113 mg) in 1,4-dioxane (2 mL) were added bis(pinacolato)diboron (114 mg), potassium acetate (86 mg), 1,1'-bis(diphenylphosphino)ferrocene palladium chloride (22 mg), and 1,1'-bis(diphenylphosphino)ferrocene (7.5 mg), and the mixture was stirred at 95° C. for 2 hours. To the reaction mixture were added the compound of Reference example 25 (150 mg), potassium carbonate (94 mg), 1,1'-bis(diphenylphosphino)ferrocene palladium chloride (22 mg), and water (0.5 ml), and the mixture was stirred at 95° C. for 2 hours. The reaction mixture was cooled to room temperature. Water was added thereto, and the mixture was extracted with ethyl acetate. The organic layer was dried over sodium sulfate, filtrated, and then concentrated in vacuo. The residue was purified by silica gel column chromatography (ethyl acetate/hexane) to give the title compound (122 mg).

LC-MS [M+H]⁺/Rt (min): 472.38/0.678 (Method A); ¹H-NMR (CDCl₃) δ: 8.94 (1H, s), 8.63-8.59 (2H, m), 8.21-8.16 (1H, m), 7.68 (1H, dd, J=8.2, 2.1 Hz), 7.31 (1H, d, J=8.2 Hz), 6.90 (1H, d, J=1.8 Hz), 5.55 (2H, s), 4.46 (2H, q, J=7.1 Hz), 3.15-3.10 (1H, m), 3.10-3.00 (2H, m), 2.84 (3H, s), 2.73-2.61 (2H, m), 1.83-1.77 (2H, m), 1.63-1.53 (2H, m), 1.46 (3H, t, J=7.1 Hz).

Examples 353-364

According to the method of Example 352, Example 353-364 were prepared by using the correspond compounds.

| Example | Chemical Structure | Instrumental analysis data |
|---|---|---|
| 353 | 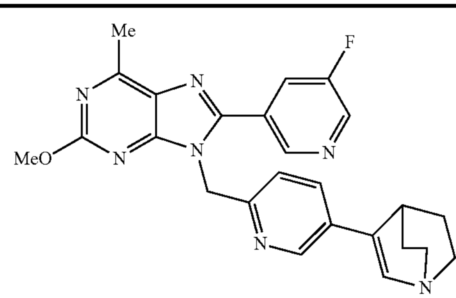 | LC-MS [M + H]⁺/Rt (min): 458.4/0.645 (Method A); ¹H-NMR (CDCl₃) δ: 8.96 (1H, s), 8.64-8.58 (2H, m), 8.23-8.17 (1H, m), 7.68 (1H, dd, J = 8.2, 2.1 Hz), 7.33 (1H, d, J = 8.2 Hz), 6.89 (1H, d, J = 1.8 Hz), 5.55 (2H, s), 4.05 (3H, s), 3.14-3.10 (1H, m), 3.08-3.00 (2H, m), 2.84 (3H, s), 2.71-2.61 (2H, m), 1.82-1.76 (2H, m), 1.63-1.52 (2H, m). |
| 354 | 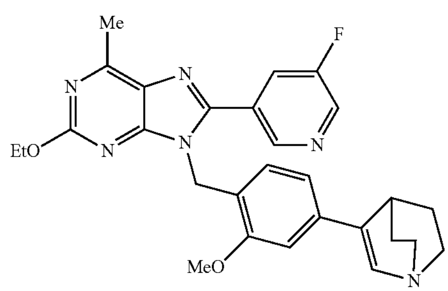 [SMILES: CCOc1nc(C)c2nc(-c3cncc(F)c3)n(Cc3ccc(C4=CN5CCC4CC5)cc3OC)c2n1] | LC-MS [M + 2H]²⁺/2/Rt (min): 251.2/0.591 (Method C); ¹H-NMR (CDCl₃) δ: 8.70-8.67 (1H, m), 8.54 (1H, d, J = 2.4 Hz), 7.75-7.71 (1H, m), 6.86-6.79 (4H, m), 5.46 (2H, s), 4.43 (2H, q, J = 7.2 Hz), 3.76 (3H, s), 3.17-2.98 (3H, m), 2.81 (3H, s), 2.75-2.63 (2H, m), 1.84-1.74 (2H, m), 1.61-1.52 (2H, m), 1.42 (3H, t, J = 7.2 Hz). |

-continued

| Example | Chemical Structure | Instrumental analysis data |
| --- | --- | --- |
| 355 | 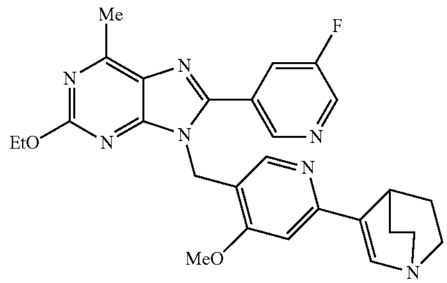 [SMILES: CCOc1nc(C)c2nc(-c3cncc(F)c3)n(Cc3cnc(C4=CN5CCC4CC5)cc3OC)c2n1] | LC-MS [M + 2H]²⁺/2/Rt (min): 251.6/0.518 (Method C); ¹H-NMR (CDCl₃) δ: 8.72-8.69 (1H, m), 8.59 (1H, d, J = 3.0 Hz), 8.11 (1H, s), 7.79-7.74 (1H, m), 7.14-7.13 (1H, m), 6.88 (1H, s), 5.45 (2H, s), 4.43 (2H, q, J = 7.0 Hz), 3.74 (3H, s), 3.59-3.54 (1H, m), 3.12-3.03 (2H, m), 2.78 (3H, s), 2.75-2.65 (2H, m), 1.83-1.74 (2H, m), 1.59-1.49 (2H, m), 1.42 (3H, t, J = 7.0 Hz). |
| 356 | 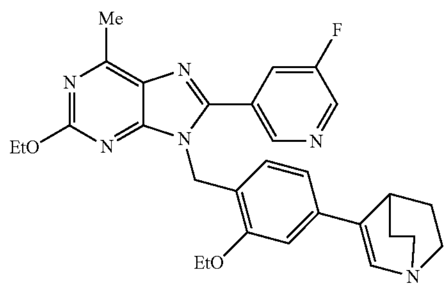 [SMILES: CCOc1nc(C)c2nc(-c3cncc(F)c3)n(Cc3ccc(C4=CN5CCC4CC5)cc3OCC)c2n1] | LC-MS [M + 2H]²⁺/2/Rt (min): 258.2/0.641 (Method C); ¹H-NMR (CDCl₃) δ: 8.68-8.66 (1H, m), 8.52 (1H, d, J = 3.0 Hz), 7.74-7.68 (1H, m), 6.85 (1H, d, J = 1.2 Hz), 6.82-6.78 (2H, m), 6.72 (1H, d, J = 7.9 Hz), 5.48 (2H, s), 4.43 (2H, q, J = 7.0 Hz), 4.03 (2H, q, J = 7.0 Hz), 3.14-2.99 (3H, m), 2.82 (3H, s), 2.73-2.63 (2H, m), 1.83-1.73 (2H, m), 1.61-1.50 (2H, m), 1.41 (3H, t, J = 7.0 Hz), 1.30 (3H, t, J = 7.0 Hz). |
| 357 | 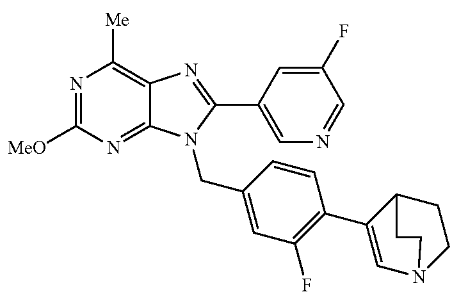 [SMILES: COc1nc(C)c2nc(-c3cncc(F)c3)n(Cc3ccc(C4=CN5CCC4CC5)c(F)c3)c2n1] | LC-MS [M + 2H]²⁺/2/Rt (min): 238.1/0.525 (Method C); ¹H-NMR (CDCl₃) δ: 8.67-8.64 (1H, m), 8.59 (1H, d, J = 2.4 Hz), 7.76-7.71 (1H, m), 7.21 (1H, t, J = 7.9 Hz), 6.83-6.75 (3H, m), 5.45 (2H, s), 4.04 (3H, s), 3.07-2.98 (3H, m), 2.83 (3H, s), 2.72-2.63 (2H, m), 1.79-1.70 (2H, m), 1.66-1.56 (2H, m). |
| 358 | 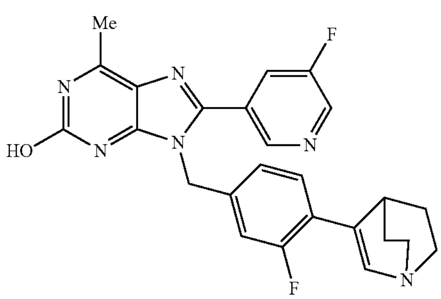 [SMILES: Cc1nc(O)nc2c1nc(-c1cncc(F)c1)n2Cc1ccc(C2=CN3CCC2CC3)c(F)c1] | LC-MS [M + H]⁺/Rt (min): 461.3/0.361 (Method C); ¹H-NMR (DMSO-D₆) δ: 12.12 (1H, br s), 8.74 (1H, d, J = 3.0 Hz), 8.68-8.67 (1H, m), 8.04-7.99 (1H, m), 7.32-7.27 (1H, m), 6.97-6.90 (1H, m), 6.85-6.81 (1H, m), 6.68-6.64 (1H, m), 5.34 (2H, s), 2.95-2.82 (3H, m), 2.56 (3H, s), 2.48-2.38 (2H, m), 1.71-1.61 (2H, m), 1.50-1.39 (2H, m). |
| 359 | 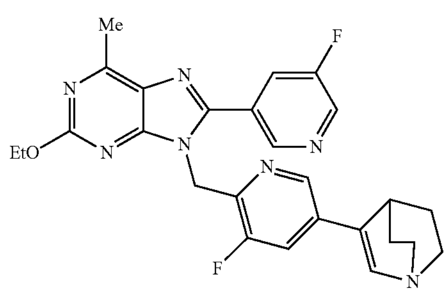 [SMILES: CCOc1nc(C)c2nc(-c3cncc(F)c3)n(Cc3ncc(C4=CN5CCC4CC5)cc3F)c2n1] | LC-MS [M + 2H]²⁺/2/Rt (min): 245.6/0.532 (Method C); ¹H-NMR (CDCl₃) δ: 8.89-8.85 (1H, m), 8.57 (1H, d, J = 3.0 Hz), 8.30-8.27 (1H, m), 8.07-8.02 (1H, m), 7.38 (1H, dd, J = 10.4, 1.8 Hz), 6.88 (1H, d, J = 1.8 Hz), 5.57 (2H, s), 4.38 (2H, q, J = 7.0 Hz), 3.07-2.97 (3H, m), 2.79 (3H, s), 2.68-2.57 (2H, m), 1.82-1.73 (2H, m), 1.58-1.47 (2H, m), 1.39 (3H, t, J = 7.0 Hz). |

| Example | Chemical Structure | Instrumental analysis data |
|---|---|---|
| 360 | (structure) | LC-MS [M + 2H]²⁺/2/Rt (min): 270.7/0.644 (Method C); ¹H-NMR (CDCl₃) δ: 8.57 (1H, d, J = 2.4 Hz), 8.54-8.52 (1H, m), 7.73-7.69 (1H, m), 7.52 (1H, d, J = 8.5 Hz), 7.27 (1H, s), 7.07 (1H, d, J = 8.5 Hz), 5.67 (2H, s), 4.39 (2H, q, J = 7.2 Hz), 3.70-3.63 (1H, m), 3.12-3.01 (2H, m), 2.84 (3H, s), 2.73-2.61 (2H, m), 1.85-1.75 (2H, m), 1.61-1.50 (2H, m), 1.39 (3H, t, J = 7.2 Hz). |
| 361 | (structure) | LC-MS [M + 2H]²⁺/2/Rt (min): 249.3/0.535 (Method C); ¹H-NMR (CDCl₃) δ: 8.62 (1H, d, J = 2.4 Hz), 8.56-8.52 (1H, m), 7.79-7.73 (1H, m), 7.59 (1H, d, J = 8.5 Hz), 7.35 (1H, d, J = 8.5 Hz), 7.27 (1H, s), 5.67 (2H, s), 4.41 (2H, q, J = 7.2 Hz), 3.76-3.68 (1H, m), 3.19-3.06 (2H, m), 2.82 (3H, s), 2.78-2.64 (2H, m), 1.90-1.79 (2H, m), 1.63-1.51 (2H, m), 1.41 (3H, t, J = 7.2 (Hz). |
| 362 | (structure) | LC-MS [M + 2H]²⁺/2/Rt (min): 245.8/0.514 (Method C) |
| 363 | (structure) | LC-MS [M + 2H]²⁺/2/Rt (min): 248.8/0.529 (Method C); ¹H-NMR (CDCl₃) δ: 8.59 (1H, d, J = 3.1 Hz), 8.55-8.53 (1H, m), 7.76-7.72 (1H, m), 7.69 (1H, d, J = 1.8 Hz), 7.51-7.48 (1H, m), 6.93 (1H, d, J = 8.5 Hz), 6.88 (1H, d, J = 1.8 Hz), 5.65 (2H, s), 4.41 (2H, q, J = 7.0 Hz), 3.12-3.00 (3H, m), 2.83 (3H, s), 2.70-2.60 (2H, m), 1.86-1.78 (2H, m), 1.60-1.50 (2H, m), 1.41 (3H, t, J = 7.0 Hz). |
| 364 | (structure) | LC-MS [M + 2H]²⁺/2/Rt (min): 229.3/0.513 (Method C); ¹H-NMR (CDCl₃) δ: 8.69-8.68 (1H, m), 8.57 (1H, d, J = 3.0 Hz), 7.70-7.65 (1H, m), 7.31-7.22 (2H, m), 7.13 (1H, s), 6.91 (1H, d, J = 7.3 Hz), 6.70 (1H, d, J = 1.2 Hz), 5.46 (2H, s), 4.05 (3H, s), 3.03-2.94 (3H, m), 2.82 (3H, s), 2.66-2.57 (2H, m), 1.80-1.69 (2H, m), 1.57-1.45 (2H, m). |

Example 365 test-Butyl 4-(3-fluoro-4-{[8-(5-fluoropyridin-3-yl)-2-methoxy-6-methyl-9H-purin-9-yl]methyl}phenyl)-3,6-dihydropyridine-1(2H)-carboxylate

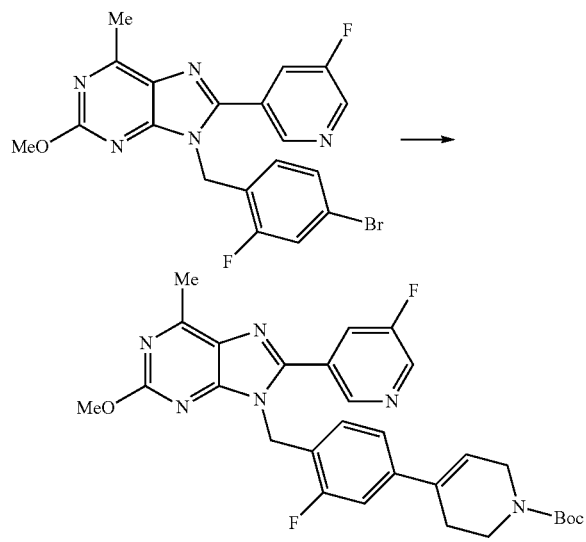

To a solution of the compound of Example 337 (89 mg) in 1,2-dimethoxyethane (4 mL) were added 1-N-tert-butoxycarbonyl-4-(4,4,5,5-tetramethyl-[1,3,2]dioxaborolan-2-yl)-3,6-dihydro-2H-pyridine (74 mg), dichlorobis(tri-o-tolylphosphine)palladium (II) (7.9 mg), potassium carbonate (83 mg), and water (1 mL), and the mixture was stirred at 100° C. for 4.5 hours. The reaction mixture was cooled to room temperature. Aqueous saturated sodium bicarbonate was added thereto, and the mixture was extracted with ethyl acetate. The organic layer was dried over sodium sulfate, filtrated, and then concentrated in vacuo. The residue was purified by silica gel column chromatography (ethyl acetate/hexane) to give the title compound (121 mg).

LC-MS [M+H]$^+$/Rt (min): 549.4/1.061 (Method C); $^1$H-NMR (CDCl$_3$) δ: 8.67-8.62 (1H, m), 8.57 (1H, d, J=3.0 Hz), 7.73-7.67 (1H, m), 7.07-6.98 (2H, m), 6.9-6.86 (1H, m), 6.06-5.93 (1H, m), 5.49 (2H, s), 4.05-4.01 (2H, m), 4.03 (3H, s), 3.63-3.53 (2H, m), 2.81 (3H, s), 2.45-2.35 (2H, m), 1.45 (9H, s).

Examples 366-367

According to the method of Example 365, Examples 366-367 were prepared by using the corresponding material compounds.

| Example | Chemical Structure | Instrumental analysis data |
|---|---|---|
| 366 | 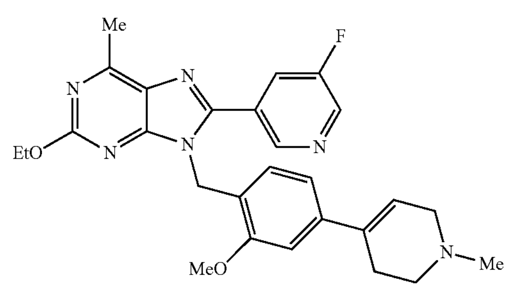 [SMILES: CCOc1nc(C)c2nc(-c3cncc(F)c3)n(Cc3ccc(C4=CCN(C)CC4)cc3OC)c2n1] | LC-MS [M + 2H]$^{2+}$/2/Rt (min): 245.7/0.463 (Method C); $^1$H-NMR (CDCl$_3$) δ: 8.72-8.70 (1H, m), 8.57 (1H, d, J = 3.0 Hz), 8.09 (1H, s), 7.77-7.72 (1H, m), 6.77 (1H, s), 6.54-6.51 (1H, m), 5.43 (2H, s), 4.42 (2H, q, J = 7.1 Hz), 3.69 (3H, s), 3.21-3.13 (2H, m), 2.77 (3H, s), 2.71-2.59 (4H, m), 2.40 (3H, s), 1.41 (3H, t, J = 7.1 Hz). |
| 367 | 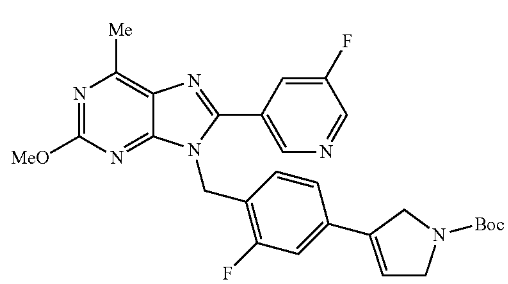 [SMILES: COc1nc(C)c2nc(-c3cncc(F)c3)n(Cc3ccc(C4=CCN(C(=O)OC(C)(C)C)C4)cc3F)c2n1] | LC-MS [M + H]$^+$/Rt (min): 535.4/1.005 (Method C); $^1$H-NMR (CDCl$_3$) δ: 8.66-8.64 (1H, m), 8.59 (1H, d, J = 2.4 Hz), 7.74-7.68 (1H, m), 7.07-6.89 (3H, m), 6.17-6.09 (1H, m), 5.51 (2H, s), 4.44-4.22 (4H, m), 4.04 (3H, s), 2.84 (3H, s), 1.50-1.45 (9H, m). |

Example 368 tert-Butyl 4-(3-fluoro-4-{[8-(5-fluoropyridin-3-yl)-2-methoxy-6-methyl-9H-purin-9-yl]methyl}benzyl)piperazine-1-carboxylate

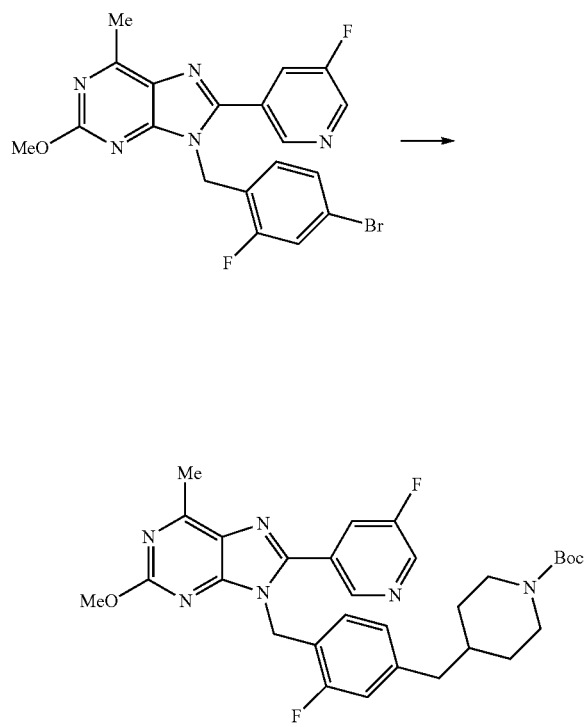

To a solution 1-tert-butoxycarbonyl-4-methylenepiperidine (178 mg) in tetrahydrofuran (3 mL) was added 9-borabicyclo[3.3.1]nonane (0.5 mol/L, tetrahydrofuran solution, 1.8 mL) at room temperature, and the mixture was stirred at 75° C. for 3 hours and 20 minutes. The reaction mixture was cooled to room temperature. The compound of Example 337 (134 mg), potassium carbonate (124 mg), [1,1'-bis(diphenylphosphino)ferrocene]palladium(II) dichloride dichloromethane adduct (25 mg), 1,2-dimethoxyethane (3 mL), and water (2 mL) were added thereto, and the mixture was stirred at 75° C. for 3 hours and 40 minutes. The reaction mixture was cooled to room temperature. Aqueous saturated sodium bicarbonate was added thereto, and the mixture was extracted with ethyl acetate. The organic layer was dried over sodium sulfate, filtrated, and then concentrated in vacuo. The obtained residue was purified by amino silica gel chromatography (hexane/ethyl acetate) and silica gel column chromatography (chloroform/methanol) to give the title compound (146 mg).

LC-MS [M+H]$^+$/Rt (min): 565.4/1.123 (Method. C); $^1$H-NMR (CDCl$_3$) δ: 8.66-8.63 (1H, m), 8.57 (1H, d, J=3.0 Hz), 7.70-7.64 (1H, m), 6.88-6.74 (3H, m), 5.48 (2H, s), 4.12-3.96 (2H, m), 4.03 (3H, s), 2.81 (3H, s), 2.68-2.53 (2H, m), 2.50-2.41 (2H, m), 1.64-1.47 (3H, m), 1.42 (9H, s), 1.15-1.01 (2H, m).

Example 369

According to the method of Example 368, Example 369 was prepared by using the corresponding material compound.

| Example | Chemical Structure | Instrumental analysis data |
|---|---|---|
| 369 | (structure shown) | LC-MS [M + H]$^+$/Rt (min): 592.4/0.670 (Method C); $^1$H-NMR (CDCl$_3$) δ: 8.72-8.67 (1H, m), 8.59 (1H, d, J = 3.0 Hz), 8.12 (1H, s), 7.78-7.72 (1H, m), 6.52 (1H, s), 5.42 (2H, s), 4.43 (2H, q, J = 7.1 Hz), 4.11-3.94 (2H, m), 3.67 (3H, br s), 2.78 (3H, s), 2.69-2.51 (4H, m), 1.93-1.83 (1H, m), 1.63-1.47 (1H, m), 1.46-1.38 (12H, m), 1.31-1.21 (1H, m), 1.18-1.06 (2H, m). |

Example 370

9-{[5-(1-Azabicyclo[2.2.2]oct-3-yl)pyridin-2-yl]methyl}-2-ethoxy-8-(5-fluoropyridin-3-yl)-6-methyl-9H-purine

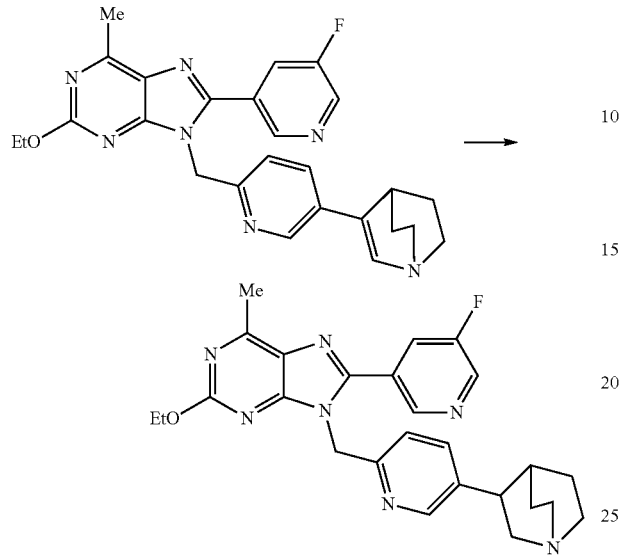

To a solution the compound of Example 352 (104 mg) in ethyl acetate (2 mL) was added 20% palladium carbon (31 mg). The reaction mixture was stirred at room temperature under hydrogen atmosphere for 6 hours, filtrated, and then concentrated in vacuo. The residue was purified by silica gel column chromatography (chloroform/methanol) to give the title compound (85 mg).

LC-MS [M+H]$^+$/Rt (min): 474.4/0.706 (Method A); $^1$H-NMR (CDCl$_3$) δ: 8.95 (1H, s), 8.60 (1H, d, J=3.0 Hz), 8.47 (1H, d, J=2.4 Hz), 8.18-8.13 (1H, m), 7.58 (1H, dd, J=8.2, 2.4 Hz), 7.29 (1H, d, J=8.2 Hz), 5.54 (2H, s), 4.46 (2H, q, J=7.1 Hz), 3.43-3.31 (1H, m), 3.07-2.86 (6H, m), 2.84 (3H, s), 1.92-1.35 (1H, m), 1.81-1.74 (2H, m), 1.65-1.54 (1H, m), 1.49-1.37 (4H, m).

Examples 371-387

According to the method of Example 370, Examples 371-387 were prepared by using the corresponding material compounds.

| Example | Chemical Structure | Instrumental analysis data |
|---|---|---|
| 371 | (structure) | $^1$H-NMR (CDCl$_3$) δ: 8.96 (1H, s), 8.60 (1H, d, J = 3.0 Hz), 8.47 (1H, d, J = 2.4 Hz), 8.19-8.15 (1H, m), 7.59 (1H, dd, J = 8.5, 3.0 Hz), 7.32 (1H, d, J = 8.5 Hz), 5.54 (2H, s), 4.05 (3H, s), 3.42-3.34 (1H, m), 3.09-2.87 (6H, m), 2.85 (3H, s), 1.98-1.91 (1H, m), 1.83-1.76 (2H, m), 1.66-1.56 (1H, m), 1.50-1.39 (1H, m). |
| 372 | (structure) | LC-MS [M + 2H]$^{2+}$/2/Rt (min): 252.2/0.590 (Method C); $^1$H-NMR (CDCl$_3$) δ: 8.68-8.66 (1H, m), 8.53 (1H, d, J = 2.4 Hz), 7.73-7.68 (1H, m), 6.81 (1H, d, J = 7.9 Hz), 6.73-6.67 (2H, m), 5.44 (2H, s), 4.44 (2H, q, J = 7.0 Hz), 3.72 (3H, s), 3.40-3.25 (1H, m), 3.12-2.83 (6H, m), 2.80 (3H, s), 2.17-1.55 (4H, m), 1.47-1.32 (1H, m), 1.42 (3H, t, J = 7.0 Hz). |

| Example | Chemical Structure | Instrumental analysis data |
|---|---|---|
| 373 | 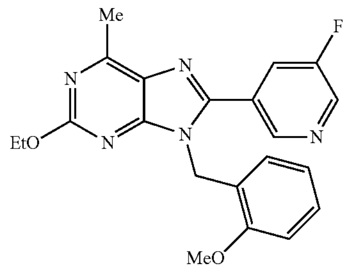 [SMILES: CCOc1nc(C)c2nc(-c3cncc(F)c3)n(Cc3ccccc3OC)c2n1] | LC-MS [M + H]⁺/Rt (min): 394.2/0.878 (Method C); ¹H-NMR (CDCl₃) δ: 8.69-8.67 (1H, m), 8.53 (1H, d, J = 3.0 Hz), 7.71-7.66 (1H, m), 7.25-7.20 (1H, m), 6.85-6.77 (3H, m), 5.47 (2H, s), 4.43 (2H, q, J = 7.2 Hz), 3.72 (3H, s), 2.81 (3H, s), 1.42 (3H, t, J = 7.2 Hz). |
| 374 | 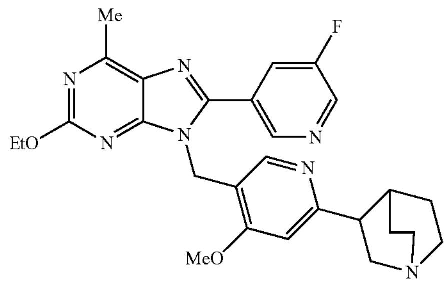 [SMILES: CCOc1nc(C)c2nc(-c3cncc(F)c3)n(Cc3cnc(C4CN5CCC4CC5)cc3OC)c2n1] | LC-MS [M + 2H]²⁺/2/Rt (min): 252.6/0.510 (Method C); ¹H-NMR (CDCl₃) δ: 8.66-8.64 (1H, m), 8.53 (1H, d, J = 3.0 Hz), 8.05 (1H, s), 7.74-7.69 (1H, m), 6.54 (1H, s), 5.43-5.33 (2H, m), 4.39 (2H, q, J = 7.0 Hz), 3.64 (3H, s), 3.54-3.46 (1H, m), 3.16-3.07 (1H, m), 3.03-2.82 (4H, m), 2.81-2.70 (1H, m), 2.74 (3H, s), 1.98-1.93 (1H, m), 1.75-1.62 (2H, m), 1.60-1.48 (1H, m), 1.38 (3H, t, J = 7.0 Hz), 1.31-1.17 (1H, m). |
| 375 | 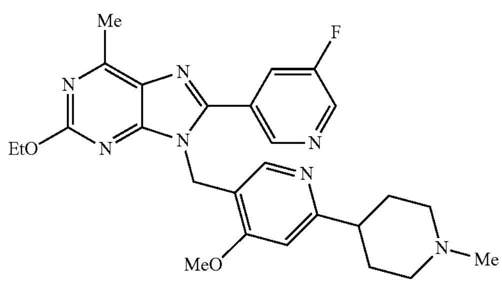 [SMILES: CCOc1nc(C)c2nc(-c3cncc(F)c3)n(Cc3cnc(C4CCN(C)CC4)cc3OC)c2n1] | LC-MS [M + 2H]²⁺/2/Rt (min): 246.6/0.436 (Method C); ¹H-NMR (CDCl₃) δ: 8.71-8.67 (1H, m), 8.58 (1H, d, J = 2.4 Hz), 8.11-8.07 (1H, m), 7.78-7.72 (1H, m), 6.64-6.60 (1H, m), 5.44-5.39 (2H, m), 4.43 (2H, q, J = 7.0 Hz), 3.71-3.64 (3H, m), 3.17-3.04 (1H, m), 2.78 (3H, s), 2.75-2.55 (1H, m), 2.48-1.51 (10H, m), 1.42 (3H, t, J = 7.0 Hz). |
| 376 | 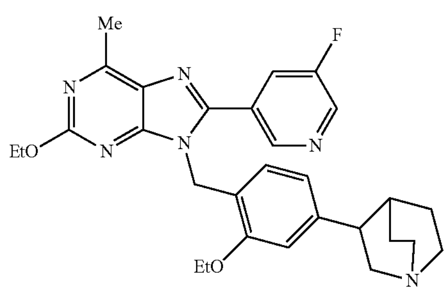 [SMILES: CCOc1nc(C)c2nc(-c3cncc(F)c3)n(Cc3ccc(C4CN5CCC4CC5)cc3OCC)c2n1] | LC-MS [M + 2H]²⁺/2/Rt (min): 259.2/0.636 (Method C); ¹H-NMR (CDCl₃) δ: 8.67-8.65 (1H, m), 8.50 (1H, d, J = 2.4 Hz), 7.69-7.64 (1H, m), 6.72-6.65 (3H, m), 5.46 (2H, s), 4.43 (2H, q, J = 7.0 Hz), 3.97 (2H, q, J = 7.0 Hz), 3.34-3.24 (1H, m), 3.07-2.83 (6H, m), 2.81 (3H, s), 2.07-1.85 (1H, m), 1.77-1.68 (2H, m), 1.65-1.54 (1H, m), 1.44-1.31 (1H, m), 1.41 (3H, t, J = 7.0 Hz), 1.25 (3H, t, J = 7.0 Hz). |
| 377 | 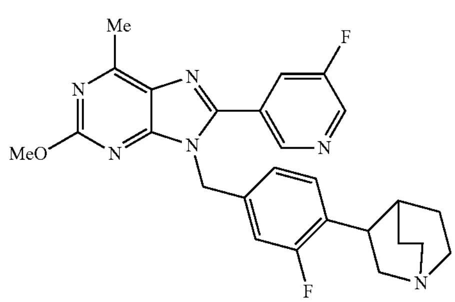 [SMILES: COc1nc(C)c2nc(-c3cncc(F)c3)n(Cc3ccc(C4CN5CCC4CC5)c(F)c3)c2n1] | LC-MS [M + 2H]²⁺/2/Rt (min): 239.1/0.528 (Method C); ¹H-NMR (CDCl₃) δ: 8.66-8.64 (1H, m), 8.58 (1H, d, J = 2.4 Hz), 7.73-7.69 (1H, m), 7.28-7.23 (1H, m), 6.83-6.74 (2H, m), 5.44 (2H, s), 4.05 (3H, s), 3.34-3.17 (2H, m), 2.99-2.79 (5H, m), 2.82 (3H, s), 1.92-1.65 (3H, m), 1.63-1.53 (1H, m), 1.43-1.33 (1H, m). |

| Example | Chemical Structure | Instrumental analysis data |
|---|---|---|
| 378 | 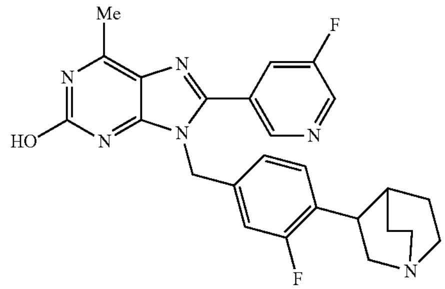 [SMILES: Cc1nc(O)nc2c1nc(-c1cncc(F)c1)n2Cc1ccc(C2CN3CCC2CC3)c(F)c1] | LC-MS [M + H]⁺/Rt (min): 463.3/0.360 (Method C); ¹H-NMR (CDCl₃) δ: 8.65-8.62 (1H, m), 8.58 (1H, d, J = 3.0 Hz), 7.69-7.64 (1H, m), 7.28-7.23 (1H, m), 6.86-6.74 (2H, m), 5.36 (2H, s), 3.38-3.21 (2H, m), 3.07-2.84 (5H, m), 2.82 (3H, s), 1.95-1.88 (1H, m), 1.86-1.68 (2H, m), 1.67-1.54 (1H, m), 1.48-1.36 (1H, m). |
| 379 | 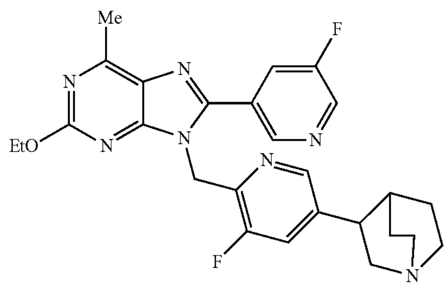 [SMILES: CCOc1nc(C)c2nc(-c3cncc(F)c3)n(Cc3ncc(C4CN5CCC4CC5)cc3F)c2n1] | LC-MS [M + 2H]²⁺/2/Rt (min): 246.7/0.515 (Method C); ¹H-NMR (CDCl₃) δ: 8.87-8.84 (1H, m), 8.55 (1H, d, J = 2.4 Hz), 8.15-8.12 (1H, m), 8.04-7.99 (1H, m), 7.32-7.26 (1H, m), 5.57-5.55 (2H, m), 4.38 (2H, q, J = 7.0 Hz), 3.42-3.31 (1H, m), 3.05-2.85 (6H, m), 2.79 (3H, s), 1.95-1.89 (1H, m), 1.81-1.72 (2H, m), 1.60-1.41 (2H, m), 1.38 (3H, t, J = 7.0 Hz). |
| 380 | 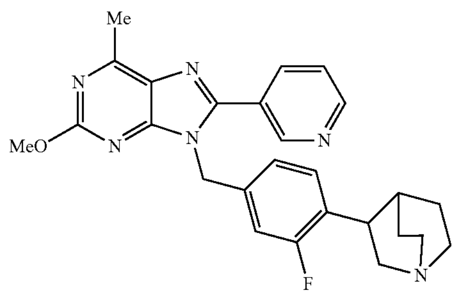 [SMILES: COc1nc(C)c2nc(-c3cccnc3)n(Cc3ccc(C4CN5CCC4CC5)c(F)c3)c2n1] | LC-MS [M + 2H]²⁺/2/Rt (min): 230.2/0.475 (Method C); ¹H-NMR (CDCl₃) δ: 8.85-8.83 (1H, m), 8.73-8.70 (1H, m), 7.96-7.91 (1H, m), 7.42-7.37 (1H, m), 7.27-7.21 (1H, m), 6.83-6.73 (2H, m), 5.40 (2H, s), 4.04 (3H, s), 3.31-3.14 (2H, m), 2.98-2.75 (5H, m), 2.81 (3H, s) 1.87-1.83 (1H, m), 1.77-1.63 (2H, m), 1.60-1.52 (1H, m), 1.40-1.29 (1H, m). |
| 381 | 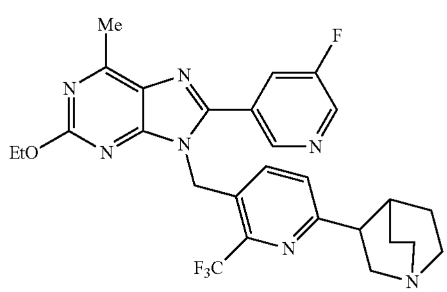 [SMILES: CCOc1nc(C)c2nc(-c3cncc(F)c3)n(Cc3ccc(C4CN5CCC4CC5)nc3C(F)(F)F)c2n1] | LC-MS [M + H]⁺/Rt (min): 542.2/0.635 (Method C); ¹H-NMR (CDCl₃) δ: 8.56 (1H, d, J = 3.0 Hz), 8.54-8.51 (1H, m), 7.72-7.66 (1H, m), 7.27-7.20 (1H, m), 7.07-7.01 (1H, m), 5.72-5.61 (2H, m), 4.39 (2H, q, J = 7.0 Hz), 3.62-3.47 (1H, m), 3.31-2.77 (6H, m), 2.84 (3H, s), 2.02-1.54 (4H, m), 1.42-1.28 (1H, m), 1.38 (3H, t, J = 7.0 Hz). |
| 382 | 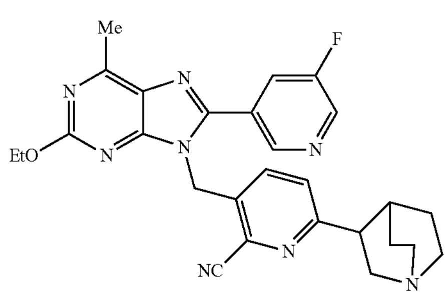 [SMILES: CCOc1nc(C)c2nc(-c3cncc(F)c3)n(Cc3ccc(C4CN5CCC4CC5)nc3C#N)c2n1] | LC-MS [M + 2H]²⁺/2/Rt (min): 250.3/0.521 (Method C); ¹H-NMR (DMSO-D₆) δ: 8.78-8.74 (2H, m), 8.18-8.13 (1H, m), 7.57 (1H, d, J = 8.2 Hz), 7.51 (1H, d, J = 8.2 Hz), 5.70 (2H, s), 4.28 (2H, q, J = 7.0 Hz), 3.27-3.16 (1H, m), 3.07-2.95 (2H, m), 2.80-2.58 (4H, m), 2.67 (3H, s), 1.90-1.86 (1H, m), 1.69-1.53 (2H, m), 1.27-1.14 (2H, m), 1.25 (3H, t, J = 7.0 Hz). |

| Example | Chemical Structure | Instrumental analysis data |
|---|---|---|
| 383 | 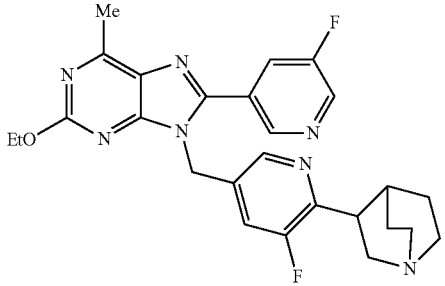 | LC-MS [M + 2H]$^{2+}$/2/Rt (min): 246.8/0.536 (Method C); $^1$H-NMR (CDCl$_3$) δ: 8.67-8.64 (1H, m), 8.62 (1H, d, J = 2.4 Hz), 8.15-8.12 (1H, m), 7.76-7.71 (1H, m), 7.12-7.06 (1H, m), 5.47 (2H, s), 4.46 (2H, q, J = 7.0 Hz), 3.70-3.60 (1H, m), 3.38-3.26 (1H, m), 3.15-3.01 (2H, m), 3.01-2.87 (2H, m), 2.86-2.72 (1H, m), 2.81 (3H, s), 2.00-1.63 (3H, m), 1.59-1.48 (1H, m), 1.44 (3H, t, J = 7.0 Hz), 1.33-1.20 (1H, m). |
| 384 | 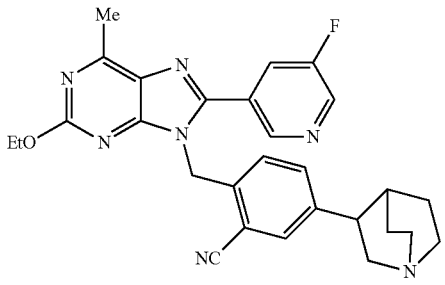 [SMILES: CCOc1nc(C)c2nc(-c3cncc(F)c3)n(Cc3ccc(C4CN5CCC4CC5)cc3C#N)c2n1] | LC-MS [M + 2H]$^{2+}$/2/Rt (min): 249.9/0.530 (Method C); $^1$H-NMR (CDCl$_3$) δ: 8.58 (1H, d, J = 2.4 Hz), 8.55-8.53 (1H, m), 7.75-7.69 (1H, m), 7.56 (1H, d, J = 1.8 Hz), 7.40-7.33 (1H, m), 6.91 (1H, d, J = 7.9 Hz), 5.64 (2H, s), 4.41 (2H, q, J = 7.0 Hz), 3.39-3.29 (1H, m), 3.04-2.79 (6H, m), 2.82 (3H, s), 1.94-1.74 (3H, m), 1.58-1.45 (1H, m), 1.45-1.35 (1H, m), 1.40 (3H, t, J = 7.0 Hz). |
| 385 | 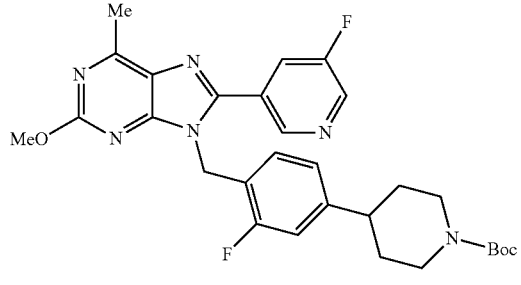 [SMILES: COc1nc(C)c2nc(-c3cncc(F)c3)n(Cc3ccc(C4CCN(C(=O)OC(C)(C)C)CC4)cc3F)c2n1] | LC-MS [M + H]$^+$/Rt (min): 551.5/1.061 (Method C); $^1$H-NMR (CDCl$_3$) δ: 8.65-8.62 (1H, m), 8.57 (1H, d, J = 2.4 Hz), 7.71-7.66 (1H, m), 6.90-6.81 (3H, m), 5.47 (2H, s), 4.30-4.13 (2H, m), 4.03 (3H, s), 2.82 (3H, s), 2.80-2.67 (2H, m), 2.63-2.52 (1H, m), 1.79-1.70 (2H, m), 1.64-1.47 (2H, m), 1.45 (9H, s). |
| 386 | 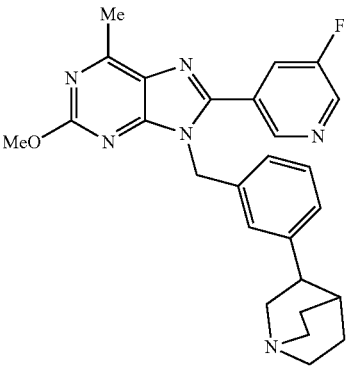 [SMILES: COc1nc(C)c2nc(-c3cncc(F)c3)n(Cc3cccc(C4CN5CCC4CC5)c3)c2n1] | LC-MS [M + H]$^+$/Rt (min): 459.4/0.492 (Method C); $^1$H-NMR (CDCl$_3$) δ: 8.68-8.66 (1H, m), 8.56 (1H, d, J = 2.4 Hz), 7.72-7.62 (1H, m), 7.28-7.21 (1H, m), 7.16 (1H, d, J = 7.9 Hz), 7.06-6.92 (1H, m), 6.88 (1H, d, J = 7.9 Hz), 5.48 (2H, s), 4.04 (3H, s), 3.44-3.23 (1H, m), 3.18-2.85 (6H, m), 2.82 (3H, s), 1.93-1.67 (3H, m), 1.65-1.48 (1H, m), 1.46-1.30 (1H, m). |
| 387 | 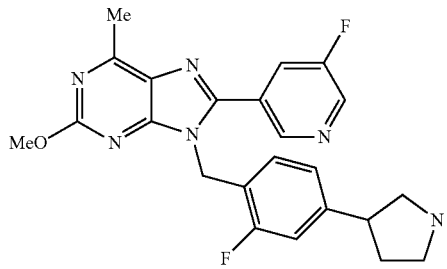 | LC-MS [M + H]$^+$/Rt (min): 537.5/0.988 (Method C); $^1$H-NMR (CDCl$_3$) δ: 8.66-8.62 (1H, m), 8.57 (1H, d, J = 3.1 Hz), 7.74-7.67 (1H, m), 6.94-6.85 (3H, m), 5.48 (2H, s), 4.02 (3H, s), 3.83-3.66 (1H, m), 3,63-3.44 (1H, m), 3.41-3.10 (3H, m), 2.81 (3H, s), 2.25-2.14 (1H, m), 1.93-1.81 (1H, m), 1.44 (9H, s). |

Example 388

9-[4-(1-Azabicyclo[2.2.2]oct-3-yl)benzyl]-8-(5-fluoropyridin-3-yl)-6-methyl-9H-purin-2-ol

Examples 390, 391

9-({6-[(3S)-1-Azabicyclo[2.2.2]oct-3-yl]pyridin-3-yl}methyl)-2-ethoxy-8-(5-fluoropyridin-3-yl)-6-methyl-9H-purine; 9-{[6-[(3R)-1-azabicyclo[2.2.2]oct-3-yl]pyridin-3-yl}methyl)-2-ethoxy-8-(5-fluoropyridin-3-yl)-6-methyl-9H-purine

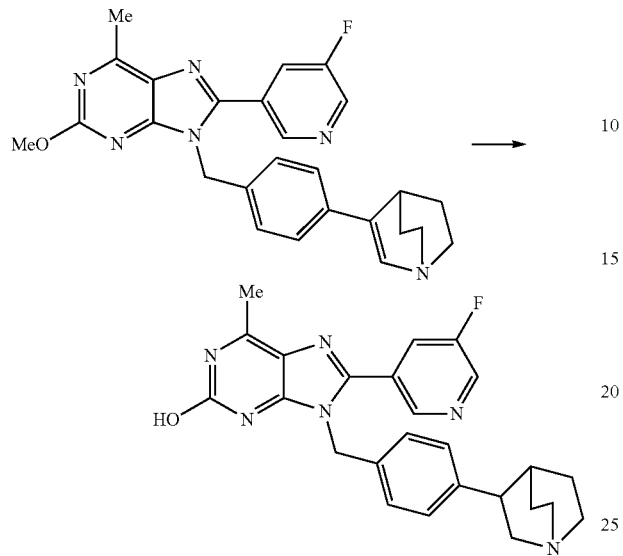

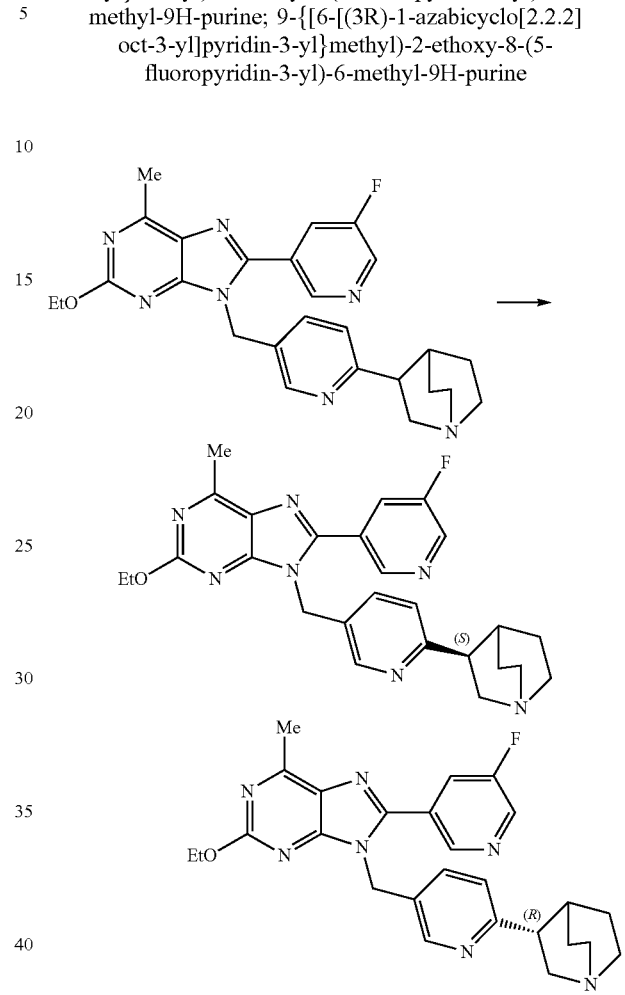

To a solution of the compound of Example 165 (88 mg) in ethyl acetate (2 mL) and methanol (0.2 mL) was added a solution of hydrochloric acid in ethyl acetate (4 mol/L, 0.055 mL) at room temperature, and the mixture was stirred at room temperature for one hour. The reaction mixture was concentrated in vacuo, and the residue was purified by amino silica gel column chromatography (chloroform/methanol) to give the title compound (15 mg).

LC-MS [M+H]$^+$/Rt (min): 445.4/0.346 (Method C); $^1$H-NMR (DMSO-D$_6$) δ: 8.69 (1H, d, J=3.0 Hz), 8.67-8.64 (1H, m), 7.99-7.94 (1H, m), 7.18 (2H, d, J=8.2 Hz), 6.94 (2H, d, J=8.2 Hz), 5.32 (2H, s), 3.69-3.00 (3H, m), 2.88-2.59 (5H, m), 2.54 (3H, s), 1.73-1.68 (1H, m), 1.66-1.52 (2H, m), 1.44-1.33 (1H, m), 1.26-1.13 (1H, m).

Example 389

According to the method of Example 388, Example 389 was prepared by using the corresponding material compound.

| Example | Chemical Structure | Instrumental analysis data |
|---|---|---|
| 389 | Me, F, HO, N, N, N, N, N, F (structure) | LC-MS [M+H]$^+$/Rt (min): 4.63.4/0.361 (Method C) |

The compound of Example 171 (25.9 mg) was optically separated in the following conditions to obtain the title compounds (Example 390: 12.0 mg-first peak: 18.2 min, Example 391: 8.9 mg-second peak: 31.4 min).

Column: CHIRALPAK™ AS-H; Solvent: Solution A: hexane/diethylamine=1/0.1%, solution B: ethanol/2-propanol/diethylamine/methanol=3/2/0.1/1%; Mobile phase condition: A/B=85/15; Flow rate: 10 mL/min; Detection UV: 220 nm; Column temperature: 40° C.

| Example | Instrumental analysis data |
|---|---|
| 390 | $^1$H-NMR (400 MHz, CDCl$_3$)δ: 8.69-8.66 (1H, m), 8.60 (1H, d, J = 3.1 Hz), 8.33 (1H, d, J = 2.4 Hz), 7.74-7.69 (1H, m), 7.32 (1H, dd, J = 7.9, 2.4 Hz), 7.10 (1H, d, J = 7.9 Hz), 5.46 (2H, s), 4.47 (2H, q, J = 7.1 Hz), 3.46-3.37 (1H, m), 3.22-3.13 (1H, m), 3.04-2.82 (4H, m), 2.81 (3H, s), 2.79-2.73 (1H, m), 2.00-1.95 (1H, m), 1.74-1.68 (2H, m), 1.59-1.47 (1H, m), 1.45 (3H, t, J = 7.1 Hz), 1.32-1.22 (1H, m). |
| 391 | $^1$H-NMR (400 MHz, CDCl$_3$)δ: 8.69-8.66 (1H, m), 8.60 (1H, d, J = 3.1 Hz), 8.33 (1H, d, J = 2.4 Hz), 7.74-7.69 (1H, m), 7.32 (1H, dd, J = 7.9, 2.4 Hz), 7.10 (1H, d, J = 7.9 Hz), 5.46 (2H, s), 4.47 (2H, q, J = 7.1 Hz), 3.46-3.37 (1H, m), 3.22-3.13 (1H, m), 3.04-2.82 (4H, m), 2.81 (3H, s), |

| Example | Instrumental analysis data |
|---|---|
|  | 2.79-2.73 (1H, m), 2.00-1.95 (1H, m), 1.74-1.68 (2H, m), 1.59-1.47 (1H, m), 1.45 (3H, t, J = 7.1 Hz), 1.32-1.22 (1H, m). |

Examples 392, 393

9-{4-[(3R)-1-Azabicyclo[2.2.2]oct-3-yl]-2-fluorobenzyl}-8-(5-fluoropyridin-3-yl)-2-methoxy-6-methyl-9H-purine; 9-{4-[(3S)-1-azabicyclo[2.2.2]oct-3-yl]-2-fluorobenzyl}-8-(5-fluoropyridin-3-yl)-2-methoxy-6-methyl-9H-purine

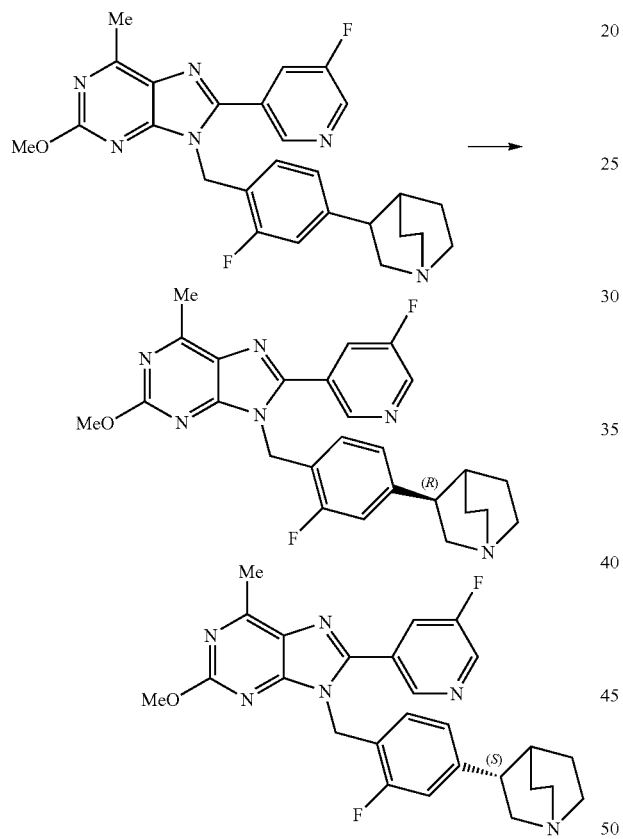

The compound of Example 314 (30.3 mg) was optically separated in the following conditions to obtain the title compounds (Example 392: 12.2 mg-first peak: 19.4 min, Example 393: 11.3 mg-second peak: 36.7 min).

Column: CHIRALPAK™ AD-H; Solvent: Solution A: hexane, Solution B: ethanol/2-propanol=1/2; Mobile phase condition: A/B/diethylamine=70/30/0.2%; Flow rate: 10 mL/min; Detection UV: 220 nm; Column temperature: 40° C.

| Example | Instrumental analysis data |
|---|---|
| 392 | $^1$H-NMR CDCl$_3$) δ: 8.70-8.67 (1H, m), 8.61 (1H, d, J = 2.4 Hz), 7.75-7.70 (1H, m), 6.99-6.91 (3H, m), 5.53 (2H, s), 4.08 (3H, s), 3.36-3.26 (1H, m), 3.01-2.80 (9H, m), 1.93-1.85 (1H, m), 1.77-1.65 (2H, m), 1.59-1.50 (1H, m), 1.42-1.30 (1H, m). |
| 393 | $^1$H-NMR (CDCl$_3$) δ: 8.70-8.67 (1H, m), 8.61 (1H, d, J = 2.4 Hz), 7.75-7.70 (1H, m), 6.99-6.91 (3H, m), 5.53 (2H, s), 4.08 (3H, s), 3.36-3.26 (1H, m), 3.01-2.80 (9H, m), 1.93-1.85 (1H, m), 1.77-1.65 (2H, m), 1.59-1.50 (1H, m), 1.42-1.30 (1H, m). |

Examples 394, 395

2-[(3R)-1-Azabicyclo[2.2.2]oct-3-yl]-5-{[2-ethoxy-8-(5-fluoropyridin-3-yl)-6-methyl-9H-purin-9-yl]methyl}benzonitrile; 2-[(3S)-1-azabicyclo[2.2.2]oct-3-yl]-5-{[2-ethoxy-8-(5-fluoropyridin-3-yl)-6-methyl-9H-purin-9-yl]methyl}benzonitrile

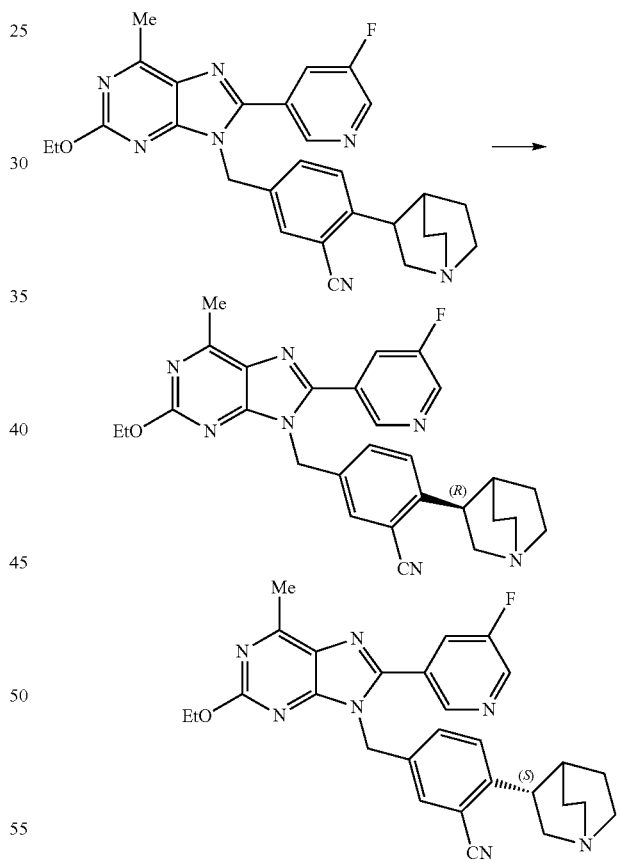

The compound of Example 316 (29.5 mg) was optically separated in the following conditions to obtain the title compounds (Example 394: 14.6 mg-first peak: 10.8 min, Example 395: 15.0 mg-second peak: 26.9 min).

Column: CHIRALPAK™ AD-H; Solvent: Solution A: hexane, Solution B: ethanol/2-propanol/methanol=6/3/1; Mobile phase condition: A/B/diethylamine=70/30/0.2%; Flow rate: 10 mL/min; Detection UV: 220 nm; Column temperature: 40° C.

| Example | Instrumental analysis data |
|---|---|
| 394 | ¹H-NMR (CDCl₃) δ: 8.68-8.60 (2H, m), 7.78-7.73 (1H, m), 7.50 (1H, d, J = 7.9 Hz), 7.40 (1H, d, J = 1.8 Hz), 7.32-7.29 (1H, m), 5.50 (2H, s), 4.50 (2H, q, J = 7.1 Hz), 3.44-3.38 (1H, m), 3.38-3.30 (1H, m), 3.10-3.00 (1H, m), 3.00-2.87 (4H, m), 2.86 (3H, s), 1.92-1.82 (2H, m), 1.79-1.73 (1H, m), 1.54-1.44 (4H, m), 1.42-1.33 (1H, m). |
| 395 | ¹H-NMR (CDCl₃) δ: 8.68-8.60 (2H, m), 7.78-7.73 (1H, m), 7.50 (1H, d, J = 7.9 Hz), 7.40 (1H, d, J = 1.8 Hz), 7.32-7.29 (1H, m), 5.50 (2H, s), 4.50 (2H, q, J = 7.1 Hz), 3.44-3.38 (1H, m), 3.38-3.30 (1H, m), 3.10-3.00 (1H, m), 3.00-2.87 (4H, m), 2.86 (3H, s), 1.92-1.82 (2H, m), 1.79-1.73 (1H, m), 1.54-1.44 (4H, m), 1.42-1.33 (1H, m). |

| Example | Instrumental analysis data |
|---|---|
| 396 | ¹H-NMR (CDCl₃) δ: 8.62 (1H, s), 8.59 (1H, d, J = 3.0 Hz), 7.74-7.69 (1H, m), 6.92 (1H, d, J = 7.9 Hz), 6.84 (1H, d, J = 7.9 Hz), 5.46 (2H, s), 4.45 (2H, q, J = 7.1 Hz), 3.50-3.43 (1H, m), 3.24-3.16 (1H, m), 3.07-2.97 (2H, m), 2.96-2.88 (2H, m), 2.87 (3H, s), 2.85-2.77 (1H, m), 2.51 (3H, s), 2.02-1.97 (1H, m), 1.75-1.68 (2H, m), 1.66-1.57 (1H, m), 1.44 (3H, t, J = 7.1 H2), 1.35-1.26 (1H, m). |
| 397 | ¹H-NMR (CDCl₃) δ: 8.62 (1H, s), 8.59 (1H, d, J = 3.0 Hz), 7.74-7.69 (1H, m), 6.92 (1H, d, J = 7.9 Hz), 6.84 (1H, d, J = 7.9 Hz), 5.46 (2H, s), 4.45 (2H, q, J = 7.1 Hz), 3.50-3.43 (1H, m), 3.24-3.16 (1H, m), 3.07-2.97 (2H, m), 2.96-2.88 (2H, m), 2.87 (3H, s), 2.85-2.77 (1H, m), 2.51 (3H, s), 2.02-1.97 (1H, m), 1.75-1.68 (2H, m), 1.66-1.57 (1H, m), 1.44 (3H, t, J = 7.1 Hz), 1.35-1.26 (1H, m), |

Examples 396, 397

9-({6-[(3S)-1-Azabicyclo[2.2.2]oct-3-yl]-2-methyl-pyridin-3-yl}methyl)-2-ethoxy-8-(5-fluoropyridin-3-yl)-6-methyl-9H-purine; 9-({6-[(3R)-1-azabicyclo[2.2.2]oct-3-yl]-2-methylpyridin-3-yl}methyl)-2-ethoxy-8-(5-fluoropyridin-3-yl)-6-methyl-9H-purine Examples 398, 399

9-({1-[(3S)-1-Azabicyclo[2.2.2]oct-3-ylmethyl]-1H-pyrazol-4-yl}methyl)-2-ethoxy-8-(3-fluoropyridin-3-yl)-6-methyl-9H-purine; 9-({1-[(3R)-1-azabicyclo[2.2.2]oct-3-ylmethyl]-1H-pyrazol-4-yl}methyl)-2-ethoxy-8-(5-fluoropyridin-3-yl)-6-methyl-9H-purine

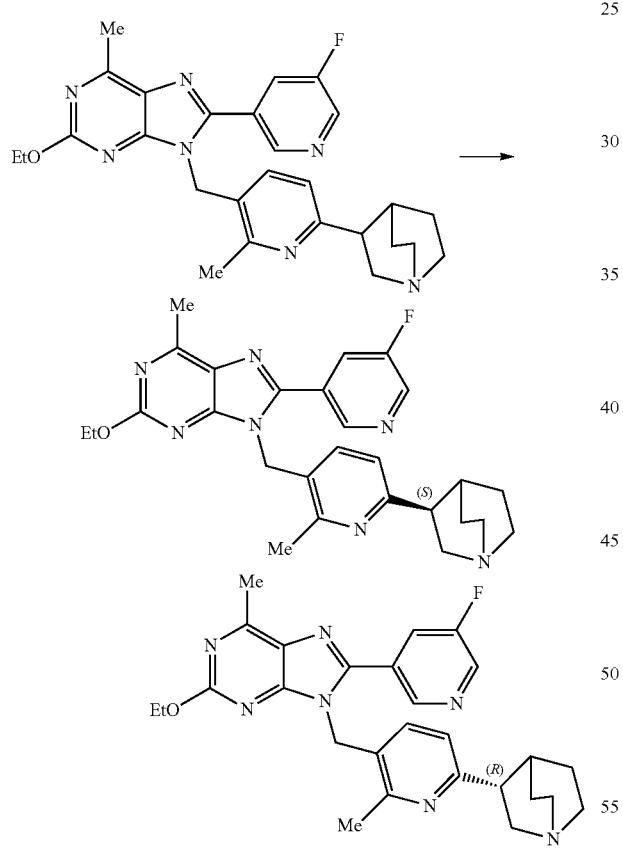

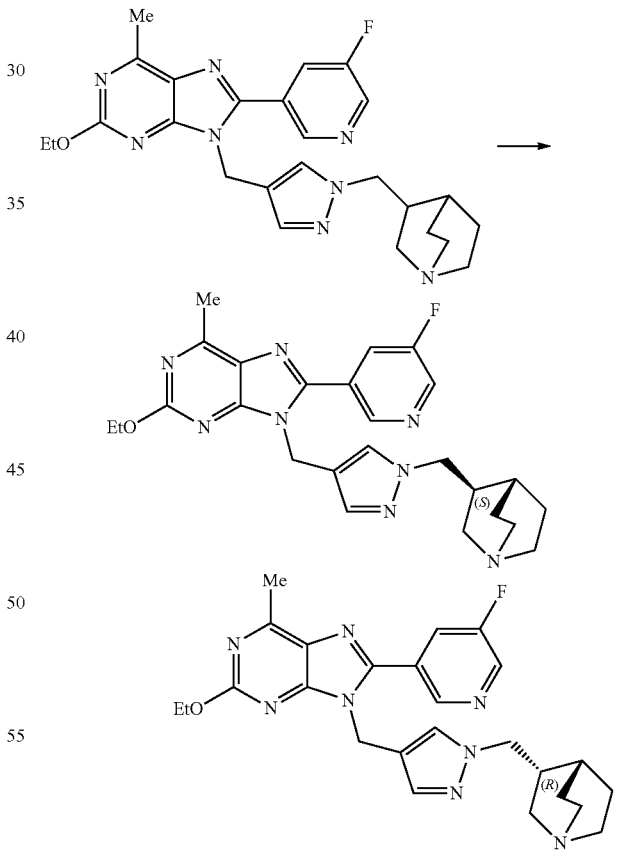

The compound of Example 315 (30.0 mg) was optically separated in the following conditions to obtain the title compounds (Example 396: 14.6 mg-first peak: 11.4 min, Example 397: 15.0 mg-second peak: 16.1 min).
Column: CHIRALPAK™ AD-H; Solvent: Solution A: hexane, Solution B: ethanol/2-propanol/methanol=1/1/1; Mobile phase condition: A/B/diethylamine=80/20/0.2%; Flow rate: 5 mL/min; Detection UV: 220 nm; Column temperature: 40° C.

The compound of Example 163 (33.0 mg) was optically separated in the following conditions to obtain the title compounds (Example 398: 16.0 mg-first peak: 28.1 min, Example 399: 16.3 mg-second peak: 38.0 min).
Column: CHIRALPAK™ AS-H; Solvent: Solution A: hexane/diethylamine=1/0.2%, Solution B: ethanol/2-propanol/diethylamine=2/1/0.2%; Mobile phase condition: A/B=90/10; Flow rate: 10 mL/min; Detection UV: 220 nm; Column temperature: 40° C.

| Example | Instrumental analysis data |
|---|---|
| 398 | $^1$H-NMR (CDCl$_3$) δ: 8.78 (1H, s), 8.62 (1H, d, J = 3.1 Hz), 7.79-7.76 (1H, m), 7.32 (1H, s), 7.22 (1H, s), 5.31 (2H, s), 4.51 (2H, q, J = 7.1 Hz), 4.00 (2H, d, J = 7.9 Hz), 2.98-2.93 (1H, m), 2.87-2.71 (7H, m), 2.38-2.33 (1H, m), 2.19-2.13 (1H, m), 1.68-1.55 (2H, m), 1.49-1.40 (6H, m). |
| 399 | $^1$H-NMR (CDCl$_3$) δ: 8.78 (1H, s), 8.62 (1H, d, J = 3.1 Hz), 7.79-7.76 (1H, m), 7.32 (1H, s), 7.22 (1H, s), 5.31 (2H, s), 4.51 (2H, q, J = 7.1 Hz), 4.00 (2H, d, J = 7.9 Hz), 2.98-2.93 (1H, m), 2.87-2.71 (7H, m), 2.38-2.33 (1H, m), 2.19-2.13 (1H, m), 1.68-1.55 (2H, m), 1.49-1.40 (6H, m). |

Examples 400, 401

2-[(3R)-1-Azabicyclo[2.2.2]oct-3-yl]-5-{[8-(5-fluoropyridin-3-yl)-2-methoxy-6-methyl-9H-purin-9-yl]methyl}benzonitrile; 2-[(3S)-1-azabicyclo[2.2.2]oct-3-yl]-5-{[8-(5-fluoropyridin-3-yl)-2-methoxy-6-methyl-9H-purin-9-yl]methyl}benzonitrile

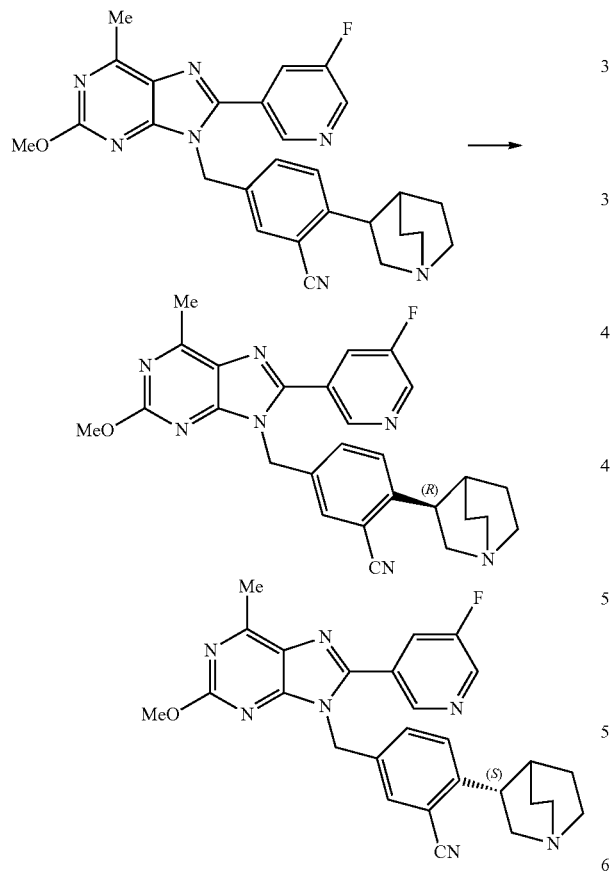

The compound of Example 318 (40.0 mg) was optically separated in the following conditions to obtain the title compounds (Example 400: 21.2 mg-first peak: 11.9 min, Example 401: 18.2 mg-second peak: 26.9 min).

Column: CHIRALPAK™ AD-H; Solvent: Solution A: hexane/diethylamine=1/0.2%, Solution B: ethanol/2-propanol/methanol/diethylamine=6/3/1/0.2%; Mobile phase condition: A/B=70/30; Flow rate: 10 mL/min; Detection UV: 220 nm; Column temperature: 40° C.

| Example | Instrumental analysis data |
|---|---|
| 400 | LC-MS [M + 2H]$^{+2}$/2/Rt (min): 242.9/0.495 (Method C); $^1$H-NMR (CDCl$_3$) δ: 8.61-8.58 (2H, m), 7.75-7.70 (1H, m), 7.46 (1H, d, J = 8.5 Hz), 7.36 (1H, d, J = 1.8 Hz), 7.27 (1H, dd, J = 8.5, 1.8 Hz), 5.47 (2H, s), 4.04 (3H, s), 3.43-3.27 (2H, m), 3.08-2.84 (5H, m), 2.83 (3H, s), 2.04-1.78 (2H, m), 1.78-1.66 (1H, m), 1.53-1.30 (2H, m). |
| 401 | LC-MS [M + H]$^{+2}$/2/Rt (min): 242.8/0.500 (Method C); $^1$H-NMR (CDCl$_3$) δ: 8.62-8.56 (2H, m), 7.77-7.71 (1H, m), 7.53-7.31 (3H, m), 5.48 (2H, s), 4.05 (3H, s), 3.64-3.54 (1H, m), 3.51-3.41 (1H, m), 3.39-2.98 (5H, m), 2.84 (3H, s), 2.15-1.83 (3H, m), 1.69-1.48 (2H, m). |

Examples 402, 403

5-(9-{4-[(3R)-1-Azabicyclo[2.2.2]oct-3-yl]-2-fluorobenzyl}-2-methoxy-6-methyl-9H-purin-8-yl)pyridine-3-carbonitrile; 5-(9-{4-[(3S)-1-azabicyclo[2.2.2]oct-3-yl]-2-fluorobenzyl}-2-methoxy-6-methyl-9H-purin-8-yl)pyridine-3-carbonitrile

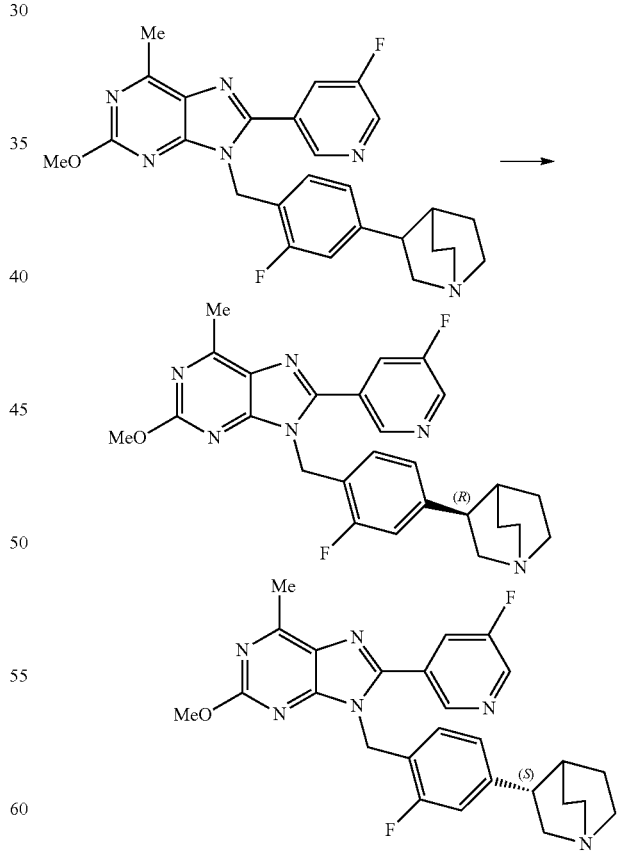

The compound of Example 344 (40.0 mg) was optically separated in the following conditions to obtain the title compounds (Example 402: 21.0 mg-first peak: 7.47 min, Example 403: 23.0 mg second peak: 13.6 min).

Column: CHIRALPAK™ AD-H; Solvent: Solution A: hexane/diethylamine=1/0.2%, Solution B: 2-propanol/diethylamine=1/0.1%; Mobile phase condition: A/B=60/40; Flow rate: 10 mL/min; Detection UV: 220 nm; Column temperature: 40° C.

| Example | Instrumental analysis data |
|---|---|
| 402 | LC-MS [M + 2H]$^{+2}$/2/Rt (min): 242.7/0.492 (Method C); $^1$H-NMR CDCl$_3$) δ: 9.02 (1H, d, J = 2.4 Hz), 8.95 (1H, d, J = 1.8 Hz), 8.21-8.19 (1H, m), 7.02-6.91 (3H, m), 5.48 (2H, s), 4.05 (3H, s), 3.41-3.32 (1H, m), 3.07-2.84 (6H, m), 2.81 (3H, s), 1.97-1.92 (1H, m), 1.81-1.74 (2H, m), 1.64-1.53 (1H, m), 1.49-1.36 (1H, m). |
| 403 | LC-MS [M + 2H]$^{+2}$/2/Rt (min): 242.8/0.491 (Method C); $^1$H-NMR (CDCl$_3$) δ: 9.03 (1H, d, J = 1.8 Hz), 8.95 (1H, d, J = 1.8 Hz), 8.22-8.20 (1H, m), 7.00-6.90 (3H, m), 5.48 (2H, s), 4.05 (3H, s), 3.31-3.23 (1H, m), 2.98-2.79 (6H, m), 2.81 (3H, s), 1.88-1.83 (1H, m), 1.73-1.61 (2H, m), 1.57-1.46 (1H, m), 1.40-1.29 (1H, m). |

Examples 404, 405

3-Fluoro-4-{[8-(5-fluoropyridin-3-yl)-2-methoxy-6-methyl-9H-purin-9-yl]methyl}phenol; 9-(2-fluoro-4-methoxybenzyl)-8-(5-fluoropyridin-3-yl)-2-methoxy-6-methyl-9H-purine

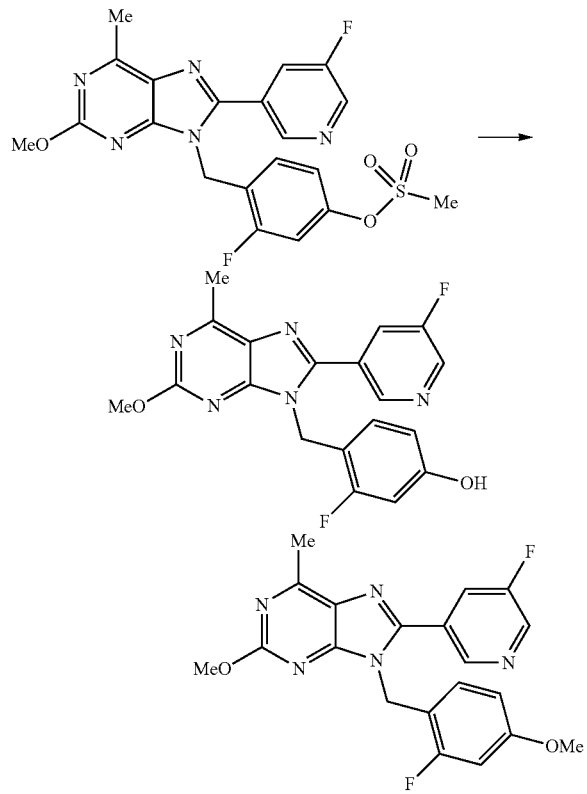

To an ice-cooled solution of the compound of Example 342 (103 mg) in methanol (2 mL)/tetrahydrofuran (2 mL) was added 1 mol/L aqueous potassium hydroxide (0.223 mL), and the mixture was stirred in ice bath for 10 hours. To the reaction mixture was added 50% aqueous potassium carbonate, and the mixture was extracted with chloroform/ethanol (3/1). The organic layer was dried over sodium sulfate, filtrated, and then concentrated in vacuo. The obtained residue was purified by amino silica gel column chromatography (chloroform/methanol) and amino silica gel column chromatography (hexane/ethyl acetate) to give the compound of Example 404 (57.0 mg) and the compound of Example 405 (10.0 mg).

Compound of Example 404: LC-MS [M+H]$^+$/Rt. (min): 384.2/0.650 (Method C); $^1$H-NMR (DMSO-D$_6$) δ: 9.95 (1H, br s), 8.75 (1H, d, J=2.4 Hz), 8.74-8.71 (1H, m), 8.14-8.08 (1H, m), 6.86-6.78 (1H, m), 6.45-6.38 (2H, m), 5.44 (2H, s), 3.95 (3H, s), 2.68 (38, s).

Compound of Example 405: LC-MS [M+H]$^+$/Rt (min): 398.3/0.801 (Method C); $^1$H-NMR (CDCl$_3$) δ: 8.67-8.66 (1H, m), 8.58 (1H, d, J=3.0 Hz), 7.70-7.66 (1H, m), 6.92 (1H, t, J=8.5 Hz), 6.57-6.52 (2H, m), 5.43 (2H, s), 4.04 (3H, s), 3.73 (3H, s), 2.80 (3H, s).

Examples 406-407

According to the method of Example 405, Examples 405-406 were prepared by using the corresponding material compounds.

| Example | Chemical Structure | Instrumental analysis data |
|---|---|---|
| 406 | ![structure] | LC-MS [M + H]$^+$/Rt (min): 446.2/0.740 (Method C) |
| 407 | ![structure] | LC-MS [M + H]$^+$/Rt (min): 3.662/0.575 (Method C) |

Example 408 tert-Butyl (3-endo)-3-(4-{[8-(5-cyanopyridin-3-yl)-2-methoxy-6-methyl-9H-purin-9-yl]methyl}-3-fluorophenoxy)-8-azabicyclo[3.2.1]octane-8-carboxylate

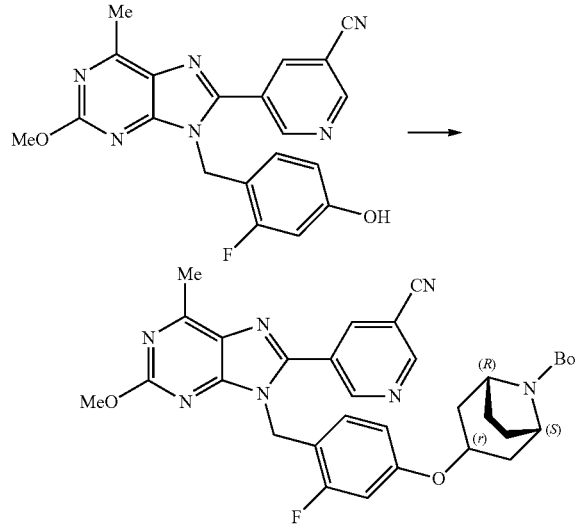

To an ice-cooled solution of the compound of Example 349 (25.0 mg) in chloroform (0.4 mL) were added tert-butyl (1R,3S,5S)-3-hydroxy-8-azabicyclo[3.2.1]octane-8-carboxylate (29.0 mg), triphenylphosphine (34.0 mg), and diisopropyl azodicarboxylate (0.025 mL), and the mixture was stirred at room temperature overnight. The reaction mixture was concentrated in vacuo, and the obtained residue was purified by amino silica gel column chromatography (hexane/ethyl acetate) to give the title compound (29.0 mg).

$^1$H-NMR (CDCl$_3$) δ: 9.07-9.04 (1H, m), 8.99-8.95 (1H, m), 8.24-8.18 (1H, m), 7.00 (1H, t, J=8.9 Hz), 6.60-6.45 (2H, m), 5.44 (2H, s), 4.55-4.48 (1H, m), 4.07 (3H, s), 3.75 (2H, s), 2.82 (3H, s), 1.99-1.91 (2H, m), 1.91-1.84 (2H, m), 1.48-1.46 (4H, m), 1.26 (9H, s).

Examples 409-421

According to the methods of Example 66 and Example 408, Examples 409-421 were prepared by using the corresponding material compounds.

| Example | Chemical Structure | Instrumental analysis data |
|---|---|---|
| 409 | 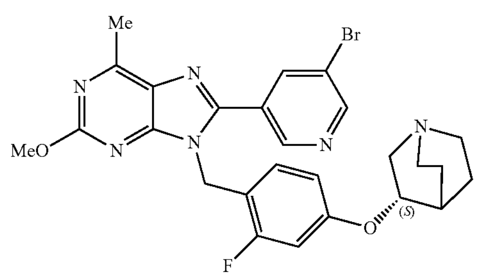 | LC-MS [M + 2H]$^{2+}$/2/Rt (min): 278.3/0.581 (Method C) |
| 410 | 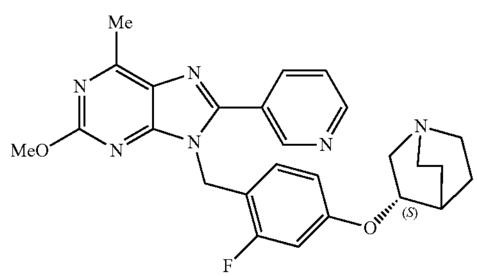 | LC-MS [M + 2H]$^{2+}$/2/Rt (min): 238.68/1.075 (Method C); $^1$H-NMR (CD$_3$OD) δ: 8.84-8.81 (1H, m), 8.70 (1H, dd, J = 4.9, 1.2 Hz), 8.12 (1H, dt, J = 7.9, 1.8 Hz), 7.57 (1H, dt, J = 7.9, 3.1 Hz), 6.97 (1H, t, J = 8.5 Hz), 6.60-6.54 (2H, m), 5.50 (2H, s), 4.45-4.37 (1H, m), 4.03 (3H, s), 3.26-3.21 (1H, m), 2.91-2.74 (3H, m), 2.72 (3H, s), 2.71-2.63 (1H, m), 2.09-2.00 (1H, m), 1.95-1.83 (1H, m), 1.79-1.68 (1H, m), 1.66-1.54 (1H, m), 1.48-1.35 (1H, m), 1.31-1.18 (H, m). |
| 411 | 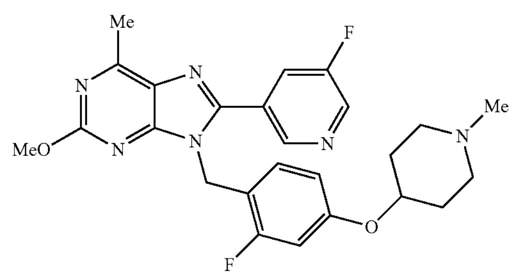 [SMILES: COc1nc(C)c2nc(-c3cncc(F)c3)n(Cc3ccc(OC4CCN(C)CC4)cc3F)c2n1] | LC-MS [M + 2H]$^{2+}$/2/Rt (min): 241.3/0.520 (Method C); $^1$H-NMR (CDCl$_3$) δ: 8.67-8.64 (1H, m), 8.58 (1H, d, J = 3.1 Hz), 7.72-7.66 (1H, m), 6.94-6.86 (1H, m), 6.59-6.50 (2H, m), 5.43 (2H, s), 4.35-4.23 (1H, m), 4.04 (3H, s), 2.80 (3H, s), 2.78-2.69 (2H, m), 2.59-2.30 (2H, m), 2.38 (3H, s), 2.16-2.02 (2H, m), 1.91-1.79 (2H, m). |

| Example | Chemical Structure | Instrumental analysis data |
|---|---|---|
| 412 | 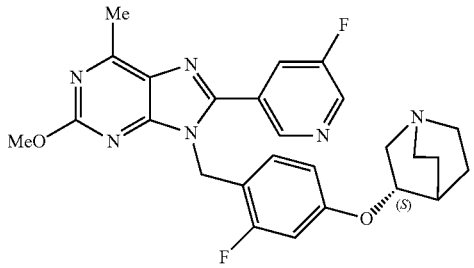 | LC-MS [M + 2H]²⁺/2/Rt (min): 247.4/0.517 (Method C); ¹H-NMR (CDCl₃) δ: 8.67-8.64 (1H, m), 8.58 (1H, d, J = 2.4 Hz), 7.72-7.67 (1H, m), 6.94-6.88 (1H, m), 6.53-6.47 (2H, m), 5.43 (2H, s), 4.45-4.25 (1H, m), 4.04 (3H, s), 3.44-3.18 (1H, m), 3.05-2.77 (5H, m), 2.80 (3H, s), 2.51-1.37 (5H, m). |
| 413 | 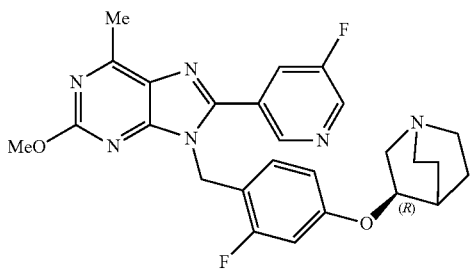 | LC-MS [M + 2H]²⁺/2/Rt (min): 247.3/0.525 (Method C); ¹H-NMR (CDCl₃) δ: 8.67-8.64 (1H, m), 8.58 (1H, d, J = 2.4 Hz), 7.72-7.66 (1H, m), 6.95-6.88 (1H, m), 6.53-6.47 (2H, m), 5.43 (2H, s), 4.40-4.29 (1H, m), 4.04 (3H, s), 3.39-3.24 (1H, m), 3.08-2.82 (5H, m), 2.80 (3H, s), 2.49-1.38 (5H, m). |
| 414 | 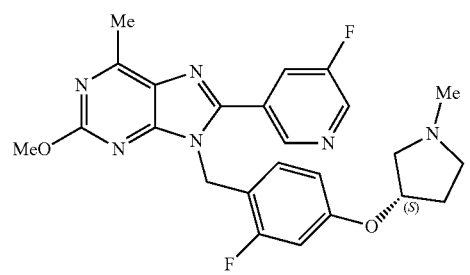 | LC-MS [M + 2H]²⁺/2/Rt (min): 234.3/0.499 (Method C); ¹H-NMR (CDCl₃) δ: 8.66-8.64 (1H, m), 8.58 (1H, d, J = 3.0 Hz), 7.71-7.65 (1H, m), 6.93-6.87 (1H, m), 6.53-6.47 (2H, m), 5.43 (2H, s), 4.79-4.72 (1H, m), 4.04 (3H, s), 3.12-2.60 (4H, m), 2.80 (3H, s), 2.48 (3H, s), 2.37-2.26 (1H, m), 2.04-1.94 (1H, m). |
| 415 | 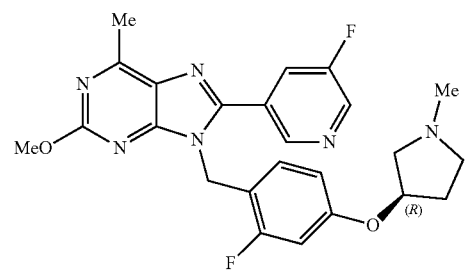 | LC-MS [M + 2H]²⁺/2/Rt (min): 234.3/0.479 (Method C); ¹H-NMR (CDCl₃) δ: 8.66-8.64 (1H, m), 8.58 (1H, d, J = 3.0 Hz), 7.71-7.66 (1H, m), 6.93-6.86 (1H, m), 6.52-6.46 (2H, m), 5.42 (2H, s), 4.78-4.71 (1H, m), 4.04 (3H, s), 3.05-2.75 (3H, m), 2.80 (3H, s), 2.70-2.55 (1H, m), 2.45 (3H, s), 2.36-2.25 (1H, m), 2.03-1.92 (1H, m). |
| 416 | 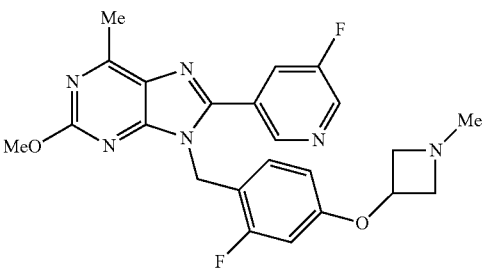 [SMILES: COc1nc(C)c2nc(-c3cncc(F)c3)n(Cc3ccc(OC4CN(C)C4)cc3F)c2n1] | LC-MS [M + 2H]²⁺/2/Rt (min): 227.2/0.473 (Method C); ¹H-NMR (CDCl₃) δ: 8.65-8.64 (1H, m), 8.58 (1H, d, J = 2.4 Hz), 7.71-7.65 (1H, m), 6.94-6.87 (1H, m), 6.45-6.37 (2H, m), 5.42 (2H, s), 4.72-4.65 (1H, m), 4.03 (3H, s), 3.93-3.86 (2H, m), 3.19-3.13 (2H, m), 2.80 (3H, s), 2.45 (3H, s). |

-continued

| Example | Chemical Structure | Instrumental analysis data |
|---|---|---|
| 417 | 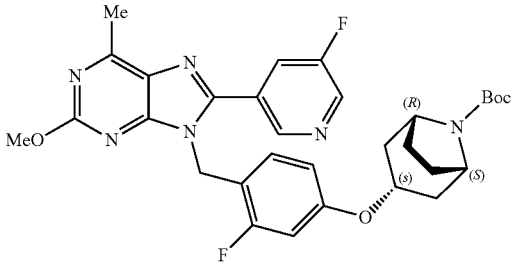 | LC-MS [M + H]⁺/Rt (min): 5.93.5/1.126 (Method C) |
| 418 | 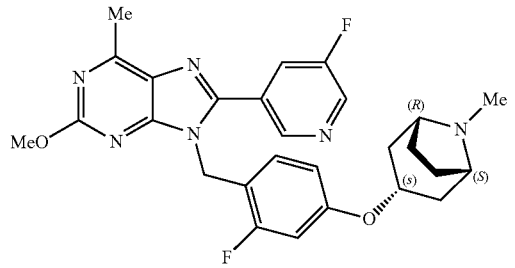 | LC-MS [M + 2H]²⁺/2/Rt (min): 254.3/0.519 (Method C); ¹H-NMR (CDCl₃) δ: 8.66-8.64 (1H, m), 8.58 (1H, d, J = 3.1 Hz), 7.71-7.66 (1H, m), 6.93-6.86 (1H, m), 6.55-6.49 (2H, m), 5.42 (2H, s), 4.48-4.37 (1H, m), 4.04 (3H, s), 3.50-3.34 (2H, m), 2.80 (3H, s), 2.47 (3H, s), 2.30-1.92 (6H, m), 1.78-1.66 (2H, m). |
| 419 | 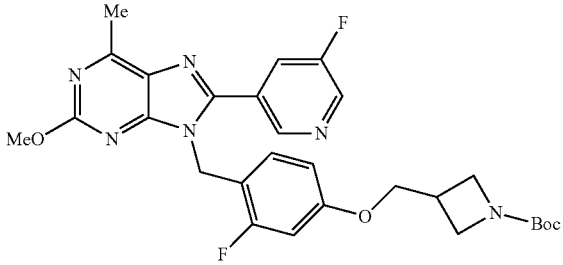 [SMILES: COc1nc(C)c2nc(-c3cncc(F)c3)n(Cc3ccc(OCC4CN(C(=O)OC(C)(C)C)C4)cc3F)c2n1] | LC-MS [M + H]⁺/Rt (min): 553.4/0.969 (Method C); ¹H-NMR (CDCl₃) δ: 8.67-8.65 (1H, m), 8.58 (1H, d, J = 2.4 Hz), 7.71-7.66 (1H, m), 6.95-6.88 (1H, m), 6.58-6.51 (2H, m), 5.44 (2H, s), 4.07-3.97 (4H, m), 4.04 (3H, s), 3.75-3.70 (2H, m), 2.97-2.85 (1H, m), 2.80 (3H, s), 1.41 (9H, s). |
| 420 | 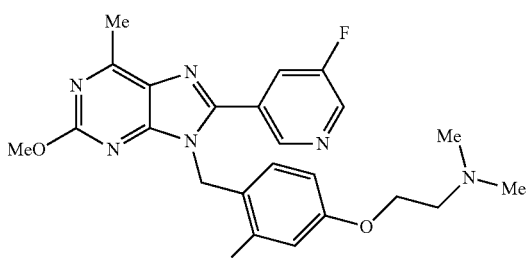 | LC-MS [M + 2H]²⁺/2/Rt (min): 228.3/0.463 (Method C); ¹H-NMR (CDCl₃) δ: 8.67-8.64 (1H, m), 8.58 (1H, d, J = 3.0 Hz), 7.71-7.66 (1H, m), 6.95-6.88 (1H, m), 6.61-6.54 (2H, m), 5.44 (2H, s), 4.24-4.11 (2H, m), 4.04 (3H, s), 3.03-2.89 (2H, m), 2.80 (3H, s), 2.53 (6H, br s). |
| 421 | 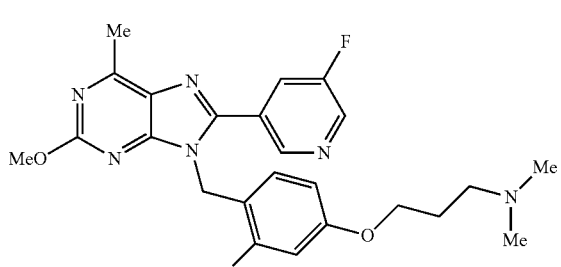 | LC-MS [M + 2H]²⁺/2/Rt (min): 235.2/0.496 (Method C); ¹H-NMR (CDCl₃) δ: 8.68-8.64 (1H, m), 8.58 (1H, d, J = 3.1 Hz), 7.71-7.65 (1H, m), 6.93-6.86 (1H, m), 6.57-6.50 (2H, m), 5.43 (2H, s), 4.04 (3H, s), 3.95 (2H, t, J = 6.1 Hz), 2.80 (3H, s), 2.71-2.61 (2H, m), 2.42 (6H, br s), 2.12-2.01 (2H, m). |

Example 422

5-(9-{4-[(3S)-1-Azabicyclo[2.2.2]oct-3-yloxy]-2-fluorobenzyl}-2-methoxy-6-methyl-9H-purin-8-yl)pyridine-3-carbonitrile

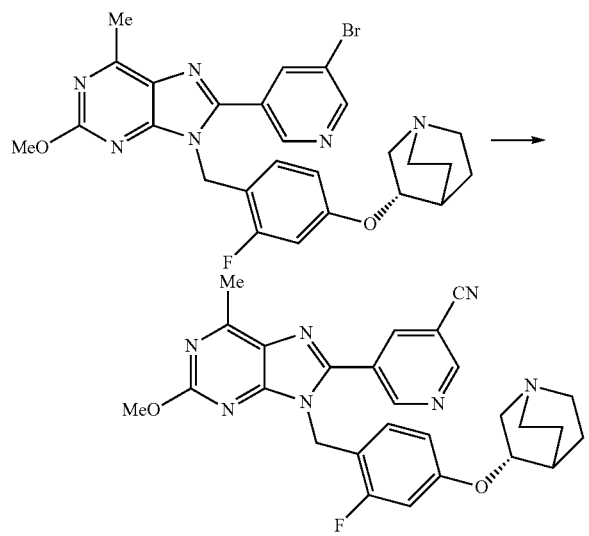

To a solution of the compound of Example 409 (50.0 mg) in N,N-dimethylformamide (1.5 mL) were added tetrakis(triphenylphosphine)palladium (10.4 mg) and zinc cyanide (12.7 mg), and the reaction solution was heated to 85° C. and stirred with heating for 2 hours. The reaction solution was filtered, and the filtrate was purified by reversed-phase column chromatography (water/acetonitrile/trifluoruacetic acid) to give the title compound (12.2 mg).

LC-MS [M+2H]$^{2+}$/2//Rt (min): 250.67/0.538; $^1$H-NMR (CD$_3$OD) δ: 9.06 (2H, s), 8.46 (1H, t, J=2.1 Hz), 7.04 (1H, t, J=8.9 Hz), 6.64-6.58 (2H, m), 5.55 (2H, s), 4.52-4.40 (1H, m), 4.08 (3H, s), 3.38-3.22 (1H, m), 2.94-2.79 (3H, m), 2.79-2.67 (2H, m), 2.76 (3H, s), 2.12-2.04 (1H, m), 1.98-1.88 (1H, m), 1.84-1.72 (1H, m), 1.70-1.58 (1H, m), 1.52-1.40 (1H, m).

Example 423

According to the method of Example 216, Example 423 was prepared by using the corresponding material compound.

| Example | Chemical Structure | Instrumental analysis data |
|---|---|---|
| 423 | *(structure shown)* | LC-MS [M + H]$^+$/Rt (min): 396.4/0.800 (Method A) |

Examples 424-437

According to the methods of Example 123 and Example 227, Examples 424-237 were prepared by using the corresponding material compounds.

| Example | Chemical Structure | Instrumental analysis data |
|---|---|---|
| 424 | *(structure shown)* | LC-MS [M + H]$^+$/Rt (min): 453.3/0.569 (Method A); |
| 425 | *(structure shown)* | LC-MS [M + H]$^+$/Rt (min): 453.3/0.572 (Method A); |

| Example | Chemical Structure | Instrumental analysis data |
|---|---|---|
| 426 | 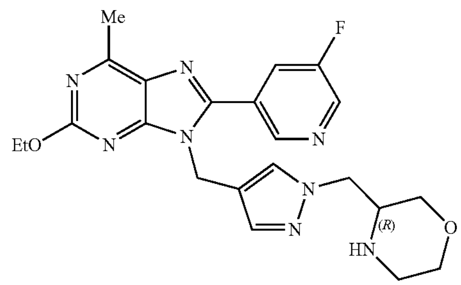 | LC-MS [M + H]+/Rt (min): 453.3/0.564 (Method A); |
| 427 | 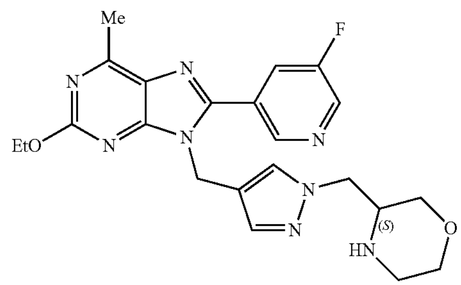 | LC-MS [M + H]+/Rt (min): 453.3/0.565 (Method A); |
| 428 | 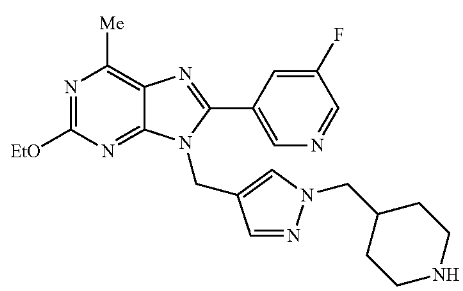 [SMILES: CCOc1nc(C)c2nc(-c3cncc(F)c3)n(Cc3cnn(CC4CCNCC4)c3)c2n1] | LC-MS [M + H]+/Rt (min): 451.3/0.589 (Method A); |
| 429 | 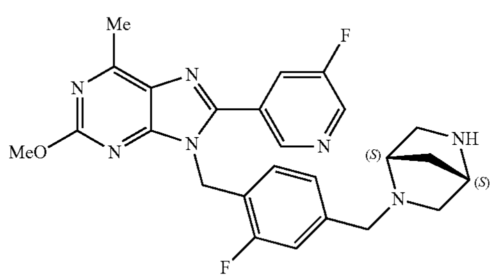 | LC-MS [M + H]+/Rt (min): 478.5/0.561 (Method A); |
| 430 | 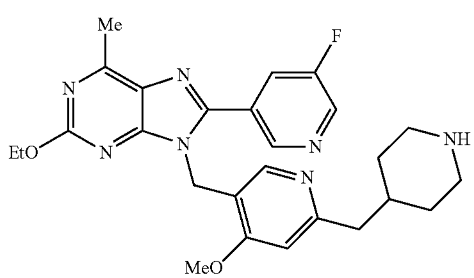 [SMILES: CCOc1nc(C)c2nc(-c3cncc(F)c3)n(Cc3cnc(CC4CCNCC4)cc3OC)c2n1] | LC-MS [M + 2H]$^{2+}$/2/Rt (min): 246.8/0.393 (Method C); $^1$H-NMR (CDCl$_3$) δ: 8.72-8.69 (1H, m), 8.58 (1H, d, J = 2.4 Hz), 8.12 (1H, s), 7.77-7.72 (1H, m), 6.50 (1H, s), 5.41 (2H, s), 4.43 (2H, q, J = 7.0 Hz), 3.65 (3H, s), 3.07-3.01 (2H, m), 2.77 (3H, s), 2.61-2.51 (4H, m), 1.91-1.69 (2H, m), 1.59-1.52 (2H, m), 1.42 (3H, t, J = 7.0 Hz), 1.29-1.14 (2H, m). |

-continued

| Example | Chemical Structure | Instrumental analysis data |
|---|---|---|
| 431 | 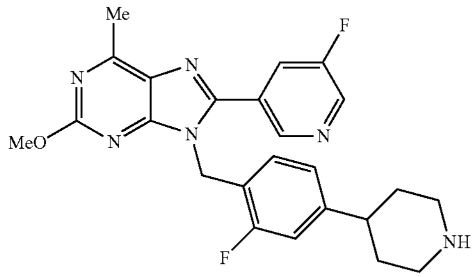 [SMILES: COc1nc(C)c2nc(-c3cncc(F)c3)n(Cc3ccc(C4CCNCC4)cc3F)c2n1] | LC-MS [M + 2H]²⁺/2/Rt (min): 226.1/0.489 (Method C) ; ¹H-NMR (CDCl₃) δ: 8.66-8.62 (1H, m), 8.57 (1H, d, J = 2.4 Hz), 7.72-7.65 (1H, m), 6.91-6.84 (3H, m), 5.47 (2H, s), 4.03 (3H, s), 3.25-3.16 (2H, m), 2.81 (3H, s), 2.77-2.67 (2H, m), 2.62-2.50 (1H, m), 2.04-1.83 (1H, m), 1.83-1.74 (2H, m), 1.68-1.54 (2H, m). |
| 432 | 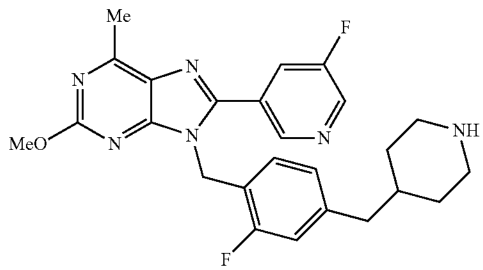 [SMILES: COc1nc(C)c2nc(-c3cncc(F)c3)n(Cc3ccc(CC4CCNCC4)cc3F)c2n1] | LC-MS [M + 2H]²⁺/2/Rt (min): 233.3/0.554 (Method C); ¹H-NMR (CDCl₃) δ: 8.65-8.63 (1H, m), 8.56 (1H, d, J = 3.1 Hz), 7.71-7.64 (1H, m), 6.88-6.73 (3H, m), 5.47 (2H, s), 4.03 (3H, s), 3.13-3.04 (2H, m), 2.81 (3H, s), 2.59-2.50 (2H, m), 2.49-2.42 (2H, m), 2.31-2.06 (1H, m), 1.67-1.49 (3H, m), 1.27-1.12 (2H, m). |
| 433 | 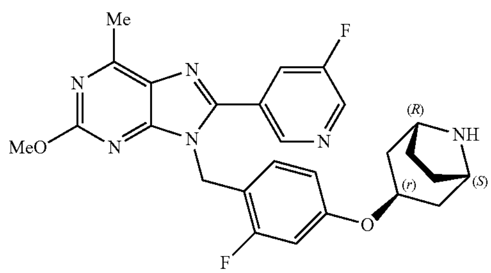 | LC-MS [M + 2H]²⁺/2/Rt (min): 247.3/0.534 (Method C); ¹H-NMR (CDCl₃) δ: 8.67-8.64 (1H, m), 8.58 (1H, d, J = 3.1 Hz), 7.72-7.66 (1H, m), 6.94-6.88 (1H, m), 6.49-6.42 (2H, m), 5.42 (2H, s), 4.50-4.41 (1H, m), 4.04 (3H, s), 3.63-3.53 (2H, m), 2.80 (3H, s), 2.31-1.75 (7H, m), 1.30-1.19 (2H, m). |
| 434 | 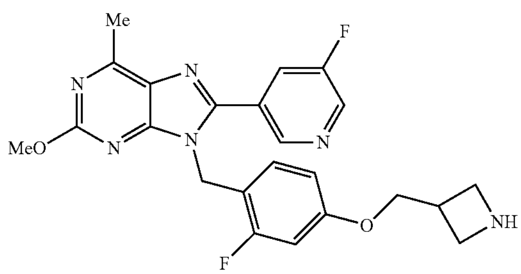 [SMILES: COc1nc(C)c2nc(-c3cncc(F)c3)n(Cc3ccc(OCC4CNC4)cc3F)c2n1] | LC-MS [M + 2H]²⁺/2/Rt (min): 227.2/0.482 (Method C); ¹H-NMR (CDCl₃) δ: 8.66-8.63 (1H, m), 8.58 (1H, d, J = 2.4 Hz), 7.72-7.66 (1H, m), 6.96-6.86 (1H, m), 6.65-6.49 (2H, m), 5.44 (2H, s), 4.32-3.90 (5H, m), 4.04 (3H, s), 3.86-3.67 (2H, m), 3.25-3.09 (1H, m), 2.80 (3H, s). |
| 435 | 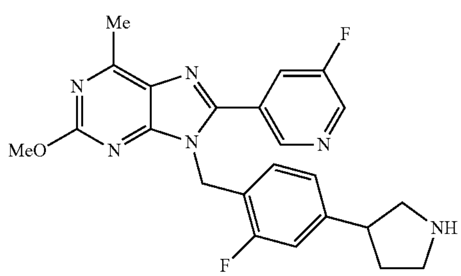 [SMILES: COc1nc(C)c2nc(-c3cncc(F)c3)n(Cc3ccc(C4CCNC4)cc3F)c2n1] | LC-MS [M + 2H]²⁺/2/Rt (min): 219.2/0.466 (Method C); ¹H-NMR (CDCl₃) δ: 8.66-8.62 (1H, m), 8.57 (1H, d, J = 3.0 Hz), 7.74-7.67 (1H, m), 6.94-6.85 (3H, m), 5.48 (2H, s), 4.03 (3H, s), 3.43-3.35 (1H, m), 3.26-3.07 (3H, m), 2.87-2.80 (1H, m), 2.81 (3H, s), 2.47-2.15 (2H, m), 1.86-1.74 (1H, m). |

| Example | Chemical Structure | Instrumental analysis data |
|---|---|---|
| 436 | 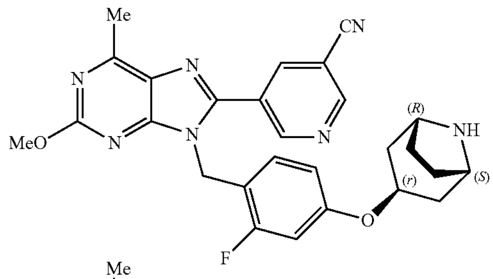 | LC-MS [M + 2H]²⁺/2/Rt (min): 250.9/0.522 (Method C); ¹H-NMR (CDCl₃) δ: 9.06 (2H, dd, J = 3.7, 2.4 Hz), 8.46 (1H, t, J = 1.8 Hz), 703 (1H, t, J = 8.9 Hz), 6.59-6.52 (2H, m), 5.56 (2H, s), 4.56-4.55 (1H, m), 4.08 (3H, s), 3.54-3.44 (2H, m), 2.77 (3H, s), 2.14-2.03 (3H, m), 1.93-1.75 (5H, m). |
| 437 | 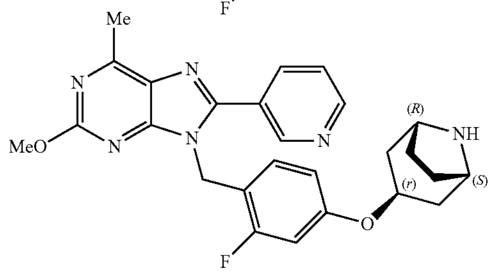 | LC-MS [M + 2H]²⁺/2/Rt (min): 238.34/0.511 (Method C) |

Example 438

According to the method of Example 232, Example 438 was prepared by using the corresponding material compound.

| Example | Chemical Structure | Instrumental analysis data |
|---|---|---|
| 438 | 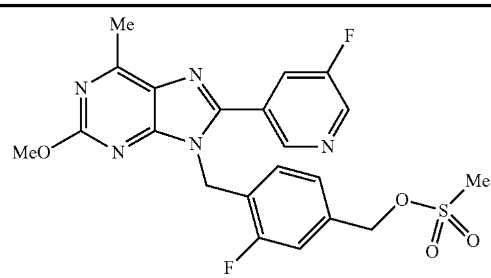 | LC-MS: [M + H]⁺/Rt (min): 476.4/0.810 (Method A) |

Examples 439-441

According to the method of Example 165 or Example 301, Examples 439-441 were prepared by using the corresponding material compounds.

| Example | Chemical Structure | Instrumental analysis data |
|---|---|---|
| 439 | 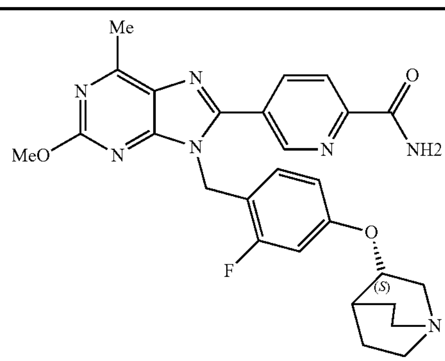 | LC-MS: [M + 2H]²⁺/2/Rt (min): 259.7/0.477 (Method C); ¹H-NMR (CDCl₃) δ: 8.82-8.76 (1H, m), 8.23 (1H, d, J = 7.3 Hz), 8.03 (1H, dd, J = 2.4, 7.9 Hz), 6.85 (1H, t, J = 8.5 Hz), 6.46-6.39 (2H, m), 5.38 (2H, s), 4.23-4.17 (1H, m), 4.00 (3H, s), 3.20-3.12 (1H, m), 2.93-2.77 (2H, m), 2.77 (3H, s), 2.75-2.63 (2H, m), 2.05-1.99 (1H, m), 1.92-1.78 (1H, m), 1.71-1.62 (1H, m), 1.51-1.41 (1H, m), 1.36-1.25 (1H, m). |

-continued

| Example | Chemical Structure | Instrumental analysis data |
|---|---|---|
| 440 | (structure) | LC-MS: [M + 2H]$^{2+}$/2/Rt (min): 263.3/0.559 (Method C); $^1$H-NMR (CD$_3$OD) δ: 8.99-8.95 (1H, m), 8.45-8.41 (1H, m), 8.27 (1H, d, J = 1.8 Hz), 8.15 (1H, d, J = 9.2 Hz), 8.04 (1H, dd, J = 2.1, 8.9 Hz), 7.65 (1H, dd, J = 4.3, 7.9 Hz), 6.98-6.91 (1H, m), 6.55-6.47 (2H, m), 5.60 (2H, s), 4.41-4.35 (1H, m), 4.07 (3H, s), 3.25-3.17 (1H, m), 2.85-2.79 (2H, m), 2.77 (3H, s), 2.67-2.62 (2H, m), 2.00-1.95 (1H, m), 1.91-1.81 (1H, m), 1.79-1.69 (1H, m), 1.64-1.53 (1H, m), 1.46-1.35 (1H, m). |
| 441 | (structure) | LC-MS [M + 2H]$^{2+}$/2/Rt (min): 238.6/0.540; $^1$H-NMR (CD$_3$OD) δ: 9.26 (1H, dd, J = 4.9, 1.8 Hz), 8.51-8.50 (1H, m), 7.90-7.87 (1H, m), 7.03 (1H, t, J = 8.5 Hz), 6.60-6.55 (2H, m), 6.11 (2H, s), 4.46-4.39 (1H, m), 4.07 (3H, s), 3.29-3.20 (1H, m), 2.91-2.81 (2H, m), 2.78 (3H, m), 2.77-2.65 (2H, m), 2.10-2.03 (1H, m), 1.98-1.87 (1H, m), 1.81-1.70 (1H, m), 1.67-1.57 (1H, m), 1.49-1.37 (1H, m). |

Example 442

According to the method of Example 352, Example 442 was prepared by using the corresponding material compound.

| Example | Chemical Structure | Instrumental analysis data |
|---|---|---|
| 442 | (structure) | LC-MS: [M + H]$^+$/Rt (min): 475.5/0.639 (Method A) |

Example 443

According to the method of Example 370, Example 443 was prepared by using the corresponding material compound.

| Example | Chemical Structure | Instrumental analysis data |
|---|---|---|
| 443 | 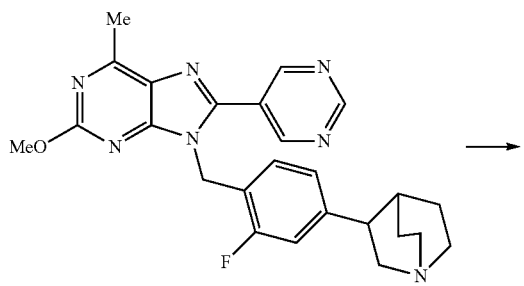 | LC-MS (M + 2H)$^{2+}$/2/Rt (min): 239.2/0.514 (Method C); $^1$H-NMR (CDCl$_3$) δ: 8.65-8.64 (1H, m), 8.58 (1H, d, J = 2.4 Hz), 7.73-7.70 (1H, m), 7.17-7.10 (1H, m), 7.05-6.98 (1H, m), 6.95-6.90 (1H, m), 5.51 (2H, s), 4.03 (3H, s), 3.39-3.29 (1H, m), 3.12-2.88 (6H, m), 2.82 (3H, s), 1.85-1.74 (3H, m), 1.58-1.47 (1H, m), 1.45-1.34 (1H, m). |

Examples 444, 445

9-{4-[(3R)-1-Azabicyclo[2.2.2]oct-3-yl]-2-fluorobenzyl}-2-methoxy-6-methyl-8-(pyrimidin-5-yl)-9H-purine; 9-{4-[(3S)-1-azabicyclo[2.2.2]oct-3-yl]-2-fluorobenzyl}-2-methoxy-6-methyl-8-(pyrimidin-5-yl)-9H-purine

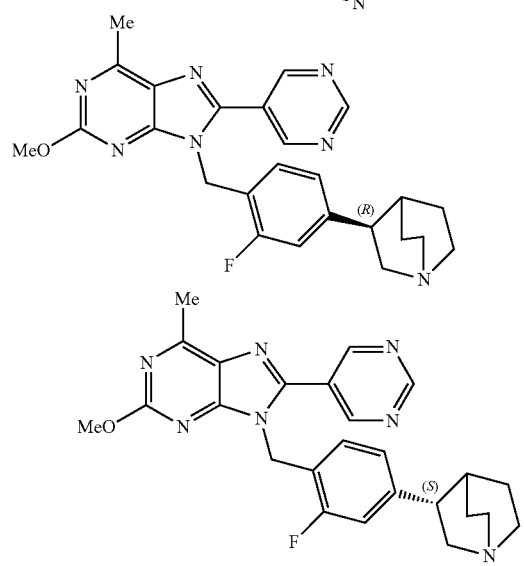

The compound of Example 346 (190 mg) was optically separated in the following conditions to obtain the title compounds (Example 444: 88.0 mg-first peak: 7.19 min, Example 445: 88.0 mg-second peak: 16.6 min.).

Column: CHIRALPAK™ AD-H; Solvent: Solution A: hexane/diethylamine=1/0.1%, Solution B: 2-propanol/diethylamine=1/0.1%; Mobile phase condition: A/B=60/40; Flow rate: 10 mL/min; Detection UV: 220 nm; Column temperature: 40° C.

| Example | Instrumental analysis data |
|---|---|
| 444 | LC-MS [M + 2H]$^{2+}$/2/Rt (min): 230.7/0.425 (Method C); $^1$H-NMR (CDCl$_3$) δ: 9.29 (1H, s), 8.98 (2H, s), 6.98-6.89 (3H, m), 5.49 (2H, s), 4.04 (3H, s), 3.47-3.29 (1H, m), 3.14-2.87 (6H, m), 2.82 (3H, s), 1.99-1.92 (1H, m), 1.87-1.72 (2H, m), 1.68-1.55 (1H, m), 1.51-1.38 (1H, m). |
| 445 | LC-MS [M + 2H]$^{2+}$/2/Rt (min): 230.7/0.428 (Method C); $^1$H-NMR (CDCl$_3$) δ: 9.29 (1H, s), 8.98 (2H, s), 6.98-6.89 (3H, m), 5.49 (2H, s), 4.04 (3H, s), 3.45-3.30 (1H, m), 3.14-2.86 (6H, m), 2.82 (3H, s), 1.98-1.91 (1H, m), 1.86-1.72 (2H, m), 1.67-1.53 (1H, m), 1.50-1.37 (1H, m). |

Reference Example 1

6-{[(Methylsulfonyl)oxy]methyl}pyridin-3-yl methanesulfonate

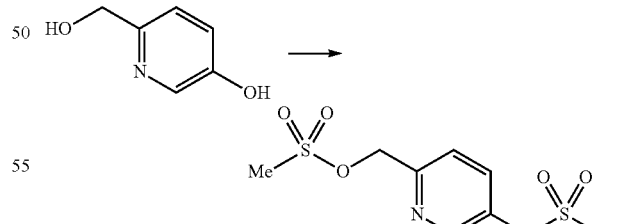

To an ice-cooled solution of 6-(hydroxymethyl)pyridin-3-ol (946 mg) in tetrahydrofuran (25 mL) were added triethylamine (2.4 mL) and methanesulfonyl chloride (1.3 mL), and the mixture was stirred in ice bath for 2 hours. To the reaction mixture was added water, and the mixture was extracted with ethyl acetate. The organic layer was washed with aqueous saturated sodium bicarbonate, dried over sodium sulfate, filtrated, and then concentrated in vacuo.

The residue was purified by silica gel column chromatography (hexane/ethyl acetate) to give the title compound (842 mg).

$^1$H-NMR (CDCl$_3$) δ: 8.56 (1H, d, J=2.6 Hz), 7.73 (1H, dd, J=2.6, 8.5 Hz), 7.57 (1H, d, J=8.5 Hz), 5.34 (2H, s), 3.24 (3H, s), 3.12 (3H, s).

Reference Example 2

Methyl 4-[(6-amino-2-ethoxy-9H-purin-9-yl)methyl]benzoate

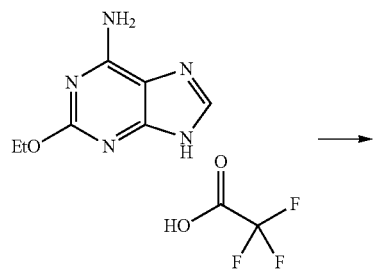 → 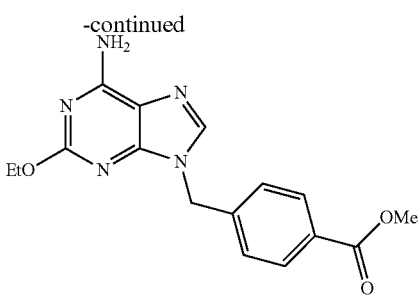

To an ice-cooled solution of 2-ethoxy-9H-purine-6-amine trifluoroacetate (2.00 g) in N,N-dimethylformamide (30 mL) were added potassium carbonate (3.01 g) and methyl 4-(bromomethyl)benzoate (2.00 g). The reaction mixture was stirred at room temperature for 28 hours. To the reaction mixture was added aqueous saturated sodium bicarbonate, and the mixture was extracted with chloroform. The organic layer was dried over sodium sulfate, filtrated, and then concentrated in vacuo. The residue was purified by silica gel column chromatography (chloroform/methanol) to give the title compound (1.57 g).

LC-MS [M+H]$^+$/Rt (min): 328.3/0.745 (Method A)

Reference Examples 3-22

According to the method of Reference example 2, Reference examples 3-22 were prepared by using the corresponding material compounds.

| Reference example | Chemical Structure | Instrumental analysis data |
|---|---|---|
| 3 | 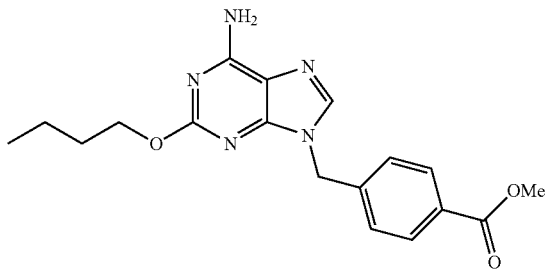 [SMILES: CCCCOc1nc(N)c2ncn(Cc3ccc(C(=O)OC)cc3)c2n1] | LC-MS: [M + H]$^+$/Rt (min): 356.1/0.858 (Method A) |
| 4 | 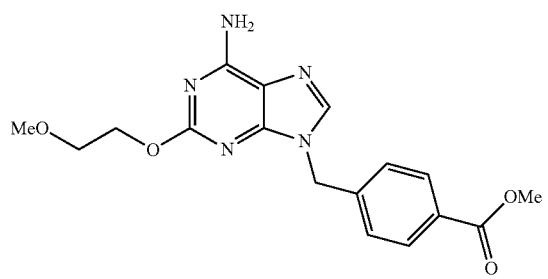 [SMILES: COCCOc1nc(N)c2ncn(Cc3ccc(C(=O)OC)cc3)c2n1] | LC-MS: [M + H]$^+$/Rt (min): 358.2/0.604 (Method A) |

| Reference example | Chemical Structure | Instrumental analysis data |
|---|---|---|
| 5 | 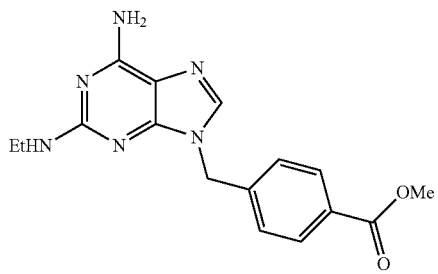 | LC-MS: [M + H]+/Rt (min): 327.3/0.652 (Method A) |
| 6 | 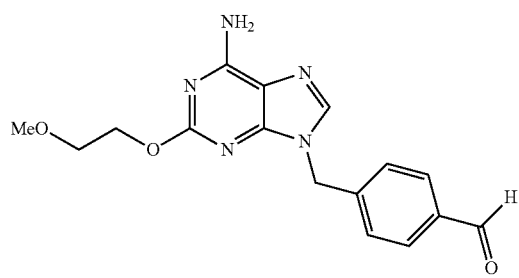 [SMILES: COCCOc1nc(N)c2ncn(Cc3ccc(C=O)cc3)c2n1] | 1H-NMR (400 MHz, DMSO-d6) δ: 9.97 (1H, s), 8.09 (1H, s), 7.89 (2H, d, J = 8.2 Hz), 7.48 (2H, d, J = 8.2 Hz), 7.30 (2H, brs), 5.38 (2H, s), 4.30 (2H, t, J = 4.7 Hz), 3.58 (2H, t, J = 4.7 Hz), 3.26 (3H, s). |
| 7 | 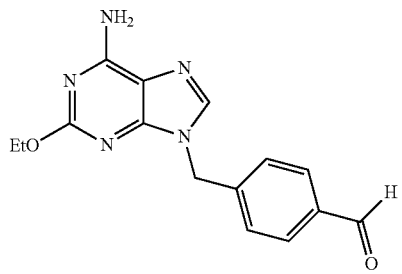 [SMILES: CCOc1nc(N)c2ncn(Cc3ccc(C=O)cc3)c2n1] | LC-MS: [M + H]+/Rt (min): 298.3/0.650 (Method A) |
| 8 | 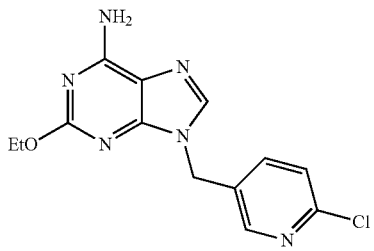 [SMILES: CCOc1nc(N)c2ncn(Cc3ccc(Cl)nc3)c2n1] | 1H-NMR (CDCl3) δ: 8.45 (1H, d, J = 2.4 Hz), 7.62-7.59 (2H, m), 7.30 (1H, d, J = 7.9 Hz), 5.61 (2H, br s), 5.27 (2H, s), 4.37 (2H, q, J = 7.1 Hz), 1.41 (3H, t, J = 7.1 Hz). |
| 9 | 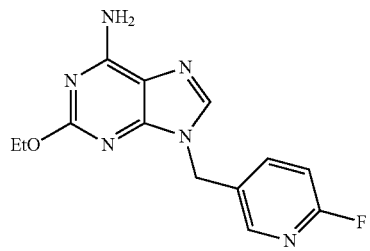 [SMILES: CCOc1nc(N)c2ncn(Cc3ccc(F)nc3)c2n1] | 1H-NMR (CDCl3) δ: 8.36 (1H, d, J = 1.8 Hz), 7.88-7.83 (1H, m), 6.92-6.89 (1H, m), 5.44 (2H, s), 5.30 (2H, s), 4.39 (2H, q, J = 7.2 Hz), 1.42 (3H, t, J = 7.2 Hz). |

-continued

| Reference example | Chemical Structure | Instrumental analysis data |
|---|---|---|
| 10 | 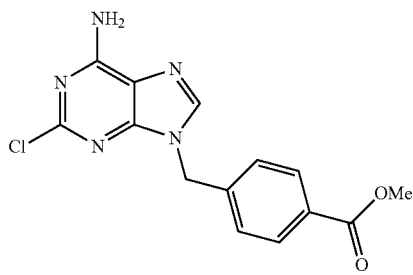 [SMILES: COC(=O)c1ccc(Cn2cnc3c(N)nc(Cl)nc32)cc1] | $^1$H-NMR (DMSO-D$_6$) δ: 8.26 (1H, s), 7.94-7.91 (2H, m), 7.81 (2H, br s), 7.35 (2H, d, J = 8.5 Hz), 5.43 (2H, s), 3.82 (3H, s). |
| 11 | 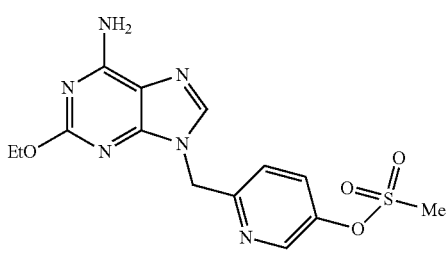 [SMILES: CCOc1nc(N)c2ncn(Cc3ccc(OS(C)(=O)=O)cn3)c2n1] | LC-MS [M + H]$^+$/Rt (min): 365.2/0.667 (Method C) |
| 12 | 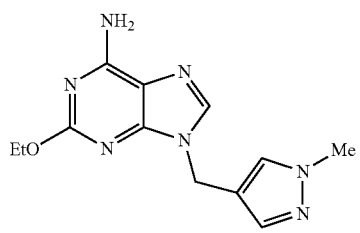 [SMILES: CCOc1nc(N)c2ncn(Cc3cnn(C)c3)c2n1] | $^1$H-NMR (CDCl$_3$) δ: 7.59 (1H, s), 7.51 (1H, s), 7.40 (1H, s), 5.47 (2H, s), 5.14 (2H, s), 4.41 (2H, q, J = 7.1 Hz), 3.87 (3H, s), 1.45-1.40 (3H, m). |
| 13 | 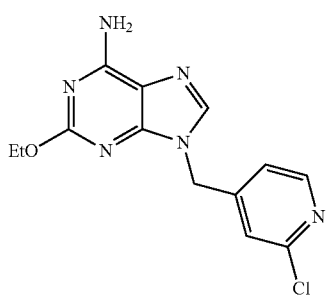 [SMILES: CCOc1nc(N)c2ncn(Cc3ccnc(Cl)c3)c2n1] | LC-MS: [M + H]$^+$/Rt (min): 305.3/0.536 (Method C); $^1$H-NMR (400 MHz, CDCl$_3$) δ: 8.34 (1H, d, J = 5.5 Hz), 7.62 (1H, s), 7.17 (1H, s), 7.05 (1H, d, J = 5.5 Hz), 5.72 (2H, s), 5.27 (2H, s), 4.34 (2H, q, J = 7.1 Hz), 1.38 (3H, t, J = 7.0 Hz). |
| 14 | 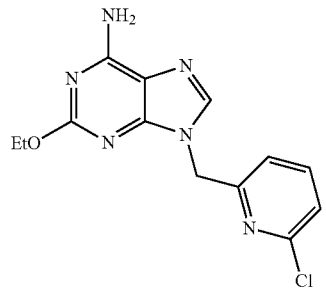 [SMILES: CCOc1nc(N)c2ncn(Cc3cccc(Cl)n3)c2n1] | LC-MS: [M + 1]$^+$/Rt (min): 305.3/0.584 (Method C); $^1$H-NMR (400 MHz, CDCl$_3$) δ: 7.79 (1H, s), 7.59 (1H, dd, J = 7.9, 7.9 Hz), 7.25 (1H, d, J = 7.9 Hz), 7.09 (1H, d, J = 7.9 Hz), 5.71 (2H, s), 5.36 (2H, s), 4.35 (2H, q, J = 7.0 Hz), 1.38 (3H, t, J = 7.0 Hz). |

| Reference example | Chemical Structure | Instrumental analysis data |
|---|---|---|
| 15 | 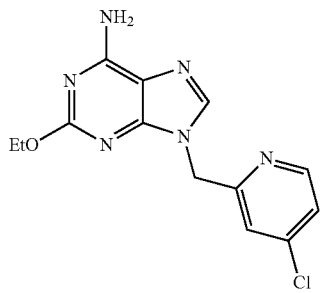 [SMILES: CCOc1nc(N)c2ncn(Cc3cc(Cl)ccn3)c2n1] | LC-MS: [M + H]⁺/Rt (min): 305.3/0.573 (Method C); $^1$H-NMR (400 MHz, CDCl$_3$) δ: 8.46 (1H, d, J = 6.1 Hz), 7.78 (1H, s), 7.24-7.23 (2H, m), 5.56 (2H, s), 5.37 (2H, s), 4.37 (2H, q, J = 7.1 Hz), 1.40 (3H, t, J = 7.1 Hz). |
| 16 | 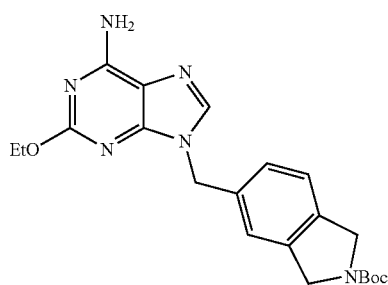 [SMILES: CCOc1nc(N)c2ncn(Cc3ccc4c(c3)CN(C(=O)OC(C)(C)C)C4)c2n1] | LC-MS: [M + H]⁺/Rt (min): 411.4/0.848 (Method C); $^1$H-NMR (400 MHz, CDCl$_3$) δ: 7.58 (1H, d, J = 2.4 Hz), 7.25-7.10 (3H, m), 5.57 (2H, s), 5.26 (2H, s), 4.69-4.57 (4H, m), 4.39 (2H, q, J = 7.1 Hz), 1.50 (9H, s), 1.41 (3H, t, J = 7.1 Hz). |
| 17 | 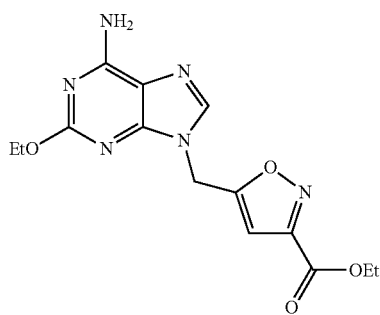 [SMILES: CCOC(=O)c1cc(Cn2cnc3c(N)nc(OCC)nc32)on1] | $^1$H-NMR (400 MHz, CDCl$_3$) δ: 7.74 (1H, s), 6.63 (1H, s), 5.62 (2H, s), 5.45 (2H, s), 4.47-4.35 (4H, m), 1.46-1.37 (6H, m). |
| 18 | 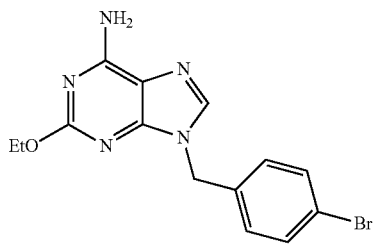 [SMILES: CCOc1nc(N)c2ncn(Cc3ccc(Br)cc3)c2n1] | $^1$H-NMR (400 MHz, CDCl$_3$) δ: 7.58 (1H, s), 7.47 (2H, d, J = 8.5 Hz), 7.17 (2H, d, J = 8.5 Hz), 5.62 (2H, s), 5.22 (2H, s), 4.38 (2H, q, J = 7.1 Hz), 1.41 (3H, t, J = 7.1 Hz). |
| 19 | 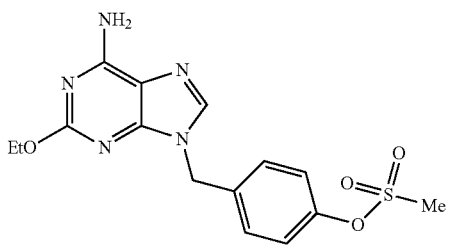 | $^1$H-NMR (400 MHz, CDCl$_3$) δ: 7.62 (1H, s), 7.37 (2H, d, J = 8.5 Hz), 7.27 (2H, d, J = 8.5 Hz), 5.63 (2H, s), 5.29 (2H, s), 4.39 (2H, q, J = 7.1 Hz), 3.14 (3H, s), 1.41 (3H, t, J = 7.1 Hz). |

| Reference example | Chemical Structure | Instrumental analysis data |
|---|---|---|
| 20 | 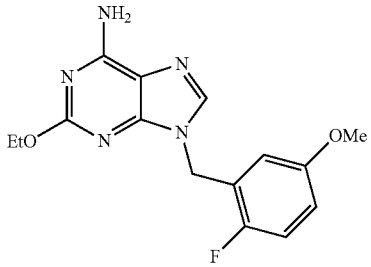 [SMILES: CCOc1nc(N)c2ncn(Cc3cc(OC)ccc3F)c2n1] | LC-MS [M + H]$^+$/Rt (min): 318.0/0.676 (Method C); $^1$H-NMR (400 MHz, CDCl$_3$) δ: 7.66 (1H, s), 7.03-6.98 (1H, m), 6.84 (1H, dd, J = 3.1, 6.1 Hz), 6.82-6.76 (1H, m), 5.67 (2H, s), 5.27 (2H, s), 4.40 (2H, q, J = 7.1 Hz), 3.71 (3H, s), 1.41 (3H, t, J = 7.0 Hz). |
| 21 | 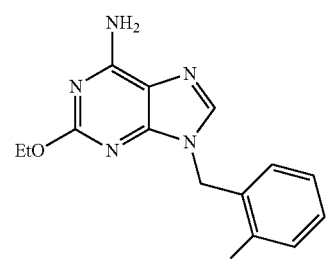 | LC-MS [M + H]$^+$/Rt (min): 288.0/0.658 (Method C); $^1$H-NMR (400 MHz, CDCl$_3$) δ: 7.67 (1H, s), 7.35-7.25 (2H, m), 7.13-7.04 (2H, m), 5.56 (2H, s), 5.32 (2H, s), 4.40 (2H, q, J = 7.1 Hz), 1.41 (3H, t, J = 7.1 Hz). |
| 22 | 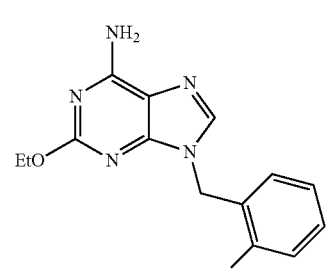 | LC-MS [M + H]$^+$/Rt (min): 295.0/0.551 (Method C); $^1$H-NMR (400 MHz, CDCl$_3$) δ: 7.78 (1H, s), 7.71 (1H, d, J = 7.9 Hz), 7.58-7.52 (1H, m), 7.46-7.40 (2H, m), 5.56 (2H, s), 5.50 (2H, s), 4.38 (2H, q, J = 7.1 Hz), 1.40 (3H, t, J = 7.1 Hz). |

Reference Example 23 tert-Butyl 4-{4-[(6-amino-2-ethoxy-9H-purin-9-yl)methyl]phenyl}-3,6-dihydropyridine-1(2H)-carboxylate

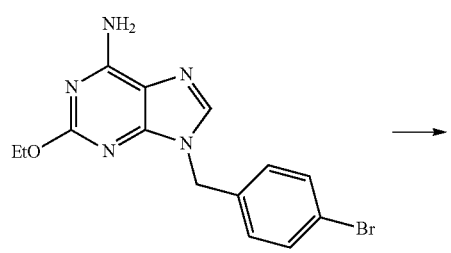

→

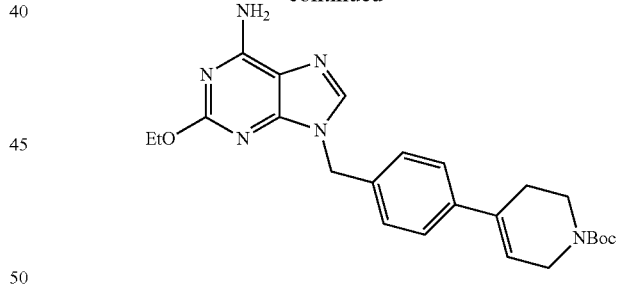

To a solution of the compound of Reference example 18 (700 mg) in a mixture of dimethylformamide (10 mL)/water (1.7 mL) were added N-Boc-1,2,5,6-tetrahydropyridine-4-(pinacolato)boronate (715 mg), potassium carbonate (834 mg), and 1,1'-bis(diphenylphosphino)ferrocene palladium chloride (221 mg), and the mixture was stirred at 80° C. for 2 hours. The reaction mixture was cooled to room temperature. Water was added thereto, and the mixture was extracted with ethyl acetate. The organic layer was dried over sodium sulfate, filtrated, and then concentrated in vacuo. The residue was purified by silica gel column chromatography (chloroform/methanol) to give the title compound (820 mg).

LC-MS [M+H]$^+$/Rt (min): 451.5/0.963 (Method C); $^1$H-NMR (400 MHz, CDCl$_3$) δ: 7.58 (1H, s), 7.34 (2H, d, J=7.9 Hz), 7.26 (2H, d, J=7.9 Hz), 6.05-5.97 (1H, m), 5.54 (2H, s), 5.25 (2H, s), 4.39 (2H, q, J=7.1 Hz), 4.09-4.03 (2H, m), 3.65-3.59 (2H, m), 2.52-2.43 (2H, m), 1.48 (9H, s), 1.41 (3H, t, J=7.1 Hz).

Reference Example 24

According to the method of Reference example 23, Reference example 24 was prepared by using the corresponding material compound.

| Reference example | Chemical Structure | Instrumental analysis data |
|---|---|---|
| 24 | 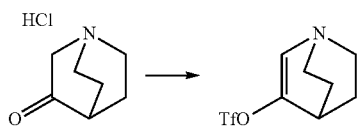 [SMILES: Cl ; O=C1CN2CCC1CC2 ; O=S(=O)(OC1=CN2CCC1CC2)C(F)(F)F] | LC-MS [M + H]⁺/Rt (min): 437.4/0.912 (Method C); ¹H-NMR (400 MHz, CDCl₃) δ: 7.61 (1H, s), 7.35 (2H, d, J = 7.8 Hz), 7.27 (2H, d, J = 7.8 Hz), 6.20-6.06 (1H, m), 5.72 (2H, s), 5.26 (2H, s), 4.56-4.20 (6H, m), 1.50 (9H, s), 1.41 (3H, t, J = 6.9 Hz). |

Reference Example 25

1-Azabicyclo[2.2.2]oct-2-en-3-yl trifluoromethanesulfonate

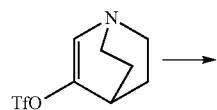

To a solution of quinuclidin-3-one (5.34 g) in tetrahydrofuran (220 mL) was added lithium bis(trimethylsilyl)amide (1.3 mol/1, 58.4 ml) at −78° C. The mixture was stirred for 30 minutes, and then N-phenyl(trifluoromethane)sulfonamide (14.15 g) was added thereto. The mixture was stirred at −78° C. for one hour, and warmed to room temperature, followed by stirring for 2 hours. The reaction mixture was cooled to 0° C. Water was added thereto, and the mixture was extracted with ethyl acetate. The organic layer was dried over sodium sulfate, filtrated, and then concentrated in vacuo. The residue was purified by silica gel column chromatography (chloroform/methanol) to give the title compound (6.15 g).

LC-MS [M+H]⁺/Rt (min): 258.1/0.374 (Method C); ¹H-NMR (400 MHz, CDCl₃) δ: 6.47 (1H, d, J=2.3 Hz), 3.01-2.91 (2H, m), 2.87-2.82 (1H, m), 2.69-2.59 m), 1.90-1.73 (4H, m).

Reference Example 26

9-[4-(1-Azabicyclo[2.2.2]oct-2-en-3-yl)benzyl]-2-ethoxy-9H-purine-6-amine

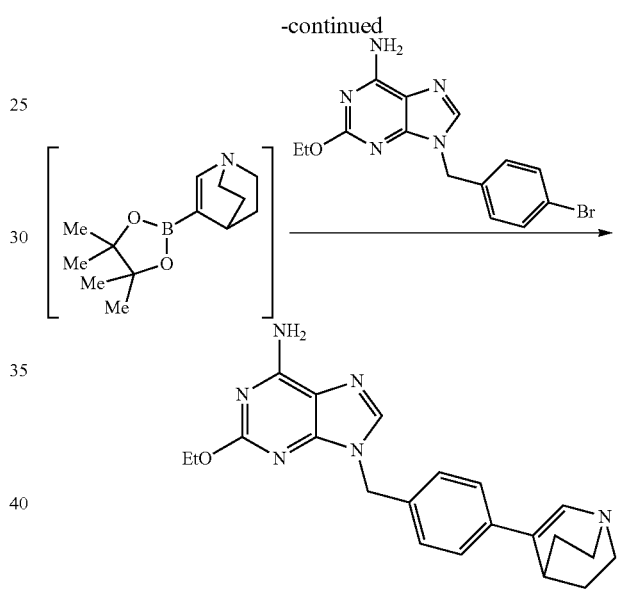

To a solution of the compound of Reference example 25 (515 mg) in 1,4-dioxane (10 mL) were added bis(pinacolato)diboron (610 mg), potassium acetate (432 mg), 1,1'-bis(diphenylphosphino)ferrocene palladium chloride (131 mg), and 1,1'-bis(diphenylphosphino)ferrocene (44.4 mg), and the mixture was stirred at 90° C. for 2 hours.

To the reaction mixture were added the compound of Reference example 18 (581 mg), potassium carbonate (461 mg), 1,1'-bis(diphenylphosphino)ferrocene palladium chloride (98 mg), and water (0.3 ml), and the mixture was stirred at 80° C. for 2 hours. The reaction mixture was cooled to room temperature. Water was added thereto, and the mixture was extracted with ethyl acetate. The organic layer was dried over sodium sulfate, filtrated, and then concentrated in vacuo. The residue was purified by silica gel column chromatography (chloroform/methanol) to give the title compound (403 mg).

¹H-NMR (400 MHz, CDCl₃) δ: 7.59 (1H, s), 7.39 (2H, d, J=7.9 Hz), 7.29 (2H, d, J=7.9 Hz), 6.81 (1H, d, J=1.2 Hz), 5.59 (2H, s), 5.26 (2H, s), 4.39 (2H, q, J=7.0 Hz), 3.16-3.11 (1H, m), 3.06-2.96 (2H, 2.69-2.59 (2H, m), 1.81-1.72 (2H, m), 1.61-1.49 (2H, m), 1.41 (3H, t, J=7.0 Hz).

Reference Examples 27-29

According to the method of Reference example 26, Reference examples 27-29 were prepared by using the corresponding material compounds.

| Reference example | Chemical Structure | Instrumental analysis data |
|---|---|---|
| 27 | 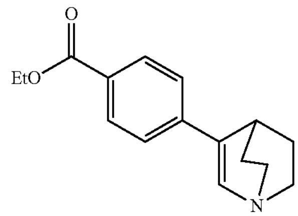 [SMILES: CCOC(=O)c1ccc(C2=CN3CCC2CC3)cc1] | LC-MS [M + H]⁺/Rt (min): 258.2/0.615 (Method C); ¹H-NMR (400 MHz, CDCl₃) δ: 8.01 (2H, d, J = 8.5 Hz), 7.46 (2H, d, J = 8.5 Hz), 6.91 (1H, d, J = 1.2 Hz), 4.38 (2H, q, J = 7.1 Hz), 3.22-3.14 (1H, m), 3.07-2.93 (2H, m), 2.73-2.57 (2H, m), 1.85-1.68 (2H, m), 1.64-1.50 (2H, m), 1.40 (3H, t, J = 7.0 Hz). |
| 28 | 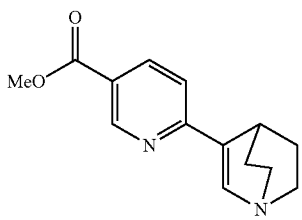 [SMILES: COC(=O)c1ccc(C2=CN3CCC2CC3)nc1] | LC-MS [M + H]⁺/Rt (min): 244.9/0.330 (Method C); ¹H-NMR (400 MHz, CDCl₃) δ: 9.18 (1H, d, J = 2.4 Hz), 8.23 (1H, dd, J = 2.4, 9.2 Hz), 7.54 (1H, d, J = 9.2 Hz), 7.32 (1H, d, J = 1.8 Hz), 3.95 (3H, s), 3.63-3.57 (1H, m), 3.09-2.99 (2H, m), 2.72-2.59 (2H, m), 1.85-1.74 (2H, m), 1.62-1.49 (2H, m). |
| 29 | 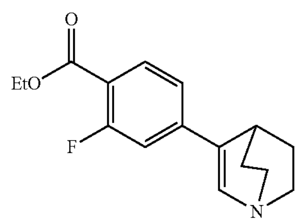 [SMILES: CCOC(=O)c1ccc(C2=CN3CCC2CC3)cc1F] | ¹H-NMR (400 MHz, CDCl₃) δ: 7.94-7.88 (1H, m), 7.26-7.22 (1H, m), 7.16 (1H, dd, J = 12.2, 1.8 Hz), 6.95 (1H, d, J = 1.8 Hz), 3.93 (3H, s), 3.15-3.11 (1H, m), 3.06-2.98 (2H, m), 2.68-2.58 (2H, m), 1.83-1.74 (2H, m), 1.60-1.50 (2H, m). |

Reference Example 30

9-[4-(1-Azabicyclo[2.2.2]oct-3-yl)benzyl]-2-ethoxy-9H-purine-6-amine

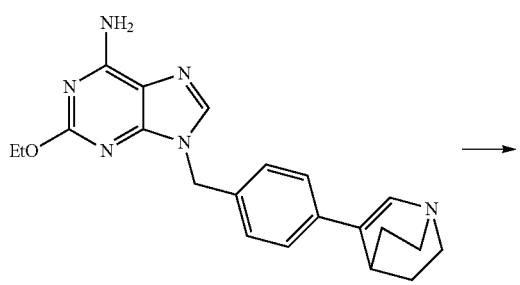

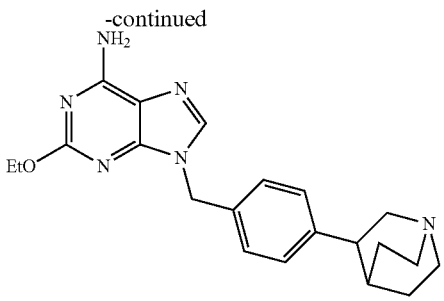

To a solution of the compound of Reference example 26 (260 mg) in ethanol (2 mL)/tetrahydrofuran (0.1 ml) were added acetic acid (0.237 ml) and 5% palladium carbon (294 mg). The reaction mixture was stirred at room temperature under hydrogen atmosphere for 10 hours, filtrated, and then concentrated in vacuo. The residue was purified by silica gel column chromatography (chloroform/methanol) to give the title compound (149 mg).

¹H-NMR (400 MHz, CDCl₃) δ: 7.59 (1H, s), 7.27 (2H, d, J=8.5 Hz), 7.24 (2H, d, J=8.5 Hz), 5.55 (2H, s), 5.24 (2H, s), 4.40 (2H, q, J=7.1 Hz), 3.37-3.24 (1H, m), 3.10-3.02 (1H, m), 3.01-2.79 (5H, m), 1.93-1.88 (1H, m), 1.79-1.69 (2H, m), 1.68-1.57 (1H, m), 1.41 (3H, t, J=7.1 Hz), 1.39-1.31 (1H, m).

Reference Examples 31-35

According to the method of Reference example 30, Reference examples 31-35 were prepared by using the corresponding material compounds.

| Reference example | Chemical Structure | Instrumental analysis data |
|---|---|---|
| 31 | (6-amino-2-ethoxy-9H-purin-9-yl)methyl-4-(1-Boc-piperidin-4-yl)phenyl derivative | LC-MS: [M + H]⁺/Rt (min): 453.5/1.01 (Method C); ¹H-NMR (400 MHz, CDCl₃) δ: 7.58 (1H, s), 7.24 (2H, d, J = 7.9 Hz), 7.17 (2H, d, J = 7.9 Hz), 5.59 (2H, s), 5.23 (2H, s), 4.39 (2H, q, J = 7.1 Hz), 4.30-4.12 (2H, m), 2.86-2.69 (2H, m), 2.68-2.57 (1H, m), 1.82-1.73 (2H, m), 1.65-1.53 (2H, m), 1.47 (9H, s), 1.41 (3H, t, J = 7.1 Hz). |
| 32 | (6-amino-2-ethoxy-9H-purin-9-yl)methyl-4-(1-Boc-pyrrolidin-3-yl)phenyl derivative | LC-MS: [M + H]⁺/Rt (min): 439.4/0.902 (Method C) |
| 33 | ethyl 4-(quinuclidin-3-yl)benzoate | LC-MS [M + H]⁺/Rt (min): 260.3/0.629 (Method C); ¹H-NMR (400 MHz, CDCl₃) δ: 8.01 (2H, d, J = 7.9 Hz), 7.34 (2H, d, J = 7.9 Hz), 4.37 (2H, q, J = 7.1 Hz), 3.41-3.28 (1H, m), 3.16-2.78 (6H, m), 1.98-1.90 (1H, m), 1.78-1.58 (3H, m), 1.39 (3H, t, J = 7.1 Hz), 1.38-1.32 (1H, m). |
| 34 | methyl 6-(quinuclidin-3-yl)nicotinate | LC-MS [M + H]⁺/Rt (min): 247.0/0.315 (Method C); ¹H-NMR (400 MHz, CDCl₃) δ: 9.18 (1H, d, J = 2.1 Hz), 8.21 (1H, dd, J = 8.2, 2.1 Hz), 7.28 (1H, d, J = 8.2 Hz), 3.94 (3H, s), 3.61-3.51 (1H, m), 3.30-3.20 (1H, m), 3.18-3.11 (1H, m), 3.11-2.99 (1H, m), 2.99-2.88 (2H, m), 2.88-2.77 (1H, m), 2.11-2.04 (1H, m), 1.81-1.66 (2H, m), 1.66-1.54 (1H, m), 1.41-1.26 (1H, m). |
| 35 | ethyl 2-fluoro-4-(quinuclidin-3-yl)benzoate | LC-MS [M + H]⁺/Rt (min): 263.9/0.368 (Method C); ¹H-NMR (400 MHz, CDCl₃) δ: 7.90 (1H, dd, J = 7.9, 12.8 Hz), 7.10 (1H, d, J = 7.9 Hz), 7.05 (1H, d, J = 12.8 Hz), 3.92 (3H, s), 3.39-3.27 (1H, m), 3.08-2.79 (6H, m), 1.99-1.93 (1H, m), 1.78-1.69 (2H, m), 1.66-1.55 (1H, m), 1.44-1.33 (1H, m). |

Reference Example 36

Methyl 4-[(6-amino-8-bromo-2-ethoxy-9H-purin-9-yl)methyl]benzoate

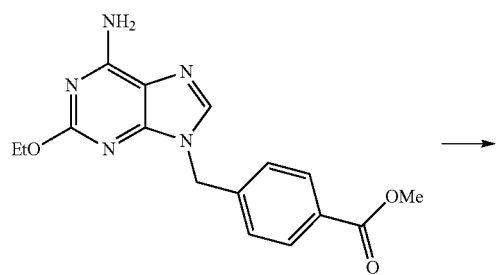

→

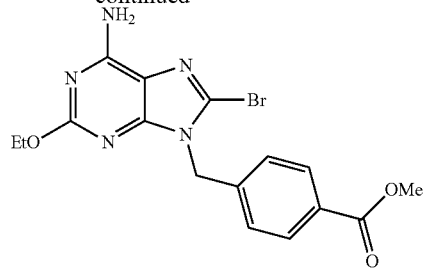

To an ice-cooled solution of the compound of Reference example 2 (1.57 g) in a mixture of chloroform (15 mL)/methanol (3 mL) were added sodium acetate (0.786 g), and then a solution of bromine (0.358 ml) in chloroform (5 mL) dropwise. The reaction mixture was stirred in ice bath for 3 hours. To the reaction mixture were added aqueous saturated sodium thiosulfate and aqueous saturated sodium bicarbonate, and the mixture was extracted with chloroform. The organic layer was dried over sodium sulfate, filtrated, and then concentrated in vacuo. The residue was purified by silica gel column chromatography (chloroform/methanol) to give the title compound (1.77 g).

LC-MS [M+H]$^+$/Rt (min): 406.3/0.876 (Method A)

Reference Examples 37-58

According to the method of Reference example 36, Reference examples 37-58 were prepared by using the corresponding material compounds.

| Reference example | Chemical Structure | Instrumental analysis data |
|---|---|---|
| 37 | 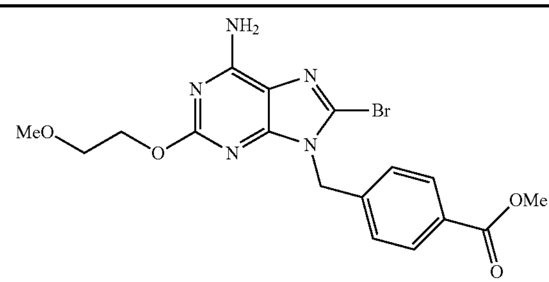 | LC-MS: [M + H]$^+$/Rt (min): 436.2/0.811 (Method A) |
| 38 | 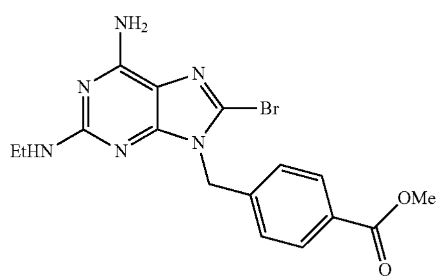 | LC-MS: [M + H]$^+$/Rt (min): 405.3/0.759 (Method A) |
| 39 | 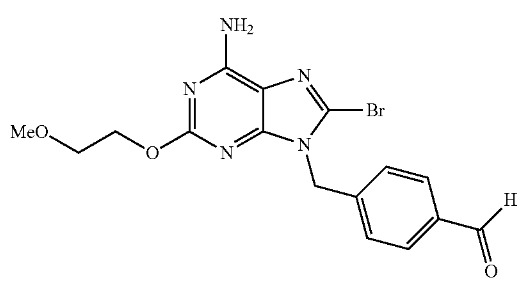 [SMILES: COCCOc1nc(N)c2nc(Br)n(Cc3ccc(C=O)cc3)c2n1] | LC-MS [M + H]$^+$/Rt (min): 406.0/0.731 (Method A) |

| Reference example | Chemical Structure | Instrumental analysis data |
| --- | --- | --- |
| 40 | 2-ethoxy-8-bromo-9-(4-formylbenzyl)-9H-purin-6-amine | LC-MS: [M + H]⁺/Rt (min): 376.3/0.792 (Method A) |
| 41 | 2-chloro-8-bromo-9-(4-(methoxycarbonyl)benzyl)-9H-purin-6-amine | ¹H-NMR (CDCl₃) δ: 8.01 (2H, d, J = 8.5 Hz), 7.34 (2H, d, J = 8.5 Hz), 5.74 (2H, br s), 5.41 (2H, s), 3.91 (3H, s). |
| 42 | 2-ethoxy-8-bromo-9-((6-chloropyridin-3-yl)methyl)-9H-purin-6-amine | ¹H-NMR (CDCl₃) δ: 8.52 (1H, d, J = 2.4 Hz), 7.68 (1H, dd, J = 2.4, 8.0 Hz), 7.29 (1H, d, J = 8.0 Hz), 5.53 (2H, br s), 5.29 (2H, s), 4.38 (2H, q, J = 7.1 Hz), 1.41 (3H, t, J = 7.1 Hz). |
| 43 | 2-ethoxy-8-bromo-9-((6-fluoropyridin-3-yl)methyl)-9H-purin-6-amine | ¹H-NMR (CDCl₃) δ: 8.36 (1H, d, J = 1.8 Hz), 7.88-7.83 (1H, m), 6.92-6.89 (1H, m), 5.44 (2H, s), 5.30 (2H, s), 4.39 (2H, q, J = 7.2 Hz), 1.42 (3H, t, J = 7.2 Hz). |
| 44 | 2-ethoxy-8-bromo-9-((5-(methylsulfonyloxy)pyridin-2-yl)methyl)-9H-purin-6-amine | ¹H-NMR (DMSO-D₆) δ: 8.50 (1H, d, J = 2.8 Hz), 7.84 (1H, dd, J = 2.8, 8.6 Hz), 7.42 (1H, d, J = 8.6 Hz), 5.39 (2H, s), 4.19 (2H, q, J = 7.1 Hz), 3.45 (3H, s), 1.21 (3H, t, J = 7.1 Hz). |
| 45 | 2-ethoxy-8-bromo-9-((1-methyl-1H-pyrazol-4-yl)methyl)-9H-purin-6-amine | ¹H-NMR (CDCl₃) δ: 7.57 (1H, s), 7.44 (1H, s), 5.41 (2H, s), 5.16 (2H, s), 4.41 (2H, q, J = 7.1 Hz), 3.84 (3H, s), 1.43 (3H, t, J = 7.3 Hz). |

| Reference example | Chemical Structure | Instrumental analysis data |
|---|---|---|
| 46 | 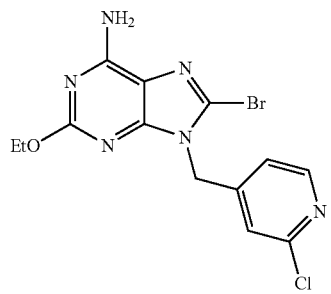 [SMILES: CCOc1nc(N)c2nc(Br)n(Cc3ccnc(Cl)c3)c2n1] | ¹H-NMR (400 MHz, CDCl₃) δ: 8.35 (1H, d, J = 5.5 Hz), 7.21 (1H, d, J = 1.2 Hz), 7.09 (1H, dd, J = 1.2, 5.5 Hz), 5.56 (2H, s), 5.28 (2H, s), 4.36 (2H, q, J = 7.0 Hz), 1.40 (3H, t, J = 7.0 Hz). |
| 47 | 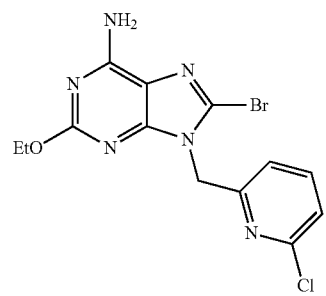 [SMILES: CCOc1nc(N)c2nc(Br)n(Cc3cccc(Cl)n3)c2n1] | ¹H-NMR (400 MHz, CDCl₃) δ: 7.57 (1H, dd, J = 7.3, 7.6 Hz), 7.24 (1H, d, J = 7.6 Hz), 6.80 (1H, d, J = 7.3 Hz), 5.55 (2H, s), 5.42 (2H, s), 4.32 (2H, q, J = 7.1 Hz), 1.36 (3H, t, J = 7.1 Hz). |
| 48 | 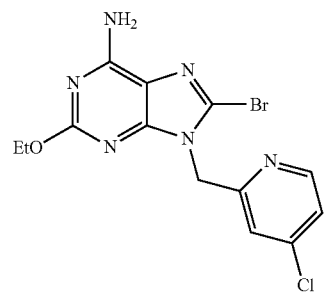 [SMILES: CCOc1nc(N)c2nc(Br)n(Cc3cc(Cl)ccn3)c2n1] | LC-MS: [M + H]⁺/Rt (min): 385.2/0.727 (Method C); ¹H-NMR (400 MHz, CDCl₃) δ: 8.45 (1H, d, J = 5.5 Hz), 7.23 (1H, dd, J = 5.5, 1.8 Hz), 7.05 (1H, d, J = 1.8 Hz), 5.58 (2H, s), 5.42 (2H, s), 4.34 (2H, q, J = 7.1 Hz), 1.37 (3H, t, J = 7.1 Hz). |
| 49 | 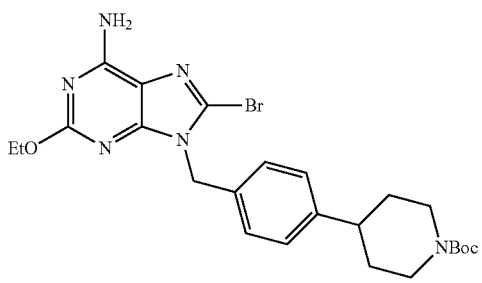 [SMILES: CCOc1nc(N)c2nc(Br)n(Cc3ccc(C4CCN(C(=O)OC(C)(C)C)CC4)cc3)c2n1] | LC-MS: [M + H]⁺/Rt (min): 533.4/1.094 (Method C); ¹H-NMR (400 MHz, CDCl₃) δ: 7.30 (2H, d, J = 7.9 Hz), 7.14 (2H, d, J = 7.9 Hz), 5.49 (2H, s), 5.26 (2H, s), 4.39 (2H, q, J = 7.1 Hz), 4.28-4.13 (2H, m), 2.83-2.70 (2H, m), 2.66-2.56 (1H, m), 1.82-1.73 (2H, m), 1.60-1.50 (2H, m), 1.47 (9H, s), 1.41 (3H, t, J = 7.1 Hz). |
| 50 | 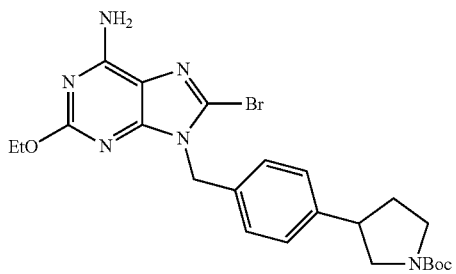 [SMILES: CCOc1nc(N)c2nc(Br)n(Cc3ccc(C4CCN(C(=O)OC(C)(C)C)C4)cc3)c2n1] | LC-MS: [M + H]⁺/Rt (min): 519.4/1.054 (Method C) |

| Reference example | Chemical Structure | Instrumental analysis data |
|---|---|---|
| 51 | 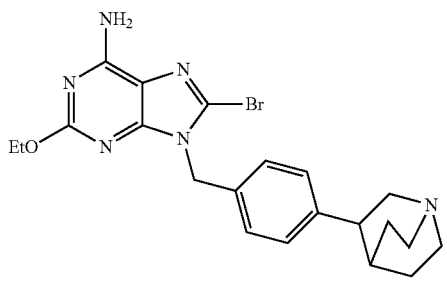 [SMILES: CCOc1nc(N)c2nc(Br)n(Cc3ccc(C4CN5CCC4CC5)cc3)c2n1] | $^1$H-NMR (400 MHz, CDCl$_3$) δ: 7.34 (2H, d, J = 8.5 Hz), 7.22 (2H, d, J = 8.5 Hz), 5.48 (2H, s), 5.28 (2H, s), 4.39 (2H, q, J = 6.9 Hz), 3.38-3.30 (1H, m), 3.13-3.04 (1H, m), 3.04-2.82 (5H, m), 2.00-1.90 (1H, m), 1.81-1.71 (2H, m), 1.70-1.60 (1H, m), 1.45-1.33 (4H, m). |
| 52 | 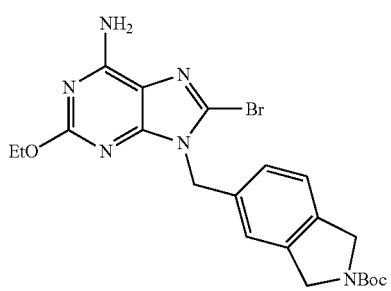 [SMILES: CCOc1nc(N)c2nc(Br)n(Cc3ccc4c(c3)CN(C(=O)OC(C)(C)C)C4)c2n1] | LC-MS: [M + H]$^+$/Rt (min): 491.35/0.987 (Method C); $^1$H-NMR (400 MHz, CDCl$_3$) δ: 7.30-7.19 (2H, m), 7.16 (1H, d, J = 11.0 Hz), 5.52 (2H, s), 5.29 (2H, s), 4.64 (2H, s), 4.60 (2H, s), 4.38 (2H, q, J = 7.1 Hz), 1.50 (9H, s), 1.41 (3H, t, J = 7.1 Hz). |
| 53 | 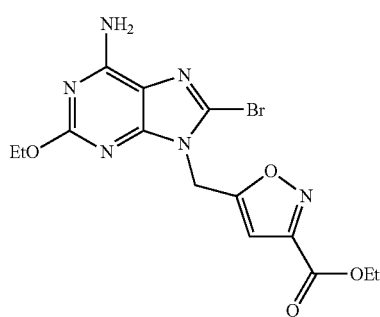 [SMILES: CCOC(=O)c1cc(Cn2c(Br)nc3c(N)nc(OCC)nc32)on1] | LC-MS: [M + H]$^+$/Rt (min): 413.3/0.763 (Method C); $^1$H-NMR (400 MHz, CDCl$_3$) δ: 6.56 (1H, s), 5.57 (2H, s), 5.47 (2H, s), 4.49-4.32 (4H, m), 1.45-1.35 (6H, m). |
| 54 | 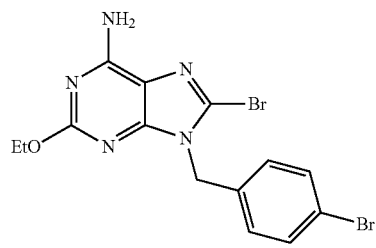 [SMILES: CCOc1nc(N)c2nc(Br)n(Cc3ccc(Br)cc3)c2n1] | LC-MS: [M + H]$^+$/Rt (min): 428.2/0.956 (Method C): $^1$H-NMR (400 MHz, CD$_3$OD) δ: 7.48 (2H, d, J = 8.5 Hz), 7.22 (2H, d, J = 8.5 Hz), 5.29 (2H, s), 4.36 (2H, q, J = 7.1 Hz), 1.35 (3H, t, J = 7.1 Hz). |
| 55 | 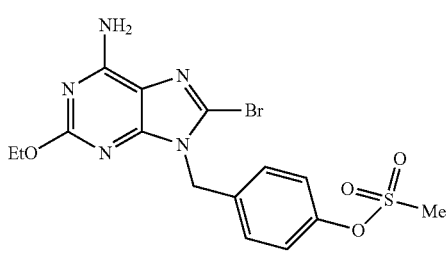 [SMILES: CCOc1nc(N)c2nc(Br)n(Cc3ccc(OS(C)(=O)=O)cc3)c2n1] | LC-MS [M + H]$^+$/Rt (min): 444.2/0.731 (Method C); $^1$H-NMR (400 MHz, CDCl$_3$) δ: 7.43 (2H, d, J = 8.5 Hz), 7.31 (2H, d, J = 8.5 Hz), 5.37 (2H, s), 4.38 (2H, q, J = 6.7 Hz), 3.19 (3H, s), 1.37 (3H, t, J = 6.7 Hz). |

| Reference example | Chemical Structure | Instrumental analysis data |
|---|---|---|
| 56 | 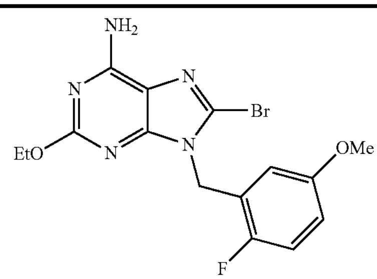 | LC-MS [M + H]⁺/Rt (min): 397.9/0.849 (Method C); ¹H-NMR (400 MHz, CDCl₃) δ: 7.04-6.97 (1H, m), 6.80-6.73 (1H, m), 6.57 (1H, dd, J = 6.1, 3.1 Hz), 5.66 (2H, s), 5.33 (2H, s), 4.36 (2H, q, J = 7.1 Hz), 3.67 (3H, s), 1.38 (3H, t, J = 7.1 Hz). |
| 57 | 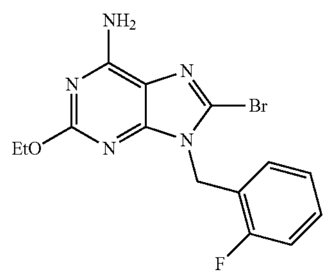 [SMILES: CCOc1nc(N)c2nc(Br)n(Cc3ccccc3F)c2n1] | LC-MS [M + H]⁺/Rt (min): 367.8/0.834 (Method C); ¹H-NMR (400 MHz, CDCl₃) δ: 7.31-7.24 (1H, m), 7.12-7.01 (3H, m), 5.76 (2H, s), 5.38 (2H, s), 4.35 (2H, q, J = 6.9 Hz), 1.38 (3H, t, J = 6.9 Hz). |
| 58 | 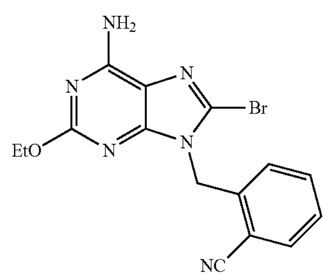 [SMILES: CCOc1nc(N)c2nc(Br)n(Cc3ccccc3C#N)c2n1] | LC-MS [M + H]⁺/Rt (min): 374.8/0.740 (Method C); ¹H-NMR (400 MHz, CDCl₃) δ: 7.72 (1H, dd, J = 7.9, 1.2 Hz), 7.53-7.48 (1H, m), 7.44-7.38 (1H, m), 7.02 (1H, d, J = 7.9 Hz), 5.58 (2H, s), 5.55 (2H, s), 4.34 (2H, q, J = 7.1 Hz), 1.37 (3H, t, J = 7.1 Hz). |

Reference Example 59

2-Chloro-6-methyl-5-nitropyrimidine-4-amine

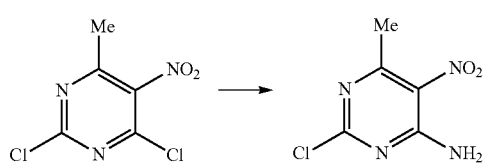 [SMILES: Cc1nc(Cl)nc(Cl)c1[N+](=O)[O-] ; Cc1nc(Cl)nc(N)c1[N+](=O)[O-]]

To a solution of 2,4-dichloro-6-methyl-5-nitropyrimidine (20 g) in tetrahydrofuran (321 mL) were added dropwise N,N-diisopropylethylamine (24.5 mL) and ammonia (7.0 mol/L methanol solution, 20.6 mL) at −10° C., and the mixture was stirred at −10° C. for 2.5 hours. To the reaction mixture was added water, and the mixture was extracted with ethyl acetate. The organic layer was washed with brine, dried over sodium sulfate, filtrated, and then concentrated in vacuo to give the title compound (17.5 g).

LC-MS [M+H]⁺/Rt (min): 188.8/0.503 (Method C)

Reference Example 60 tert-Butyl 3-(4-{[(2-chloro-6-methyl-5-nitropyrimidin-4-yl)amino]methyl}phenyl)pyrrolidine-1-carboxylate

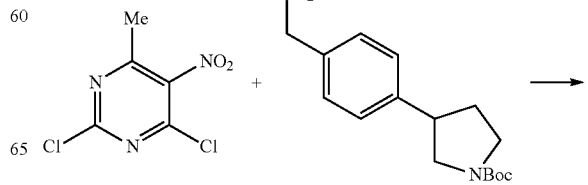

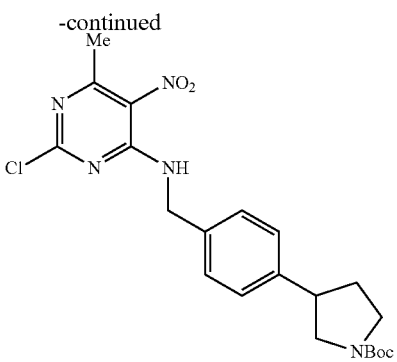

To an ice-cooled solution of 2,4-dichloro-6-methyl-5-nitropyrimidine (502 mg) in tetrahydrofuran (10 mL) were added N,N-diisopropylethylamine (0.506 ml), and a solution of tert-butyl 3-(4-(aminomethyl)phenyl)pyrrolidine-1-carboxylate (714 mg) in tetrahydrofuran (15 mL). The reaction mixture was warmed to room temperature, and then stirred for 30 minutes. To the mixture in ice bath was water, and the mixture was extracted with ethyl acetate. The organic layer was dried over sodium sulfate, filtrated, and then concentrated in vacuo. The residue was purified by silica gel column chromatography (hexane/ethyl acetate) to give the title compound (1.06 g).

$^1$H-NMR (400 MHz, CDCl$_3$) δ: 8.40 (1H, t, J=5.5 Hz), 7.31 (2H, d, J=7.9 Hz), 7.24 (2H, d, J=7.9 Hz), 4.76 (2H, d, J=5.5 Hz), 3.87-3.72 (1H, m), 3.66-3.52 (1H, m), 3.45-3.22 (3H, m), 2.73 (3H, s), 2.32-2.21 (1H, m), 2.02-1.93 (1H, m), 1.47 (9H, s).

Reference Example 61 tert-Butyl 3-(4-{[(2-ethoxy-6-methyl-5-nitropyrimidin-4-yl)amino]methyl}phenyl)pyrrolidine-1-carboxylate

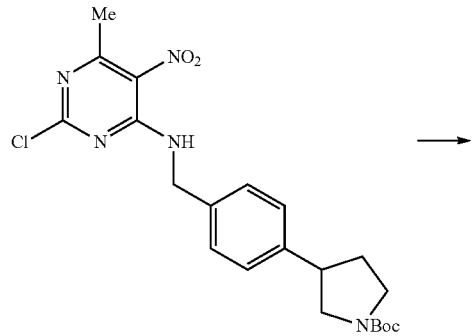

⟶

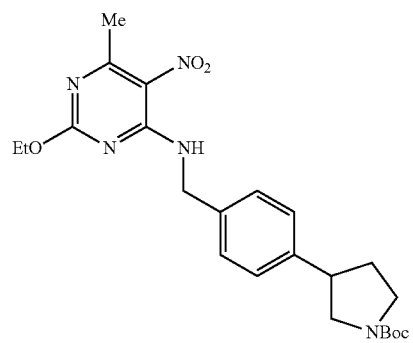

To an ice-cooled solution of the compound of Reference example 60 (479 mg) in ethanol (6 mL) was added 20% sodium ethoxide solution (1.09 mL). The reaction mixture was warmed to room temperature, and then stirred for one hour. To the reaction mixture was added aqueous saturated ammonium chloride, and the mixture was extracted with chloroform. The organic layer was dried over sodium sulfate, filtrated, and then concentrated in vacuo. The residue was purified by silica gel column chromatography (hexane/ethyl acetate) to give the title compound (291 mg).

LC-MS [M+H]$^+$/Rt (min): 459.4/1.220 (Method D); $^1$H-NMR (400 MHz, CDCl$_3$) δ: 8.80 (1H, t, J=5.5 Hz), 7.29 (2H, d, J=7.9 Hz), 7.23 (2H, d, J=7.9 Hz), 4.76 (2H, d, J=5.5 Hz), 4.40 (2H, q, J=7.0 Hz), 3.87-3.72 m), 3.69-3.50 (1H, m), 3.45-3.20 (3H, m), 2.74 (3H, s), 2.31-2.19 (1H, m), 2.07-1.90 (1H, m), 1.47 (9H, s), 1.39 (3H, t, J=7.0 Hz).

Reference Examples 62-65

According to the method of Reference example 61, Reference examples 62-65 were prepared by using the corresponding material compounds.

| Reference example | Chemical Structure | Instrumental analysis data |
|---|---|---|
| 62 | ![structure] | LC-MS [M + H]$^+$/Rt (min): 445.3/1.166 (Method D); $^1$H-NMR (400 MHz, CDCl$_3$) δ: 8.79 (1H, t, J = 5.5 Hz), 7.29 (2H, d, J = 7.9 Hz), 7.23 (2H, d, J = 7.9 Hz), 4.77 (2H, d, J = 5.5 Hz), 3.98 (3H, s), 3.88-3.72 (1H, m), 3.68-3.50 (1H, m), 3.46-3.21 (3H, m), 2.74 (3H, s), 2.29-2.22 (1H, m), 2.01-1.91 (1H, m), 1.47 (9H, s). |

| Reference example | Chemical Structure | Instrumental analysis data |
|---|---|---|
| 63 | Me, NO2, MeO, NH2 pyrimidine | LC-MS [M + H]+/Rt (min): 184.7/0.554 (Method D) |
| 64 | Me, NO2, EtO, NH2 pyrimidine | $^1$H-NMR (CDCl$_3$) δ: 7.89 (1H, br s), 5.89 (1H, br s), 4.43-4.37 (2H, m), 2.75 (3H, s), 1.45-1.38 (3H, m). |
| 65 | Me, NO2, PrO, NH2 pyrimidine | LC-MS ([M + ]+/Rt (min)): 212.9/0.779 (Method A) |

Reference Example 66 tert-Butyl (2-ethoxy-6-methyl-5-nitropyrimidin-4-yl)carboxylate

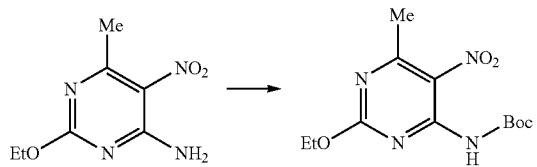 [SMILES: CCOc1nc(C)c([N+](=O)[O-])c(N)n1 ; CCOc1nc(C)c([N+](=O)[O-])c(NC(=O)OC(C)(C)C)n1]

To an ice-cooled solution of the compound of Reference example 64 (1.8 g) in tetrahydrofuran (30 mL) were added dimethylaminopyridine (110 mg) and di-tert-butyl dicarbonate (3.71 g). The reaction mixture was warmed to room temperature and then stirred for 4 hours. To the reaction mixture was added 20% sodium ethoxide solution (6.2 mL), and the mixture was stirred for one more hour. To the reaction mixture was added aqueous saturated ammonium chloride, and the mixture was extracted with chloroform. The organic layer was dried over sodium sulfate, filtrated, and then concentrated in vacuo. The residue was purified by silica gel column chromatography (hexane/ethyl acetate) to give the title compound (2.54 g).

LC-MS [M+H]+/Rt (min): 299.2/1.035 (Method C); $^1$H-NMR (400 MHz, CDCl$_3$) δ: 9.26 (1H, s), 4.51 (2H, q, J=7.1 Hz), 2.70 (3H, s), 1.53 (9H, s), 1.43 (3H, t, J=7.1 Hz).

Reference Examples 67-68

According to the method of Reference example 66, Reference examples 67-68 were prepared by using the corresponding material compounds.

| Reference example | Chemical Structure | Instrumental analysis data |
|---|---|---|
| 67 | Me, NO2, MeO, NHBoc pyrimidine | $^1$H-NMR (CDCl$_3$) δ: 9.22 (1H, brs), 4.08 (3H, s), 2.71 (3H, s), 1.46 (9H, s). |
| 68 | Me, NO2, PrO, NHBoc pyrimidine | LC-MS [M + H]+/Rt (min): 313.5/1.096 (Method A) |

Reference Example 69 tert-Butyl (2-ethoxy-6-methyl-5-nitropyrimidin-4-yl)[(6-fluoropyridin-3-yl)methyl]carboxylate

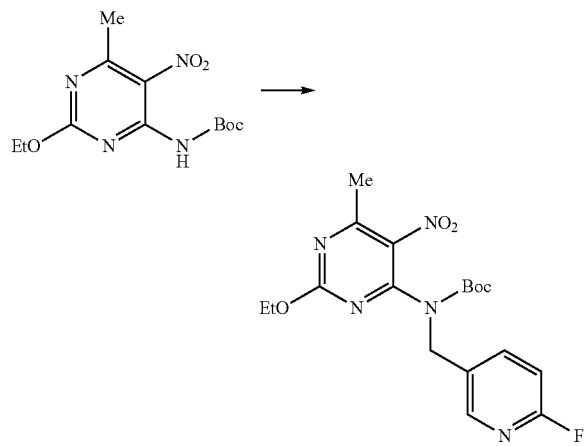

To an ice-cooled solution of the compound of Reference example 66 (0.8 g) in N,N-dimethylformamide (13 mL) were added potassium carbonate (0.56 g), tetrabutylammonium iodide (50 mg), and 5-(chloromethyl)-2-fluoropyridine (0.59 g), and the mixture was stirred at room temperature for 28 hours. To the reaction mixture was added water, and the mixture was extracted with ethyl acetate. The organic layer was washed with brine, dried over sodium sulfate, filtrated, and then concentrated in vacuo. The obtained residue was purified by silica gel column chromatography (hexane/ethyl acetate) to give the title compound (0.96 g).

$^1$H-NMR (CDCl$_3$) δ: 8.23 (1H, d, J=2.4 Hz), 7.97-7.93 (1H, m), 6.92-6.89 (1H, m), 5.15 (2H, s), 4.42 (2H, q, J=7.1 Hz), 2.61 (3H, s), 1.44-1.38 (12H, m).

Reference Examples 70-73

According to the method of Reference example 69, Reference examples 70-73 were prepared by using the corresponding material compounds.

| Reference example | Chemical Structure | Instrumental analysis data |
|---|---|---|
| 70 | 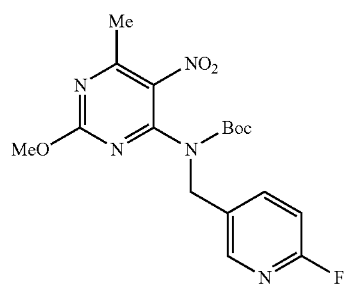 [SMILES: COc1nc(C)c([N+](=O)[O-])c(N(Cc2ccc(F)nc2)C(=O)OC(C)(C)C)n1] | $^1$H-NMR (CDCl$_3$) δ: 8.23 (1H, d, J = 2.4 Hz), 7.98-7.93 (1H, m), 6.92-6.89 (1H, m), 5.15 (2H, s), 4.02 (3H, s), 2.62 (3H, s), 1.40 (9H, s). |
| 71 | 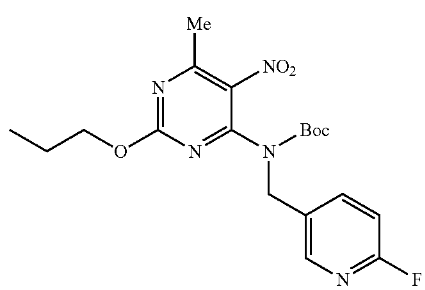 [SMILES: CCCOc1nc(C)c([N+](=O)[O-])c(N(Cc2ccc(F)nc2)C(=O)OC(C)(C)C)n1] | $^1$H-NMR (CDCl$_3$) δ: 8.22 (1H, s), 7.97-7.93 (1H, m), 6.92-6.90 (1H, m), 5.15 (2H, s), 4.30 (2H, t, J = 6.7 Hz), 2.61 (3H, s), 1.84-1.80 (2H, m), 1.40 (9H, s), 1.03 (3H, t, J = 7.3 Hz). |
| 72 | 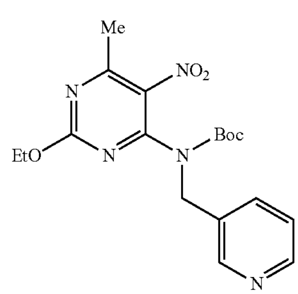 [SMILES: CCOc1nc(C)c([N+](=O)[O-])c(N(Cc2cccnc2)C(=O)OC(C)(C)C)n1] | LC-MS [M + H]$^+$/Rt (min): 390.3/0.959 (Method C); $^1$H-NMR (400 MHz, CDCl$_3$) δ: 8.64-8.61 (1H, m), 8.51 (1H, dd, J = 4.6, 1.5 Hz), 7.83-7.78 (1H, m), 7.27 (3H, dd, J = 4.6, 7.6 Hz), 5.17 (2H, s), 4.39 (2H, q, J = 7.1 Hz), 2.61 (3H, s), 1.44-1.35 (12H, m). |

| Reference example | Chemical Structure | Instrumental analysis data |
|---|---|---|
| 73 | 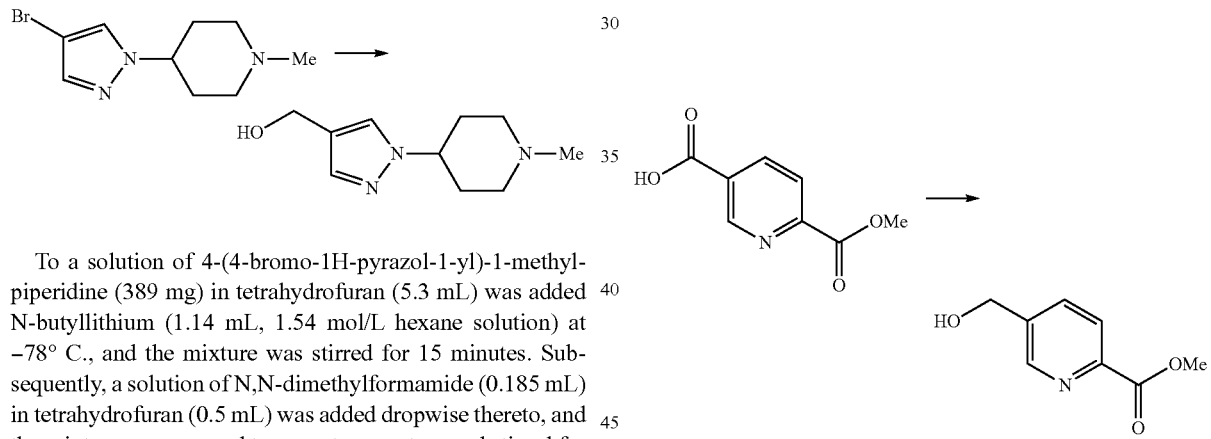 | LC-MS [M + H]⁺/Rt (min): 448.3/1.158 (Method C); ¹H-NMR (400 MHz, CDCl₃) δ: 9.12 (1H, d, J = 3.1 Hz), 8.27 (1H, dd, J = 2.1, 7.9 Hz), 7.51 (1H, d, J = 7.9 Hz), 5.33 (2H, s), 4.22 (2H, q, J = 6.9 Hz), 3.94 (3H, s), 2.64 (3H, s), 1.37 (9H, s), 1.29 (3H, t, J = 6.9 Hz). |

Reference Example 74

[1-(1-Methylpiperidin-4-yl)-1H-pyrazol-4-yl]methanol

To a solution of 4-(4-bromo-1H-pyrazol-1-yl)-1-methylpiperidine (389 mg) in tetrahydrofuran (5.3 mL) was added N-butyllithium (1.14 mL, 1.54 mol/L hexane solution) at −78° C., and the mixture was stirred for 15 minutes. Subsequently, a solution of N,N-dimethylformamide (0.185 mL) in tetrahydrofuran (0.5 mL) was added dropwise thereto, and the mixture was warmed to room temperature and stirred for one hour. To the reaction mixture was added water, and the mixture was extracted with chloroform. The organic layer was dried over sodium sulfate, filtrated, and then concentrated in vacuo.

The obtained crude product (308 mg) was dissolved in methanol (12.5 mL). Sodium borohydride (121 mg) was slowly added to the solution in ice bath, and the mixture was stirred at 0° C. for 30 minutes. To the reaction mixture were added aqueous saturated ammonium chloride and then aqueous saturated sodium bicarbonate, and the mixture was extracted with chloroform/methanol. The organic layer was dried over sodium sulfate, filtrated, and then concentrated in vacuo. The residue was purified by amino silica gel column chromatography (chloroform/methanol) to give the title compound (132 mg).

¹H-NMR (CDCl₃) δ: 7.49 (1H, s), 7.45 (1H, s), 4.59 (2H, s), 4.13-4.05 (1H, m), 2.97-2.94 (2H, m), 2.32 (3H, s), 2.15-2.09 (4H, m), 2.02-1.99 (2H, m), 1.63 (1H, br s).

Reference Example 75

Methyl 5-(hydroxymethyl)pyridine-2-carboxylate

To a solution of 6-(methoxycarbonyl)nicotinic acid (2.03 g) in tetrahydrofuran (50 ml) were added ethyl chloroformate (1.14 ml) and triethylamine (1.75 ml) at 0° C., and the mixture was stirred for one hour. Then, the reaction mixture was filtrated, and the filtrate was added to a solution of sodium borohydride (0.892 mg) in water (3 ml) at 0° C. The reaction mixture was stirred for 30 minutes. To the reaction mixture was added aqueous saturated ammonium chloride, and the mixture was extracted with ethyl acetate. The organic layer was dried over sodium sulfate, filtrated, and then concentrated in vacuo. The residue was purified by silica gel column chromatography (ethyl acetate/hexane) to give the title compound (990 mg).

¹H-NMR (400 MHz, CDCl₃) δ: 9.16 (1H, d, J=1.2 Hz), 8.29 (1H, dd, J=7.3, 1.2 Hz), 7.36 (1H, d, J=7.3 Hz), 4.83 (2H, d, J=4.9 Hz), 3.96 (3H, s), 3.63 (1H, t, J=4.9 Hz).

Reference Example 76

According to the method of Reference example 75, Reference example 76 was prepared by using the corresponding material compound.

| Reference example | Chemical Structure | Instrumental analysis data |
|---|---|---|
| 76 | ![structure] HO-CH2-C6H4-pyrrolidine-N-Boc | $^1$H-NMR (400 MHz, CDCl$_3$) δ: 7.29 (2H, d, J = 7.3 Hz), 7.15 (2H, d, J = 7.3 Hz), 4.78 (1H, br s), 4.66 (2H, s), 3.69-3.44 (2H, m), 2.36-2.22 (1H, m), 1.96-1.60 (4H, m), 1.19 (9H, s). |

Reference Example 77

[4-(1-Azabicyclo[2.2.2]oct-3-yl)phenyl]methanol

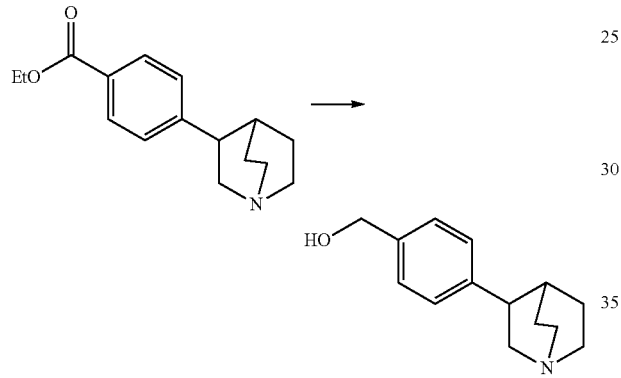

To a solution of lithium aluminum hydride (121 mg) in tetrahydrofuran (4 mL) was added a solution of the compound of Reference example 33 (332 mg) in tetrahydrofuran (4 mL) at 0° C. The mixture was stirred in ice bath for 1.5 hours, and water (0.121 ml), 15% aqueous sodium hydroxide (0.121 ml), and then water (0.363 ml) were added thereto at 0° C. The reaction mixture was stirred for one hour, filtrated, and then concentrated in vacuo. The residue was purified by silica gel column chromatography (chloroform/methanol) to give the title compound (196 mg).

LC-MS [M+H]$^+$/Rt (min): 218.2/0.442 (Method C); $^1$H-NMR (400 MHz, CDCl$_3$) δ: 7.33 (2H, d, J=7.9 Hz), 7.24 (2H, d, J=7.9 Hz), 4.65 (2H, s), 3.28-3.19 (1H, m), 2.99-2.74 (6H, m), 1.93-1.88 (1H, m), 1.75-1.68 (2H, m), 1.67-1.58 (1H, 1.38-1.26 (1H m).

Reference Examples 78-79

According to the method of Reference example 77, Reference examples 78-79 were prepared by using the corresponding material compounds.

| Reference example | Chemical Structure | Instrumental analysis data |
|---|---|---|
| 78 | HO-CH2-pyridine-azabicyclo | LC-MS [M + H]$^+$/Rt (min): 219.0/0.151 (Method C); $^1$H-NMR (400 MHz, CDCl$_3$) δ: 8.55 (1H, d, J = 2.4 Hz), 7.66 (1H, dd, J = 7.9, 2.4 Hz), 7.18 (1H, d, J = 7.9 Hz), 4.68 (2H, s), 3.37 (1H, ddd, J = 1.8, 6.7, 13.4 Hz), 3.20-3.11 (1H, m), 3.09-3.02 (1H, m), 2.97-2.82 (3H, m), 2.80-2.71 (1H, m), 2.07-2.02 (1H, m), 1.80-1.58 (3H, m), 1.35-1.25 (1H, m). |
| 79 | HO-CH2-C6H3(F)-azabicyclo | LC-MS [M + H]$^+$/Rt (min): 235.9/0.207 (Method C); $^1$H-NMR (400 MHz, CDCl$_3$) δ: 7.37 (1H, dd, J = 7.9, 11.6 Hz), 7.04 (1H, dd, J = 1.5, 7.9 Hz), 6.96 (1H, dd, J = 1.5, 11.6 Hz), 4.72 (2H, s), 3.33-3.23 (1H, m), 3.00-2.76 (6H, m), 1.95-1.90 (1H, m), 1.76-1.68 (2H, m), 1.68-1.56 (1H, m), 1.41-1.31 (1H, m). |

Reference Example 80

[4-(1-Methylpyrrolidin-2-yl)phenyl]methanol

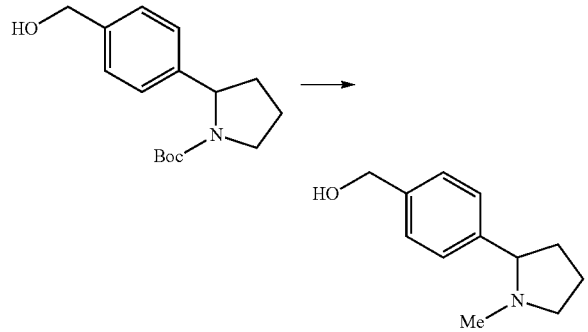

To a solution of lithium aluminum hydride (166 mg) in tetrahydrofuran (5 mL) was added a solution of tert-butyl 2-(4-(hydroxymethyl)phenyl)pyrrolidine-1-carboxylate (304 mg) in tetrahydrofuran (5 mL) at 0° C. The reaction solution was heated, and then stirred under reflux for one hour. The reaction solution was cooled to 0° C., and water (0.166), 15% aqueous sodium hydroxide (0.166 mL), and then water (0.332 mL) were added thereto at 0° C. The reaction mixture was stirred for one hour, filtrated, and then concentrated in vacuo. The residue was purified by silica gel column chromatography (chloroform/methanol) to give the title compound (214 mg).

LC-MS [M+H]$^+$/Rt (min): 191.9/0.182 (Method C); $^1$H-NMR (400 MHz, CDCl$_3$) δ: 7.39-7.28 (4H, m), 4.67 (2H, d, J=6.7 Hz), 3.30-3.17 (1H, m), 3.09-2.96 (1H, m), 2.27 (1H, t, J=6.7 Hz), 2.21-2.08 (4H, m), 2.01-1.86 (1H, m), 1.86-1.66 (3H, m).

Reference Example 81

Ethyl 1-(1-azabicyclo[2.2.2]oct-3-yl)-1H-pyrazole-4-carboxylate

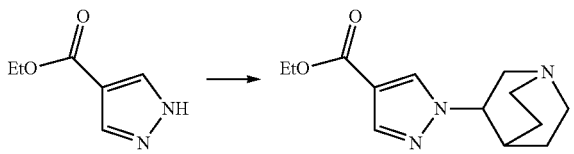 [SMILES: CCOC(=O)c1cn[nH]c1 ; CCOC(=O)c1cnn(C2CN3CCC2CC3)c1]

To an ice-cooled solution of ethyl 1H-pyrazole-4-carboxylate (1.0 g) in tetrahydrofuran (23.8 mL) were added 3-quinuclidinol (1.36 g) and cyanomethylenetributylphosphorane (2.8 mL), and the mixture was stirred at 80° C. for 4 hours. To the reaction mixture was added water, and the mixture was extracted with chloroform. The organic layer was dried over sodium sulfate, filtrated, and then concentrated in vacuo. The residue was purified by silica gel column chromatography (chloroform/methanol) to give the title compound (1.63 g).

$^1$H-NMR (CDCl$_3$) δ: 7.99 (1H, s), 7.93 (1H, s), 4.39-4.27 (3H, m), 3.54-3.48 (1H, m), 3.43-3.36 (1H, m), 3.11-3.03 (1H, m), 2.96-2.81 (3H, m), 2.22-2.18 (1H, m), 1.82-1.61 (3H, m), 1.47-1.33 (4H, m).

Reference Example 82

[1-(1-Azabicyclo[2.2.2]oct-3-yl)-1H-pyrazol-4-yl]methanol

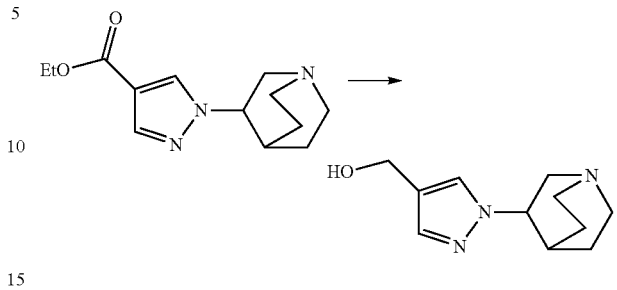

To an ice-cooled solution of the compound of Reference example 81 (1.63 g) in tetrahydrofuran (32.7 mL) was added diisobutylaluminum hydride (19.2 mL, 1.02 mol/L hexane solution), and the mixture was stirred at 0° C. for 2 hours. To the reaction mixture in ice bath was added aqueous saturated potassium sodium tartrate, and the mixture was extracted with chloroform/methanol. The organic layer was washed with brine, dried over sodium sulfate, filtrated, and concentrated in vacuo to give the title compound (0.41 g).

$^1$H-NMR (CDCl$_3$) δ: 7.53 (1H, s), 7.50 (1H, s), 4.59 (2H, s), 4.35-4.30 (1H, m), 3.53-3.48 (1H, m), 3.38-3.32 (1H, m), 3.10-3.02 (1H, m), 2.94-2.79 (3H, m), 2.18-2.14 (1H, m), 1.93 (1H, br s), 1.80-1.65 (3H, m), 1.44-1.36 (1H, m).

Reference Example 83 tert-Butyl {[1-(1-azabicyclo[2.2.2]oct-3-yl)-1H-pyrazol-4-yl]methyl}(2-ethoxy-6-methyl-5-nitropyrimidin-4-yl)carboxylate

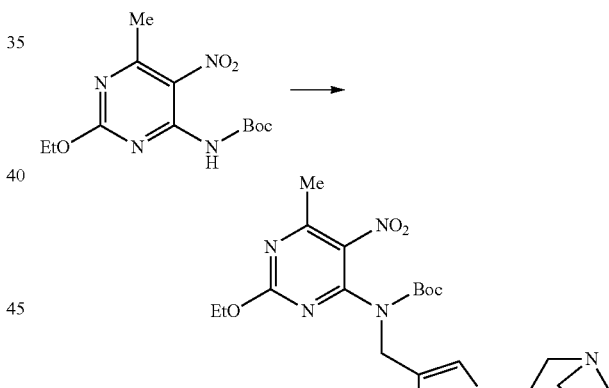

To ice-cooled solution of the compound of Reference example 66 (1.14 g) in tetrahydrofuran (12.7 mL) were added (1-quinuclidin-3-yl)-1H-pyrazol-4-yl)methanol (950 mg), triphenylphosphine (1.50 g), and diisopropyl azodicarboxylate (1.12 mL), and the mixture was stirred at room temperature for 12 hours. To the reaction mixture was added water, and the mixture was extracted with ethyl acetate/methanol. The organic layer was washed with brine, dried over sodium sulfate, filtrated, and then concentrated in vacuo. The residue was purified by silica gel column chromatography (chloroform/methanol) to give the title compound (1.21 g).

$^1$H-NMR (CDCl$_3$) δ: 7.61 (1H, s), 7.53 (1H, s), 5.01 (2H, s), 4.46 (2H, q, J=7.1 Hz), 4.34-4.29 (1H, m), 3.53-3.48 (1H, m), 3.38-3.32 (1H, m), 3.08-3.00 (1H, m), 2.94-2.80 (3H, m), 2.60 (3H, s), 2.13-2.11 (1H, m), 1.79-1.66 (2H, m), 1.63-1.50 (1H, m), 1.50-1.33 (13H, m).

Reference Examples 84-90

According to the method of Reference example 83, Reference examples 84-90 were prepared by using the corresponding material compounds.

| Reference example | Chemical Structure | Instrumental analysis data |
|---|---|---|
| 84 | 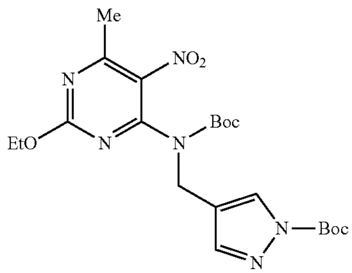 [SMILES: CCOc1nc(C)c([N+](=O)[O-])c(N(Cc2cnn(C(=O)OC(C)(C)C)c2)C(=O)OC(C)(C)C)n1] | $^1$H-NMR (CDCl$_3$) δ: 8.14 (1H, s), 7.79 (1H, s), 5.00 (2H, s), 4.45 (2H, q, J = 7.1 Hz), 2.61 (3H, s), 1.63 (9H, s), 1.44 (9H, s), 1.26 (3H, t, J = 7.1 Hz). |
| 85 | 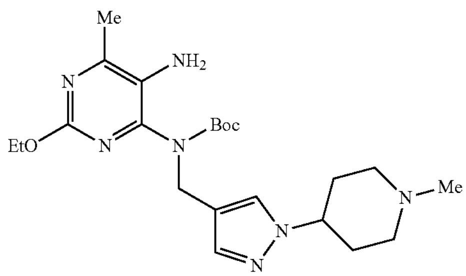 [SMILES: CCOc1nc(C)c(N)c(N(Cc2cnn(C3CCN(C)CC3)c2)C(=O)OC(C)(C)C)n1] | $^1$H-NMR (CDCl$_3$) δ: 7.53 (1H, s), 7.50 (1H, s), 4.99 (2H, s), 4.46 (2H, q, J = 7.0 Hz), 4.10-4.03 (1H, m), 2.96-2.93 (2H, m), 2.60 (3H, s), 2.31 (3H, s), 2.15-2.12 (4H, m), 2.03-1.96 (2H, m), 1.46-1.42 (12H, m). |
| 86 | 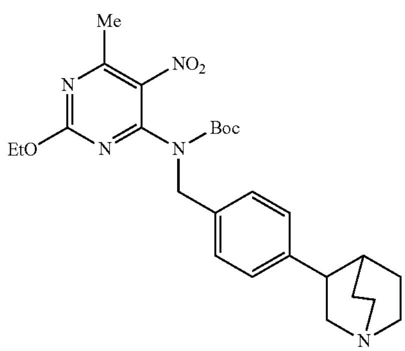 [SMILES: CCOc1nc(C)c([N+](=O)[O-])c(N(Cc2ccc(C3CN4CCC3CC4)cc2)C(=O)OC(C)(C)C)n1] | LC-MS [M + H]$^+$/Rt (min): 484.2/0.752 (Method C); $^1$H-NMR (400 MHz, CDCl$_3$) δ: 7.35 (2H, d, J = 7.9 Hz), 7.20 (2H, d, J = 7.9 Hz), 5.16 (2H, s), 3.96 (3H, s), 3.32-3.23 (1H, m), 3.08-3.00 (1H, m), 2.97-2.78 (5H, m), 2.60 (3H, s), 1.89-1.84 (1H, m), 1.74-1.66 (2H, m), 1.65-1.56 (1H, m), 1.39-1.29 (10H, m). |
| 87 | 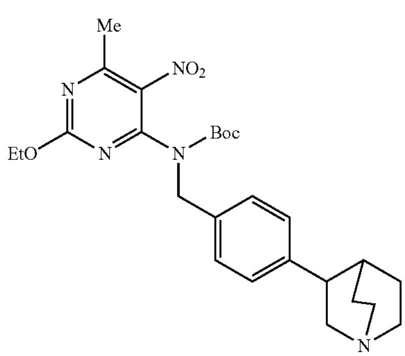 [SMILES: CCOc1nc(C)c([N+](=O)[O-])c(N(Cc2ccc(C3CN4CCC3CC4)cc2)C(=O)OC(C)(C)C)n1] | LC-MS [M + H]$^+$/Rt (min): 493.5/0.9331 (Method C); $^1$H-NMR (400 MHz, CDCl$_3$) δ: 7.35 (2H, d, J = 8.2 Hz), 7.21 (2H, d, J = 8.2 Hz) 5.16 (2H, s), 4.36 (2H, q, J = 7.2 Hz), 3.34-3.24 (1H, m), 3.09-2.99 (1H, m), 2.98-2.77 (5H, m), 2.60 (3H, s), 1.91-1.85 (1H, m), 1.75-1.68 (2H, m), 1.68-1.57 (1H, m), 1.42-1.32 (13H, m). |

| Reference example | Chemical Structure | Instrumental analysis data |
|---|---|---|
| 88 | Me, NO2, EtO, N, Boc, N-Me pyrrolidine benzyl structure | LC-MS [M + H]+/Rt (min): 472.2/0.700 (Method C); 1H-NMR (400 MHz, CDCl3) δ: 7.33 (2H, d, J = 7.3 Hz) 7.27 (2H, d, J = 7.3 Hz), 5.15 (2H, s), 4.35 (2H, q, J = 7.3 Hz), 3.26-3.18 (1H, m), 3.03-2.96 (1H, m), 2.61 (3H, s), 2.26 (1H, dd, J = 9.0, 18.0 Hz), 2.19-2.08 (4H, m), 2.01-1.84 (1H, m), 1.84-1.65 (2H, m), 1.41-1.30 (12H, m). |
| 89 | Me, NO2, EtO, N, Boc, pyridyl-quinuclidine structure | LC-MS [M + H]+/Rt (min): 499.1/0.759 (Method C): 1H-NMR (400 MHz, CDCl3) δ: 8.56 (1H, d, J = 2.4 Hz), 7.74 (1H, dd, J = 7.9, 2.4 Hz), 7.18 (1H, d, J = 7.9 Hz), 5.16 (2H, s), 4.40 (2H, q, J = 7.1 Hz), 3.51-3.42 (1H, m), 3.27-3.17 (1H, m), 3.10-2.85 (4H, m), 2.85-2.75 (1H, m), 2.61 (3H, s), 2.06-2.00 (1H, m), 1.81-1.67 (2H, m), 1,62-1.53 (1H, m), 1.47-1.35 (13H, m). |
| 90 | Me, NO2, EtO, N, Boc, F-aryl-quinuclidine structure | 1H-NMR (400 MHz, CDCl3) δ: 7.42 (1H, dd, J = 7.9, 11.6 Hz), 7.00 (1H, dd, J = 1.2, 7.9 Hz), 6.93 (1H, dd, J = 1.2, 11.6 Hz), 5.22 (2H, s), 4.36 (2H, q, J = 7.1 Hz), 3.37-3.26 (1H, m), 3.06-2.77 (6H, m), 2.62 (3H, s), 1.93-1.87 (1H, m), 1.76-1.67 (2H, m), 1.61-1.55 (1H, m), 1.42-1.31 (13H, m). |

Reference Example 91

2-Ethoxy-N-[(6-fluoropyridin-3-yl)methyl]-6-methyl-5-nitropyrimidine-4-amine

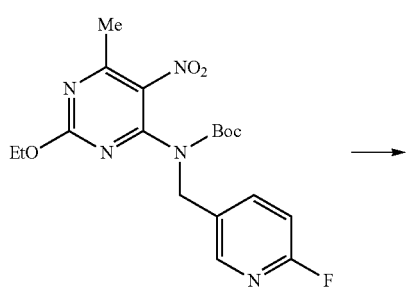

→

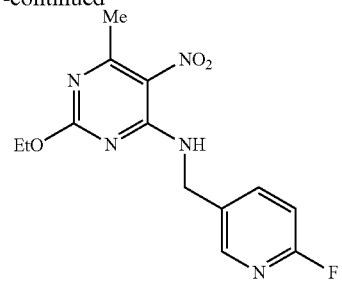

To an ice-cooled solution of the compound of Reference example 69 (930 in dichloromethane (7.6 mL) was added trifluoroacetic acid (1.8 mL), and the mixture was stirred at 40° C. for 3 hours. The reaction mixture was poured to 28% ammonia in ice bath, and the mixture was extracted with chloroform. The organic layer was dried over sodium sulfate, filtrated, and then concentrated in vacuo. The obtained residue was purified by silica gel column chromatography (hexane/ethyl acetate) to give the title compound (680 mg).

$^1$H-NMR (CDCl$_3$) δ: 8.85 (1H, br s), 8.23 (1H, s), 7.79-7.75 (1H, m), 6.94 (1H, dd, J=8.5, 3.0 Hz), 4.79 (2H, d, J=5.9 Hz), 4.38 (2H, q, J=7.2 Hz), 2.75 (3H, d, J=1.8 Hz), 1.39 (3H, t, J=7.2 Hz).

Reference Examples 92-105

According to the method of Reference example 91, Reference examples 92-105 were prepared by using the corresponding material compounds.

| Reference example | Chemical Structure | Instrumental analysis data |
| --- | --- | --- |
| 92 | (structure) | $^1$H-NMR (CDCl$_3$) δ: 8.84 (1H, s), 8.24 (1H, d, J = 2.4 Hz), 7.80-7.76 (1H, m) 6.95-6.92 (1H, m), 4.79 (2H, d, J = 6.1 Hz), 3.97 (3H, s), 2.75 (3H, s). |
| 93 | (structure) | $^1$H-NMR (CDCl$_3$) δ: 8.85 (1H, s), 8.23 (1H, s), 7.79-7.75 (1H, m), 6.95-6.92 (1H, m), 4.79 (2H, d, J = 6.1 Hz), 4.27 (2H, t, J = 6.7 Hz), 2.75 (3H, s), 1.83-1.74 (2H, m), 1.01 (3H, t, J = 7.3 Hz). |
| 94 | (structure) | LC-MS [M + H]$^+$/Rt (min): 279.0/0.624 (Method C) |
| 95 | (structure) | LC-MS [M + H]$^+$/Rt (min): 376.0/0.495 (Method C) |
| 96 | (structure) | LC-MS [M + H]$^+$/Rt (min): 388.3/0.575 (Method D) |

-continued

| Reference example | Chemical Structure | Instrumental analysis data |
|---|---|---|
| 97 | (structure: 5-amino-2-ethoxy-6-methyl-4-[(1H-pyrazol-4-ylmethyl)amino]pyrimidine) | $^1$H-NMR (CDCl$_3$) δ: 7.60 (2H, s), 5.43 (2H, br s), 4.56 (2H, d, J = 5.5 Hz), 4.33 (2H, q, J = 7.1 Hz), 2.47 (2H, s), 2.28 (3H, s), 1.39 (3H, t, J = 7.1 Hz). |
| 98 | (structure: 2-ethoxy-6-methyl-5-nitro-4-{[1-(1-methylpiperidin-4-yl)-1H-pyrazol-4-ylmethyl]amino}pyrimidine) | LC-MS [M + H]$^+$/Rt (min): 346.0/0.190 Method D) |
| 99 | (structure: 2-ethoxy-6-methyl-5-nitro-4-[(pyridin-3-ylmethyl)amino]pyrimidine) | LC-MS [M + H]$^+$/Rt (min): 290.2/0.582 (Method C); $^1$H-NMR (400 MHz, CD$_3$OD) δ: 8.99-8.97 (1H, m), 8.84 (1H, d, J = 6.1 Hz), 8.73-8.71 (1H, m), 8.12 (1H, dd, J = 6.1, 7.9 Hz), 5.13 (2H, s), 4.52 (2H, q, J = 7.1 Hz), 2.75 (3H, s), 1.37 (3H, t, J = 7.1 Hz). |
| 100 | (structure: methyl 5-{[(2-ethoxy-6-methyl-5-nitropyrimidin-4-yl)amino]methyl}pyridine-2-carboxylate) | LC-MS [M + H]$^+$/Rt (min): 348.24/0.911 (Method C); $^1$H-NMR (400 MHz, CD$_3$OD) δ: 9.27 (1H, s), 8.95 (1H, d, J = 7.9 Hz), 8.17 (1H, d, J = 7.9 Hz), 5.35 (2H, s), 4.43 (2H, q, J = 6.9 Hz), 4.02 (3H, s), 2.79 (3H, s), 1.32 (3H, t, J = 6.9 Hz). |
| 101 | (structure: 2-methoxy-6-methyl-5-nitro-4-{[4-(quinuclidin-3-yl)benzyl]amino}pyrimidine) | $^1$H-NMR (400 MHz, CDCl$_3$) δ: 8.78 (1H, br s), 7.30 (2H, d, J = 7.9 Hz), 7.26 (2H, d, J = 7.9 Hz), 4.76 (2H, d, J = 5.5 Hz), 3.93 (3H, s), 3.35-3.26 (1H, m), 3.09-3.01 (1H, m), 2.99-2.80 (5H, m), 2.73 (3H, s), 1.93-1.86 (1H, m), 1.76-1.69 (2H, m), 1.67-1.59 (1H, m), 1.40-1.28 (1H, m). |

| Reference example | Chemical Structure | Instrumental analysis data |
|---|---|---|
| 102 | 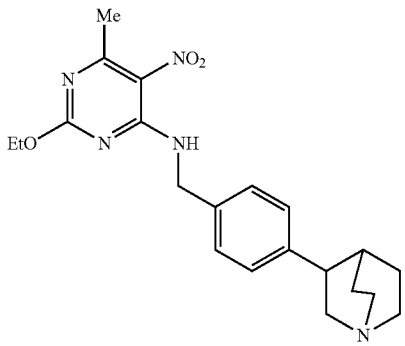 [SMILES: CCOc1nc(C)c([N+](=O)[O-])c(NCc2ccc(C3CN4CCC3CC4)cc2)n1] | $^1$H-NMR (400 MHz, CDCl$_3$) δ: 8.80 (1H, s), 7.30 (2H, d, J = 8.5 Hz), 7.26 (2H, d, J = 8.5 Hz), 4.76 (2H, d, J = 5.5 Hz), 4.40 (2H, q, J = 7.1 Hz), 3.38-3.26 (1H, m), 3.13-3.02 (1H, m), 3.02-2.80 (5H, m), 2.74 (3H, s), 1.95-1.89 (1H, m), 1.80-1.70 (2H, m), 1.70-1.60 (1H, m), 1.38 (3H, t, J = 7.1 Hz), 1.37-1.31 (1H, m). |
| 103 | 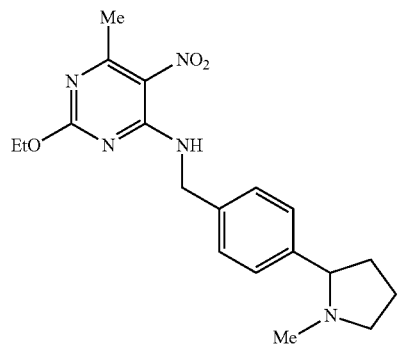 | LC-MS [M + H]$^+$/Rt (min): 372.04/0.535 (Method C); $^1$H-NMR (400 MHz, CDCl$_3$) δ: 8.80 (1H, t, J = 5.5 Hz), 7.33 (2H, d, J = 7.9 Hz), 7.27 (2H, d, J = 7.9 Hz), 4.76 (2H, d, J = 5.5 Hz), 4.40 (2H, q, J = 7.1 Hz), 3.26-3.20 (1H, m), 3.03 (1H, dd, J = 8.2, 9.0 Hz), 2.74 (3H, s), 2.28 (1H, dd, J = 9.0, 18.0 Hz), 2.20-2.12 (4H, m), 1.99-1.88 (1H, m), 1.85-1.67 (2H, m), 1.38 (3H, t, J = 7.1 Hz). |
| 104 | 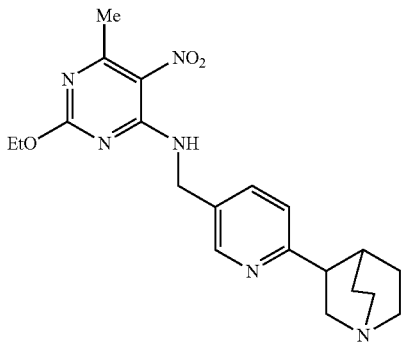 [SMILES: CCOc1nc(C)c([N+](=O)[O-])c(NCc2ccc(C3CN4CCC3CC4)nc2)n1] | LC-MS [M + H]$^+$/Rt (min): 399.0/0.505 (Method C); $^1$H-NMR (400 MHz, CDCl$_3$) δ: 8.83 (1H, t, J = 5.5 Hz), 8.58 (1H, d, J = 2.4 Hz), 7.58 (1H, dd, J = 2.4, 7.9 Hz), 7.20 (1H, d, J = 7.9 Hz), 4.78 (2H, d, J = 5.5 Hz), 4.40 (2H, q, J = 7.1 Hz), 3.53-3.45 (1H, m), 3.28-3.20 (1H, m), 3.10-2.90 (4H, m), 2.86-2.77 (1H, m), 2.74 (3H, s) ( 2.07-2.02 (1H, m), 1.81-1.68 (2H, m), 1.44-1.30 (5H, m). |
| 105 | 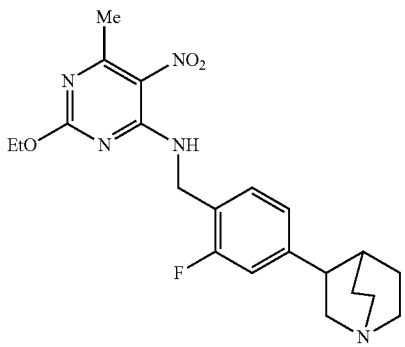 [SMILES: CCOc1nc(C)c([N+](=O)[O-])c(NCc2ccc(C3CN4CCC3CC4)cc2F)n1] | LC-MS [M + H]$^+$/Rt (min): 416.36/0.678 (Method C); $^1$H-NMR (400 MHz, CDCl$_3$) δ: 8.81 (1H, s), 7.29 (1H, d, J = 7.9 Hz), 7.05-6.98 (2H, m), 4.81 (2H, d, J = 5.5 Hz), 4.42 (2H, q, J = 7.1 Hz), 3.37-3.29 (1H, m), 3.06-2.84 (6H, m), 2.73 (3H, s), 1.94-1.90 (1H, m), 1.77-1.70 (2H, m), 1.64-1.58 (1H, m), 1.43-1.34 (4H, m). |

Reference Example 106 tert-Butyl 3-(4-{[(5-amino-2-ethoxy-6-methylpyrimidin-4-yl)amino]methyl}phenyl)pyrrolidine-1-carboxylate

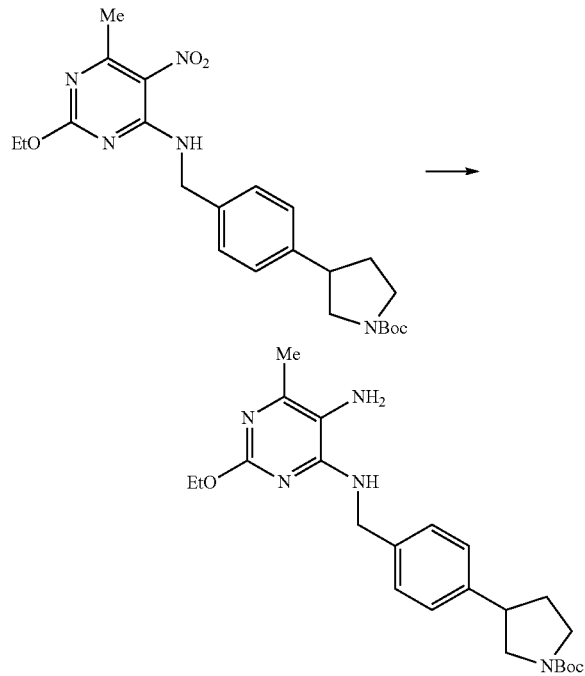

To a solution of the compound of Reference example 61 (209 mg) in tetrahydrofuran (1 ml)/water (1 mL) were added ammonium chloride (244 mg) and zinc (149 mg) at room temperature. The reaction mixture was stirred under reflux for 2 hours, cooled to room temperature, filtrated, and concentrated in vacuo. The residue was purified by silica gel column chromatography (chloroform/methanol) to give the title compound (165 mg).

LC-MS ([M+H]$^+$/Rt (min)): 428.4/0.797 (Method C); $^1$H-NMR (400 MHz, CDCl$_3$) δ: 7.30 (2H, d, J=7.9 Hz), 7.20 (2H, d, J=7.9 Hz), 5.58 (1H, t, J=5.5 Hz), 4.63 (2H, d, J=5.5 Hz), 4.29 (2H, q, J=7.1 Hz), 3.87-3.68 (1H, m), 3.67-3.52 (1H, m), 3.44-3.21 (3H, m), 2.28 (3H, s), 2.26-2.20 (1H, m), 2.03-1.90 (1H, m), 1.47 (9H, s), 1.35 (3H, t, J=7.1 Hz).

Reference Example 107

N$^4$-[4-(1-Azabicyclo[2.2.2]oct-3-yl)benzyl]-2-methoxy-6-methylpyrimidine-4,5-diamine

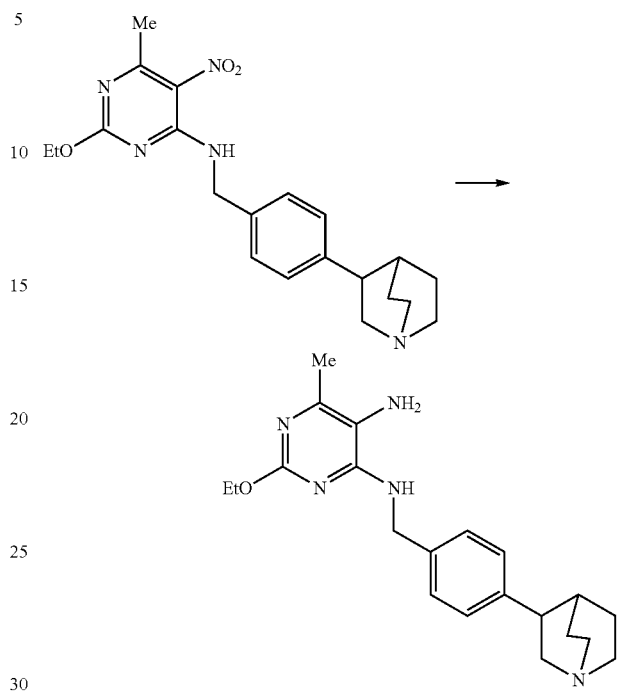

To a solution of the compound of Reference example 101 (319 mg) in methanol (8 ml) was added tin(II) chloride (789 mg) at room temperature. The reaction mixture was stirred under reflux for 3 hours, and cooled to room temperature. Aqueous ammonia was added thereto, and the mixture was stirred. The reaction solution was filtrated, and the filtrate was concentrated in vacuo. The residue was purified by silica gel column chromatography (chloroform/methanol) to give the title compound (300 mg).

$^1$H-NMR (400 MHz, CDCl$_3$) δ: 7.31 (2H, d, J=7.9 Hz), 7.22 (2H, d, J=7.9 Hz), 5.57 (1H, br s), 4.62 (2H, d, J=6.1 Hz), 3.88 (3H, s), 3.34-3.26 (1H, m), 3.09-2.99 (1H, m), 2.99-2.79 (5H, m), 2.43 (2H, s), 2.28 (3H, s), 1.92-1.87 (1H, m), 1.77-1.69 (3H, m), 1.39-1.28 (1H, m).

Reference Examples 108-120

According to the methods of Reference example 106 and Reference example 107, Reference examples 108-120 were prepared by using the corresponding material compounds.

| Reference example | Chemical Structure | Instrumental analysis data |
|---|---|---|
| 108 | 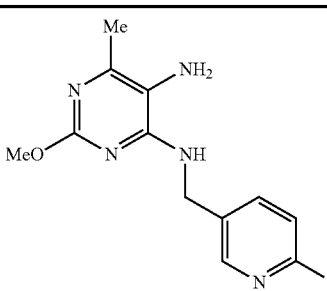 | $^1$H-NMR (CDCl$_3$) δ: 8.13 (1H, s), 7.81-7.77 (1H, m), 6.89-6.86 (1H, m), 5.79 (1H, s), 4.66 (2H, d, J = 6.1 Hz), 3.86 (3H, s), 2.53 (2H, br s), 2.30 (3H, s). |

-continued

| Reference example | Chemical Structure | Instrumental analysis data |
|---|---|---|
| 109 | (structure: 2-ethoxy-4-[(6-fluoropyridin-3-yl)methylamino]-6-methylpyrimidin-5-amine) | ¹H-NMR (CDCl₃) δ: 8.20 (1H, d, J = 1.8 Hz), 7.83-7.79 (1H, m), 6.89 (1H, dd, J = 8.5, 3.0 Hz), 6.04 (1H, s), 4.67 (2H, d, J = 5.9 Hz), 4.28 (2H, q, J = 7.2 Hz), 2.30 (3H, s), 1.76 (2H, br s), 1.35 (3H, t, J = 7.2 Hz). |
| 110 | (structure: 4-[(6-fluoropyridin-3-yl)methylamino]-6-methyl-2-propoxypyrimidin-5-amine) | ¹H-NMR (CDCl₃) δ: 8.85 (1H, s), 8.23 (1H, s) 7.79-7.75 (1H, m), 6.95-6.92 (1H, m), 4.79 (2H, d, J = 6.1 Hz), 4.27 (2H, t, J = 6.7 Hz), 2.75 (3H, s), 1.83-1.74 (2H, m), 1.01 (3H, t, J = 7.3 Hz). |
| 111 | (structure: 2-ethoxy-6-methyl-4-[[1-(quinuclidin-3-yl)pyrazol-4-yl]methylamino]pyrimidin-5-amine) | LC-MS [M + H]⁺/Rt (min): 358.3/0.361 (Method D) |
| 112 | (structure: 2-ethoxy-6-methyl-4-[(1H-pyrazol-4-yl)methylamino]pyrimidin-5-amine) | ¹H-NMR (CDCl₃) δ: 7.60 (2H, s), 5.43 (2H, br s), 4.56 (2H, d, J = 5.5 Hz), 4.33 (2H, q, J = 7.1 Hz), 2.47 (2H, s), 2.28 (3H, s), 1.39 (3H, t, J = 7.1 Hz). |
| 113 | (structure: 2-ethoxy-6-methyl-4-[[1-(1-methylpiperidin-4-yl)pyrazol-4-yl]methylamino]pyrimidin-5-amine) | LC-MS [M + H]⁺/Rt (min): 346.0/0.190 (Method D) |

-continued

| Reference example | Chemical Structure | Instrumental analysis data |
|---|---|---|
| 114 | 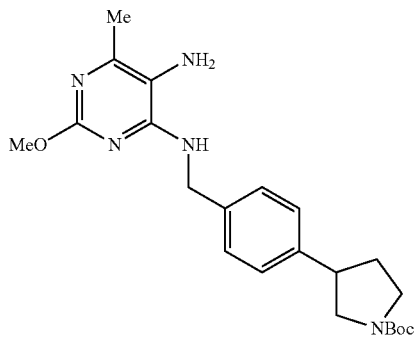 [SMILES: COc1nc(C)c(N)c(NCc2ccc(C3CCN(C(=O)OC(C)(C)C)C3)cc2)n1] | LC-MS ([M + H]$^+$/Rt (min)): 519.42/1.048 (Method D); $^1$H-NMR (400 MHz, CDCl$_3$) δ: 7.31 (2H, d, J = 7.9 Hz), 7.20 (2H, d, J = 7.9 Hz) 5.64 (1H, t, J = 5.5 Hz), 4.63 (2H, d, J = 5.5 Hz), 3.89 (3H, m), 3.87-3.69 (1H, m), 3.66-3.51 (1H, m), 3.43-3.23 (3H, m), 2.30 (3H, s), 2.26-2.20 (1H, m), 2.02-1.91 (1H, m), 1.47 (9H, s). |
| 115 | 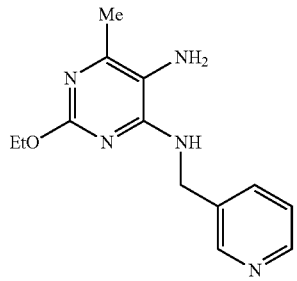 | LC-MS [M + H]$^+$/Rt (min): 260.2/0.409 (Method C); $^1$H-NMR (400 MHz, CDCl$_3$) δ: 8.60-8.58 (1H, m), 8.50 (1H, dd, J = 4.9, 1.2 Hz), 7.68-7.63 (1H, m), 7.24 (1H, dd, J = 7.9, 4.9 Hz), 5.77 (1H, t, J = 6.1 Hz), 4.67 (2H, d, J = 6.1 Hz), 4.27 (2H, q, J = 7.1 Hz), 2.53 (2H, s), 2.29 (3H, s), 1.34 (3H, t, J = 7.1 Hz). |
| 116 | 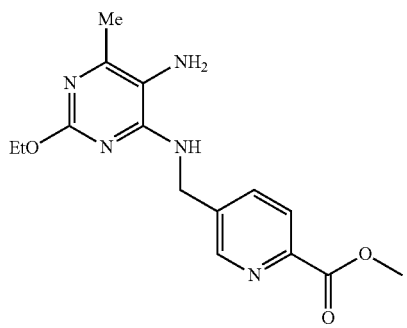 [SMILES: CCOc1nc(C)c(N)c(NCc2ccc(C(=O)OC)nc2)n1] | LC-MS [M + H]$^+$/Rt (min): 318.25/0.501 (Method C); $^1$H-NMR (400 MHz, CDCl$_3$) δ: 9.17 (1H, s), 8.24 (1H, d, J = 8.5 Hz), 7.37 (1H, d, J = 7.9 Hz), 6.42 (1H, t, J = 5.5 Hz), 4.83 (2H, d, J = 5.5 Hz), 4.25 (2H, q, J = 7.1 Hz), 3.95 (3H, s), 2.30 (3H, s), 1.34 (3H, t, J = 7.1 Hz). |
| 117 | 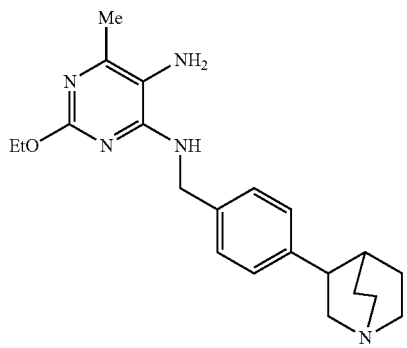 | $^1$H-NMR (400 MHz, CDCl$_3$) δ: 7.31 (2H, d, J = 7.9 Hz), 7.24 (2H, d, J = 7.9 Hz), 5.58 (1H, t, J = 5.5 Hz) 4.63 (2H, d, J = 5.5 Hz), 4.30 (2H, q, J = 7.1 Hz), 3.36-3.26 (1H, m), 3.10-3.02 (1H, m), 3.00-2.82 (5H, m), 2.28 (3H, s), 1.92-1.88 (1H, m), 1.76-1.69 (2H, m), 1.69-1.61 (1H, m), 1.39-1.31 (4H, m). |

| Reference example | Chemical Structure | Instrumental analysis data |
|---|---|---|
| 118 | 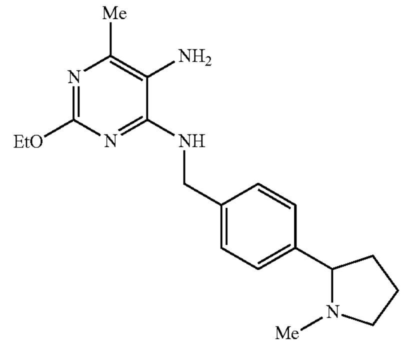 | $^1$H-NMR (400 MHz, CDCl$_3$) δ: 7.28 (2H, d, J = 8.5 Hz), 7.25 (2H, d, J = 8.5 Hz), 4.59 (2H, s), 4.27 (2H, q, J = 7.1 Hz), 3.26-3.19 (1H, m), 3.00 (1H, dd, J = 8.2, 9.0 Hz), 2.26 (1H, dd, J = 9.0, 17.2 Hz), 2.19-2.10 (7H, m), 2.00-1.88 (1H, m), 1.84-1.70 (2H, m), 1.35 (3H, t, J = 7.1 Hz). |
| 119 | 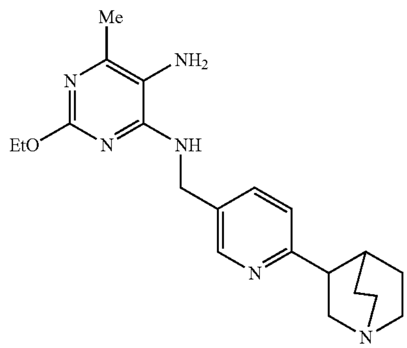 | LC-MS [M + H]$^+$/Rt (min): 369.1/0.138 (Method C); $^1$H-NMR (400 MHz, CDCl$_3$) δ: 8.56 (1H, d, J = 1.8 Hz), 7.61 (1H, dd, J = 1.8, 7.9 Hz), 7.16 (1H, d, J = 7.9 Hz), 5.67 (1H, t, J = 6.1 Hz), 4.65 (2H, d, J = 6.1 Hz), 4.29 (2H, q, J = 7.1 Hz), 3.51-3.44 (1H, m), 3.27-3.19 (1H, m), 3.09-2.86 (4H, m), 2.86-2.76 (1H, m), 2.48 (2H, s), 2.29 (3H, s), 2.07-2.02 (1H, m), 1.81-1.58 (3H, m), 1.39-1.26 (4H, m). |
| 120 | 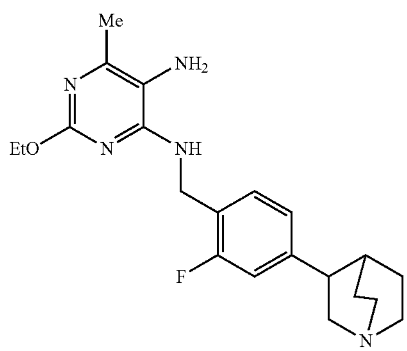 [SMILES: CCOc1nc(C)c(N)c(NCc2ccc(C3CN4CCC3CC4)cc2F)n1] | LC-MS [M + H]$^+$/Rt (min): 386.4/0.418 (Method C); $^1$H-NMR (400 MHz, CDCl$_3$) δ: 7.33 (1H, dd, J = 8.2, 8.6 Hz), 7.02-6.95 (2H, m), 5.64 (1H, t, J = 5.5 Hz), 4.69 (2H, d, J = 5.5 Hz), 4.31 (2H, q, J = 7.1 Hz), 3.35-3.27 (1H, m), 3.05-2.79 (6H, m), 2.48 (2H, s), 2.28 (3H, s), 1.93-1.88 (1H, m), 1.76-1.68 (2H, m), 1.64-1.57 (1H, m), 1.41-1.30 (4H, m). |

Reference Example 121

N'-[2-Ethoxy-8-(5-fluoropyridin-3-yl)-9-(4-hydroxybenzyl)-9H-purin-6-yl]-N,N-dimethylimidoformamide

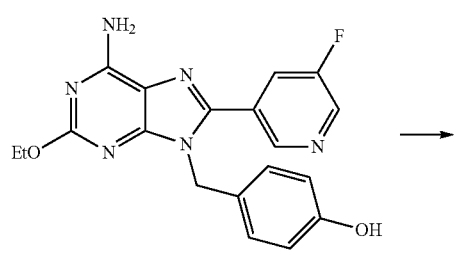

→

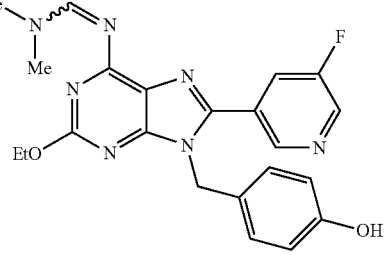

To a solution of the compound of Example 208 (570 mg) in N,N-dimethylformamide (5.0 mL) was added N,N-dimethylformamide dimethyl acetal (0.602 mL), and the mixture was stirred at 60° C. for one hour. To the reaction mixture was added water, and the mixture was extracted with chloroform. The organic layer was washed with brine, dried over sodium sulfate, filtrated, and then concentrated in vacuo to give the title compound (602 mg).

LC-MS [M+H]⁺/Rt (min): 436.4/0.658 (Method B)

Reference Example 122

According to the method of Reference example 121, Reference example 122 was prepared by using the corresponding material compound.

| Reference example | Chemical Structure | Instrumental analysis data |
|---|---|---|
| 122 | *[structure: 2-ethoxy-6-(N,N-dimethylimidoformamide)-8-(5-fluoropyridin-3-yl)-9-(4-bromobenzyl)-9H-purine]* | LC-MS ([M + H]⁺/Rt (min)): 500.3/0.776 (Method C); ¹H-NMR (400 MHz, CD₃OD) δ: 8.95 (1H, s), 8.64 (1H, s), 8.59 (1H, d, J = 2.4 Hz), 7.92-7.88 (1H, m), 7.43 (2H, d, J = 8.5 Hz), 6.97 (2H, d, J = 8.5 Hz), 5.49 (2H, m), 4.43 (2H, q, J = 7.3 Hz), 3.24 (6H, s), 1.39 (3H, t, J = 7.3 Hz). |

Reference Example 123

N'-{2-Ethoxy-8-(5-fluoropyridin-3-yl)-9-[4-(4-methyl-piperazin-1-yl)benzyl]-9H-purin-6-yl}-N,N-dimethylimidoformamide

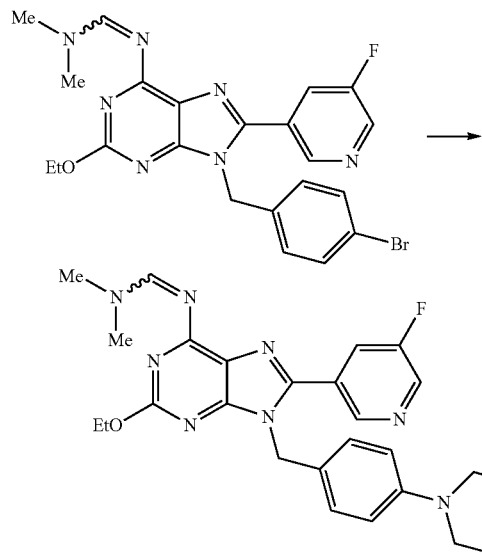

To a solution of the compound of Reference example 122 (80.9 mg) in 1,4-dioxane (2 mL) were added 1-methylpiperazine (0.045 mL), lithium bis(trimethylsilyl)amide (1.3 mol/0.25 mL), tris(dibenzylideneacetone)dipalladium (14.9 mg), and 2-(dicyclohexylphosphino)-2'-(N,N-dimethylamino)biphenyl (6.4 mg), and the mixture was stirred at 35° C. for 4 hours. The reaction mixture was cooled to room temperature. Water was added thereto, and the mixture was extracted with chloroform/methanol. The organic layer was dried over sodium sulfate, filtrated, and then concentrated in vacuo. The residue was purified by silica gel column chromatography (chloroform/methanol) to give the title compound (14.0 mg).

¹H-NMR (400 MHz, CDCl₃) δ: 8.97 (1H, s), 8.73 (1H, s), 8.50 (1H, d, J=3.1 Hz), 7.77-7.72 (1H, m), 6.95 (2H, d, J=8.5 Hz), 6.79 (2H, d, J=8.5 Hz), 5.61 (2H, s), 5.38 (2H, s), 4.46 (2H, q, J=6.5 Hz), 3.19-3.14 (4H, m), 2.61-2.52 (4H, m), 2.38-2.32 (9H, m), 1.44 (3H, t, J=6.5 Hz).

Reference Examples 124-128

According to the method of Example 69, Reference examples 124-128 were prepared by using the corresponding material compounds.

| Reference example | Chemical Structure | Instrumental analysis data |
|---|---|---|
| 124 | *[structure: 6-amino-2-ethoxy-8-bromo-9-[(6-((R)-1-methylpyrrolidin-3-yloxy)pyridin-3-yl)methyl]-9H-purine]* | ¹H-NMR (CDCl₃) δ: 8.24 (1H, d, J = 2.4 Hz), 7.63 (1H, dd, J = 2.4, 8.5 Hz), 6.59 (1H, d, J = 8.5 Hz), 5.41 (3H, br s), 5.21 (2H, s), 4.40 (2H, q, J = 7.0 Hz), 2.88-2.79 (2H, m), 2.73-2.69 (1H, m), 2.37-2.30 (5H, m), 1.99-1.90 (1H, m), 1.43 (3H, t, J = 7.0 Hz). |

-continued

| Reference example | Chemical Structure | Instrumental analysis data |
|---|---|---|
| 125 | (structure: 6-amino-2-ethoxy-8-bromopurine with N9-CH2-pyridine-O-(S)-pyrrolidinyl(N-Me)) | ¹H-NMR (CDCl₃) δ: 8.24 (1H, d, J = 2.4 Hz), 7.63 (1H, dd, J = 2.4, 8.9 Hz), 5.69 (1H, d, J = 8.9 Hz), 5.42-5.38 (3H, m), 5.21 (2H, s), 4.40 (2H, q, J = 7.1 Hz), 2.87-2.79 (2H, m), 2.73-2.69 (1H, m), 2.37-2.32 (5H, m), 1.98-1.92 (1H, m), 1.43 (3H, t, J = 7.3 Hz). |
| 126 | (structure: 6-amino-2-ethoxy-8-bromopurine with N9-CH2-pyridine-O-(S)-quinuclidinyl) | ¹H-NMR (CDCl₃) δ: 8.23 (1H, d, J = 3.1 Hz), 7.67-7.64 (1H, m), 6.68 (1H, d, J = 8.5 Hz), 5.41 (2H, s), 5.21 (2H, s), 5.01-4.97 (1H, m), 4.40 (2H, q, J = 7.1 Hz), 3.36-3.30 (1H, m), 2.98-2.73 (5H, m), 2.14-2.10 (1H, m), 1.98-1.89 (1H, m), 1.75-1.55 (2H, m), 1.45-1.34 (4H, m). |
| 127 | (structure: 6-amino-2-ethoxy-8-bromopurine with N9-CH2-pyridine-O-(R)-quinuclidinyl) | ¹H-NMR (CDCl₃) δ: 8.23 (1H, d, J = 1.8 Hz), 7.65 (1H, dd, J = 2.4, 8.5 Hz), 6.68 (1H, d, J = 8.5 Hz), 5.48 (2H, br s), 5.21 (2H, s), 5.01-4.97 (1H, m), 4.40 (2H, q, J = 7.1 Hz), 3.36-3.30 (1H, 2.98-2.73 (5H, m), 2.14-2.10 (1H, m), 1.98-1.89 (1H, m), 1.75-1.56 (2H, m), 1.44-1.34 (4H, m). |
| 128 | (structure: 6-amino-2-ethoxy-8-bromopurine with N9-CH2-pyridine-O-(CH2)3-N(Me)2) | ¹H-NMR (CDCl₃) δ: 8.26 (1H, d, J = 2.4 Hz), 7.64 (1H, dd, J = 2.4, 8.5 Hz), 6.67 (1H, d, J = 8.5 Hz), 5.43 (2H, s), 5.21 (2H, s), 4.40 (2H, q, J = 7.0 Hz), 4.31 (2H, t, J = 6.4 Hz), 2.40 (2H, t, J = 7.3 Hz), 2.23 (6H, br s), 1.96-1.89 (2H, m), 1.43 (3H, t, J = 7.0 Hz). |

Reference Examples 129-132

According to the method of Example 80, Reference examples 129-132 were prepared by using the corresponding material compounds.

| Reference example | Chemical Structure | Instrumental analysis data |
|---|---|---|
| 129 | (structure: 6-amino-2-ethoxy-8-bromopurine with N9-CH2-pyridine-CH2-N(Me)2) | LC-MS [M]⁺/Rt (min) 405.3/0.531 (Method A) |

| Reference example | Chemical Structure | Instrumental analysis data |
|---|---|---|
| 130 | 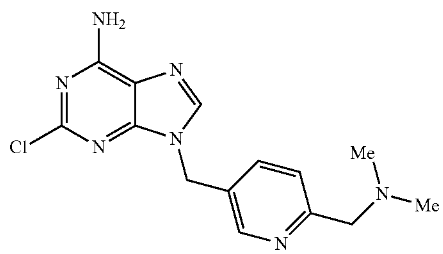 [SMILES: CN(C)Cc1ccc(Cn2cnc3c(N)nc(Cl)nc32)cn1] | $^1$H-NMR (CDCl$_3$) δ: 7.70 (1H, s), 7.32 (2H, d, J = 7.9 Hz), 7.26-7.24 (2H, m), 5.84 (2H, br s), 5.31 (2H, s), 3.43 (2H, s), 2.24 (6H, s). |
| 131 | 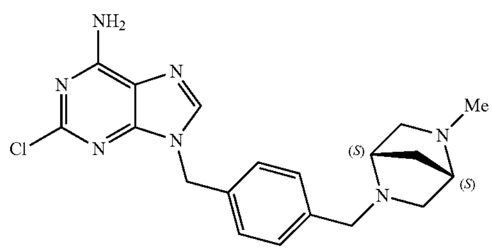 | $^1$H-NMR (DMSO-D$_6$) δ: 8.23 (1H, s), 7.76 (2H, br s), 7.28 (2H, d, J = 7.9 Hz), 7.19 (2H, d, J = 7.9 Hz), 5.29 (2H, s), 3.59 (2H, q, J = 13.6 Hz), 3.15 (1H, s), 3.07 (1H, s), 2 64 (1H, d, J = 9.2 Hz), 2.55-2.44 (3H, m), 2.22 (3H, s), 1.56 (2H, s). |
| 132 | 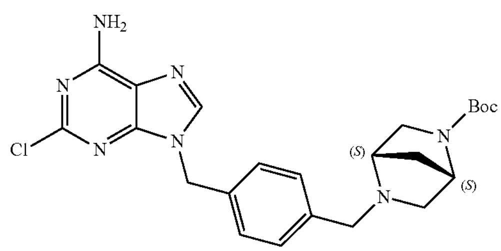 | LC-MS [M + H]$^+$/Rt (min): 470.4/0.600 (Method B) |

Reference Example 133

Methyl 4-{[6-chloro-2-ethoxy-8-(5-fluoropyridin-3-yl)-9H-purin-9-yl]methyl}benzoate

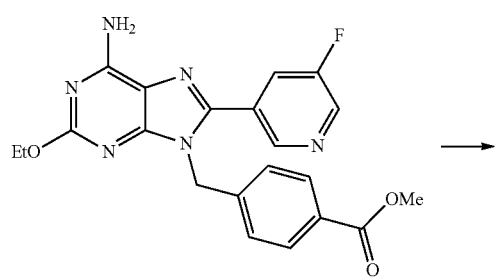

→

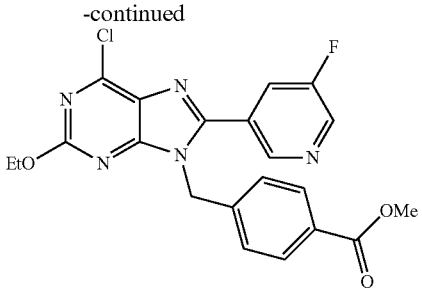

To a solution of the compound of Example 182 (1.93 g) in dichloromethane (30 mL) were added benzyltriethylammonium chloride (2.08 g), chlorotrimethylsilane (5.79 mL), and tert-butyl nitrite (3.00 mL), and the mixture was stirred under reflux for 3 hours. To the reaction mixture in ice bath was added aqueous saturated sodium bicarbonate, and the mixture was extracted with chloroform. The organic layer was dried over sodium sulfate, filtrated, and then concentrated in vacuo. The residue was purified by silica gel column chromatography (chloroform/methanol) to give the title compound (1.57 g).

LC-MS [M+H]⁺/Rt (min): 442.4/1.029 (Method A)

Reference Examples 134-135

According to the method of Reference example 133, Reference examples 134-135 were prepared by using the corresponding material compounds.

| Reference example | Chemical Structure | Instrumental analysis data |
|---|---|---|
| 134 | 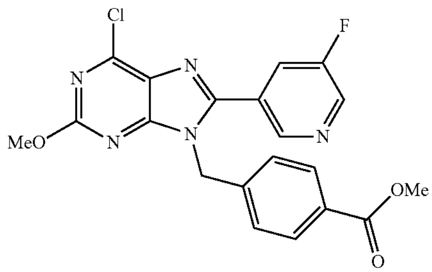 | LC-MS [M + H]⁺/Rt (min): 428.3/0.972 (Method A) |
| 135 | 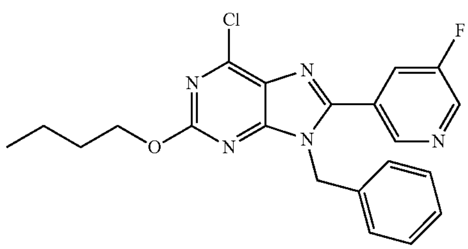 [SMILES: CCCCOc1nc(Cl)c2nc(-c3cncc(F)c3)n(Cc3ccccc3)c2n1] | $^1$H-NMR (400 MHz, DMSO-d$_6$) δ: 8.77 (1H, d, J = 2.7 Hz), 8.75-8.74 (1H, m), 8.10-8.06 (1H, m), 7.29-7.23 (2H, m), 7.06-7.03 (2H, m), 5.60 (2H s), 4.38 (2H, t, J = 6.6 Hz), 1.71 (2H, tt, J = 6.6, 7.9 Hz), 1.40 (2H, qt, J = 7.3, 7.9 Hz), 0.93 (3H, t, J = 7.3 Hz). |

Reference Examples 136-141

According to the method of Example 150, Reference examples 136-141 were prepared by using the corresponding material compounds. As appropriate, microwave irradiation was used.

| Reference example | Chemical Structure | Instrumental analysis data |
|---|---|---|
| 136 | 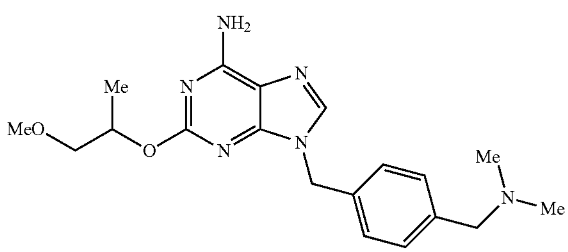 [SMILES: COCC(C)Oc1nc(N)c2ncn(Cc3ccc(CN(C)C)cc3)c2n1] | LC-MS [M + H]⁺/Rt (min): 371.3/0.507 (Method B) |
| 137 | 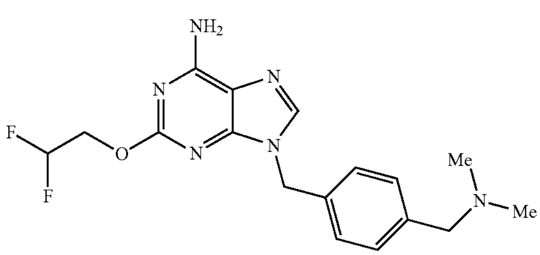 [SMILES: CN(C)Cc1ccc(Cn2cnc3c(N)nc(OCC(F)F)nc32)cc1] | $^1$H-NMR (CDCl$_3$) δ: 7.64 (1H, s), 7.33 (2H, d, J = 7.9 Hz), 7.26-7.24 (2H, m), 6.13 (1H, tt, J = 55.8, 4.3 Hz), 5.57 (2H, br s), 5.26 (2H, s), 4.55 (2H, td, J = 13.1, 4.3 Hz), 3.47 (2H, s), 2.27 (6H, s). |

| Reference example | Chemical Structure | Instrumental analysis data |
|---|---|---|
| 138 | (2-cyclopropylmethoxy-9-{4-[(dimethylamino)methyl]benzyl}-9H-purin-6-amine) | ¹H-NMR (CDCl₃) δ: 7.58 (1H, s), 7.30 (2H, d, J = 7.9 Hz), 7.26-7.24 (2H, m), 5.47 (2H, br s), 5.25 (2H, s), 4.16 (2H, d, J = 6.7 Hz), 3.44 (2H, s), 2.25 (6H, s), 1.35-1.28 (1H, m), 0.61-0.57 (2H, m), 0.38-0.34 (2H, m). |
| 139 | (9-{4-[(dimethylamino)methyl]benzyl}-2-propoxy-9H-purin-6-amine) | ¹H-NMR (CDCl₃) δ: 7.58 (1H, s), 7.29-7.24 (4H, m), 5.47 (2H, s), 5.25 (2H, s), 4.29 (2H, t, J = 6.7 Hz), 3.40 (2H, s), 2.22 (6H, s), 1.87-1.78 (2H, m), 1.04 (3H, t, J = 7.2 Hz). |
| 140 | (2-methoxy-9-{4-[(5-methyl-2,5-diazabicyclo[2.2.1]heptan-2-yl)oxy]benzyl}-9H-purin-6-amine) | ¹H-NMR (CDCl₃) δ: 7.59 (1H, s), 7.32 (2H, d, J = 7.9 Hz), 7.26-7.23 (2H, m), 5.51 (2H, s), 5.25 (2H, s), 3.97 (3H, s), 3.74-3.64 (2H, m), 3.25-3.20 (2H, m), 2.87 (1H, d, J = 9.8 Hz), 2.73-2.57 (3H, m), 2.39 (3H, s), 1.72 (2H, s). |
| 141 | (Boc-protected analog) | LC-MS [M + H]⁺/Rt (min): 466.5/0.581 (Method B) |

Reference Examples 142-145

According to the method of Reference example 2, Reference examples 142-145 were prepared by using the corresponding material compounds.

| Reference example | Chemical Structure | Instrumental analysis data |
|---|---|---|
| 142 | (9-(3-cyanobenzyl)-2-ethoxy-9H-purin-6-amine) | LC-MS [M + H]⁺/Rt (min): 294.96/0.590 (Method C); ¹H-NMR (CDCl₃) δ: 7.65-7.59 (3H, m), 7.56-7.51 (1H, m), 7.50-7.45 (1H, m), 5.63 (2H, s), 5.32 (2H, s), 4.39 (2H, q, J = 7.1 Hz), 1.42 (3H, t, J = 7.1 Hz). |

-continued

| Reference example | Chemical Structure | Instrumental analysis data |
|---|---|---|
| 143 | (purine with NH2, EtO, 9-benzyl bearing 2-OCHF2) | LC-MS [M + H]+/Rt (min): 337.2/0.845 (Method A); 1H-NMR (CDCl3) δ: 7.69 (1H, s), 7.39-7.30 (2H, m), 7.21-7.11 (2H, m), 5.63 (2H, s), 6.62 (1H, t, J = 73.4 Hz), 5.35 (2H, s), 4.40 (2H, q, J = 7.1 Hz), 1.42 (3H, t, J = 7.1 Hz). |
| 144 | (purine with NH2, EtO, 9-(2,5-difluorobenzyl)) | LC-MS [M + H]+/Rt (min): 305.9/0.673 (method C); 1H-NMR (CDCl3) δ: 7.68 (1H, s), 7.10-6.94 (3H, m), 5.54 (2H, s), 5.29 (2H, s), 4.40 (2H, q, J = 7.1 Hz), 1.42 (3H, t, J = 7.1 Hz). |
| 145 | (purine with NH2, EtO, 9-(3-cyano-4-fluorobenzyl)) | LC-MS [M + H]+/Rt (min): 313.5/0.688 (method A); 1H-NMR (CDCl3) δ: 7.69-7.66 (2H, m), 7.66-7.61 (1H, m), 7.22 (1H, dd, J = 8.8, 8.8 Hz), 5.60 (2H, s), 5.34 (2H, s), 4.39 (2H, q, J = 7.0 Hz), 1.42 (3H, t, J = 7.0 Hz). |

Reference Examples 146-147

According to the method of Reference example 26, Reference examples 146-147 were prepared by using the corresponding material compounds.

| Reference example | Chemical Structure | Instrumental analysis data |
|---|---|---|
| 146 | (methyl 2-methoxy-6-(quinuclidin-3-yl)nicotinate) | LC-MS [M + H]+/Rt (min): 275.1/0.389 (Method C) |
| 147 | (methyl 4-methyl-6-(quinuclidin-3-yl)nicotinate) | LC-MS [M + H]+/Rt (min): 259.1/0.394 (Method C) |

Reference Examples 143-149

According to the method of Reference example 30, Reference examples 148-149 were prepared by using the corresponding material compounds.

| Reference example | Chemical Structure | Instrumental analysis data |
|---|---|---|
| 148 | MeO-C(=O)-pyridine(OMe)-quinuclidine | LC-MS [M + H]⁺/Rt (min): 277.1/0.377 (Method C) |
| 149 | MeO-C(=O)-pyridine(Me)-quinuclidine | LC-MS [M + H]⁺/Rt (min): 261.1/0.409 (Method C) |

Reference Examples 150-153

According to the method of Reference example 36, Reference examples 150-153 were prepared by using the corresponding material compounds.

| Reference example | Chemical Structure | Instrumental analysis data |
|---|---|---|
| 150 | 6-NH₂, 2-EtO, 8-Br purine with 3-cyanobenzyl at N9 | ¹H-NMR (CDCl₃) δ: 7.66 (1H, s), 7.64-7.58 (2H, m), 7.50-7.44 (1H, m), 5.70 (2H, s), 5.33 (2H, s), 4.39 (2H, q, J = 7.1 Hz), 1.43 (3H, t, J = 7.1 Hz). |
| 151 | 6-NH₂, 2-EtO, 8-Br purine with 2-(OCHF₂)benzyl at N9 | LC-MS [M + H]⁺/Rt (min): 416.16/0.985 (Method A); ¹H-NMR (CDCl₃) δ: 7.35-7.30 (1H, m), 7.20-7.11 (2H, m), 6.92 (1H, d, J = 7.9 Hz), 6.66 (1H, t, J = 73.4 Hz), 5.58 (2H, s), 5.42 (2H, s), 4.35 (2H, q, J = 7.1 Hz), 1.39 (3H, t, J = 7.1 Hz). |
| 152 | 6-NH₂, 2-EtO, 8-Br purine with 2,5-difluorobenzyl at N9 | LC-MS [M + H]⁺/Rt (min): 385.8/0.310 (method A); ¹H-NMR (CDCl₃) δ: 7.09-7.02 (1H, m), 7.00-6.92 (1H, m), 6.80-6.74 (1H, m), 5.72 (2H, s), 5.34 (2H, s), 4.36 (2H, q, J = 7.1 Hz), 1.39 (3H, t, J = 7.1 Hz). |

| Reference example | Chemical Structure | Instrumental analysis data |
|---|---|---|
| 153 | (structure: 2-ethoxy-6-amino-8-bromo-9-[(2-fluoro-5-cyanobenzyl)]purine) | LC-MS [M + H]⁺/Rt (min): 393.1/0.834 (method A); ¹H-NMR (CDCl₃) δ: 7.65-7.60 (1H, m), 7.42 (1H, d, J = 5.9 Hz), 7.25-7.19 (1H, m), 5.58 (2H, s), 5.38 (2H, s), 4.35 (2H, q, J = 6.9 Hz), 1.40 (3H, t, J = 6.9 Hz). |

Reference Examples 154-164

According to the method of Reference example 69, Reference examples 154-161 were prepared by using the corresponding material compounds.

| Reference example | Chemical Structure | Instrumental analysis data |
|---|---|---|
| 154 | (structure with Me, NO₂, MeO, Boc, N-benzyl with MeO and Br substituents) | LC-MS [M + H]⁺/Rt (min): 497.2/1.296 (Method C); ¹H-NMR (CDCl₃) δ: 7.20 (1H, d, J = 8.2 Hz), 7.02 (1H, dd, J = 8.2, 1.8 Hz), 6.94 (1H, d, J = 1.8 Hz), 5.08 (2H, s), 4.32 (2H, q, J = 7.0 Hz), 3.70 (3H, s), 2.60 (3H, s), 1.36 (9H, s), 1.34 (3H, t, J = 7.3 Hz). |
| 155 | (structure with Me, NO₂, MeO, Boc, N-benzyl with F and CO₂Me substituents) | LC-MS ([M + H]⁺/Rt (min)): 451.4/1.212 (Method A) |
| 156 | (structure with Me, NO₂, MeO, Boc, N-benzyl with F and CHO substituents) | LC-MS ([M + H]⁺/Rt (min)): 421.4/1.130 (Method A) |

-continued
| Reference example | Chemical Structure | Instrumental analysis data |
|---|---|---|
| 157 | 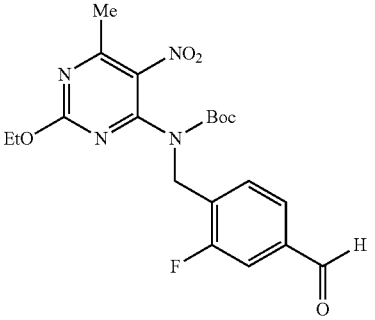 [SMILES: CCOc1nc(C)c([N+](=O)[O-])c(N(Cc2ccc(C=O)cc2F)C(=O)OC(C)(C)C)n1] | LC-MS [M + H]+/Rt (min): 435.4/1.186 (Method A) |
| 158 | 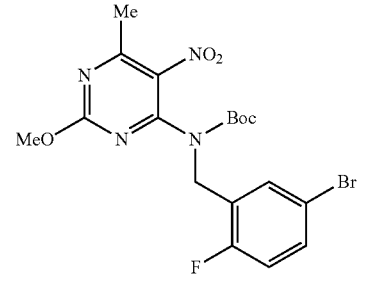 | LC-MS [M + H]+/Rt (min): 471.3/1.284 (Method A) |
| 159 | 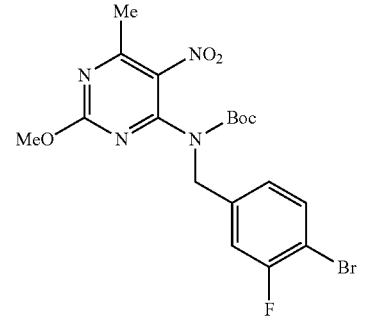 [SMILES: COc1nc(C)c([N+](=O)[O-])c(N(Cc2ccc(Br)c(F)c2)C(=O)OC(C)(C)C)n1] | LC-MS [M + H]+/Rt (min): 471.1/1.245 (Method C) |
| 160 | 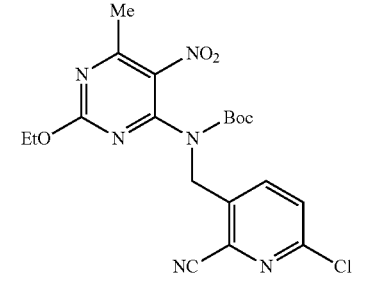 [SMILES: CCOc1nc(C)c([N+](=O)[O-])c(N(Cc2ccc(Cl)nc2C#N)C(=O)OC(C)(C)C)n1] | LC-MS [M + H]+/Rt (min): 449.2/1.161 (Method C) |
| 161 | 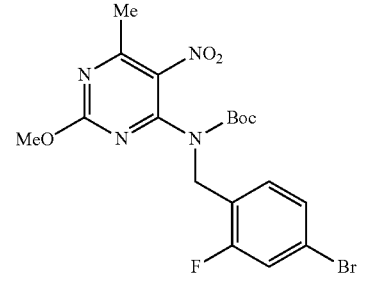 [SMILES: COc1nc(C)c([N+](=O)[O-])c(N(Cc2ccc(Br)cc2F)C(=O)OC(C)(C)C)n1] | LC-MS [M + H]+/Rt (min): 471.3/1.259 (Method C) |

| Reference example | Chemical Structure | Instrumental analysis data |
|---|---|---|
| 162 | (Me, NO₂, EtO, N-Boc, pyridine with Cl, F substituted pyrimidine) | LC-MS [M + H]⁺/Rt (min): 442.3/1.182 (Method C) |
| 163 | (Me, NO₂, EtO pyrimidine, N-Boc, benzyl with CN and Br) | LC-MS [M + H]⁺/Rt (min): 492.3/1.246 (Method C) |
| 164 | (Me, NO₂, MeO pyrimidine, N-Boc, 3-bromobenzyl) | LC-MS [M + H]⁺/Rt (min): 453.2/1.235 (Method C) |

Reference Examples 165-166

According to the method of Reference example 77, Reference examples 165-166 were prepared by using the corresponding material compounds.

| Reference example | Chemical Structure | Instrumental analysis data |
|---|---|---|
| 165 | (HO-CH₂-pyridine with MeO, quinuclidine substituent) | LC-MS [M + H]⁺/Rt (min): 249.1/0.305 (Method C); (CDCl₃) δ: 7.47 (1H, d, J = 7.3 Hz), 6.73 (1H, d, J = 7.3 Hz), 4.60 (2H, s), 3.98 (3H, s), 3.61-3.52 (1H, m), 3.20-3.05 (2H, m), 3.02-2.80 (4H, m), 2.00-1.95 (1H, m), 1.86-1.65 (3H, m), 1.37-1.27 (1H, m). |
| 166 | (HO-CH₂-pyridine with Me, quinuclidine substituent) | LC-MS [M + H]⁺/Rt (min): 233.1/0.148 (Method C) |

Reference Example 167

Ethyl 2-fluoro-4-(oxiran-2-yl)benzoate

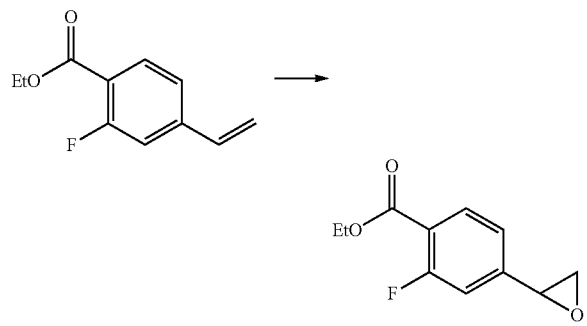

To an ice-cooled solution of ethyl 2-fluoro-4-vinylbenzoate (1.30 g) in dichloromethane (50 mL) was added 3-chloroperbenzoic acid (2.66 and the mixture was stirred at room temperature overnight. To the reaction mixture were added aqueous sodium bicarbonate and aqueous saturated sodium thiosulfate, and the mixture was extracted with chloroform. The organic layer was washed with aqueous saturated sodium bicarbonate, dried over sodium sulfate, filtrated, and then concentrated in vacuo. The residue was purified by silica gel column chromatography (hexane/ethyl acetate) to give the title compound (1.36 g).

$^1$H-NMR (CDCl$_3$) δ: 7.89 (1H, dd, J=7.9 Hz), 7.11 (1H, dd, J=1.8, 7.9 Hz), 7.02 (1H, dd, J=1.8, 11.3 Hz), 4.37 (2H, q, J=7.1 Hz), 3.86 (1H, dd, J=2.4, 4.0 Hz), 3.16 (1H, dd, J=4.0, 5.5 Hz), 2.73 (1H, dd, J=2.4, 5.5 Hz), 1.37 (3H, t, J=7.1).

Reference Example 168

Ethyl 2-fluoro-4-{1-hydroxy-2-[(2-hydroxyethyl)amino]ethyl}benzoate

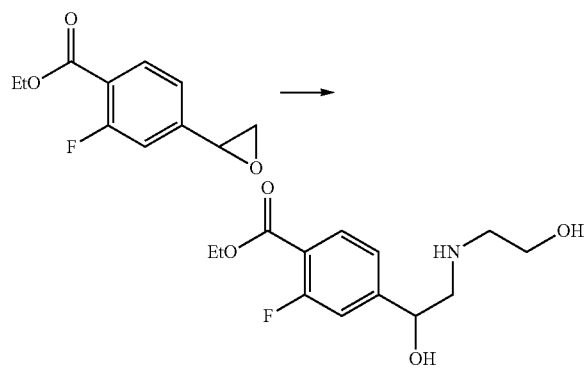

To a solution of the compound of Reference example 167 (1.36 g) in tetrahydrofuran (50 mL) was added 2-aminoethanol (3.9 mL), and the mixture was stirred at room temperature for one day, and then at 60° C. for 12 hours. To the reaction mixture was added aqueous sodium bicarbonate, and the mixture was extracted with a mixture of chloroform and ethanol. The organic layer was washed with aqueous saturated sodium bicarbonate, dried over sodium sulfate, fil- trated, and then concentrated in vacuo. The residue was purified by silica gel column chromatography (chloroform/methanol) to give the title compound (1.36 g).

LC-MS [M+H]$^+$/Rt (min): 272.2/0.486 (Method A)

Reference Example 169

Ethyl 4-(2-{[(benzyloxy)carbonyl](2-hydroxyethyl)amino}-1-hydroxyethyl)-2-fluorobenzoate

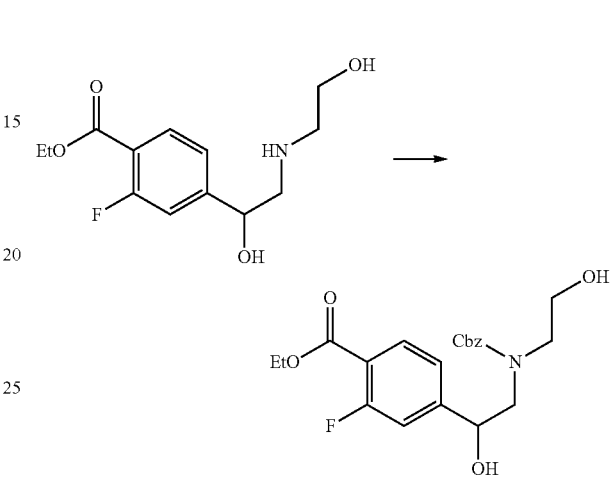

To a solution of the compound of Reference example 168 (1.15 g) in a mixture of tetrahydrofuran (20 mL) and water (10 mL) were added sodium bicarbonate (0.535 mg) and benzyl chloroformate (0.893 mL), and the mixture was stirred at room temperature overnight. To the reaction mixture was added aqueous saturated sodium bicarbonate, and the mixture was extracted with chloroform. The organic layer was dried over sodium sulfate, filtrated, and then concentrated in vacuo. The residue was purified by silica gel column chromatography (chloroform/methanol) to give the title compound (913 mg).

LC-MS [M+H]$^+$/Rt. (min): 406.3/0.887 (Method A)

Reference Example 170

Benzyl 2-[4-(ethoxycarbonyl)-3-fluorophenyl]morpholine-4-carboxylate

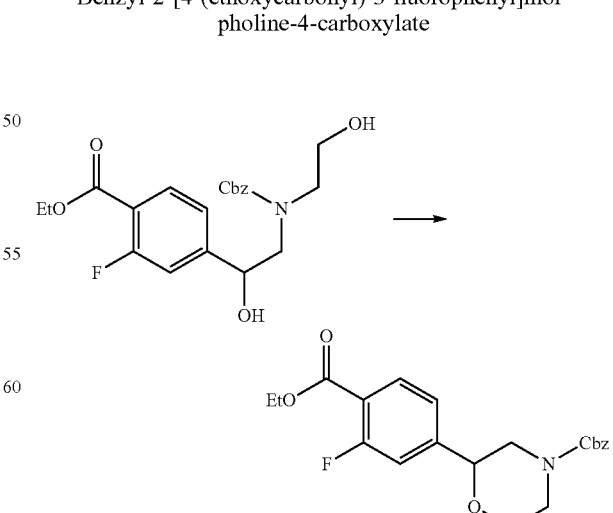

To a solution of the compound of Reference example 169 (910 mg) in toluene (45 mL) were added triphenylphosphine (913 mg) and diisopropyl azodicarboxylate (0.665 mL), and the mixture was stirred at room temperature for 20 hours. The reaction mixture was concentrated in vacuo, and then the obtained residue was purified by silica gel column chromatography (hexane/ethyl acetate) to give the title compound (583 mg).

LC-MS [M+H]$^+$/Rt (min): 388.2/1.145 (Method A)

Reference Example 171

[2-Fluoro-4-(4-methylmorpholin-2-yl)phenyl]methanol

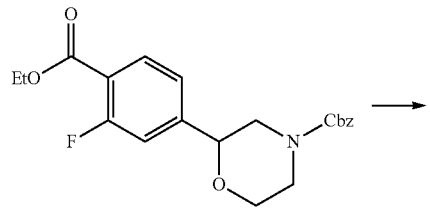

→

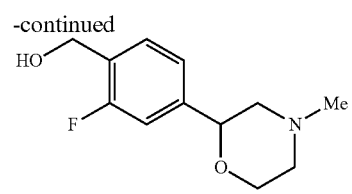

To an ice-cooled solution of the compound of Reference example 170 (581 mg) in tetrahydrofuran (45 mL) was added diisobutylaluminum hydride (1.02 mol/L hexane solution, 3.38 mL), and the mixture was stirred for one hour. Further, diisobutylaluminum hydride (1.02 mol/L hexane solution, 9.0 mL) was added thereto, and the mixture was stirred in ice bath for 5 hours. To the reaction mixture in ice bath were slowly added water (0.47 mL), aqueous sodium hydroxide (4 mol/L, 0.47 mL), and water (1.41 mL), and the mixture was stirred at room temperature for 15 minutes. The reaction mixture was filtered and concentrated in vacuo. The residue was purified by silica gel column chromatography (chloroform/methanol) to give the title compound (177 mg).

LC-MS [M+H]$^+$/Rt (min): 226.1/0.346 (Method A)

Reference Examples 172-185

According to the method of Reference example 83, Reference examples 172-185 were prepared by using the corresponding material compounds.

| Reference example | Chemical Structure | Instrumental analysis data |
|---|---|---|
| 172 | (pyrimidine with Me, NO$_2$, MeO, N-Boc, CH$_2$-(2-fluorophenyl)-quinuclidine) | $^1$H-NMR (CDCl$_3$) δ: 7.44 (1H, dd, J = 11.6, 7.9 Hz), 7.02 (1H, d, J = 7.9 Hz), 6.95 (1H, d, J = 11.6 Hz), 5.25 (2H, s), 3.98 (3H, s), 3.37-3.28 (1H, m), 3.07-2.98 (1H, m), 2.98-2.81 (5H, m), 2.63 (3H, s), 1.93-1.87 (1H, m), 1.76-1.66 (2H, m), 1.65-1.57 (1H, m), 1.44-1.31 (10H, m). |
| 173 | (pyrimidine with Me, NO$_2$, EtO, N-Boc, CH$_2$-(6-methylpyridin-3-yl)-quinuclidine) | LC-MS [M + H]$^+$/Rt (min): 513.4/0.908 (Method A); $^1$H-NMR (CDCl$_3$) δ: 7.62 (1H, d, J = 7.9 Hz), 7.03 (1H, d, J = 7.9 Hz), 5.18 (2H, s), 4.33 (2H, q, J = 7.1 Hz), 3.51-3.44 (1H, m), 3.27-3.17 (1H, m), 3.09-2.98 (2H, m), 2.98-2.89 (2H, m), 2.89-2.75 (1H, m), 2.64 (3H, s), 2.59 (3H, s), 2.05-1.99 (1H, m), 1.71-1.59 (3H, m), 1.42-1.24 (13H, m). |

-continued
| Reference example | Chemical Structure | Instrumental analysis data |
|---|---|---|
| 174 | 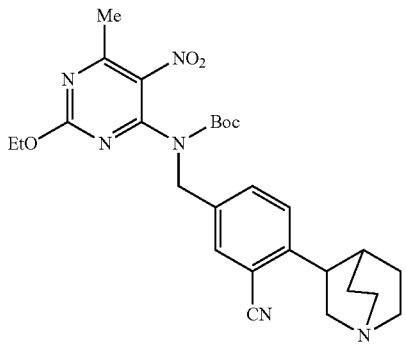 [SMILES: CCOc1nc(C)c([N+](=O)[O-])c(N(Cc2ccc(C3CN4CCC3CC4)c(C#N)c2)C(=O)OC(C)(C)C)n1] | ¹H-NMR (CDCl₃) δ: 7.72-7.56 (1H, m), 7.55-7.51 (1H, m), 5.17 (2H, s), 4.42 (2H, q, J = 7.1 Hz), 3.47-3.40 (1H, m), 3.40-3.30 (1H, m), 3.17-3.06 (1H, m), 3.06-2.86 (4H, m), 2.65 (3H, s), 1.94-1.83 (2H, m), 1.79-1.68 (1H, m), 1.61-1.50 (1H, m), 1.46-1.34 (13H, m). |
| 175 | 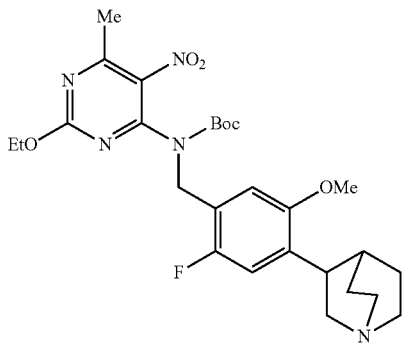 [SMILES: CCOc1nc(C)c([N+](=O)[O-])c(N(Cc2cc(OC)c(C3CN4CCC3CC4)cc2F)C(=O)OC(C)(C)C)n1] | LC-MS [M + H]⁺/Rt (min): 546.5/0.941 (Method A); ¹H-NMR (CDCl₃) δ: 7.06 (1H, d, J = 6.7 Hz), 6.97 (1H, d, J = 11.6 Hz), 5.29 (2H, s), 4.41 (2H, q, J = 7.1 Hz), 3.77 (3H, s), 3.37-3.28 (1H, m), 3.28-3.23 (1H, m), 3.00-2.89 (3H, m), 2.88-2.77 (2H, m), 2.63 (3H, s), 1.91-1.85 (1H, m), 1.75-1.62 (3H, m), 1.45 (9H, s), 1.43-1.35 (4H, m). |
| 176 | 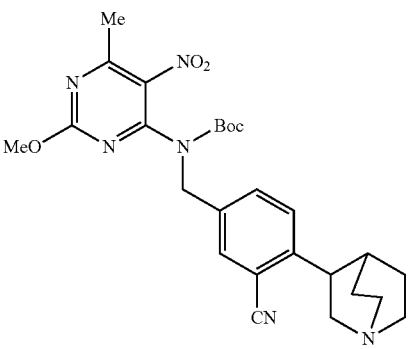 [SMILES: COc1nc(C)c([N+](=O)[O-])c(N(Cc2ccc(C3CN4CCC3CC4)c(C#N)c2)C(=O)OC(C)(C)C)n1] | ¹H-NMR (CDCl₃) δ: 7.73 (1H, s), 7.57-7.46 (2H, m), 5.18 (2H, s), 4.02 (3H, s), 3.48-3.41 (1H, m), 3.39-3.31 (1H, m), 3.15-3.08 (1H, m), 3.07-2.89 (4H, m), 2.66 (3H, s), 1.90-1.84 (2H, m), 1.80-1.71 (1H, m), 1.61-1.50 (1H, m), 1.46-1.35 (10H, m). |
| 177 | 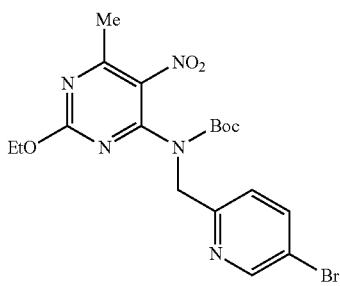 [SMILES: CCOc1nc(C)c([N+](=O)[O-])c(N(Cc2ccc(Br)cn2)C(=O)OC(C)(C)C)n1] | LC-MS [M + H]⁺/Rt (min): 468.3/1.324 (Method A); ¹H-NMR (CDCl₃) δ: 8.59 (1H, d, J = 2.4 Hz), 7.81 (1H, dd, J = 8.5, 2.4 Hz), 7.37 (1H, d, J = 8.5 Hz), 5.26 (2H, s), 4.29 (2H, q, J = 7.1 Hz), 2.65 (3H, s), 1.41 (9H, s), 1.34 (3H, t, J = 7.1 Hz). |

-continued

| Reference example | Chemical Structure | Instrumental analysis data |
|---|---|---|
| 178 | (structure: 2-methoxy-6-methyl-5-nitro-4-[Boc-N-((5-bromopyridin-2-yl)methyl)amino]pyrimidine) | LC-MS [M + H]⁺/Rt (min): 456.2/1.288 (Method A); ¹H-NMR (CDCl₃) δ: 8.59 (1H, d, J = 2.4 Hz), 7.81 (1H, dd, J = 8.5, 2.4 Hz), 7.37 (1H, d, J = 8.5 Hz), 5.27 (2H, s), 3.90 (3H, s), 2.66 (3H, s), 1.41 (9H, s). |
| 179 | (structure: 2-ethoxy-6-methyl-5-nitro-4-[Boc-N-((6-methoxy-5-(quinuclidin-3-yl)pyridin-3-yl)methyl...) pyrimidine with pyridyl-quinuclidine substituent] | LC-MS [M + H]⁺/Rt (min): 529.4/0.873 (Method C) |
| 180 | (structure: 2-ethoxy-6-methyl-5-nitro-pyrimidine with Boc-N-(2-fluoro-4-(4-methylmorpholin-2-yl)benzyl)amino) | LC-MS ([M + H]⁺/Rt (min)): 506.3/0.866 (Method A) |
| 181 | (structure: 2-ethoxy-6-methyl-5-nitro-pyrimidine with Boc-N-((4-methyl-6-(quinuclidin-3-yl)pyridin-3-yl)methyl)amino) | LC-MS [M + H]⁺/Rt (min): 513.4/0.787 (Method C) |

| Reference example | Chemical Structure | Instrumental analysis data |
|---|---|---|
| 182 | 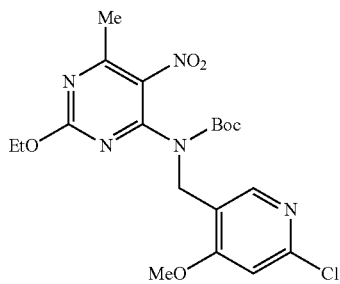 [SMILES: CCOc1nc(C)c([N+](=O)[O-])c(N(Cc2cnc(Cl)cc2OC)C(=O)OC(C)(C)C)n1] | LC-MS [M + H]⁺/Rt (min): 454.2/1.082 (Method C) |
| 183 | 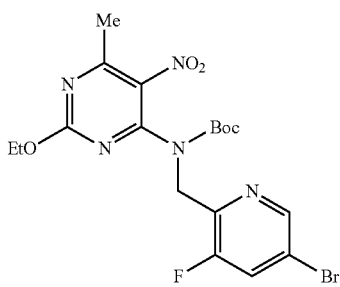 [SMILES: CCOc1nc(C)c([N+](=O)[O-])c(N(Cc2ncc(Br)cc2F)C(=O)OC(C)(C)C)n1] | LC-MS [M + H]⁺/Rt (min): 486.2/1.207 (Method C); ¹H-NMR (CDCl₃) δ 8.37-8.34 (1H, m), 7.58-7.53 (1H, m), 5.23-5.21 (2H, m), 4.14 (2H, q, J = 7.2 Hz), 2.60 (3H, s), 1.40 (9H s), 1.25 (3H, t, J = 7.2 Hz). |
| 184 | 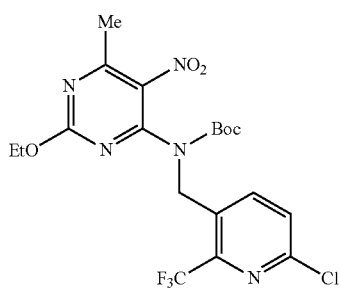 [SMILES: CCOc1nc(C)c([N+](=O)[O-])c(N(Cc2ccc(Cl)nc2C(F)(F)F)C(=O)OC(C)(C)C)n1] | LC-MS [M + H]⁺/Rt (min): 492.3/1.275 (Method C) |
| 185 | 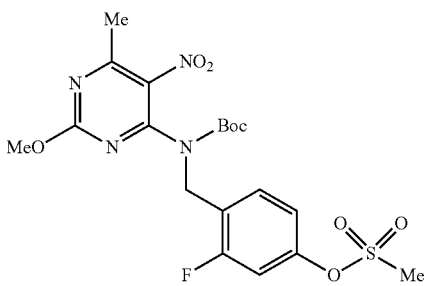 [SMILES: COc1nc(C)c([N+](=O)[O-])c(N(Cc2ccc(OS(C)(=O)=O)cc2F)C(=O)OC(C)(C)C)n1] | LC-MS [M + H]⁺/Rt (min): 487.3/1.065 (Method C) |

Reference Examples 186-187

According to the methods Examples 352 and 365, Reference examples 186-187 were prepared by using the corresponding material compounds.

| Reference example | Chemical Structure | Instrumental analysis data |
|---|---|---|
| 186 | 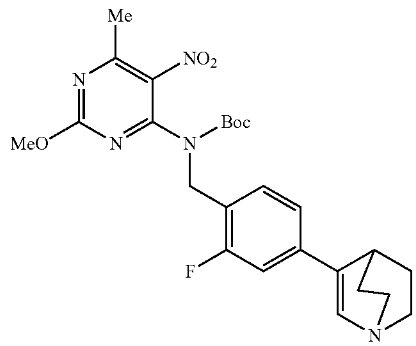 [SMILES: COc1nc(C)c([N+](=O)[O-])c(N(Cc2ccc(C3=CN4CCC3CC4)cc2F)C(=O)OC(C)(C)C)n1] | LC-MS [M + H]$^+$/Rt (min): 500.4/0.708 (Method C) |
| 187 | 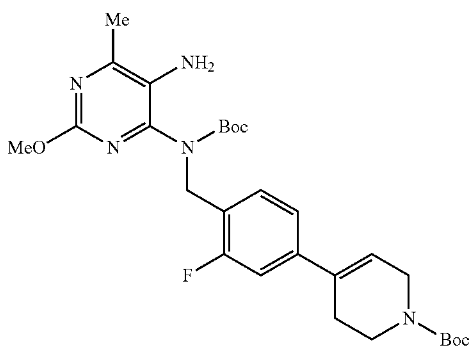 [SMILES: COc1nc(C)c(N)c(N(Cc2ccc(C3=CCN(C(=O)OC(C)(C)C)CC3)cc2F)C(=O)OC(C)(C)C)n1] | LC-MS [M + H]$^+$/Rt (min): 444.4/0.721 (Method C) |

Reference Examples 188-189

According to the method of Example 80, Reference examples 188-189 were prepared by using the corresponding material compounds.

| Reference example | Chemical Structure | Instrumental analysis data |
|---|---|---|
| 188 | 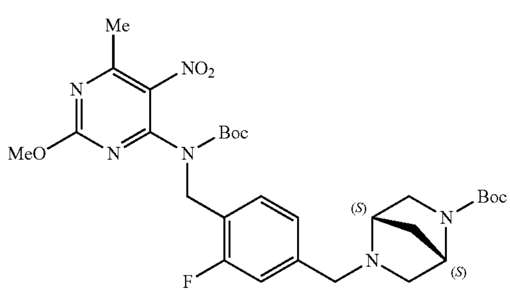 | LC-MS ([M + H]$^+$/Rt (min)): 603.5/0.880 (Method A) |

| Reference example | Chemical Structure | Instrumental analysis data |
|---|---|---|
| 189 | 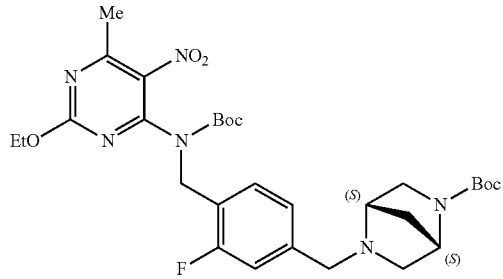 | LC-MS ([M + H]⁺/Rt (min)): 617.5/0.0932 (Method A) |

Reference Example 190, Reference Example 191

N-(4-Bromo-2-fluorobenzyl)-2-methoxy-6-methyl-5-nitropyrimidine-4-amine; 4-[(4-bromo-2-fluorobenzyl)amino]-6-methyl-5-nitropyrimidin-2-ol

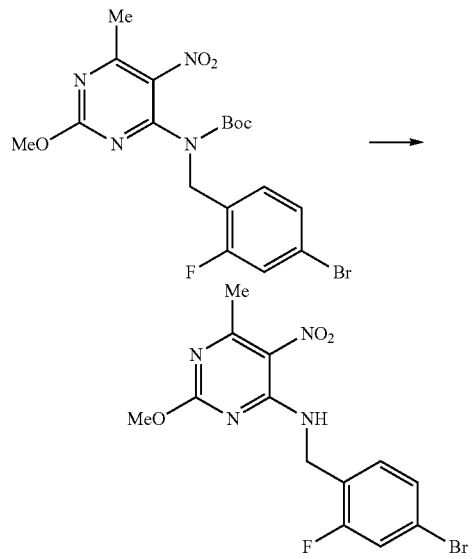

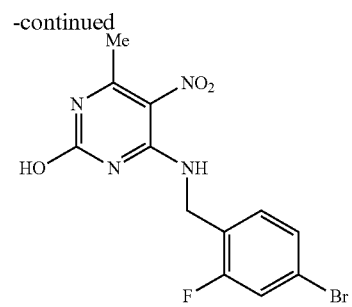

To an ice-cooled solution of the compound of Reference example 161 (4.6 g) in ethyl acetate (10 mL) was added a solution of hydrochloric acid in ethyl acetate (4 mol/L, 49 mL), and the mixture was stirred at room temperature for 2 hours, and at 50° C. for 2 hours. The reaction mixture was cooled to room temperature, and then the solvent was removed under reduced pressure to give the two title compounds (4.7 g) as a mixture.

Reference example 190: LC-MS [M+H]⁺/Rt (min): 370.9/1.008

Reference example 191: LC-MS [M+H]⁺/Rt (min): 357.0/0.709

Reference Examples 192-218

According to the method of Reference example 91, Reference examples 192-218 were prepared by using the corresponding material compounds.

| Reference example | Chemical Structure | Instrumental analysis data |
|---|---|---|
| 192 | 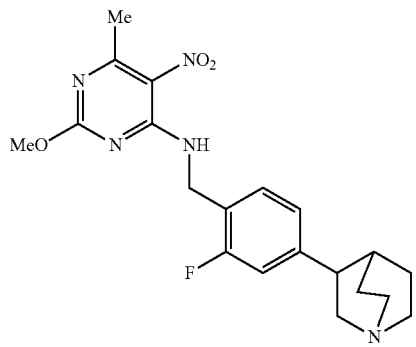 [SMILES: COc1nc(C)c([N+](=O)[O-])c(NCc2ccc(C3CN4CCC3CC4)cc2F)n1] | LC-MS [M + H]⁺/Rt (min): 402.0/0.514 (Method C); ¹H-NMR (CDCl₃) δ: 8.83-8.81 (1H, br m), 7.34-7.28 (1H, m), 7.06-6.39 (2H, m), 4.84 (2H, d, J = 5.5 Hz), 4.03 (3H, s), 3.41-3.31 (1H, m), 3.09-2.84 (6H, m), 2.75 (3H, s), 2.02-1.90 (1H, m), 1.80-1.71 (2H, m), 1.69-1.61 (1H, m), 1.45-1.33 (1H, m). |

| Reference example | Chemical Structure | Instrumental analysis data |
|---|---|---|
| 193 | 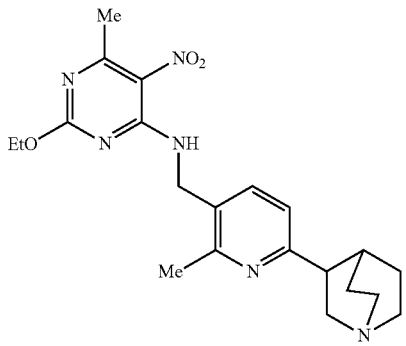 [SMILES: CCOc1nc(C)c([N+](=O)[O-])c(NCc2ccc(C3CN4CCC3CC4)nc2C)n1] | LC-MS [M + H]⁺/Rt (min): 413.4/0.659 (Method A); ¹H-NMR (CDCl₃) δ: 8.74-8.68 (1H, m), 7.48 (1H, d, J = 7.9 Hz), 7.05 (1H, d, J = 7.9 Hz), 4.77 (2H, d, J = 5.5 Hz), 4.41 (2H, q, J = 7.1 Hz), 3.52-3.46 (1H, m), 3.27-3.19 (1H, m), 3.10-2.99 (2H, m), 2.99-2.89 (2H, m), 2.88-2.78 (1H, m), 2.77 (3H, s), 2.60 (3H, s), 2.07-2.01 (1H, m), 1.77-1.63 (3H, m), 1.40 (3H, t, J = 7.1 Hz), 1.37-1.22 (1H, m). |
| 194 | 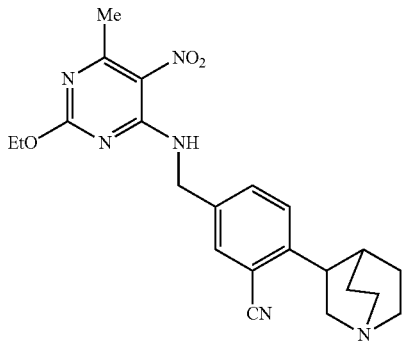 [SMILES: CCOc1nc(C)c([N+](=O)[O-])c(NCc2ccc(C3CN4CCC3CC4)c(C#N)c2)n1] | LC-MS [M + H]⁺/Rt (min): 423.4/0.700 (Method A); ¹H-NMR (CDCl₃) δ: 8.88 1H, t, J = 5.5 Hz), 7.69-7.61 (1H, m), 7.61-7.51 (2H, m), 4.81 (2H, d, J = 5.5 Hz), 4.39 (2H, q, J = 7.1 Hz), 3.50-3.43 (1H, m), 3.43-3.31 (1H, m), 3.19-3.09 (1H, m), 3.09-2.89 (4H, m), 2.77 (3H, s), 1.98-1.87 (2H, m), 1.83-1.73 (1H, m), 1.63-1.51 (1H, m), 1.47-1.34 (4H, m). |
| 195 | 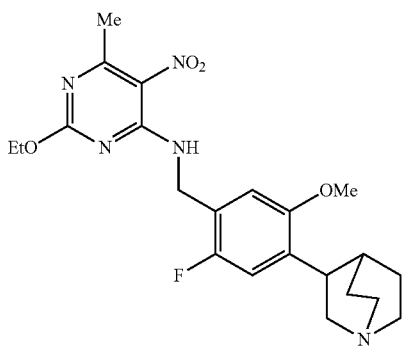 [SMILES: CCOc1nc(C)c([N+](=O)[O-])c(NCc2cc(OC)c(C3CN4CCC3CC4)cc2F)n1] | LC-MS [M + H]⁺/Rt (min): 446.4/0.785 (Method A); ¹H-NMR (CDCl₃) δ: 8.80 (1H, t, J = 5.5 Hz), 7.05 (1H, d, J = 11.0 Hz), 6.81 (1H, d, J = 6.1 Hz), 4.81 (2H, d, J = 5.5 Hz), 4.46 (2H, q, J = 7.1 Hz), 3.79 (3H, s), 3.41-3.33 (1H, m), 3.30-3.24 (1H, m), 3.02-2.80 (5H, m), 2.75 (3H, s), 1.93-1.89 (1H, m), 1.82-1.65 (3H, m), 1.47-1.34 (4H, m). |
| 196 | 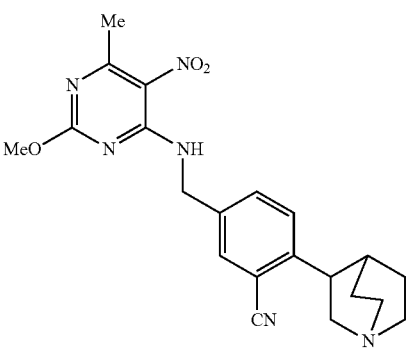 [SMILES: COc1nc(C)c([N+](=O)[O-])c(NCc2ccc(C3CN4CCC3CC4)c(C#N)c2)n1] | LC-MS [M + H]⁺/Rt (min): 409.4/0.712 (Method A); ¹H-NMR (CDCl₃) δ: 8.86 (6H, t, J = 6.1 Hz), 7.65 (1H, s), 7.60-7.52 (2H, m), 4.82 (2H, d, J = 6.1 Hz), 3.97 (3H, s), 3.49-3.43 (1H, m), 3.41-3.32 (1H, m), 3.16-3.08 (1H, m), 3.08-2.88 (4H, m), 2.78 (3H, s), 1.96-1.85 (2H, m), 1.81-1.72 (1H, m), 1.61-1.52 (1H, m), 1.43-1.36 (1H, m). |

-continued

| Reference example | Chemical Structure | Instrumental analysis data |
|---|---|---|
| 197 | 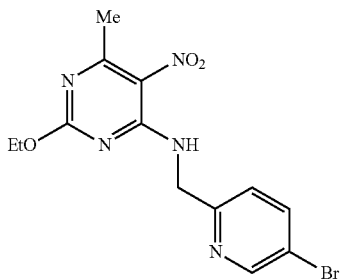 | LC-MS [M + H]⁺/Rt (min): 370.2/1.100 (Method A); ¹H-NMR (CDCl₃) δ: 9.35 (1H, t, J = 5.5 Hz), 8.69 (1H, d, J = 2.4 Hz), 7.83 (1H, dd, J = 7.9, 2.4 Hz), 7.21 (1H, d, J = 8.5 Hz), 4.86 (2H, d, J = 5.5 Hz), 4.40 (2H, q, J = 7.1 Hz), 2.77 (3H, s), 1.40 (4H, t, J = 7.1 Hz). |
| 198 | 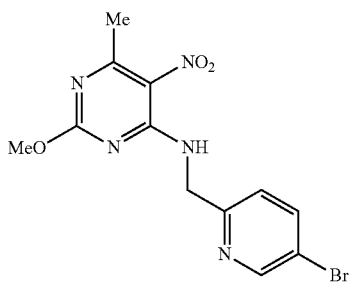 | LC-MS [M + H]⁺/Rt (min): 356.1/1.018 (Method A); ¹H-NMR (CDCl₃) δ: 9.35 (1H, t, J = 4.9 Hz), 8.69 (1H, d, J = 2.4 Hz), 7.83 (1H, dd, J = 8.5, 2.4 Hz), 7.22 (1H, d, J = 8.5 Hz), 4.87 (3H, d, J = 4.9 Hz), 3.98 (3H, s), 2.77 (3H, s). |
| 199 | 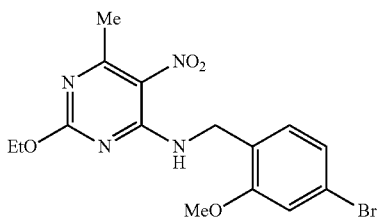 [SMILES: CCOc1nc(C)c([N+](=O)[O-])c(NCc2ccc(Br)cc2OC)n1] | LC-MS [M + H]⁺/Rt (min): 397.1/1.130 (Method C) |
| 200 | 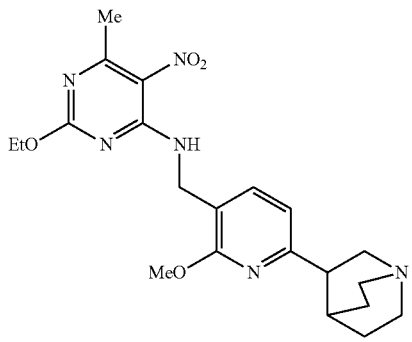 [SMILES: CCOc1nc(C)c([N+](=O)[O-])c(NCc2ccc(C3CN4CCC3CC4)nc2OC)n1] | LC-MS [M + 2H]²⁺/2/Rt (min): 215.1/0.671 (Method C); ¹H-NMR (CDCl₃) δ: 9.04-8.95 (1H, m), 7.42 (1H, d, J = 7.3 Hz), 6.69 (1H, d, J = 7.3 Hz), 4.68 (2H, d, J = 5.5 Hz), 4.40 (2H, q, J = 7.0 Hz), 4.00 (3H, s), 3.55-3.47 (1H, m), 3.17-3.02 (2H, m), 2.98-2.77 (4H, m), 2.69 (3H, s), 1.97-1.93 (1H, m), 1.83-1.62 (3H, m), 1.38 (3H, t, J = 7.0 Hz), 1.34-1.21 (1H, m). |
| 201 | 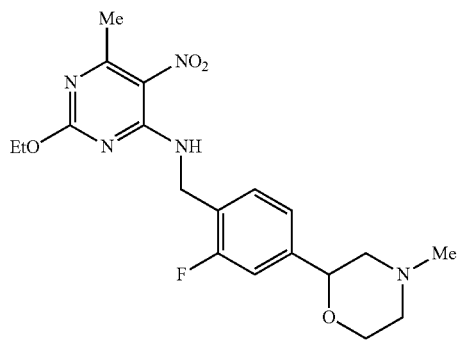 [SMILES: CCOc1nc(C)c([N+](=O)[O-])c(NCc2ccc(C3CN(C)CCO3)cc2F)n1] | LC-MS [M + H]⁺/Rt (min): 406.5/0.729 (Method A) |

-continued

| Reference example | Chemical Structure | Instrumental analysis data |
|---|---|---|
| 202 | 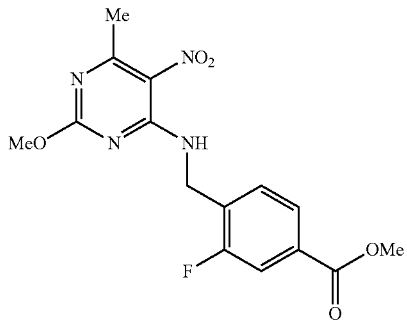 [SMILES: COC(=O)c1ccc(CNc2nc(OC)nc(C)c2[N+](=O)[O-])c(F)c1] | LC-MS [M + H]⁺/Rt (min): 350.9/0.984 (Method A) |
| 203 | 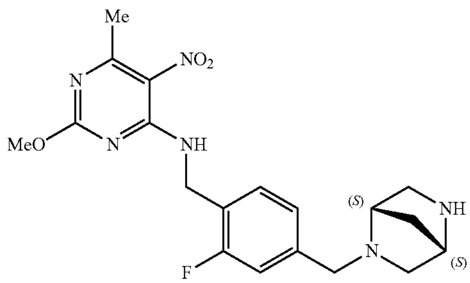 | LC-MS [M + H]⁺/Rt (min): 403.4/0.523 (Method A) |
| 204 | 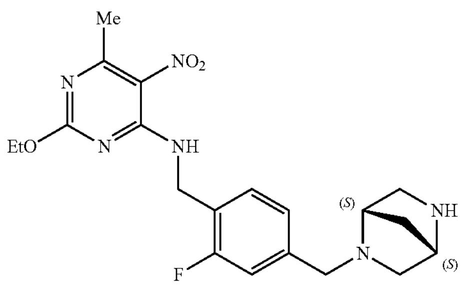 | LC-MS [M + H]⁺/Rt (min): 417.4/0.592 (Method A) |
| 205 | 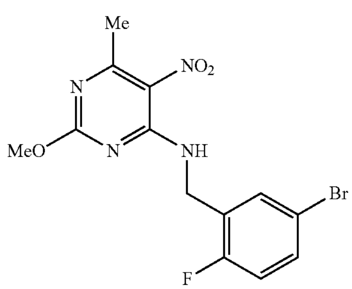 [SMILES: COc1nc(C)c([N+](=O)[O-])c(NCc2cc(Br)ccc2F)n1] | LC-MS [M + H]⁺/Rt (min): 371.2/1.074 (Method A) |
| 206 | 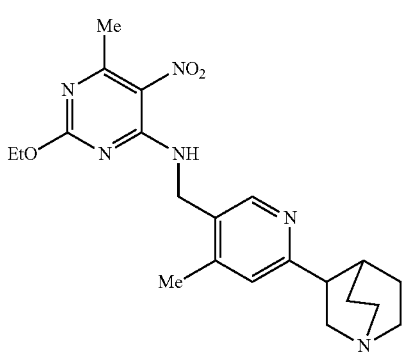 [SMILES: CCOc1nc(C)c([N+](=O)[O-])c(NCc2cnc(C3CN4CCC3CC4)cc2C)n1] | LC-MS [M + 2H]²⁺/2/Rt (min): 207.0/0.561 (Method C) |

| Reference example | Chemical Structure | Instrumental analysis data |
| --- | --- | --- |
| 207 | (2-ethoxy-6-methyl-5-nitropyrimidin-4-yl)-[(6-chloro-4-methoxypyridin-3-yl)methyl]amine | LC-MS [M + H]+/Rt (min): 354.1/0.856 (Method C) |
| 208 | (2-methoxy-6-methyl-5-nitropyrimidin-4-yl)-[(4-bromo-3-fluorophenyl)methyl]amine | LC-MS [M + H]+/Rt (min): 370.9/1.008 (Method C) |
| 209 | 2-hydroxy-6-methyl-5-nitro-4-[(4-bromo-3-fluorobenzyl)amino]pyrimidine | LC-MS [M + H]+/Rt (min): 357.1/0.709 (Method C) |
| 210 | (2-ethoxy-6-methyl-5-nitropyrimidin-4-yl)-[(4-bromo-2-fluorophenyl)methyl]amine | LC-MS [M + H]+/Rt (min): 386.0/1.005 (Method C) |
| 211 | (2-ethoxy-6-methyl-5-nitropyrimidin-4-yl)-[(6-chloro-2-trifluoromethylpyridin-3-yl)methyl]amine | LC-MS [M + H]+/Rt (min): 392.1/1.038 (Method C) |

| Reference example | Chemical Structure | Instrumental analysis data |
|---|---|---|
| 212 | (structure: 2-ethoxy-6-methyl-5-nitro-4-[(6-chloro-2-cyanopyridin-3-yl)methylamino]pyrimidine) | LC-MS [M + H]⁺/Rt (min): 349.2/0.903 (Method C) |
| 213 | (structure: 2-methoxy-6-methyl-5-nitro-4-[(4-bromo-2-fluorobenzyl)amino]pyrimidine) | LC-MS [M + H]⁺/Rt (min): 371.2/1.036 (Method C) |
| 214 | (structure: 2-ethoxy-6-methyl-5-nitro-4-[(6-chloro-5-fluoropyridin-3-yl)methylamino]pyrimidine) | LC-MS [M + H]⁺/Rt (min): 342.2/0.904 (Method C) |
| 215 | (structure: 2-ethoxy-6-methyl-5-nitro-4-[(4-bromo-2-cyanobenzyl)amino]pyrimidine) | LC-MS [M + H]⁺/Rt (min): 392.2/1.006 (Method C) |
| 216 | (structure: 2-ethoxy-6-methyl-5-nitro-4-[[2-fluoro-4-(quinuclidin-3-en-3-yl)benzyl]amino]pyrimidine) | LC-MS [M + H]⁺/Rt (min): 400.2/0.554 (Method C) |

| Reference example | Chemical Structure | Instrumental analysis data |
|---|---|---|
| 217 | (2-methoxy-6-methyl-5-nitropyrimidin-4-yl)-NH-CH2-(3-bromophenyl) | LC-MS [M + H]⁺/Rt (min): 353.1/0.998 (Method C) |
| 218 | (2-methoxy-6-methyl-5-nitropyrimidin-4-yl)-NH-CH2-(2-fluoro-4-(methanesulfonyloxy)phenyl) | LC-MS [M + H]⁺/Rt (min): 387.2/0.832 (Method C) |

Reference Examples 219-222

According to the method of Example 127, Reference examples 219-222 were prepared by using the corresponding material compounds.

| Reference example | Chemical Structure | Instrumental analysis data |
|---|---|---|
| 219 | (2-methoxy-6-methyl-5-nitropyrimidin-4-yl)-NH-CH2-[2-fluoro-4-((S,S)-5-methyl-2,5-diazabicyclo[2.2.1]heptan-2-ylmethyl)phenyl] | LC-MS [M + H]⁺/Rt (min): 417.4/0.581 (Method A) |
| 220 | (2-methoxy-6-methyl-5-nitropyrimidin-4-yl)-NH-CH2-[2-fluoro-4-((S,S)-5-ethyl-2,5-diazabicyclo[2.2.1]heptan-2-ylmethyl)phenyl] | LC-MS [M + H]⁺/Rt (min): 431.45/0.596 (Method A) |

| Reference example | Chemical Structure | Instrumental analysis data |
|---|---|---|
| 221 | 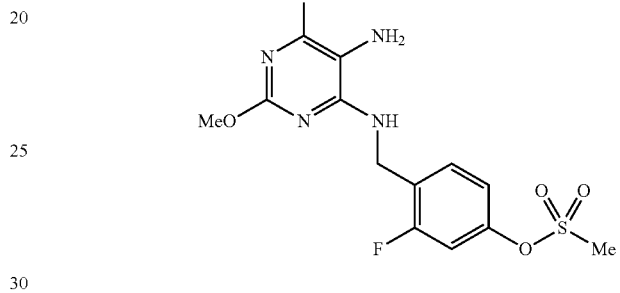 | LC-MS [M + H]⁺/Rt (min): 431.4/0.651 (Method A) |

Reference Example 222

4-{[(5-Amino-2-methoxy-6-methylpyrimidin-4-yl)amino]methyl}-3-fluorophenylmethanesulfonate

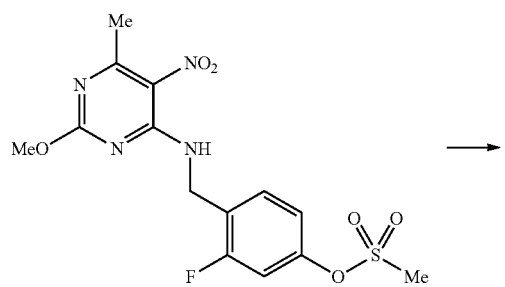

To a solution of the compound of Reference example 218 (7.38 g) in ethanol (100 mL) was added 5% palladium carbon (1.13 g) at room temperature. The reaction mixture was stirred at room temperature under ambient-pressure hydrogen atmosphere for 3 hours, and then filtrated through Celite. The filtrate was concentrated in vacuo, and the residue was purified by silica gel column chromatography (chloroform/methanol) to give the title compound (4.22 g).

LC-MS [M+H]⁺/Rt (min): 357.2/0.441 (Method C)

Reference Examples 223-249

According to the methods of Reference example 106, Reference example 107, and Reference example 222, Reference examples 223-249 were prepared by using the corresponding material compounds.

| Reference example | Chemical Structure | Instrumental analysis data |
|---|---|---|
| 223 | 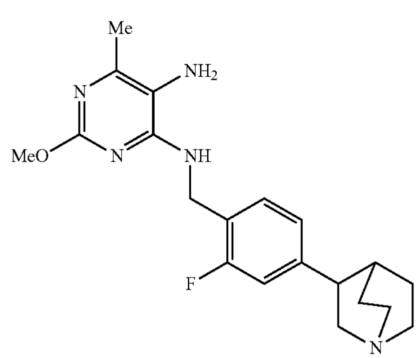 | LC-MS [M + 2H]²⁺/2/Rt (min): 186.6/0.252 (Method C); ¹H-NMR (CDCl₃) δ: 7.39-7.33 (1H, m), 7.04-6.96 (2H, m), 5.68 (1H, t, J = 6.1 Hz), 4.71 (2H, d, J = 6.1 Hz), 3.91 (3H, s), 3.37-3.29 (1H, m), 3.07-2.81 (6H, m), 2.50 (2H, s), 2.31 (3H, s), 1.94-1.90 (1H, m), 1.78-1.69 (2H, m), 1.69-1.64 (1H, m), 1.44-1.32 (1H, m). |

-continued

| Reference example | Chemical Structure | Instrumental analysis data |
|---|---|---|
| 224 | 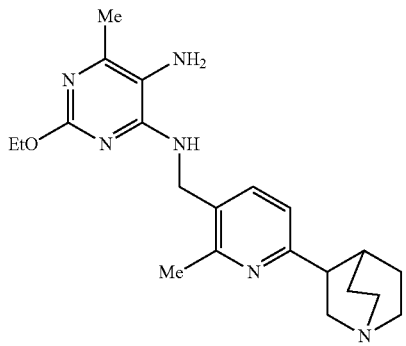 [SMILES: CCOc1nc(C)c(N)c(NCc2ccc(C3CN4CCC3CC4)nc2C)n1] | ¹H-NMR (CDCl₃) δ: 7.50 (1H, d, J = 7.9 Hz), 7.03 (1H, d, J = 7.9 Hz), 5.53 (1H, t, J = 5.5 Hz), 4.64 (2H, d, J = 5.5 Hz), 4.30 (2H, q, J = 6.9 Hz), 3.51-3.42 (1H, m), 3.29-3.18 (1H, m), 3.09-2.99 (2H, m), 2.99-2.89 (2H, m), 2.89-2.77 (1H, m), 2.58 (3H, s), 2.51 (2H, s), 2.32 (3H, s), 2.07-2.00 (1H, m), 1-77-1.62 (3H, m), 1.37 (3H, t, J = 6.9 Hz), 1.34-1.27 (1H, m). |
| 225 | 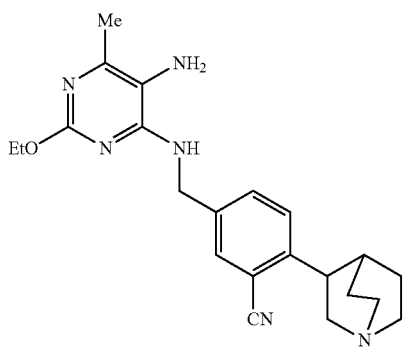 [SMILES: CCOc1nc(C)c(N)c(NCc2ccc(C3CN4CCC3CC4)c(C#N)c2)n1] | ¹H-NMR (CDCl₃) δ: 7.64 (1H, d, J = 1.2 Hz), 7.57 (1H, dd, J = 7.9, 1.2 Hz), 7.50 (1H, d, J = 7.9 Hz), 5.79 (1H, t, J = 6.1 Hz), 4.69 (2H, d, J = 6.1 Hz), 4.28 (2H, q, J = 6.9 Hz), 3.47-3.40 (1H, m), 3.38-3.30 (1H, m), 3.15-3.07 (1H, m), 3.03-2.87 (4H, m), 2.53 (2H, s), 2.32 (3H, s), 1.94-1.83 (2H, m), 1.80-1.73 (1H, m), 1.60-1.52 (1H, m), 1.43-1.32 (4H, m). |
| 226 | 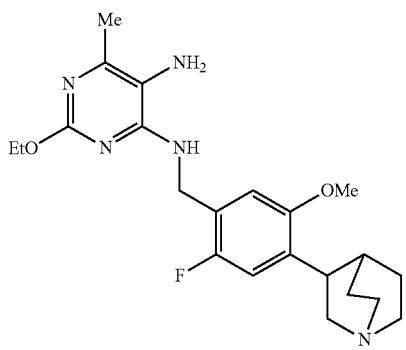 [SMILES: CCOc1nc(C)c(N)c(NCc2cc(OC)c(C3CN4CCC3CC4)cc2F)n1] | LC-MS [M + H]⁺/Rt (min): 416.4/0.485 (Method A); ¹H-NMR (CDCl₃) δ: 7.02 (1H, d, J = 11.6 Hz), 6.92 (1H, d, J = 6.1 Hz), 5.66 (1H, t, J = 5.5 Hz), 4.69 (2H, d, J = 5.5 Hz), 4.34 (2H, q, J = 7.1 Hz), 3.78 (3H s), 3.43-3.32 (1H, m), 3.31-3.25 (1H, m), 3.04-2.92 (3H, m), 2.92-2.82 (2H, m), 2.50 (2H, s), 2.30 (3H, s), 1.97-1.90 (1H, m), 1.83-1.68 (3H, m), 1.48-1.34 (4H, m). |
| 227 | 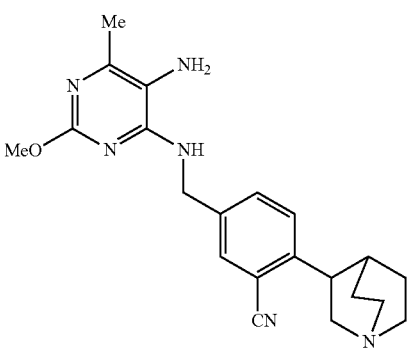 | ¹H-NMR (CDCl₃) δ: 7.65 (1H, d, J = 1.8 Hz), 7.59 (1H, dd, J = 7.9, 1.8 Hz), 7.50 (1H, d, J = 7.9 Hz), 5.82 (1H, t, J = 5.5 Hz), 4.70 (2H, d, J = 5.5 Hz), 3.87 (3H, s), 3.51-3.44 (1H, m), 3.41-3.33 (1H, m), 3.19-3.12 (1H, m), 3.08-2.92 (4H, m), 2.54 (2H, s), 2.34 (3H, s), 1.99-1.87 (2H, m), 1.82-1.74 (1H, m), 1.65-1.55 (1H, m), 1.46-1.36 (1H, m). |

-continued

| Reference example | Chemical Structure | Instrumental analysis data |
|---|---|---|
| 228 | 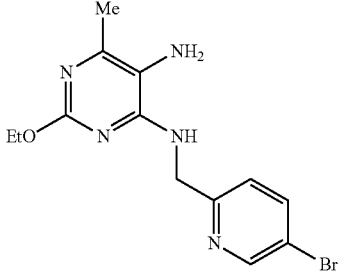 [SMILES: CCOc1nc(C)c(N)c(NCc2ccc(Br)cn2)n1] | LC-MS [M + H]⁺/Rt (min): 340.1/0.649 (Method A); ¹H-NMR (CDCl₃) δ: 8.64 (1H, d, J = 1.8 Hz), 7.78 (1H, dd, J = 7.9, 1.8 Hz), 7.24 (1H, d, J = 7.9 Hz), 6.40 (1H, t, J = 5.5 Hz), 4.74 (2H, d, J = 5.5 Hz), 4.29 (2H, q, J = 7.1 Hz), 2.32 (3H, s), 1.36 (3H, t, J = 7.1 Hz). |
| 229 | 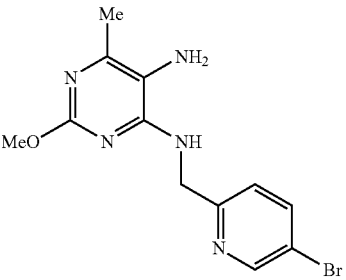 | LC-MS [M + H]⁺/Rt (min): 326.1/0.585 (Method A); ¹H-NMR (CDCl₃) δ: 8.63 (1H, d, J = 2.4 Hz), 7.78 (1H, dd, J = 8.5, 2.4 Hz), 7.24 (1H, d, J = 8.5 Hz), 6.37 (1H, t, J = 5.5 Hz), 4.74 (2H, d, J = 5.5 Hz), 3.87 (3H, s), 2.32 (3H, s). |
| 230 | 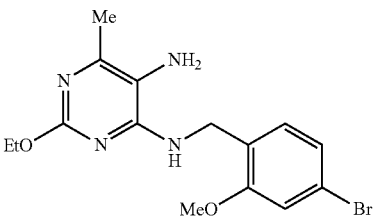 | LC-MS [M + H]⁺/Rt (min): 367.0/0.654 (Method C); ¹H-NMR (CDCl₃) δ: 7.15 (1H, d, J = 8.2 Hz), 7.02-6.98 (2H, m), 6.14 (1H, br s), 4.59 (2H, d, J = 5.9 Hz), 4.29 (2H, q, J = 7.2 Hz), 3.84 (3H, s), 2.27 (3H, s), 1.33 (3H, t, J = 7.2 Hz). |
| 231 | 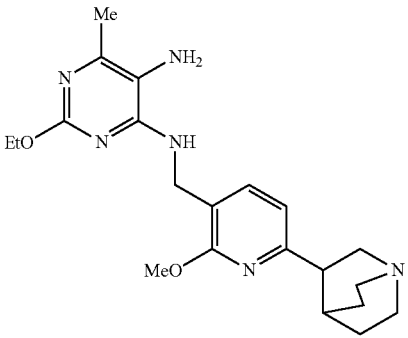 [SMILES: CCOc1nc(C)c(N)c(NCc2ccc(C3CN4CCC3CC4)nc2OC)n1] | LC-MS [M + 2H]²⁺/2/Rt (min): 200.1/0.392 (Method C); ¹H-NMR (CDCl₃) δ: 7.48 (1H, d, J = 7.3 Hz), 6.68 (1H, d, J = 7.3 Hz), 5.78 (1H, t, J = 6.0 Hz), 4.57 (2H, d, J = 6.0 Hz), 4.27 (2H, q, J = 7.0 Hz), 3.98 (3H, s), 3.68-3.55 (1H, m), 3.24-3.09 (2H, m), 3.05-2.82 (4H, m), 2.53-2.42 (2H, m), 2.25 (3H, s), 2.03-1.95 (1H, m), 1.90-1.67 (3H, m), 1.40-1.29 (1H, m), 1.34 (3H, t, J = 7.0 Hz). |
| 232 | 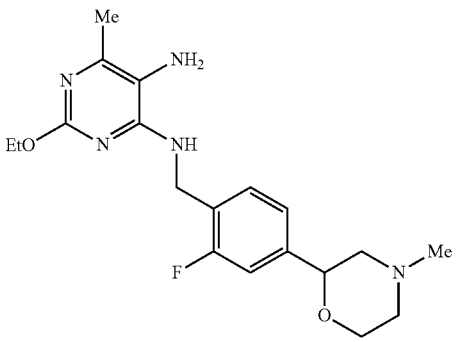 | LC-MS ([M + H]⁺/Rt (min)): 376.5/0.457 (Method A) |

-continued
| Reference example | Chemical Structure | Instrumental analysis data |
|---|---|---|
| 233 | 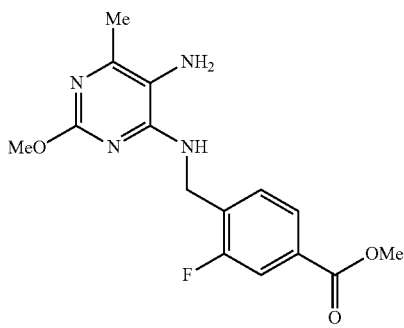 | LC-MS ([M + H]⁺/Rt (min)): 321.3/0.598 (Method A) |
| 234 | 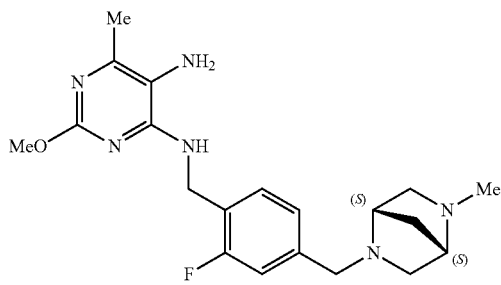 | LC-MS [M + H]⁺/Rt (min): 387.4/0.348 (Method A) |
| 235 | 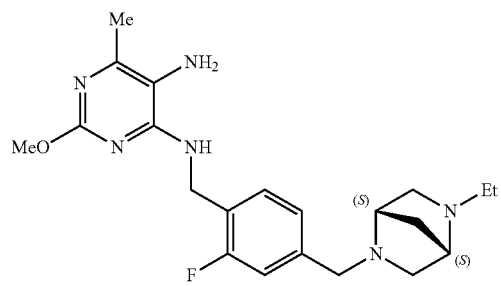 | LC-MS [M + H]⁺/Rt (min): 401.4/0361 (Method A) |
| 236 | 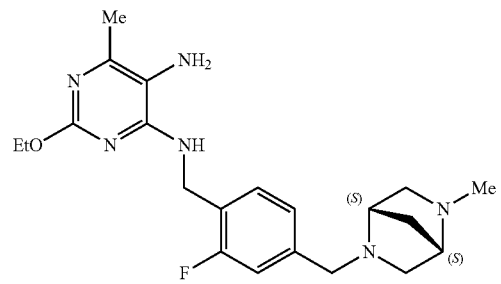 | LC-MS ([M + H]⁺/Rt (min)): 401.4/0.389 (Method A) |
| 237 | 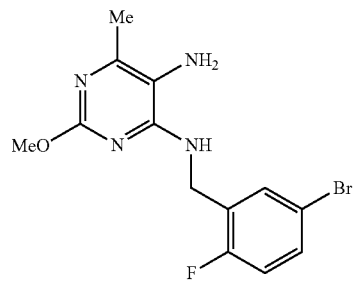 | LC-MS [M + H]⁺/Rt (min): 341.2/0.630 (Method A) |

-continued

| Reference example | Chemical Structure | Instrumental analysis data |
|---|---|---|
| 238 | 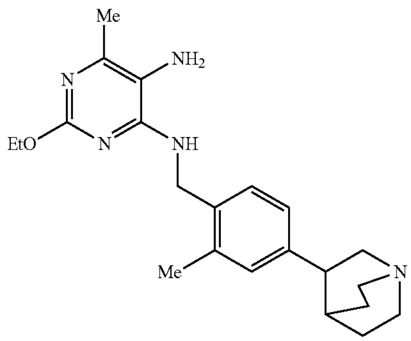 [SMILES: CCOc1nc(C)c(N)c(NCc2ccc(C3CN4CCC3CC4)cc2C)n1] | LC-MS [M + 2H]²⁺/Rt (min): 192.1/0.287 (Method C) |
| 239 | 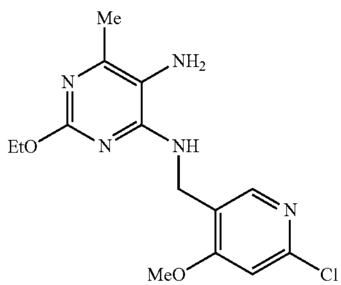 | LC-MS [M + H]⁺/Rt (min): 324.1/0.453 (Method C) |
| 240 | 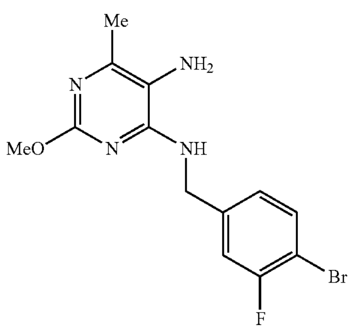 [SMILES: COc1nc(C)c(N)c(NCc2ccc(Br)c(F)c2)n1] | LC-MS [M + H]⁺/Rt (min): 341.0/0.578 (Method C) |
| 241 | 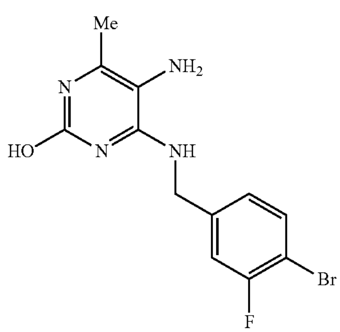 | LC-MS [M + H]⁺/Rt (min): 327.0/0.456 (Method C) |
| 242 | 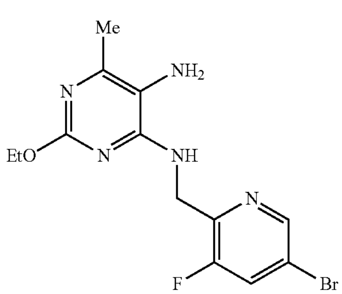 [SMILES: CCOc1nc(C)c(N)c(NCc2ncc(Br)cc2F)n1] | LC-MS [M + H]⁺/Rt (min): 356.0/0.512 (Method C) |

| Reference example | Chemical Structure | Instrumental analysis data |
| --- | --- | --- |
| 243 | (structure) | LC-MS [M + H]+/Rt (min): 362.1/0.601 (Method C) |
| 244 | (structure) | LC-MS [M + H]+/Rt (min): 319.2/0.498 (Method C) |
| 245 | (structure) | LC-MS [M + H]+/Rt (min): 341.1/0.585 (Method C) |
| 246 | (structure) | LC-MS [M + H]+/Rt (min): 312.2/0.489 (Method C) |
| 247 | (structure) | LC-MS [M + H]+/Rt (min): 362.2/0.592 (Method C) |

| Reference example | Chemical Structure | Instrumental analysis data |
|---|---|---|
| 248 | 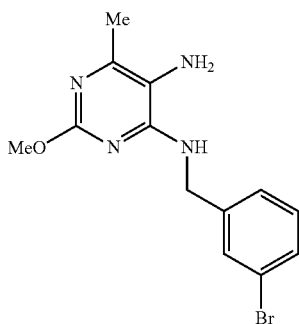 | LC-MS [M + H]⁺/Rt (min): 323.2/0.552 (Method C) |
| 249 | 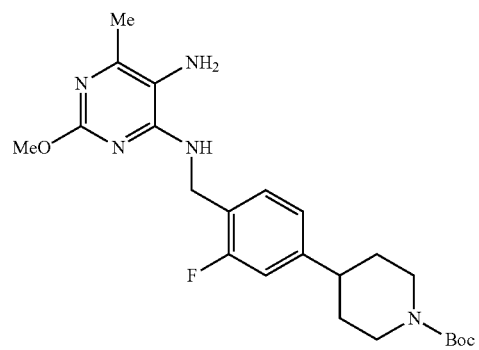 [SMILES: COc1nc(C)c(N)c(NCc2ccc(C3CCN(C(=O)OC(C)(C)C)CC3)cc2F)n1] | LC-MS [M + H]⁺/Rt (min): 446.4/0.721 (Method C) |

Reference Example 250

4-{[(5-Amino-2-methoxy-6-methylpyrimidin-4-yl)amino]methyl}-3-fluorophenol

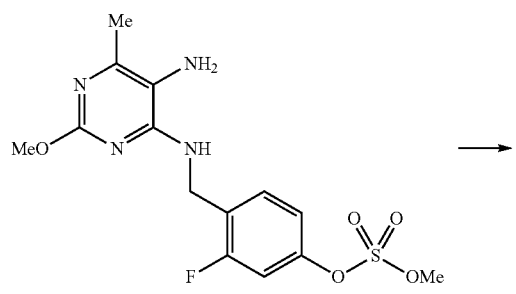

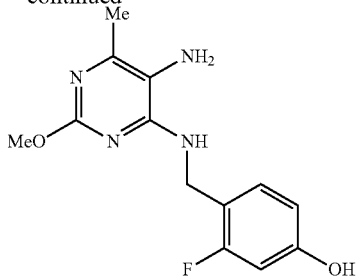

To an ice-cooled solution of the compound of Reference example 222 (1.70 g) in methanol (20 mL)/tetrahydrofuran (20 mL) was added 5 mol/L aqueous sodium hydroxide (4.77 mL), and the mixture was stirred in ice bath for 15 hours. To the reaction mixture was added 50% aqueous potassium carbonate, and the mixture was extracted with chloroform/ethanol (3/1). The organic layer was dried over sodium sulfate, filtrated, and then concentrated in vacuo. The residue was purified by silica gel column chromatography (chloroform/methanol) to give the title compound (0.914 q).

LC-MS [M+H]⁺/Rt (min): 279.2/0.390 (Method C)

Reference Examples 251-252

According to the method of Reference example 106, Reference example 107, and Reference example 222, Reference examples 251-252 were prepared by using the corresponding material compounds.

| Reference example | Chemical Structure | Instrumental analysis data |
|---|---|---|
| 251 | 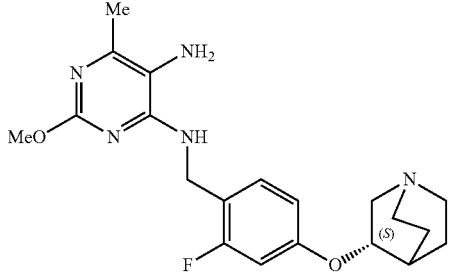 | LC-MS [M + 2H]²⁺/2/Rt (min): 195.0/0.248 Method C) |
| 252 | 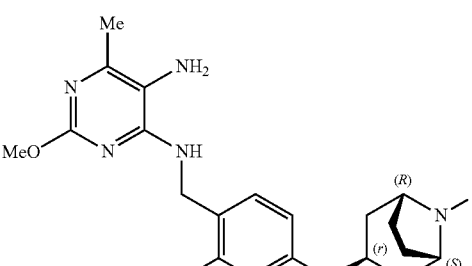 | LC-MS [M + H]⁺/Rt (min): 488.4/0.755 (Method C) |

Reference Example 253

According to the method of Reference example 2, Reference example 253 was prepared by using the corresponding material compound.

| Reference example | Chemical Structure | Instrumental analysis data |
|---|---|---|
| 253 | 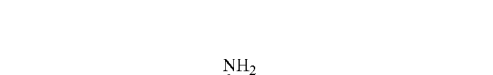 | ¹H-NMR (DMSO-d₆) δ: 9.97 (1H, s), 8.08 (1H, s), 7.86-7.84 (2H, m), 7.69-7.66 (1H, m), 7.62-7.57 (1H, m), 7.24 (2H, brs), 5.37 (2H, s), 4.19 (2H, t, J = 6.4 Hz), 1.62 (2H, tt, J = 6.4, 7.9 Hz), 1.39 (2H, qt, J = 7.3, 7.9 Hz), 0.90 (3H, t, J = 7.3 Hz). |

Reference Examples 254-255

According to the method of Reference example 36, Reference examples 254-255 were prepared by using the corresponding material compounds.

| Reference example | Chemical Structure | Instrumental analysis data |
|---|---|---|
| 254 | [structure: 6-amino-2-(2-methoxyethoxy)-8-bromo-9-(3-formylbenzyl)purine] | $^1$H-NMR (DMSO-$d_6$) δ: 10.0 (1H, s), 7.88-7.85 (1H, m), 7.76 (1H, brs), 7.62-7.56 (2H, m), 7.48 (2H, brs), 5.36 (2H, s), 4.33 (2H, t, J = 4.7 Hz), 3.60 (2H, t, J = 4.7 Hz), 3.27 (3H, s). |
| 255 | [structure: 6-amino-2-butoxy-8-bromo-9-(4-formylbenzyl)purine] | $^1$H-NMR (DMSO-$d_6$) δ: 9.98 (1H, s), 7.90 (2H, d, J = 7.9 Hz), 7.45 (2H, brs), 7.41 (2H, d, J = 7.9 Hz), 5.37 (2H, s), 4.19 (2H, t, J = 6.4 Hz), 1.64 (2H, tt, J = 6.4, 7.9 Hz), 1.37 (2H, qt, J = 7.3, 7.9 Hz), 0.90 (3H, t, J = 7.3 Hz). |

Reference Examples 256-261

According to the method of Example 80, Reference examples 256-261 were prepared by using the corresponding material compounds.

| Reference example | Chemical Structure | Instrumental analysis data |
|---|---|---|
| 256 | [structure: 6-amino-2-(2-methoxyethoxy)-8-bromo-9-(3-((dimethylamino)methyl)benzyl)purine] | $^1$H-NMR (DMSO-$d_6$) δ: 7.46 (2H, brs), 7.31-7.27 (1H, m), 7.25-7.18 (2H, m), 7.11-7.09 (1H, m), 5.25 (2H, s), 4.34 (2H, t, J = 4.7 Hz), 3.61 (2H, t, J = 4.7 Hz), 3.33 (2H, s), 3.28 (3H s), 2.10 (6H, s). |
| 257 | [structure: 6-amino-2-(2-methoxyethoxy)-8-bromo-9-(3-(morpholinomethyl)benzyl)purine] | $^1$H-NMR (DMSO-$d_6$) δ: 7.48 (2H, brs), 7.32-7.27 (1H, m), 7.23-7.19 (2H, m), 7.13-7.10 (1H, m), 5.25 (2H, s), 4.32 (2H, t, J = 4.7 Hz), 3.61 (2H, t, J = 4.7 Hz), 3.55-3.49 (4H, m), 3.45-3.33 (5H, m), 3.27 (3H, s). |

| Reference example | Chemical Structure | Instrumental analysis data |
|---|---|---|
| 258 | MeO-CH2CH2-O-[2-methoxyethoxy purine with 6-NH2, 8-Br, 9-(4-((dimethylamino)methyl)benzyl)] | $^1$H-NMR (DMSO-$d_6$) δ: 7.45 (2H, brs), 7.26 (2H, d, J = 7.9 Hz), 7.19 (2H, d, J = 7.9 Hz), 5.23 (2H, s), 4.33 (2H, t, J = 4.7 Hz), 3.61 (2H, t, J = 4.7 Hz), 3.33 (2H, s), 3.28 (3H, s), 2.10 (6H, s). |
| 259 | MeO-CH2CH2-O-[purine 6-NH2, 8-Br, 9-(4-(pyrrolidin-1-ylmethyl)benzyl)] | $^1$H-NMR (DMSO-$d_6$) δ: 7.46 (2H, brs), 7.27 (2H, d, J = 7.9 Hz), 7.20 (2H, d, J = 7.9 Hz), 5.23 (2H, s), 4.32 (2H, t, J = 4.7 Hz), 3.61 (2H, t, J = 4.7 Hz), 3.55-3.52 (4H, m), 3.38 (2H, s), 3.27 (3H, s), 2.34-2.28 (4H, m). |
| 260 | n-Butyl-O-[purine 6-NH2, 8-Br, 9-(3-((dimethylamino)methyl)benzyl)] | $^1$H-NMR (DMSO-$d_6$) δ: 7.41 (2H, brs), 7.31-7.27 (1H, m), 7.23-7.18 (2H, m), 7.12-7.09 (1H, m), 5.25 (2H, s), 4.22 (2H, t, J = 6.4 Hz), 3.31 (2H, s), 2.10 (6H, s), 1.66 (2H, tt, J = 6.4, 7.9 Hz), 1.39 (2H, qt, J = 7.3, 7.9 Hz), 0.91 (3H, t, J = 7.3 Hz). |
| 261 | n-Butyl-O-[purine 6-NH2, 8-Br, 9-(3-(morpholinomethyl)benzyl)] | $^1$H-NMR (DMSO-$d_6$) δ: 7.42 (2H, brs), 7.32-7.27 (1H, m), 7.24-7.20 (2H, m), 7.14-7.11 (1H, m), 5.24 (2H, s), 4.21 (2H, t, J = 6.4 Hz), 3.58-3.48 (4H, m), 3.42 (2H, s), 2.32-2.26 (4H, m), 1.65 (2H, tt, J = 6.4, 7.9 Hz), 1.39 (2H, qt, J = 7.3, 7.9 Hz), 0.91 (3H, t, J = 7.3 Hz). |

Next, the pharmacological activities of the typical compounds of the present invention are explained in more detail with the following Tests.

Test 1: Test for Evaluating the Inhibition of the Activation of Human TLR7

As human TLR7 expressing cell line, HEK293 cell line was bought from IMGENEX Corporation (TLR7/NF-ηB/SEAPorter™ HEK293 cell), which is human embryonic kidney cell line and stably expresses full-length human TLR7 gene and secreted alkaline phosphatase (SEAP) reporter gene under the transcriptional control of an NE-ηB response element. The TLR7/NF-ηB/SEAPorter™ HEK293 cell was cultivated with DMEM containing 10% fetal bovine serum (FBS) and 10 μg/mL blasticidin S at 37° C. in the presence of 5% $CO_2$. The TLR7/NF-ηB/SEAPorter™ HEK293 cell was seeded into 96-well microtiter plate at $5 \times 10^4$ cell/90 μL/well, and the place was cultivated at 37° C. in a $CO_2$ incubator overnight. Each test compound that was diluted with the medium was added to the wells (10 μL/well), wherein each final concentration was adjusted to 0.001, 0.003, 0.01, 0.03, 0.1, 0.3, 1, 3, and 10 μmol/L, or 0.01, 0.03, 0.1, 0.3, 1, 3, 10, 30, and 100 μmol/L. After 0.5 hour, R-848 that is TLR7/8 ligand was added to each well (10 μL/well), wherein each final concentration was adjusted to 200 nmol/L. The total volume was adjusted to 110 μL/well, the test samples were incubated in $CO_2$ incubator for 20±1 hours, and then the SEAP activity was measured as activation of TLR7. The SEAP activity was evaluated as follows: p-nitro-phenyl phosphate (pNPP) (Invitrogen) was added to the incubated sample (50 μL/well); after 15 minutes, 4 mol/L sodium hydroxide solution (nacalai tesque) was added thereto (50 μL/well) to quench the reaction; and the absorbance of each sample was measured at 405 nm with microplate reader Elx808 (BioTek). The 50% inhibitory concentration ($IC_{50}$ value) of each sample compound was calculated based on 100% of the SEAP activity wherein the test sample comprises no sample compound.

Each compound prepared in the Examples was evaluated by Test 1. Each concentration of each test compound shown in the table below denotes the concentration to inhibit the cell growth by 50% ($IC_{50}$ value; μmol/L).

| Example | TLR7 IC$_{50}$ (μmol/L) |
|---|---|
| 1 | 2.3 |
| 2 | 5.5 |
| 3 | 9.2 |
| 4 | 7.8 |
| 5 | 1.4 |
| 6 | 9.6 |
| 7 | 7.8 |
| 8 | 9.3 |
| 9 | 12.8 |
| 10 | 0.80 |
| 11 | 10.9 |
| 12 | 9.2 |
| 13 | 9.3 |
| 14 | 8.2 |
| 15 | 4.1 |
| 16 | 13.9 |
| 17 | 1.1 |
| 18 | 2.7 |
| 19 | 1.4 |
| 20 | 22.5 |
| 21 | 0.70 |
| 22 | 2.0 |
| 23 | 9.1 |
| 24 | 13.7 |
| 25 | 3.5 |
| 26 | 18.7 |
| 27 | 1.4 |
| 28 | 9.5 |
| 29 | 1.0 |
| 30 | 2.8 |
| 31 | 7.7 |
| 32 | 8.6 |
| 33 | 0.82 |
| 34 | 1.7 |
| 35 | 18.1 |
| 36 | 2.9 |
| 37 | 2.7 |
| 38 | 0.52 |
| 39 | 0.82 |
| 40 | 0.12 |
| 41 | 0.14 |
| 42 | 0.55 |
| 43 | 2.0 |
| 44 | 0.75 |
| 45 | 0.95 |
| 46 | 0.025 |
| 47 | 0.030 |
| 48 | 0.099 |
| 49 | 0.067 |
| 50 | 0.077 |
| 51 | 0.059 |
| 52 | 0.089 |
| 53 | 0.060 |
| 54 | 0.42 |
| 55 | 0.62 |
| 56 | 0.66 |
| 57 | 1.8 |
| 58 | 0.81 |
| 59 | 0.28 |
| 60 | 0.23 |
| 61 | 0.62 |
| 62 | 1.43 |
| 63 | 5.8 |
| 64 | 0.68 |
| 65 | 0.55 |
| 66 | 0.021 |
| 67 | 0.051 |
| 68 | 0.18 |
| 69 | 0.13 |
| 70 | 0.11 |
| 71 | 0.058 |
| 72 | 0.081 |
| 73 | 0.16 |
| 74 | 1.4 |
| 75 | 0.20 |
| 76 | 0.40 |
| 77 | 2.4 |
| 78 | 1.3 |
| 79 | 3.5 |
| 80 | 0.54 |
| 81 | 0.060 |
| 82 | 0.40 |
| 83 | 1.3 |
| 84 | 0.50 |
| 85 | 0.80 |
| 86 | 0.30 |
| 87 | 2.5 |
| 88 | 0.90 |
| 89 | 1.4 |
| 90 | 4.2 |
| 91 | 0.25 |
| 92 | 0.37 |
| 93 | 0.29 |
| 94 | 0.020 |
| 95 | 0.050 |
| 96 | 0.080 |
| 97 | 0.10 |
| 98 | 0.071 |
| 99 | 0.146 |
| 100 | 0.096 |
| 101 | 0.056 |
| 102 | 0.81 |
| 103 | 1.6 |
| 104 | 0.76 |
| 105 | 0.059 |
| 106 | 0.062 |
| 107 | 0.027 |
| 108 | 0.16 |
| 109 | 0.010 |
| 110 | 0.005 |
| 111 | 0.20 |
| 112 | 0.10 |
| 113 | 1.0 |
| 114 | 0.30 |
| 115 | 0.10 |
| 116 | 0.16 |
| 117 | 7.0 |
| 118 | 0.95 |
| 119 | 0.028 |
| 120 | 0.051 |
| 121 | 1.3 |
| 122 | 0.23 |
| 123 | 0.033 |
| 124 | 0.22 |
| 125 | 0.085 |
| 126 | 0.15 |
| 127 | 0.053 |
| 128 | 0.019 |
| 129 | 0.071 |
| 130 | 0.043 |
| 131 | 0.007 |
| 132 | 0.019 |
| 133 | 0.013 |
| 134 | 0.17 |
| 135 | 0.085 |
| 136 | 0.020 |
| 137 | 0.84 |
| 138 | 0.049 |
| 139 | 0.084 |
| 140 | 0.12 |
| 141 | 3.3 |
| 142 | 6.6 |
| 143 | 1.57 |
| 144 | 2.6 |
| 145 | 2.1 |
| 146 | 1.7 |
| 147 | 3.5 |
| 148 | 0.016 |
| 149 | 0.46 |
| 150 | 0.50 |
| 151 | 16.6 |
| 152 | 2.9 |

| Example | TLR7 IC$_{50}$ (μmol/L) |
|---|---|
| 153 | 5.8 |
| 154 | 13.6 |
| 155 | 8.1 |
| 156 | 5.0 |
| 157 | 8.9 |
| 158 | 13.7 |
| 159 | 0.93 |
| 160 | 1.3 |
| 161 | 0.028 |
| 162 | 0.21 |
| 163 | 0.010 |
| 164 | 0.17 |
| 165 | 0.016 |
| 166 | 0.050 |
| 167 | 0.11 |
| 168 | 1.4 |
| 169 | 0.007 |
| 170 | 0.082 |
| 171 | 0.018 |
| 172 | 0.003 |
| 173 | 0.063 |
| 174 | 0.026 |
| 175 | 0.094 |
| 176 | 0.011 |
| 177 | 0.010 |
| 178 | 0.003 |
| 179 | 16.2 |
| 181 | 19.7 |
| 237 | 2.02 |
| 238 | 2.17 |
| 240 | 0.357 |
| 242 | 2.68 |
| 243 | 2.66 |
| 244 | 0.445 |
| 245 | 0.198 |
| 246 | 0.3 |
| 247 | 0.085 |
| 248 | 0.248 |
| 249 | 0.1 |
| 250 | 0.2 |
| 251 | 0.18 |
| 252 | 0.028 |
| 258 | 0.169 |
| 259 | 0.028 |
| 260 | 0.018 |
| 261 | 1.16 |
| 262 | 0.027 |
| 263 | 0.102 |
| 264 | 0.063 |
| 265 | 0.057 |
| 266 | 0.029 |
| 268 | 0.027 |
| 269 | 0.019 |
| 270 | 0.272 |
| 271 | 0.099 |
| 272 | 0.261 |
| 273 | 0.2 |
| 274 | 0.1 |
| 275 | 0.033 |
| 276 | 0.024 |
| 277 | 0.023 |
| 278 | 0.072 |
| 279 | 0.040 |
| 280 | 0.003 |
| 281 | 0.142 |
| 282 | 0.008 |
| 283 | 0.021 |
| 284 | 0.003 |
| 285 | 0.002 |
| 286 | 0.026 |
| 287 | 0.029 |
| 288 | 0.062 |
| 289 | 0.030 |
| 290 | 0.022 |
| 291 | 0.017 |
| 292 | 0.039 |
| 293 | 0.018 |
| 294 | 0.019 |
| 295 | 0.013 |
| 296 | 0.021 |
| 297 | 0.050 |
| 300 | 0.028 |
| 301 | 0.043 |
| 302 | 0.067 |
| 303 | 0.007 |
| 304 | 0.004 |
| 305 | 0.005 |
| 306 | 0.040 |
| 307 | 0.057 |
| 308 | 0.027 |
| 309 | 0.020 |
| 310 | 0.028 |
| 311 | 0.011 |
| 312 | 0.025 |
| 313 | 0.008 |
| 314 | 0.008 |
| 315 | 0.053 |
| 316 | 0.007 |
| 317 | 1.61 |
| 318 | 0.007 |
| 322 | 0.013 |
| 323 | 0.070 |
| 325 | 1.52 |
| 326 | 0.389 |
| 327 | 0.023 |
| 329 | 0.120 |
| 330 | 0.213 |
| 332 | 6.48 |
| 337 | 1.34 |
| 338 | 0.667 |
| 339 | 0.160 |
| 340 | 0.026 |
| 342 | 0.816 |
| 343 | 0.067 |
| 344 | 0.012 |
| 345 | 0.036 |
| 346 | 0.019 |
| 347 | 0.035 |
| 348 | 0.092 |
| 352 | 0.505 |
| 353 | 0.504 |
| 354 | 0.036 |
| 355 | 1.60 |
| 356 | 0.463 |
| 357 | 0.062 |
| 358 | 0.018 |
| 359 | 0.855 |
| 360 | 1.72 |
| 361 | 0.582 |
| 363 | 0.592 |
| 364 | 0.011 |
| 365 | 0.291 |
| 366 | 1.13 |
| 368 | 0.355 |
| 369 | 1.69 |
| 370 | 0.117 |
| 371 | 0.264 |
| 372 | 0.011 |
| 373 | 0.209 |
| 374 | 1.63 |
| 375 | 0.199 |
| 376 | 0.084 |
| 377 | 0.007 |
| 379 | 0.506 |
| 380 | 0.225 |
| 381 | 1.39 |
| 382 | 0.575 |
| 383 | 0.083 |
| 384 | 0.270 |
| 385 | 0.094 |

-continued

| Example | TLR7 IC$_{50}$ (µmol/L) |
|---|---|
| 386 | 0.013 |
| 388 | 1.35 |
| 389 | 2.04 |
| 390 | 0.31 |
| 391 | 0.038 |
| 392 | 0.013 |
| 393 | 0.001 |
| 394 | 0.114 |
| 395 | 0.005 |
| 396 | 0.061 |
| 397 | 0.031 |
| 398 | 0.021 |
| 399 | 0.039 |
| 400 | 0.263 |
| 401 | 0.006 |
| 402 | 0.132 |
| 403 | 0.021 |
| 404 | 0.846 |
| 405 | 3.41 |
| 410 | 0.070 |
| 411 | 0.026 |
| 412 | 0.005 |
| 413 | 0.009 |
| 414 | 0.016 |
| 415 | 0.016 |
| 416 | 0.050 |
| 418 | 0.019 |
| 419 | 0.712 |
| 420 | 0.139 |
| 421 | 0.073 |
| 424 | 0.1 |
| 425 | 0.093 |
| 426 | 0.2 |
| 427 | 0.028 |
| 428 | 0.210 |
| 430 | 0.549 |
| 431 | 0.008 |
| 432 | 0.062 |
| 433 | 0.009 |
| 434 | 0.09 |
| 435 | 0.018 |
| 436 | 0.037 |
| 437 | 0.016 |
| 439 | 0.134 |
| 440 | 0.084 |
| 441 | 0.176 |
| 443 | 0.017 |
| 444 | 0.098 |
| 445 | 0.021 |

The compounds of the present invention exhibited potent inhibitory effect against TLR7 in the test for evaluating inhibition of the activation of TLR7. In particular, the compounds of Examples 46, 47, 48, 49, 50, 51, 52, 53, 66, 67, 69, 70, 71, 72, 81, 94, 95, 96, 98, 100, 101, 105, 106, 107, 109, 110, 119, 123, 125, 127, 128, 129, 130, 131, 132, 133, 135, 136, 138, 139, 148, 161, 163, 165, 166, 169, 171, 172, 173, 174, 175, 176, 177, 178, 252, 259, 260, 262, 264, 265, 266, 275, 276, 277, 278, 279, 280, 282, 283, 284, 285, 286, 287, 288, 289, 290, 291, 292, 293, 294, 295, 296, 297, 300, 301, 302, 303, 304, 305, 306, 307, 308, 309, 310, 311, 312, 313, 314, 315, 316, 318, 322, 323, 327, 340, 343, 344, 345, 346, 347, 348, 372, 376, 377, 383, 386, 391, 392, 393, 395, 396, 397, 398, 399, 401, 403, 410, 411, 412, 413, 414, 415, 416, 418, 421, 431, 432, 433, 436, 437, 443, and 445 exhibited potent inhibitory effect against TLR7.

Test 2: Test for Evaluating the Inhibition of the Activation of Human TLR8

As human TLR8 expressing cell line, HEK293 cell line was bought from IMGENEX Corporation (TLR8/NF-ηB/ SEAPorter™ HEK293 cell), which is human embryonic kidney cell line and stably expresses full-length human TLR8 gene and secreted alkaline phosphatase (SEAP) reporter gene under the transcriptional control of an NF-ηB response element. The TLR8/NF-ηB/SEAPorter™ HEK293 cell was cultivated with DMEM containing 10% fetal bovine serum (FBS) and 10 µg/mL blasticidin S at 37° C. in the presence of 5% $CO_2$. The TLR8/NF-ηB/SEAPorter™ HEK293 cell was seeded into 96-well microtiter plate at $5 \times 10^4$ cell/90 µL/well, and the place was cultivated at 37° C. in a $CO_2$ incubator overnight. Each test compound that was diluted with the medium was added to the wells (10 µL/well), wherein each final concentration was adjusted to 0.01, 0.03, 0.1, 0.3, 1, 3, 10, 30, and 100 µmol/L. After 0.5 hour, R-848 that is TLR7/8 ligand was added to each well (10 µL/well), wherein each final concentration was adjusted to 30 µmol/L. The total volume was adjusted to 110 µL/well, the test samples were incubated in $CO_2$ incubator for 20±1 hours, and then the SEAP activity was measured as activation of TLR8. The SEAP activity was evaluated as follows: p-nitro-phenyl phosphate (pNPP, Invitrogen) was added to the incubated sample (50 µL/well); after 15 minutes, 4 mol/L sodium hydroxide solution (nacalai tesque) was added thereto (50 µL/well) to quench the reaction; and the absorbance of each sample was measured at 405 nm with microplate reader Elx808 (BioTek). The 50% inhibitory concentration (IC$_{50}$ value) of each sample compound was calculated based on 100% of the SEAP activity wherein the test sample comprises no sample compound.

Test 3: Test for Evaluating the Inhibition of the Activation of Human TLR9

As human TLR9 expressing cell line, HEK293 cell line was bought from IMGENEX Corporation (TLR9/NF-ηB/ SEAPorter™ HEK293 cell), which is human embryonic kidney cell line and stably expresses full-length human TLR9 gene and the secreted alkaline phosphatase (SEAP) reporter gene under the transcriptional control of an NF-ηB response element. The TLR9/NE-ηB/SEAPorter™ HEK293 cell was cultivated with DMEM containing 10% fetal bovine serum (FBS) and 10 µg/mL blasticidin S at 37° C. in the presence of 5% $CO_2$. The TLR9/NF-ηB/SEAPorter™ HEK293 cell was suede into 96-well microtiter plate at $5 \times 10^4$ cell/90 µL/well, and the place was cultivated at 37° C. in a $CO_2$ incubator overnight. Each test compound that was diluted with the medium was added to the wells (10 µL/well), wherein each concentration was adjusted to 0.01, 0.03, 0.1, 0.3, 1, 3, 10, 30, and 100 µmol/L. After 0.5 hour, CpG-B DNA (CpG2006, Hokkaido System Science Co., Ltd.) that is TLR9 ligand was added to each well (10 µL/well), wherein each final concentration was adjusted to 500 nmol/L. The total volume was adjusted to 110 µL/well, that test samples were incubated in $CO_2$ incubator for 20±1 hours, and then the SEAP activity was measured as activation TLR9. The SEAP activity was evaluated as follows: p-nitro-phenyl phosphate (pNPP) (Invitrogen) was added to the incubated sample (50 µL/well); after 15 minutes, 4 mol/L sodium hydroxide solution (nacalai tesque) was added thereto (50 µL/well) to quench the reaction; and the absorbance of each sample was measured at 405 nm with microplate reader Elx808 (BioTek). The 50% inhibitory concentration (IC$_{50}$ value) of each sample compound was calculated based on 100% of the SEAP activity wherein the test sample comprises no sample compound.

Test 4: Pharmacokinetic Study with Mice

For the evaluation of pharmacokinetic study of each sample, 11-week-old mouse (Jcl: ICR, male, CLEA Japan, Inc.) was used. In order to implement the single-dose oral administration to a mouse herein, each compound suspended in 0.5% methylcellulose solution was administered at 10, 30, or 100 mg/kg. As for tail vein injection, each compound dissolved in saline was administered at 1 mg/kg. The blood collection was once with a heparinized syringe, 0.5 hour, 1 hour, 2 hours, 4 hours, 6 hours, and 24 hours after the oral administration; and 5 minutes, 15 minutes, 0.5 hour, 1 hour, 2 hours, 4 hours, 6 hours, and 24 hours after the tail vein injection. Each collected blood was centrifuged to give its plasma. The plasma was diluted with methanol, wherein the final concentration of methanol was adjusted to 80%, centrifuged, and then filtrated to deproteinize the plasma. The obtained filtrate was analyzed with an LC-MS/MS (API4000, 5500Qtrap, 6500Qtrap, AB SCIEX) to detect and assay the test compound. For the assay, the calibration curve was prepared from mouse plasma comprising known amount of the compound, and phenytoin was used as an internal standard.

Test 5: Test for Evaluating the Inhibition of the Activation of Mouse TLR7

As mouse TLR7 expressing cell line, mouse TLR7 gene-stably-expressing HEK293 cell line which is human embryonic kidney cell line was bought from InvivoGen (293XL-mTLR7 cell). The 293XL-mTLR7 cell was cultivated with DMEM containing 10% fetal bovine serum (FBS) and 10 µg/mL blasticidin S at 37° C. in the presence of 5% $CO_2$. The 293XL-mTLR7 cell was seeded into 6-well plate (collagen-coated) at $3 \times 10^5$ cell/2 mL/well, and the place was cultivated an 37° C. in a $CO_2$ incubator overnight. pNF-ηB-Luc plasmid (Agilent Technologies) that was diluted with FuGENER™ 6 Transfection Reagent (Promega) and the medium was added to the 293XL-mTLR7 cell-cultivating plate (1 µg/100 µL/well), the plate was cultivated at 37° C. in a $CO_2$ incubator overnight. The pNF-ηB-Luc plasmid-transfected 293XL-mTLR7 cell was seeded into 96-well plate for fluorescence/luminescence assay at $2 \times 10^4$ cell/90 µL/well. Each test compound that was diluted with the medium was added to the wells (10 µL/well), wherein each final concentration was adjusted to 0.001, 0.003, 0.01, 0.03, 0.1, 0.3, 1, 3, 10 µmol/L, or 0.01, 0.03, 0.1, 0.3, 1, 3, 10, 30, 100 µmol/L. After 0.5 hour, R-848 that is TLR7/8 ligand was added to each well (10 µL/well), wherein each final concentration was adjusted to 200 nmol/L. The total volume was adjusted to 110 µL/well, the test samples were incubated in $CO_2$ incubator for 6 hours, and then the luciferase activity was measured as activation of TLR7. The luciferase activity was evaluated as follows: Bright-Glo™ Luciferase Assay System (Promega) was added to the incubated sample (100 µL/well); after 2 minutes, the luminescence intensity of each sample was measured with a luminometer (Envision). The 50% inhibitory concentration ($IC_{50}$ value) of each sample compound was calculated based on 100% of the luciferase activity wherein the test sample comprises no sample compound.

Test 6: Test for Evaluating the Inhibition of the Activation of Mouse TLR9

As mouse TLR9 expressing cell line, mouse TLR9 gene-stably-expressing HEK293 cell line which is human embryonic kidney cell line was bought from InvivoGen (293-mTLR9 cell). The 293-mTLR9 cell was cultivated with DMEM containing 10% fetal bovine serum (FBS) and 10 µg/mL blasticidin S at 37° C. in the presence of 5% $CO_2$. The 293-mTLR9 cell was seeded into 6-well plate (collagen-coated) at $3 \times 10^5$ cell/2 mL/well, and the place was cultivated at 37° C. in a $CO_2$ incubator overnight to prepare 293-mTLR9 (pNF-ηB-Luc) cell. The 293-mTLR9 (pNF-ηB-Luc) cell was seeded into 96-well plate for fluorescence/luminescence assay at $2 \times 10^4$ cell/90 µL/well. Each test compound that was diluted with the medium was added to the wells (10 µL/well), wherein each final concentration was adjusted to 0.01, 0.03, 0.1, 0.3, 1, 3, 10, 30, 100 µmol/L. After 0.5 hour, CpG-B DNA (CpG1826, Hokkaido System Science Co., Ltd.) that is TLR9 ligand was added to each well (10 µL/well), wherein each final concentration was adjusted to 100 nM. The total volume was adjusted to 110 µL/well, the test samples were incubated in $CO_2$ incubator for 6 hours, and then the luciferase activity was measured as activation of TLR9. The luciferase activity was evaluated as follows: Bright-Glo™ Luciferase Assay System (Promega) was added to the incubated sample (100 µL/well); after 2 minutes, the luminescence intensity of each sample was measured with a luminometer (Envision). The 50% inhibitory concentration ($IC_{50}$ value) of each sample compound was calculated based on 100% of the luciferase activity wherein the test sample comprises no sample compound.

Test 7: Test for Evaluating the Inhibition of Blood Cytokine Production in Mouse Treated with Oral Single Administration 6 to 17-week-old mice (ICR, male, CHARLES RIVER LABORATORIES JAPAN, INC.; or BALB/c, female, Japan SLC, Inc.) were used in the present test. Each example compound dissolved or suspended in 0.5% methylcellulose solution was orally administered to the mouse. Three or six hours later, R848 which is a TLR7 agonist was subcutaneously administered to the back of the mouse at 15 µg/200 µL/head. 1.5 hours after the administration of R848, the blood was collected with a heparinized syringe, and the induced IL-6 in the plasma was assayed with a commercially available ELISA kit (Quantikine Mouse IL-6 ELISA; R&D system (# M6000B).

Test 8: Test for Evaluating Drug in Case of Prophylactic Administration with NZBW F1 Mouse NZBW F1 mice (Japan SLC, Inc., female) used herein were consumed when they were 22 weeks old. The urinary albumin/creatinine ratio (UACR) of the mice when they were 24 weeks old was measured, and the mice were grouped based on their weight and UACR (vehicle control group (0.5% methylcellulose), Example compound group, and prednisolone group). Mice whose creatinine concentration was over 100 mg/g when they were 24 weeks old were excluded as onset individual. The test mice received daily oral administration (once a day) for 13 weeks since they were 25 weeks old. The urine was collected from all the mice with a metabolism cage once in one or two weeks. 14 weeks after the start of the administration (38-week-old), the blood was collected and the kidney was extirpated from all the mice. The UACR was measured with an autoanalyzer. The blood dsDNA antibody titer was assayed with a Mouse Anti-dsDNA ELISA KIT (Shibayagi Corporation). The extirpated kidney was tested about histopathological workup.

The compounds of the present invention exhibited potent pharmacological effect in a dose-dependent manner at the drug efficiency evaluation with NZBW F1 mice receiving prophylactic administration.

Test 9: Test for Evaluating Drug in case of
Therapeutic Administration with NZBW F1 Mouse NZBW F1 mice (Japan SLC, inc., female) used herein were consumed when they were 22 weeks old. The mice whose urinary albumin/creatinine ratio (UACR) was 300-4000 (mg/g creatinine) were chosen, which were grouped (vehicle control group (0.5% methylcellulose), and Example compound group). The administration was sequentially started after onset of each individual, and the oral administration was continued every day for 4 weeks. The urine was collected from all the mice with a metabolism cage once a week, and the UACR was measured with an autoanalyzer. Four weeks after the start of the administration, the blood was collected and the kidney was extirpated from all the alive mice. The extirpated kidney was tested about histopathological work-up.

The compounds of the present invention exhibited potent pharmacological effect in an administration-frequency-dependent manner at the drug efficiency evaluation with NZBW F1 mice receiving therapeutic administration.

Test 10: Test for Evaluating Drug in Case of
Prophylactic Administration with NZW×BXSB F1
Mouse NZW×BXSB F1 mice (Japan SLC, Inc., female) used herein were consumed when they were 4 weeks old. The blood of the 6-week-old NZW×BXSB F1 mice was partially collected from their neck at 100 μL/head, which was treated with EDTA, and the mice were grouped based on the platelet count in blood and the body weight (vehicle control group (0.5% methylcellulose), Example compound group, and prednisolone group). The platelet count was measured with a Sysmex XT-1800I. From the next day of the grouping, the test mice received daily oral administration (once a day) for 12 weeks. Every 3 weeks after the start of the administration, the blood was partially collected from the neck, which was treated with EDTA. The effect that the test drug can inhibit the platelet depletion was studied by monitoring the platelet count with time. From the mice which received the last administration, the urine was collected with a metabolism cage, and the urinary albumin/creatinine ratio (UACR) was measured with an autoanalyzer. The weights of kidney and spleen were measured.

The compounds of the present invention exhibited potent pharmacological effect in a dose-dependent manner at the drug efficiency evaluation with NZBW F1 mice receiving prophylactic administration.

INDUSTRIAL APPLICABILITY

Thus, the compounds of the present invention have inhibitory effect to TLR, which are useful for preventing and/or treating autoimmune disease.

The invention claimed is:
1. A compound of formula (1):

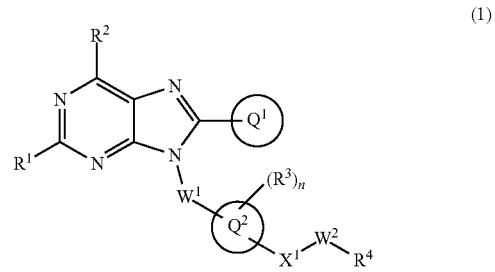

or a pharmaceutically acceptable salt thereof
wherein
$R^1$ is optionally-substituted $C_{1-6}$ alkoxy, optionally-substituted $C_{3-7}$ cycloalkoxy, optionally-substituted 4- to 10-membered saturated heterocyclyloxy, optionally-substituted $C_{1-6}$ alkyl, optionally-substituted $C_{3-7}$ cycloalkyl, optionally-substituted $C_{1-6}$ alkylthio, optionally-substituted 4- to 10-membered saturated heterocyclyl, optionally-substituted amino, halogen atom, or hydroxy;
$R^2$ is optionally-substituted $C_{1-6}$ alkyl, optionally-substituted $C_{3-7}$ cycloalkyl, or optionally-substituted amino;
$W^1$ is single bond, or optionally-substituted $C_{1-4}$ alkylene;
Ring $Q^1$ is
(1) pyridyl which may be substituted with 1-5 the same or different substituents selected from the group consisting of
(a) halogen atom,
(b) cyano,
(c) $C_{1-6}$ alkyl which may be substituted with 1-3 the same or different halogen atoms, and
(d) $C_{1-6}$ alkoxy which may be substituted with 1-3 the same or different halogen atoms, or
(2) pyrimidinyl which may be substituted with 1-3 the same or different substituents selected from the group consisting of (a)-(d) in the above (1),
Ring $Q^2$ is $C_{6-10}$ aromatic carbocyclyl, or 5- to 10-membered aromatic heterocyclyl;
n is 1, 2, 3, or 4;
$R^3$ is, independently if there are plural $R^3$, hydrogen atom, halogen atom, cyano, hydroxy, optionally-substituted $C_{1-6}$ alkyl, optionally-substituted $C_{1-6}$ alkoxy, optionally-substituted $C_{3-7}$ cycloalkyl, optionally-substituted $C_{3-7}$ cycloalkoxy, or optionally-substituted amino;
$Q^2$-$X^1$— is $Q^2$-(single bond)-, $Q^2$-$(CH_2)_m$—O—, $Q^2$-$(CH_2)_m$—S—, $Q^2$-$(CH_2)_m$—$S(O)_2$—, $Q^2$-$(CH_2)_m$—$NR^aS(O)_2$—, $Q^2$-$(CH_2)_m$—$S(O)_2NR^a$—, $Q^2$-$(CH_2)_m$—C(O)—, $Q^2$-$(CH_2)_m$—$NR^a$—, $Q^2$-$(CH_2)_m$—$NR^aC(O)$—, or $Q^2$-$(CH_2)_m$—$C(O)NR^a$—, wherein $R^a$ is hydrogen atom or $C_{1-6}$ alkyl; m is 0, 1, or 2;
$W^2$ is single bond, or optionally-substituted $C_{1-8}$ alkylene; and
$R^4$ is hydrogen atom, —$OR^b$ (wherein $R^b$ is hydrogen atom, optionally-substituted $C_{1-6}$ alkyl, optionally-substituted $C_{1-6}$ alkylcarbonyl, optionally-substituted aminocarbonyl, or optionally-substituted $C_{1-6}$ alkylsulfonyl), —$NR^cR^d$ (wherein $R^c$ is hydrogen atom or optionally-substituted $C_{1-6}$ alkyl; and $R^d$ is hydrogen atom, optionally-substituted $C_{1-6}$ alkyl, optionally-substituted $C_{1-6}$ alkylcarbonyl, optionally-substituted $C_{1-6}$ alkoxycarbonyl, or optionally-substituted $C_{1-6}$ alkylsulfonyl), optionally-substituted 4- to 10-membered saturated heterocyclyl, or optionally-substituted 5- to 10-membered heteroaryl.

2. The compound of claim 1 or a pharmaceutically acceptable salt thereof, wherein
$R^1$ is
(1) $C_{1-6}$ alkoxy which may be substituted with 1-3 the same or different substituents selected from the group consisting of
  (a) halogen atom,
  (b) hydroxy,
  (c) $C_{1-6}$ alkoxy which may be substituted with 1-3 the same or different halogen atoms,
  (d) $C_{3-7}$ cycloalkyl which may be substituted with 1-4 the same or different substituents selected from the group consisting of halogen atom, $C_{1-6}$ alkyl, and $C_{1-6}$ alkoxy,
  (e) $C_{3-7}$ cycloalkoxy which may be substituted with 1-4 the same or different substituents selected from the group consisting of halogen atom, $C_{1-6}$ alkyl, and $C_{1-6}$ alkoxy,
  (f) phenyl which may be substituted with 1-4 the same or different substituents selected from the group consisting of halogen atom, $C_{1-6}$ alkyl, and $C_{1-6}$ alkoxy,
  (g) 5- or 6-membered heteroaryl which may be substituted with 1-4 the same or different substituents selected from the group consisting of halogen atom, $C_{1-6}$ alkyl, and $C_{1-6}$ alkoxy, and
  (h) 4- to 7-membered saturated heterocyclyl which may be substituted with 1-4 the same or different substituents selected from the group consisting of halogen atom, $C_{1-6}$ alkyl, and $C_{1-6}$ alkoxy,
(2) $C_{3-7}$ cycloalkoxy which may be substituted with 1-4 the same or different substituents selected from the group consisting of halogen atom, $C_{1-6}$ alkyl, and $C_{1-6}$ alkoxy,
(3) 4- to 10-membered saturated heterocyclyloxy which may be substituted with 1-4 the same or different substituents selected from the group consisting of halogen atom, $C_{1-6}$ alkyl, and $C_{1-6}$ alkoxy,
(4) $C_{1-6}$ alkyl which may be substituted with 1-3 the same or different substituents selected from the group consisting of halogen atom, hydroxy, and $C_{1-6}$ alkoxy,
(5) $C_{3-7}$ cycloalkyl which may be substituted with 1-4 the same or different substituents selected from the group consisting of halogen atom, $C_{1-6}$ alkyl, and $C_{1-6}$ alkoxy,
(6) $C_{1-6}$ alkylthio which may be substituted with 1-3 the same or different halogen atoms,
(7) 4- to 10-membered saturated heterocyclyl which may be substituted with 1-4 the same or different substituents selected from the group consisting of halogen atom, $C_{1-6}$ alkyl, and $C_{1-6}$ alkoxy,
(8) amino which may be substituted with 1-2 the same or different $C_{1-6}$ alkyl which may be substituted with 1-3 the same or different halogen atoms,
(9) halogen atom, or
(10) hydroxy;
$R^2$ is $C_{1-6}$ alkyl (which may be substituted with 1-3 the same or different halogen atoms), $C_{3-7}$ cycloalkyl, or amino (which may be substituted with 1-2 the same or different $C_{1-6}$ alkyl);
Ring $Q^1$ is
(1) pyridyl which may be substituted with 1-5 the same or different substituents selected from the group consisting of
  (a) halogen atom,
  (b) cyano,
  (c) $C_{1-6}$ alkyl which may be substituted with 1-3 the same or different halogen atom, and
  (d) $C_{1-6}$ alkoxy which may be substituted with 1-3 the same or different halogen atoms, or
(2) pyrimidinyl which may be substituted with 1-3 the same or different substituents selected from the group consisting of (a)-(d) in the above (1);
$W^1$ is single bond, or $C_{1-4}$ alkylene which may be substituted with 1-4 the same or different substituents selected from the group consisting of halogen atom, hydroxy, and $C_{1-6}$ alkoxy,
Ring $Q^2$ is $C_{6-10}$ aromatic carbocyclyl, or 5- to 10-membered aromatic heterocyclyl;
n is 1, 2, 3, or 4;
$R^3$ is, independently if there are plural $R^3$,
(1) hydrogen atom,
(2) halogen atom,
(3) cyano,
(4) hydroxy,
(5) $C_{1-6}$ alkyl which may be substituted with 1-3 the same or different substituents selected from the group consisting of halogen atom, hydroxy, and $C_{1-6}$ alkoxy,
(6) $C_{1-6}$ alkoxy which may be substituted with 1-3 the same or different substituents selected from the group consisting of halogen atom, hydroxy, and $C_{1-6}$ alkoxy,
(7) $C_{3-7}$ cycloalkyl which may be substituted with 1-4 the same or different substituents selected from the group consisting of halogen atom, $C_{1-6}$ alkyl, and $C_{1-6}$ alkoxy,
(8) $C_{3-7}$ cycloalkoxy which may be substituted with 1-4 the same or different substituents selected from the group consisting of halogen atom, $C_{1-6}$ alkyl, and $C_{1-6}$ alkoxy, or
(9) amino which may be substituted with 1-2 the same or different $C_{1-6}$ alkyl which may be substituted with 1-3 the same or different halogen atoms;
$Q^2$-$X^1$— is $Q^2$-(single bond)-, $Q^2$-$(CH_2)_m$—O—, $Q^2$-$(CH_2)_m$—S—, $Q^2$-$(CH_2)_m$—$S(O)_2$—, $Q^2$-$(CH_2)_m$—$NR^aS(O)_2$—, $Q^2$-$(CH_2)_m$—$S(O)_2NR^a$—, $Q^2$-$(CH_2)_m$—C(O)—, $Q^2$-$(CH_2)_m$—$NR^a$—, $Q^2$-$(CH_2)_m$—$NR^aC(O)$—, or $Q^2$-$(CH_2)_m$—$C(O)NR^a$—, wherein $R^a$ is hydrogen atom or $C_{1-6}$ alkyl; m is 0, 1, or 2;
$W^2$ is single bond, or $C_{1-8}$ alkylene which may be substituted with 1-4 the same or different substituents selected from the group consisting of halogen atom, hydroxy, and $C_{1-6}$ alkoxy; and
$R^4$ is
(1) hydrogen atom,
(2) —$OR^b$ wherein $R^b$ is hydrogen atom, $C_{1-6}$ alkyl, $C_{1-6}$ alkylcarbonyl, mono- or di-$C_{1-6}$ alkyl-aminocarbonyl, or $C_{1-6}$ alkylsulfonyl,
(3) —$NR^cR^d$ wherein $R^c$ is hydrogen atom or $C_{1-6}$ alkyl which may be substituted with 1-3 the same or different halogen atoms; and $R^d$ is hydrogen atom, $C_{1-6}$ alkyl (which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy), $C_{1-6}$ alkylcarbonyl (which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy), $C_{1-6}$ alkoxycarbonyl, or $C_{1-6}$ alkylsulfonyl,
(4) 4- to 10-membered saturated heterocyclyl which may be substituted with 1-4 the same or different substituents selected from the group consisting of
  (a) halogen atom,
  (b) hydroxy,
  (c) cyano, (d) $C_{1-6}$ alkyl which may be substituted with 1-3 the same or different substituents selected from the group consisting of halogen atom, hydroxy, and $C_{1-6}$ alkoxy, (e) $C_{1-6}$ alkoxy which may be substituted with 1-3 the same or different substituents selected from the group consisting of halogen atom, hydroxy, and $C_{1-6}$ alkoxy, (f) $C_{3-7}$ cycloalkyl, (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, (h) $C_{1-6}$ alkoxycarbonyl, (i) 4- to 7-membered saturated heterocyclyl which may be substituted with 1-4 the same or different substituents selected from the group consisting of halogen atom, $C_{1-6}$ alkyl, and $C_{1-6}$ alkoxy, (j) phenyl which may be substituted with 1-4 the same or different substituents selected from the group consisting of halogen atom, $C_{1-6}$ alkyl, and $C_{1-6}$ alkoxy, (k) 5- or 6-membered heteroaryl which may be substituted with 1-4 the same or different substituents selected from the group consisting of halogen atom, $C_{1-6}$ alkyl, and $C_{1-6}$ alkoxy, and (l) oxo, or (5) 5- to 10-membered heteroaryl which may be substituted with 1-4 the same or different substituents selected from the group consisting of halogen atom, $C_{1-6}$ alkyl, and $C_{1-6}$ alkoxy.

3. The compound of claim 1 or a pharmaceutically acceptable salt thereof, wherein $R^1$ is $C_{1-6}$ alkoxy (which may be substituted with 1-3 the same or different substituents selected from the group consisting of halogen atom, hydroxy, $C_{1-6}$ alkoxy, $C_{3-7}$ cycloalkyl and 4- to 7-membered saturated heterocyclyl), 4- to 10-membered saturated heterocyclyloxy (which may be substituted with 1-4 the same or different substituents selected from the group consisting of halogen atom, and $C_{1-6}$ alkyl), $C_{1-6}$ alkyl (which may be substituted with 1-3 the same or different substituents selected from the group consisting of halogen atom, hydroxy, and $C_{1-6}$ alkoxy), 4- to 10-membered saturated heterocyclyl (which may be substituted with 1-4 the same or different substituents selected from the group consisting of halogen atom, $C_{1-6}$ alkyl, and $C_{1-6}$ alkoxy), amino (which may be substituted with 1-2 the same or different $C_{1-6}$ alkyl), halogen atom, or hydroxy.

4. The compound of claim 1 or a pharmaceutically acceptable salt thereof, wherein $R^1$ is $C_{1-6}$ alkoxy (which may be substituted with 1-3 the same or different substituents selected from the group consisting of halogen atom, hydroxy, and $C_{1-6}$ alkoxy), or halogen atom.

5. The compound of claim 1 or a pharmaceutically acceptable salt thereof, wherein $R^2$ is $C_{1-6}$ alkyl or amino.

6. The compound of claim 1 or a pharmaceutically acceptable salt thereof, wherein $W^1$ is methylene.

7. The compound of claim 1 or a pharmaceutically acceptable salt thereof, wherein Ring $Q^2$ is benzene ring group, or 5- or 6-membered aromatic heterocyclyl.

8. The compound of claim 1 or a pharmaceutically acceptable salt thereof, wherein Ring $Q^2$ is pyridine ring group, pyrazole ring group, isoxazole ring group, or benzene ring group.

9. The compound of claim 1 or a pharmaceutically acceptable salt thereof, wherein $R^3$ is hydrogen atom, halogen atom, cyano, hydroxy, $C_{1-6}$ alkyl (which may be substituted with 1-3 the same or different halogen atoms), or $C_{1-6}$ alkoxy (which may be substituted with 1-3 the same or different halogen atoms).

10. The compound of claim 1 or a pharmaceutically acceptable salt thereof, wherein $Q^2$-$X^1$— is $Q^2$-(single bond)-, $Q^2$-$(CH_2)_m$—O—, $Q^2$-$(CH_2)_m$—C(O)—, $Q^2$-$(CH_2)_m$—$NR^a$—, or $Q^2$-$(CH_2)_m$—C(O)$NR^a$—, wherein $R^a$ is hydrogen atom or $C_{1-6}$ alkyl; m is 0, 1, or 2.

11. The compound of claim 1 or a pharmaceutically acceptable salt thereof, wherein $X^1$ is single bond or —O—.

12. The compound of claim 1 or a pharmaceutically acceptable salt thereof, wherein $W^2$ is single bond or $C_{1-3}$ alkylene.

13. The compound of claim 1 or a pharmaceutically acceptable salt thereof, wherein $W^2$ is single bond or methylene.

14. The compound of claim 1 or a pharmaceutically acceptable salt thereof, wherein $R^4$ is (1) hydrogen atom, (2) —$OR^b$ wherein $R^b$ is hydrogen atom, $C_{1-6}$ alkyl, or $C_{1-6}$ alkylsulfonyl, (3) —$NR^cR^d$ wherein $R^c$ and $R^d$ are independently hydrogen atom or $C_{1-6}$ alkyl which may be substituted with 1-3 the same or different halogen atoms, (4) 4- to 10-membered saturated heterocyclyl which may be substituted with 1-4 the same or different substituents selected from the group consisting of (a) halogen atom, (b) hydroxy, (c) cyano, (d) $C_{1-6}$ alkyl which may be substituted with 1-3 the same or different substituents selected from the group consisting of halogen atom, hydroxy, and $C_{1-6}$ alkoxy, (e) $C_{1-6}$ alkoxy which may be substituted with 1-3 the same or different substituents selected from the group consisting of halogen atom, hydroxy, and $C_{1-6}$ alkoxy, (f) $C_{3-7}$ cycloalkyl, (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, (h) $C_{1-6}$ alkoxycarbonyl, (i) 4- to 7-membered saturated heterocyclyl which may be substituted with 1-4 the same or different substituents selected from the group consisting of halogen atom, $C_{1-6}$ alkyl, and $C_{1-6}$ alkoxy, and (j) oxo, or (5) 5- to 10-membered heteroaryl which may be substituted with 1-4 the same or different substituents selected from the group consisting of halogen atom, $C_{1-6}$ alkyl, and $C_{1-6}$ alkoxy.

15. The compound of claim 1 or a pharmaceutically acceptable salt thereof, wherein $R^4$ is (1) —$NR^cR^d$ wherein $R^c$ and $R^d$ are independently hydrogen atom or $C_{1-6}$ alkyl which may be substituted with 1-3 the same or different halogen atoms, or (2) 4- to 10-membered saturated nitrogen-containing heterocyclyl which may be substituted with 1-4 the same or different substituents selected from the group consisting of (a) halogen atom, (b) hydroxy, (c) cyano, (d) $C_{1-6}$ alkyl which may be substituted with 1-3 the same or different substituents selected from the group consisting of halogen atom, hydroxy, and $C_{1-6}$ alkoxy, (e) $C_{1-6}$ alkoxy which may be substituted with 1-3 the same or different substituents selected from the group consisting of halogen atom, hydroxy, and $C_{1-6}$ alkoxy, (f) $C_{3-7}$ cycloalkyl, (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, and (h) 4- to 7-membered saturated heterocyclyl.

16. The compound of claim 1 or a pharmaceutically acceptable salt thereof, wherein formula (1) is represented as formula (1a):

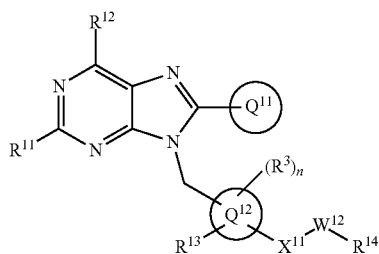

(1a)

wherein $R^{11}$ is $C_{1-6}$ alkoxy (which may be substituted with 1-3 the same or different substituents selected from the group consisting of halogen atom, hydroxy, $C_{1-6}$ alkoxy, $C_{3-7}$ cycloalkyl and 4- to 7-membered saturated heterocyclyl), 4- to 10-membered saturated heterocyclyloxy (which may be substituted with 1-4 the same or different substituents selected from the group consisting of halogen atom, and $C_{1-6}$ alkyl), $C_{1-6}$ alkyl (which may be substituted with 1-3 the same or different substituents selected from the group consisting of halogen atom, hydroxy, and $C_{1-6}$ alkoxy), 4- to 10-membered saturated heterocyclyl (which may be substituted with 1-4 the same or different substituents selected from the group consisting of halogen atom, $C_{1-6}$ alkyl, and $C_{1-6}$ alkoxy), amino (which may be substituted with 1-2 the same or different $C_{1-6}$ alkyl), halogen atom, or hydroxy;

$R^{12}$ is $C_{1-6}$ alkyl or amino;

Ring $Q^{11}$ is (1) pyridyl which may be substituted with 1-4 the same or different substituents selected from the group consisting of (a) halogen atom, (b) cyano, (c) $C_{1-6}$ alkyl which may be substituted with 1-3 the same or different halogen atoms, and (d) $C_{1-6}$ alkoxy which may be substituted with 1-3 the same or different halogen atoms, or (2) pyrimidinyl which may be substituted with 1-3 the same or different substituents selected from the group consisting of (a)-(d) in the above (1);

Ring $Q^{12}$ is benzene ring group, or 5- or 6-membered aromatic heterocyclyl;

$R^{13}$ is hydrogen atom, halogen atom, hydroxy, $C_{1-6}$ alkyl (which may be substituted with 1-3 the same or different halogen atoms), or $C_{1-6}$ alkoxy (which may be substituted with 1-3 the same or different halogen atoms);

$Q^2$-$X^{11}$— is $Q^{12}$-(single bond)-, $Q^{12}$-$(CH_2)_m$—O—, $Q^{12}$-$(CH_2)_m$—C(O)—, $Q^{12}$-$(CH_2)_m$—NR$^a$—, or $Q^{12}$-$(CH_2)_m$—C(O)NR$^a$—, wherein R$^a$ is hydrogen atom or $C_{1-6}$ alkyl; m is 0, 1, or 2;

$W^{12}$ is single bond or $C_{1-3}$ alkylene; and $R^{14}$ is (1) hydrogen atom, (2) —OR$^b$ wherein R$^b$ is hydrogen atom, $C_{1-6}$ alkyl, or $C_{1-6}$ alkylsulfonyl, (3) —NR$^c$R$^d$ wherein R$^c$ and R$^d$ are independently hydrogen atom, or $C_{1-6}$ alkyl which may be substituted with 1-3 the same or different halogen atoms, (4) 4- to 10-membered saturated heterocyclyl which may be substituted with 1-4 the same or different substituents selected from the group consisting of (a) halogen atom, (b) hydroxy, (d) $C_{1-6}$ alkyl which may be substituted with 1-3 the same or different substituents selected from the group consisting of halogen atom, hydroxy, and $C_{1-6}$ alkoxy, (e) $C_{1-6}$ alkoxy which may be substituted with 1-3 the same or different substituents selected from the group consisting of halogen atom, hydroxy, and $C_{1-6}$ alkoxy, (f) $C_{3-7}$ cycloalkyl, (g) $C_{1-6}$ alkylcarbonyl which may be substituted with 1-3 the same or different substituents selected from the group consisting of halogen atom, hydroxy, amino (which may be substituted with 1-2 the same or different $C_{1-6}$ alkyl), and $C_{1-6}$ alkoxy, (h) $C_{1-6}$ alkoxycarbonyl, (i) 4- to 7-membered saturated heterocyclyl which may be substituted with 1-4 the same or different substituents selected from the group consisting of halogen atom, $C_{1-6}$ alkyl, and $C_{1-6}$ alkoxy, and (j) oxo, or (5) 5- to 10-membered heteroaryl which may be substituted with 1-4 the same or different substituents selected from the group consisting of halogen atom, $C_{1-6}$ alkyl, and $C_{1-6}$ alkoxy.

17. The compound of claim 16 or a pharmaceutically acceptable salt thereof, wherein $R^{12}$ is $C_{1-4}$ alkyl.

18. The compound of claim 16 or a pharmaceutically acceptable salt thereof, wherein $R^{13}$ is hydrogen atom or halogen atom.

19. The compound of claim 16 or a pharmaceutically acceptable salt thereof, wherein Ring $Q^{11}$ is 5-fluoropyridin-3-yl, 5-cyanopyridin-3-yl, pyridin-3-yl, or pyrimidinyl.

20. The compound of claim 16 or a pharmaceutically acceptable salt thereof, wherein Ring $Q^{12}$ is pyridine ring group, pyrazole ring group, isoxazole ring group, or benzene ring group.

21. The compound of claim 16 or a pharmaceutically acceptable salt thereof, wherein $R^{14}$ is the following formula (2), (3), (4), (5), (6), (8), (9), (10), (11), (12), (13), (14), (15), or (16):

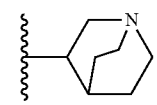

(2)

-continued

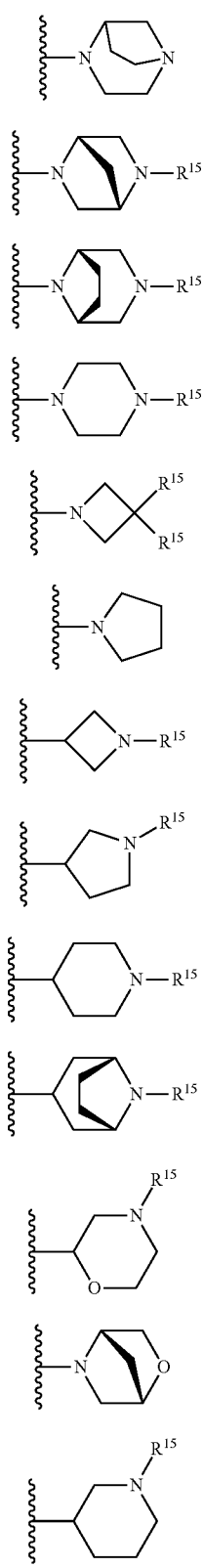

wherein
R[15] is halogen, hydroxy, C[1-6] alkyl (which may be substituted with 1-3 the same or different substituents selected from the group consisting of halogen atom, hydroxy, and C[1-6] alkoxy), C[3-7] cycloalkyl, C[1-6] alkylcarbonyl (which may be substituted with one amino which may be substituted with 1-2 the same or different C[1-6] alkyl), or 4- to 7-membered saturated heterocyclyl.

22. The compound of claim 16 or a pharmaceutically acceptable salt thereof, wherein R[14] is the following formula (2), (3), (4), (5), (6), (8), (9), or (10):

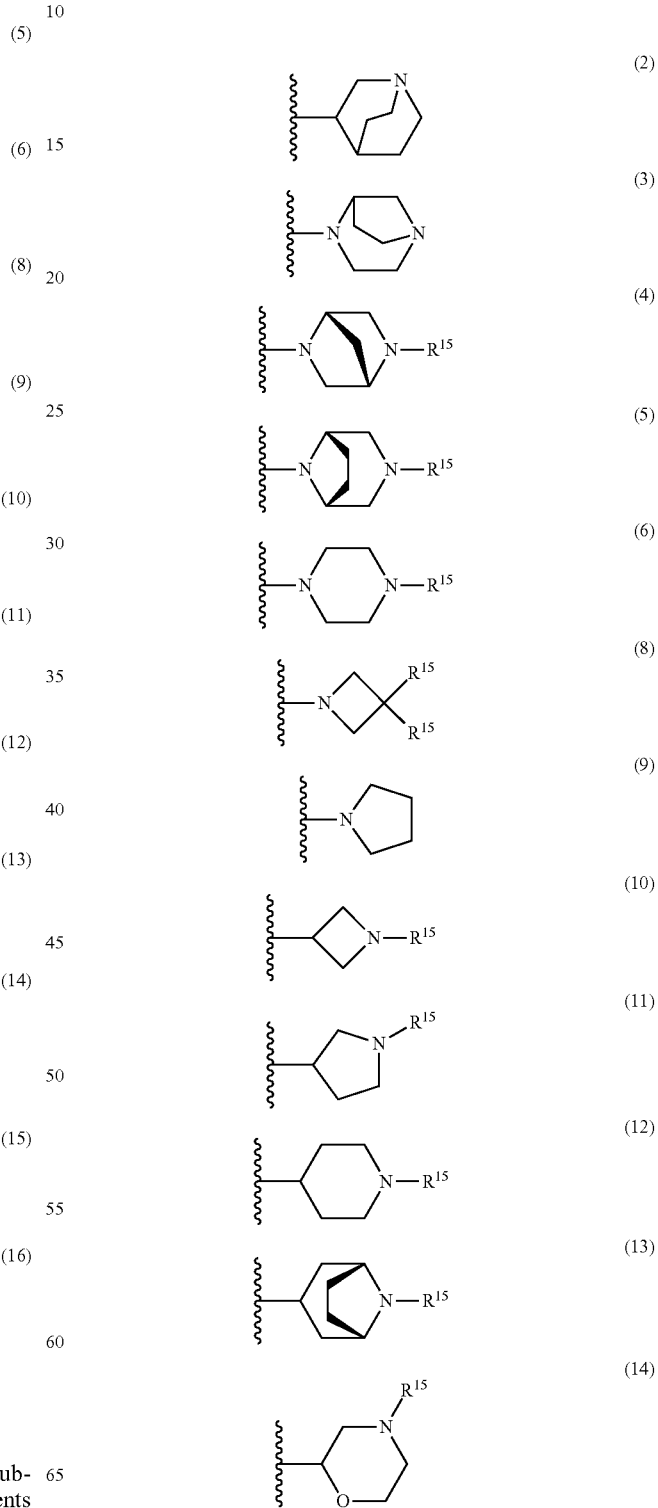

-continued

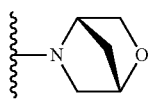
(15)

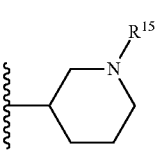
(16)

wherein
R[15] is halogen, hydroxy, $C_{1-6}$ alkyl (which may be substituted with 1-3 the same or different substituents selected from the group consisting of halogen atom, hydroxy, and $C_{1-6}$ alkoxy), $C_{3-7}$ cycloalkyl, $C_{1-6}$ alkylcarbonyl (which may be substituted with one amino which may be substituted with 1-2 the same or different $C_{1-6}$ alkyl), or 4- to 7-membered saturated heterocyclyl.

23. The compound of claim 1 which is selected from the following compounds, or a pharmaceutically acceptable salt thereof:

9-({6-[(3S)-1-azabicyclo[2.2.2]oct-3-yloxy]pyridin-3-yl}methyl)-8-(5-fluoropyridin-3-yl)-2-methoxy-6-methyl-9H-purine, 9-({6-[(3S)-1-azabicyclo[2.2.2]oct-3-yloxy]pyridin-3-yl}methyl)-2-ethoxy-8-(5-fluoropyridin-3-yl)-6-methyl-9H-purine, 8-(5-fluoropyridin-3-yl)-2-methoxy-6-methyl-9-(4-{[(1 S,4S)-5-methyl-2,5-diazabicyclo[2.2.1]hept-2-yl]methyl}benzyl)-9H-purine, 2-ethoxy-8-(5-fluoropyridin-3-yl)-6-methyl-9-(4-{[(1 S,4S)-5-methyl-2,5-diazabicyclo[2.2.1]hept-2-yl]methyl}benzyl)-9H-purine, 2-ethoxy-8-(5-fluoropyridin-3-yl)-6-methyl-9-(4-{[(1R,4R)-5-methyl-2,5-diazabicyclo[2.2.1]hept-2-yl]methyl}benzyl)-9H-purine, 2-ethoxy-9-(4-{[(1 S,4S)-5-ethyl-2,5-diazabicyclo[2.2.1]hept-2-yl]methyl}benzyl)-8-(5-fluoropyridin-3-yl)-6-methyl-9H-purine, 9-(4-{[(1 S,4S)-5-ethyl-2,5-diazabicyclo[2.2.1]hept-2-yl]methyl}benzyl)-8-(5-fluoropyridin-3-yl)-2-methoxy-6-methyl-9H-purine, 8-(5-fluoropyridin-3-yl)-2-methoxy-6-methyl-9-(4-{[(1 S,4S)-5-propyl-2,5-diazabicyclo[2.2.1]hept-2-yl]methyl}benzyl)-9H-purine, 9-{4-[(5R)-1,4-diazabicyclo[3.2.1]oct-4-ylmethyl]benzyl}-2-ethoxy-8-(5-fluoropyridin-3-yl)-6-methyl-9H-purine, 9-{4-[(3S)-1-azabicyclo[2.2.2]oct-3-yl]benzyl}-8-(5-fluoropyridin-3-yl)-2-methoxy-6-methyl-9H-purine, 2-ethoxy-8-(5-fluoropyridin-3-yl)-6-methyl-9-{4-[(4-methylpiperazine-1-yl)methyl]benzyl}-9H-purin, 9-[4-(1-azabicyclo[2.2.2]oct-3-yl)-2-methoxybenzyl]-2-ethoxy-8-(5-fluoropyridin-3-yl)-6-methyl-9H-purine, 2-(1-azabicyclo[2.2.2]oct-3-yl)-5-{[2-ethoxy-8-(5-fluoropyridin-3-yl)-6-methyl-9H-purin-9-yl]methyl}benzonitrile, 9-{[1-(1-azabicyclo[2.2.2]oct-3-ylmethyl)-1H-pyrazol-4-yl]methyl}-2-ethoxy-8-(5-fluoropyridin-3-yl)-6-methyl-9H-purine, 2-(1-azabicyclo[2.2.2]oct-3-yl)-5-{[8-(5-fluoropyridin-3-yl)-2-methoxy-6-methyl-9H-purin-9-yl]methyl}benzonitrile, 9-[2-fluoro-4-[(1-methylpiperidin-4-yl)methyl]benzyl}-8-(5-fluoropyridin-3-yl)-2-methoxy-6-methyl-9H-purine, 9-[2-fluoro-4-[(1-methylazetidin-3-yl)methoxy]benzyl]-8-(5-fluoropyridin-3-yl)-2-methoxy-6-methyl-9H-purine, 5-f 9-[4-(1-ethylpiperidin-4-yl)-2-fluorobenzyl]-2-methoxy-6-methyl-9H-purin-8-yl)pyridine-3-carbonitrile, 9-[2-fluoro-4-(1-methylpyrrolidin-3-yl)benzyl]-8-(5-fluoropyridin-3-yl)-2-methoxy-6-methyl-9H-purine, 9-[4-(1-ethylpyrrolidin-3-yl)-2-fluorobenzyl]-8-(5-fluoropyridin-3-yl)-2-methoxy-6-methyl-9H-purine, 9-[2-fluoro-4-(1-methylpiperidin-4-yl)benzyl]-2-methoxy-6-methyl-8-(pyridin-3-yl)-9H-purine, 9-[4-(1-ethylpiperidin-4-yl)-2-fluorobenzyl]-2-methoxy-6-methyl-8-(pyridin-3-yl)-9H-purine, 9-(2-fluoro-4-{[(3-endo)-8-methyl-8-azabicyclo[3.2.1]oct-3-yl]oxy}benzyl)-2-methoxy-6-methyl-8-(pyridin-3-yl)-9H-purine, 9-{4-[(3S)-1-azabicyclo[2.2.2]oct-3-yloxy]-2-fluorobenzyl}-2-methoxy-6-methyl-8-(pyrimidin-5-yl)-9H-purine, 9-[4-(1-azabicyclo[2.2.2]oct-3-yl)-3-fluorobenzyl]-8-(5-fluoropyridin-3-yl)-2-methoxy-6-methyl-9H-purine, 9-[3-(1-azabicyclo[2.2.2]oct-3-yl)benzyl]-8-(5-fluoropyridin-3-yl)-2-methoxy-6-methyl-9H-purine, 9-{[6-(1-azabicyclo[2.2.2]oct-3-yl)-2-methylpyridin-3-yl]methyl}-2-ethoxy-8-(5-fluoropyridin-3-yl)-6-methyl-9H-purine, 9-{4-[(3S)-1-azabicyclo[2.2.2]oct-3-yloxy]-2-fluorobenzyl}-2-methoxy-6-methyl-8-(pyridin-3-yl)-9H-purine, 9-{2-fluoro-4-[(1-methylpiperidin-4-yl)oxy]benzyl}-8-(5-fluoropyridin-3-yl)-2-methoxy-6-methyl-9H-purine, 9-(2-fluoro-4-{[(3S)-1-methylpyrrolidin-3-yl]oxy}benzyl)-8-(5-fluoropyridin-3-yl)-2-methoxy-6-methyl-9H-purine, 9-(2-fluoro-4-{[(3R)-1-methylpyrrolidin-3-yl]oxy}benzyl)-8-(5-fluoropyridin-3-yl)-2-methoxy-6-methyl-9H-purine, 9-{2-fluoro-4-[(1-methylazetidin-3-yl)oxy]benzyl}-8-(5-fluoropyridin-3-yl)-2-methoxy-6-methyl-9H-purine, 1-(3-fluoro-4-{[8-(5-fluoropyridin-3-yl)-2-methoxy-6-methyl-9H-purin-9-yl]methyl}phenyl)-N,N-dimethylmethanamine, 9-[4-(azetidin-1-ylmethyl)-2-fluorobenzyl]-8-(5-fluoropyridin-3-yl)-2-methoxy-6-methyl-9H-purine, 9-(2-fluoro-4-{[(1 S,4S)-5-methyl-2,5-diazabicyclo[2.2.1]hept-2-yl]methyl}benzyl)-8-(5-fluoropyridin-3-yl)-2-methoxy-6-methyl-9H-purine, 9-[2-fluoro-4-(1-methylpiperidin-4-yl)benzyl]-8-(5-fluoropyridin-3-yl)-2-methoxy-6-methyl-9H-purine, 9-[4-(1-ethylpiperidin-4-yl)-2-fluorobenzyl]-8-(5-fluoropyridin-3-yl)-2-methoxy-6-methyl-9H-purine, 9-(2-fluoro-4-{[(3-endo)-8-methyl-8-azabicyclo[3.2.1]oct-3-yl]oxy}benzyl)-8-(5-fluoropyridin-3-yl)-2-methoxy-6-methyl-9H-purine, 9-(2-fluoro-4-{[(3-endo)-8-methyl-8-azabicyclo[3.2.1]oct-3-yl]oxy}benzyl)-2-methoxy-6-methyl-8-(pyrimidin-5-yl)-9H-purine, 5-[9-(2-fluoro-4-{[(3-endo)-8-methyl-8-azabicyclo[3.2.1]oct-3-yl]oxy}benzyl}-2-methoxy-6-methyl-9H-purin-8-yl]pyridine-3-carbonitrile, 5-[9-(4-{[(3-endo)-8-ethyl-8-azabicyclo[3.2.1]oct-3-yl]oxy}-2-fluorobenzyl)-2-methoxy-6-methyl-9H-purin-8-yl]pyridine-3-carbonitrile, 9-[4-(1-azabicyclo[2.2.2]oct-3-yl)-2-fluorobenzyl]-2-methoxy-6-methyl-8-(pyridin-3-yl)-9H-purine, 9-[4-(1-azabicyclo[2.2.2]oct-3-yl)-2-fluorobenzyl]-2-methoxy-6-methyl-8-(4-methylpyridin-3-yl)-9H-purine, 9-[4-(1-azabicyclo[2.2.2]oct-3-yl)-2-fluorobenzyl]-2-methoxy-6-methyl-8-(5-methylpyridin-3-yl)-9H-purine, 5-[9-(2-fluoro-4-{[(1 S,4S)-5-methyl-2,5-diazabicyclo[2.2.1]hept-2-yl]methyl}benzyl)-2-methoxy-6-methyl-9H-purin-8-yl]pyridine-3-carbonitrile, 5-[9-(4-{[(1 S,4S)-5-ethyl-2,5-diazabicyclo[2.2.1]hept-2-yl]methyl}-2-fluorobenzyl)-2-methoxy-6-methyl-9H-purin-8-yl]pyridine-3-carbonitrile, 9-(2-fluoro-4-{[(1 S,4S)-5-methyl-2,5-diazabicyclo[2.2.1]hept-2-yl]methyl}benzyl)-2-methoxy-6-methyl-8-(pyridin-3-yl)-9H-purine, 5-[2-ethoxy-9-(2-fluoro-4-{[(1 S,4S)-5-methyl-2,5-diazabicyclo[2.2.1]hept-2-yl]methyl}benzyl)-6-methyl-9H-purin-8-yl]pyridine-3-carbonitrile, 2-ethoxy-9-(2-fluoro-4-{[(1 S,4S)-5-methyl-2,5-diazabicyclo[2.2.1]hept-2-yl]methyl}benzyl)-6-methyl-8-(pyrimidin-5-yl)-9H-purine, 2-ethoxy-9-(2-fluoro-4-{[(1 S,4S)-5-methyl-2,5-diazabicyclo[2.2.1]hept-2-yl]methyl}benzyl)-8-(5-fluoropyridin-3-yl)-6-methyl-9H-purine, 5-(9-{4-[(3S)-1-azabicyclo[2.2.2]oct-3-yloxy]-2-fluorobenzyl}-2-methoxy-6-methyl-9H-purin-8-yl)pyridine-3-carbonitrile, 9-{[6-(1-azabicyclo[2.2.2]oct-3-yl)pyridin-3-yl]methyl}-2-ethoxy-8-(5-fluoropyridin-3-yl)-6-methyl-9H-purine, 9-[4-(1-azabicyclo[2.2.2]oct-3-yl)-2-fluorobenzyl]-8-(5-fluoropyridin-3-yl)-2-methoxy-6-methyl-9H-purine, 5-{9-[4-(1-azabicyclo[2.2.2]oct-3-yl)-2-fluorobenzyl]-2-methoxy-6-methyl-9H-purin-8-yl}pyridine-3-carbonitrile, 9-{4-[(3S)-1-azabicyclo[2.2.2]oct-3-yloxy]-2-fluorobenzyl}-8-(5-fluoropyridin-3-yl)-2-methoxy-6-methyl-9H-purine, 9-{4-[(3R)-1-azabicyclo[2.2.2]oct-3-yloxy]-2-fluorobenzyl}-8-(5-fluoropyridin-3-yl)-2-methoxy-6-methyl-9H-purine, 9-(2-fluoro-4-{[(3-exo)-8-methyl-8-azabicyclo[3.2.1]oct-3-yl]oxy}benzyl)-8-(5-fluoropyridin-3-yl)-2-methoxy-6-methyl-9H-purine, and 9-[5-(1-azabicyclo[2.2.2]oct-3-yl)-2-fluorobenzyl]-8-(5-fluoropyridin-3-yl)-2-methoxy-6-methyl-9H-purine.

24. The compound of claim 1 which is selected from the following compounds, or a pharmaceutically acceptable salt thereof:

1-(3-fluoro-4-{[8-(5-fluoropyridin-3-yl)-2-methoxy-6-methyl-9H-purin-9-yl]methyl}phenyl)-N,N-dimethyl-methanamine, 9-[4-(azetidin-1-ylmethyl)-2-fluorobenzyl]-8-(5-fluoropyridin-3-yl)-2-methoxy-6-methyl-9H-purine, 9-(2-fluoro-4-[(1 S,4S)-5-methyl-2,5-diazabicyclo[2.2.1]hept-2-yl]methyl}benzyl)-8-(5-fluoropyridin-3-yl)-2-methoxy-6-methyl-9H-purine, 9-[2-fluoro-4-(1-methylpiperidin-4-yl)benzyl]-8-(5-fluoropyridin-3-yl)-2-methoxy-6-methyl-9H-purine, 9-[4-(1-ethylpiperidin-4-yl)-2-fluorobenzyl]-8-(5-fluoropyridin-3-yl)-2-methoxy-6-methyl-9H-purine, 9-(2-fluoro-4-{[(3-endo)-8-methyl-8-azabicyclo[3.2.1]oct-3-yl]oxy}benzyl)-8-(5-fluoropyridin-3-yl)-2-methoxy-6-methyl-9H-purine, 9-(2-fluoro-4-{[(3-endo)-8-methyl-8-azabicyclo[3.2.1]oct-3-yl]oxy}benzyl)-2-methoxy-6-methyl-8-(pyrimidin-5-yl)-9H-purine, 5-[9-(2-fluoro-4-{[(3-endo)-8-methyl-8-azabicyclo[3.2.1]oct-3-yl]oxy}benzyl)-2-methoxy-6-methyl-9H-purin-8-yl]pyridine-3-carbonitrile, 5-[9-(4-{[(3-endo)-8-ethyl-8-azabicyclo[3.2.1]oct-3-yl]oxy}-2-fluorobenzyl)-2-methoxy-6-methyl-9H-purin-8-yl]pyridine-3-carbonitrile, 9-[4-(1-azabicyclo[2.2.2]oct-3-yl)-2-fluorobenzyl]-2-methoxy-6-methyl-8-(pyridin-3-yl)-9H-purine, 9-[4-(1-azabicyclo[2.2.2]oct-3-yl)-2-fluorobenzyl]-2-methoxy-6-methyl-8-(4-methylpyridin-3-yl)-9H-purine, 9-[4-(1-azabicyclo[2.2.2]oct-3-yl)-2-fluorobenzyl]-2-methoxy-6-methyl-8-(5-methylpyridin-3-yl)-9H-purine, 5-[9-(2-fluoro-4-{[(1 S,4S)-5-methyl-2,5-diazabicyclo[2.2.1]hept-2-yl]methyl}benzyl}-2-methoxy-6-methyl-9H-purin-8-yl]pyridine-3-carbonitrile, 5-({[(1 S,4S)-5-ethyl-2,5-diazabicyclo[2.2.1]hept-2-yl]methyl}-2-fluorobenzyl)-2-methoxy-6-methyl-9H-purin-8-yl]pyridine-3-carbonitrile, 9-(2-fluoro-4-{[(1 S,4S)-5-methyl-2,5-diazabicyclo[2.2.1]hept-2-yl]methyl}benzyl)-2-methoxy-6-methyl-8-(pyridin-3-yl)-9H-purine, 5-[2-ethoxy-9-(2-fluoro-4-{[(1 S,4S)-5-methyl-2,5-diazabicyclo[2.2.1]hept-2-yl]methyl}benzyl)-6-methyl-9H-purin-8-yl]pyridine-3-carbonitrile, 2-ethoxy-9-(2-fluoro-4-{[(1 S,4S)-5-methyl-2,5-diazabicyclo[2.2.1]hept-2-yl]methyl}benzyl)-6-methyl-8-(pyrimidin-5-yl)-9H-purine, 2-ethoxy-9-(2-fluoro-4-{[(1 S,4S)-5-methyl-2,5-diazabicyclo[2.2.1]hept-2-yl]methyl}benzyl}-8-(5-fluoropyridin-3-yl)-6-methyl-9H-purine, 5-(9-{4-[(3S)-1-azabicyclo[2.2.2]oct-3-yloxy]-2-fluorobenzyl}-2-methoxy-6-methyl-9H-purin-8-yl)pyridine-3-carbonitrile, 9-{[6-(1-azabicyclo[2.2.2]oct-3-yl)pyridin-3-yl]methyl}-2-ethoxy-8-(5-fluoropyridin-3-yl)-6-methyl-9H-purine, 9-[4-(1-azabicyclo[2.2.2]oct-3-yl)-2-fluorobenzyl]-8-(5-fluoropyridin-3-yl)-2-methoxy-6-methyl-9H-purine, 5-f 9-[4-(1-azabicyclo[2.2.2]oct-3-yl)-2-fluorobenzyl]-2-methoxy-6-methyl-9H-purin-8-yl}pyridine-3-carbonitrile, 9-{4-[(3S)-1-azabicyclo[2.2.2]oct-3-yloxy]-2-fluorobenzyl}-8-(5-fluoropyridin-3-yl)-2-methoxy-6-methyl-9H-purine, 9-f 4-[(3R)-1-azabicyclo[2.2.2]oct-3-yloxy]-2-fluorobenzyl}-8-(5-fluoropyridin-3-yl)-2-methoxy-6-methyl-9H-purine, 9-(2-fluoro-4-1f[(3-exo)-8-methyl-8-azabicyclo[3.2.1]oct-3-yl]oxy}benzyl)-8-(5-fluoropyridin-3-yl)-2-methoxy-6-methyl-9H-purin, and 9-[5-(1-azabicyclo[2.2.2]oct-3-yl)-2-fluorobenzyl]-8-(5-fluoropyridin-3-yl)-2-methoxy-6-methyl-9H-purine.

25. A pharmaceutical composition comprising the compound of claim 1 or a pharmaceutically acceptable salt thereof as an active ingredient, and a carrier.

26. A method for treating autoimmune disease, comprising administering a therapeutically effective amount of the compound of claim 1 or a pharmaceutically acceptable salt thereof to a mammal.

27. A method for treating systemic lupus erythematosus, lupus nephritis, Sjogren's syndrome, idiopathic thrombocytopenic purpura, psoriasis, rheumatoid arthritis, polymyositis, dermatomyositis, Behcet's disease, multiple sclerosis, or pemphigus, comprising administering a therapeutically effective amount of the compound of claim 1 or a pharmaceutically acceptable salt thereof to a mammal.

\* \* \* \* \*

UNITED STATES PATENT AND TRADEMARK OFFICE
CERTIFICATE OF CORRECTION

PATENT NO. : 10,703,755 B2  
APPLICATION NO. : 16/095822  
DATED : July 7, 2020  
INVENTOR(S) : Shingo Tojo et al.

Page 1 of 1

It is certified that error appears in the above-identified patent and that said Letters Patent is hereby corrected as shown below:

In the Claims

In Claim 22, Columns 416-417, Delete:

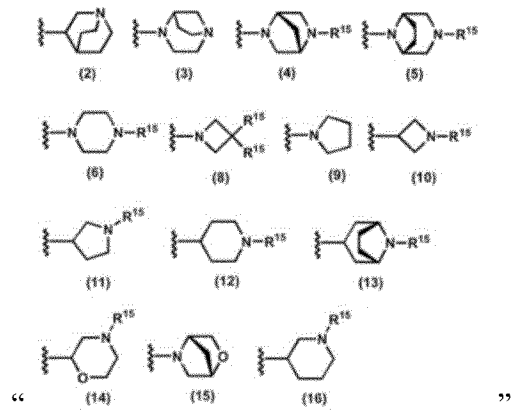

" And insert:

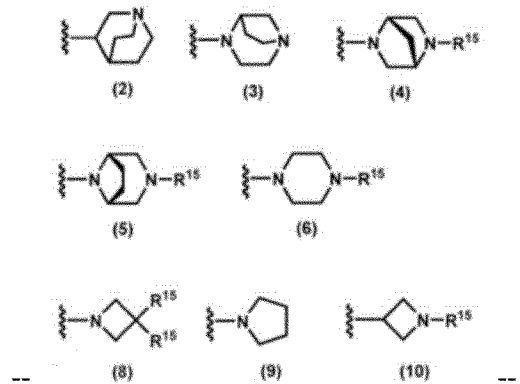

Signed and Sealed this  
Eighth Day of December, 2020

Andrei Iancu  
*Director of the United States Patent and Trademark Office*